United States Patent
Wilson et al.

(10) Patent No.: US 7,928,107 B2
(45) Date of Patent: Apr. 19, 2011

(54) QUINAZOLINES USEFUL AS MODULATORS OF ION CHANNELS

(75) Inventors: Dean Wilson, San Diego, CA (US); Andreas Termin, Encinitas, CA (US); Jesus Gonzalez, San Diego, CA (US); Lev Fanning, San Marcos, CA (US); Timothy Neubert, San Diego, CA (US); Paul Krenitsky, San Diego, CA (US); Pramod Joshi, San Diego, CA (US); Dennis Hurley, San Marcos, CA (US); Urvi Sheth, San Diego, CA (US)

(73) Assignee: Vertex Pharmaceuticals Incorporated, Cambridge, MA (US)

(*) Notice: Subject to any disclaimer, the term of this patent is extended or adjusted under 35 U.S.C. 154(b) by 1320 days.

(21) Appl. No.: 11/367,954

(22) Filed: Mar. 3, 2006

(65) Prior Publication Data

US 2009/0312342 A1    Dec. 17, 2009

Related U.S. Application Data

(63) Continuation-in-part of application No. 11/216,376, filed on Aug. 31, 2005, which is a continuation-in-part of application No. PCT/US2005/31146, filed on Aug. 31, 2005.

(60) Provisional application No. 60/607,150, filed on Sep. 2, 2004, provisional application No. 60/607,037, filed on Sep. 2, 2004, provisional application No. 60/607,033, filed on Sep. 2, 2004, provisional application No. 60/607,036, filed on Sep. 2, 2004.

(51) Int. Cl.
*A61K 31/496* (2006.01)
*A61K 31/517* (2006.01)
*C07D 239/94* (2006.01)

(52) U.S. Cl. ........... 514/252.17; 514/266.2; 514/266.22; 544/293

(58) Field of Classification Search ............. 514/252.17, 514/266.2, 266.22; 544/293
See application file for complete search history.

(56) References Cited

U.S. PATENT DOCUMENTS

| | | |
|---|---|---|
| 3,340,260 A | 9/1967 | Morton Blatter Herbert |
| 3,637,693 A | 1/1972 | Otterstedt et al. |
| 3,819,628 A | 6/1974 | Simpson et al. |
| 4,306,065 A | 12/1981 | Chen |
| 4,377,582 A | 3/1983 | Chen |
| 6,169,088 B1 | 1/2001 | Matsuno et al. |
| 6,184,226 B1 | 2/2001 | Chakravarty et al. |
| 6,608,056 B1 | 8/2003 | Hayakawa et al. |
| 6,613,772 B1 | 9/2003 | Schindler et al. |
| 7,189,733 B2 | 3/2007 | Scarborough et al. |
| 2002/0151544 A1 | 10/2002 | Hayakawa et al. |
| 2004/0248890 A1 | 12/2004 | Gonzales et al. |
| 2006/0154935 A1 | 7/2006 | Wilson et al. |
| 2006/0166963 A1 | 7/2006 | Silva et al. |
| 2006/0173018 A1 | 8/2006 | Wilson et al. |
| 2006/0217377 A1 | 9/2006 | Gonzales et al. |
| 2008/0167305 A1 | 7/2008 | Wilson et al. |

FOREIGN PATENT DOCUMENTS

| | | |
|---|---|---|
| DE | 119051 | 4/1965 |
| DE | 2121031 | 11/1972 |
| EP | 1231211 | 5/1995 |
| EP | 1277738 | 1/2003 |
| EP | 0655456 | 6/2010 |
| GB | 2295387 A | 5/1996 |
| JP | 58-172379 | 10/1983 |
| JP | 08003144 | 1/1996 |
| JP | 2000229950 | 8/2000 |
| JP | 2001-89452 | 4/2001 |
| WO | 98/14431 | 4/1998 |
| WO | 98/25895 | 6/1998 |
| WO | 99/32460 | 7/1999 |
| WO | 01/32632 | 5/2001 |
| WO | 02/14271 | 2/2002 |
| WO | 02/24667 | 3/2002 |
| WO | 03/097615 | 11/2003 |
| WO | 2004/030672 | 4/2004 |
| WO | 2004/078733 | 9/2004 |
| WO | 2006/028904 | 3/2006 |
| WO | 2007058989 | 5/2007 |

OTHER PUBLICATIONS

ERB et. al., J. Het. Chemistry, vol. 37 (2000), pp. 253-260.*
Gorvin, J. of Chem. Research Synopses 9, pp. 294-295 (1989).
Baig et al., J of Chem. Society, Perkin Transaction 1: Organic & Biorganic Chemistry 5, pp. 999-1003 (1984).
Partridge et al., J. of Chem. Society, Section C: Organic 19 pp. 2641-2647 (1970).
Dass et al., J. of Scientific & Industrial Research 11B, p. 461-463 (1952).
Petridou-Fischer J. et al., Journal of Heterocyclic Chemistry, vol. 20, 1983, pp. 1159-1167, XP002394184 p. 1160, left hand Column.
Berge, et al., J. Pharm. Sci., 66(1), 1977, pp. 1-19.
Jordan, V.C. Nature Reviews: Drug Discovery, 2, 2003, p. 205.
Cardellini et al., IL Farmaco Ed, Sci., vol. 30, No. 7, pp. 536-543, 1975.
Lee et al., "Discovery of Potent Cyclic GMP Phosphodiesterase Inhibitors. 2-Pyridyl-and 2- Imidazolyquinazolines Possessing Cyclic GMP Phosphodiesterase and Thromboxane Synthesis Inhibitory Activities", J. Med. Chem., vol. 38, No. 18, pp. 3547-3557, 1995.
Suma et al., "Na and High-voltage-activated Ca2+ Channel Blocking Actions of NS-7, a Novel Neuroprotective Agent, in NG108-15 Cells", Euro. Journal of Pharmacology vol. 336, No. 2/3, pp. 283-290, 1997.

(Continued)

Primary Examiner — James O Wilson
Assistant Examiner — Tamthom N Truong
(74) Attorney, Agent, or Firm — Nancy K. Brennan

(57) ABSTRACT

The present invention relates to compounds useful as inhibitors of voltage-gated sodium channels. The invention also provides pharmaceutically acceptable compositions comprising the compounds of the invention and methods of using the compositions in the treatment of various disorders.

5 Claims, No Drawings

OTHER PUBLICATIONS

Taylor et al., "Na Channels as Targets for Neuroprotective Drugs", Elsevier Science Ltd., vol. 16, No. 9, pp. 309-316, 1995.

ERB et al., "Synthesis of 2-Aminoquinazoline-4(3H)-one Derivatives as Potential Potassium Channel Openers", J. Heterocyclic Chem., vol. 37, pp. 253-260, 2000.

Gupta et al., "Drugs Acting on the Central Nervous System. Syntheses of Substituted Quinazolones and Quinazolines and Triazepino- and Triazocinoquinazolenes", J. Chem., Am. Chem. Soc., vol. 11, No. 2 pp. 392-395, 1968.

Bodajla et al., Chem. Papers 48 (6), 432-436 (1994).

Bodajla et al., Coll. of Czech. Chem. Comm. 59(6), 1463-1466 (1994).

Dorwald, F. Zaragoza. Side Reactions In Organic Synthesis: A Guide to Successful Synthesis Design, Weinheim: WILEY-VCH Verlag Gmbh & Co. KgaA, 2005, Preface.

* cited by examiner

QUINAZOLINES USEFUL AS MODULATORS OF ION CHANNELS

CROSS-REFERENCE TO RELATED APPLICATIONS

This application, as a continuation-in-part application, claims the benefit under 35 U.S.C. §120 of U.S. patent application Ser. No. 11/216,376, filed Aug. 31, 2005, entitled "Quinazolines Useful as Modulators of Ion Channels" and of International Patent application number PCT/US2005/31146, filed Aug. 31, 2005 entitled "Quinazolines Useful as Modulators of Ion Channels", both of which claim the benefit under 35 U.S.C. §119 to U.S. Provisional application Ser. No. 60/607,150, filed Sep. 2, 2004, U.S. Provisional application Ser. No. 60/607,037, filed Sep. 2, 2004, U.S. Provisional application Ser. No. 60/607,033, filed Sep. 2, 2004, and U.S. Provisional application Ser. No. 60/607,036, filed Sep. 2, 2004, the entire contents of each of the above applications being incorporated herein by reference.

TECHNICAL FIELD OF THE INVENTION

The present invention relates to compounds useful as inhibitors of ion channels. The invention also provides pharmaceutically acceptable compositions comprising the compounds of the invention and methods of using the compositions in the treatment of various disorders.

BACKGROUND OF THE INVENTION

Na channels are central to the generation of action potentials in all excitable cells such as neurons and myocytes. They play key roles in excitable tissue including brain, smooth muscles of the gastrointestinal tract, skeletal muscle, the peripheral nervous system, spinal cord and airway. As such they play key roles in a variety of disease states such as epilepsy (ee, Moulard, B. and D. Bertrand (2002) "Epilepsy and sodium channel blockers" *Expert Opin. Ther. Patents* 12(1): 85-91)), pain (See, Waxman, S. G., S. Dib-Hajj, et al. (1999) "Sodium channels and pain" *Proc Natl Acad Sci USA* 96(14): 7635-9 and Waxman, S. G., T. R. Cummins, et al. (2000) "Voltage-gated sodium channels and the molecular pathogenesis of pain: a review" *J Rehabil Res Dev* 37(5): 517-28), myotonia (See, Meola, G. and V. Sansone (2000) "Therapy in myotonic disorders and in muscle channelopathies" *Neurol Sci* 21(5): S953-61 and Mankodi, A. and C. A. Thornton (2002) "Myotonic syndromes" *Curr Opin Neurol* 15(5): 545-52), ataxia (See, Meisler, M. H., J. A. Kearney, et al. (2002) "Mutations of voltage-gated sodium channels in movement disorders and epilepsy" *Novartis Found Symp* 241: 72-81), multiple sclerosis (See, Black, J. A., S. Dib-Hajj, et al. (2000) "Sensory neuron-specific sodium channel SNS is abnormally expressed in the brains of mice with experimental allergic encephalomyelitis and humans with multiple sclerosis" *Proc Natl Acad Sci USA* 97(21): 11598-602, and Renganathan, M., M. Gelderblom, et al. (2003) "Expression of Na(v)1.8 sodium channels perturbs the firing patterns of cerebellar purkinje cells" *Brain Res* 959(2): 235-42), irritable bowel (See Su, X., R. E. Wachtel, et al. (1999) "Capsaicin sensitivity and voltage-gated sodium currents in colon sensory neurons from rat dorsal root ganglia" *Am J Physiol* 277(6 Pt 1): G1180-8, and Laird, J. M., V. Souslova, et al. (2002) "Deficits in visceral pain and referred hyperalgesia in Nav1.8 (SNS/PN3)-null mice" *J Neurosci* 22(19): 8352-6), urinary incontinence and visceral pain (See, Yoshimura, N., S. Seki, et al. (2001) "The involvement of the tetrodotoxin-resistant sodium channel Na(v)1.8 (PN3/SNS) in a rat model of visceral pain" *J Neurosci* 21(21): 8690-6), as well as an array of psychiatry dysfunctions such as anxiety and depression (See, Hurley, S. C. (2002) "Lamotrigine update and its use in mood disorders" *Ann Pharmacother* 36(5): 860-73).

Voltage gated Na channels comprise a gene family consisting of 9 different subtypes (NaV1.1-NaV1.9). These subtypes show tissue specific localization and functional differences (See, Goldin, A. L. (2001) "Resurgence of sodium channel research" *Annu Rev Physiol* 63: 871-94). Three members of the gene family (NaV1.8, 1.9, 1.5) are resistant to block by the well-known Na channel blocker TTX, demonstrating subtype specificity within this gene family. Mutational analysis has identified glutamate 387 as a critical residue for TTX binding (See, Noda, M., H. Suzuki, et al. (1989) "A single point mutation confers tetrodotoxin and saxitoxin insensitivity on the sodium channel II" *FEBS Lett* 259(1): 213-6).

In general, voltage-gated sodium channels (NaVs) are responsible for initiating the rapid upstroke of action potentials in excitable tissue in nervous system, which transmit the electrical signals that compose and encode normal and aberrant pain sensations. Antagonists of NaV channels can attenuate these pain signals and are useful for treating a variety of pain conditions, including but not limited to acute, chronic, inflammatory, and neuropathic pain. Known NaV antagonists, such as TTX, lidocaine (See Mao, J. and L. L. Chen (2000) "Systemic lidocaine for neuropathic pain relief" *Pain* 87(1): 7-17.) bupivacaine, phenyloin (See, Jensen, T. S. (2002) "Anticonvulsants in neuropathic pain: rationale and clinical evidence" *Eur J Pain* 6 (Suppl A): 61-8), lamotrigine (See, Rozen, T. D. (2001) "Antiepileptic drugs in the management of cluster headache and trigeminal neuralgia" *Headache* 41 Suppl 1: S25-32 and Jensen, T. S. (2002) "Anticonvulsants in neuropathic pain: rationale and clinical evidence" *Eur J Pain* 6 (Suppl A): 61-8), and carbamazepine (See, Backonja, M. M. (2002) "Use of anticonvulsants for treatment of neuropathic pain" *Neurology* 59(5 Suppl 2): S14-7), have been shown to be useful attenuating pain in humans and animal models.

Hyperalgesia (extreme sensitivity to something painful) that develops in the presence of tissue injury or inflammation reflects, at least in part, an increase in the excitability of high-threshold primary afferent neurons innervating the site of injury. Voltage sensitive sodium channels activation is critical for the generation and propagation of neuronal action potentials. There is a growing body of evidence indicating that modulation of NaV currents is an endogenous mechanism used to control neuronal excitability (See, Goldin, A. L. (2001) "Resurgence of sodium channel research" *Annu Rev Physiol* 63: 871-94). Several kinetically and pharmacologically distinct voltage-gated sodium channels are found in dorsal root ganglion (DRG) neurons. The TTX-resistant current is insensitive to micromolar concentrations of tetrodotoxin, and displays slow activation and inactivation kinetics and a more depolarized activation threshold when compared to other voltage-gated sodium channels. TTX-resistant sodium currents are primarily restricted to a subpopulation of sensory neurons likely to be involved in nociception. Specifically, TTX-resistant sodium currents are expressed almost exclusively in neurons that have a small cell-body diameter; and give rise to small-diameter slow-conducting axons and that are responsive to capsaicin. A large body of experimental evidence demonstrates that TTX-resistant sodium channels are expressed on C-fibers and are important in the transmission of nociceptive information to the spinal cord.

Intrathecal administration of antisense oligo-deoxynucleotides targeting a unique region of the TTX-resistant sodium channel (NaV1.8) resulted in a significant reduction in $PGE_2$-induced hyperalgesia (See, Khasar, S. G., M. S. Gold, et al. (1998) "A tetrodotoxin-resistant sodium current mediates inflammatory pain in the rat" *Neurosci Lett* 256(1): 17-20). More recently, a knockout mouse line was generated by Wood and colleagues, which lacks functional NaV1.8. The mutation has an analgesic effect in tests assessing the animal's response to the inflammatory agent carrageenan (See, Akopian, A. N., V. Souslova, et al. (1999) "The tetrodotoxin-resistant sodium channel SNS has a specialized function in pain pathways" *Nat Neurosci* 2(6): 541-8). In addition, deficit in both mechano- and thermoreception were observed in these animals. The analgesia shown by the Nav1.8 knockout mutants is consistent with observations about the role of TTX-resistant currents in nociception.

Immunohistochemical, in-situ hybridization and in-vitro electrophysiology experiments have all shown that the sodium channel NaV1.8 is selectively localized to the small sensory neurons of the dorsal root ganglion and trigeminal ganglion (See, Akopian, A. N., L. Sivilotti, et al. (1996) "A tetrodotoxin-resistant voltage-gated sodium channel expressed by sensory neurons" *Nature* 379(6562): 257-62). The primary role of these neurons is the detection and transmission of nociceptive stimuli. Antisense and immunohistochemical evidence also supports a role for NaV1.8 in neuropathic pain (See, Lai, J., M. S. Gold, et al. (2002) "Inhibition of neuropathic pain by decreased expression of the tetrodotoxin-resistant sodium channel, NaV1.8" *Pain* 95(1-2): 143-52, and Lai, J., J. C. Hunter, et al. (2000) "Blockade of neuropathic pain by antisense targeting of tetrodotoxin-resistant sodium channels in sensory neurons" *Methods Enzymol* 314: 201-13). NaV1.8 protein is upregulated along uninjured C-fibers adjacent to the nerve injury. Antisense treatment prevents the redistribution of NaV1.8 along the nerve and reverses neuropathic pain. Taken together the gene-knockout and antisense data support a role for NaV1.8 in the detection and transmission of inflammatory and neuropathic pain.

Several Na channel blockers are currently used or being tested in the clinic to treat epilepsy (See, Moulard, B. and D. Bertrand (2002) "Epilepsy and sodium channel blockers" *Expert Opin. Ther. Patents* 12(1): 85-91); acute (See, Wiffen, P., S. Collins, et al. (2000) "Anticonvulsant drugs for acute and chronic pain" *Cochrane Database Syst Rev* 3), chronic (See, Wiffen, P., S. Collins, et al. (2000) "Anticonvulsant drugs for acute and chronic pain" *Cochrane Database Syst Rev* 3, and Guay, D. R. (2001) "Adjunctive agents in the management of chronic pain" *Pharmacotherapy* 21(9): 1070-81), inflammatory (See, Gold, M. S. (1999) "Tetrodotoxin-resistant Na+ currents and inflammatory hyperalgesia." *Proc Natl Acad Sci USA* 96(14): 7645-9), and neuropathic pain (See, Strichartz, G. R., Z. Zhou, et al. (2002) "Therapeutic concentrations of local anaesthetics unveil the potential role of sodium channels in neuropathic pain" *Novartis Found Symp* 241: 189-201, and Sandner-Kiesling, A., G. Rumpold Seitlinger, et al. (2002) "Lamotrigine monotherapy for control of neuralgia after nerve section" *Acta Anaesthesiol Scand* 46(10): 1261-4); cardiac arrhythmias (See, An, R. H., R. Bangalore, et al. (1996) "Lidocaine block of LQT-3 mutant human $Na^+$ channels" *Circ Res* 79(1): 103-8, and Wang, D. W., K. Yazawa, et al. (1997) "Pharmacological targeting of long QT mutant sodium channels" *J Clin Invest* 99(7): 1714-20); neuroprotection (ee Taylor, C. P. and L. S, Narasimhan (1997) "Sodium channels and therapy of central nervous system diseases" *Adv Pharmacol* 39: 47-98) and as anesthetics (See, Strichartz, G. R., Z. Zhou, et al. (2002) "Therapeutic concentrations of local anaesthetics unveil the potential role of sodium channels in neuropathic pain." *Novartis Found Symp*, 241: 189-201).

Various animal models with clinical significance have been developed for the study of sodium channel modulators for numerous different pain indications. E.g., malignant chronic pain, see, Kohase, H., et al., Acta Anaesthesiol Scand. 2004; 48(3):382-3; femur cancer pain (see, Kohase, H., et al., Acta Anaesthesiol Scand. 2004; 48(3):382-3); non-malignant chronic bone pain (see, Ciocon, J. O. et al., J Am Geriatr Soc. 1994; 42(6):593-6); rheumatoid arthritis (see, Calvino, B. et al., Behav Brain Res. 1987; 24(1):11-29); osteoarthritis (see, Guzman, R. E., et al., Toxicol Pathol. 2003; 31(6):619-24); spinal stenosis (see, Takenobu, Y. et al., J Neurosci Methods. 2001; 104(2):191-8); Neuropathic low back pain (see, Hines, R., et al., Pain Med. 2002; 3(4):361-5; Massie, J. B., et al., J Neurosci Methods. 2004; 137(2):283-9; neuropathic low back-pain (see, Hines, R., et al., Pain Med. 2002; 3(4):361-5; Massie, J. B., et al., J Neurosci Methods. 2004; 137(2):283-9); myofascial pain syndrome (see, Dalpiaz & Dodds, J Pain Palliat Care Pharmacother. 2002; 16(1):99-104; Sluka K A et al., Muscle Nerve. 2001; 24(1):37-46); fibromyalgia (see, Bennet & Tai, Int J Clin Pharmacol Res. 1995; 15(3):115-9); temporomandibular joint pain (see, Ime H, Ren K, Brain Res Mol Brain Res. 1999; 67(1):87-97); chronic visceral pain, including, abdominal (see, Al-Chaer, E. D., et al., Gastroenterology. 2000; 119(5):1276-85); pelvic/perineal pain, (see, Wesselmann et al., Neurosci Lett. 1998; 246(2):73-6); pancreatic (see, Vera-Portocarrero, L. B., et al., Anesthesiology. 2003; 98(2):474-84); IBS pain (see, Verne, G. N., et al., Pain. 2003; 105(1-2):223-30; La J H et al., World Gastroenterol. 2003; 9(12):2791-5); chronic headache pain (see, Willimas & Stark, Cephalalgia. 2003; 23(10):963-71); migraine (see, Yamamura, H., et al., J. Neurophysiol. 1999; 81(2):479-93); tension headache, including, cluster headaches (see, Costa, A., et al., Cephalalgia. 2000; 20(2):85-91); chronic neuropathic pain, including, post-herpetic neuralgia (see, Attal, N., et al., Neurology. 2004; 62(2):218-25; Kim & Chung 1992, Pain 50:355); diabetic neuropathy (see, Beidoun A et al., Clin J. Pain. 2004; 20(3):174-8; Courteix, C., et al., Pain. 1993; 53(1):81-8); HIV-associated neuropathy (see, Portegies & Rosenberg, Ned Tijdschr Geneeskd. 2001; 145(15):731-5; Joseph E K et al., Pain. 2004; 107(1-2):147-58; Oh, S. B., et al., J. Neurosci. 2001; 21(14):5027-35); trigeminal neuralgia (see, Sato, J., et al., Oral Surg Oral Med Oral Pathol Oral Radiol Endod. 2004; 97(1):18-22; Imamura Y et al., Exp Brain Res. 1997; 116(1):97-103); Charcot-Marie Tooth neuropathy (see, Sereda, M., et al., Neuron. 1996; 16(5):1049-60); hereditary sensory neuropathies (see, Lee, M. J., et al., Hum Mol. Genet. 2003; 12(15):1917-25); peripheral nerve injury (see, Attal, N., et al., Neurology. 2004; 62(2):218-25; Kim & Chung 1992, Pain 50:355; Bennett & Xie, 1988, Pain 33:87; Decostered, I. & Woolf, C. J., 2000, Pain 87:149; Shir, Y. & Seltzer, Z. 1990; Neurosci Lett 115:62); painful neuromas (see, Nahabedian & Johnson, Ann Plast Surg. 2001; 46(1):15-22; Devor & Raber, Behav Neural Biol. 1983; 37(2):276-83); ectopic proximal and distal discharges (see, Liu, X. et al., Brain Res. 2001; 900(1):119-27); radiculopathy (see, Devers & Galer, (see, Clin J. Pain. 2000; 16(3):205-8; Hayashi N et al., Spine. 1998; 23(8):877-85); chemotherapy induced neuropathic pain (see, Aley, K. O., et al., Neuroscience. 1996; 73(1):259-65); radiotherapy-induced neuropathic pain; post-mastectomy pain (see, Devers & Galer, Clin J. Pain. 2000; 16(3):205-8); central pain (Cahana, A., et al., Anesth Analg. 2004; 98(6):1581-4), spinal cord injury pain (see, Hains, B. C., et al., Exp Neurol. 2000; 164(2):426-37); post-stroke pain; thalamic pain (see, LaBuda, C. J., et al., Neurosci Lett. 2000; 290(1):79-83); complex regional pain syndrome (see, Wallace, M. S., et al., Anesthesiology. 2000; 92(1):75-83; Xantos D et al., J. Pain. 2004; 5(3 Suppl 2):S1); phantom pain (see, Weber, W. E., Ned Tijdschr Geneeskd.

2001; 145(17):813-7; Levitt & Heyback, Pain. 1981; 10(1): 67-73); intractable pain (see, Yokoyama, M., et al., Can J. Anaesth. 2002; 49(8):810-3); acute pain, acute post-operative pain (see, Koppert, W., et al., Anesth Analg. 2004; 98(4): 1050-5; Brennan, T. J., et al., Pain. 1996; 64(3):493-501); acute musculoskeletal pain; joint pain (see, Gotoh, S., et al., Ann Rheum Dis. 1993; 52(11):817-22); mechanical low back pain (see, Kehl, L. J., et al., Pain. 2000; 85(3):333-43); neck pain; tendonitis; injury/exercise pain (see, Sesay, M., et al., Can J. Anaesth. 2002; 49(2):137-43); acute visceral pain, including, abdominal pain; pyelonephritis; appendicitis; cholecystitis; intestinal obstruction; hernias; etc (see, Giambernardino, M. A., et al., Pain. 1995; 61(3):459-69); chest pain, including, cardiac Pain (see, Vergona, R. A., et al., Life Sci. 1984; 35(18):1877-84); pelvic pain, renal colic pain, acute obstetric pain, including, labor pain (see, Segal, S., et al., Anesth Analg. 1998; 87(4):864-9); cesarean section pain; acute inflammatory, burn and trauma pain; acute intermittent pain, including, endometriosis (see, Cason, A. M., et al., Horm Behav. 2003; 44(2):123-31); acute herpes zoster pain; sickle cell anemia; acute pancreatitis (see, Toma, H; Gastroenterology. 2000; 119(5):1373-81); breakthrough pain; orofacial pain, including, sinusitis pain, dental pain (see, Nusstein, J., et al., J. Endod. 1998; 24(7):487-91; Chidiac, J. J., et al., Eur J. Pain. 2002; 6(1):55-67); multiple sclerosis (MS) pain (see, Sakurai & Kanazawa, J Neurol Sci. 1999; 162(2):162-8); pain in depression (see, Greene B, Curr Med Res Opin. 2003; 19(4):272-7); leprosy pain; behcet's disease pain; adiposis dolorosa (see, Devillers & Oranje, Clin Exp Dermatol. 1999; 24(3):240-1); phlebitic pain; Guillain-Barre pain; painful legs and moving toes; Haglund syndrome; erythromelalgia pain (see, Legroux-Crespel, E., et al., Ann Dermatol Venereol. 2003; 130(4):429-33); Fabry's disease pain (see, Germain, D. P., J Soc Biol. 2002; 196(2):183-90); Bladder and urogenital disease, including, urinary incontinence (see, Berggren, T., et al., J. Urol. 1993; 150(5 Pt 1):1540-3); hyperactivity bladder (see, Chuang, Y. C., et al., Urology. 2003; 61(3):664-70); painful bladder syndrome (see, Yoshimura, N., et al., J. Neurosci. 2001; 21(21):8690-6); interstitial cyctitis (IC) (see, Giannakopoulos & Campilomatos, Arch Ital Urol Nefrol Androl. 1992; 64(4):337-9; Boucher, M., et al., J. Urol. 2000; 164(1):203-8); and prostatitis (see, Mayersak, J. S., Int Surg. 1998; 83(4):347-9; Keith, I. M., et al., J. Urol. 2001; 166(1):323-8).

Unfortunately, as described above, the efficacy of currently used sodium channel blockers and calcium channel blockers for the disease states described above has been to a large extent limited by a number of side effects. These side effects include various CNS disturbances such as blurred vision, dizziness, nausea, and sedation as well more potentially life threatening cardiac arrhythmias and cardiac failure. Such undesirable side effects may be avoided by using a Na channel blocker that exhibit a degree of selectivity in its activity against a Na channel subtype. However, Na channel blockers currently in the market lack such selectivity. Perhaps because of this lack of molecular selectivity, drugs currently in the market exhibit use-dependent block and generally show higher affinity at depolarized potentials resulting in the preferential targeting of actively firing neurons, believed to be a key factor in the therapeutic window of existing Na channel blocking drugs. While every drug has it own unique therapeutic profile, current Na channel blockers are generally associated with central nervous system (CNS) and cardiovascular (CV) side effects, including blood pressure changes, which are often dose-limiting. Dizziness, sedation, nausea, ataxia, and confusion are some of the specific side effects observed for Phenyloin™, Mexiletine™, and Lidocaine™.

There is also a need to develop Na channel blockers that have minimal or no inhibitory activity against the hERG channel. hERG (human ether a-go-go related gene) encodes a potassium ion channel (hERG channel) that is involved in cardiac repolarization. See, e.g., Pearlstein, R., R. Vaz, et al. (2003). "Understanding the Structure-Activity Relationship of the Human Ether-a-go-go-Related Gene Cardiac K(+) Channel. A Model for Bad Behavior." J Med Chem 46(11): 2017-22. Interaction with the hERG channel is one indicator of potential cardiac toxicity. hERG-block increases the likelihood of cardiac QT-interval prolongation and dispersion. A subset of compounds that prolong the QT interval can cause ventricular fibrillation and cardiac failure. Belardinelli, L., C. Antzelevitch and M. A. Vos (2003). "Assessing predictors of drug-induced torsade de pointes". Trends Pharmacol Sci. 24 (12): 619-25; Al-Khatib, S. M., N. M. LaPointe, et al. (2003). "What clinicians should know about the QT interval." Jama 289(16): 2120-7; http://www.fenichel.net/pages/site_map.htm.

There is also a need to develop Na channel blockers that have minimal or no inhibitory activity against the Cytochrome P450 enzyme family. Within this family, CYP 3A4 isoform is believed to be the major isoform present in the liver and small intestines. Other key isoforms include CYP 2D6, CYP 2C9, and CYP 1A2. See, e.g., U.S. Pat. No. 6,514,687, the disclosure whereof is incorporated herein by reference. A Na channel blocker that inhibits one or more of the isoforms can cause undesirable side effect or can cause undesirable drug-drug interactions when administered with another drug that interacts with that isoform. See, e.g., Davit, B., et al. (1999), "FDA Evaluations Using In Vitro Metabolism to Predict and Interpret In Vivo Metabolic Drug-Drug Interactions: Impact on Labeling," J. Clin. Pharmacol., 39: 899-910; "Drug Metabolism/Drug Interaction Studies in the Drug Development Process: Studies In Vitro, Dept. of Health and Human Services, U.S.F.D.A (http://www.fda.gov/cder/guidance-.htm).

There is also a need to develop Na channel blockers that exhibit selectivity against a certain sub-type of Na channel. Particularly useful are compounds that have a desirably low activity against NaV 1.2.

There is also a need to develop Na channel blockers that have a desirably low activity against L-type calcium channel 1.2. CaV1.2 calcium channels are abundantly expressed in smooth and striated muscle, especially in the heart, brain and endocrine cells. Blocking these channels can be therapeutically useful, but it can also result in significant side effects. The most significant concerns are impairment of cardiac contractility (that is, a negative inotropic effect) and slowing of electrical conduction in the pacemaker regions of the heart. See, e.g., Kizer, J. R., et al., "Epidemiologic Review of the Calcium Channel Blocker Drugs," Arch. Intern Med. 2001; 161: 1145-1158.

There is also a need to Na channel blockers that have a desirably low activity against potassium channel 1.5 ("Kv1.5"; also known as KCNA5). Kv1.5 is found primarily in human atrial cells, but also in brain. See, e.g., Gutman, G. A., et al., "Compendium of Voltage-Gated Ion Channels Potassium Channels," Pharmacol. Rev., 55: 583-585 (2003). Unwanted block of Kv1.5 could produce convulsion or ataxia.

There is also a need to develop Na channel blockers that have improved pharmacokinetic and/or pharmacodynamic properties and, therefore, are better suited for in-vivo administration for therapeutic purposes. Such properties include aqueous solubility, bioavailability, clearance kinetics, etc. See, e.g., Shargel, L., Yu, A., Ed's "Applied Biopharmaceutics & Pharmacokinetics", 4th Ed., McGraw-Hill, New York, 1999; Yacobi, A., Skelly, J. P., Shah, V. P., Benet, L. Z., Ed's. "Integration of Pharmacokinetics, Pharmacodynamics, and Toxicokinetics in Rational Drug Development", Plenum Press, New York, 1993; Lee, J. S., Obach, R. S., Fisher, M. B., Ed's. "Drug Metabolizing Enzymes Cytochrome P450 and Other Enzymes in Drug Discovery and Development", Marcel Dekker, New York, 2003; Birkett, D. J. "Pharmacokinetics Made Easy", McGraw-Hill Australia, Roseville, Australia, 2002; Katzung, B. G. "Basic & Clinical Pharmacology", McGraw-Hill, New York, 2001; Welling, P. G., Tse, F. L. S., Ed's. "Pharmcokinetics", Marcel Dekker, New York, 1988; Thomas, G. "Medicinal Chemistry An Introduction", Wiley & Sons, New York, 2000; and Gennaro, A. R., et al., "Remington: The Science and Practice of Pharmacy," 20th Ed., Lippincott, Williams, & Wilkins (2003).

A Na channel blocker that meets one or more of the above unmet needs would be a very desirable improvement over the currently marketed Na channel blockers and would greatly benefit patients in need of a therapy therewith.

SUMMARY OF THE INVENTION

The present invention provides compounds of formula I:

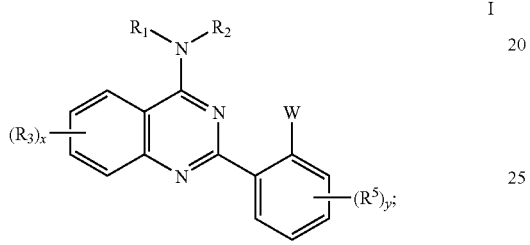

I or a pharmaceutically acceptable salt or derivative thereof.

These compounds and pharmaceutically acceptable compositions are useful for treating or lessening the severity of a variety of diseases, disorders, or conditions, including, but not limited to, acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, or cancer pain.

DETAILED DESCRIPTION OF THE INVENTION

I. General Description of Compounds of the Invention

The present invention provides a compound of formula I:

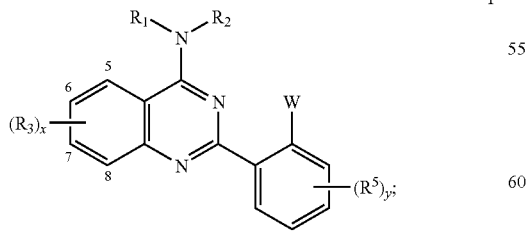

I or a pharmaceutically acceptable salt or derivative thereof, wherein:

$R^1$ and $R^2$, taken together with the nitrogen atom, form a substituted ring selected from:

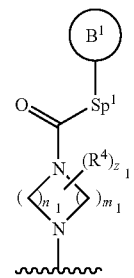
(A)

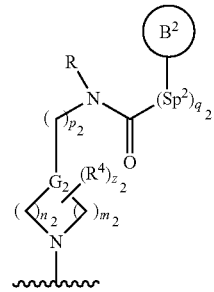
(B)

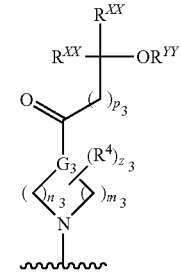
(C)

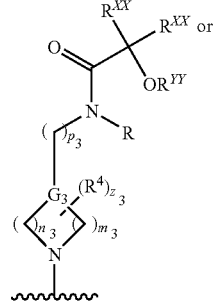
(D)

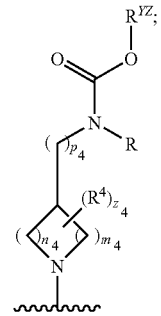
(E)

wherein, in ring (A):
each of $m_1$ and $n_1$ is independently 0-3, provided that $m_1+n_1$ is 2-6;
$z_1$ is 0-4;
$Sp^1$ is —O—, —S—, —NR'—, or a C1-C6 alkylidene linker, wherein up to two methylene units are optionally and independently replaced by —O—, —S—, —CO—, —CS—, —COCO—, —CONR'—, —CONR'NR'—, —CO₂—, —OCO—, —NR'CO₂—, —NR'CONR'—, —OCONR'—, —NR'NR', —NR'NR'CO—, —NR'CO—, —SO, —SO₂—, —NR'—, —SO₂NR'—, NR'SO₂—, or —NR'SO₂NR'—, provided that Sp¹ is attached to the carbonyl group through an atom other than carbon;

ring B¹ is a 4-8 membered, saturated, partially unsaturated, or aromatic, monocyclic heterocyclic ring having 1-4 heteroatoms selected from O, S, or N, wherein ring B¹ is optionally substituted with $w_1$ independent occurrences of —R¹¹, wherein $w_1$ is 0-4;

wherein, in ring (B):
  $G_2$ is —N—, or CH;
  each of $m_2$ and $n_2$ is independently 0-3, provided that $m_2+n_2$ is 2-6;
  $p_2$ is 0-2; provided that when $G_2$ is N, then $p_2$ is not 0;
  $q_2$ is 0 or 1;
  $z_2$ is 0-4;
  Sp² is a bond or a C1-C6 alkylidene linker, wherein up to two methylene units are optionally and independently replaced by —O—, —S—, —CO—, —CS—, —COCO—, —CONR'—, —CONR'NR'—, —CO₂—, —OCO—, —NR'CO₂—, —NR'CONR'—, —OCONR'—, —NR'NR', —NR'NR'CO—, —NR'CO—, —SO, —SO₂—, —NR'—, —SO₂NR'—, NR'SO₂—, or —NR'SO₂NR'—;
  ring B² is a 4-8 membered, saturated, partially unsaturated, or aromatic, monocyclic heterocyclic ring having 1-4 heteroatoms selected from O, S, or N, wherein ring B is optionally substituted with w independent occurrences of —R¹², wherein $w_2$ is 0-4;

wherein, in ring (C) or ring (D):
  $G_3$ is —N—, —CH—NH—, or —CH—CH₂—NH—;
  each of $m_3$ and $n_3$ is independently 0-3, provided that $m_3+n_3$ is 2-6;
  $p_3$ is 0-2;
  $z_3$ is 0-4;
  each $R^{XX}$ is hydrogen, $C_{1-6}$ aliphatic group, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; wherein $R^{XX}$ is optionally substituted with $W_3$ independent occurrences of —R¹³, wherein $W_3$ is 0-3;
  provided that both $R^{XX}$ are not simultaneously hydrogen;
  $R^{YY}$ is hydrogen, —COR', —CO₂R', —CON(R')₂, —SOR', —SO₂R', —SO₂N(R')₂, —COCOR', —COCH₂COR', —P(O)(OR')₂, —P(O)₂OR', or —PO(R');

wherein, in ring (E):
  each of $m_4$ and $n_4$ is independently 0-3, provided that $m_4+n_4$ is 2-6;
  $p_4$ is 1-2;
  $z_4$ is 0-4;
  $R^{YZ}$ is $C_1-C_6$ aliphatic group, optionally substituted with $w_4$ independent occurrences of —R¹⁴, wherein $w_4$ is 0-3;
  x and y, each, is independently 0-4;
  W is $OR^{XY}$;
  $R^{XY}$ is hydrogen or a group selected from:

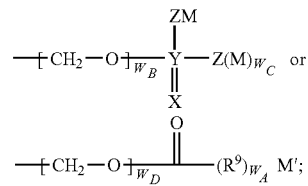

wherein:
  each of $w_A$, $w_B$, $w_C$, and $w_D$ is independently 0 or 1;
  each M is independently selected from hydrogen, Li, Na, K, Mg, Ca, Ba, —N(R⁷)₄, $C_1-C_{12}$-alkyl, $C_2-C_{12}$-alkenyl, or —R⁶; wherein 1 to 4-CH₂ radicals of the alkyl or alkenyl group, other than the —CH₂ that is bound to Z, is optionally replaced by a heteroatom group selected from O, S, S(O), S(O₂), or N(R⁷); and wherein any hydrogen in said alkyl, alkenyl or R⁶ is optionally replaced with a substituent selected from oxo, —OR⁷, —R⁷, N(R⁷)₂, N(R⁷)₃, R⁷OH, —CN, —CO₂R⁷, —C(O)—N(R⁷)₂, S(O)₂—N(R⁷)₂, N(R⁷)—C(O)—R⁷, C(O)R⁷, —S(O)ₙ—R⁷, OCF₃, —S(O)ₙ—R⁶, N(R⁷)—S(O)₂(R⁷), halo, —CF₃, or —NO₂;
  n is 0-2;
  M' is H, $C_1-C_{12}$-alkyl, $C_2-C_{12}$-alkenyl, or —R⁶; wherein 1 to 4-CH₂ radicals of the alkyl or alkenyl group is optionally replaced by a heteroatom group selected from O, S, S(O), S(O₂), or N(R⁷); and wherein any hydrogen in said alkyl, alkenyl or R⁶ is optionally replaced with a substituent selected from oxo, —OR⁷, —R⁷, —N(R⁷)₂, N(R⁷)₃, —R⁷OH, —CN, —CO₂R⁷, —C(O)—N(R⁷)₂, —S(O)₂—N(R⁷)₂, —N(R⁷)—C(O)—R⁷, —C(O)R⁷, —S(O)ₙ—R⁷, —OCF₃, —S(O)ₙ—R⁶, —N(R⁷)—S(O)₂ (R⁷), halo, —CF₃, or —NO₂;
  Z is —CH₂—, —O—, —S—, —N(R⁷)₂—; or, when M is absent, then Z is hydrogen, =O, or =S;
  Y is P or S, wherein when Y is S, then Z is not S;
  X is O or S;
  each R⁷ is independently selected from hydrogen, or $C_1-C_4$ aliphatic, optionally substituted with up to two $Q_1$;
  each $Q_1$ is independently selected from a 3-7 membered saturated, partially saturated or unsaturated carbocyclic ring system; or a 5-7 membered saturated, partially saturated or unsaturated heterocyclic ring containing one or more heteroatom or heteroatom group selected from O, N, NH, S, SO, or SO₂; wherein Q, is optionally substituted with up to three substituents selected from oxo, —OH, —O($C_1-C_4$ aliphatic), —$C_1-C_4$ aliphatic, —NH₂, NH($C_1-C_4$ aliphatic), —N($C_1-C_4$ aliphatic)₂, —N($C_1-C_4$ aliphatic)-C(O)—$C_1-C_4$ aliphatic, —($C_1-C_4$ aliphatic)-OH, —CN, —CO₂H, —CO₂($C_1-C_4$ aliphatic), —C(O)—NH₂, —C(O)—NH($C_1-C_4$ aliphatic), —C(O)—N($C_1-C_4$ aliphatic)₂, halo or —CF₃;
  R⁶ is a 5-6 membered saturated, partially saturated or unsaturated carbocyclic or heterocyclic ring system, or an 8-10 membered saturated, partially saturated or unsaturated bicyclic ring system; wherein any of said heterocyclic ring systems contains one or more heteroatoms selected from O, N, S, S(O)ₙ or N(R⁷); and wherein any of said ring systems optionally contains 1 to 4 substituents independently selected from OH, $C_1-C_4$ alkyl, O—$C_1-C_4$ alkyl or O—C(O)—$C_1-C_4$ alkyl;

$R^9$ is $C(R^7)_2$, O or $N(R^7)$;

each occurrence of $R^{11}$, $R^{12}$, $R^{13}$, $R^{14}$, $R^3$, $R^4$, and $R^5$ is independently Q-$R^X$; wherein Q is a bond or is a $C_1$-$C_6$ alkylidene chain wherein up to two non-adjacent methylene units of Q are optionally and independently replaced by —NR—, —S—, —O—, —CS—, —$CO_2$—, —OCO—, —CO—, —COCO—, —CONR—, —NRCO—, —$NRCO_2$—, —$SO_2$NR—, —$NRSO_2$—, —CONRNR—, —NRCONR—, —OCONR—, —NRNR—, —$NRSO_2$NR—, —SO—, —$SO_2$—, —PO—, —$PO_2$—, —OP(O)(OR)—, or —POR—; and each occurrence of $R^X$ is independently selected from —R', halogen, =O, =NR', —$NO_2$, —CN, —OR', —SR', —$N(R')_2$, —NR'COR', —NR'CON$(R')_2$, —NR'$CO_2$R', —COR', —$CO_2$R', —OCOR', —CON$(R')_2$, —OCON$(R')_2$, —SOR', —$SO_2$R', —$SO_2$N$(R')_2$, —NR'$SO_2$R', —NR'$SO_2$N$(R')_2$, —COCOR', —$COCH_2$COR', —OP(O)(OR')$_2$, —P(O)(OR')$_2$, —OP(O)$_2$OR', —P(O)$_2$OR', —PO$(R')_2$, or —OPO$(R')_2$; and each occurrence of R is independently hydrogen or $C_{1-6}$ aliphatic group having up to three substituents; and each occurrence of R is independently hydrogen or $C_{1-6}$ aliphatic group, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur, wherein R' has up to four substituents; or R and R', two occurrences of R, or two occurrences of R', are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur.

2. Compounds and Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. In some embodiments, "cycloaliphatic" (or "carbocycle" or "cycloalkyl") refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule wherein any individual ring in said bicyclic ring system has 3-7 members. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "heteroaliphatic", as used herein, means aliphatic groups wherein one or two carbon atoms are independently replaced by one or more of oxygen, sulfur, nitrogen, phosphorus, or silicon. Heteroaliphatic groups may be substituted or unsubstituted, branched or unbranched, cyclic or acyclic, and include "heterocycle", "heterocyclyl", "heterocycloaliphatic", or "heterocyclic" groups.

The term "heterocycle", "heterocyclyl", "heterocycloaliphatic", or "heterocyclic" as used herein means non-aromatic, monocyclic, bicyclic, or tricyclic ring systems in which one or more ring members are an independently selected heteroatom. In some embodiments, the "heterocycle", "heterocyclyl", "heterocycloaliphatic", or "heterocyclic" group has three to fourteen ring members in which one or more ring members is a heteroatom independently selected from oxygen, sulfur, nitrogen, or phosphorus, and each ring in the system contains 3 to 7 ring members.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated", as used herein, means that a moiety has one or more units of unsaturation.

The term "alkoxy", or "thioalkyl", as used herein, refers to an alkyl group, as previously defined, attached to the principal carbon chain through an oxygen ("alkoxy") or sulfur ("thioalkyl") atom.

The terms "haloalkyl", "haloalkenyl" and "haloalkoxy" means alkyl, alkenyl or alkoxy, as the case may be, substituted with one or more halogen atoms. The term "halogen" means F, Cl, Br, or I.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined hereinbelow.

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroarylalkoxy and the like) group may contain one or more substituents and thus may be "optionally substituted". Unless otherwise defined above and herein, suitable substituents on the unsaturated carbon atom of an aryl or heteroaryl group are generally selected from halogen; —$R^o$; —$OR^o$; —$SR^o$; phenyl (Ph) optionally substituted with $R^o$; —O(Ph) optionally substituted with $R^o$; —$(CH_2)_{1-2}$(Ph), optionally substituted with $R^o$; —CH═CH(Ph), optionally substituted with $R^o$; —$NO_2$; —CN; —$N(R^o)_2$; —$NR^oC(O)R^o$; —$NR^oC(S)R^o$; —$NR^oC(O)N(R^o)_2$; —$NR^oC(S)N(R^o)_2$; —$NR^oCO_2R^o$; —$NR^oNR^oC(O)R^o$; —$NR^oNR^oC(O)N(R^o)_2$; —$NR^oNR^oCO_2R^o$; —$C(O)C(O)R^o$; —$C(O)CH_2C(O)R^o$; —$CO_2R^o$; —$C(O)R^o$; —$C(S)R^o$; —$C(O)N(R^o)_2$; —$C(S)N(R^o)_2$; —$OC(O)N(R^o)_2$; —$OC(O)R^o$; —$C(O)N(OR^o)R^o$; —$C(NOR^o)R^o$; —$S(O)_2R^o$; —$S(O)_3R^o$; —$SO_2N(R^o)_2$; —$S(O)R^o$; —$NR^oSO_2N(R^o)_2$; —$NR^oSO_2R^o$; —$N(OR^o)R^o$; —C(═NH)—$N(R^o)_2$; —$P(O)_2R^o$; —$PO(R^o)_2$; —$OPO(R^o)_2$; —$(CH_2)_{0-2}NHC(O)R^o$; phenyl (Ph) optionally substituted with $R^o$; —O(Ph) optionally substituted with $R^o$; —$(CH_2)_{1-2}$(Ph), optionally substituted with $R^o$; or —CH═CH(Ph), optionally substituted with $R^o$; wherein each independent occurrence of $R^o$ is selected from hydrogen, optionally substituted $C_{1-6}$ aliphatic, an unsubstituted 5-6 membered heteroaryl or heterocyclic ring, phenyl, —O(Ph), or —$CH_2$(Ph), or, notwithstanding the definition above, two independent occurrences of $R^o$, on the same substituent or different substituents, taken together with the atom(s) to which each $R^o$ group is bound, to form an optionally substituted 3-12 membered saturated, partially unsaturated, or fully unsaturated monocyclic or bicyclic ring having 0-4 heteroatoms independently selected from nitrogen, oxygen, or sulfur.

Optional substituents on the aliphatic group of $R^o$ are selected from $NH_2$, $NH(C_{1-4}$aliphatic), $N(C_{1-4}$aliphatic$)_2$, halogen, $C_{1-4}$aliphatic, OH, $O(C_{1-4}$aliphatic), $NO_2$, CN, $CO_2H$, $CO_2(C_{1-4}$aliphatic), O(halo$C_{1-4}$ aliphatic), or halo$C_{1-4}$ aliphatic, wherein each of the foregoing $C_{1-4}$aliphatic groups of $R^o$ is unsubstituted.

An aliphatic or heteroaliphatic group, or a non-aromatic heterocyclic ring may contain one or more substituents and thus may be "optionally substituted". Unless otherwise defined above and herein, suitable substituents on the saturated carbon of an aliphatic or heteroaliphatic group, or of a non-aromatic heterocyclic ring are selected from those listed above for the unsaturated carbon of an aryl or heteroaryl group and additionally include the following: ═O, ═S, ═NNHR*, ═NN(R*)$_2$, ═NNHC(O)R*, ═NNHCO$_2$(alkyl), ═NNHSO$_2$(alkyl), or ═NR*, where each R* is independently selected from hydrogen or an optionally substituted $C_{1-6}$ aliphatic group.

Unless otherwise defined above and herein, optional substituents on the nitrogen of a non-aromatic heterocyclic ring are generally selected from —$R^+$, —$N(R^+)_2$, —$C(O)R^+$, —$CO_2R^+$, —$C(O)C(O)R^+$, —$C(O)CH_2C(O)R^+$, —$SO_2R^+$, —$SO_2N(R^+)_2$, —C(═S)N(R$^+$)$_2$, —C(═NH)—N(R$^+$)$_2$, or —$NR^+SO_2R^+$; wherein $R^+$ is hydrogen, an optionally substituted $C_{1-6}$ aliphatic, optionally substituted phenyl, optionally substituted —O(Ph), optionally substituted —$CH_2$(Ph), optionally substituted —$(CH_2)_{1-2}$(Ph); optionally substituted —CH═CH(Ph); or an unsubstituted 5-6 membered heteroaryl or heterocyclic ring having one to four heteroatoms independently selected from oxygen, nitrogen, or sulfur, or, notwithstanding the definition above, two independent occurrences of $R^+$, on the same substituent or different substituents, taken together with the atom(s) to which each $R^+$ group is bound, form an optionally substituted 3-12 membered saturated, partially unsaturated, or fully unsaturated monocyclic or bicyclic ring having 0-4 heteroatoms independently selected from nitrogen, oxygen, or sulfur.

Optional substituents on the aliphatic group or the phenyl ring of $R^+$ are selected from —$NH_2$, —$NH(C_{1-4}$ aliphatic), —$N(C_{1-4}$ aliphatic$)_2$, halogen, $C_{1-4}$ aliphatic, —OH, —$O(C_{1-4}$ aliphatic), —$NO_2$, —CN, —$CO_2H$, —$CO_2(C_{1-4}$ aliphatic), —O(halo $C_{1-4}$ aliphatic), or halo($C_{1-4}$ aliphatic), wherein each of the foregoing $C_{1-4}$aliphatic groups of $R^+$ is unsubstituted.

The term "alkylidene chain" refers to a straight or branched carbon chain that may be fully saturated or have one or more units of unsaturation and has two points of attachment to the rest of the molecule.

As detailed above, in some embodiments, two independent occurrences of $R^o$ (or $R^+$, R, R' or any other variable similarly defined herein), are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur.

Exemplary rings that are formed when two independent occurrences of $R^o$ (or $R^+$, R, R' or any other variable similarly defined herein), are taken together with the atom(s) to which each variable is bound include, but are not limited to the following: a) two independent occurrences of $R^o$ (or $R^+$, R, R' or any other variable similarly defined herein) that are bound to the same atom and are taken together with that atom to form a ring, for example, $N(R^o)_2$, where both occurrences of $R^o$ are taken together with the nitrogen atom to form a piperidin-1-yl, piperazin-1-yl, or morpholin-4-yl group; and b) two independent occurrences of $R^o$ (or $R^+$, R, R' or any other variable similarly defined herein) that are bound to different atoms and are taken together with both of those atoms to form a ring, for example where a phenyl group is substituted with two occurrences of $OR^o$

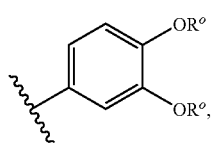

these two occurrences of $R^o$ are taken together with the oxygen atoms to which they are bound to form a fused 6-membered oxygen containing ring:

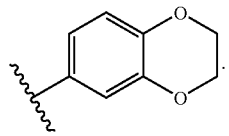

It will be appreciated that a variety of other rings can be formed when two independent occurrences of $R^o$ (or $R^+$, R, R' or any other variable similarly defined herein) are taken together with the atom(s) to which each variable is bound and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this invention. Such compounds are useful, for example, as analytical tools or probes in biological assays.

3. Description of Exemplary Compounds

In one embodiment, R is hydrogen. Or, R is C1-C6 aliphatic. Exemplary R includes C1-C6 alkyl, e.g., methyl, ethyl, propyl, or butyl.

In one embodiment, R' is hydrogen.

In one embodiment, R' is a C1-C8 aliphatic group, optionally substituted with up to 3 substituents selected from halo, CN, $CF_3$, $CHF_2$, $OCF_3$, or $OCHF_2$, wherein up to two methylene units of said C1-C8 aliphatic is optionally replaced with —CO—, —CONH(C1-C4 alkyl)-, —$CO_2$—, —OCO—, —N(C1-C4 alkyl)$CO_2$—, —O—, —N(C1-C4 alkyl)CON(C1-C4 alkyl)-, —OCON(C1-C4 alkyl)-, —N(C1-C4 alkyl)CO—, —S—, —N(C1-C4 alkyl)-, —$SO_2$N(C1-C4 alkyl)-, N(C1-C4 alkyl)$SO_2$—, or —N(C1-C4 alkyl)$SO_2$N(C1-C4 alkyl)-.

In one embodiment, R' is a 3-8 membered saturated, partially unsaturated, or fully unsaturated monocyclic ring having 0-3 heteroatoms independently selected from nitrogen, oxygen, or sulfur, wherein R' is optionally substituted with up to 3 substituents selected from halo, CN, $CF_3$, $CHF_2$, $OCF_3$, $OCHF_2$, or C1-C6 alkyl, wherein up to two methylene units of said C1-C6 alkyl is optionally replaced with —CO—, —CONH(C1-C4 alkyl)-, —$CO_2$—, —OCO—, —N(C1-C4 alkyl)$CO_2$—, —O—, —N(C1-C4 alkyl)CON(C1-C4 alkyl)-, —OCON(C1-C4 alkyl)-, —N(C1-C4 alkyl)CO—, —S—, —N(C1-C4 alkyl)-, —$SO_2$N(C1-C4 alkyl)-, N(C1-C4 alkyl)$SO_2$—, or —N(C1-C4 alkyl)$SO_2$N(C1-C4 alkyl)-.

In one embodiment, R' is an 8-12 membered saturated, partially unsaturated, or fully unsaturated bicyclic ring system having 0-5 heteroatoms independently selected from nitrogen, oxygen, or sulfur; wherein R' is optionally substituted with up to 3 substituents selected from halo, CN, $CF_3$, $CHF_2$, $OCF_3$, $OCHF_2$, or C1-C6 alkyl, wherein up to two methylene units of said C1-C6 alkyl is optionally replaced with —CO—, —CONH(C1-C4 alkyl)-, —$CO_2$—, —OCO—, —N(C1-C4 alkyl)$CO_2$—, —O—, —N(C1-C4 alkyl)CON(C1-C4 alkyl)-, —OCON(C1-C4 alkyl)-, —N(C1-C4 alkyl)CO—, —S—, —N(C1-C4 alkyl)-, —$SO_2$N(C1-C4 alkyl)-, N(C1-C4 alkyl)$SO_2$—, or —N(C1-C4 alkyl)$SO_2$N(C1-C4 alkyl)-.

In one embodiment, two occurrences of R' are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur, wherein R' is optionally substituted with up to 3 substituents selected from halo, CN, $CF_3$, $CHF_2$, $OCF_3$, $OCHF_2$, or C1-C6 alkyl, wherein up to two methylene units of said C1-C6 alkyl is optionally replaced with —CO—, —CONH(C1-C4 alkyl)-, —$CO_2$—, —OCO—, —N(C1-C4 alkyl)$CO_2$—, —O—, —N(C1-C4 alkyl)CON(C1-C4 alkyl)-, —OCON(C1-C4 alkyl)-, —N(C1-C4 alkyl)CO—, —S—, —N(C1-C4 alkyl)-, —$SO_2$N(C1-C4 alkyl)-, N(C1-C4 alkyl)$SO_2$—, or —N(C1-C4 alkyl)$SO_2$N(C1-C4 alkyl)-.

In another embodiment, W is OH.

In still another embodiment, $R^{XY}$ is:

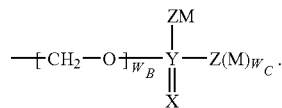

In certain embodiment, Y is P and X is O.

In another embodiment, each Z is —O—.

In yet another embodiment, $R^{XY}$ is selected from:

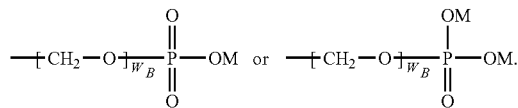

In yet another embodiment, $R^{XY}$ is selected from:

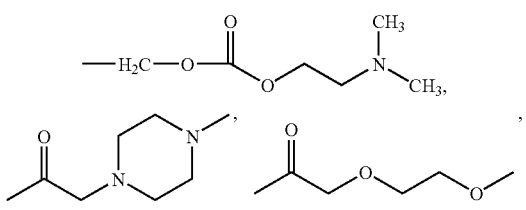

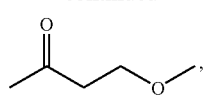

-(L)-lysine, —PO$_3$Na$_2$,

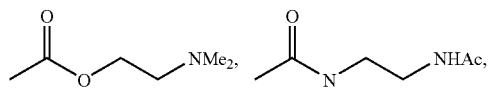

-(L)-tyrosine,

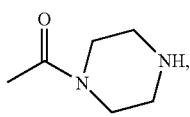

—PO$_3$Mg, —PO$_3$(NH$_4$)$_2$, —CH$_2$—OPO$_3$Na$_2$,

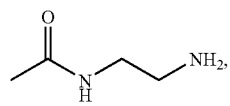

-(L)-serine, —SO$_3$Na$_2$,

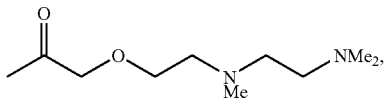

—SO$_3$Mg, —SO$_3$(NH$_4$)$_2$, —CH$_2$—OSO$_3$Na$_2$, —CH$_2$—OSO$_3$(NH$_4$)$_2$,

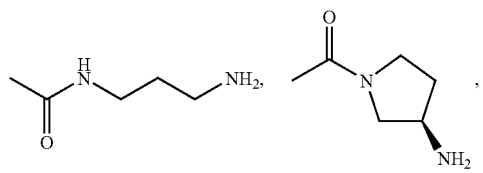

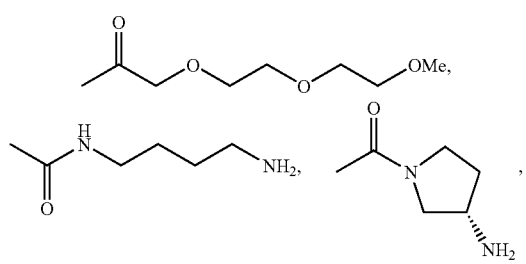

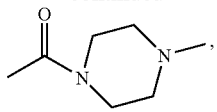

acetyl,

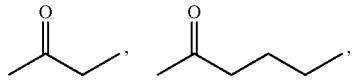

-(L)-valine, -(L)-glutamic acid, -(L)-aspartic acid, -(L)-γ-t-butyl-aspartic acid,

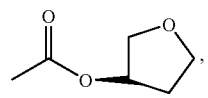

-(L)-3-pyridylalanine, -(L)-histidine,

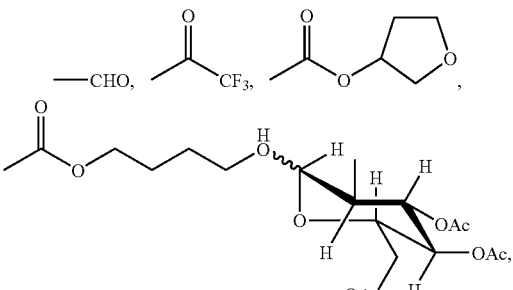

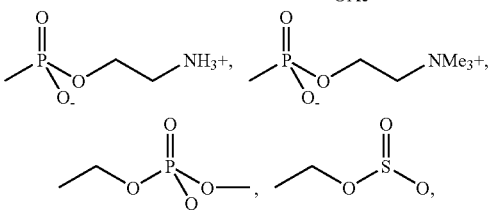

PO$_3$K$_2$, PO$_3$Ca, PO$_3$-spermine, PO$_3$-(spermidine)$_2$ or PO$_3$-(meglamine)$_2$.

In yet another embodiment, R$^{XY}$ is selected from:

| R$^{XY}$ |
|---|
| 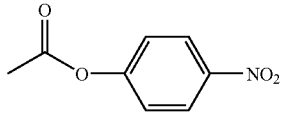 |
| 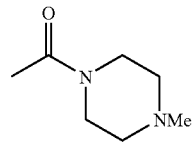 |

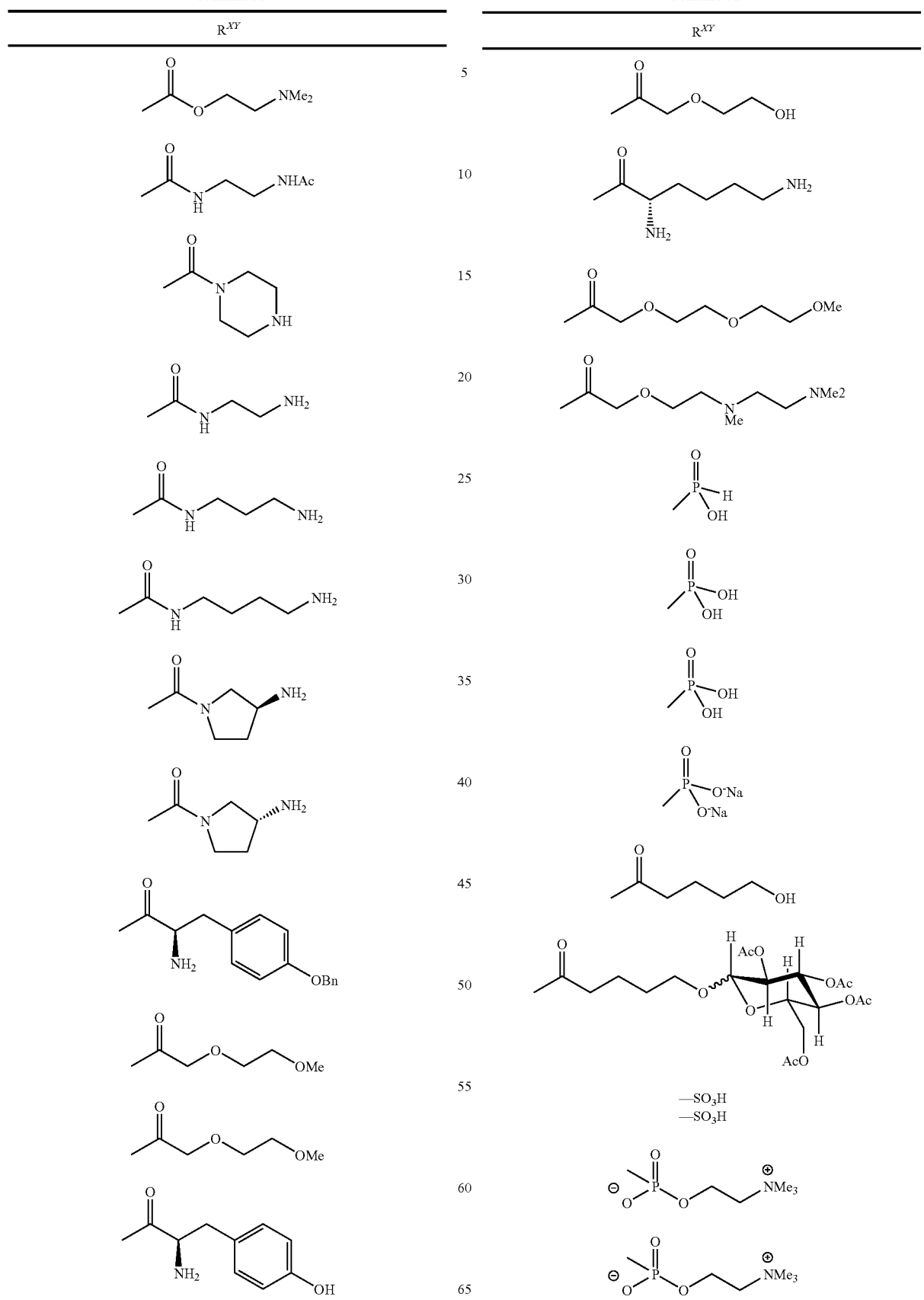

-continued

R^XY

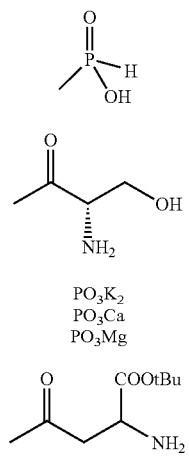

PO$_3$K$_2$
PO$_3$Ca
PO$_3$Mg

In one embodiment, x is 0-2. Or, x is 1 or 2. Or, x is 1.

In one embodiment, R$^3$ is present at the 6- or 7-position of the quinazoline ring.

In another embodiment, R$^3$ is selected from halo, CN, NO$_2$, —N(R')$_2$, —CH$_2$N(R')$_2$, —OR', —CH$_2$OR', —SR', —CH$_2$SR', —COOR', —NRCOR', —CON(R')$_2$, —OCON(R')$_2$, COR', —NHCOOR', —SO$_2$R', —SO$_2$N(R')$_2$, or an optionally substituted group selected from C$_1$-C$_6$aliphatic, aryl, heteroaryl, cycloaliphatic, heterocycloaliphatic, arylC$_1$-C$_6$alkyl, heteroarylC$_1$-C$_6$alkyl, cycloaliphaticC$_1$-C$_6$alkyl, or heterocycloaliphaticC$_1$-C$_6$alkyl.

In one embodiment, R$^3$ is independently Cl, Br, F, CF$_3$, —OCF$_3$, Me, Et, CN, —COOH, —NH$_2$, —N(CH$_3$)$_2$, —N(Et)$_2$, —N(iPr)$_2$, —O(CH$_2$)$_2$OCH$_3$, —CONH$_2$, —COOCH$_3$, —OH, —OCH$_3$, —OCH$_2$CH$_3$, —CH$_2$OH, —NHCOCH$_3$, —NHCOCH(CH$_3$)$_2$, —SO$_2$NH$_2$, —CONH(cyclopropyl), —CONHCH$_3$, —CONHCH$_2$CH$_3$, or an optionally substituted group selected from -piperidinyl, piperizinyl, morpholino, phenyl, phenyloxy, benzyl, or benzyloxy.

In another embodiment, each R$^3$ group is independently halogen, CN, optionally substituted C$_1$-C$_6$alkyl, OR', N(R')$_2$, CON(R')$_2$, or NRCOR'.

In one embodiment, x is 1 or 2, and each R$^3$ group is —Cl, —CH$_3$, —CH$_2$CH$_3$, —F, —CF$_3$, —OCF$_3$, —CONHCH$_3$, —CONHCH$_2$CH$_3$, —CONH(cyclopropyl), —OCH$_3$, —NH$_2$, —OCH$_2$CH$_3$, or —CN.

In yet another embodiment, x is 1 and R$^3$ is at the 6-position of the quinazoline ring and is selected from —Cl, —CH$_3$, —CH$_2$CH$_3$, —F, —CF$_3$, —OCF$_3$, —CONHCH$_3$, —CONHCH$_2$CH$_3$, —CONH(cyclopropyl), —OCH$_3$, —NH$_2$, —OCH$_2$CH$_3$, or —CN.

In yet another embodiment, x is 1 and R$^3$ is at the 6-position of the quinazoline ring and is —Cl, —CH$_3$, —CH$_2$CH$_3$, —F, —CF$_3$, —OCF$_3$, —OCH$_3$, or —OCH$_2$CH$_3$.

In one embodiment, R$^3$ is at the 6-position of the quinazoline ring and is —CON(R')$_2$, or NRCOR'.

In another embodiment, x is 1 and R$^3$ is at the 7-position of the quinazoline ring and is selected from —Cl, —CH$_3$, —CH$_2$CH$_3$, —F, —CF$_3$, —OCF$_3$, —CONHCH$_3$, —CONHCH$_2$CH$_3$, —CONH(cyclopropyl), —OCH$_3$, —NH$_2$, —OCH$_2$CH$_3$, or —CN.

In yet another embodiment, x is 1 and R$^3$ is at the 7-position of the quinazoline ring and is —Cl, —CH$_3$, —CH$_2$CH$_3$, —F, —CF$_3$, —OCF$_3$, —OCH$_3$, or —OCH$_2$CH$_3$. Or, x is 1 and R$^3$ is at the 7-position of the quinazoline ring and is —CON(R')$_2$, or NRCOR'.

In one embodiment, y is 0-4 and R$^5$ is independently halogen, CN, NO$_2$, —N(R')$_2$, —CH$_2$N(R')$_2$, —OR', —CH$_2$OR', —SR', —CH$_2$SR', —NRCOR', —CON(R')$_2$, —S(O)$_2$N(R')$_2$, —OCOR', —COR', —CO$_2$R', —OCON(R')$_2$, —NR'SO$_2$R', —OP(O)(OR')$_2$, —P(O)(OR')$_2$, —OP(O)$_2$OR', —P(O)$_2$OR', —PO(R')$_2$, —OPO(R')$_2$, or an optionally substituted group selected from C$_1$-C$_6$aliphatic, aryl, heteroaryl, cycloaliphatic, heterocycloaliphatic, arylC$_1$-C$_6$alkyl, heteroarylC$_1$-C$_6$alkyl, cycloaliphaticC$_1$-C$_6$alkyl, or heterocycloaliphaticC$_1$-C$_6$alkyl.

In another embodiment, R$^5$ is independently Cl, Br, F, CF$_3$, Me, Et, CN, —COOH, —NH$_2$, —N(CH$_3$)$_2$, —N(Et)$_2$, —N(iPr)$_2$, —O(CH$_2$)$_2$OCH$_3$, —CONH$_2$, —COOCH$_3$, —OH, —OCH$_3$, —OCH$_2$CH$_3$, —CH$_2$OH, —NHCOCH$_3$, —SO$_2$NH$_2$, —SO$_2$NHC(CH$_3$)$_2$, —OCOC(CH$_3$)$_3$, —OCOCH$_2$C(CH$_3$)$_3$, —O(CH$_2$)$_2$N(CH$_3$)$_2$, 4-CH$_3$-piperazin-1-yl, OCOCH(CH$_3$)$_2$, OCO(cyclopentyl), —COCH$_3$, optionally substituted phenoxy, or optionally substituted benzyloxy.

In certain embodiments, each of z$_1$, z$_2$, z$_3$, or z$_4$ is independently 0-2. In other embodiments, each of z$_1$, z$_2$, z$_3$, or z$_4$ is 0 and the ring is unsubstituted. Preferred R$^4$ groups, when present, are each independently halogen, CN, NO$_2$, —N(R')$_2$, —CH$_2$N(R')$_2$, —OR', —CH$_2$OR', —SR', —CH$_2$SR', —COOR', —NRCOR', —CON(R')$_2$, —OCON(R')$_2$, COR', —NHCOOR', —SO$_2$R', —SO$_2$N(R')$_2$, or an optionally substituted group selected from C$_1$-C$_6$aliphatic, aryl, heteroaryl, cycloaliphatic, heterocycloaliphatic, arylC$_1$-C$_6$alkyl, heteroarylC$_1$-C$_6$alkyl, cycloaliphaticC$_1$-C$_6$alkyl, or heterocycloaliphatic C$_1$-C$_6$alkyl. Other exemplary R$^4$ groups are Cl, Br, F, CF$_3$, CH$_3$, —CH$_2$CH$_3$, CN, —COOH, —N(CH$_3$)$_2$, —N(Et)$_2$, —N(iPr)$_2$, —O(CH$_2$)$_2$OCH$_3$, —CONH$_2$, —COOCH$_3$, —OH, —CH$_2$OH, —NHCOCH$_3$, —SO$_2$NH$_2$, —SO$_2$(CH$_2$)$_3$CH$_3$, —SO$_2$CH(CH$_3$)$_2$, —SO$_2$N(CH$_3$)$_2$, —SO$_2$CH$_2$CH$_3$, —C(O)OCH$_2$CH(CH$_3$)$_2$, —C(O)NHCH$_2$CH(CH$_3$)$_2$, —NHCOOCH$_3$, —C(O)C(CH$_3$)$_3$, —COO(CH$_2$)$_2$CH$_3$, —C(O)NHCH(CH$_3$)$_2$, —C(O)CH$_2$CH$_3$, or an optionally substituted group selected from piperidinyl, piperizinyl, morpholino, C$_{1-4}$alkoxy, phenyl, phenyloxy, benzyl, benzyloxy, —CH$_2$cyclohexyl, pyridyl, —CH$_2$pyridyl, or —CH$_2$thiazolyl In certain embodiments, x is 0-2. In other embodiments, x is 1 or 2. In still other embodiments x is 1 and R$^3$ is substituted at the 6- or 7-position of the quinazoline ring. When the quinazoline ring is substituted (x is 1-4), R$^3$ groups are halogen, CN, NO$_2$, —N(R')$_2$, —CH$_2$N(R')$_2$, —OR', —CH$_2$OR', —SR', —CH$_2$SR', —COOR', —NRCOR', —CON(R')$_2$, —OCON(R')$_2$, COR', —NHCOOR', —SO$_2$R', —SO$_2$N(R')$_2$, or an optionally substituted group selected from C$_1$-C$_6$aliphatic, aryl, heteroaryl, cycloaliphatic, heterocycloaliphatic, arylC$_1$-C$_6$alkyl, heteroarylC$_1$-C$_6$alkyl, cycloaliphaticC$_1$-C$_6$alkyl, or heterocycloaliphaticC$_1$-C$_6$alkyl. In still other embodiments, each occurrence of R$^3$ is independently Cl, Br, F, CF$_3$, —OCF$_3$, Me, Et, CN, —COOH, —NH$_2$, —N(CH$_3$)$_2$, —N(Et)$_2$, —N(iPr)$_2$, —O(CH$_2$)$_2$OCH$_3$, —CONH$_2$, —COOCH$_3$, —OH, —OCH$_3$, —OCH$_2$CH$_3$, —CH$_2$OH, —NHCOCH$_3$, —NHCOCH(CH$_3$)$_2$, —SO$_2$NH$_2$, —CONH(cyclopropyl), —CONHCH$_3$, —CONHCH$_2$CH$_3$, or an optionally substituted group selected from -piperidinyl, piperizinyl, morpholino, phenyl, phenyloxy, benzyl, or benzyloxy. In still other embodiments, x is 1 or 2 and each R$^3$ group is independently halogen, CN, optionally substituted C$_1$-C$_6$alkyl, OR', N(R')$_2$, CON(R')$_2$, or NRCOR'. In yet other embodiments, x is 1 or 2, and each R$^3$ group is —Cl, —CH$_3$, —CH$_2$CH$_3$, —F, —CF$_3$, —OCF$_3$, —CONHCH$_3$, —CONHCH$_2$CH$_3$, —CONH(cyclopropyl), —OCH$_3$, —NH$_2$, —OCH$_2$CH$_3$, or —CN. In still other embodiments, x is 1 and R$^3$ is at the 6-position of the quinazoline ring and is —Cl, —CH$_3$, —CH$_2$CH$_3$, —F, —CF$_3$, —OCF$_3$, —CONHCH$_3$, —CONHCH$_2$CH$_3$, —CONH(cyclopropyl), —OCH$_3$, —NH$_2$, —OCH$_2$CH$_3$, or —CN. IN yet other embodiments, x is 1 and R$^3$ is at the 7-position of the quinazoline ring and is —Cl, —CH$_3$, —CH$_2$CH$_3$, —F, —CF$_3$, —OCF$_3$, —CONHCH$_3$, —CONHCH$_2$CH$_3$, —CONH(cyclopropyl), —OCH$_3$, —NH$_2$, —OCH$_2$CH$_3$, or —CN. In other embodiments, x is 1 and R$^3$ is at the 6-position of the quinazoline ring and is —Cl, —CH$_3$, —CH$_2$CH$_3$, —F, —CF$_3$, —OCF$_3$, —OCH$_3$, or —OCH$_2$CH$_3$. In still other embodiments, x is 1 and R$^3$ is at the 7-position of the quinazoline ring and is —Cl, —CH$_3$, —CH$_2$CH$_3$, —F, —CF$_3$, —OCF$_3$, —OCH$_3$, or —OCH$_2$CH$_3$. In other embodiments, x is 1 and R$^3$ is at the 6-position of the quinazoline ring and is —CON(R')$_2$, or NRCOR'. In yet other embodiments, x is 1 and R$^3$ is at the 7-position of the quinazoline ring and is —CON(R')$_2$, or NRCOR'.

In some embodiments, y is 0-4 and R$^5$ group, when present, is each independently halogen, CN, NO$_2$, —N(R')$_2$, —CH$_2$N(R')$_2$, —OR', —CH$_2$OR', —SR', —CH$_2$SR', —NRCOR', —CON(R')$_2$, —S(O)$_2$N(R')$_2$, —OCOR', —COR', —CO$_2$R', —OCON(R')$_2$, —NR'SO$_2$R', —OP(O)(OR')$_2$, —P(O)(OR')$_2$, —OP(O)$_2$OR', —P(O)$_2$OR', —PO(R')$_2$, —OPO(R')$_2$, or an optionally substituted group selected from C$_1$-C$_6$aliphatic, aryl, heteroaryl, cycloaliphatic, heterocycloaliphatic, arylC$_1$-C$_6$alkyl, heteroarylC$_1$-C$_6$alkyl, cycloaliphaticC$_1$-C$_6$alkyl, or heterocycloaliphaticC$_1$-C$_6$alkyl.

In yet other embodiments, y is 0-4 and each occurrence of R$^5$ is independently Cl, Br, F, CF$_3$, Me, Et, CN, —COOH, —NH$_2$, —N(CH$_3$)$_2$, —N(Et)$_2$, —N(iPr)$_2$, —O(CH$_2$)$_2$OCH$_3$, —CONH$_2$, —COOCH$_3$, —OH, —OCH$_3$, —OCH$_2$CH$_3$, —CH$_2$OH, —NHCOCH$_3$, —SO$_2$NH$_2$, —SO$_2$NHC(CH$_3$)$_2$, —OCOC(CH$_3$)$_3$, —OCOCH$_2$C(CH$_3$)$_3$, —O(CH$_2$)$_2$N(CH$_3$)$_2$, 4-CH$_3$-piperazin-1-yl, OCOCH(CH$_3$)$_2$, OCO(cyclopentyl), —COCH$_3$, optionally substituted phenoxy, or optionally substituted benzyloxy.

In yet another embodiment, each of z$_1$, z$_2$, z$_3$, or z$_4$ is 0-4, and R$^4$ groups, when present, are each independently halogen, CN, NO$_2$, —N(R')$_2$, —CH$_2$N(R')$_2$, —OR', —CH$_2$OR', —SR', —CH$_2$SR', —COOR', —NRCOR', —CON(R')$_2$, —OCON(R')$_2$, COR', —NHCOOR', —SO$_2$R', —SO$_2$N(R')$_2$, or an optionally substituted group selected from C$_1$-C$_6$aliphatic, aryl, heteroaryl, cycloaliphatic, heterocycloaliphatic, arylC$_1$-C$_6$alkyl, heteroarylC$_1$-C$_6$alkyl, cycloaliphaticC$_1$-C$_6$alkyl, or heterocycloaliphaticC$_1$-C$_6$alkyl.

In still other embodiments, each of z$_1$, z$_2$, z$_3$, or z$_4$ is 0-4 and R$^4$ groups are each independently Cl, Br, F, CF$_3$, CH$_3$, —CH$_2$CH$_3$, CN, —COOH, —N(CH$_3$)$_2$, —N(Et)$_2$, —N(iPr)$_2$, —O(CH$_2$)$_2$OCH$_3$, —CONH$_2$, —COOCH$_3$, —OH, —CH$_2$OH, —NHCOCH$_3$, —SO$_2$NH$_2$, —SO$_2$(CH$_2$)$_3$CH$_3$, —SO$_2$CH(CH$_3$)$_2$, —SO$_2$N(CH$_3$)$_2$, —SO$_2$CH$_2$CH$_3$, —C(O)OCH$_2$CH(CH$_3$)$_2$, —C(O)NHCH$_2$CH(CH$_3$)$_2$, —NHCOOCH$_3$, —C(O)C(CH$_3$)$_3$, —COO(CH$_2$)$_2$CH$_3$, —C(O)NHCH(CH$_3$)$_2$, —C(O)CH$_2$CH$_3$, or an optionally substituted group selected from -piperidinyl, piperizinyl, morpholino, C$_{1-4}$alkoxy, phenyl, phenyloxy, benzyl, benzyloxy, —CH$_2$cyclohexyl, pyridyl, —CH$_2$pyridyl, or —CH$_2$thiazolyl.

For compounds described directly above, in some embodiments, x is 0-4, and R$^3$ groups, when present, are each independently halogen, CN, NO$_2$, —N(R')$_2$, —CH$_2$N(R')$_2$, —OR', —CH$_2$OR', —SR', —CH$_2$SR', —COOR', —NRCOR', —CON(R')$_2$, —OCON(R')$_2$, COR', —NHCOOR', —SO$_2$R', —SO$_2$N(R')$_2$, or an optionally substituted group selected from C$_1$-C$_6$aliphatic, aryl, heteroaryl, cycloaliphatic, heterocycloaliphatic, arylC$_1$-C$_6$alkyl, heteroarylC$_1$-C$_6$alkyl, cycloaliphaticC$_1$-C$_6$alkyl, or heterocycloaliphaticC$_1$-C$_6$alkyl.

In yet other embodiments, x is 1 or 2, and each occurrence of R$^3$ is independently Cl, Br, F, CF$_3$, —OCF$_3$, Me, Et, CN, —COOH, —NH$_2$, —N(CH$_3$)$_2$, —N(Et)$_2$, —N(iPr)$_2$, —O(CH$_2$)$_2$OCH$_3$, —CONH$_2$, —COOCH$_3$, —OH, —OCH$_3$, —OCH$_2$CH$_3$, —CH$_2$OH, —NHCOCH$_3$, —NHCOCH(CH$_3$)$_2$, —SO$_2$NH$_2$, —CONH(cyclopropyl), —CONHCH$_3$, —CONHCH$_2$CH$_3$, or an optionally substituted group selected from -piperidinyl, piperizinyl, morpholino, phenyl, phenyloxy, benzyl, or benzyloxy.

In still other embodiments, x is 1 or 2 and each R$^3$ group is independently halogen, CN, optionally substituted C$_1$-C$_6$alkyl, OR', N(R')$_2$, CON(R')$_2$, or NRCOR'.

In yet other embodiments, x is 1 or 2, and each R$^3$ group is —Cl, —CH$_3$, —CH$_2$CH$_3$, —F, —CF$_3$, —OCF$_3$, —CONHCH$_3$, —CONHCH$_2$CH$_3$, —CONH(cyclopropyl), —OCH$_3$, —NH$_2$, —OCH$_2$CH$_3$, or —CN.

In still other embodiments, x is 1 and R$^3$ is at the 6-position of the quinazoline ring and is —Cl, —CH$_3$, —CH$_2$CH$_3$, —F, —CF$_3$, —OCF$_3$, —CONHCH$_3$, —CONHCH$_2$CH$_3$, —CONH(cyclopropyl), —OCH$_3$, —NH$_2$, —OCH$_2$CH$_3$, or —CN.

In yet other embodiments, x is 1 and R$^3$ is at the 7-position of the quinazoline ring and is —Cl, —CH$_3$, —CH$_2$CH$_3$, —F, —CF$_3$, —OCF$_3$, —CONHCH$_3$, —CONHCH$_2$CH$_3$, —CONH(cyclopropyl), —OCH$_3$, —NH$_2$, —OCH$_2$CH$_3$, or —CN.

In still other embodiments, x is 1 and R$^3$ is at the 6-position of the quinazoline ring and is —Cl, —CH$_3$, —CH$_2$CH$_3$, —F, —CF$_3$, —OCF$_3$, —OCH$_3$, or —OCH$_2$CH$_3$.

In yet other embodiments, x is 1 and R$^3$ is at the 7-position of the quinazoline ring and is —Cl, —CH$_3$, —CH$_2$CH$_3$, —F, —CF$_3$, —OCF$_3$, —OCH$_3$, or —OCH$_2$CH$_3$.

In still other embodiments, x is 1 and R$^3$ is at the 6-position of the quinazoline ring and is —CON(R')$_2$, or NRCOR'.

In yet other embodiments, x is 1 and R$^3$ is at the 7-position of the quinazoline ring and is —Cl, —CH$_3$, —CH$_2$CH$_3$, —F, —CF$_3$, —OCF$_3$, —OCH$_3$, or —OCH$_2$CH$_3$.

In yet other embodiments for compounds described directly above, x is 1 and R$^3$ is at the 6-position of the quinazoline ring and is —Cl, —CH$_3$, —CH$_2$CH$_3$, —F, —CF$_3$, —OCF$_3$, —CONHCH$_3$, —CONHCH$_2$CH$_3$, —CONH(cyclopropyl), —OCH$_3$, —NH$_2$, —OCH$_2$CH$_3$, or —CN. In still other embodiments, x is 1 and R$^3$ is at the 7-position of the quinazoline ring and is —Cl, —CH$_3$, —CH$_2$CH$_3$, —F, —CF$_3$, —OCF$_3$, —CONHCH$_3$, —CONHCH$_2$CH$_3$, —CONH(cyclopropyl), —OCH$_3$, —NH$_2$, —OCH$_2$CH$_3$, or —CN. In yet other embodiments, x is 1 and R$^3$ is at the 6-position of the quinazoline ring and is —Cl, —CH$_3$, —CH$_2$CH$_3$, —F, —CF$_3$, —OCF$_3$, —OCH$_3$, or —OCH$_2$CH$_3$. In still other embodiments, x is 1 and R$^3$ is at the 7-position of the quinazoline ring and is —Cl, —CH$_3$, —CH$_2$CH$_3$, —F, —CF$_3$, —OCF$_3$, —OCH$_3$, or —OCH$_2$CH$_3$. In yet other embodiments, x is 1 and R$^3$ is at the 6-position of the quinazoline ring and is —CON(R')$_2$, or NRCOR'. In yet other embodiments, x is 1 and R$^3$ is at the 7-position of the quinazoline ring and is —CON(R')$_2$, or NRCOR'.

In one embodiment, the present invention provides compounds of formula I-A:

wherein x, y, $n_1$, $m_1$, $z_1$, $R^{XY}$, $R^4$, $R^5$, $Sp^1$, and ring $B^1$ are as defined above.

In one embodiment, $Sp^1$ is selected from —O—, —S—, or —NR'—. Or, $Sp^1$ is —O—. Or, $Sp^1$ is —O—$CH_2$—. In another embodiment, $Sp^1$ is —NR'—. Or, $Sp^1$ is —NH—. Or, $Sp^1$ is —NH—$CH_2$—.

In one embodiment, each of $m_1$ and $n_1$ is 1. In another embodiment, each of $m_1$ and $n_1$ is 2.

In one embodiment, ring $B^1$ is a 4-8 membered, saturated, partially unsaturated, or aromatic, monocyclic heterocyclic ring having 1-4 heteroatoms selected from O, S, or N, wherein ring $B^1$ is optionally substituted with w independent occurrences of —$R^{11}$, wherein $w_1$ is 0-4.

In another embodiment, ring $B^1$ is a 4-8 membered, saturated, monocyclic heterocyclic ring having 1-4 heteroatoms selected from O, S, or N, wherein ring $B^1$ is optionally substituted with w independent occurrences of —$R^{11}$, wherein $w_1$ is 0-4.

In yet another embodiment, ring $B^1$ is a 5-6 membered, saturated, monocyclic heterocyclic ring having 1-2 heteroatoms selected from O, S, or N, wherein ring $B^1$ is optionally substituted with w independent occurrences of —$R^{11}$, wherein $w_1$ is 0-4.

In one embodiment, $w_1$ is 0.

In another embodiment, ring $B^1$ is tetrahydrofuranyl.

In yet another embodiment, $Sp^1$ is a bond, 0, or —O—$CH_2$—; R is hydrogen; and $n_1$ and $m_1$ are both simultaneously 1 or 2.

In one embodiment, R is hydrogen. Or, R is $C_1$-$C_6$ alkyl. Preferred R include methyl, ethyl, propyl, or butyl.

In another embodiment, $z_1$ is 0.

According to another embodiment, ring $B^1$ is tetrahydrofuranyl, tetrahydro-[2H]-pyranyl, pyridyl, or phenyl.

According to yet another embodiment, $Sp^1$ is a bond, —O—, —O—$CH_2$—, or —NH—$CH_2$.

In one embodiment:
$n_1$ and $m_1$ each is 2;
$R^{xy}$ is hydrogen;
y is 0 or 1 and $R^5$ is fluoro;
x is 1 and $R^3$ is Me at 7-position or fluoro at 6-position;
$z_1$ is 0;
$Sp^1$ is —O—$CH_2$—;
$w_1$ is 0; and
ring $B^1$ is tetrahydrofuran-3-yl, phenyl, pyridine-3-yl, pyridine-4-yl, or tetrahydro[2H]-pyran-4-yl.

According to another embodiment, the present invention provides compounds of formula I-B:

wherein x, y, $n_2$, $m_2$, $z_2$, $q_2$, R, $Sp^2$, ring $B^2$, $R^{XY}$, $R^3$, $R^4$, and $R^5$ are as defined above.

In one embodiment, $G_2$ is N. Or, $G_2$ is CH.

In one embodiment, $p_2$ is 0. Or, $p_2$ is 1. Or, $p_2$ is 2.

In another embodiment, $q_2$ is 0. Or, $q_2$ is 1.

In one embodiment, $p_2$ is 1, and $q_2$ is 1.

In another embodiment, $G_2$ is CH, $p_2$ is 0, and $q_2$ is 1.

In one embodiment, $m_2$ and $n_2$ each is 1. Or, $m_2$ and $n_2$ each is 2. Or, $n_2$ is 1 and $m_2$ is 2. Or, $n_2$ is 1, and $m_2$ is 3.

In another embodiment, $Sp^2$ is selected from —O—, —S—, or —NR'—. In one embodiment, $Sp^2$ is —O—. Or, $Sp^2$ is —NR'—. Or, $Sp^2$ is —NH—.

In one embodiment, ring $B^2$ is a 4-8 membered, saturated, partially unsaturated, or aromatic, monocyclic heterocyclic ring having 1-4 heteroatoms selected from O, S, or N, wherein ring B is optionally substituted with w independent occurrences of —$R^{12}$, wherein $w_2$ is 0-4.

In another embodiment, ring $B^2$ is a 4-8 membered, saturated, monocyclic heterocyclic ring having 1-4 heteroatoms selected from O, S, or N, wherein ring B is optionally substituted with w independent occurrences of —$R^{12}$, wherein $w_2$ is 0-4.

In yet another embodiment, ring $B^2$ is a 5-6 membered, saturated, monocyclic heterocyclic ring having 1-2 heteroatoms selected from O, S, or N, wherein ring $B^2$ is optionally substituted with w independent occurrences of —$R^{12}$, wherein $w_2$ is 0-4.

In one embodiment, $w_2$ is 0.

According to yet another embodiment, $Sp^2$ is a bond, —O—, or —O—$CH_2$—.

In another embodiment, ring $B^2$ is tetrahydrofuranyl, tetrahydro[2H]pyranyl, or pyridyl.

In yet another embodiment,
i) $Sp^2$ is a bond, 0, or —O—$CH_2$—;
ii) $p_2$ is 1;
iii) R is hydrogen; and
iv) $n_2$ is 1 and $m_2$ is 2 or 3.

In one embodiment, R is hydrogen. Or, R is C1-C6 alkyl. Preferred R include methyl, ethyl, propyl, or butyl.

In one embodiment, compounds of formula I-B have formula I-B-i or formula I-B-ii:

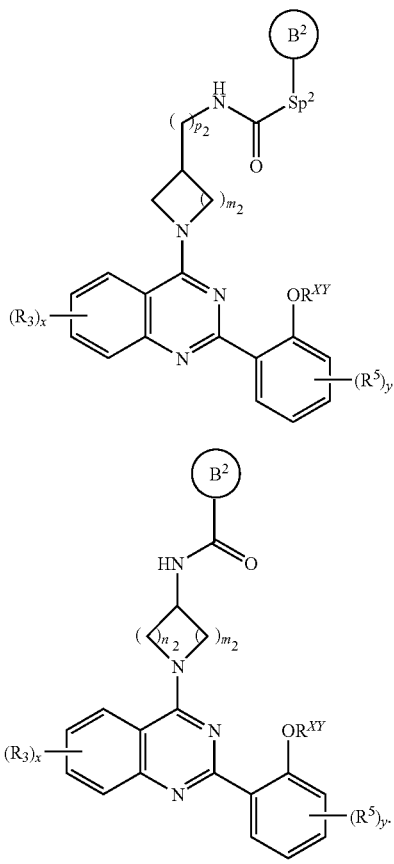

According to one embodiment, the present invention provides compounds of formula I-C or formula I-D:

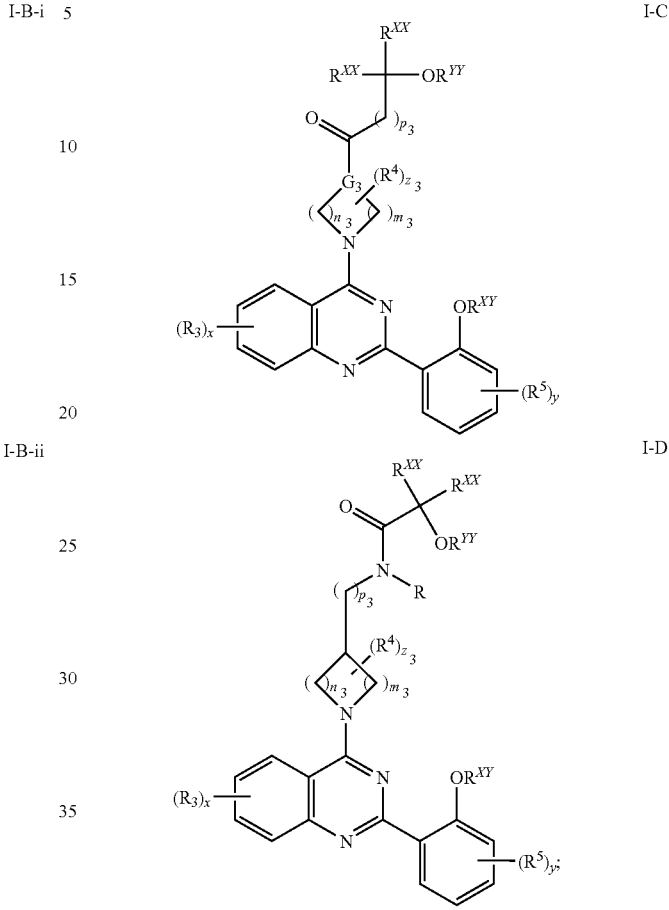

In one embodiment of formula I-B-i:
i) $p_2$ is 1;
ii) $m_2$ is 3;
iii) $Sp^2$ is —O—;
iv) y is 0 or 1, and $R^5$ is fluoro;
v) x is 1 and $R^3$ is 7-Me; and
vi) ring B is tetrahydrofuranyl.

In another embodiment of formula I-B-i:
i) $p_2$ is 0 or 1;
ii) $m_2$ is 1 or 2, preferably 2;
iii) $Sp^2$ is —O— or —O—$CH_2$—;
iv) y is 0;
v) x is 1 and $R^3$ is 7-Me; and
vi) ring $B^2$ is tetrahydrofuranyl, tetrahydro[2H]pyranyl, pyridyl, or phenyl.

In one embodiment of formula I-B-ii:
(i) $n_2$ is 1, $m_2$ is 1 or 2, preferably 2;
(ii) y is 0 or 1, and $R^5$ is fluoro;
(iii) x is 1 and $R^3$ is 7-Me or 6-F; and
(iv) ring $B^2$ is cyclopropyl optionally substituted with C1-C4 alkyl, or pyridyl.

In one embodiment of formula I-B-ii:
(i) $n_2$ and $m_2$ both are 2;
(ii) y is 0;
(iii) x is 1 and $R^3$ is C1-C4 alkyl at the 7-position; and
(iv) ring $B^2$ is an optionally substituted tetrahydrofuranyl.

In one embodiment of formula I-B-i or formula I-B-ii, $R^{XY}$ is hydrogen.

wherein x, y, $n_3$, $m_3$, $z_3$, $p_3$, $R^{XX}$, $R^{YY}$, $R^{XY}$, $R^3$, $R^4$, and $R^5$ are as defined above.

In one embodiment of the present invention, one $R^{XX}$ is hydrogen and the other $R^{XX}$ is not hydrogen.

In another embodiment of the present invention, both $R^{XX}$ are not hydrogen.

In another embodiment, one $R^{XX}$ is hydrogen and the other $R^{XX}$ is C1-C6 alkyl optionally substituted with halo. Or, both $R^{XX}$ are simultaneously C1-C6 alkyl. Exemplary alkyl include methyl, ethyl, isopropyl, n-propyl, n-butyl, sec-butyl, or t-butyl.

In one embodiment of the present invention, $p_3$ is 0. Or, $p_3$ is 1. Or, $p_3$ is 2.

In one embodiment of the present invention, $m_3$ and $n_3$ each is 1. Or, $m_3$ and $n_3$ each is 2. Or, $m_3$ and $n_3$ each is 3.

In one embodiment of the present invention, $R^{XX}$ is $C_{1-6}$ aliphatic group, wherein $R^{XX}$ is optionally substituted with w independent occurrences of —$R^{13}$, wherein $w_3$ is 0-3. Or, $R^{XX}$ is C1-C6 alkyl group optionally substituted with $w_3$ independent occurrences of —$R^{13}$, wherein $w_3$ is 0-3.

In one embodiment of the present invention, $R^{XX}$ is C1-C6 alkyl group.

In another embodiment of the present invention, $R^{XX}$ is a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur, wherein $R^{XX}$ is optionally substituted with $w_3$ independent occurrences of $—R^{13}$, wherein $w_3$ is 0-3.

In another embodiment, $R^{XX}$ is a 3-8-membered saturated, partially unsaturated, or fully unsaturated monocyclic ring having 0-3 heteroatoms independently selected from nitrogen, oxygen, or sulfur, wherein $R^{XX}$ is optionally substituted with w independent occurrences of $—R^{13}$, wherein $w_3$ is 0-3.

In another embodiment, $R^{XX}$ is an 8-12 membered saturated, partially unsaturated, or fully unsaturated bicyclic ring system having 0-5 heteroatoms independently selected from nitrogen, oxygen, or sulfur, wherein $R^{XX}$ is optionally substituted with $W_3$ independent occurrences of $—R^{13}$, wherein $w_3$ is 0-3.

In another embodiment, $R^{YY}$ is hydrogen, $—COR'$, $—CO_2R'$, $—CON(R')_2$, $—SOR'$, $—SO_2R'$, $—SO_2N(R')_2$, $—COCOR'$, $—COCH_2COR'$, $—P(O)(OR')_2$, $—P(O)_2OR'$, or $—PO(R')$.

Or, $R^{YY}$ is hydrogen.

In another embodiment, $R^{YY}$ is $—COR'$, $—CO_2R'$, $—CON(R')_2$, $—SOR'$, $—SO_2R'$, $—SO_2N(R')_2$, $—COCOR'$, $—COCH_2COR'$, $—P(O)(OR')_2$, $—P(O)_2OR'$, or $—PO(R')$.

In another embodiment, $R^{YY}$ is $R^{XY}$.

In one embodiment, R is hydrogen. Or, R is C1-C6 alkyl. Preferred R include methyl, ethyl, propyl, or butyl.

In one embodiment, the present invention provides a compound of formula I-C-i or formula I-D-i:

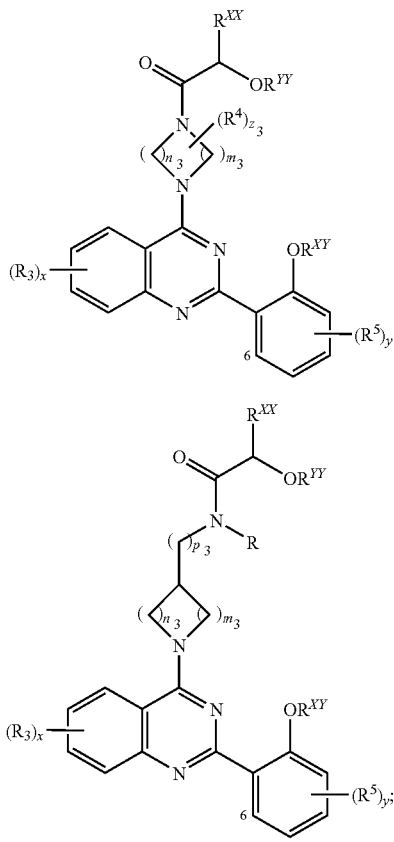

wherein x, y, $n_3$, $m_3$, $z_3$, $p_3$, $R^{XX}$, $R^{YY}$, $R^{XY}$, $R^3$, $R^4$, and $R^5$ are as defined above.

In one embodiment of 1-C-i or I-D-i, $R^{XX}$ is C1-C6 alkyl. In another embodiment, x is 1, and $R^3$ is C1-C4 alkyl at the 7-position. Or, x is 1 and $R^3$ is F, CN, or $CF_3$ at the 6-position.

In one embodiment, $R^{XX}$ is methyl, n-propyl, isopropyl, n-butyl, sec-butyl, or t-butyl.

In one embodiment, $R^3$ is C1-C6 alkyl. Or, $R^3$ is methyl, n-propyl, isopropyl, n-butyl, sec-butyl, or t-butyl.

In one embodiment of 1-C-i or I-D-i, $R^{XY}$ is hydrogen, and y is 0. Or, $R^{XY}$ is hydrogen, y is 1 and $R^5$ is 6-F.

In another embodiment, the present invention provides a compound of formula I-C-ii:

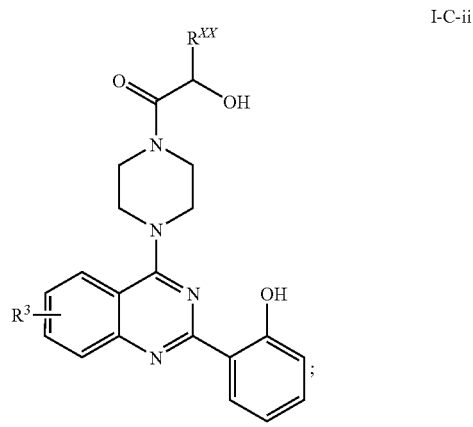

wherein $R^3$ and $R^{XX}$ are as defined above.

In another embodiment, $R^3$ is methyl at the 6- or 7-position of the quinazoline ring.

In another embodiment of formula I-C-ii, $R^{XX}$ is $CH_2C(O)OH$ or $CH_2C(O)NH_2$.

According to one embodiment, the present invention provides a compound of formula I-E:

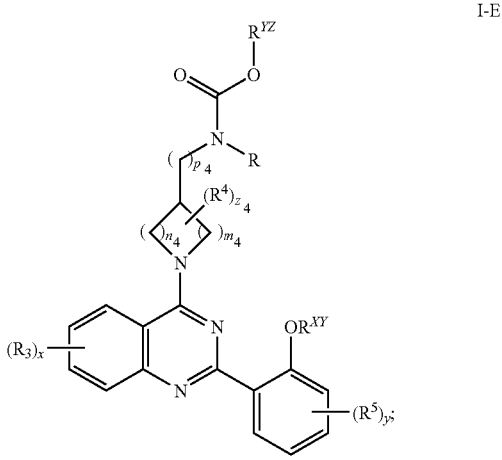

wherein x, y, $n_4$, $m_4$, $z_4$, $p_4$, $R^{YZ}$, $R^{XY}$, $R^3$, $R^4$, and $R^5$ are as defined above.

In one embodiment, $p_4$ is 1. Or, $p_4$ is 2.

In one embodiment, $m_4$ and $n_4$ each is 1. Or, $m_4$ and $n_4$ each is 2. Or, $m_4$ and $n_4$ each is 3. In one embodiment, $n_4$ is 1 and $m_4$ is 3. In another embodiment, $n_4$ is 1 and $m_4$ is 2.

In one embodiment, $n_4$ is 1, $m_4$ is 3, $Z_4$ is 0, $p_4$ is 1, y is 0 or 1, and x is 1.

In another embodiment, $n_4$ is 1, $m_4$ is 2, $z_4$ is 0, $p_4$ is 1, y is 0 or 1, and x is 1.

In one embodiment, $n_4$ is 1, $m_4$ is 3, $Z_4$ is 0, $p_4$ is 1, y is 0 or 1, x is 1, and R and $R^{XY}$ both are hydrogen.

In another embodiment, $n_4$ is 1, $m_4$ is 2, $Z_4$ is 0, $p_4$ is 1, y is 0 or 1, x is 1, and R and $R^{XY}$ both are hydrogen.

In one embodiment, $R^{YZ}$ is C1-C6 alkyl, optionally substituted with $W_4$ independent occurrences of —$R^{14}$, wherein $w_4$ is 0-3. In another embodiment, $R^{YZ}$ is C1-C4 alkyl group optionally substituted with $w_4$ independent occurrences of —$R^{14}$, wherein $W_4$ is 0-3. Or, $R^Y$ is C1-C6 alkyl group.

In one embodiment, R is hydrogen. Or, R is C1-C6 alkyl. Preferred R include methyl, ethyl, propyl, or butyl.

In another embodiment:
(i) $n_4$ is 1 and $m_4$ is 3;
(ii) $p_4$ is 1;
(iii) $z_4$ is 0;
(iv) $R^{YZ}$ is C1-C6 alkyl, wherein up to two —CH$_2$— groups therein is optionally replaced by —O—;
(v) y is 0 or 1, and $R^5$ is 6-fluoro; and
(vi) x is 1 and $R^3$ is C1-C4 alkyl.

In another embodiment:
(i) $n_4$ is 1 and $m_4$ is 2;
(ii) $p_4$ is 1;
(iii) $Z_4$ is 0;
(iv) $R^{YZ}$ is C1-C6 alkyl, wherein up to two —CH$_2$— groups therein is optionally replaced by —O—;
(v) y is 0 or 1, and $R^5$ is 6-fluoro; and
(vi) x is 1 and $R^3$ is C1-C4 alkyl.

In another embodiment:
(i) $n_4$ is 1 and $m_4$ is 3;
(ii) $p_4$ is 1;
(iii) $Z_4$ is 0;
(iv) $R^{YZ}$ is benzyl;
(v) y is 0 or 1, and $R^5$ is 6-fluoro; and
(vi) x is 1 and $R^3$ is C1-C4 alkyl.

In one embodiment, the present invention provides compounds shown below in Table 2.

TABLE 2

101

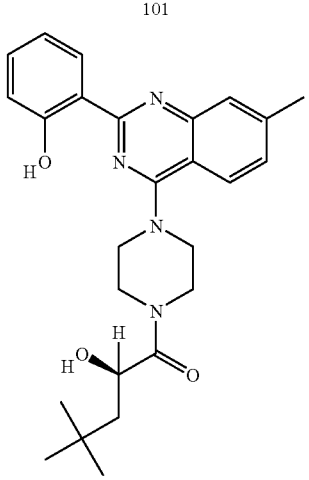

TABLE 2-continued

102

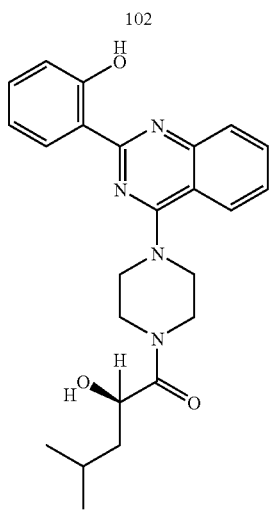

103

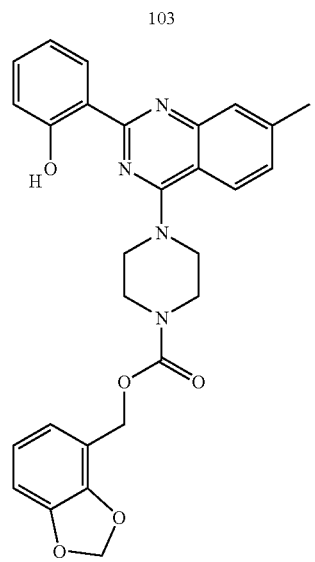

104

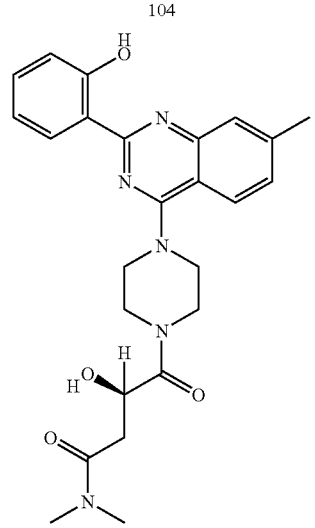

TABLE 2-continued
105
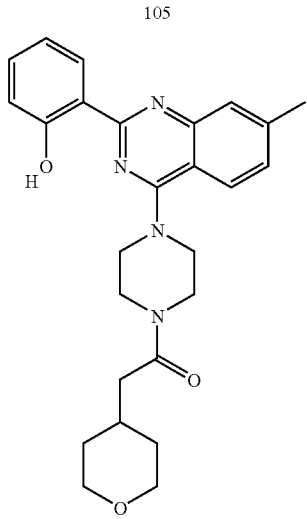
106
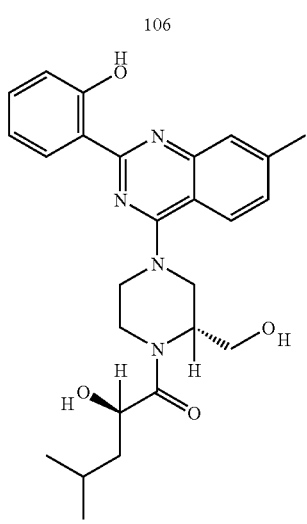
107
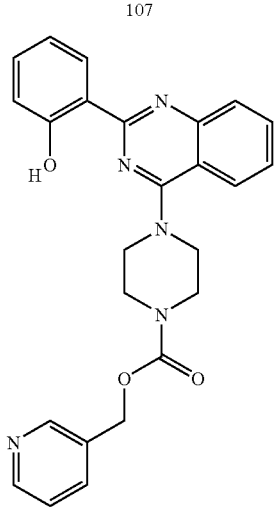
TABLE 2-continued
108
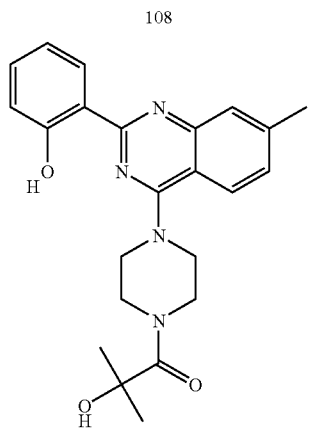
109
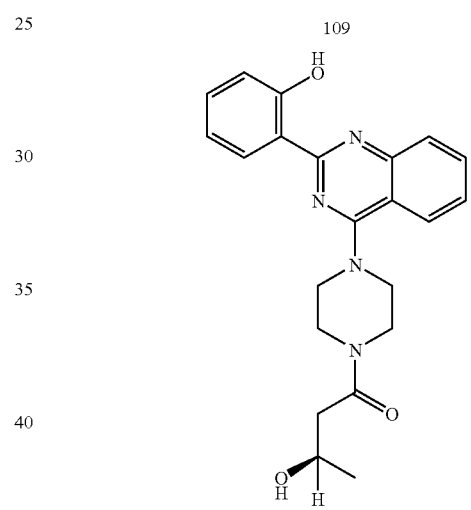
110
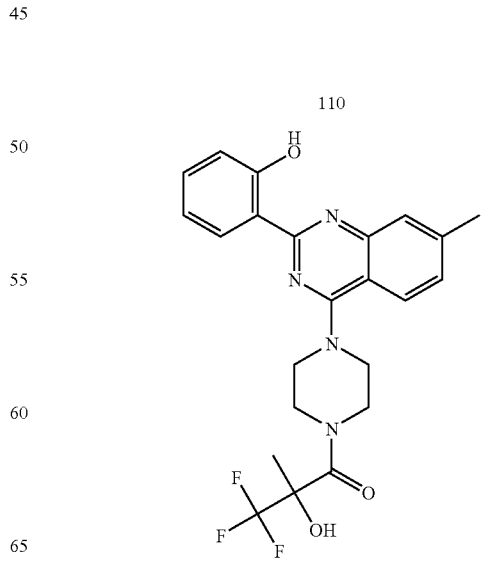

TABLE 2-continued
111
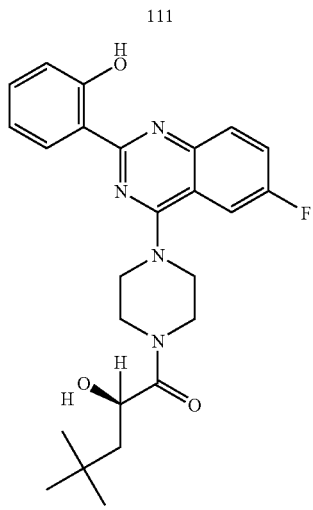
112
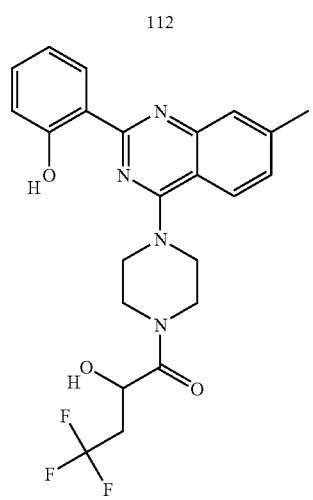
113
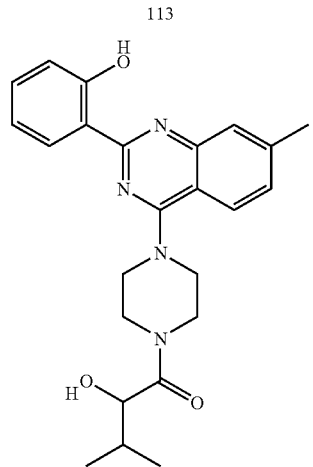
TABLE 2-continued
114
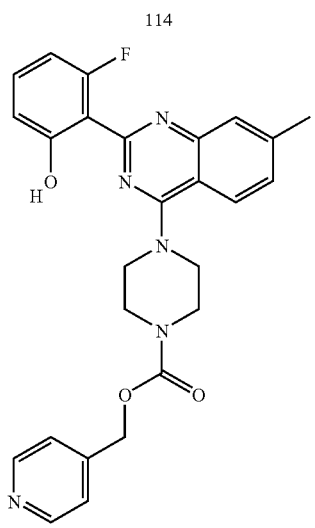
115
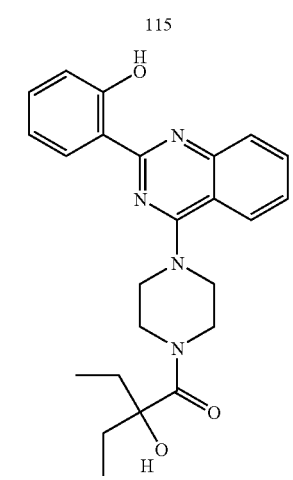
116
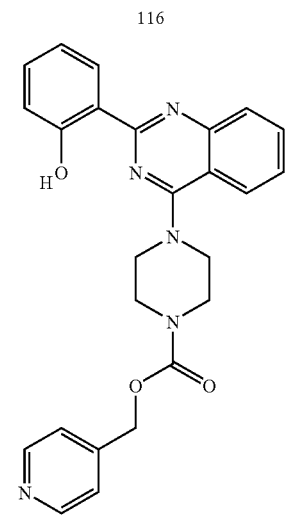

TABLE 2-continued
117
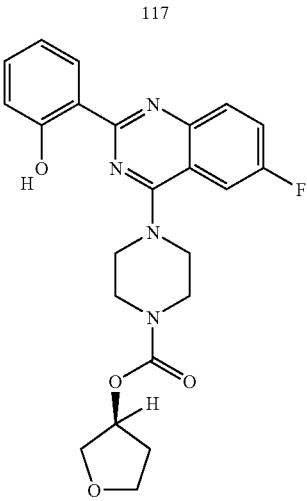
118
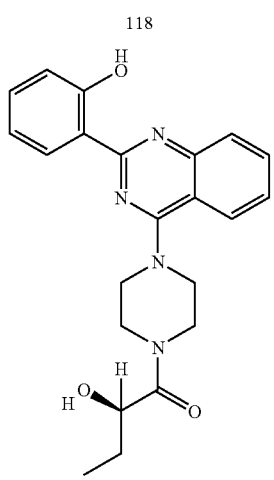
119
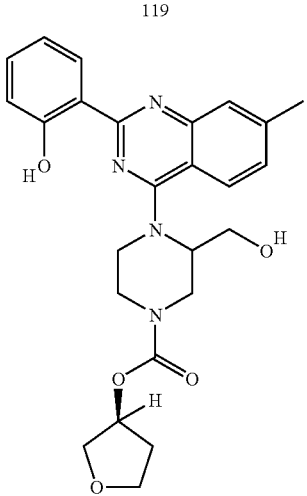
TABLE 2-continued
120
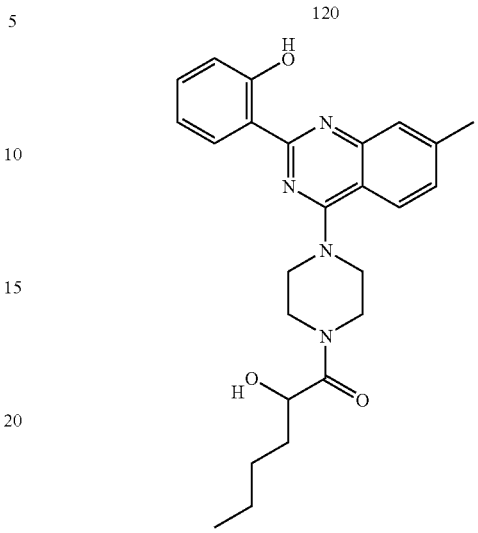
121
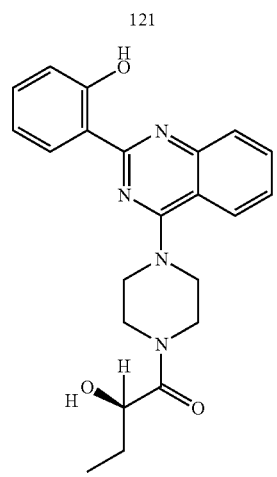
122
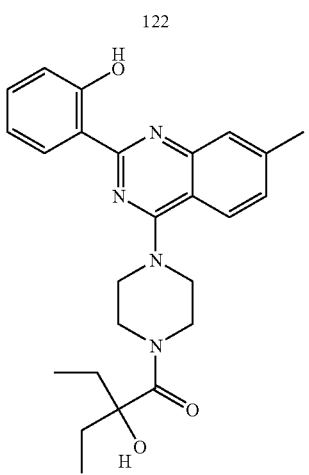

TABLE 2-continued
123
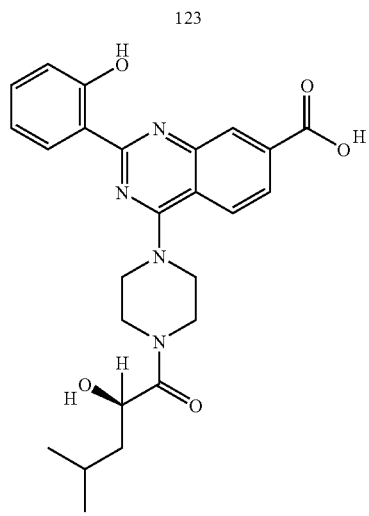
124
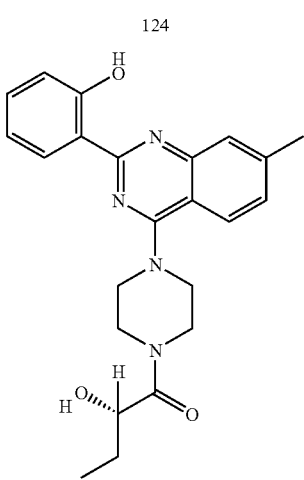
125
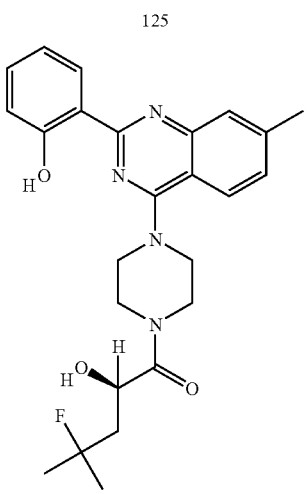
TABLE 2-continued
126
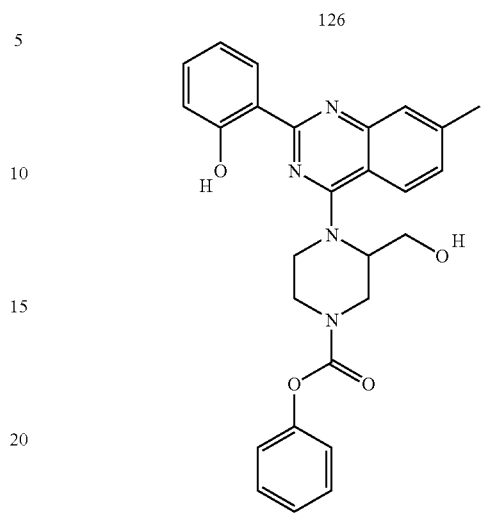
127
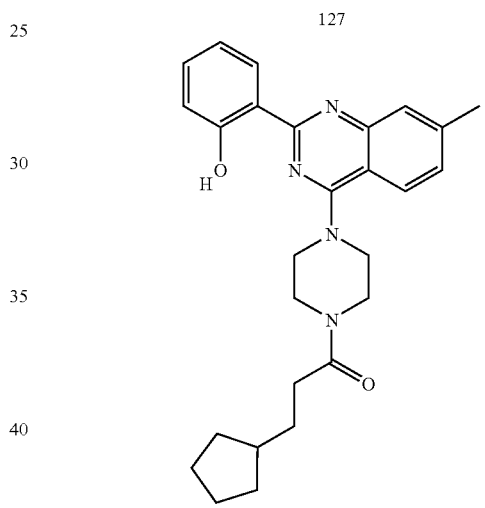
128
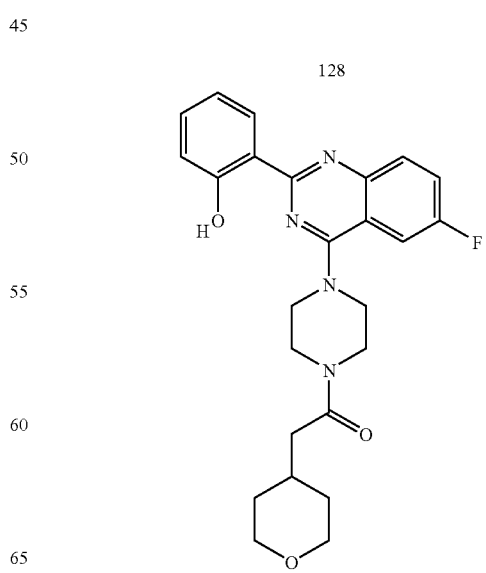

TABLE 2-continued
129
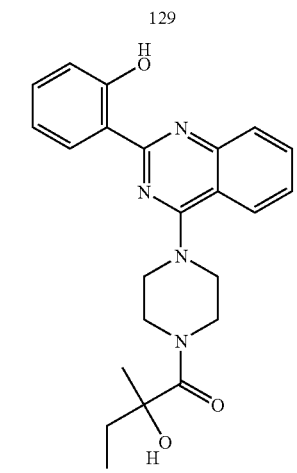
130
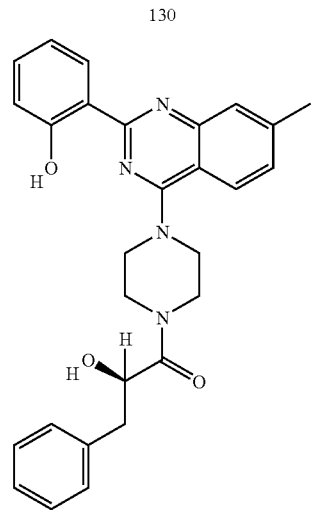
131
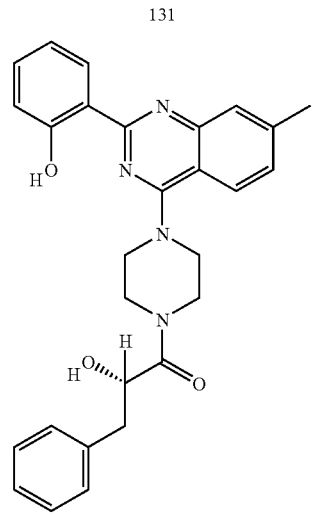
TABLE 2-continued
132
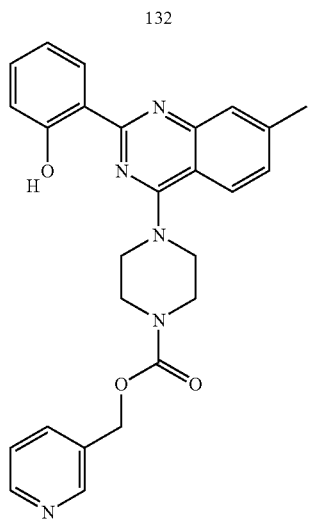
133
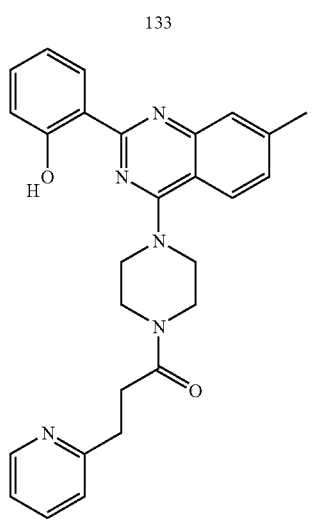
134
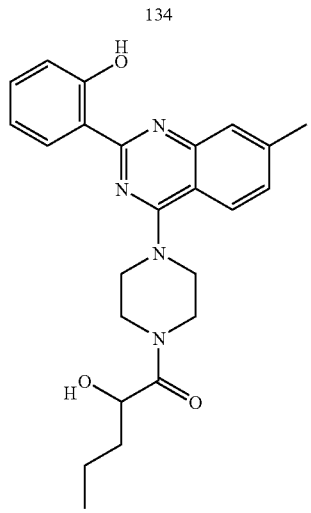

TABLE 2-continued
135
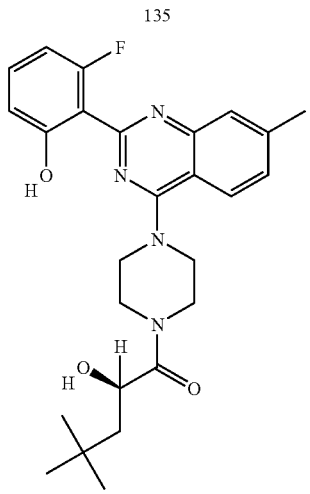
136
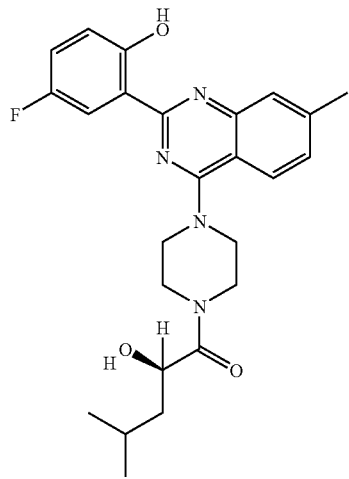
137
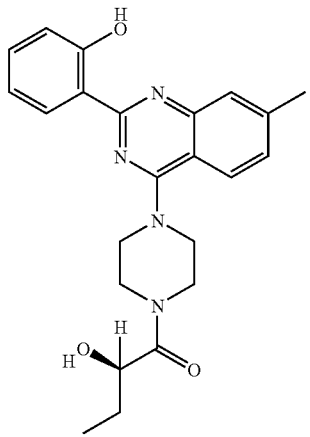
TABLE 2-continued
138
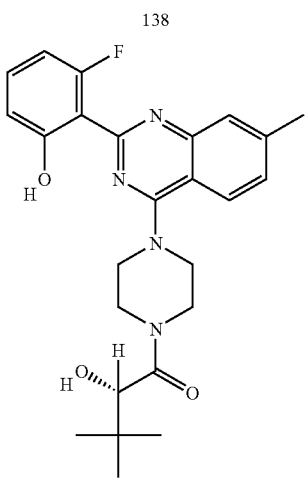
139
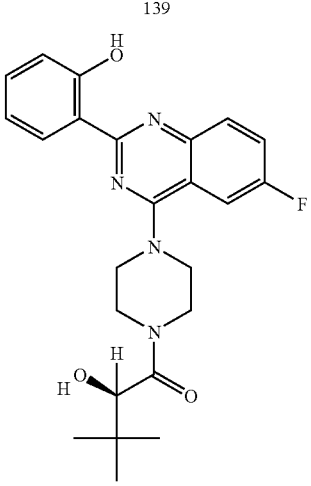
140
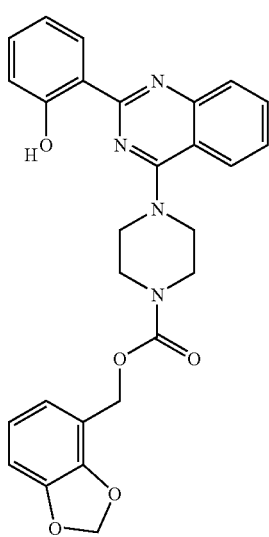

TABLE 2-continued
141
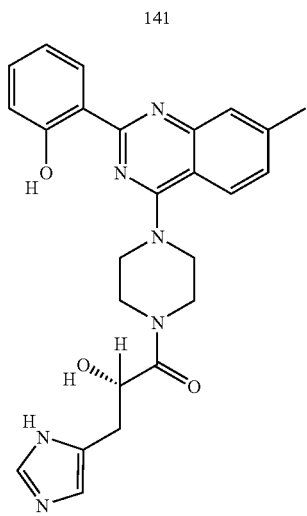
142
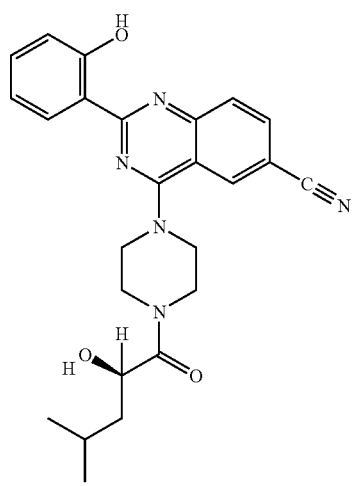
143
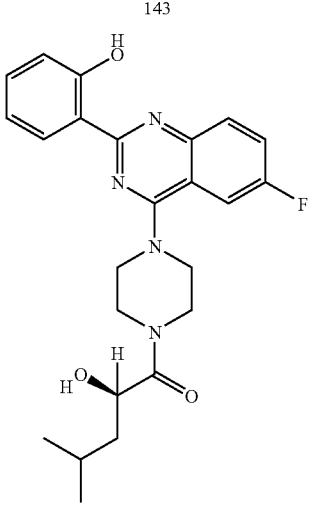
TABLE 2-continued
144
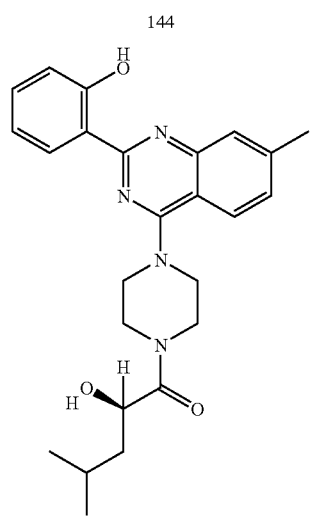
145
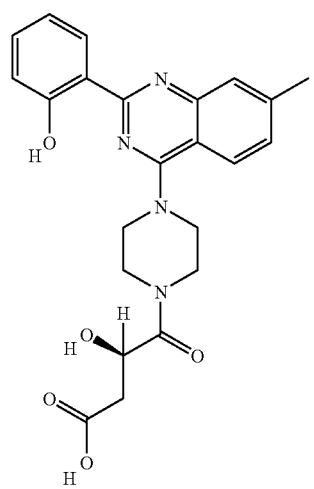
146
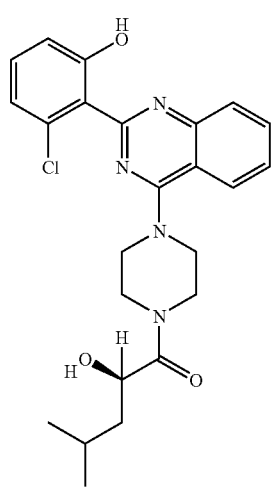

TABLE 2-continued
147
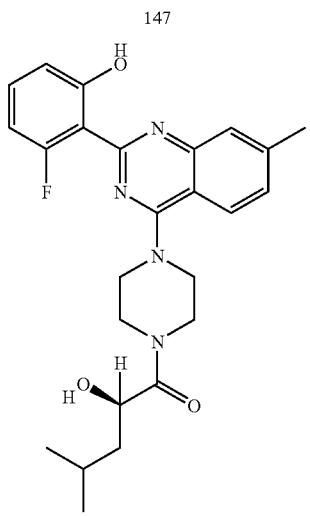
148
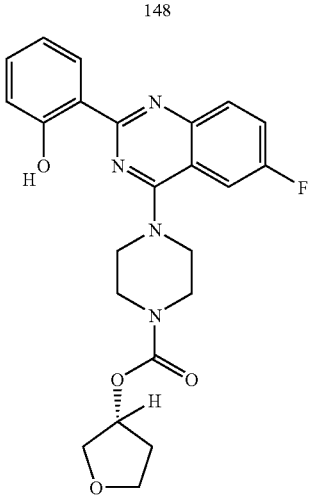
149
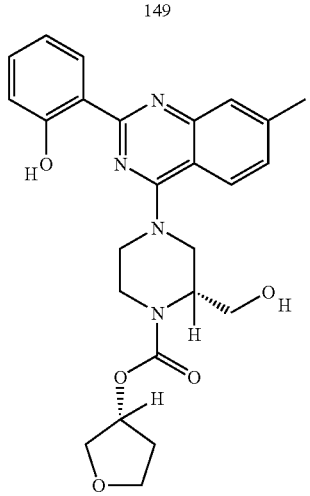
TABLE 2-continued
150
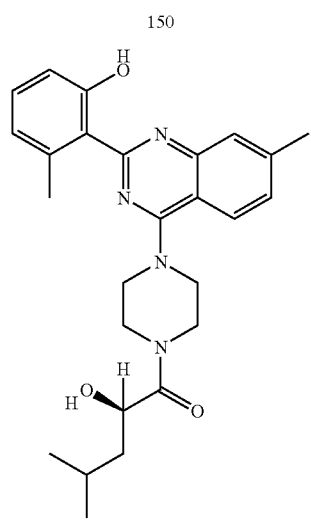
151
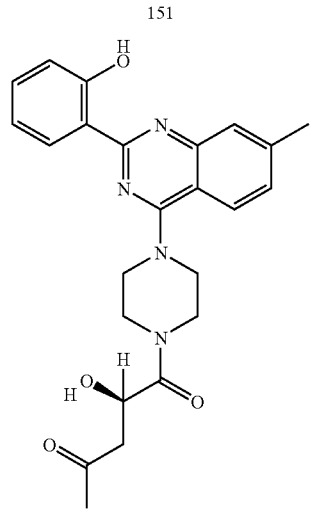
152
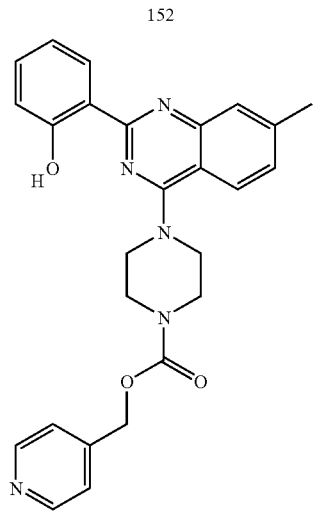

TABLE 2-continued
153
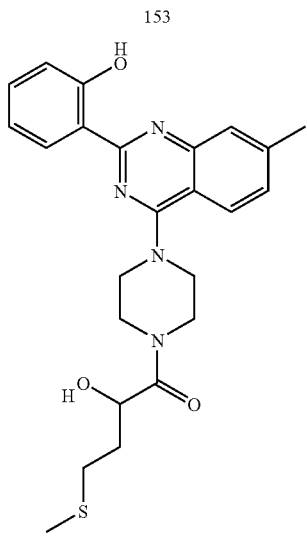
154
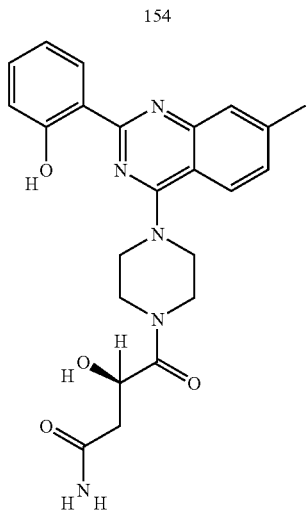
155
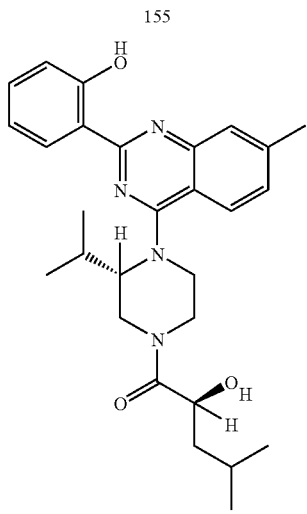
TABLE 2-continued
156
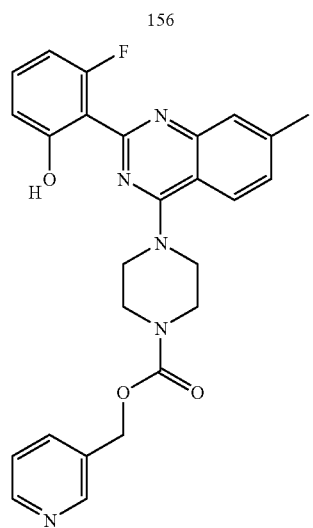
157
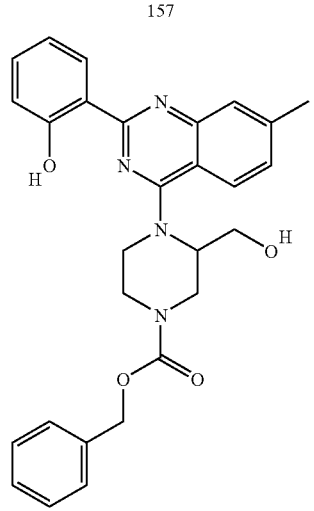
158
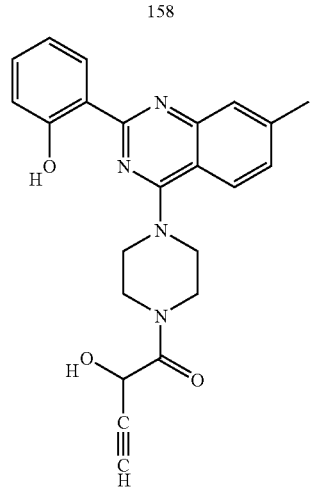

TABLE 2-continued
159
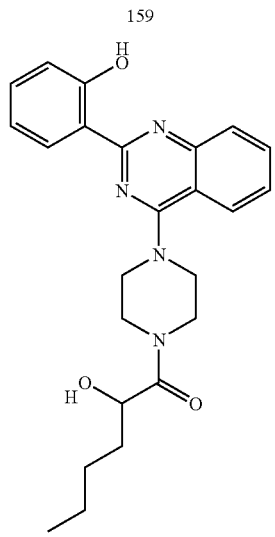
160
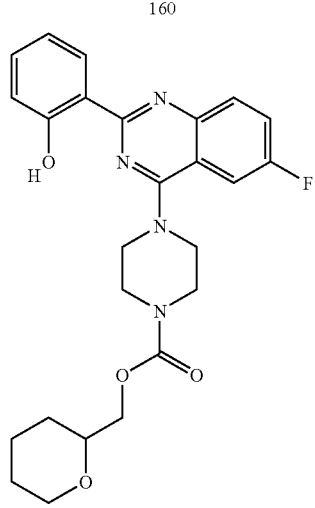
162
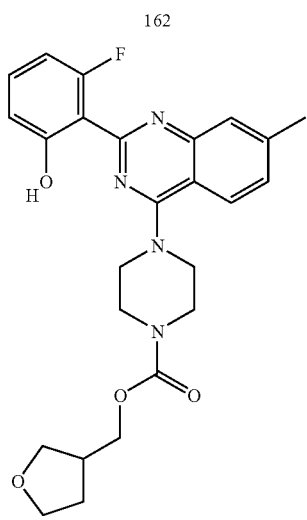
163
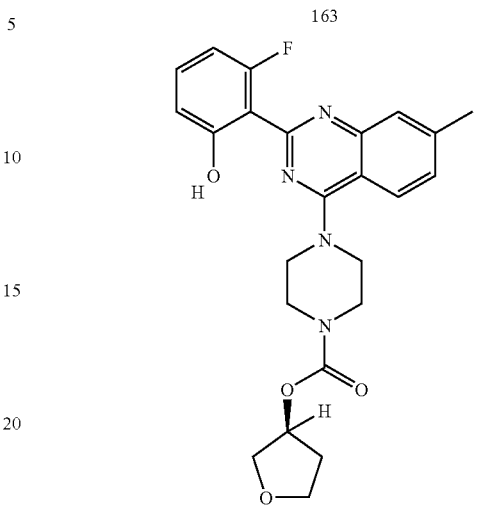
164
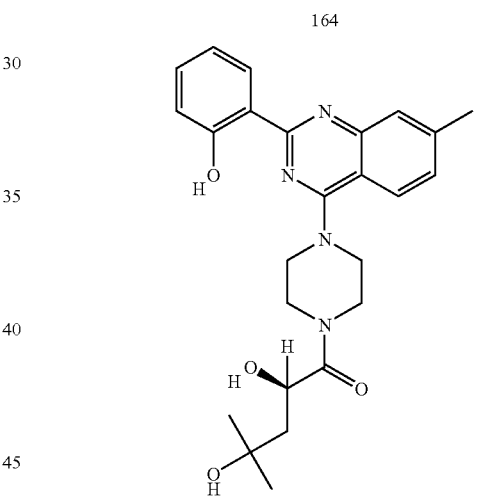
165
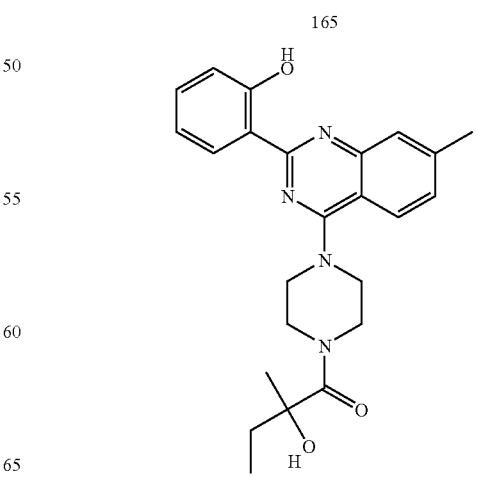

TABLE 2-continued
166
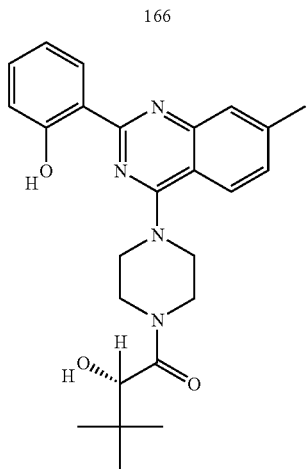
167
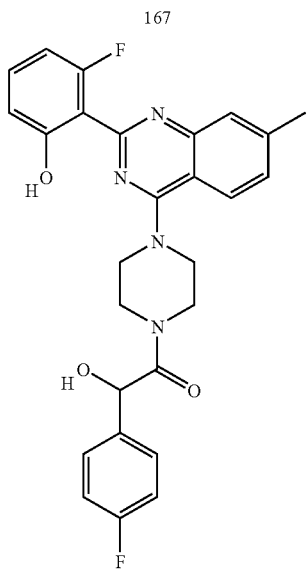
168
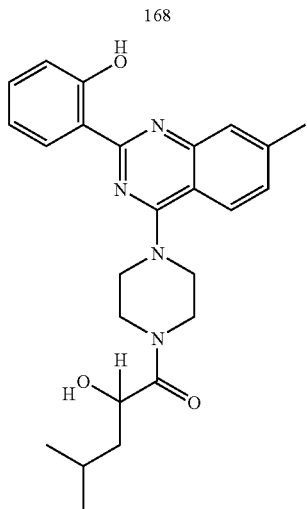
TABLE 2-continued
169
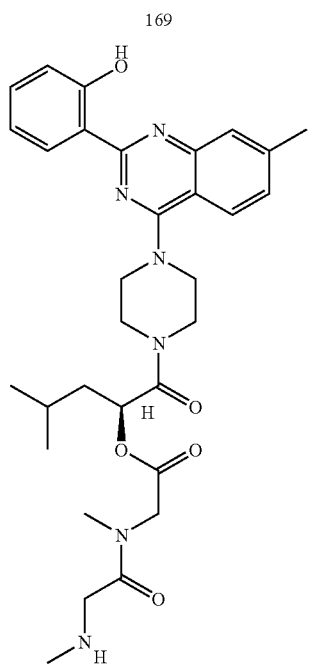
170
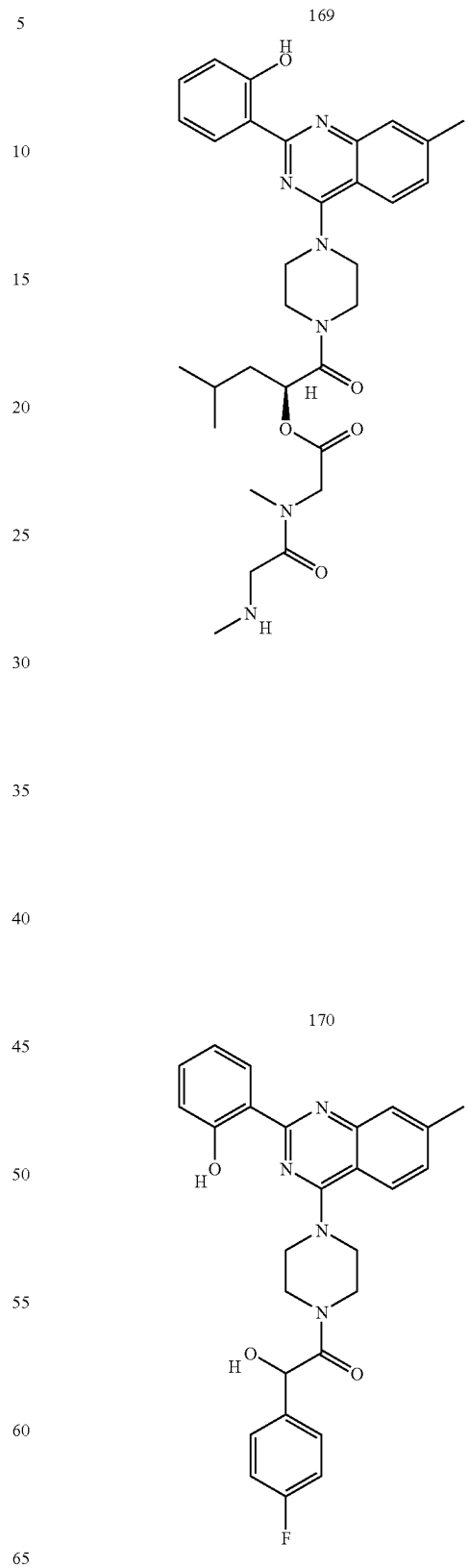

TABLE 2-continued
171
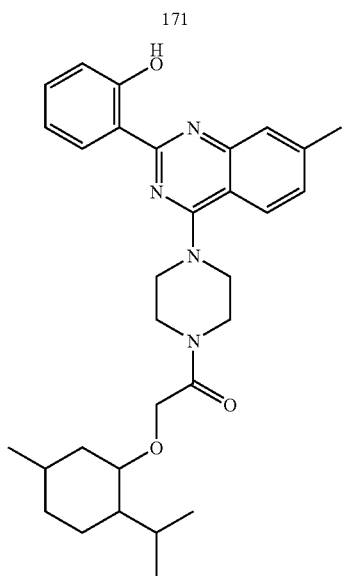
172
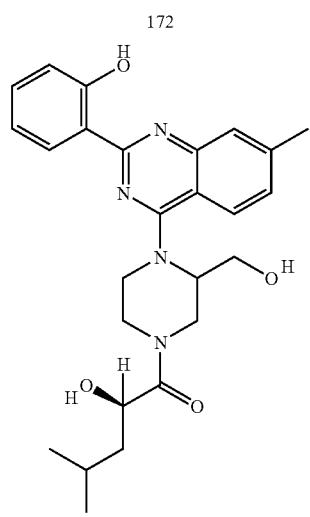
173
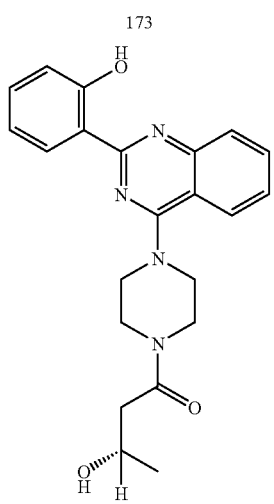
TABLE 2-continued
174
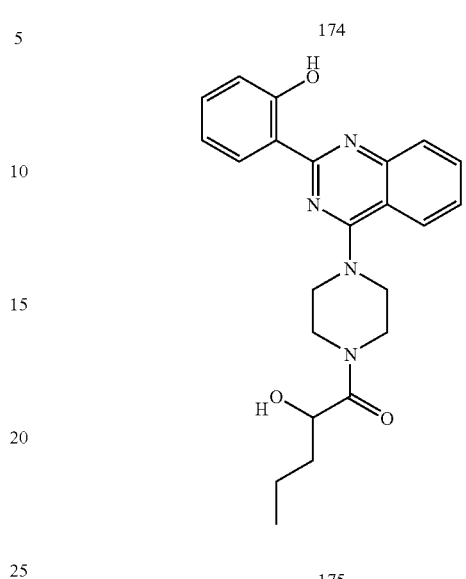
175
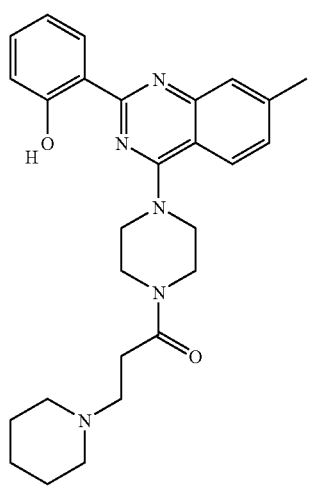
176
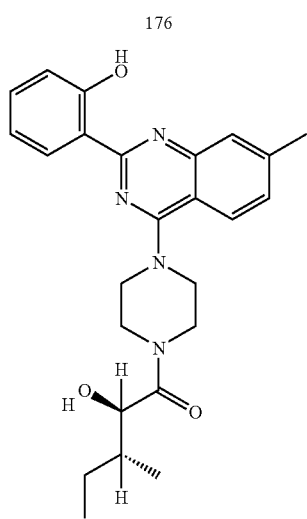

TABLE 2-continued
177
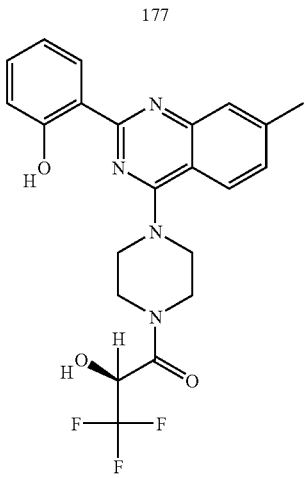
178
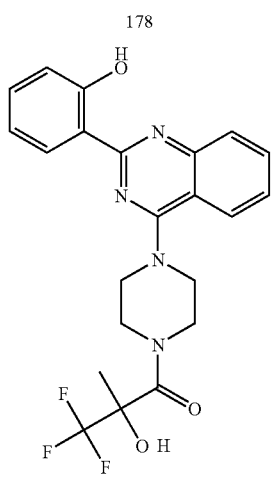
179
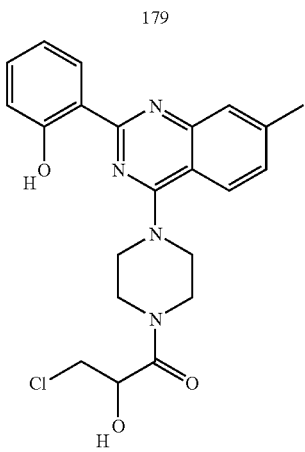
TABLE 2-continued
180
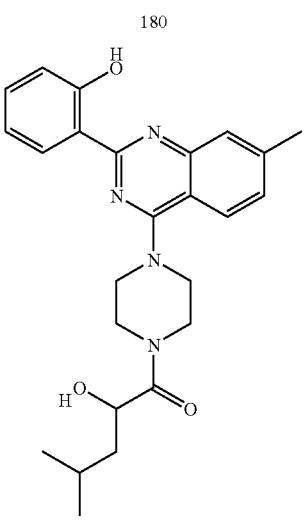
181
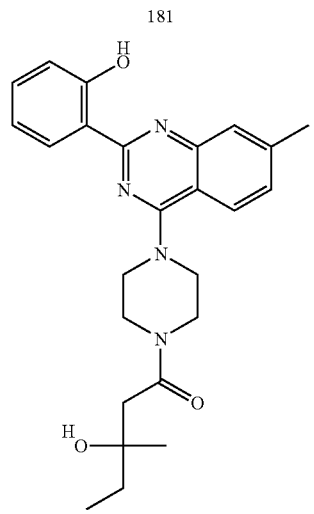
182
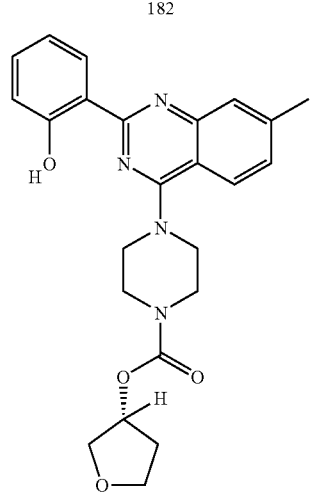

TABLE 2-continued
183
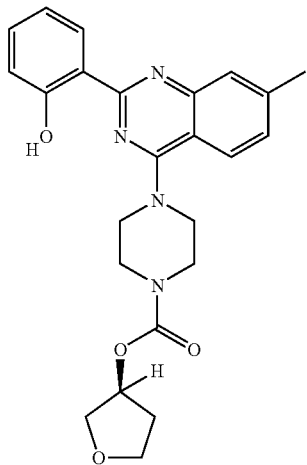
184
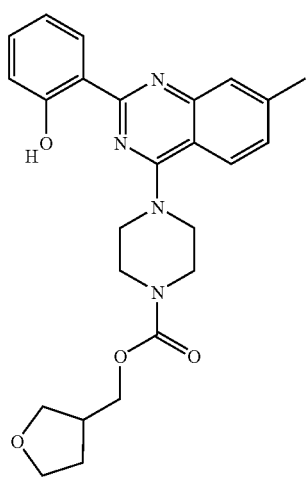
185
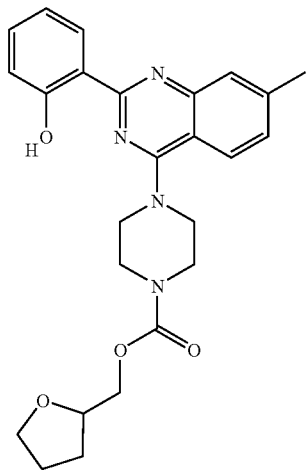
TABLE 2-continued
201
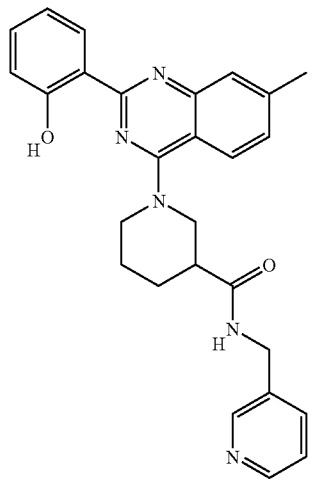
203
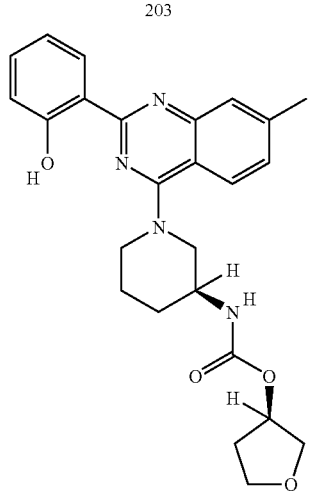
204
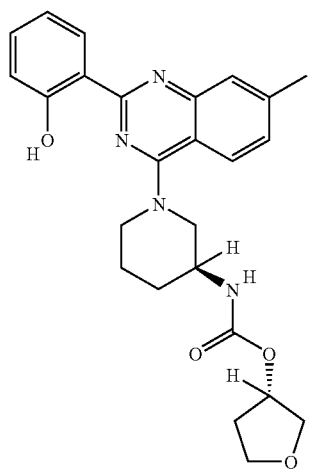

TABLE 2-continued
205
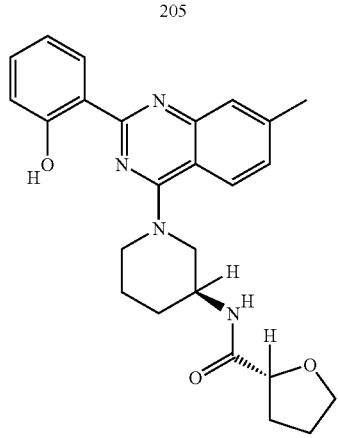
206
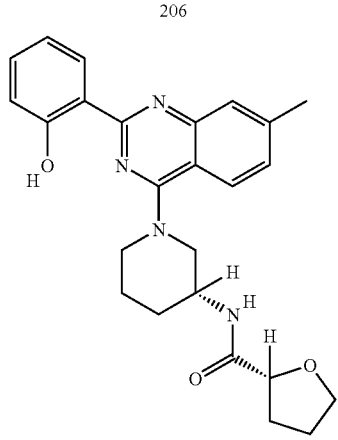
207
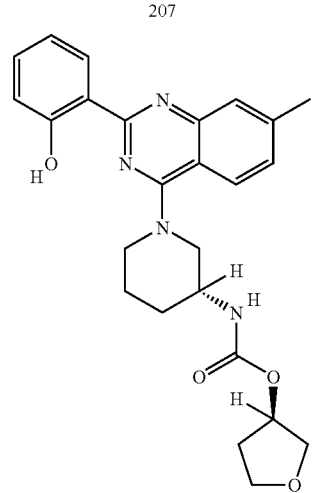
TABLE 2-continued
208
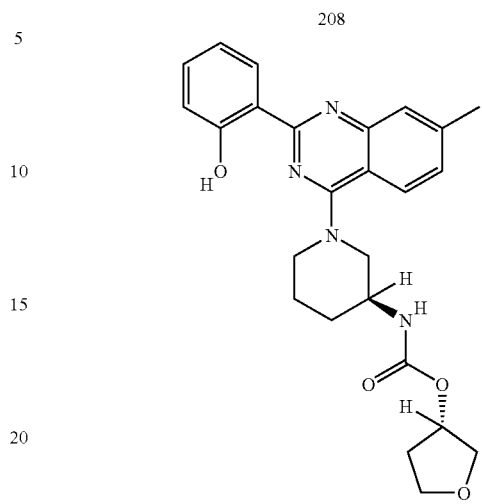
209
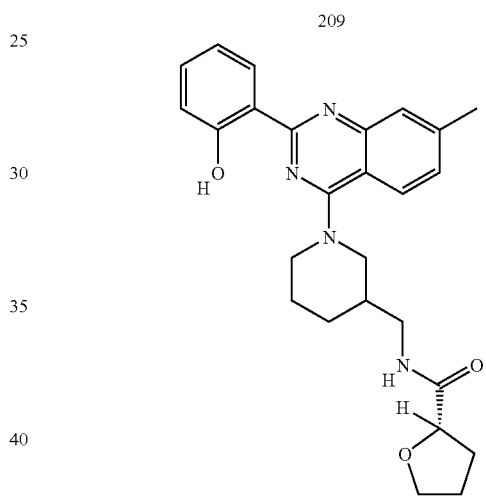
210
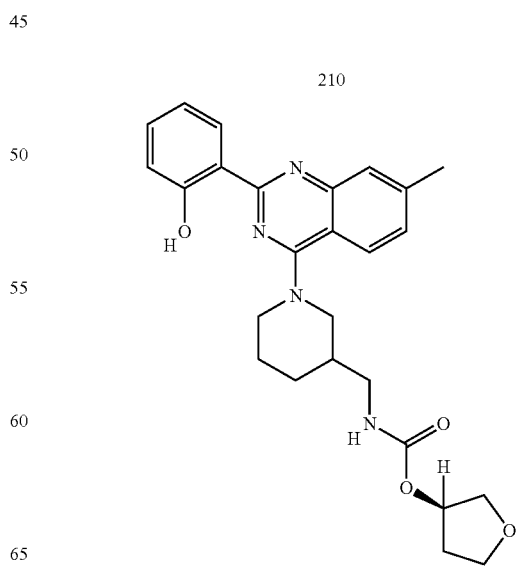

TABLE 2-continued
211
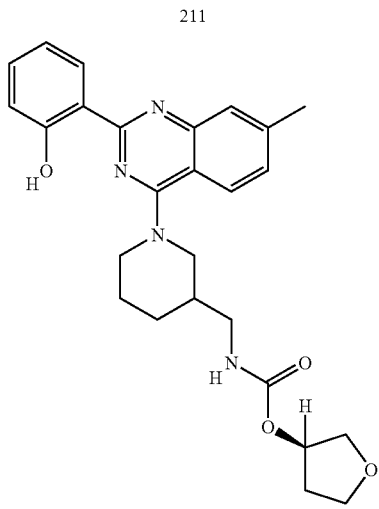
212
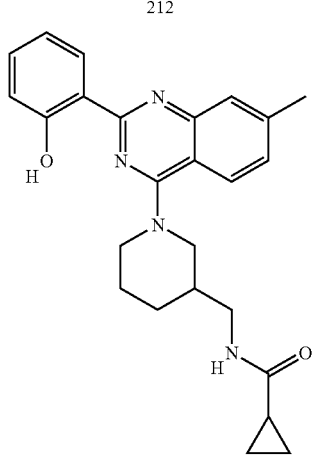
213
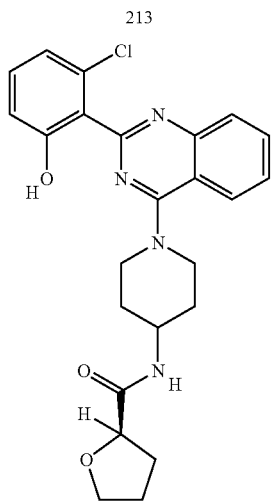
TABLE 2-continued
214
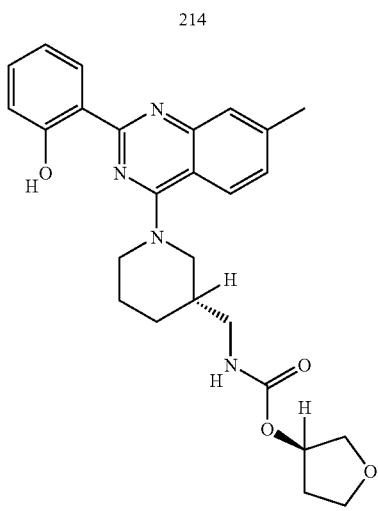
215
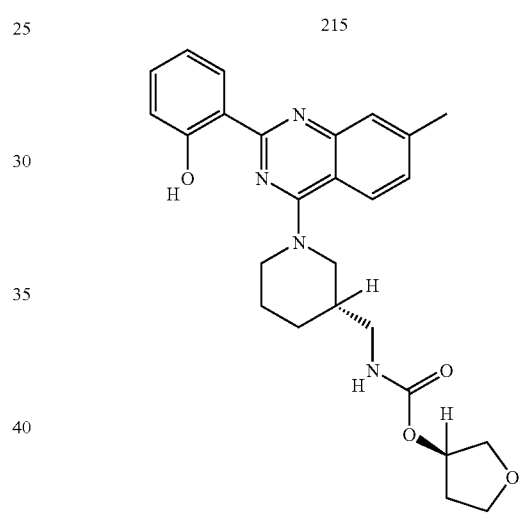
216
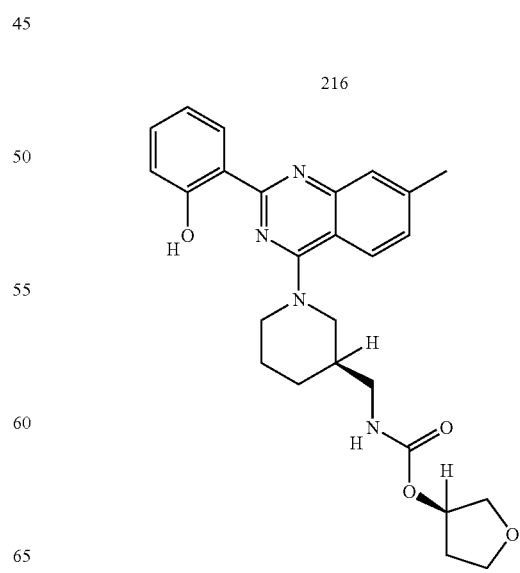

TABLE 2-continued
217
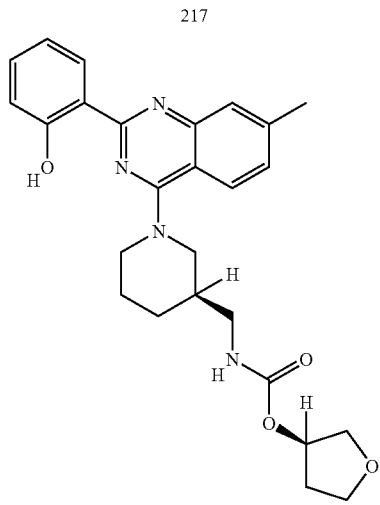
218
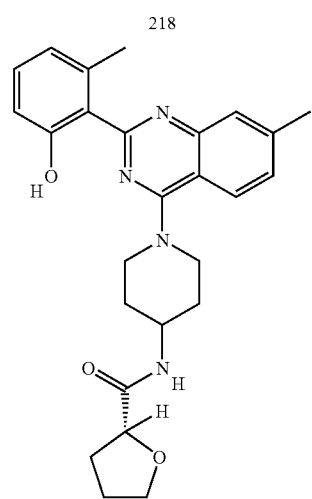
219
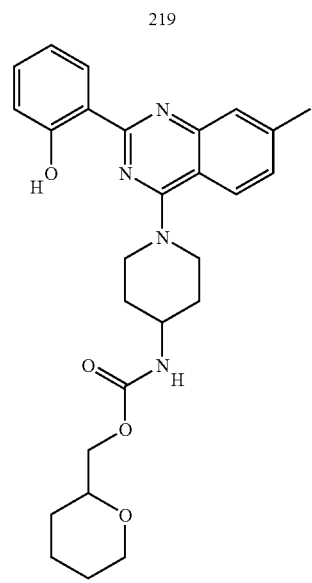
TABLE 2-continued
220
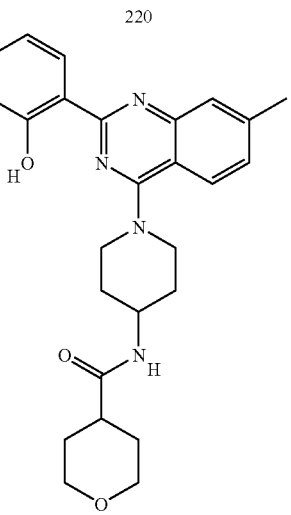
221
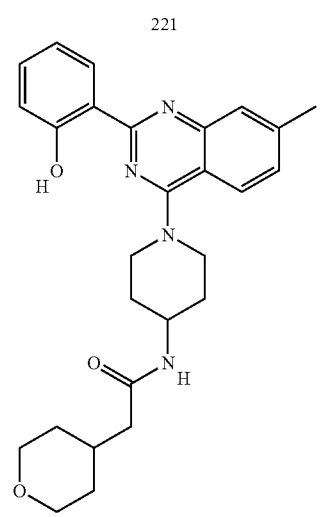
222
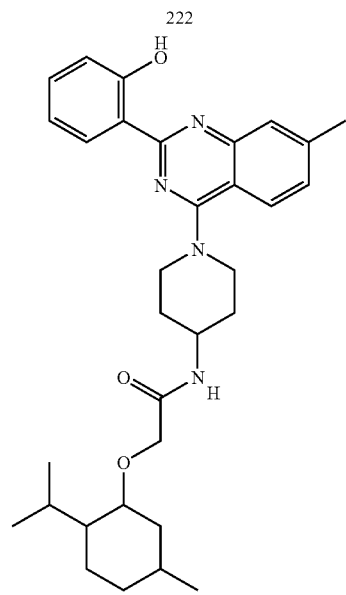

TABLE 2-continued
223
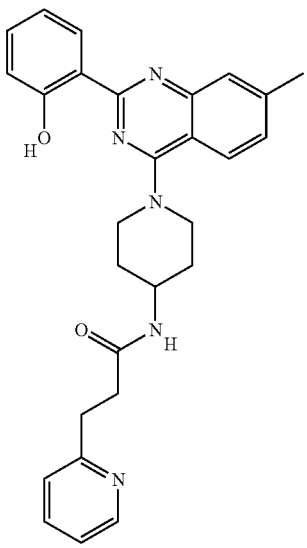
224
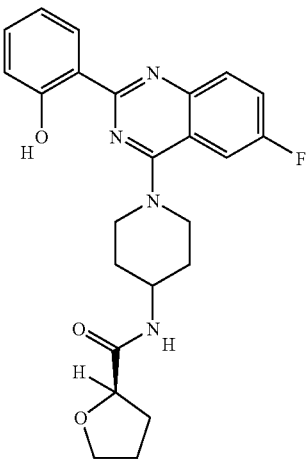
225
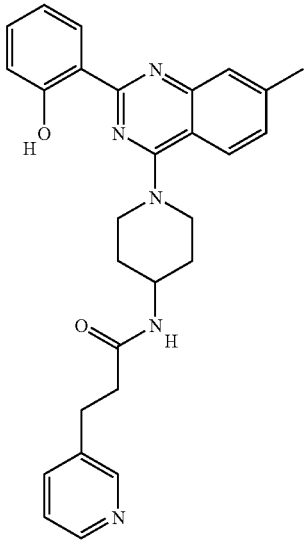
TABLE 2-continued
226
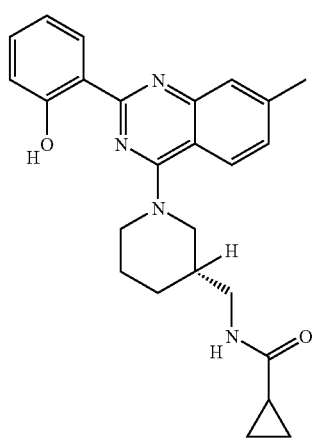
227
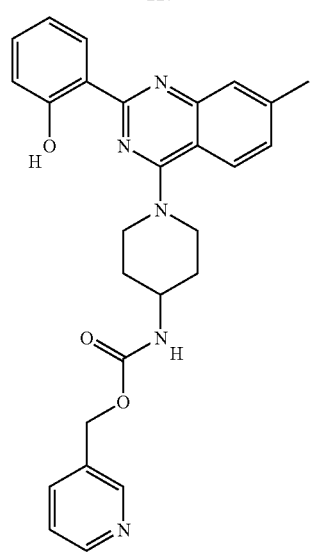
228
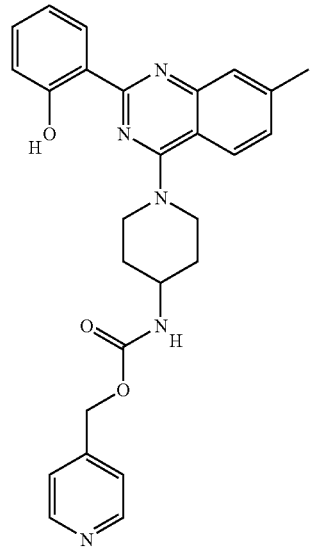

TABLE 2-continued
229
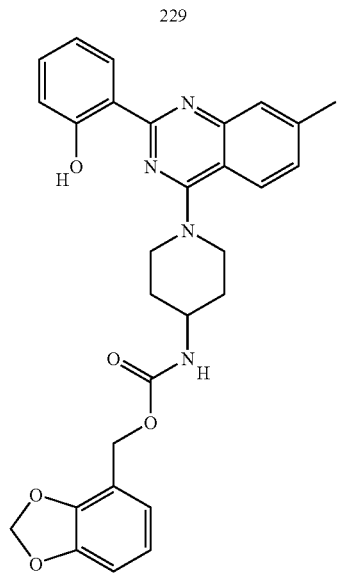
230
231
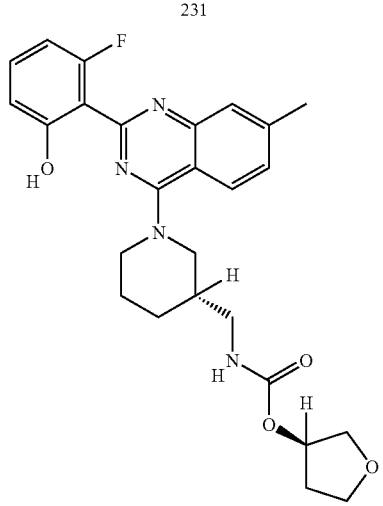
TABLE 2-continued
232
233
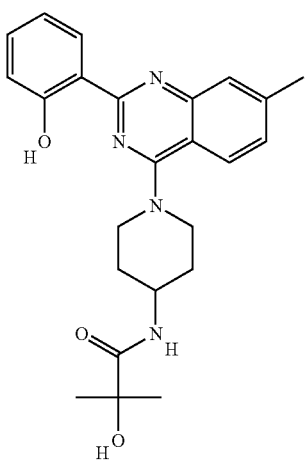
234
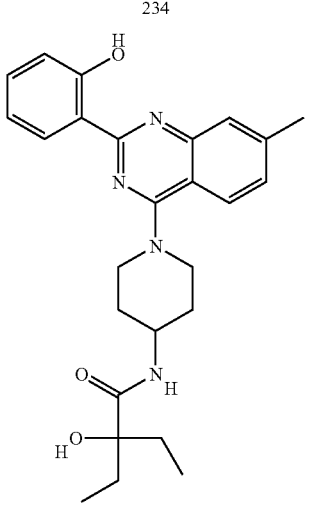

235
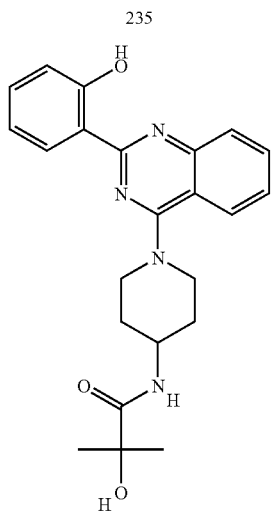
236
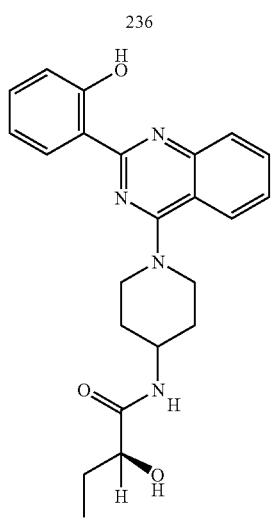
237
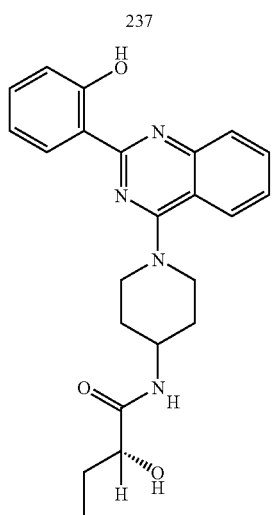
238
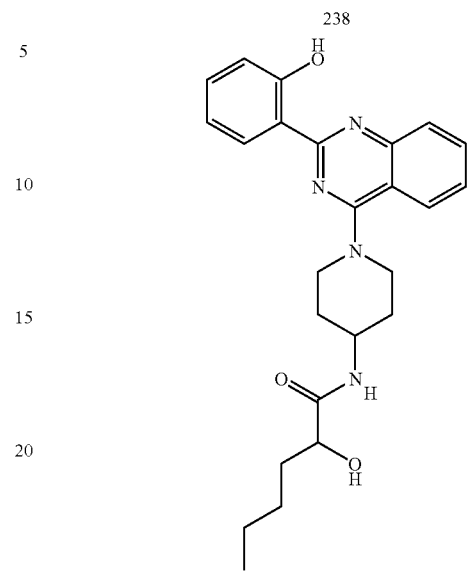
239
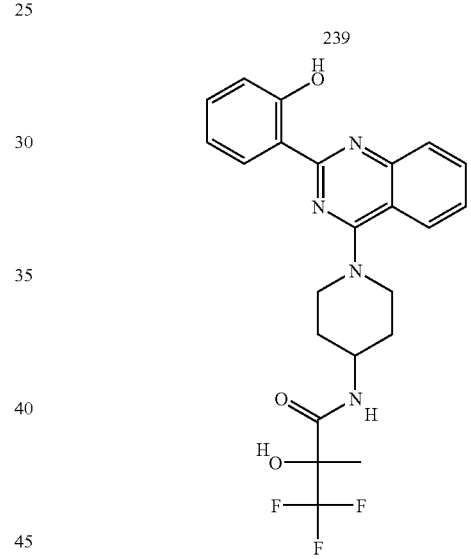
240
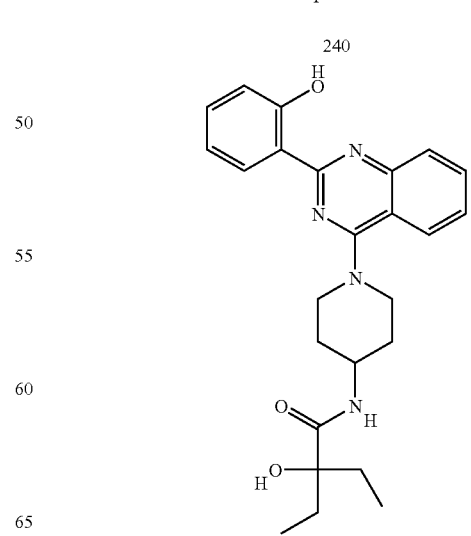

TABLE 2-continued
241
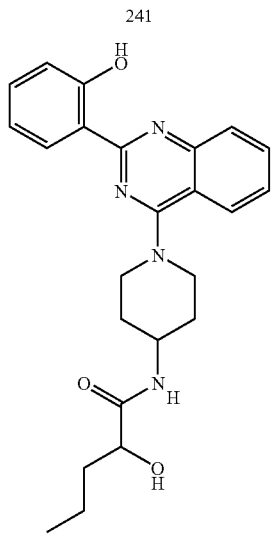
242
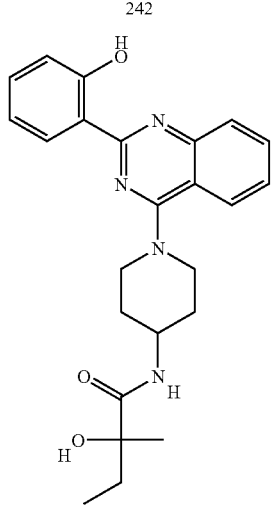
243
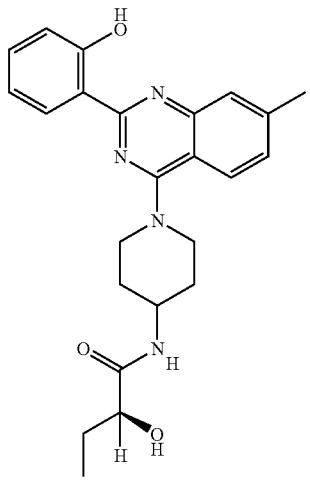
TABLE 2-continued
244
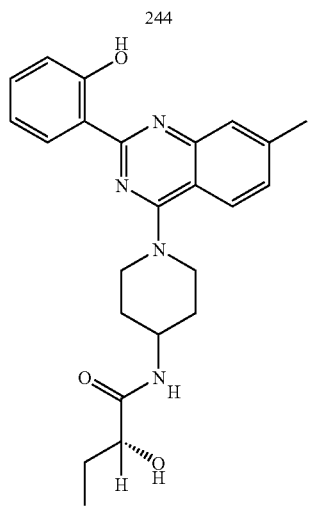
245
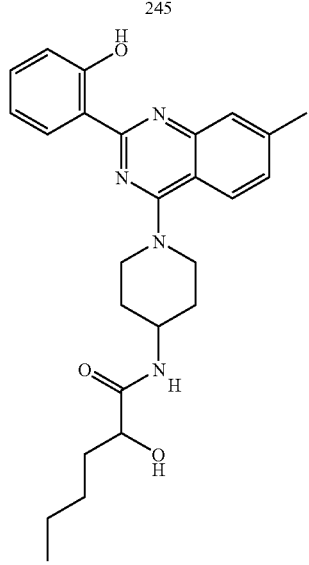
246
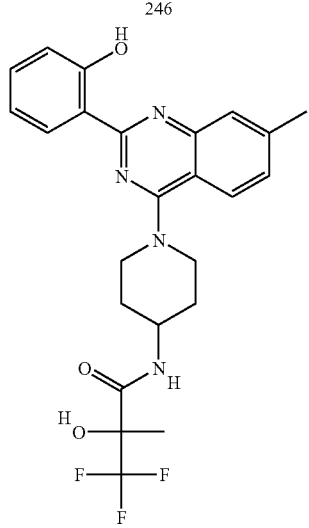

TABLE 2-continued
247
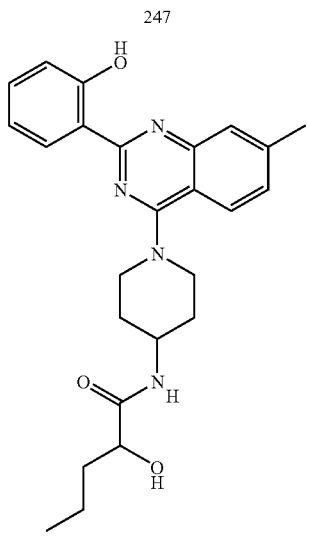
248
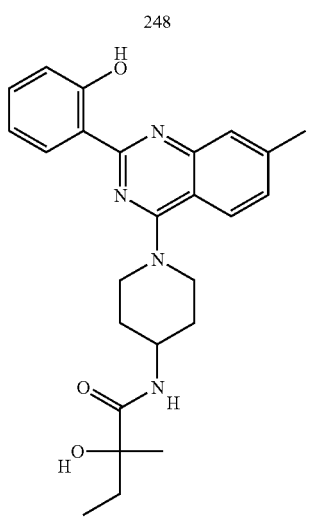
249
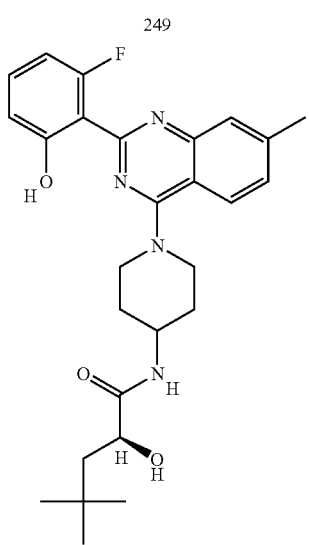
TABLE 2-continued
250
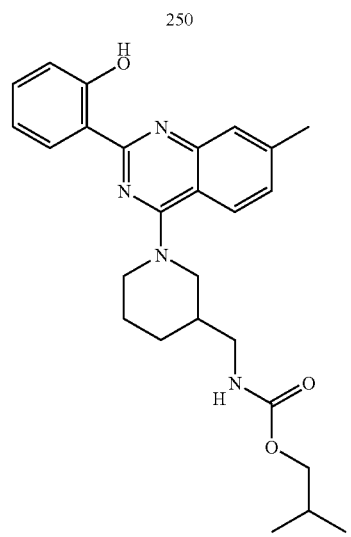
251
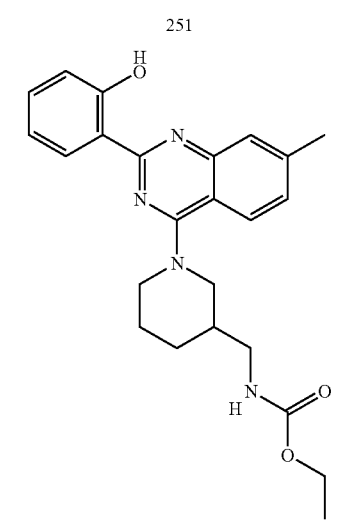
252
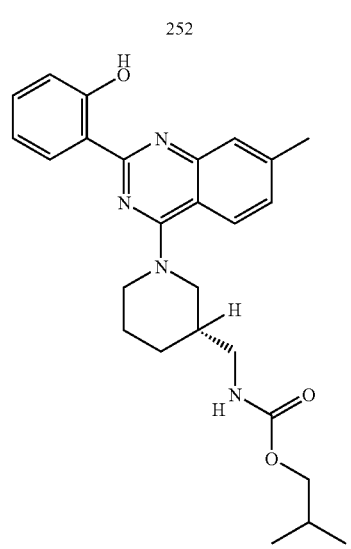

TABLE 2-continued
253
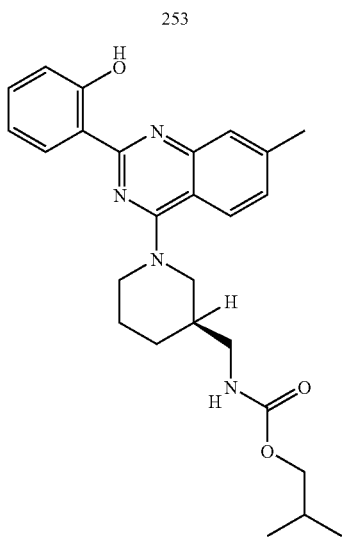
254
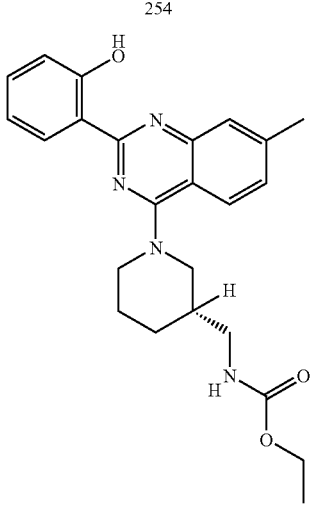
255
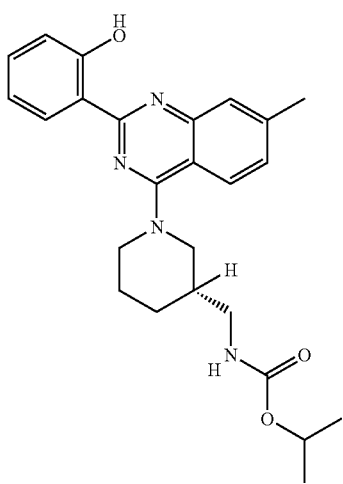
TABLE 2-continued
256
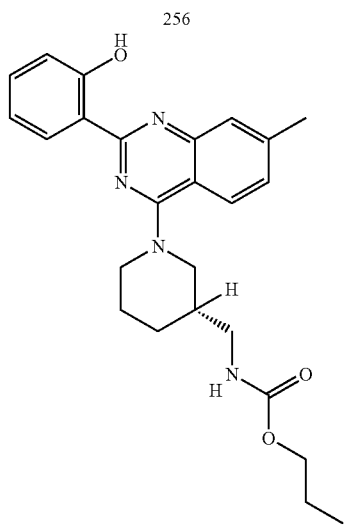
257
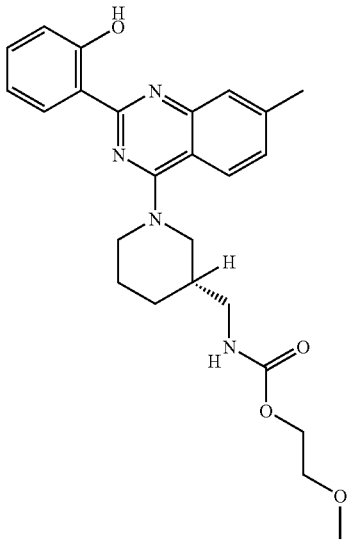
258
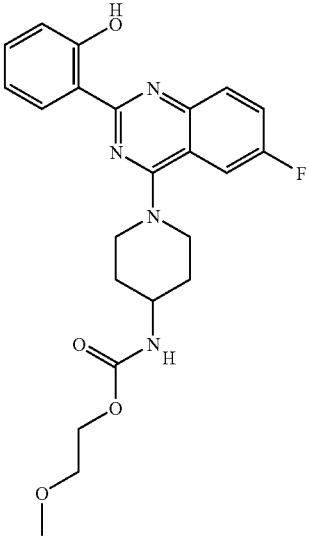

TABLE 2-continued
259
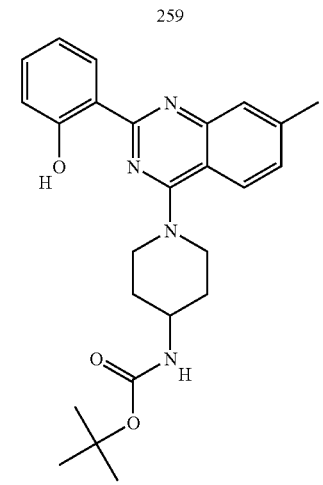
260
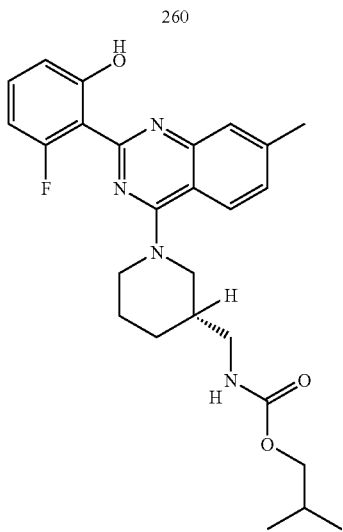
261
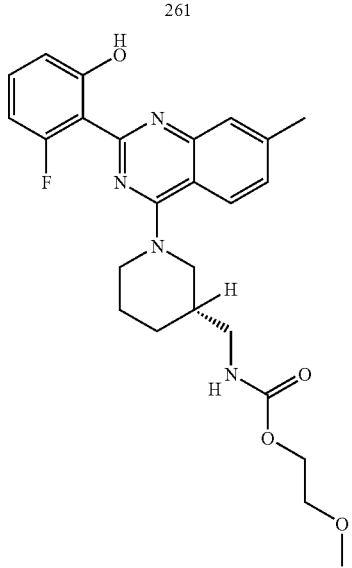
TABLE 2-continued
262
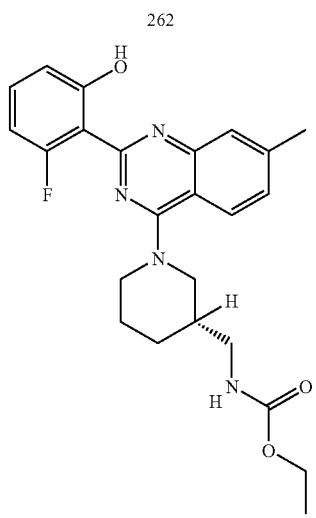
264
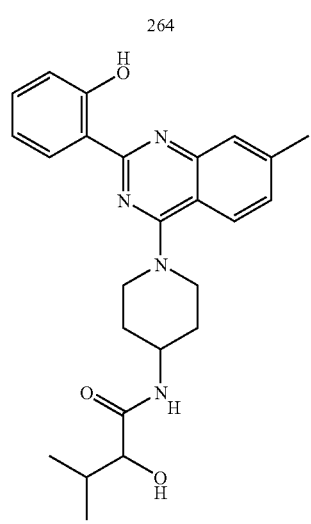
265
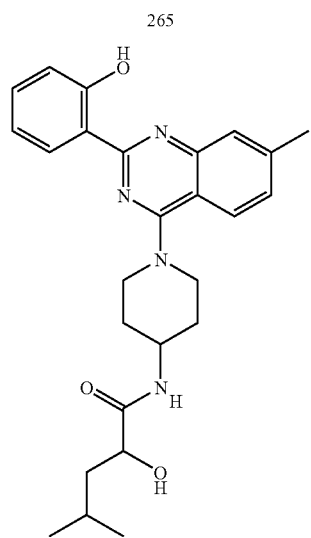

TABLE 2-continued
266
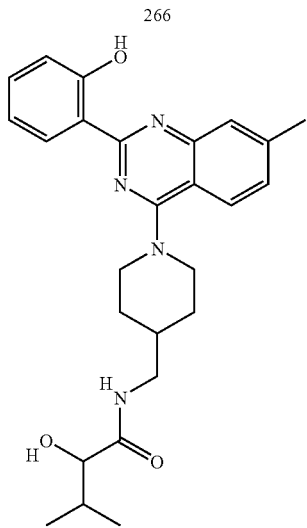
267
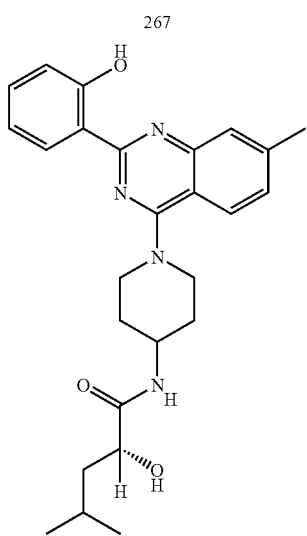
268
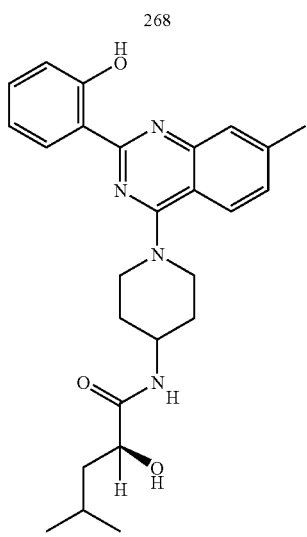
TABLE 2-continued
269
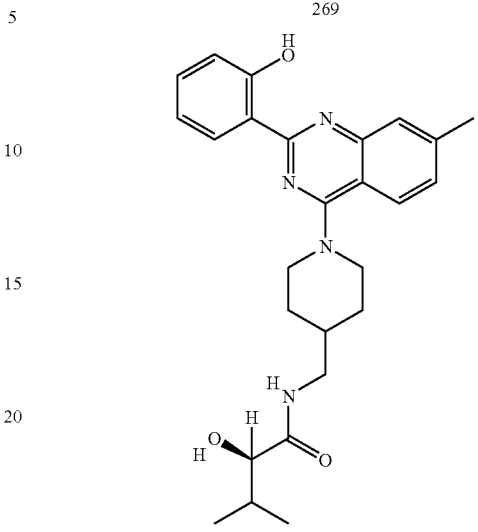
270
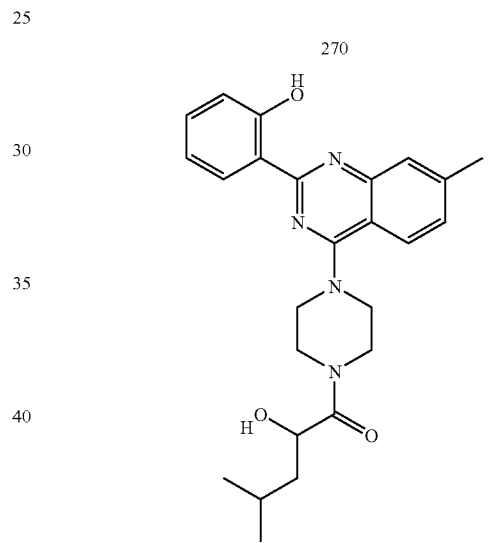
271
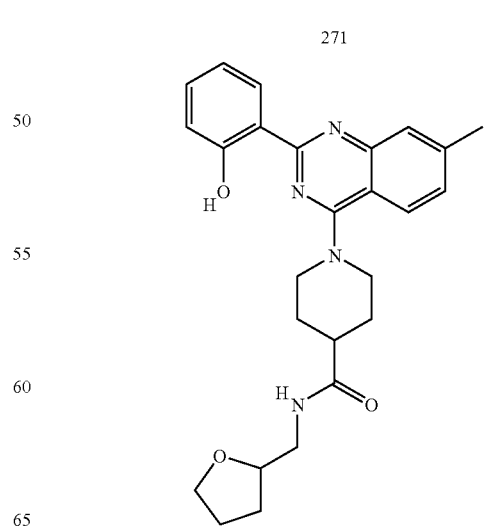

TABLE 2-continued
272
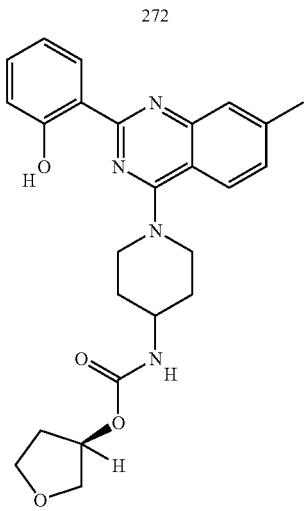
273
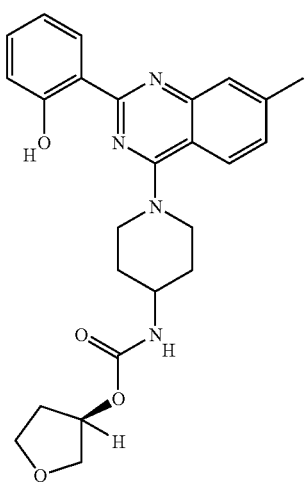
274
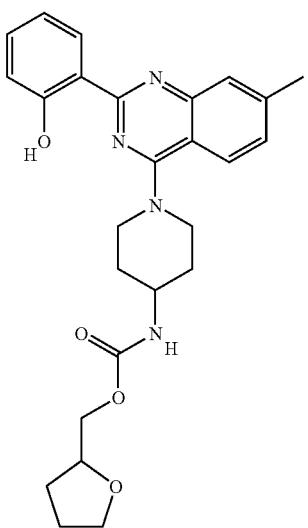
TABLE 2-continued
275
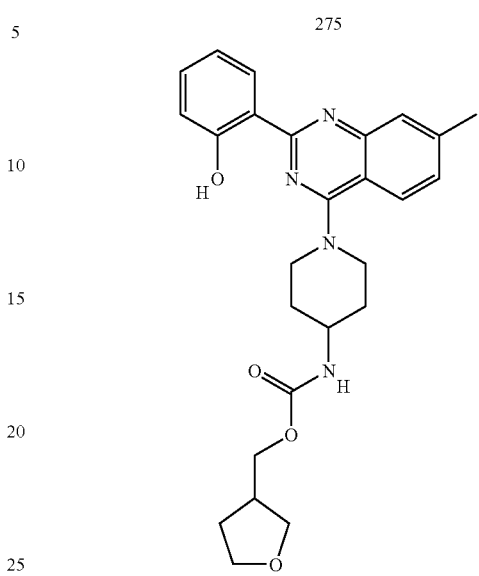
276
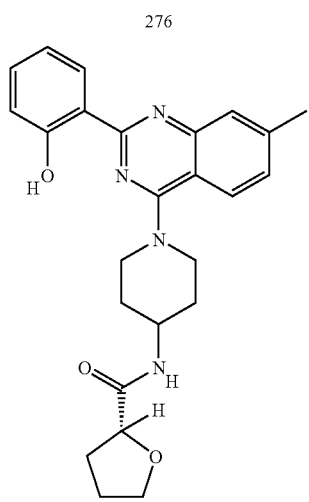
277
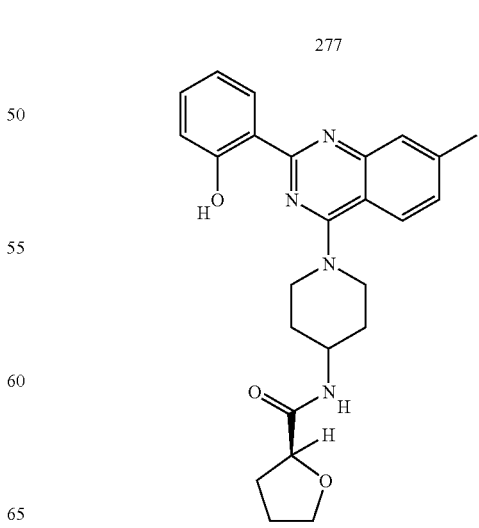

TABLE 2-continued
278
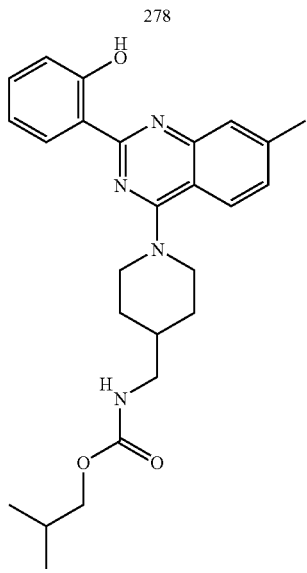
279
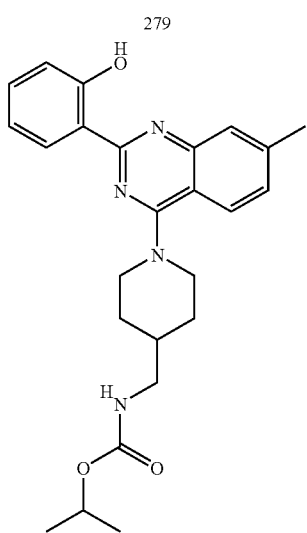
301
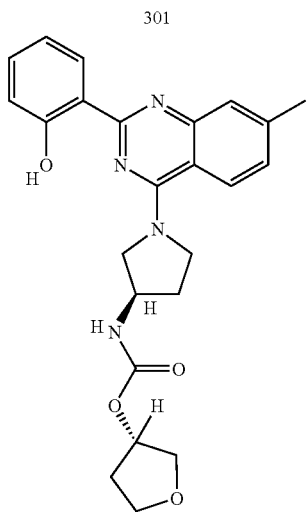
TABLE 2-continued
302
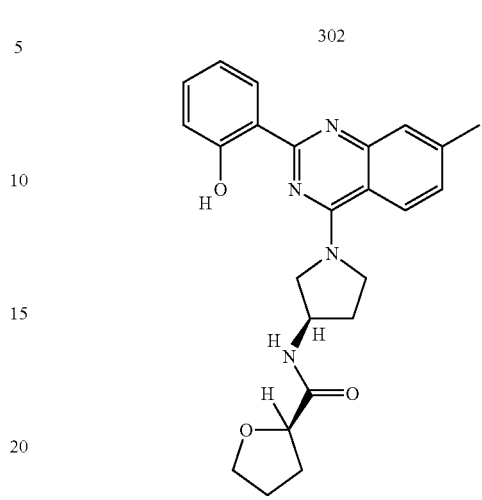
303
304

TABLE 2-continued
305
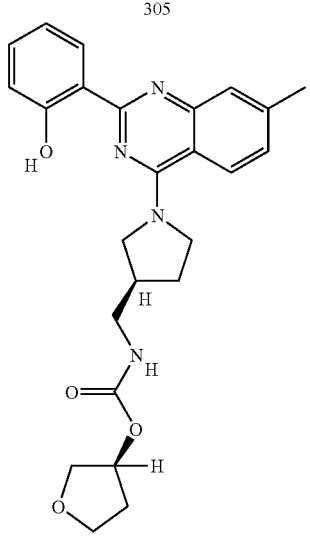
306
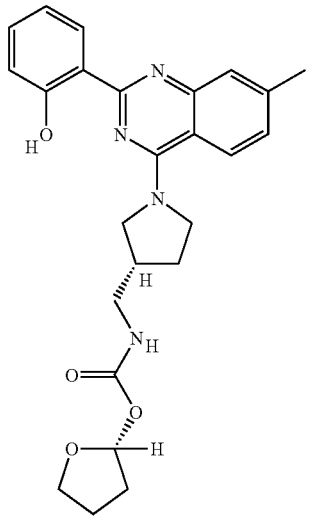
307
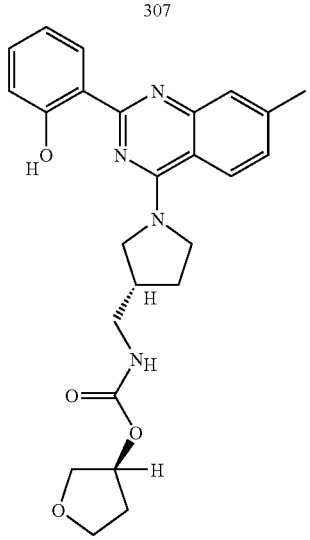
TABLE 2-continued
308
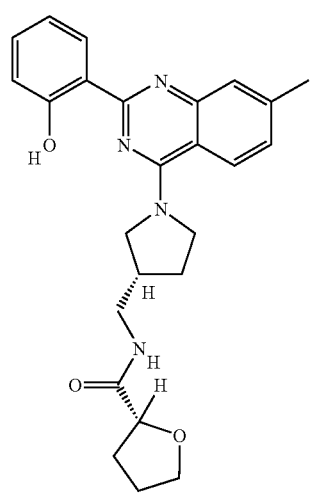
309
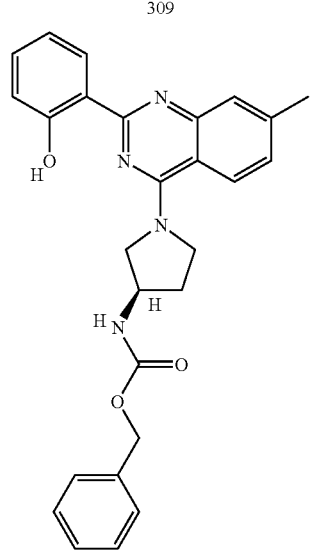
310
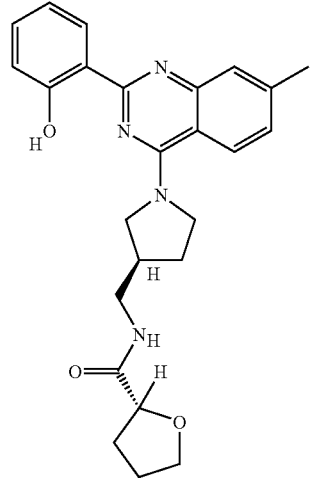

TABLE 2-continued
311
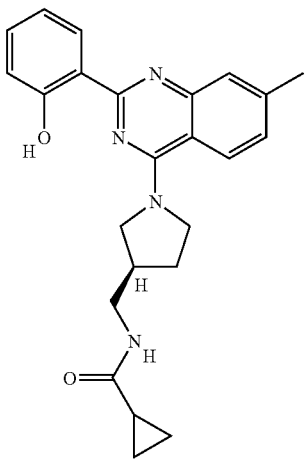
312
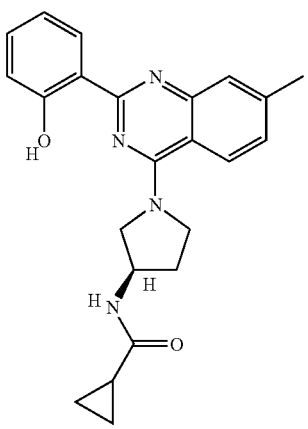
313
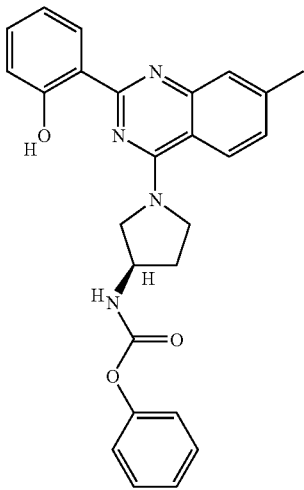
TABLE 2-continued
314
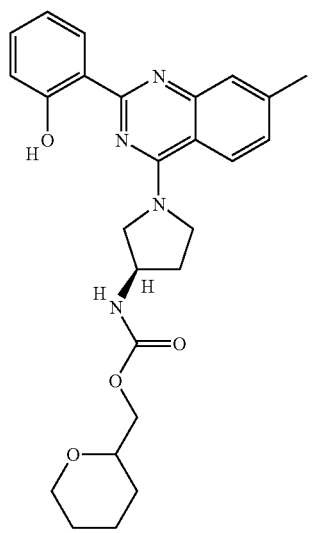
315
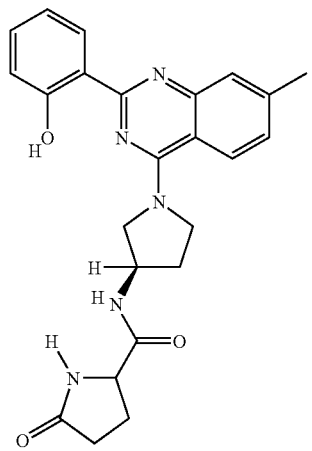
316
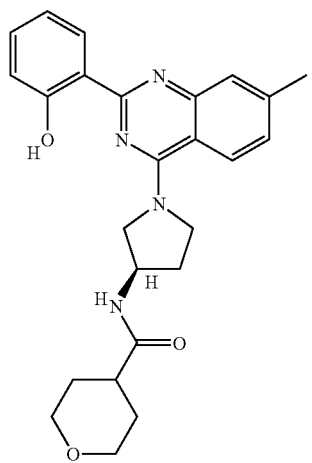

TABLE 2-continued
317
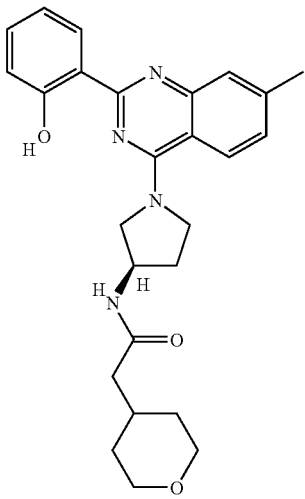
318
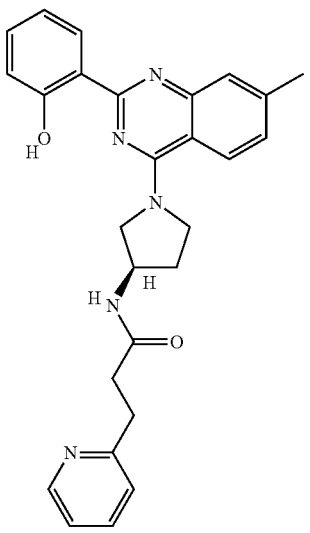
319
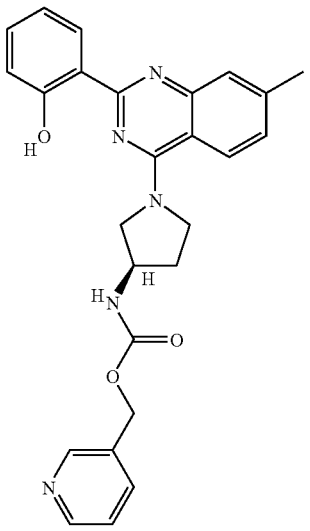
TABLE 2-continued
320
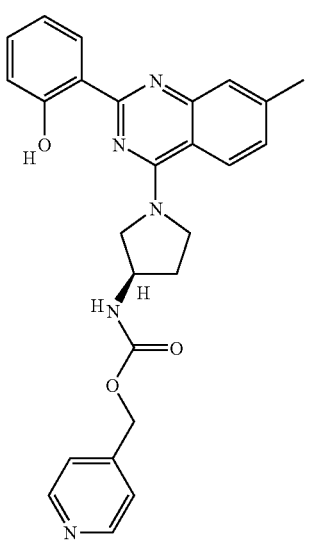
321
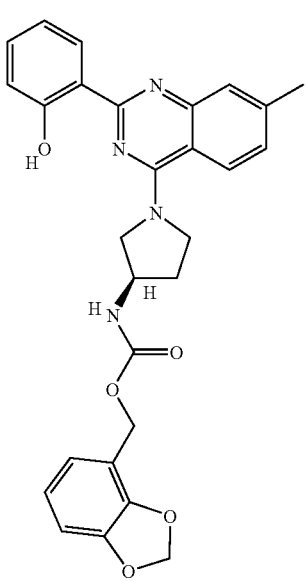

TABLE 2-continued
322
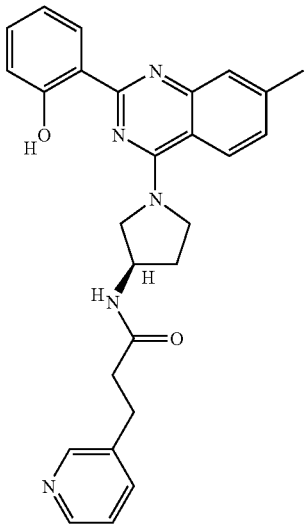
323
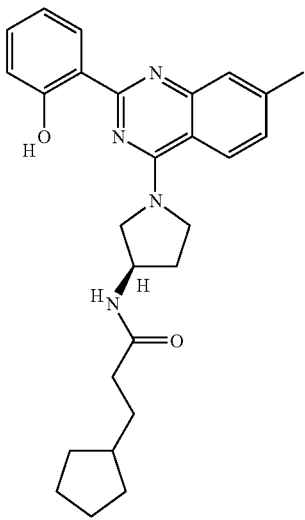
324
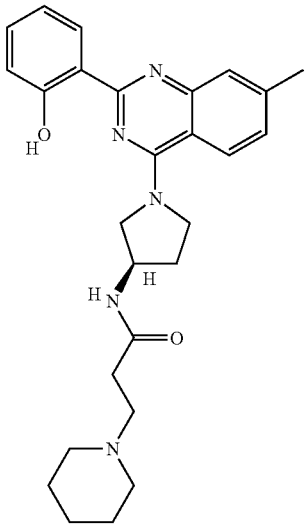
TABLE 2-continued
325
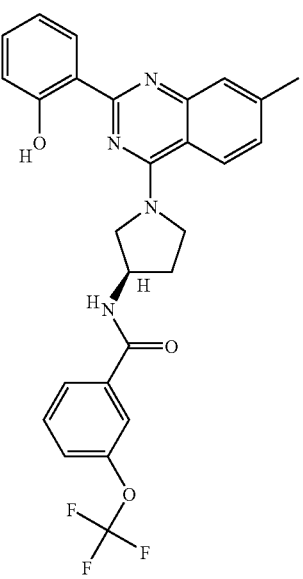
326
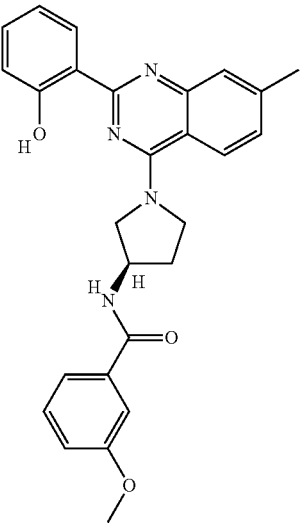

TABLE 2-continued
327
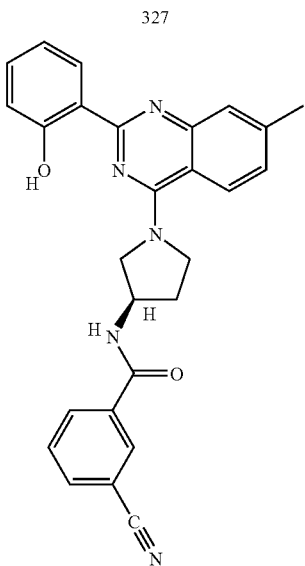
328
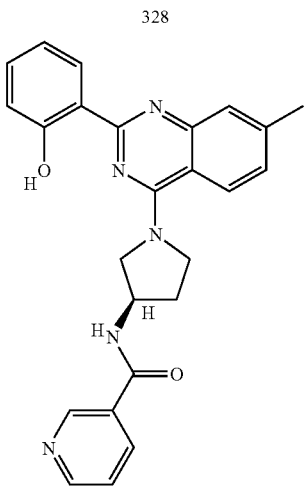
329
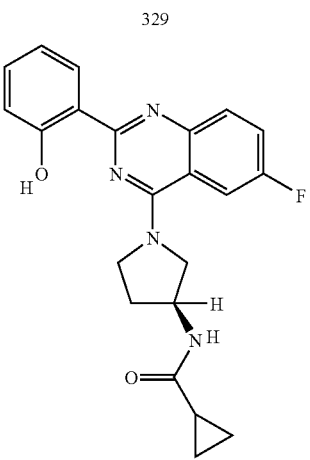
TABLE 2-continued
330
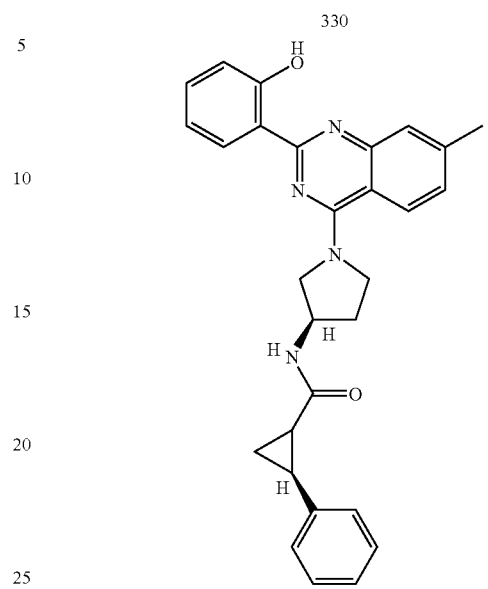
331
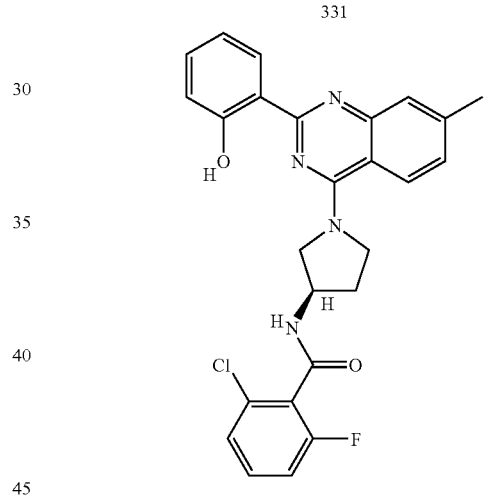
332
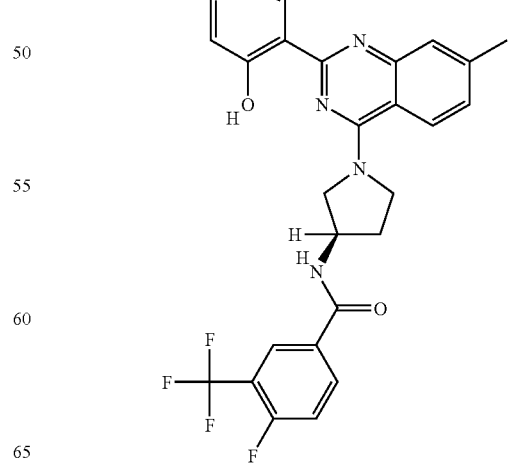

TABLE 2-continued
333
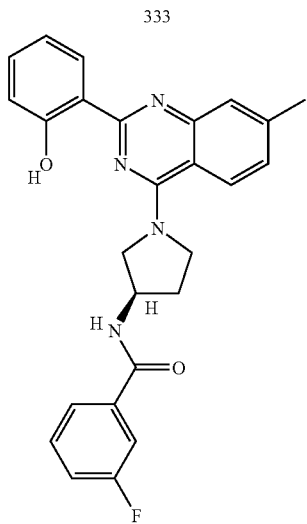
334
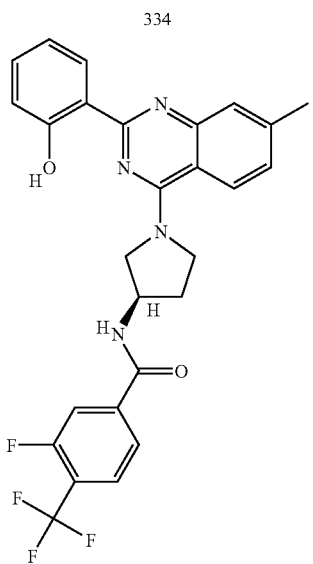
335
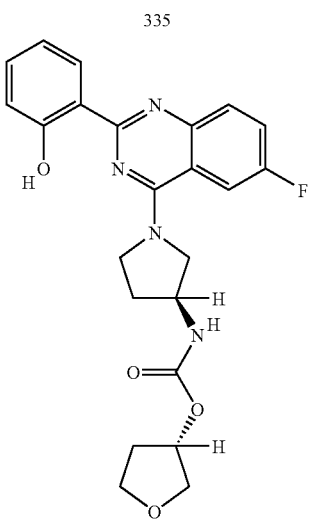
TABLE 2-continued
336
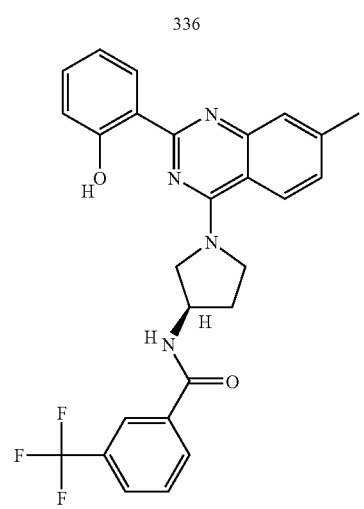
337
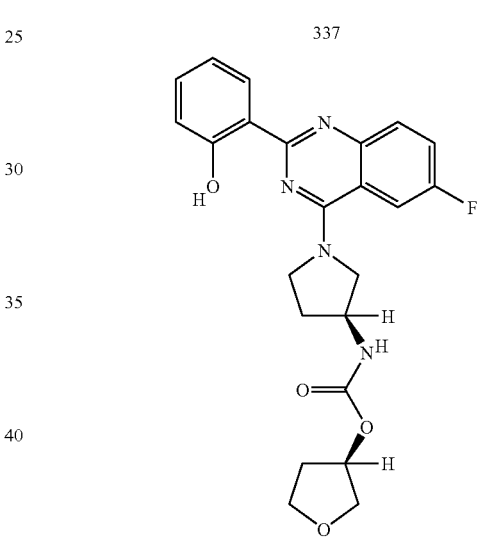
338
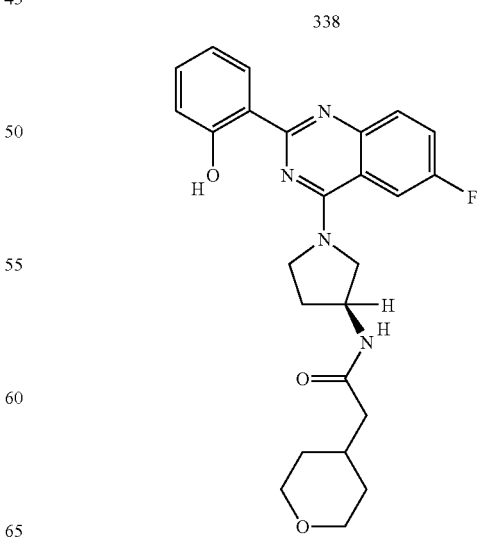

TABLE 2-continued
339
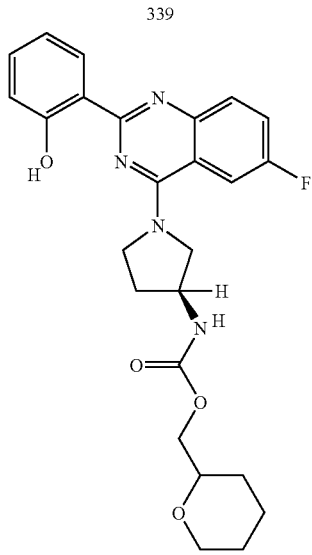
340
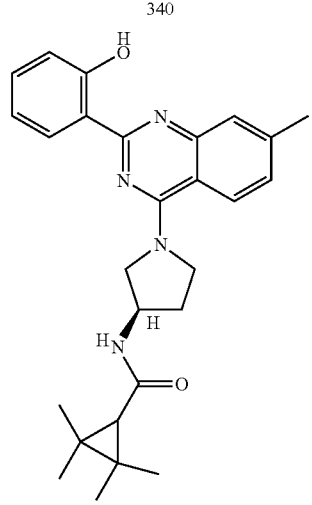
341
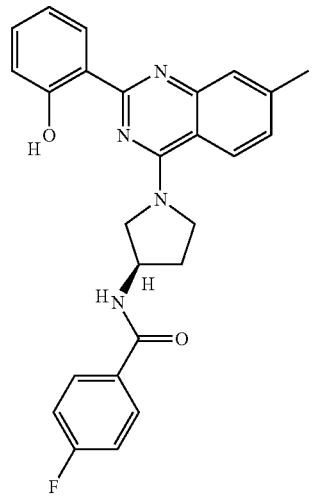
TABLE 2-continued
342
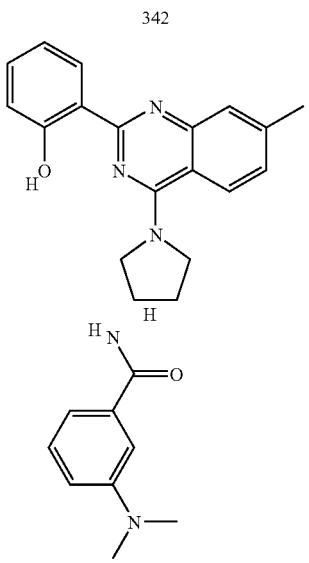
343
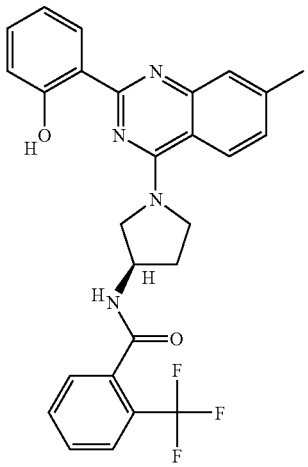
344
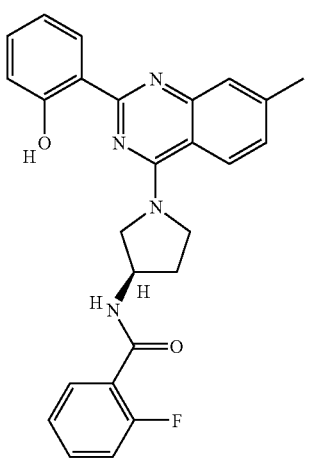

TABLE 2-continued
345
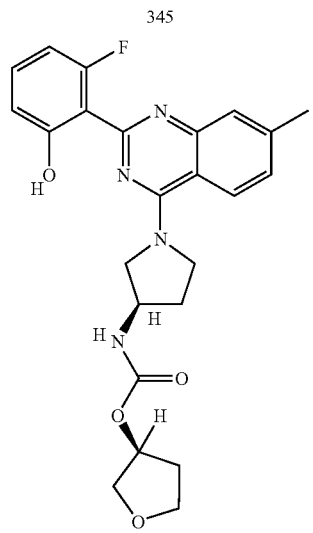
346
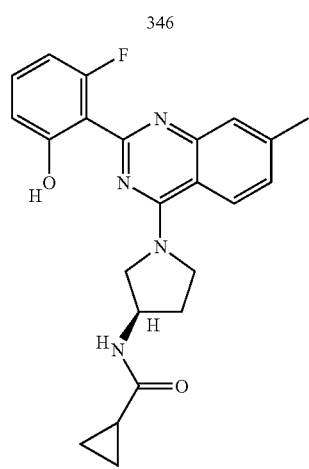
347
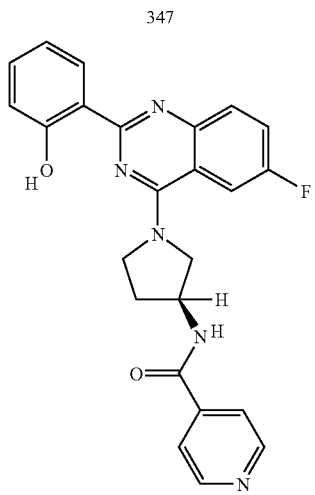
TABLE 2-continued
348
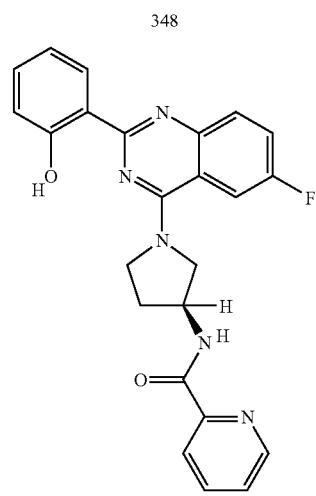
349
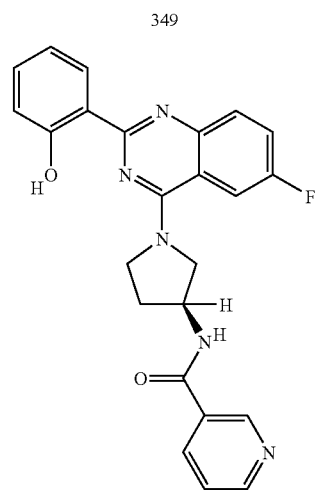
350
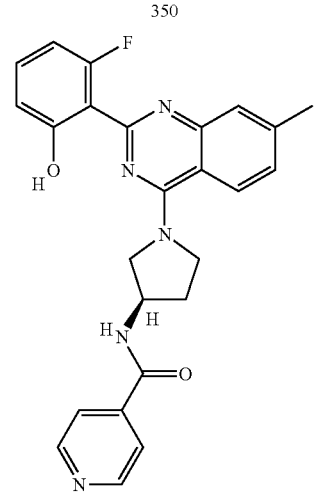

TABLE 2-continued
351
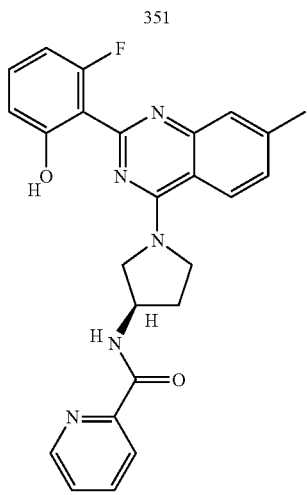
352
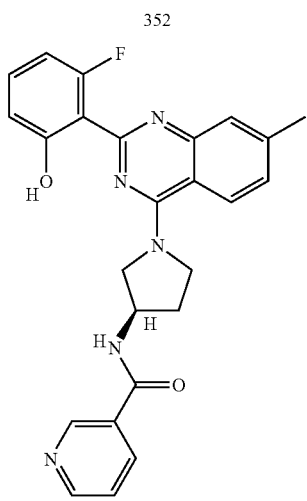
353
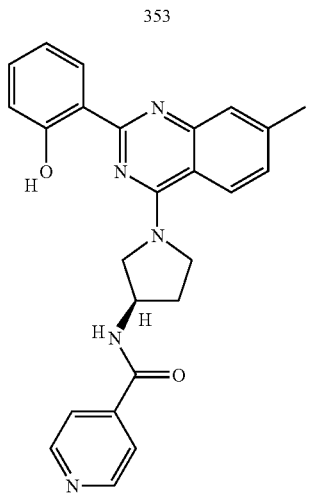
TABLE 2-continued
354
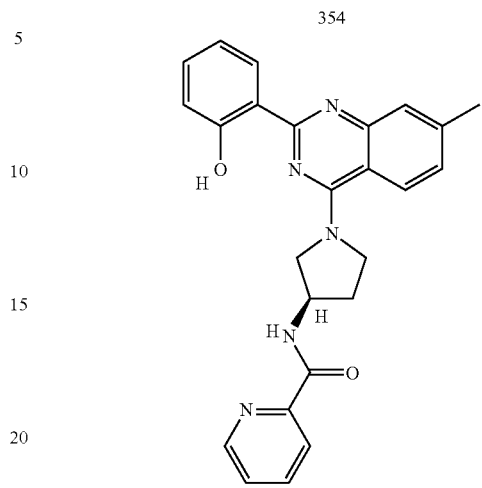
355
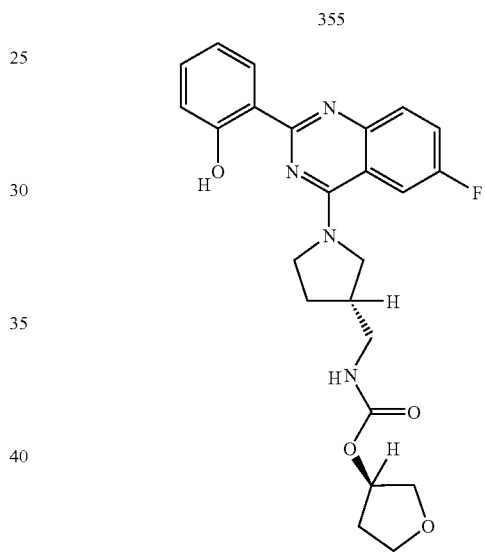
356
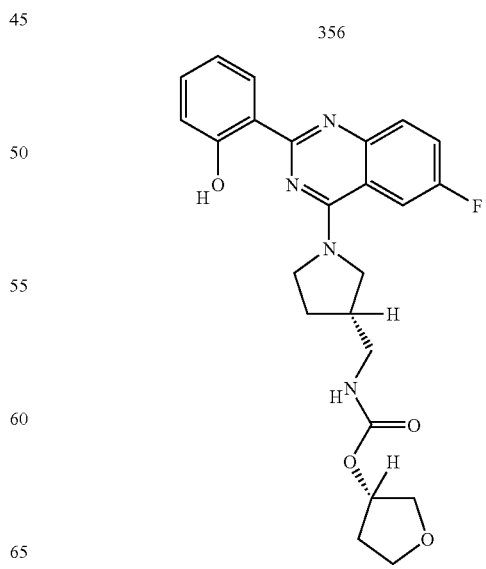

TABLE 2-continued
357
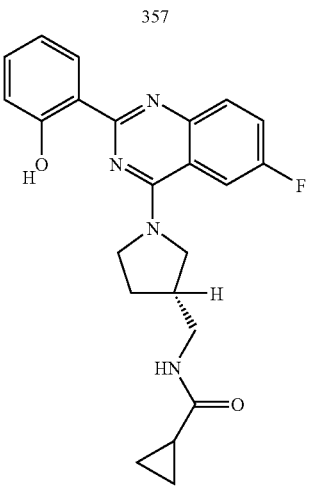
358
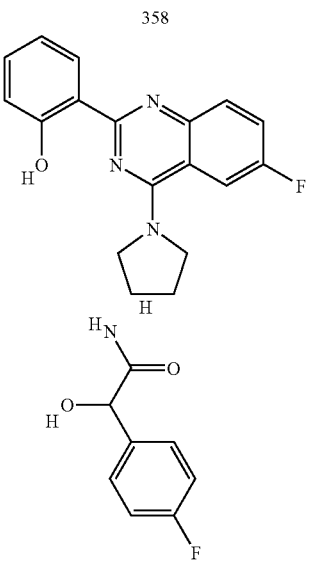
359
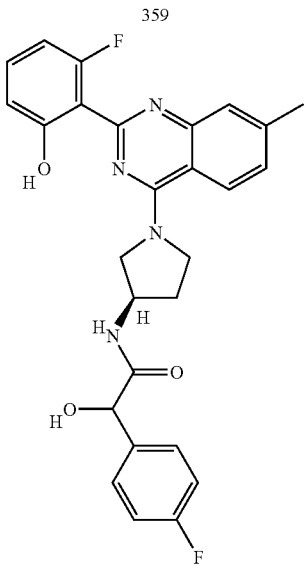
TABLE 2-continued
360
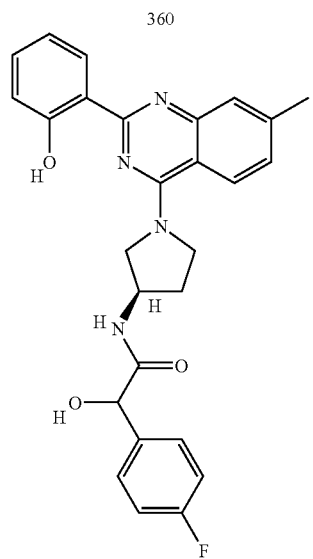
361
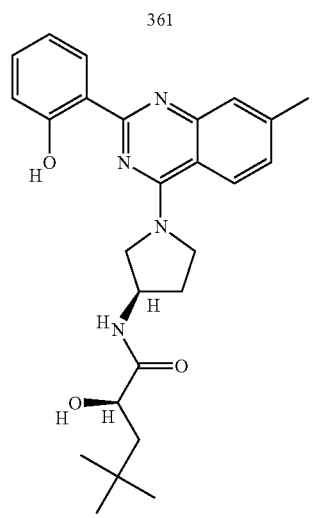
362
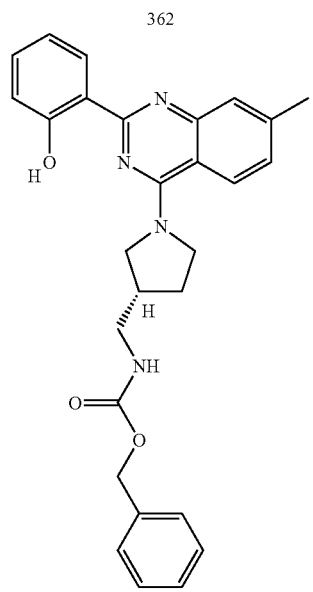

TABLE 2-continued
363
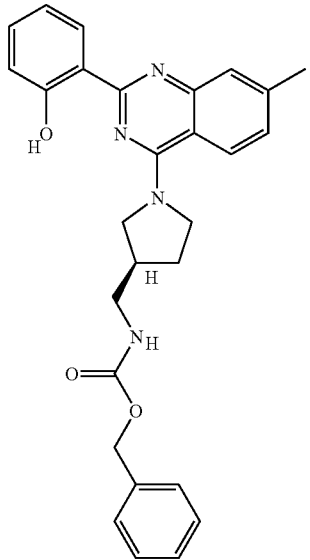
364
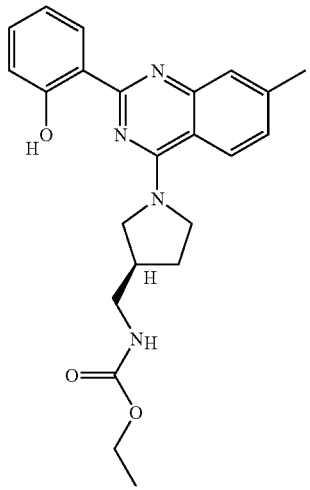
365
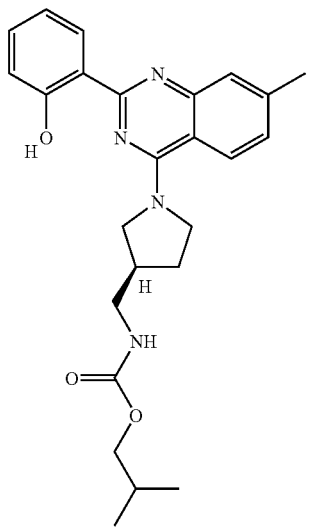
TABLE 2-continued
366
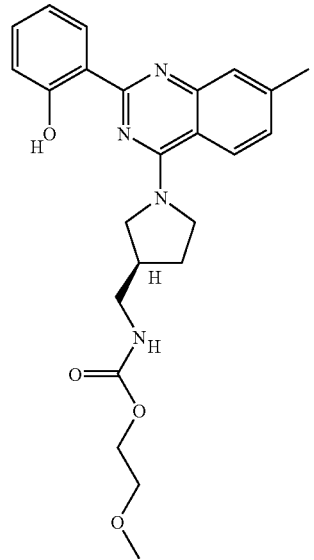
367
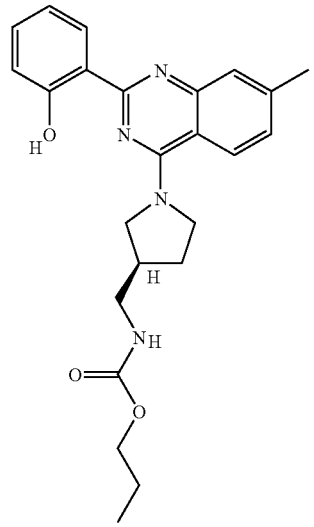
368
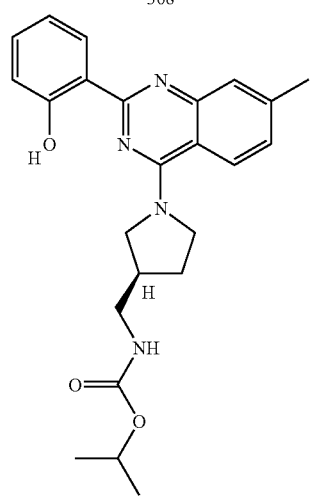

TABLE 2-continued
369
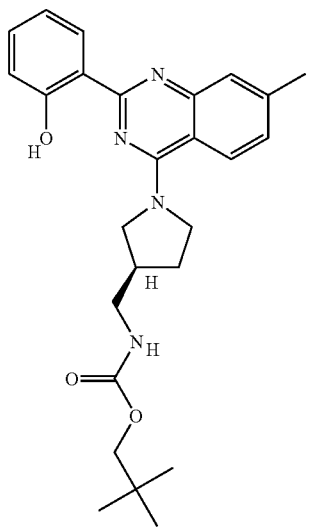
370
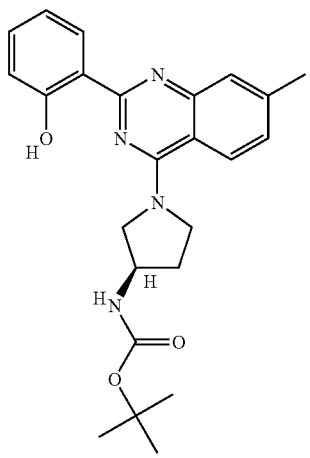
371
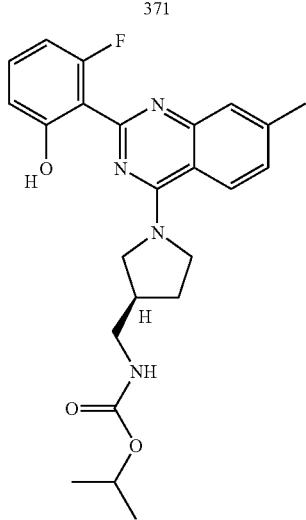
TABLE 2-continued
372
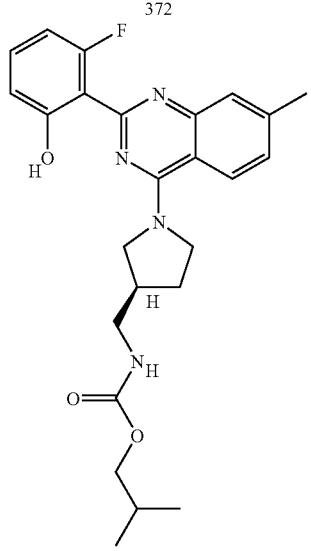
373
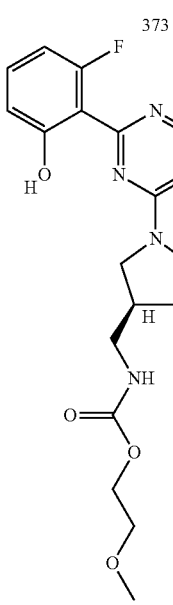
374
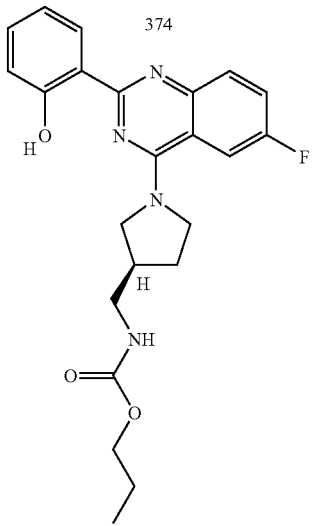

TABLE 2-continued
375
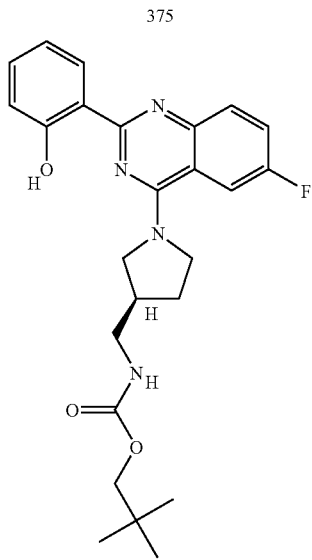
376
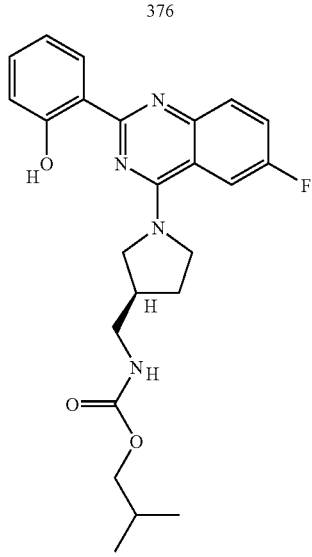
377
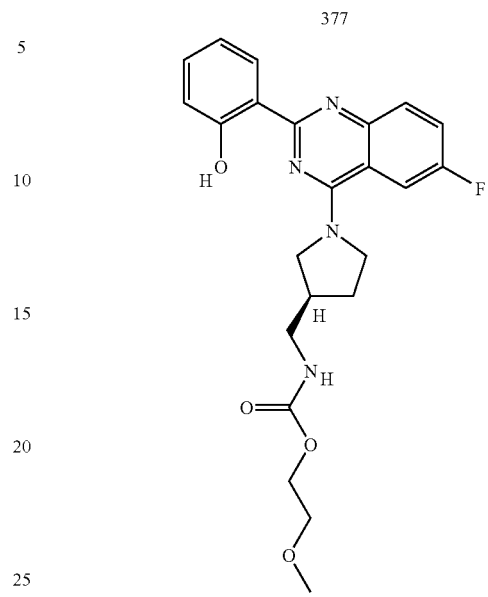
401
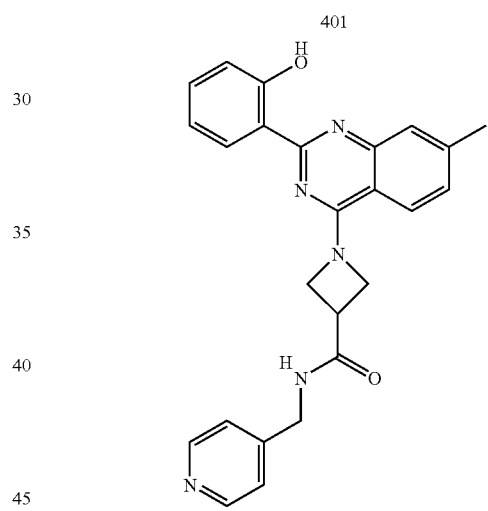
402
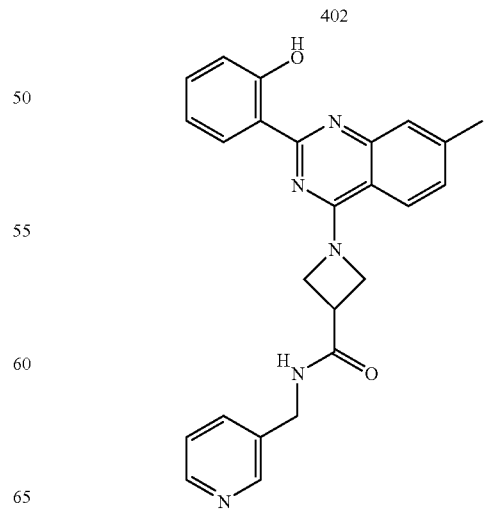

TABLE 2-continued
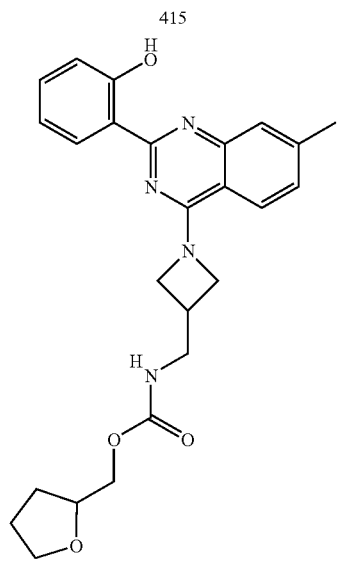
415
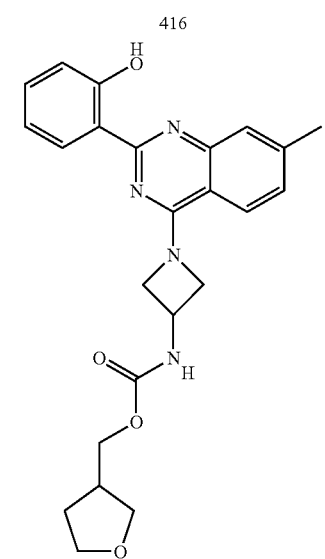
416
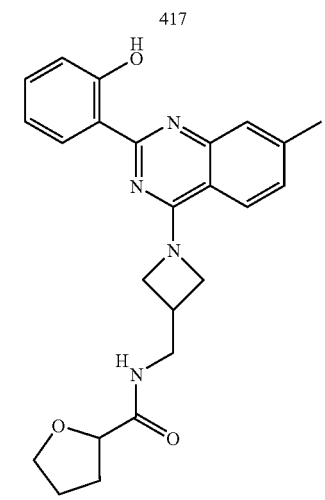
417
TABLE 2-continued
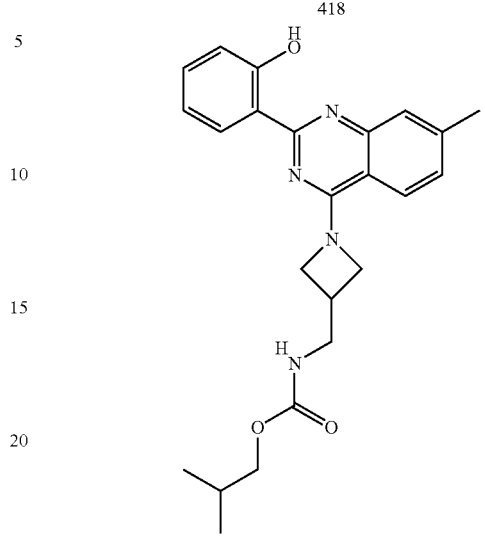
418
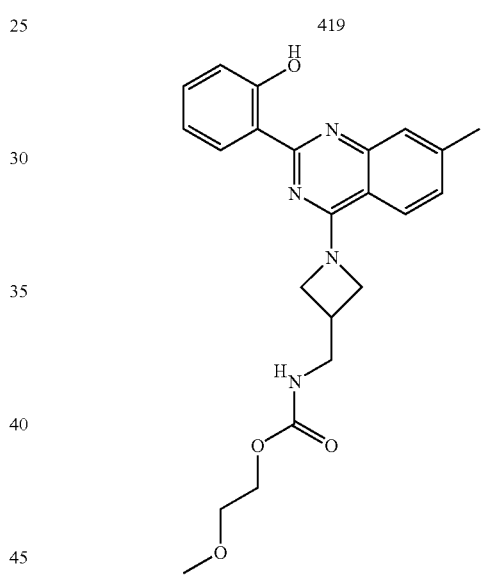
419
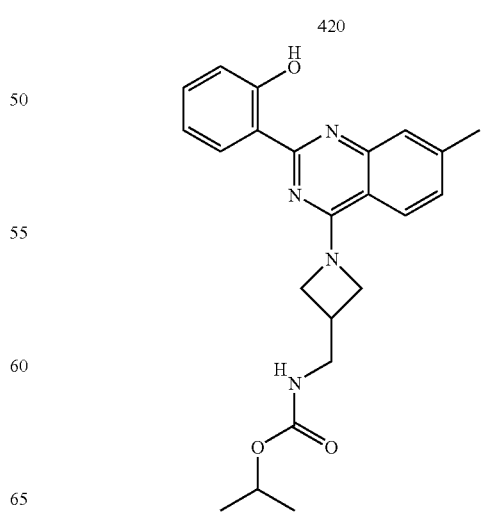
420

TABLE 2-continued
186
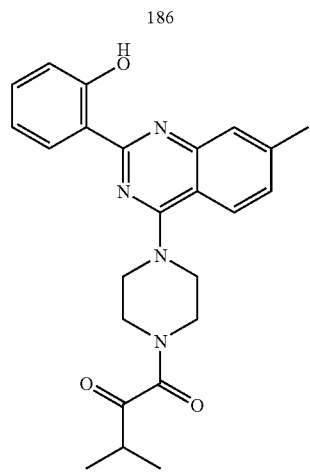
187
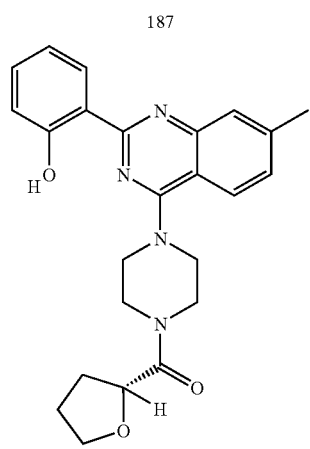
188
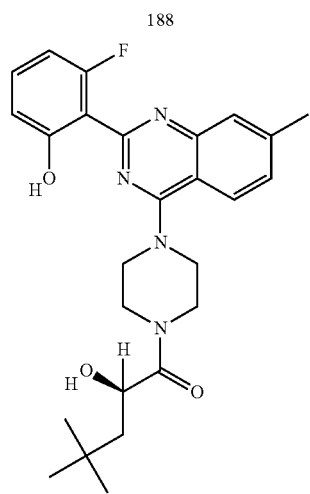
TABLE 2-continued
189
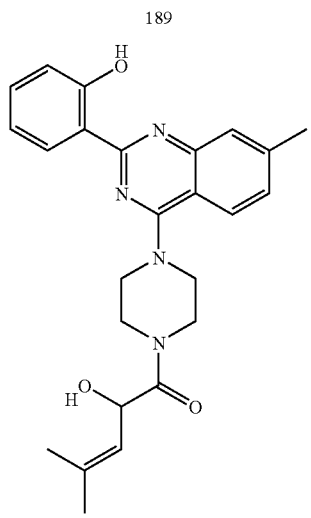
190
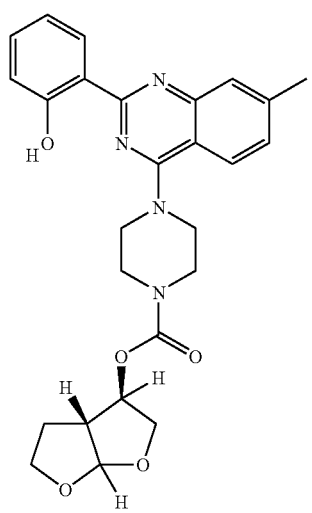
191
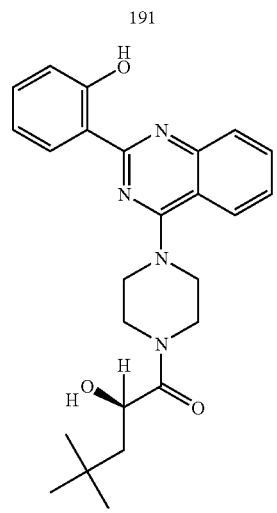

TABLE 2-continued
192
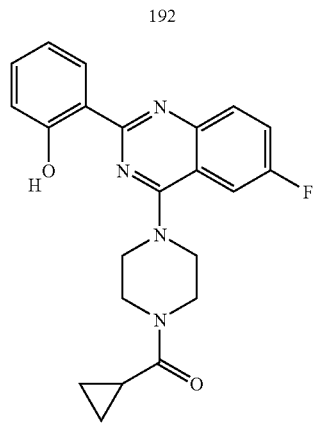
193
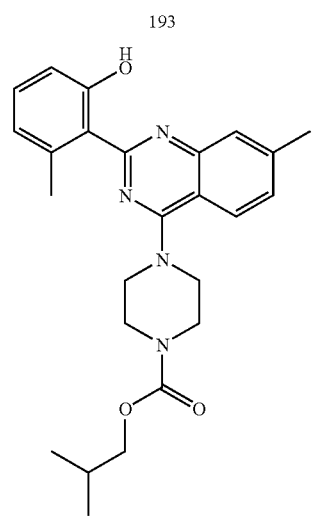
194
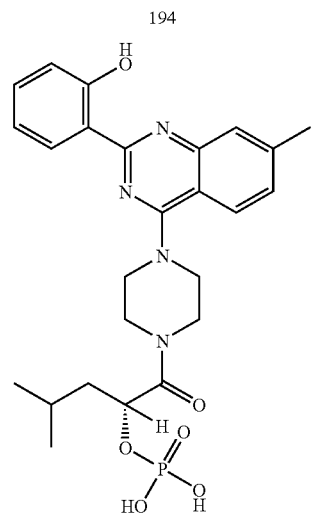
TABLE 2-continued
195
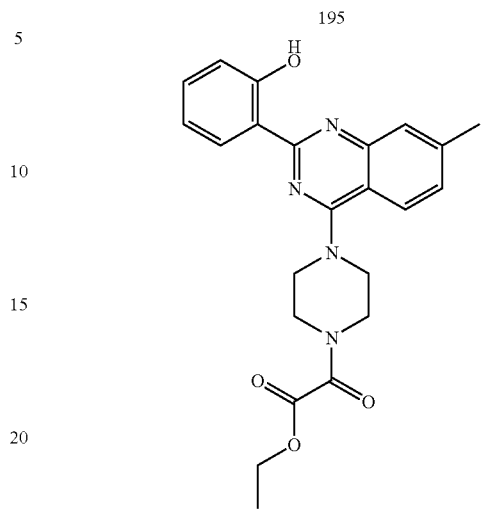
196
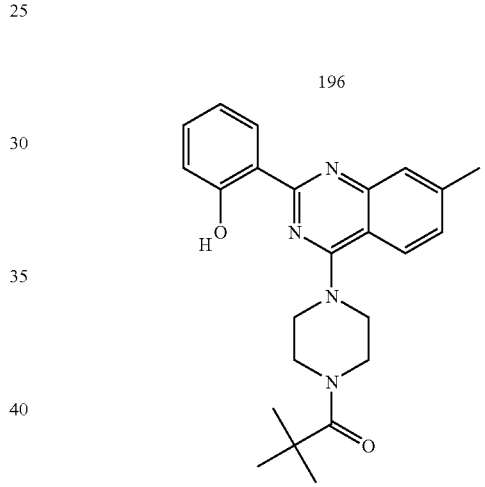
197
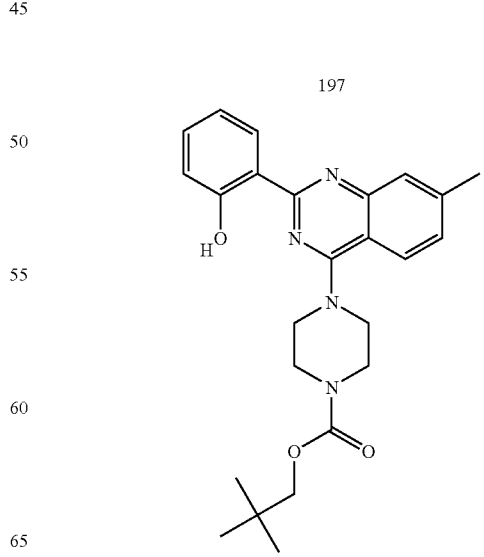

TABLE 2-continued
280
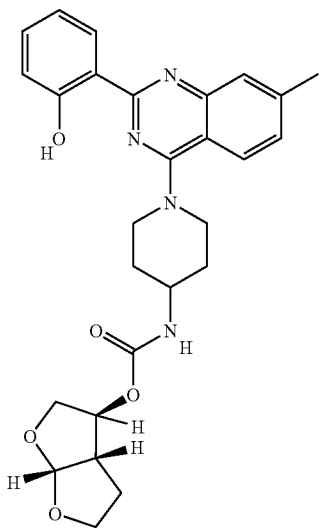
281
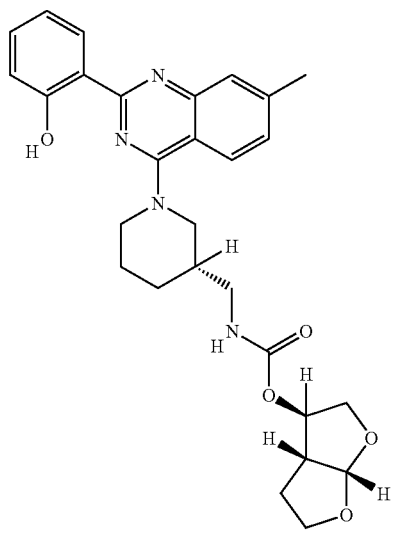
282
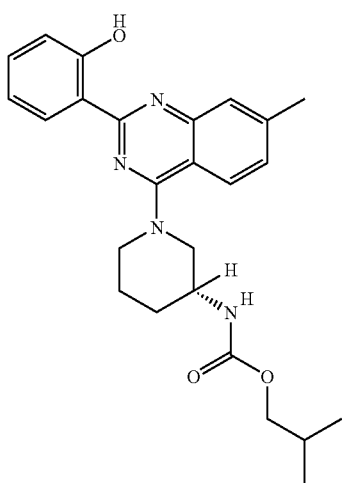
TABLE 2-continued
283
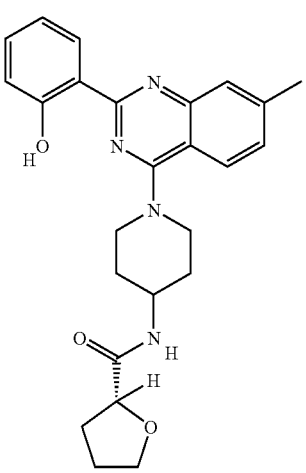
378
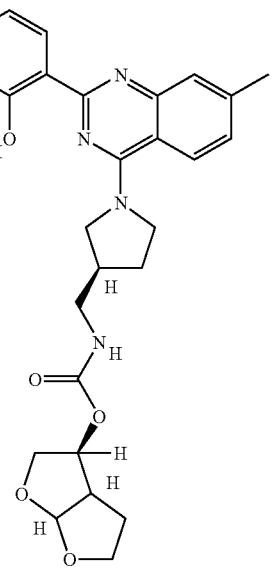

TABLE 2-continued
379
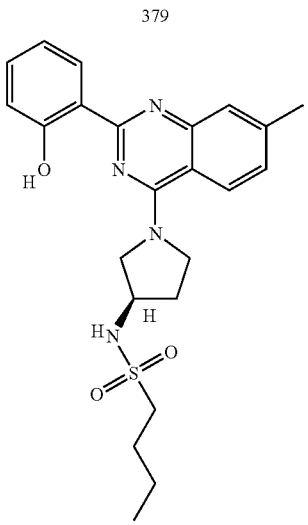
380
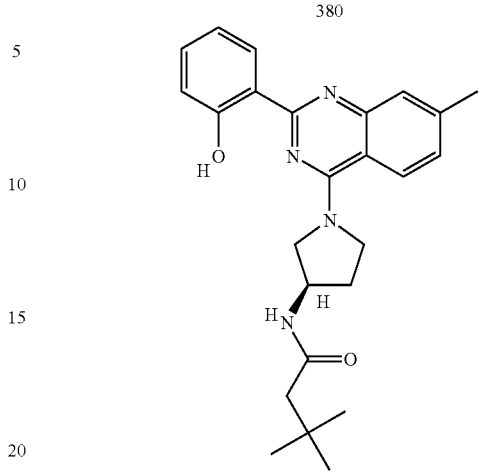
4. General Synthetic Methodology
The compounds of this invention may be prepared in general by methods known to those skilled in the art for analogous compounds, as illustrated by the general schemes below, and the preparative examples that follow.
Scheme A: General Preparations via 4-Chloroquinazolines
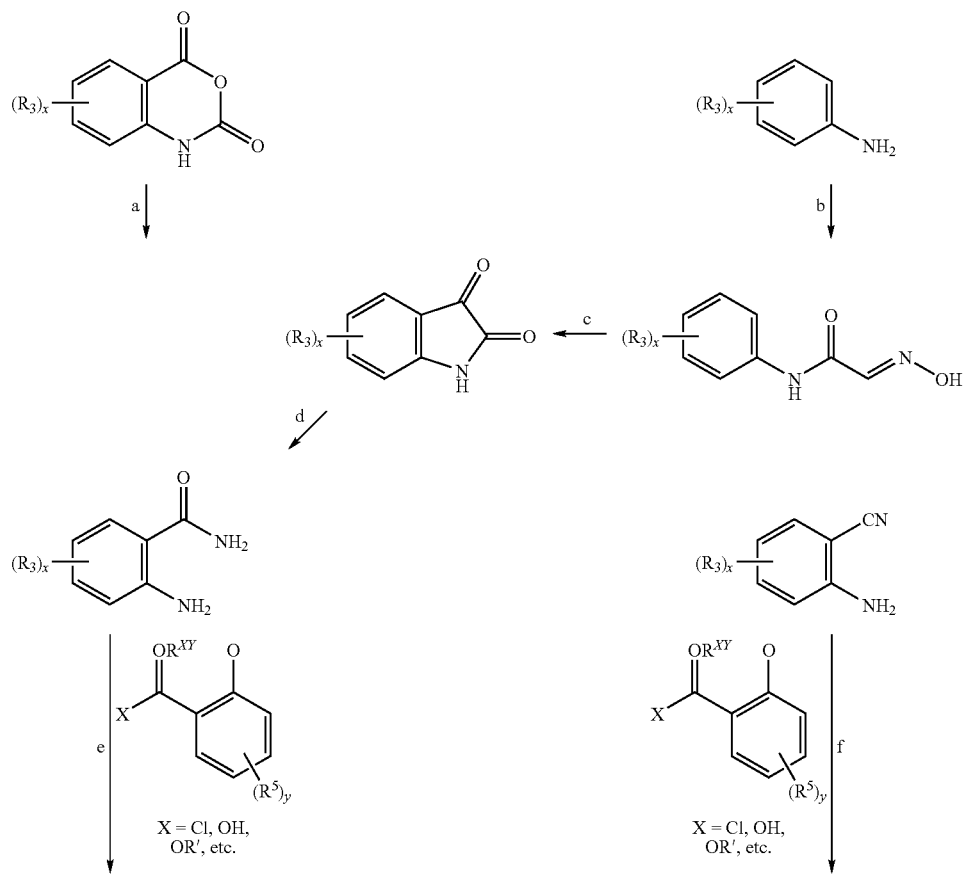

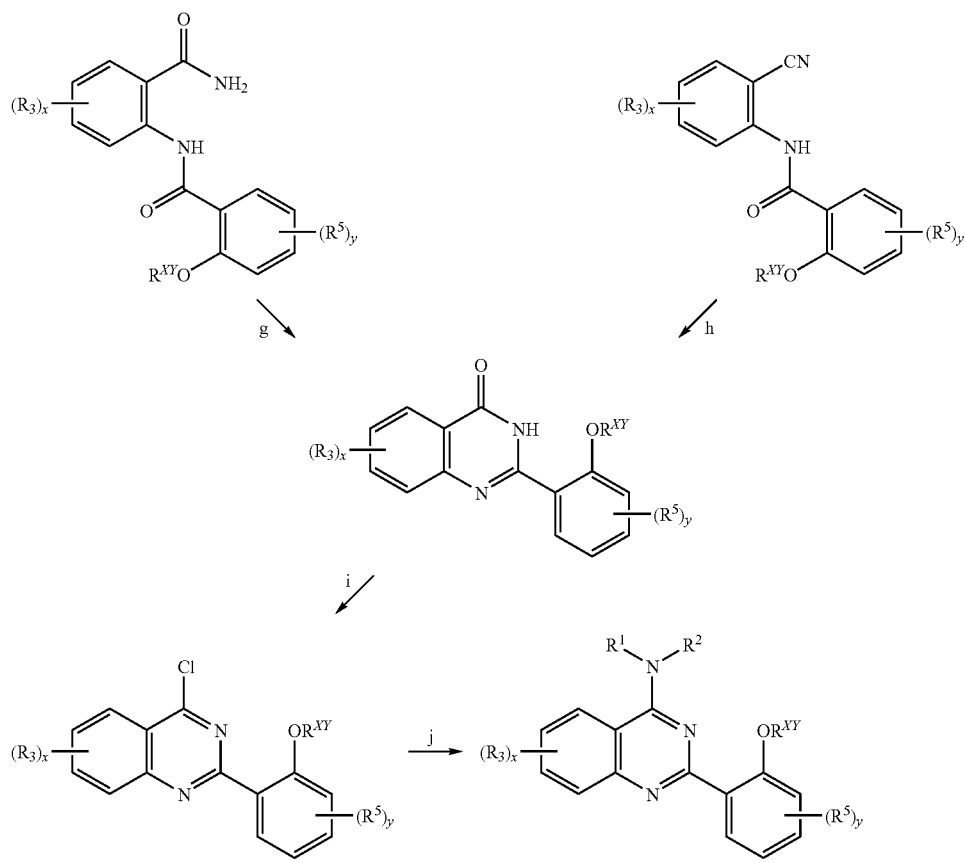
Conditions: a) aq. NH₄OH; b) chloral hydrate, HCl, Na₂SO₄, HONH₂*HCl c) H₂SO₄; d) acetic acid, H₂SO₄, aq. H₂O₂; e) Et₃N, THF; f) Et₃N, DMAP, CH₂Cl₂; g) aq. NaOH; h) aq. NaOH, aq. H₂O₂ i) POCl₃, N,N-dimethylaniline, benzene; j) R¹R²NH, Et₃N, CH₂Cl₂
Scheme B: General Preparations via 2,4-Dichloroquinazolines
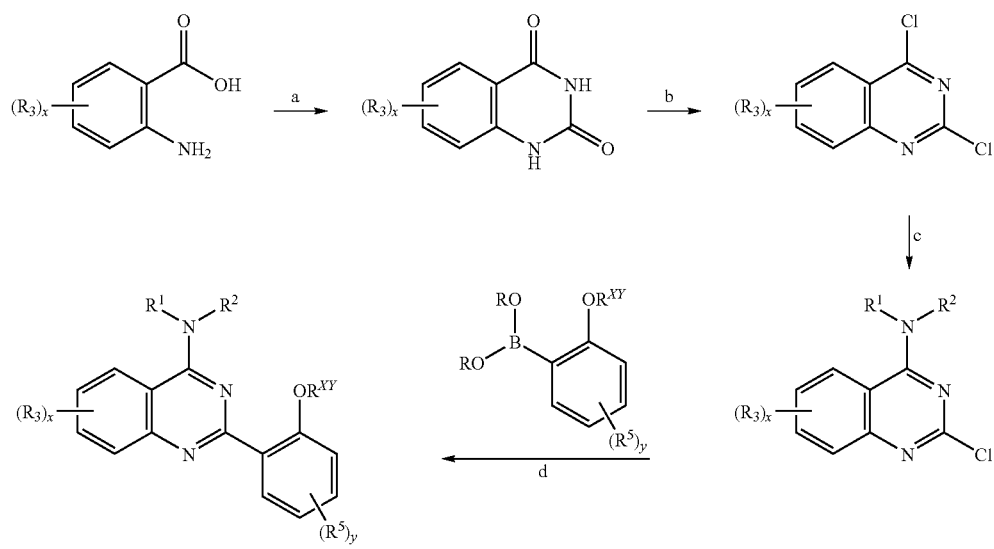
Conditions: a) AcOH, KOCN; b) POCl₃; c) Et₃N, DCM, R¹R²NH; d) Pd(PPh₃)₄, K₂CO₃, CH₃CN, H₂O Scheme I-A for formula I-A:

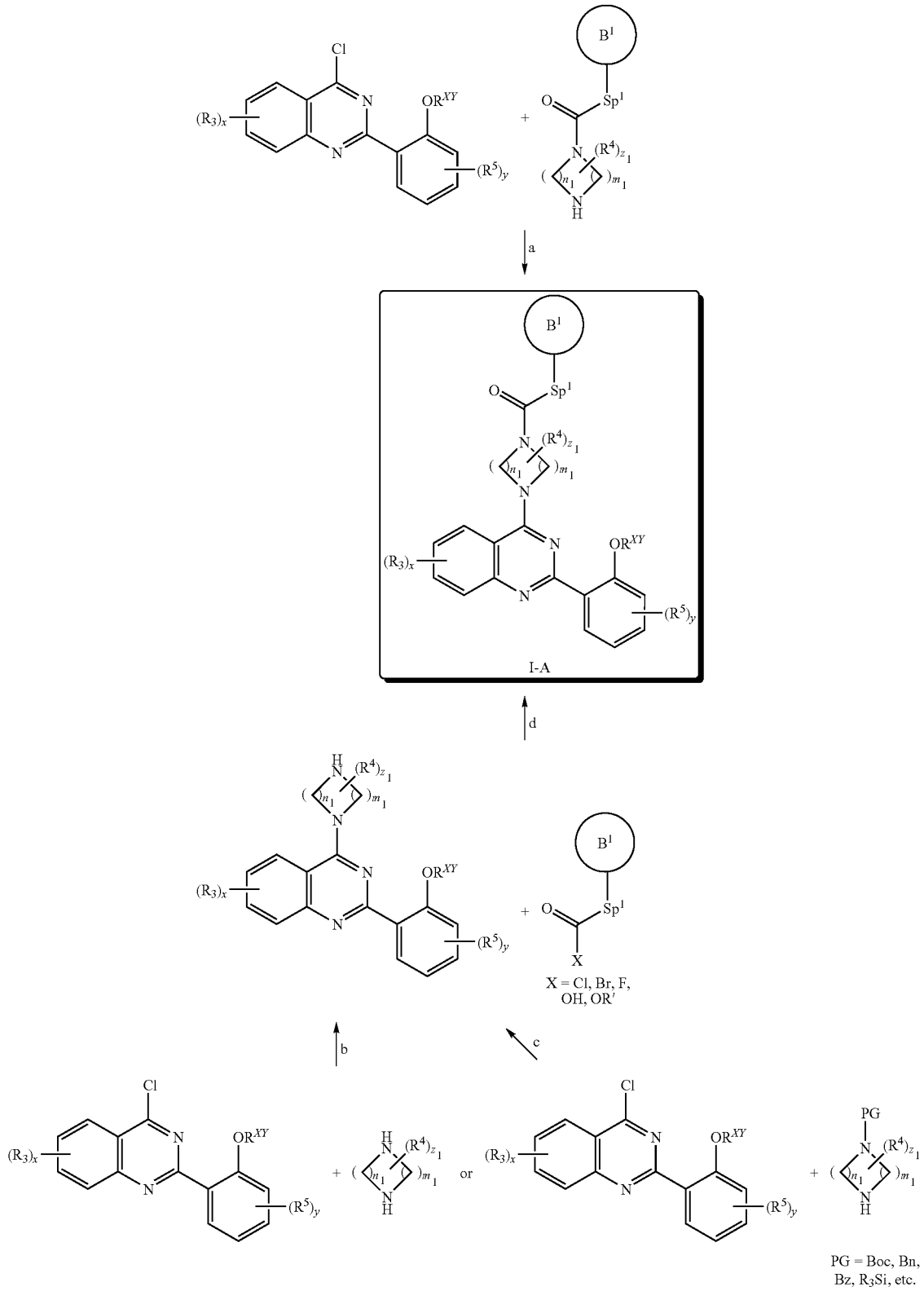

Conditions: a) DCM or THF, triethylamine, 0° C. to room temperature; b) DCM or THF, triethylamine, 0° C. to room temperature c) i. DCM or THF, triethylamine, 0° C. to room temperature, ii. Deprotect: 1:1 TFA/DCM, rt, for Boc; H₂, Pd/C for Bn; NaOH for Bz, TBAF for R3Si, etc,; d) For acid halides, DCM or THF, triethylamine; for carboxylic acids, EDC, HOBt, triethylamine, DMF; for X = OR', THF or DMF, heat.

Scheme I-B for compounds of formula I-B:
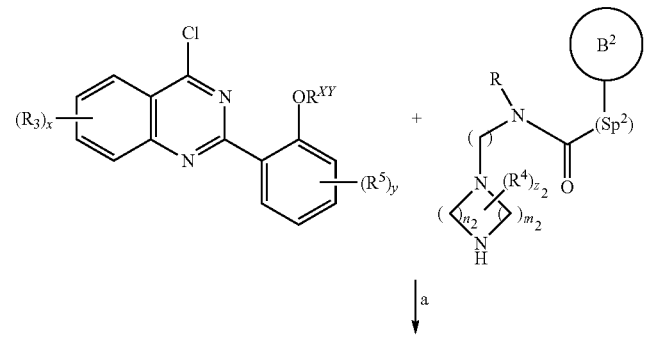
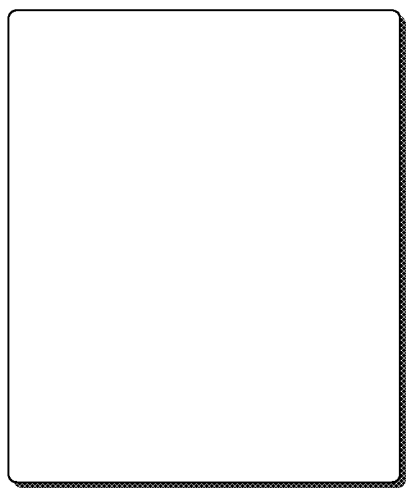
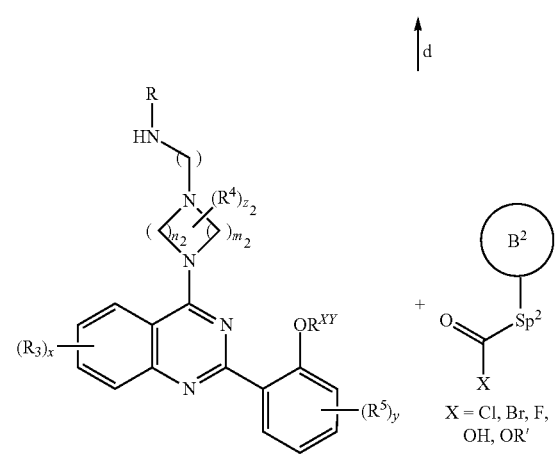

-continued

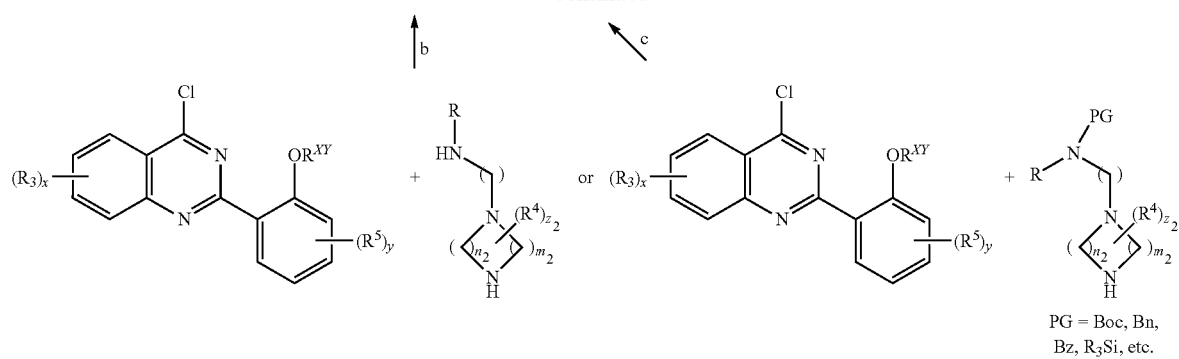

PG = Boc, Bn, Bz, R₃Si, etc.

Conditions: a) DCM or THF, triethylamine, 0° C. to room temperature; b) DCM or THF, triethylamine, 0° C. to room temperature c) i. DCM or THF, triethylamine, 0° C. to room temperature, ii. Deprotect: 1:1 TFA/DCM, rt, for Boc; H$_2$, Pd/C for Bn; NaOH for Bz, TBAF for R3Si, etc.; d) For acid halides, DCM or THF, triethylamine; for carboxylic acids, EDC, HOBt, triethylamine, DMF; for X = OR', THF or DMF, heat.

Scheme I-C for formula I-C:

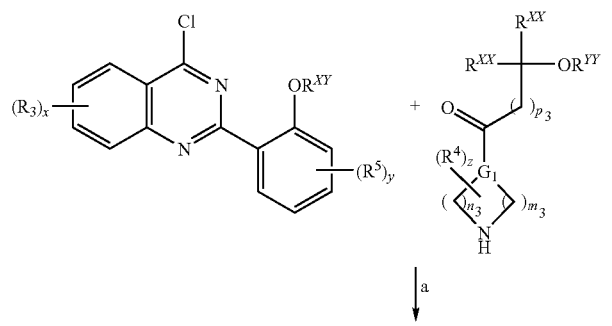

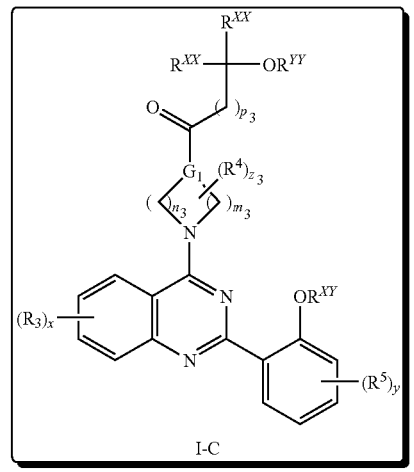

I-C

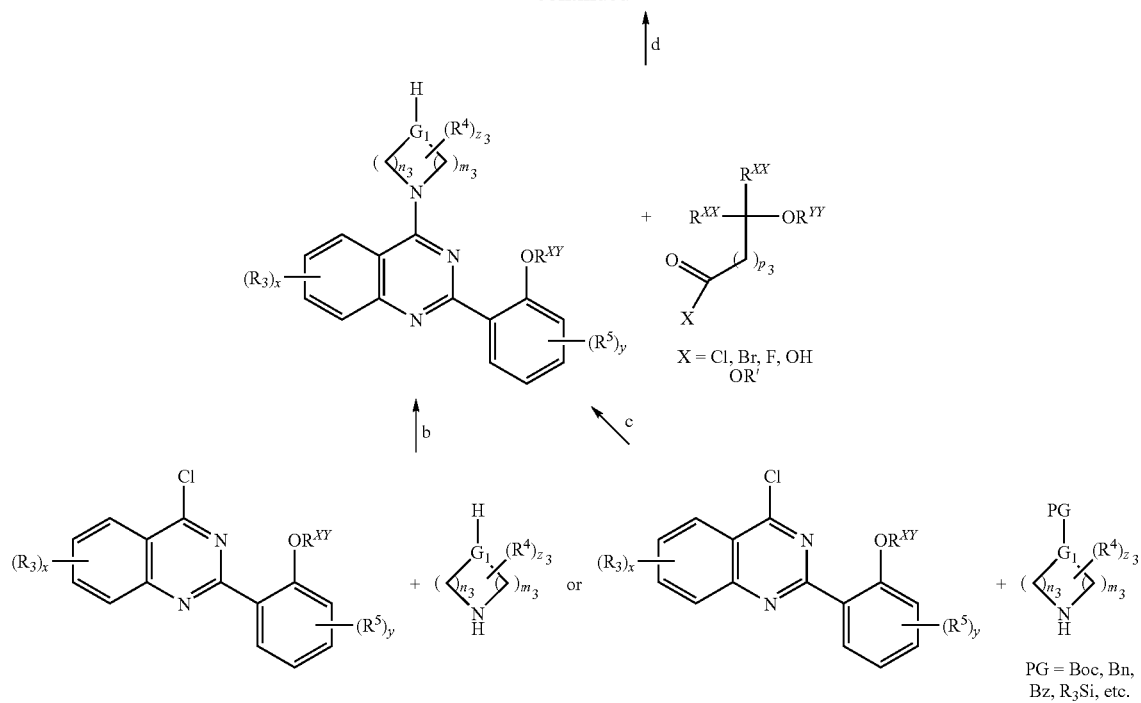

Conditions: a) DCM or THF, triethylamine, 0° C. to room temperature; b) DCM or THF, triethylamine, 0° C. to room temperature c) i. DCM or THF, triethylamine, 0° C. to room temperature, ii. Deprotect: 1:1 TFA/DCM, rt, for Boc; $H_2$, Pd/C for Bn; NaOH for Bz, TBAF for $R_3Si$, etc.; d) For acid halides, DCM or THF, triethylamine; for carboxylic acids, EDC, HOBt, triethylamine, DMF; for X = OR', THF or DMF, heat.

Scheme I-D for formula I-D:

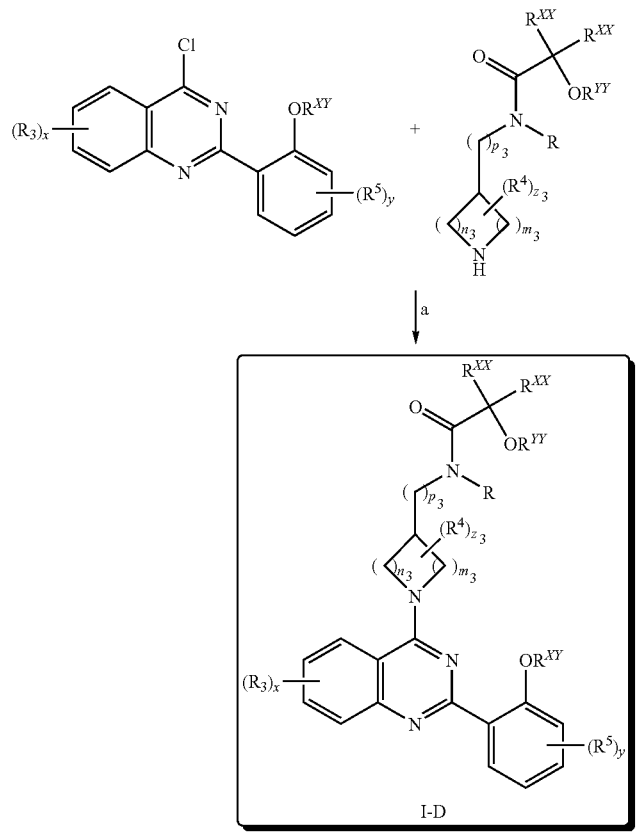

-continued

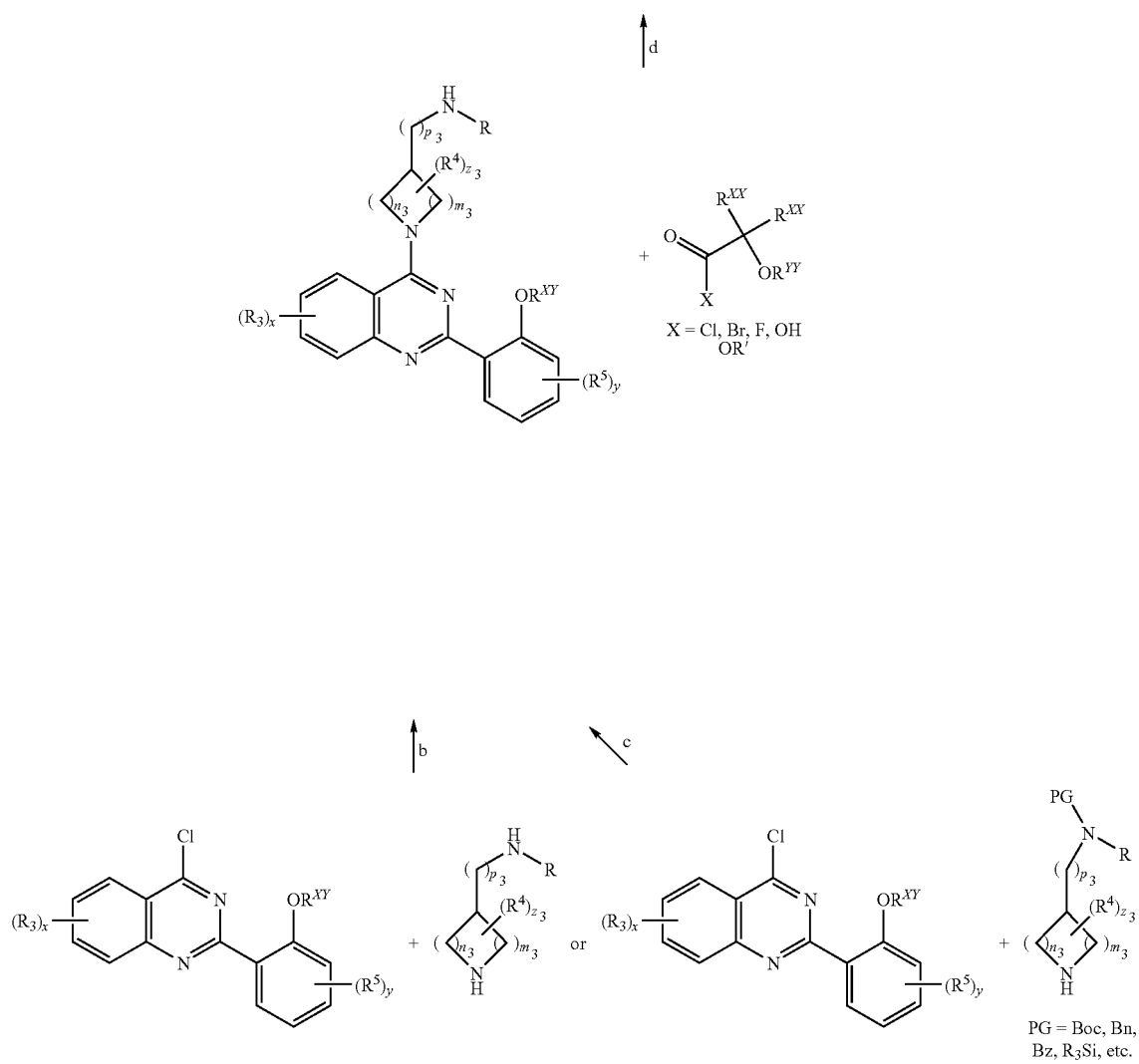

Conditions: a) DCM or THF, triethylamine, 0° C. to room temperature; b) DCM or THF, triethylamine, 0° C. to room temperature c) i. DCM or THF, triethylamine, 0° C. to room temperature, ii. Deprotect: 1:1 TFA/DCM, rt, for Boc; $H_2$, Pd/C for Bn; NaOH for Bz, TBAF for R3Si, etc.; d) For acid halides, DCM or THF, triethylamine; for carboxylic acids, EDC, HOBt, triethylamine, DMF; for X = OR′, THF or DMF, heat.

Scheme I-E for formula I-E:

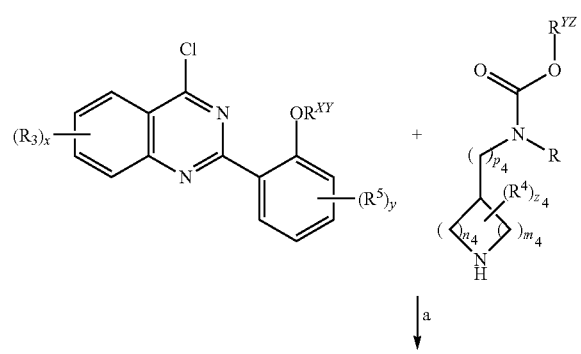

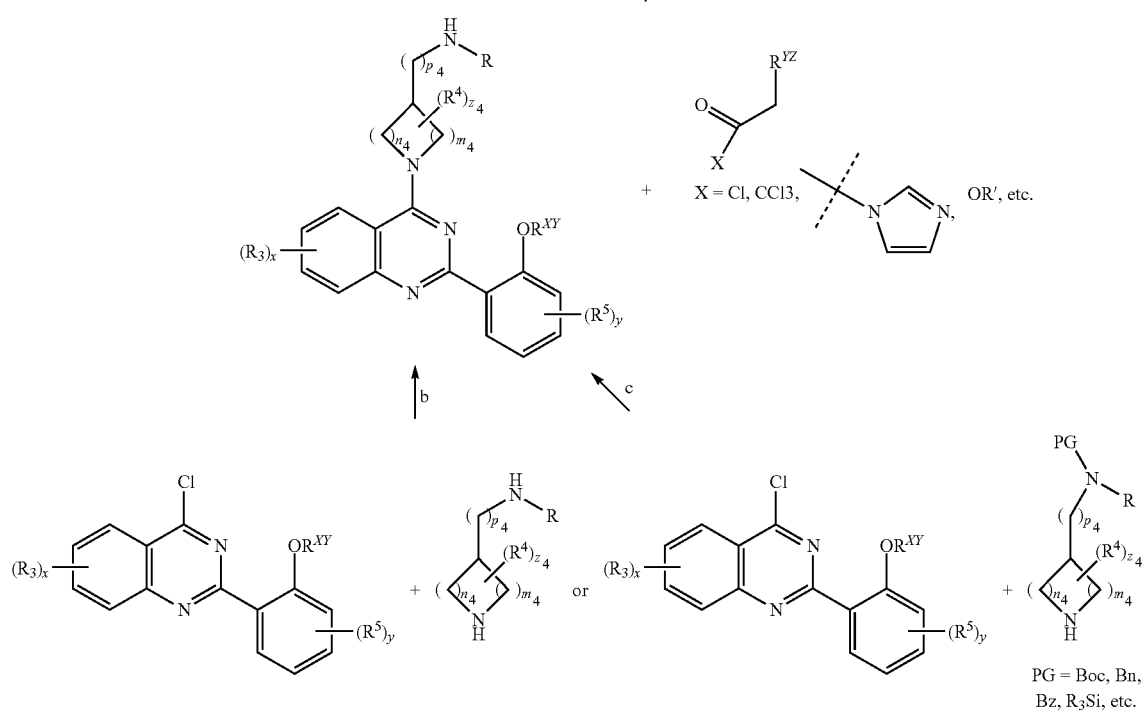

Conditions: a) DCM or THF, triethylamine, 0° C. to room temperature; b) DCM or THF, triethylamine, 0° C. to room temperature; c) i. DCM or THF, triethylamine, 0° C. to room temperature, ii. Deprotect: 1:1 TFA/DCM, rt, for Boc; H₂, Pd/C for Bn; NaOH for Bz, TBAF for R3Si, etc.; d) For X = Cl, CCl₃, imidazolyl, OR', etc., DCM or THF, triethylamine, rt or heat.

5. Uses, Formulation and Administration

WO 2004/078733 discloses a genus of sodium channel blockers that encompasses the compounds of the present invention. However, the compounds of the present invention exhibit unexpected properties set forth below that render them therapeutically more useful.

In one embodiment, certain compounds of the present invention are useful as improved inhibitors of sodium channels.

In another embodiment, certain compounds of the present invention possess improved selectivity in inhibiting one sodium channel, e.g., NaV 1.8, over one or more of the other sodium channels. Particularly useful are compounds that have a desirably low activity against NaV 1.2 or NaV 1.5.

In another embodiment, certain compounds of the present invention are improved inhibitors of NaV 1.8.

In another embodiment, certain compounds of the present invention have improved aqueous solubility, e.g., at physiologically relevant pH.

In yet another embodiment, certain compounds of the present invention have improved pharmacokinetic and/or pharmacodynamic properties and, therefore, are better suited for in-vivo administration for therapeutic purposes. Such properties include oral bioavailability, clearance kinetics, efficacy, etc.

In another embodiment, certain compounds of the present invention have desirably low activity against the hERG channel.

In another embodiment, certain compounds of the present invention have desirably low activity against the key isoforms of the cytochrome P450 enzyme family, including isozymes CYP3A4, CYP2C9, CYP1A2, CYP2C19, or CYP2D6.

In another embodiment, certain compounds of the present invention have desirably low activity against the CaV 1.2 channel and/or Kv 1.5.

Thus, in one embodiment of the present invention, the compounds have one or more of the following unexpected and therapeutically beneficial features: potent inhibition of NaV 1.8 channel, selectivity for one sodium channel, e.g., NaV 1.8 over one or more of the other sodium channels, improved aqueous solubility, improved pharmacokinetic and/or pharmacodynamic properties, desirably low activity against the hERG channel, desirably low activity against the key isoforms of the cytochrome P450 enzyme family, or desirably low activity against L-type CaV 1.2 and/or Kv1.5. The presence of such features, individually or in combination, renders the compounds more suitable for administration to humans to treat various diseases as set forth below.

The phrase "desirably low activity" as used herein means a level of activity of a compound against a target/enzyme that is low enough such that said activity would be considered advantageous (e.g., mitigating a risk factor), when evaluating the suitability of said compound for administration in humans.

The present compounds are useful for the treatment of diseases, disorders, and conditions including, but not limited to acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, and incontinence. Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

According to one embodiment, the compounds of the present invention are useful for treating a disease selected from femur cancer pain; non-malignant chronic bone pain; rheumatoid arthritis; osteoarthritis; spinal stenosis; neuropathic low back pain; neuropathic low back pain; myofascial pain syndrome; fibromyalgia; temporomandibular joint pain; chronic visceral pain, including, abdominal; pancreatic; IBS pain; chronic headache pain; migraine; tension headache, including, cluster headaches; chronic neuropathic pain, including, post-herpetic neuralgia; diabetic neuropathy; HIV-associated neuropathy; trigeminal neuralgia; Charcot-Marie Tooth neuropathy; hereditary sensory neuropathies; peripheral nerve injury; painful neuromas; ectopic proximal and distal discharges; radiculopathy; chemotherapy induced neuropathic pain; radiotherapy-induced neuropathic pain; post-mastectomy pain; central pain; spinal cord injury pain; post-stroke pain; thalamic pain; complex regional pain syndrome; phantom pain; intractable pain; acute pain, acute post-operative pain; acute musculoskeletal pain; joint pain; mechanical low back pain; neck pain; tendonitis; injury/exercise pain; acute visceral pain, including, abdominal pain; pyelonephritis; appendicitis; cholecystitis; intestinal obstruction; hernias; etc; chest pain, including, cardiac Pain; pelvic pain, renal colic pain, acute obstetric pain, including, labor pain; cesarean section pain; acute inflammatory, burn and trauma pain; acute intermittent pain, including, endometriosis; acute herpes zoster pain; sickle cell anemia; acute pancreatitis; breakthrough pain; orofacial pain, including, sinusitis pain, dental pain; multiple sclerosis (MS) pain; pain in depression; leprosy pain; Behcet's disease pain; adiposis dolorosa; phlebitic pain; Guillain-Barre pain; painful legs and moving toes; Haglund syndrome; erythromelalgia pain; Fabry's disease pain; bladder and urogenital disease, including, urinary incontinence; hyperactivity bladder; painful bladder syndrome; interstitial cystitis (IC); and prostatitis.

In another embodiment, the compounds of the present invention are useful in treating lower urinary tract disorders. See, e.g., International Patent Publication No. WO 2004/066990, the contents of which are incorporated herein by reference.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitory active metabolite or residue thereof. As used herein, the term "inhibitorily active metabolite or residue thereof" means that a metabolite or residue thereof is also an inhibitor of the targeted channel.

Pharmaceutically acceptable salts are well known in the art. For example, S. M. Berge, et al. describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

In yet another aspect, a method for the treatment or lessening the severity of acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, or cancer pain is provided comprising administering an effective amount of a compound, or a pharmaceutically acceptable composition comprising a compound to a subject in need thereof. In certain embodiments, a method for the treatment or lessening the severity of acute, chronic, neuropathic, or inflammatory pain is provided comprising administering an effective amount of a compound or a pharmaceutically acceptable composition to a subject in need thereof. In certain other embodiments, a method for the treatment or lessening the severity of radicular pain, sciatica, back pain, head pain, or neck pain is provided comprising administering an effective amount of a compound or a pharmaceutically acceptable composition to a subject in need thereof. In still other embodiments, a method for the treatment or lessening the severity of severe or intractable pain, acute pain, postsurgical pain, back pain, or cancer pain is provided comprising administering an effective amount of a compound or a pharmaceutically acceptable composition to a subject in need thereof.

In certain embodiments of the present invention an "effective amount" of the compound or pharmaceutically acceptable composition is that amount effective for treating or lessening the severity of one or more of acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, or cancer pain.

The compounds and compositions, according to the method of the present invention, may be administered using any amount and any route of administration effective for treating or lessening the severity of one or more of acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, or cancer pain. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsulated matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated". For example, exemplary additional therapeutic agents include, but are not limited to: nonopioid analgesics (indoles such as Etodolac, Indomethacin, Sulindac, Tolmetin; naphthylalkanones such as Nabumetone; oxicams such as Piroxicam; para-aminophenol derivatives, such as Acetaminophen; propionic acids such as Fenoprofen, Flurbiprofen, Ibuprofen, Ketoprofen, Naproxen, Naproxen sodium, Oxaprozin; salicylates such as Asprin, Choline magnesium trisalicylate, Diflunisal; fenamates such as meclofenamic acid, Mefenamic acid; and pyrazoles such as Phenylbutazone); or opioid (narcotic) agonists (such as Codeine, Fentanyl, Hydromorphone, Levorphanol, Meperidine, Methadone, Morphine, Oxycodone, Oxymorphone, Propoxyphene, Buprenorphine, Butorphanol, Dezocine, Nalbuphine, and Pentazocine). Additionally, nondrug analgesic approaches may be utilized in conjunction with administration of one or more compounds of the invention. For example, anesthesiologic (intraspinal infusion, neural blockade), neurosurgical (neurolysis of CNS pathways), neurostimulatory (transcutaneous electrical nerve stimulation, dorsal column stimulation), physiatric (physical therapy, orthotic devices, diathermy), or psychologic (cognitive methods-hypnosis, biofeedback, or behavioral methods) approaches may also be utilized. Additional appropriate therapeutic agents or approaches are described generally in The Merck Manual, Seventeenth Edition, Ed. Mark H. Beers and Robert Berkow, Merck Research Laboratories, 1999, and the Food and Drug Administration website, www.fda.gov, the entire contents of which are hereby incorporated by reference.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating an implantable medical device, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

Another aspect of the invention relates to inhibiting NaV1.8 activity in a biological sample or a patient, which method comprises administering to the patient, or contacting said biological sample with a compound of the present invention or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of NaV1.8 activity in a biological sample is useful for a variety of purposes that are known to one of skill in the art. Examples of such purposes include, but are not limited to, the study of sodium ion channels in biological and pathological phenomena; and the comparative evaluation of new sodium ion channel inhibitors.

In order that the invention described herein may be more fully understood, the following examples are set forth. It should be understood that these examples are for illustrative purposes only and are not to be construed as limiting this invention in any manner.

EXAMPLES

General LC/MS Methods

LC/MS data were acquired using a PESciex API-150-EX LC/MS, Shimadzu LC-8A pumps, Gilson 215 autosampler, Gilson 819 injection module, 3.0 mL/min flow rate, 10-99% $CH_3CN$ (0.035% TFA)/$H_2O$ (0.05% TFA) gradient, Phenom-

Example 101

(R)-2-Hydroxy-1-(4-(2-(2-hydroxyphenyl)-7-methylquinazolin-4-yl)piperazin-1-yl)-4,4-dimethylpentan-1-one

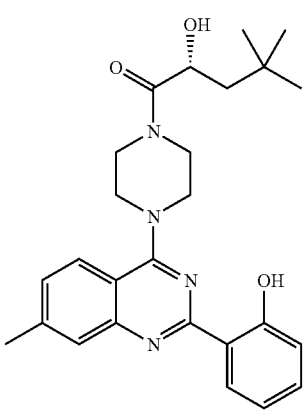

N-(2-Cyano-5-methyl-phenyl)-2-methoxy-benzamide

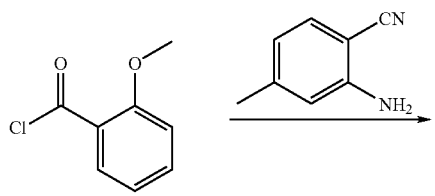

To a stirred solution of 4-methyl-2-aminobenzonitrile (100 g, 0.75 mol) in 800 mL CH$_2$Cl$_2$ was added triethylamine (77.4 g, 0.76 mol) and dimethylaminopyridine (4.62 g, 0.037 mol). The solution was cooled to 0-5° C., and o-anisoyl chloride (129 g, 0.75 mol) was added over 1 h while maintaining the reaction temperature at 0-5° C. The reaction was then stirred at 30-40° C. for 3 h. Water (400 mL) was added, and the mixture was stirred for 15 minutes. The organic layer was separated, and the aqueous solution was extracted with CH$_2$Cl$_2$ (600 mL). The combined organic layers were dried over sodium sulfate, filtered, and concentrated in vacuo to yield a solid residue, to which 800 mL hexane were added. The slurry was stirred and filtered to give N-(2-cyano-5-methyl-phenyl)-2-methoxy-benzamide as a yellow powder (180 g, 90%). mp 147-149° C. $^1$H NMR (CDCl$_3$) δ 2.429 (s, 3H), 4.2 (s, 3H), 6.8-7.2 (m, 3H), 7.4-7.6 (m, 2H), 8.2-8.4 (d, 1H), 8.6 (s, 1H), 10.8 (bs, 1H); M/z (obs., [m+H]$^+$)=268.

2-(2-Methoxyphenyl)-7-methyl-3H-quinazolin-4-one

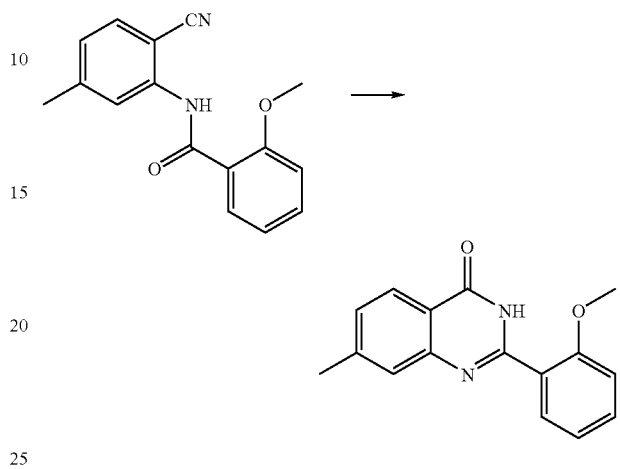

To a mechanically stirred suspension of N-(2-cyano-5-methylphenyl)-2-methoxybenzamide (180 g, 0.67 mol) in 1.8 L ethanol under an N$_2$ atmosphere was added 6 N sodium hydroxide solution (310 g in 1.25 L water). To the above mixture, 30% hydrogen peroxide (350 mL, 3.64 mol) was slowly added. The solution was then slowly heated to 80° C. and maintained at this temperature for 4 h. The reaction mixture was concentrated under reduced pressure to remove ethanol, giving a suspension, which was quenched with ice-cold water (1.8 L) and acidified with acetic acid to pH 5-6 to give a solid residue. The solid was filtered and washed with water, then dissolved in 5.5 L CH$_2$Cl$_2$ and washed with water (2×18 L). The organic layer was dried over sodium sulfate, and the solvent was removed under reduced pressure to give a light yellow solid (100 g, 54%). mp 165-170° C.

4-Chloro-2-(2-methoxy-phenyl)-7-methyl-quinazoline

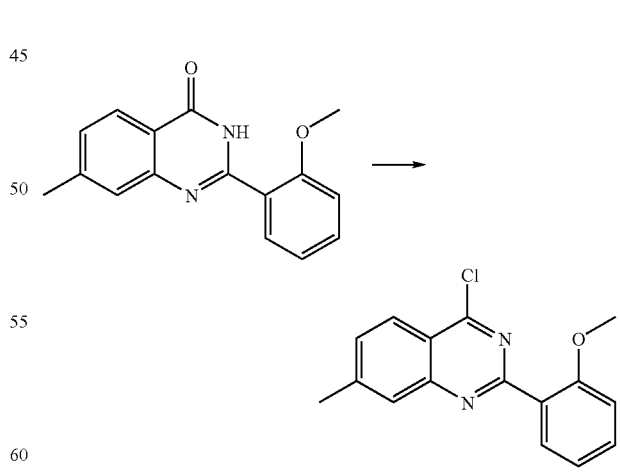

To a mechanically stirred suspension of 2-(2-methoxyphenyl)-7-methyl-3H-quinazolin-4-one (100 g, 0.37 mol) in 1 L toluene was added diisopropyl ethylamine (100 mL), followed by phosphorus oxychloride (69 g, 0.45 mol). The reaction was then heated to 80° C. for 4 h. The reaction mixture was distilled under reduced pressure to remove toluene, and the resulting residue was dissolved in 2.2 L $CH_2Cl_2$. Ice water was added, and the pH was adjusted to 8-9 with saturated aqueous sodium bicarbonate solution while maintaining the temperature below 20° C. The resulting organic layer was separated and the aqueous solution extracted with $CH_2Cl_2$, then the combined the organic layers were dried over sodium sulfate and distilled under reduced pressure. The crude product was dissolved 2:1 $CH_2Cl_2$/hexane, and the solution was passed through silica gel (2.5 kg, 60-120 mesh), followed by washing the silica bed with 2:1 $CH_2Cl_2$/hexane until the product eluted. The pure fractions were collected and combined, and the solvent was removed under reduced pressure. Hexane (500 mL) was added, and the mixture was stirred and filtered to give 4-chloro-2-(2-methoxy-phenyl)-7-methyl-quinazoline as a white to off-white solid (77 g, 72%). mp 161-164° C. $^1$H NMR ($CDCl_3$) δ 2.6 (s, 3H), 3.9 (s, 3H), 6.9-7.2 (m, 2H), 7.4-7.6 (m, 2H), 7.7-8 (d, 2H), 8.2 (d, 1H) ppm; $^{13}$C NMR ($CDCl_3$) δ 22.23, 56.06, 112.2, 120.26, 120.69, 125.34, 127.94, 130.45, 131.08, 131.08. M/z (obs., [m+H]$^+$)=285.

2-(7-Methyl-4-piperazin-1-yl-quinazolin-2-yl)-phenol

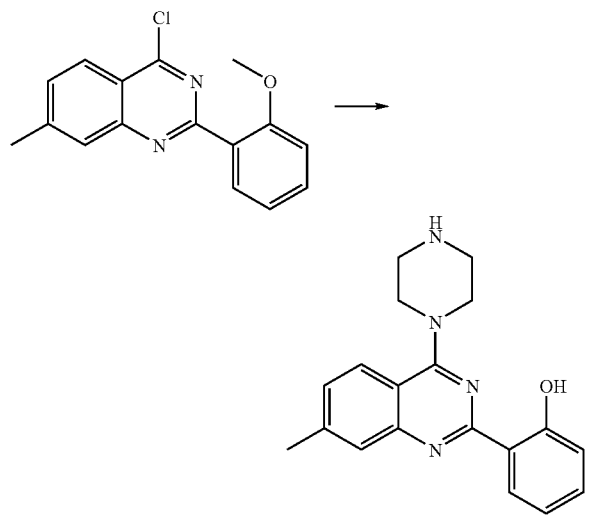

A stirring solution of 4-chloro-2-(2-methoxyphenyl)-7-methylquinazoline (91 g, 320 mmol) and $CH_2Cl_2$ (2.0 L) under an $N_2$ atmosphere was cooled to −30° C. Boron tribromide (957 mL, 957 mmol, 1.0 M in $CH_2Cl_2$) was added dropwise over a period of 30 minutes at −30 to −40° C. The cooling bath was removed, and the mixture was allowed to warm to 25° C. The mixture was carefully poured into a stirring solution of saturated aqueous $NaHCO_3$ (4.0 L). The organic portion was separated, dried over $MgSO_4$, and evaporated to dryness. The resulting solid was suspended in $CH_2Cl_2$ (400 mL) under an $N_2$ atmosphere, followed by the addition of triethylamine (64.8 g, 640 mmol). The solution was cooled to −10° C. A solution of piperazine (55.0 g, 640 mmol) in $CH_2Cl_2$ (400 mL) was added in a single portion, and the solution was stirred at ambient temperature for 1 hour. The solution temperature rose to 23° C. upon addition of the piperazine. The solution was partitioned between $CH_2Cl_2$ and $H_2O$. The organic portion was dried over $MgSO_4$ and evaporated to dryness. The residue was purified via silica gel chromatography using 5% MeOH in $CH_2Cl_2$ to obtain a tan solid. The resulting solid was triturated with 1:1 $Et_2O$/hexanes to obtain a yellow solid which was vacuum dried to give 2-(7-methyl-4-piperazin-1-yl-quinazolin-2-yl)-phenol as a light yellow solid (93.0 g, 290 mmol, 91%). LC/MS: m/z 321.1 (M+H)$^+$ at 2.34 min (10%-99% $CH_3CN$ (0.035% TFA)/$H_2O$ (0.05% TFA)).

(R)-2-Hydroxy-1-(4-(2-(2-hydroxyphenyl)-7-methylquinazolin-4-yl)piperazin-1-yl)-4,4-dimethylpentan-1-one

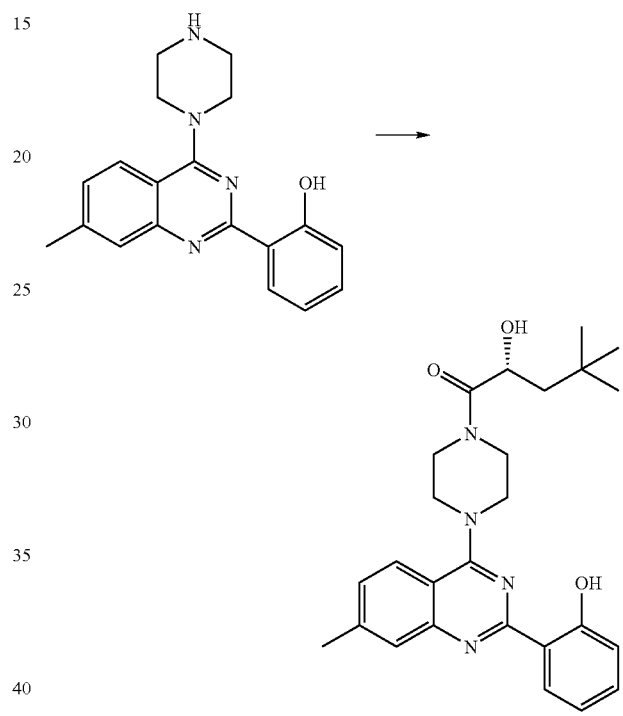

Method A 2-(7-Methyl-4-(piperazin-1-yl)quinazolin-2-yl)phenol (50 mg, 0.16 mmol) was placed in a tube charged with a stir bar followed by (R)-2-hydroxy-4,4-dimethylpentanoic acid in 1 ml of DMF and triethylamine (31.57 mg, 0.312 mmol), and the reaction was cooled to 0° C. HATU (71 mg, 0.187 mmol) was then added, and the reaction was allowed to stir at 0° C. for 10 minutes and then allowed to warm to room temperature. The reaction was complete after 40 minutes, filtered, and purified by reverse phase HPLC to give the TFA salt of (R)-2-hydroxy-1-(4-(2-(2-hydroxyphenyl)-7-methylquinazolin-4-yl)piperazin-1-yl)-4,4-dimethylpentan-1-one. LC/MS: m/z 449.3 (M+H)$^+$ at 2.75 min (10%-99% $CH_3CN$ (0.035% TFA)/$H_2O$ (0.05% TFA)).

Method B 2-(7-Methyl-4-(piperazin-1-yl)quinazolin-2-yl)phenol (250 mg, 0.74 mmol) was suspended in anhydrous DMF (5 mL) and cooled to 0° C. internal temperature. Under an $N_2$ atmosphere, (R)-2-hydroxy-4,4-dimethylpentanoic acid (125.4 mg, 0.858 mmol) was added followed by triethylamine (0.218 mL, 1.56 mmol). To this stirring solution was added HATU (356 mg, 0.936 mmol). After the complete addition of HATU, the mixture was allowed to warm to 10° C. After 45 min the reaction was complete, and it was quenched with an equal portion of ice water. A yellow precipitate formed which was collected by vacuum filtration and dissolved in CH₂Cl₂. This solution was desiccated with Na₂SO₄, filtered, and concentrated to give a viscous yellow-orange oil. The crude material was purified via silica gel chromatography using 88% CH₂Cl₂-hexanes (1:1) and 12% EtOAc to afford (R)-2-hydroxy-1-(4-(2-(2-hydroxyphenyl)-7-methylquinazolin-4-yl)piperazin-1-yl)-4,4-dimethylpentan-1-one as a faint yellow foam (265 mg, 76%). LC/MS: m/z 449.3 (M+H)⁺ at 2.75 min (10%-99% CH₃CN (0.035% TFA)/H₂O (0.05% TFA)). ¹H NMR (400 MHz, DMSO-d6) δ 8.46 (dd, J=8.2, 1.8 Hz, 1H), 8.02 (d, J=8.5 Hz, 1H), 7.70 (s, 1H), 7.41-7.37 (m, 2H), 6.97-6.93 (m, 2H), 4.89 (d, J=7.2 Hz, 1H), 4.49-4.44 (m, 1H), 4.06-3.67 (m, 8), 2.52 (s, 3H), 1.56 (dd, J=14.3, 3.0 Hz, 1H), 1.42 (dd, J=14.3, 8.8 Hz, 1H), 0.97 (s, 9H) ppm.

(R)-2-Hydroxy-1-(4-(2-(2-hydroxyphenyl)-7-methylquinazolin-4-yl)piperazin-1-yl)-4,4-dimethylpentan-1-one hydrochloride

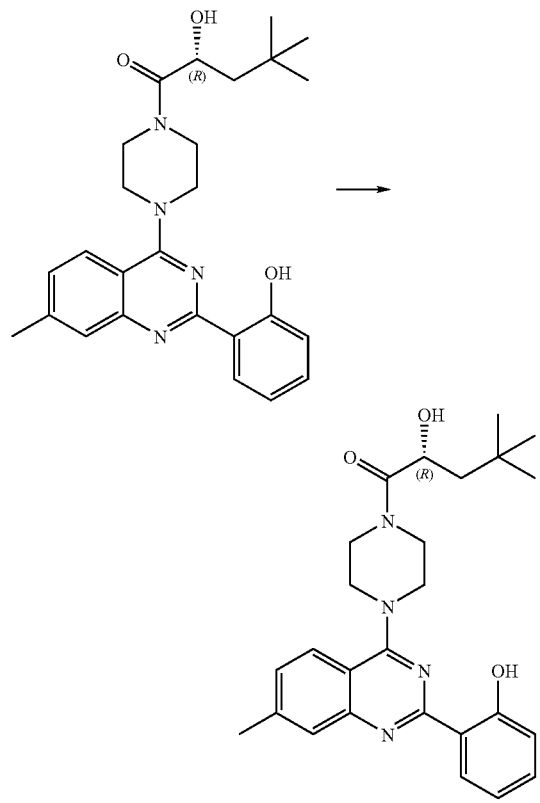

(R)-2-Hydroxy-1-(4-(2-(2-hydroxyphenyl)-7-methylquinazolin-4-yl)piperazin-1-yl)-4,4-dimethylpentan-1-one (265 mg, 0.367 mmol) was dissolved in anhydrous CH₂Cl₂ (3 mL) followed by the addition of Et₂O (6 mL) under an N₂ atmosphere. A 2.0 M HCl solution in Et₂O (0.296 mL, 0.591 mmol) was added over a 1 minute period. The reaction solution changed from a clear yellow solution to a creamy off white slurry. After complete addition of the HCl solution, the reaction was allowed to stir for an additional 10 minutes. The product was collected by vacuum filtration, washed with 3 mL of Et₂O and dried under vacuum to obtain (R)-2-hydroxy-1-(4-(2-(2-hydroxyphenyl)-7-methylquinazolin-4-yl)piperazin-1-yl)-4,4-dimethylpentan-1-one hydrochloride as a white solid (261 mg, 91%). LC/MS: m/z 449.3 (M+H)⁺ at 2.79 min (10%-99% CH₃CN (0.035% TFA)/H₂O (0.05% TFA)). ¹H NMR (400 MHz, DMSO-d6) δ 8.33 (d, J=7.6 Hz, 1H), 8.07 (d, J=8.6 Hz, 1H), 7.75 (s, 1H), 7.47-7.43 (m, 2H), 7.04-6.98 (m, 2H), 4.47-4.44 (m, 1H), 4.13-4.04 (m, 4H), 3.91-3.68 (m, 4H), 2.54 (s, 3H), 1.57 (dd, J=14.3, 3.1 Hz, 1H), 1.42 (dd, J=14.3, 8.8 Hz, 1H), 0.97 (s, 9H) ppm.

Example 102

(R)-2-Hydroxy-1-(4-(2-(2-hydroxyphenyl)quinazolin-4-yl)piperazin-1-yl)-4-methylpentan-1-one

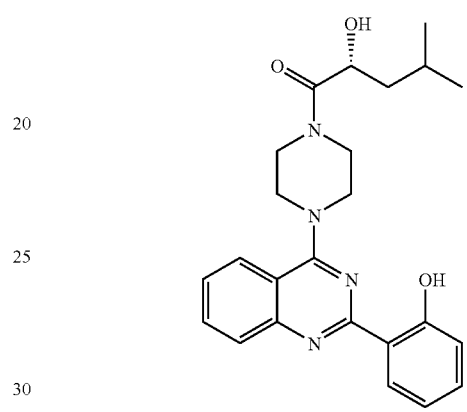

2-(2-Methoxyphenyl)quinazolin-4(3H)-one

Method A

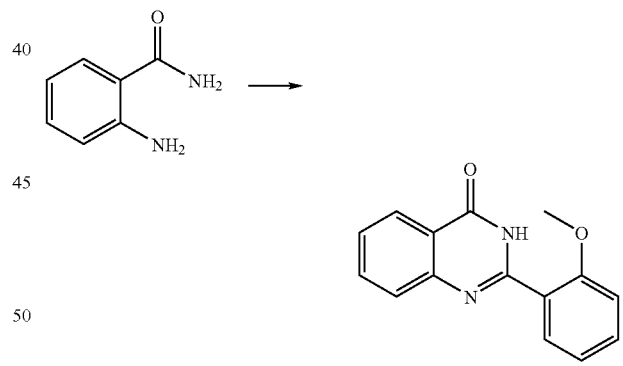

To a cooled (0-5° C.) mixture of anthranilamide (350 g, 2.57 mol) and triethylamine (286 g, 2.83 mol) in THF (2.5 L) was added dropwise o-anisoyl chloride (437 g, 2.57 mol) while maintaining the temperature between 0-20° C. The resulting suspension was stirred at room temperature overnight. The solvent was evaporated in vacuo, and the residue was washed several times with water. The wet residue was suspended in 2 M aq. NaOH (13 L), and the mixture was heated to reflux. After 20 minutes a clear solution was obtained. After 1 h of reflux the clear solution was cooled in an ice water bath and then acidified to pH 6 with conc. aq. HCl. The suspension was filtered, and the residue was washed thoroughly with water. The white solid was dried by azeotropic distillation with toluene. 2-(2-Methoxyphenyl)quinazolin-4(3H)-one (567 g) was obtained in 82%. ¹H-NMR (200 MHz, Me₂SO-d₆): δ 3.90 (s, 3 H), 7.20 (m, 2 H), 7.60 (t, 2 H), 7.85 (m, 3 H), 8.20 (d, 1 H), 12.20 (s, 1 H).

Method B

In a 2 L three-necked round-bottomed flask equipped with an overhead stirrer and reflux condenser, anthranilamide (20.0 g, 147 mmol) and potassium carbonate (28.4 g, 206 mmol) were suspended in 1 L dry ether and heated to reflux. o-Anisoyl chloride (32.5 g, 191 mmol) was added slowly to the refluxing mixture. After 3 hours at reflux, the reaction mixture was allowed to cool to room temperature, the ether was removed under reduced pressure, and the resulting residue was filtered and washed with water. The resulting solid was then suspended in 600 mL of 5% aq. NaOH solution and boiled for one hour. The reaction was allowed to cool to room temperature, and it was neutralized with acetic acid, upon which 2-(2-methoxyphenyl)quinazolin-4(3H)-one was precipitated. The product was collected by filtration, washed with water, and dried overnight in vacuo to yield 27 g (73%) of pure 2-(2-methoxyphenyl)quinazolin-4(3H)-one. LC/MS: m/z 253.0 (M+H)⁺ at 3.22 min (10%-99% CH₃CN (0.035% TFA)/H₂O (0.05% TFA)). ¹H NMR (DMSO) 63.86 (s, 3H), δ 7.09 (t, 1H), δ 7.18 (d, 1H), δ 7.53 (m, 2H), δ 7.70 (m, 2H), δ 7.80 (m, 1H), δ 8.14 (d, 1H), δ 12.11 (s, 1H) ppm; ¹³C NMR (DMSO) δ 55.75, δ 111.86, δ 120.89, δ 120.97, δ 122.74, δ 125.75, δ 126.45, δ 127.26, δ 130.41, δ 132.13, δ 134.32, δ 148.97, δ 152.48, δ157.12, δ 161.35.

4-Chloro-2-2-(2-methoxyphenyl)quinazoline

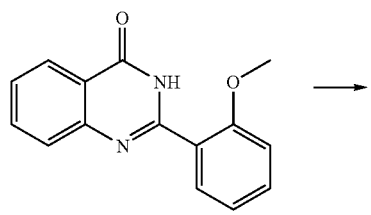

A suspension of 2-(2-methoxyphenyl)quinazolin-4(3H)-one (567 g, 2.1 mol) in phosphoryl chloride (2 L, 21 mol) and a catalytic amount of N,N-dimethyl aniline was brought to reflux. The reaction started immediately with the evolution of gas (HCl) upon the addition of N,N-dimethyl aniline. After the production of gas had ceased the mixture was cooled to room temperature. The excess POCl₃ was evaporated. The resulting dark solution was cooled to room temperature and slowly poured on ice and water, while maintaining the temperature below 5° C. The cold suspension was extracted with dichloromethane. The extract was dried over sodium sulfate and filtered, and the solvent was removed in vacuo. The crude material was purified by column chromatography (silica gel, CH₂Cl₂). Yield: 189 g (33%) of 4-chloro-2-(2-methoxyphenyl) quinazoline. ¹H-NMR (300 MHz, Me₂SO-d₆): δ 3.85 (s, 3 H), 7.15 (t, 1 H), 7.25 (d, 1 H), 7.60 (t, 2 H), 7.70 (d, 1 H), 7.8 (d, 1 H), 7.9 (t, 1 H), 8.2 (d, 1 H).

2-(4-Chloroquinazolin-2-yl)phenol

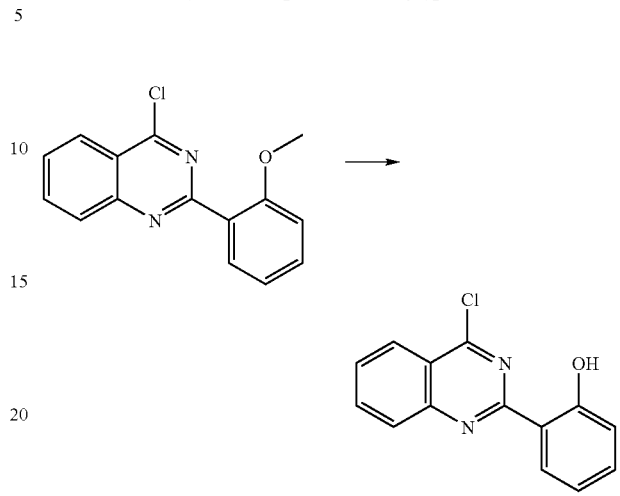

To a solution of 4-chloro-2-(2-methoxyphenyl)quinazoline (1.0 g, 3.7 mmol) in 40 mL CH₂Cl₂ at −78° C. was added 5 equivalents of 1 M BBr₃ dropwise. After complete addition the cooling bath was removed and the reaction was quenched with NaHCO₃ after 90 minutes. The product was extracted twice with CH₂Cl₂, dried over Na₂SO₄, filtered, and concentrated. Purification via silica gel chromatography using 60:40 CH₂Cl₂: hexanes gave 2-(4-chloroquinazolin-2-yl)phenol (700 mg, 74%). LC/MS: m/z 257.1 (M+H)⁺ at 3.75 min (10%-99% CH₃CN (0.035% TFA)/H₂O (0.05% TFA)). ¹H NMR (400 MHz, DMSO-d6) δ 8.44 (m, 1H), 8.24 (m, 3H), 7.89 (m, 1H), 7.49 (m, 1H), 7.05 (m, 2H) ppm.

2-(4-(piperazin-1-yl)quinazolin-2-yl)phenol

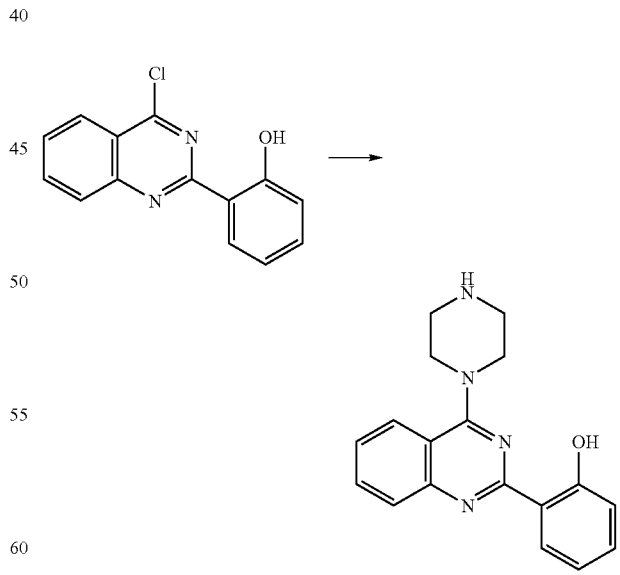

To a solution of 2-(4-chloroquinazolin-2-yl)phenol (2.0 g, 7.8 mmol) in CH₂Cl₂ at 0° C. was rapidly added a solution of piperazine (2.01 g, 23.4 mmol) and triethylamine (2.17 mL, 15.6 mmol) in 10 mL CH₂Cl₂. The reaction was warmed to room temperature and stirred for 5 hours. The reaction was quenched with 25 mL of water and extracted with (3×15) mL of $CH_2Cl_2$. The organic layer was dried over $Na_2SO_4$, filtered, and concentrated to afford 2-(4-(piperazin-1-yl)quinazolin-2-yl)phenol (1.98 g, 83%). LC/MS: m/z 307.3 (M+H)$^+$ at 1.47 min (10%-99% $CH_3CN$ (0.035% TFA)/$H_2O$ (0.05% TFA)). $^1$H NMR (400 MHz, DMSO-d6) δ 8.43 (d, J=10.1 Hz, 1H), 8.04 (d, J=8.3 Hz, 1H), 7.85 (m, 2H), 7.53 (m, 1H), 7.38 (m, 1H), 6.95 (m, 2H), 3.85 (t, J=4.8 Hz, 4H), 2.94 (t, J=4.8 Hz, 4H) ppm.

(R)-2-Hydroxy-1-(4-(2-(2-hydroxyphenyl)quinazolin-4-yl)piperazin-1-yl)-4-methylpentan-1-one

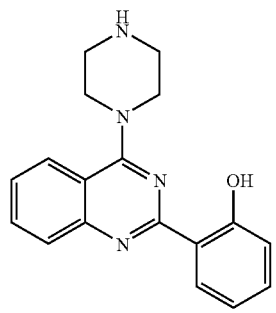

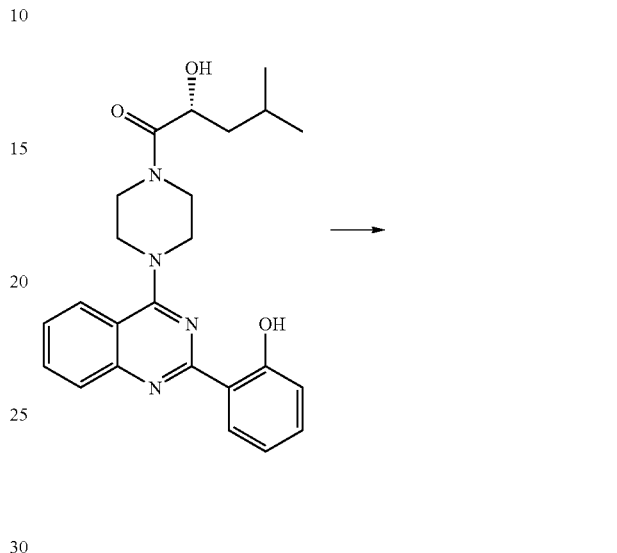

(R)-2-Hydroxy-1-(4-(2-(2-hydroxyphenyl)quinazolin-4-yl)piperazin-1-yl)-4-methylpentan-1-one hydrochloride

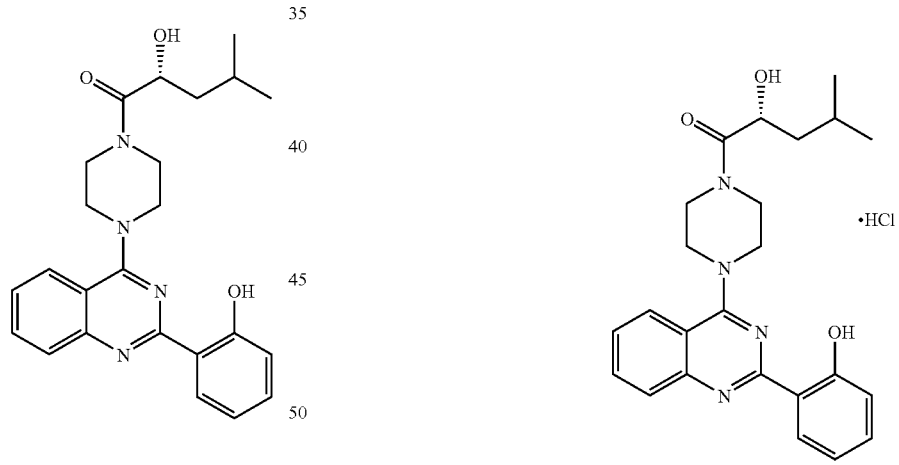

To a solution of 2-(4-(piperazin-1-yl)quinazolin-2-yl)phenol (250 mg, 0.82 mmol) in $CH_2Cl_2$ (6 mL) was added triethylamine (227 μL, 1.63 mmol) followed by the addition of (R)-2-hydroxy-4-methylpentanoic acid (140 mg, 1.06 mmol) and HATU (403 mg, 1.06 mmol). The reaction mixture was stirred at room temperature for 3 h and then quenched with $H_2O$. The aqueous layer was extracted twice with $CH_2Cl_2$, dried over $MgSO_4$, filtered, and concentrated. Purification via silica gel chromatography using 0-10% EtOAc in 50:50 $CH_2Cl_2$:hexanes gave (R)-2-hydroxy-1-(4-(2-(2-hydroxyphenyl)quinazolin-4-yl)piperazin-1-yl)-4-methylpentan-1-one (265 mg, 77%). LC/MS: m/z 421.30 (M+H)$^+$ at 2.57 min (10%-99% $CH_3CN$ (0.035% TFA)/$H_2O$ (0.05% TFA)). $^1$H NMR (400 MHz, DMSO-d6) δ 8.47 (dd, J=8.3, 1.7 Hz, 1H), 8.12 (d, J=8.3 Hz, 1H) 7.88 (m, 2H), 7.57 (m, 1H), 7.40 (m, 1H), 6.96 (m, 2H), 4.92 (d, J=7.2 Hz, 1H), 4.39 (m, 1H), 3.95 (m, 4H), 3.76 (m, 4H), 1.80 (m, 1H), 1.43 (m, 2H), 0.92 (q, J=3.8 Hz, 6H).

To a solution of (R)-2-hydroxy-1-(4-(2-(2-hydroxyphenyl)quinazolin-4-yl)piperazin-1-yl)-4-methylpentan-1-one (265 mg, 0.63 mmol) in $CH_2Cl_2$ (3 mL) under inert atmosphere was added 10 mL of ether followed by the dropwise addition of 2 M HCl (0.315 mL, 0.63 mmol). The reaction was stirred for 30 min before the formed precipitate was filtered to afford (R)-2-hydroxy-1-(4-(2-(2-hydroxyphenyl)quinazolin-4-yl)piperazin-1-yl)-4-methylpentan-1-one hydrochloride (261 mg, 91%). LC/MS: m/z 421.3 (M+H)$^+$ at 2.60 min (10%-99% $CH_3CN$ (0.035% TFA)/$H_2O$ (0.05% TFA)). $^1$H NMR (400 MHz, DMSO-d6) δ 8.28 (dd, J=7.9, 1.6 Hz, 1H), 8.19 (d, J=8.4 Hz, 1H), 7.96 (d, J=3.9 Hz, 2H), 7.65 (m, 1H), 7.48 (m, 1H), 7.04 (m, 2H), 4.37 (m, 1H), 4.10 (m, 4H), 3.80 (m, 4H), 1.77 (m, 1H), 1.41 (m, 2H), 0.91 (dd, J=6.6, 3.1 Hz, 6H) ppm.

Example 103

(Benzo[d][1,3]dioxol-7-yl)methyl 4-(2-(2-hydroxyphenyl)-7-methylquinazolin-4-yl)piperazine-1-carboxylate

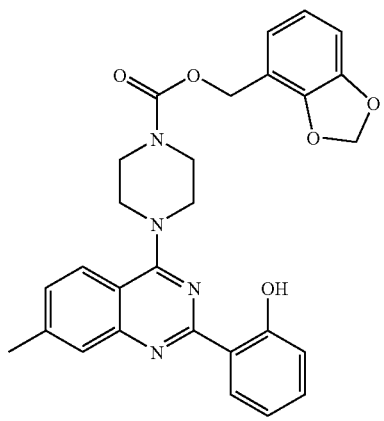

(Benzo[d][1,3]dioxol-7-yl)methyl 1H-imidazole-1-carboxylate

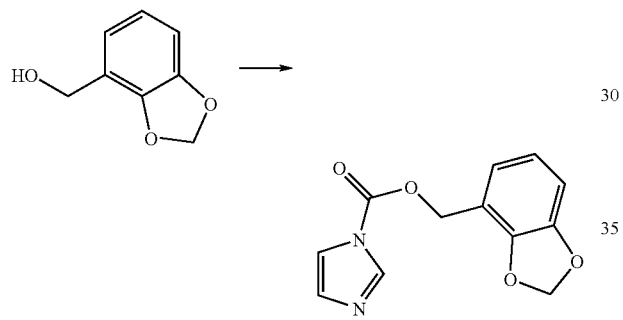

A solution of (benzo[d][1,3]dioxol-7-yl)methanol (2 g, 13.14 mmol) and di(1H-imidazol-1-yl)methanone (4.26 g, 26.28 mmol) in 20 mL $CH_2Cl_2$ was heated overnight at 50° C. The reaction was quenched with water, extracted with $CH_2Cl_2$, dried over $Na_2SO_4$, filtered, and concentrated. Purification via silica gel chromatography using 10-70% EtOAc in $CH_2Cl_2$ gave (benzo[d][1,3]dioxol-7-yl)methyl 1H-imidazole-1-carboxylate (2.8 g, 86%).

(Benzo[d][1,3]dioxol-7-yl)methyl 4-(2-(2-hydroxyphenyl)-7-methylquinazolin-4-yl)piperazine-1-carboxylate

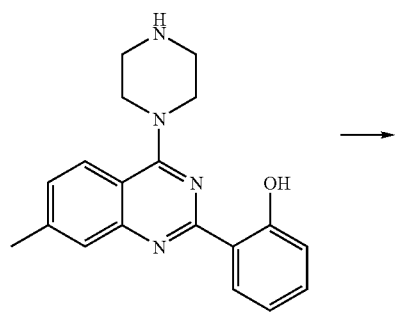

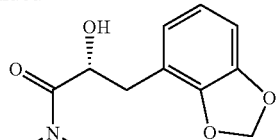

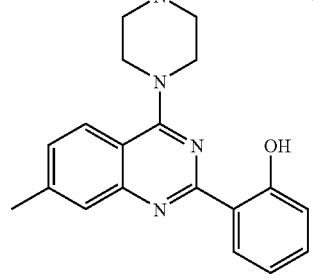

A solution of 2-(7-methyl-4-(piperazin-1-yl)quinazolin-2-yl)phenol (50 mg, 0.16 mmol), (benzo[d][1,3]dioxol-7-yl)methyl 1H-imidazole-1-carboxylate (78 mg, 0.32 mmol) and triethylamine (44.6 µL, 0.32 mmol) in DMSO (500 µL) was heated in a microwave synthesizer at 200° C. for 10 minutes. Purification using reverse phase HPLC (10%-99% $CH_3CN$ (0.035% TFA)/$H_2O$ (0.05% TFA)) gave (benzo[d][1,3]dioxol-7-yl)methyl 4-(2-(2-hydroxyphenyl)-7-methylquinazolin-4-yl)piperazine-1-carboxylate as the TFA salt. LC/MS: m/z 499.3 (M+H)⁺ at 2.97 min (10%-99% $CH_3CN$ (0.035% TFA)/$H_2O$ (0.05% TFA)).

Example 104

(R)-3-Hydroxy-4-(4-(2-(2-hydroxyphenyl)-7-methylquinazolin-4-yl)piperazin-1-yl)-N,N-dimethyl-4-oxobutanamide

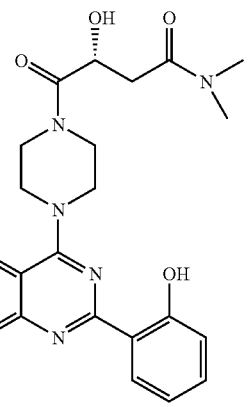

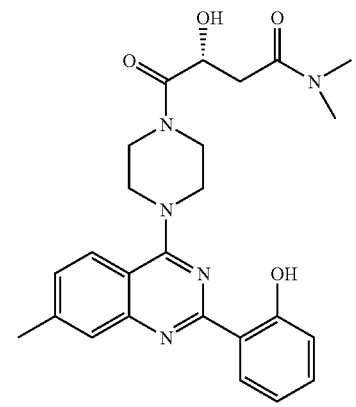

(R)-3-(Methoxycarbonyl)-2-hydroxypropanoic acid

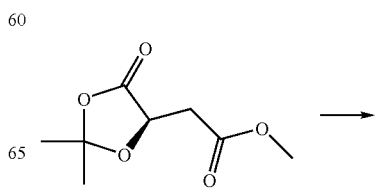

-continued

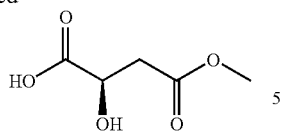

Methyl 2-((R)-2,2-dimethyl-5-oxo-1,3-dioxolan-4-yl)acetate (17.1 g, 90.9 mmol) was stirred in a 1:1 mixture of THF: 1 M HCl (200 mL) for 1 h at room temperature. After addition of NaCl to nearly saturate the aqueous layer, the mixture was extracted with EtOAc, and the extracts were dried over Na$_2$SO$_4$ and concentrated to obtain (R)-3-(methoxycarbonyl)-2-hydroxypropanoic acid as an oil. $^1$H NMR (400 MHz, CDCl$_3$) δ 4.58-4.55 (m, 1H), 3.75 (s, 3H), 2.98-2.84 (m, 2H) ppm.

4-((R)-2-Hydroxy-3-methoxycarbonyl-propionyl)-piperazine-1-carboxylic acid benzyl ester

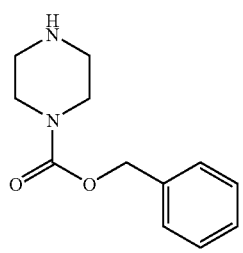
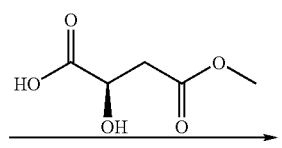

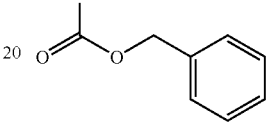

EDCI (3.6 g, 19 mmol) was added to a solution of (R)-3-(methoxycarbonyl)-2-hydroxypropanoic acid (2.8 g, 19 mmol) and HOBt (2.6 g, 19 mmol) in DMF (200 mL). After stirring this mixture for 5 min, benzyl piperazine-1-carboxylate (4.2 g, 3.6 mL, 19 mmol) and triethylamine (2.6 mL, 19 mmol) were added and stirred for 3 days at room temperature. The reaction mixture was poured into water and extracted with EtOAc. After washing the organic layers with brine and water, drying over Na$_2$SO$_4$ and concentrating, purification via silica gel chromatography using 0-10% MeOH/CH$_2$Cl$_2$ gave 4-((R)-2-hydroxy-3-methoxycarbonyl-propionyl)-piperazine-1-carboxylic acid benzyl ester as an oil (2.19 g, 33%). $^1$H NMR (400 MHz, CDCl$_3$) δ 7.40-7.31 (m, 5H), 5.15 (s, 2H), 4.79-4.74 (m, 1H), 3.95 (d, J=8.0 Hz, 1H), 3.79-3.74 (m, 1H), 3.74 (s, 3H), 3.71-3.44 (m, 7H), 2.62 (d, J=5.8 Hz, 2H) ppm.

(R)-Methyl 3-hydroxy-4-(4-(2-(2-hydroxyphenyl)-7-methylquinazolin-4-yl)piperazin-1-yl)-4-oxobutanoate

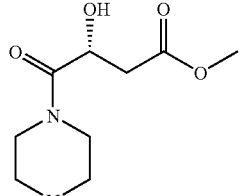

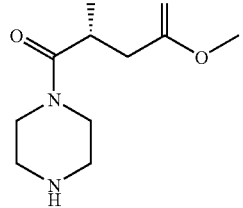

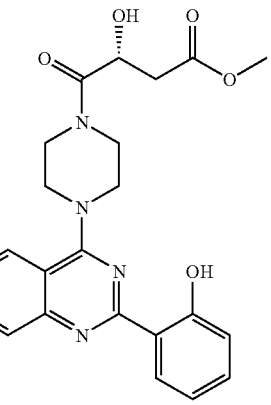

4-((R)-2-Hydroxy-3-methoxycarbonyl-propionyl)-piperazine-1-carboxylic acid benzyl ester (0.52 g, 1.5 mmol) and MeOH (15 mL) were stirred with 10% Pd/C under an H$_2$ atmosphere at ambient pressure overnight. After filtration and evaporation of the solvent the residue was taken up in CH$_2$Cl$_2$, and 2-(4-chloro-7-methylquinazolin-2-yl)phenol (0.40 g, 1.50 mmol) plus triethylamine (0.41 mL, 3.00 mmol) were added. The reaction mixture was stirred at room temperature overnight, washed with water, dried over Na$_2$SO$_4$, and concentrated. Purification via silica gel chromatography using 0-10% MeOH/CH$_2$Cl$_2$ provided (R)-methyl 3-hydroxy-4-(4-(2-(2-hydroxyphenyl)-7-methylquinazolin-4-yl)piperazin-1-yl)-4-oxobutanoate (0.38 g, 57%). LC/MS: m/z 451.1 (M+H)$^+$ at 2.18 min (10%-99% CH$_3$CN (0.035% TFA)/H$_2$O (0.05% TFA)).

159

(R)-3-Hydroxy-4-{4-[2-(2-hydroxy-phenyl)-7-methyl-quinazolin-4-yl]-piperazin-1-yl}-4-oxo-butyric acid

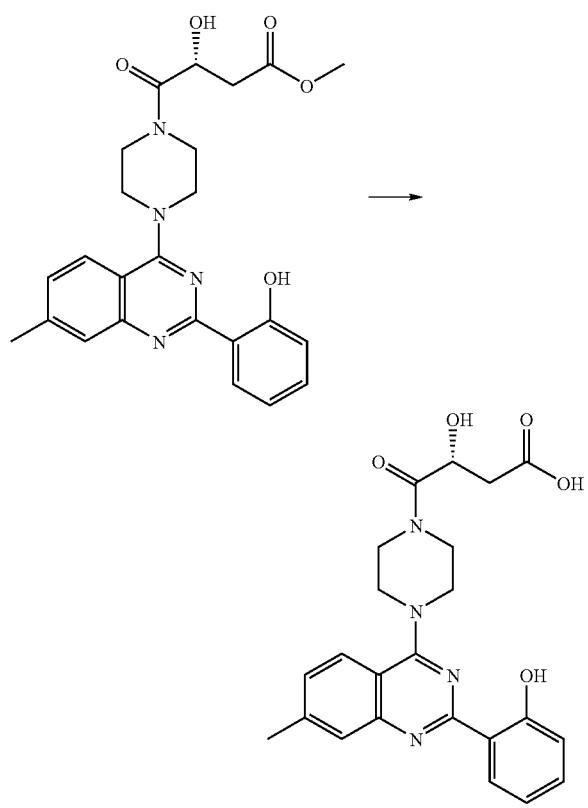

LiOH.H₂O (19.8 mg, 0.47 mmol) was added to a solution of (R)-3-hydroxy-4-{4-[2-(2-hydroxy-phenyl)-7-methyl-quinazolin-4-yl]-piperazin-1-yl}-4-oxo-butyric acid methyl ester (71 mg, 0.16 mmol) in 2 mL THF:H₂O (1:1) and stirred at room temperature for 3 h. The reaction mixture was acidified with 1 M HCl and then extracted with EtOAc. After drying the organic layer over Na₂SO₄, it was concentrated and then purified via silica gel chromatography using 0-15% MeOH/CH₂Cl₂ to provide (R)-3-hydroxy-4-{4-[2-(2-hydroxy-phenyl)-7-methyl-quinazolin-4-yl]-piperazin-1-yl}-4-oxo-butyric acid (52 mg, 75%). LC/MS: m/z 437.3 (M+H)⁺ at 2.04 min (10%-99% CH₃CN (0.035% TFA)/H₂O (0.05% TFA)).

(R)-3-Hydroxy-4-(4-(2-(2-hydroxyphenyl)-7-methylquinazolin-4-yl)piperazin-1-yl)-N,N-dimethyl-4-oxobutanamide

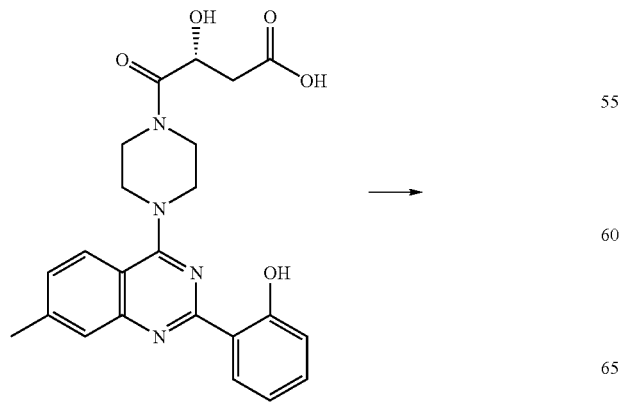

160

-continued

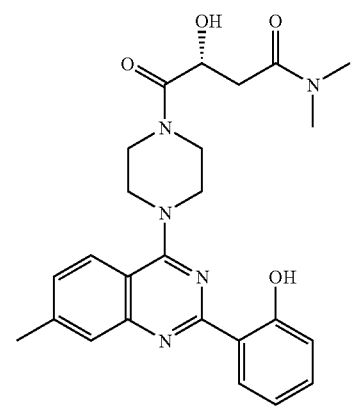

(R)-3-Hydroxy-4-{4-[2-(2-hydroxy-phenyl)-7-methyl-quinazolin-4-yl]-piperazin-1-yl}-4-oxo-butyric acid (17 mg, 0.039 mmol) and HATU (16 mg, 0.043 mmol) were stirred in DMF (0.5 mL). After adding dimethylamine (2 M in THF, 0.10 mL, 0.19 mmol), the reaction mixture was stirred at room temperature for 5 h. Purification via preparative reverse-phase HPLC (10%-99% CH₃CN (0.035% TFA)/H₂O (0.05% TFA)) gave (R)-3-hydroxy-4-(4-(2-(2-hydroxyphenyl)-7-methylquinazolin-4-yl)piperazin-1-yl)-N,N-dimethyl-4-oxobutanamide as the TFA salt. LC/MS: m/z 436.3 (M+H)⁺ at 1.94 min (10%-99% CH₃CN (0.035% TFA)/H₂O (0.05% TFA)).

Example 105

(2-(Tetrahydro-2H-pyran-4-yl)-1-(4-(2-(2-hydroxyphenyl)-7-methylquinazolin-4-yl)piperazin-1-yl)ethanone

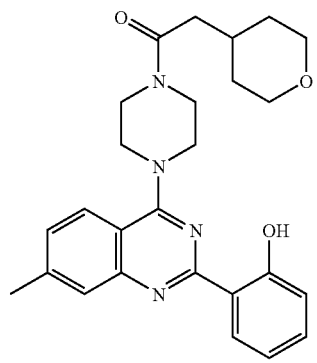

161

(2-(Tetrahydro-2H-pyran-4-yl)-1-(4-(2-(2-hydroxyphenyl)-7-methylquinazolin-4-yl)piperazin-1-yl)ethanone

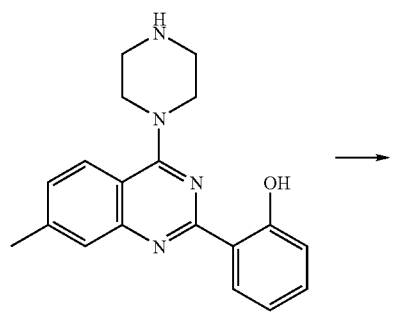

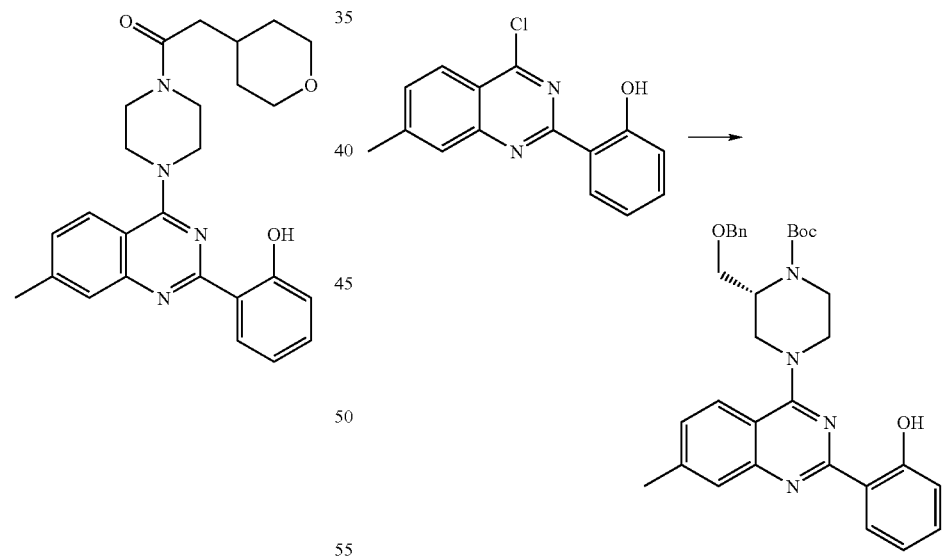

To a solution of 2-(7-methyl-4-(piperazin-1-yl)quinazolin-2-yl)phenol (30 mg, 0.09 mmol) in DMF (1 mL) was added 2-(tetrahydro-2H-pyran-4-yl)acetic acid (13.5 mg, 0.09 mmol) followed by the addition of triethylamine (25 µL), then HATU (44 mg) at room temperature. The reaction was stirred overnight. Purification using reverse phase HPLC (10%-99% CH$_3$CN (0.035% TFA)/H$_2$O (0.05% TFA)) gave (2-(tetrahydro-2H-pyran-4-yl)-1-(4-(2-(2-hydroxyphenyl)-7-methylquinazolin-4-yl)piperazin-1-yl)ethanone as the TFA salt. LC/MS: m/z 447.10 (M+H)$^+$ at 2.32 min (10%-99% CH$_3$CN (0.035% TFA)/H$_2$O (0.05% TFA)).

162

Example 106

(R)-2-Hydroxy-1-((R)-2-(hydroxymethyl)-4-(2-(2-hydroxyphenyl)-7-methylquinazolin-4-yl)piperazin-1-yl)-4-methylpentan-1-one

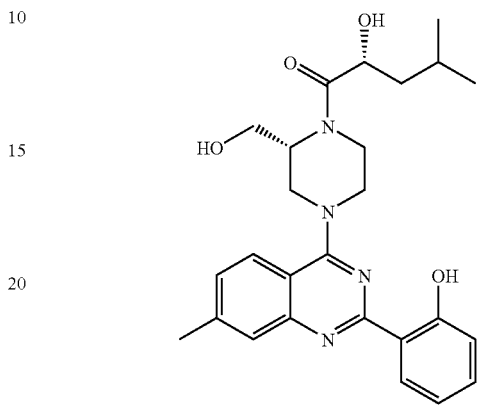

(R)-tert-Butyl 2-((benzyloxy)methyl)-4-(2-(2-hydroxyphenyl)-7-methylquinazolin-4-yl)piperazine-1-carboxylate To a solution of 2-(4-chloro-7-methylquinazolin-2-yl)phenol (450 mg, 1.66 mmol) in 10 mL DMF was added a solution of (R)-tert-butyl 2-((benzyloxy)methyl)piperazine-1-carboxylate (610 mg, 1.99 mmol) in DMF and triethylamine (0.46 mL). The reaction mixture was then refluxed at 85° C. for 30 minutes, quenched with water, extracted twice with CH$_2$Cl$_2$, dried over Na$_2$SO$_4$, and concentrated to give (R)-tert-butyl 2-((benzyloxy)methyl)-4-(2-(2-hydroxyphenyl)-7-methylquinazolin-4-yl)piperazine-1-carboxylate (760 mg, 85%). This material was used in the next step without further purification. LC/MS: m/z 541.5 (M+H)+ at 3.37 min (10%-99% CH₃CN (0.035% TFA)/H₂O (0.05% TFA)).

2-(4-((R)-3-((Benzyloxy)methyl)piperazin-1-yl)-7-methylquinazolin-2-yl)phenol

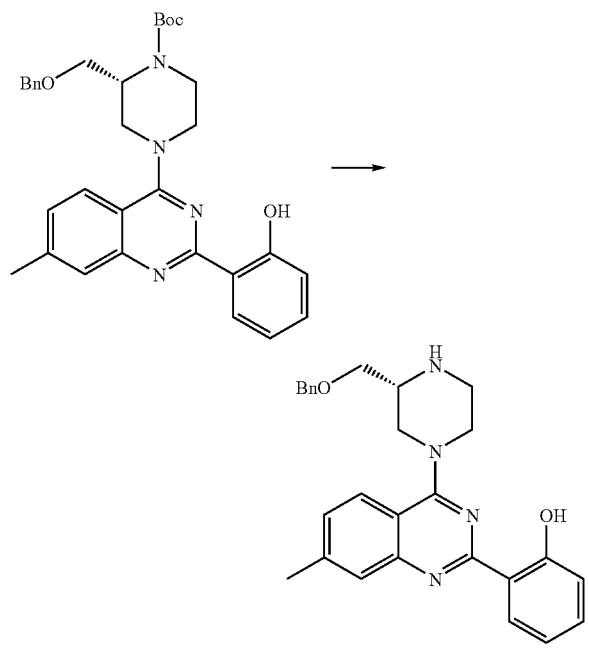

To a solution of (R)-tert-butyl 2-((benzyloxy)methyl)-4-(2-(2-hydroxyphenyl)-7-methylquinazolin-4-yl)piperazine-1-carboxylate (760 mg, 1.72 mmol) in 15 mL CH₂Cl₂ was added 10 mL of TFA. The reaction was stirred for 1 hour. TFA was removed under vacuum and the reaction was neutralized using a 1 M NaOH solution. The aqueous layer was extracted twice with CH₂Cl₂, dried over Na₂SO₄, filtered, and concentrated to obtain 2-(4-((R)-3-((benzyloxy)methyl)piperazin-1-yl)-7-methylquinazolin-2-yl)phenol (570 mg, 92%). This material was used in the next step without further purification. LC/MS: m/z 441.5 (M+H)+ at 2.44 min (10%-99% CH₃CN (0.035% TFA)/H₂O (0.05% TFA)).

(R)-1-((R)-2-((Benzyloxy)methyl)-4-(2-(2-hydroxyphenyl)-7-methylquinazolin-4-yl)piperazin-1-yl)-2-hydroxy-4-methylpentan-1-one

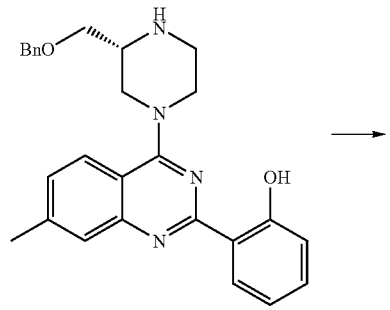

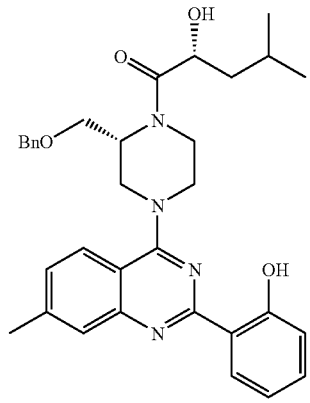

To a solution of 2-(4-((R)-3-((benzyloxy)methyl)piperazin-1-yl)-7-methylquinazolin-2-yl)phenol (100 mg, 0.22 mmol) in DMF (1 mL) was added (R)-2-hydroxy-4-methylpentanoic acid (30 mg, 0.22 mmol) followed by the addition of triethylamine (61 µL), then HATU (109 mg) at room temperature. The reaction was stirred overnight. Purification using reverse phase HPLC (10%-99% CH₃CN (0.035% TFA)/H₂O (0.05% TFA)) gave (R)-1-((R)-2-((benzyloxy)methyl)-4-(2-(2-hydroxyphenyl)-7-methylquinazolin-4-yl)piperazin-1-yl)-2-hydroxy-4-methylpentan-1-one as the TFA salt. LC/MS: m/z 555.7 (M+H)+ at 3.13 min (10%-99% CH₃CN (0.035% TFA)/H₂O (0.05% TFA)).

(R)-2-Hydroxy-1-((R)-2-(hydroxymethyl)-4-(2-(2-hydroxyphenyl)-7-methylquinazolin-4-yl)piperazin-1-yl)-4-methylpentan-1-one

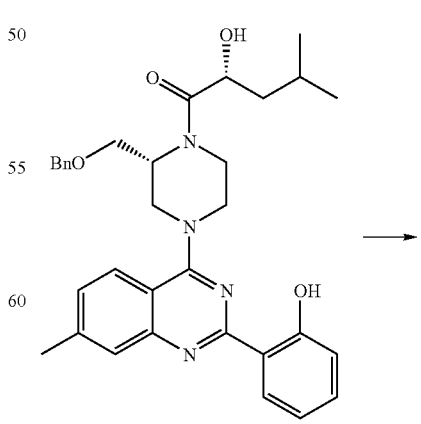

-continued

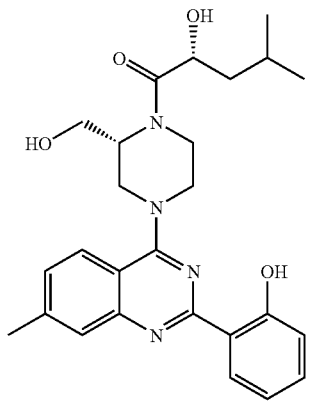

To a solution of (R)-1-((R)-2-((benzyloxy)methyl)-4-(2-(2-hydroxyphenyl)-7-methylquinazolin-4-yl)piperazin-1-yl)-2-hydroxy-4-methylpentan-1-one trifluoroacetate salt (29.6 mg, 0.053 mmol) in ethanol was added Pd(OH)$_2$ (188 mg), and the reaction was heated at 50° C. under H$_2$ atmosphere at ambient pressure. The reaction was filtered, and purification using reverse phase HPLC (10%-99% CH$_3$CN (0.035% TFA)/H$_2$O (0.05% TFA)) gave (R)-2-hydroxy-1-((R)-2-(hydroxymethyl)-4-(2-(2-hydroxyphenyl)-7-methylquinazolin-4-yl)piperazin-1-yl)-4-methylpentan-1-one as the TFA salt. LC/MS: m/z 465.50 (M+H)$^+$ at 2.47 min (10%-99% CH$_3$CN (0.035% TFA)/H$_2$O (0.05% TFA)).

Example 107

(Pyridin-3-yl)methyl 4-(2-(2-hydroxyphenyl)quinazolin-4-yl)piperazine-1-carboxylate

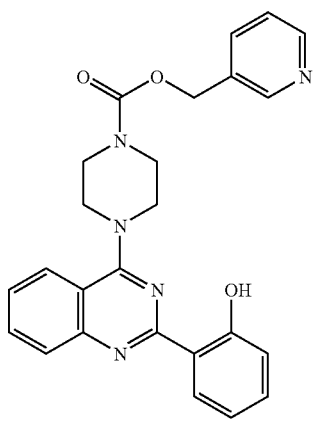

(Pyridin-3-yl)methyl 1H-imidazole-1-carboxylate

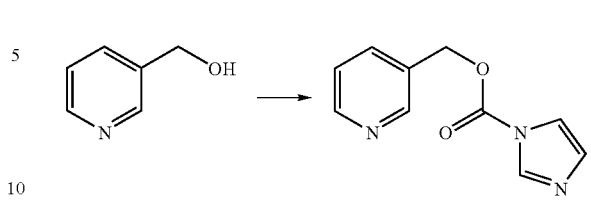

A solution of (pyridin-3-yl)methanol (2 g, 18.32 mmol) and di(1H-imidazol-1-yl)methanone (5.94 g, 36.65 mmol) in 20 mL CH$_2$Cl$_2$ was heated overnight at 50° C. The reaction was quenched with water, extracted twice with CH$_2$Cl$_2$, dried over Na$_2$SO$_4$, filtered, and concentrated. Purification via silica gel chromatography using 10-70% EtOAc in CH$_2$Cl$_2$ gave (pyridin-3-yl)methyl 1H-imidazole-1-carboxylate (3.1 g, 84%). LC/MS: m/z 204.1 (M+H)$^+$ at 0.39 min (10%-99% CH$_3$CN (0.035% TFA)/H$_2$O (0.05% TFA)). $^1$H NMR (400 MHz, CDCl$_3$) d 8.74 (d, J=1.9 Hz, 1H), 8.68 (dd, J=4.8, 1.4 Hz, 1H), 8.16 (s, 1H), 7.81 (m, 1H), 7.44 (s, 1H), 7.38 (m, 1H), 7.09 (s, 1H), 5.46 (s, 2H) ppm.

(Pyridin-3-yl)methyl 4-(2-(2-hydroxyphenyl)quinazolin-4-yl)piperazine-1-carboxylate

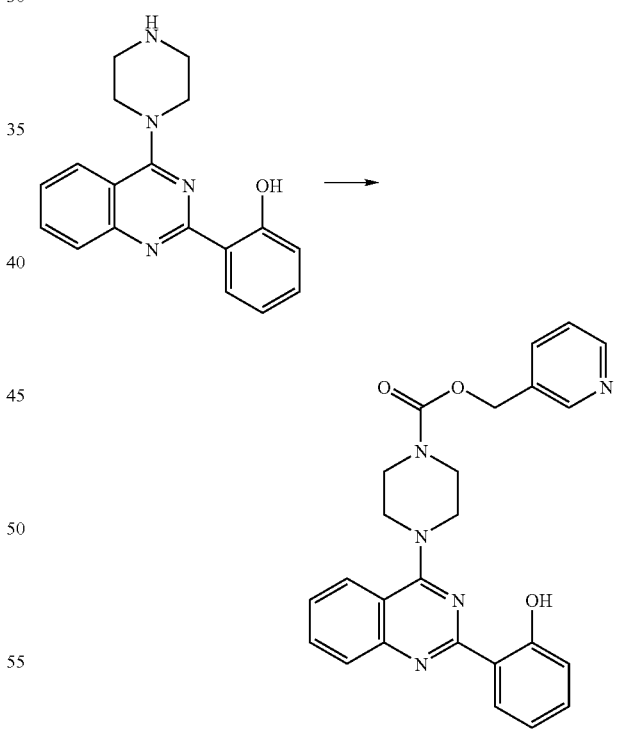

A solution of 2-(4-(piperazin-1-yl)quinazolin-2-yl)phenol (50 mg, 0.16 mmol), (pyridin-3-yl)methyl 1H-imidazole-1-carboxylate (67 mg, 0.32 mmol) and triethylamine (44.6 µL, 0.32 mmol) in DMSO (500 µL) was heated in a microwave synthesizer at 200° C. for 10 minutes. Purification using reverse phase HPLC (10%-99% CH$_3$CN (0.035% TFA)/H$_2$O (0.05% TFA)) gave (pyridin-3-yl)methyl 4-(2-(2-hydroxyphenyl)quinazolin-4-yl)piperazine-1-carboxylate as the TFA salt. LC/MS: m/z 442.50 (M+H)⁺ at 1.97 min (10%-99% CH₃CN (0.035% TFA)/H₂O (0.05% TFA)).

Example 108

2-Hydroxy-1-(4-(2-(2-hydroxyphenyl)-7-methylquinazolin-4-yl)piperazin-1-yl)-2-methylpropan-1-one

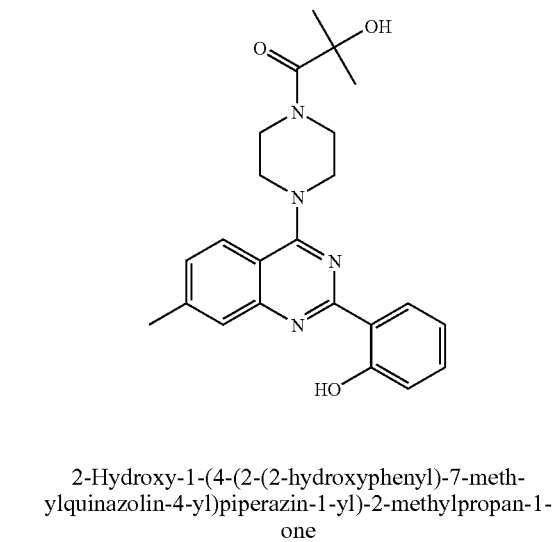

2-Hydroxy-1-(4-(2-(2-hydroxyphenyl)-7-methylquinazolin-4-yl)piperazin-1-yl)-2-methylpropan-1-one A solution of 2-(7-methyl-4-(piperazin-1-yl)quinazolin-2-yl)phenol (70 mg, 0.22 mmol) in DMF (0.5 mL) was added to 2-hydroxy-2-methylpropanoic acid (29.6 mg, 0.284 mmol). It was followed by the addition of triethylamine (61 µL), then a solution of HATU (108 mg) in 0.5 mL DMF at room temperature. The reaction was stirred overnight. Purification using reverse phase HPLC (10%-99% CH₃CN (0.035% TFA)/H₂O (0.05% TFA)) gave 2-hydroxy-1-(4-(2-(2-hydroxyphenyl)-7-methylquinazolin-4-yl)piperazin-1-yl)-2-methylpropan-1-one as the TFA salt. LC/MS: m/z 407.50 (M+H)⁺ at 2.21 min (10%-99% CH₃CN (0.035% TFA)/H₂O (0.05% TFA)).

Example 109

(S)-3-Hydroxy-1-(4-(2-(2-hydroxyphenyl)quinazolin-4-yl)piperazin-1-yl)butan-1-one

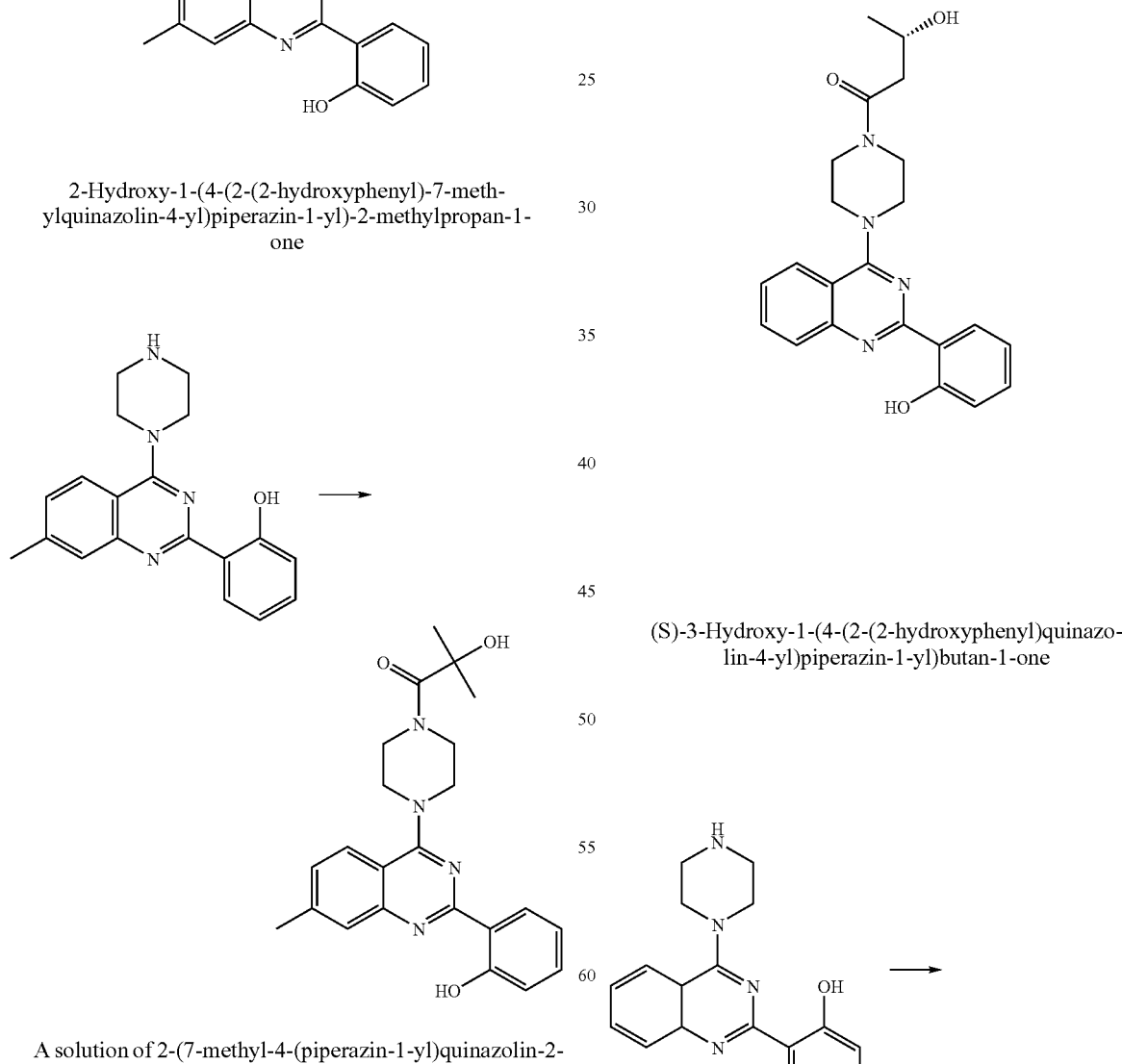

(S)-3-Hydroxy-1-(4-(2-(2-hydroxyphenyl)quinazolin-4-yl)piperazin-1-yl)butan-1-one 169
-continued

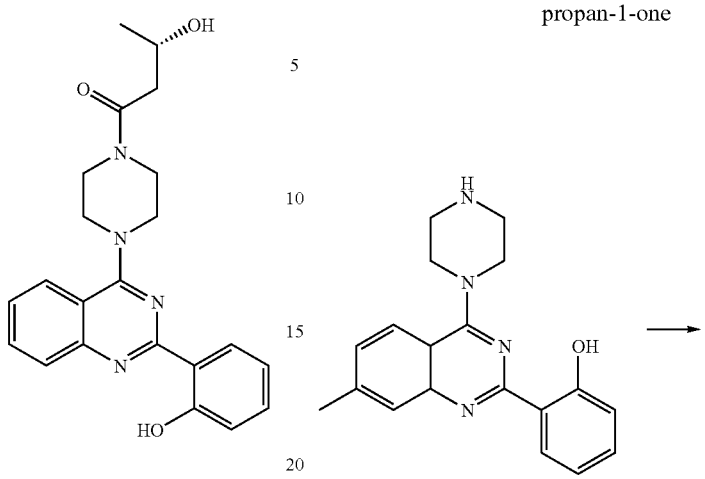

A solution of 2-(4-(piperazin-1-yl)quinazolin-2-yl)phenol (70 mg, 0.23 mmol) in DMF (0.5 mL) was added to (S)-3-hydroxybutanoic acid (31.0 mg, 0.297 mmol). It was followed by the addition of triethylamine (63 µL), then a solution of HATU (113 mg) in 0.5 mL DMF at room temperature. The reaction was stirred overnight. Purification using reverse phase HPLC (10%-99% CH$_3$CN (0.035% TFA)/H$_2$O (0.05% TFA)) gave (S)-3-hydroxy-1-(4-(2-(2-hydroxyphenyl)quinazolin-4-yl)piperazin-1-yl)butan-1-one as the TFA salt. LC/MS: m/z 393.1 (M+H)$^+$ at 2.04 min (10%-99% CH$_3$CN (0.035% TFA)/H$_2$O (0.05% TFA)).

Example 110

2-(Trifluoromethyl)-2-hydroxy-1-(4-(2-(2-hydroxyphenyl)-7-methylquinazolin-4-yl)piperazin-1-yl)propan-1-one

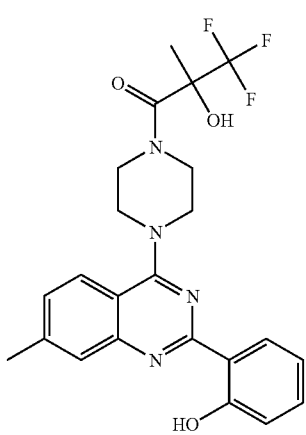

170

2-(Trifluoromethyl)-2-hydroxy-1-(4-(2-(2-hydroxyphenyl)-7-methylquinazolin-4-yl)piperazin-1-yl)propan-1-one

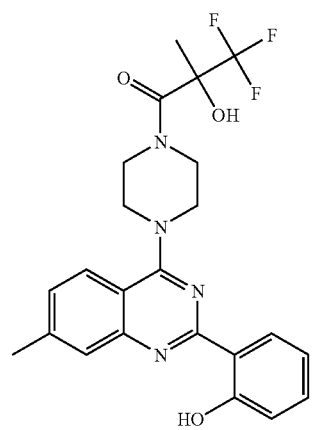

A solution of 2-(7-methyl-4-(piperazin-1-yl)quinazolin-2-yl)phenol (70 mg, 0.22 mmol) in DMF (0.5 mL) was added to 2-(trifluoromethyl)-2-hydroxypropanoic acid (45 mg, 0.284 mmol). It was followed by the addition of triethylamine (61 µL), then a solution of HATU (108 mg) in 0.5 mL DMF at room temperature. The reaction was stirred overnight. Purification using reverse phase HPLC (10%-99% CH$_3$CN (0.035% TFA)/H$_2$O (0.05% TFA)) gave 2-(trifluoromethyl)-2-hydroxy-1-(4-(2-(2-hydroxyphenyl)-7-methylquinazolin- 4-yl)piperazin-1-yl)propan-1-one as the TFA salt. LC/MS: m/z 461.1 (M+H)+ at 2.56 min (10%-99% CH₃CN (0.035% TFA)/H₂O (0.05% TFA)).

Example 111

(R)-1-(4-(6-Fluoro-2-(2-hydroxyphenyl)quinazolin-4-yl)piperazin-1-yl)-2-hydroxy-4,4-dimethylpentan-1-one

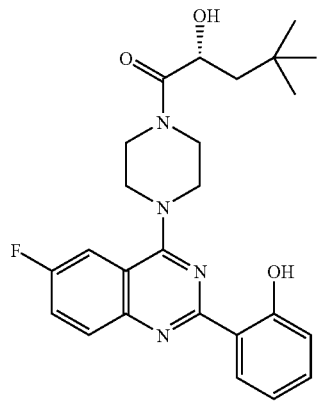

(E)-N-(4-Fluorophenyl)-2-(hydroxyimino)acetamide

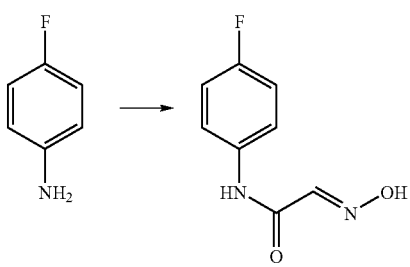

4-Fluoroaniline (58.2 g, 0.50 mol) was added slowly to 10% aqueous HCl solution. This suspension was added to a mixture of chloral hydrate (95 g, 0.55 mol) and sodium sulfate (0.5 kg) in 750 mL water with mechanical stirring. Hydroxylamine hydrochloride (116 g, 1.63 mol) dissolved in water (250 mL) was added, and the resulting slurry was heated at 100° C. After this temperature was reached, the heating mantle was removed immediately, and the solution was cooled to room temperature. The formed precipitate was collected by filtration, washed with water (2×300 mL), and dried in a vacuum oven at 60° C. Yield: 78.2 g of N-(4-fluorophenyl)-2-hydroxyiminoacetamide as an off-white solid.

5-Fluoroindoline-2,3-dione

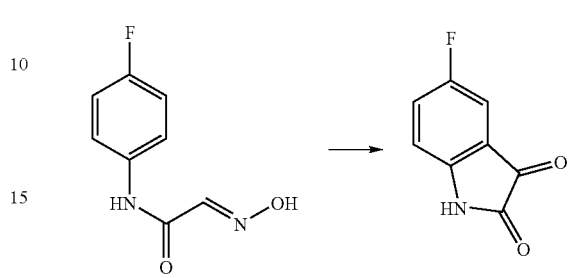

Concentrated sulfuric acid (200 mL) was heated at 50° C., and N-(4-fluorophenyl)-2-hydroxyiminoacetamide was slowly added. The black solution was carefully heated at 90° C. At this temperature, some slight cooling was necessary to keep the temperature at 90° C. When no more heat had developed, the reaction mixture was heated at 90° C. for an additional half hour. The dark-red solution was cooled to room temperature and poured onto 3 L ice water and 1 L ethyl acetate with vigorous stirring. The layers were separated, and the aqueous layer was extracted with ethyl acetate (1×1 L, 1×0.5 L). The combined organic extracts were dried over sodium sulfate, filtered, and evaporated to dryness. Yield: 35.3 g (52%) of a dark red solid, 5-fluoro-1H-indole-2,3-dione.

2-Amino-5-fluorobenzamide

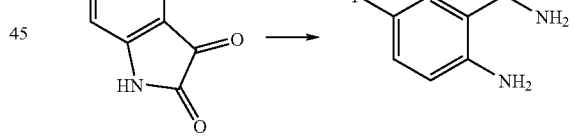

5-Fluoro-1H-indole-2,3-dione (35.3 g, 213 mmol) was heated in acetic acid (300 mL), 1 mL concentrated sulfuric acid, and 22 mL 35% aq. hydrogen peroxide at 70° C. The solution was kept at that temperature one and a half hours during which time a solid formed in the reaction mixture. After cooling to room temperature this solid was collected by filtration and was washed three times with water. The wet solid was suspended in 150 mL water, and 40 mL of a 25% aq. ammonia solution was added. This mixture was stirred at room temperature 3 days. The formed solid was collected by filtration and was washed twice with water. The solid was dried by azeotropic distillation with toluene (3×100 mL) to yield 2-amino-5-fluorobenzamide (9.5 g). The combined filtrates were extracted with ethyl acetate (2×100 mL). The combined extracts were dried over sodium sulfate, filtered, and evaporated to dryness to yield 2-amino-5-fluorobenza-

6-Fluoro-2-(2-methoxyphenyl)-3H-quinazolin-4-one

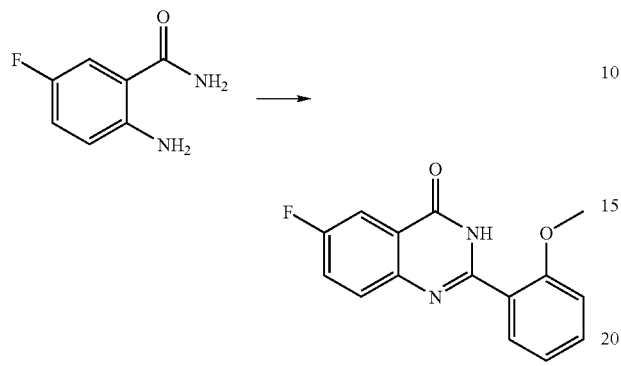

o-Anisoyl chloride (15.7 g, 92 mmol) was added dropwise to a solution of 2-amino-5-fluorobenzamide (13.0 g, 84 mmol) and triethylamine (16 mL, 110 mmol) in tetrahydrofuran (100 mL) cooled in an ice bath. Immediately a precipitate started forming. Stirring of the solution was continued for 5 hours at room temperature. The formed precipitate was collected by filtration and was washed twice with diethyl ether and dried at 50° C. in vacuo. The dried solid was suspended in 2 N aqueous sodium hydroxide solution (250 mL) and heated at reflux until a clear solution was obtained (3 hours). The reaction mixture was cooled to room temperature and filtered. The filtrate was acidified to pH<1 with concentrated aqueous HCl. The formed precipitate was collected by filtration and washed twice with water, twice with methanol, and twice with diethyl ether. The solid was dried in an oven at 45° C. to yield 6-fluoro-2-(2-methoxyphenyl)-3H-quinazolin-4-one (18.2 g, 80%) as a white solid.

4-Chloro-6-fluoro-2-(2-methoxyphenyl)quinazoline

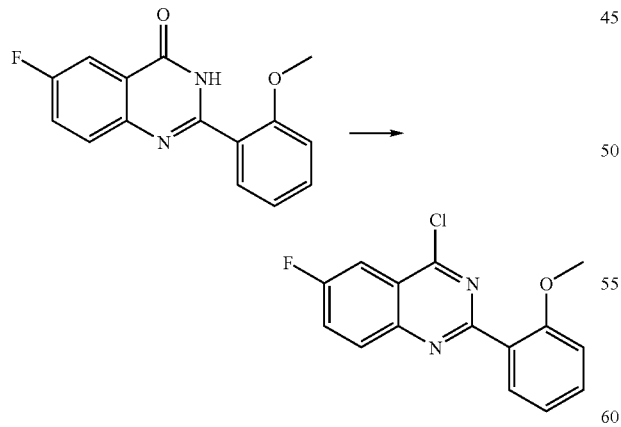

A suspension of 6-fluoro-2-(2-methoxyphenyl)-3H-quinazolin-4-one (14.0 g, 52 mmol), N,N-dimethylaniline (6.6 mL, 52 mmol), and phosphorus oxychloride (4.8 mL, 52 mmol) in benzene (100 mL) was heated at reflux until a clear, dark solution was obtained (1 hour). The reaction mixture was cooled to room temperature, and the volume was reduced under reduced pressure. The black, oily residue was poured into 300 g of ice. Dichloromethane (600 mL) was added with vigorous stirring, and the temperature was kept below 5° C. at all times. The pH was monitored, and aqueous 1 N sodium hydroxide was added until the pH was 10-11. The mixture was stirred for one hour at a temperature below 5° C., and the pH was kept between 10-11 by addition of 1 N aqueous sodium hydroxide. The layers were separated, and the organic layer was washed with ice-cold 1 N aqueous sodium hydroxide (2×200 mL). Heptanes (300 mL) were added to the organic layer. This mixture was filtered through a short plug of silica gel and eluted with dichloromethane/heptanes (2:1). All fractions containing product were combined and evaporated to dryness. The residue was triturated with heptanes to yield 4-chloro-6-fluoro-2-(2-methoxyphenyl)-quinazoline (11.5 g, 76%) as a white solid.

2-(4-Chloro-6-fluoroquinazolin-2-yl)phenol

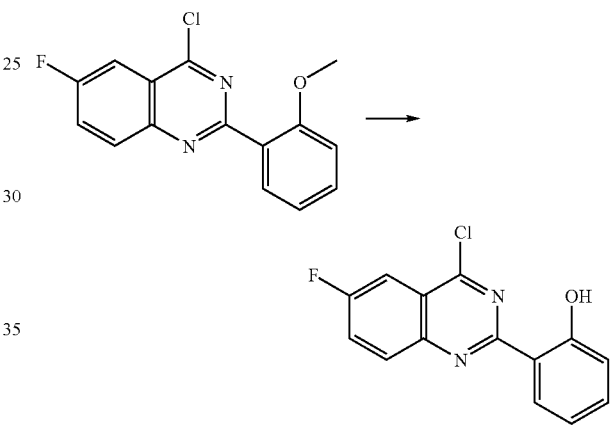

A solution of 4-chloro-6-fluoro-2-(2-methoxyphenyl) quinazoline (3.0 g, 10.3 mmol) in $CH_2Cl_2$ (15 mL) was cooled to −78° C. Then, 1 M $BBr_3$ (51.95 mL, 59.95 mmol) was added dropwise. The reaction was warmed to room temperature and was quenched with $NaHCO_3$ and extracted twice with $CH_2Cl_2$. The organic layer was dried over $MgSO_4$, filtered, and concentrated. Purification via silica gel chromatography using 5-20% $CH_2Cl_2$ in hexanes gave 2-(4-chloro-6-fluoroquinazolin-2-yl)phenol (1.61 g, 57%). LC/MS: m/z 275.1 $(M+H)^+$ at 3.8 min (10%-99% $CH_3CN$ (0.035% TFA)/ $H_2O$ (0.05% TFA)).

2-(6-Fluoro-4-(piperazin-1-yl)quinazolin-2-yl)phenol

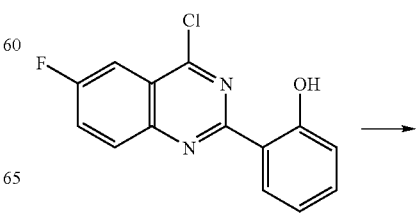

-continued

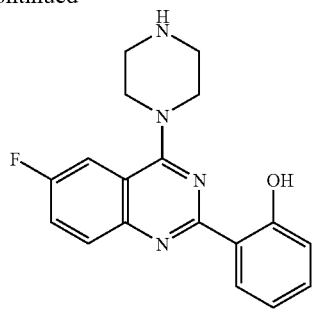

To a stirring solution of 2-(4-chloro-6-fluoroquinazolin-2-yl)phenol (500 mg, 1.82 mmol) in CH$_2$Cl$_2$ (20 mL) at 0° C., under an N$_2$ atmosphere was rapidly added a solution of piperazine (0.263 g, 7.28 mmol) and triethylamine (0.35 mL, 2.55 mmol) in CH$_2$Cl$_2$. The mixture was stirred for 1 h and then quenched with H$_2$O, extracted twice with CH$_2$Cl$_2$, dried over Na$_2$SO$_4$, filtered, and concentrated. Purification via silica gel chromatography using 0-5% MeOH in CH$_2$Cl$_2$ gave 2-(6-fluoro-4-(piperazin-1-yl)quinazolin-2-yl)phenol (400 mg, 68%). LC/MS: m/z 325.5 (M+H)$^+$ at 2.12 min (10%-99% CH$_3$CN (0.035% TFA)/H$_2$O (0.05% TFA)). $^1$H NMR (400 MHz, DMSO-d6) δ 8.42 (m, 1H), 7.97 (m, 1H), 7.78 (m, 2H), 7.39 (m, 1H), 6.95 (m, 2H), 3.83 (t, J=4.9 Hz, 4H), 2.92 (t, J=4.9 Hz, 4H) ppm.

(R)-1-(4-(6-Fluoro-2-(2-hydroxyphenyl)quinazolin-4-yl)piperazin-1-yl)-2-hydroxy-4,4-dimethylpentan-1-one Method A To a solution of 2-(6-fluoro-4-(piperazin-1-yl)quinazolin-2-yl)phenol (25 mg, 0.08 mmol) in DMF (1 mL) was added (R)-2-hydroxy-4,4-dimethylpentanoic acid (20.28 mg, 0.14 mmol) followed by the addition of triethylamine (25 µL), then HATU (44 mg) at room temperature. The reaction was stirred overnight. Purification using reverse phase HPLC (10%-99% CH$_3$CN (0.035% TFA)/H$_2$O (0.05% TFA))-H$_2$O) gave (R)-1-(4-(6-fluoro-2-(2-hydroxyphenyl)quinazolin-4-yl)piperazin-1-yl)-2-hydroxy-4,4-dimethylpentan-1-one as the TFA salt. LC/MS: m/z 453.52 (M+H)$^+$ at 3.21 min (10%-99% CH$_3$CN (0.035% TFA)/H$_2$O (0.05% TFA)).

Method B

To a solution of 2-(6-fluoro-4-(piperazin-1-yl)quinazolin-2-yl)phenol (200 mg, 0.61 mmol) in CH$_2$Cl$_2$ (5 mL) was added triethylamine (170 µL, 1.22 mmol) followed by the addition of (R)-2-hydroxy-4,4-dimethylpentanoic acid (116 mg, 0.79 mmol), then HATU (301 mg, 0.79 mmol). An additional 3 mL of CH$_2$Cl$_2$ was added, and the reaction was stirred for 3 h. After quenching with water, the mixture was extracted twice with CH$_2$Cl$_2$. The organic phase was dried over MgSO$_4$ and concentrated. Purification via silica gel chromatography using 0-10% EtOAc in 50:50 CH$_2$Cl$_2$:hexanes yielded (R)-1-(4-(6-fluoro-2-(2-hydroxyphenyl)quinazolin-4-yl)piperazin-1-yl)-2-hydroxy-4,4-dimethylpentan-1-one (240 mg, 86%). m/z: M+1 obs=453.5; t$_R$=3.19 minutes; $^1$H NMR (400 MHz, DMSO-d6) d 8.46 (m, 1H), 8.01 (m, 1H), 7.84 (m, 2H), 7.40 (m, 1H), 6.96 (m, 2H), 4.89 (d, J=7.1 Hz, 1H), 4.45 (m, 1H), 3.97 (m, 4H), 3.76 (m, 4H), 1.56 (m, 1H), 1.42 (m, 1H), 0.97 (s, 9H) ppm.

(R)-1-(4-(6-Fluoro-2-(2-hydroxyphenyl)quinazolin-4-yl)piperazin-1-yl)-2-hydroxy-4,4-dimethylpentan-1-one hydrochloride

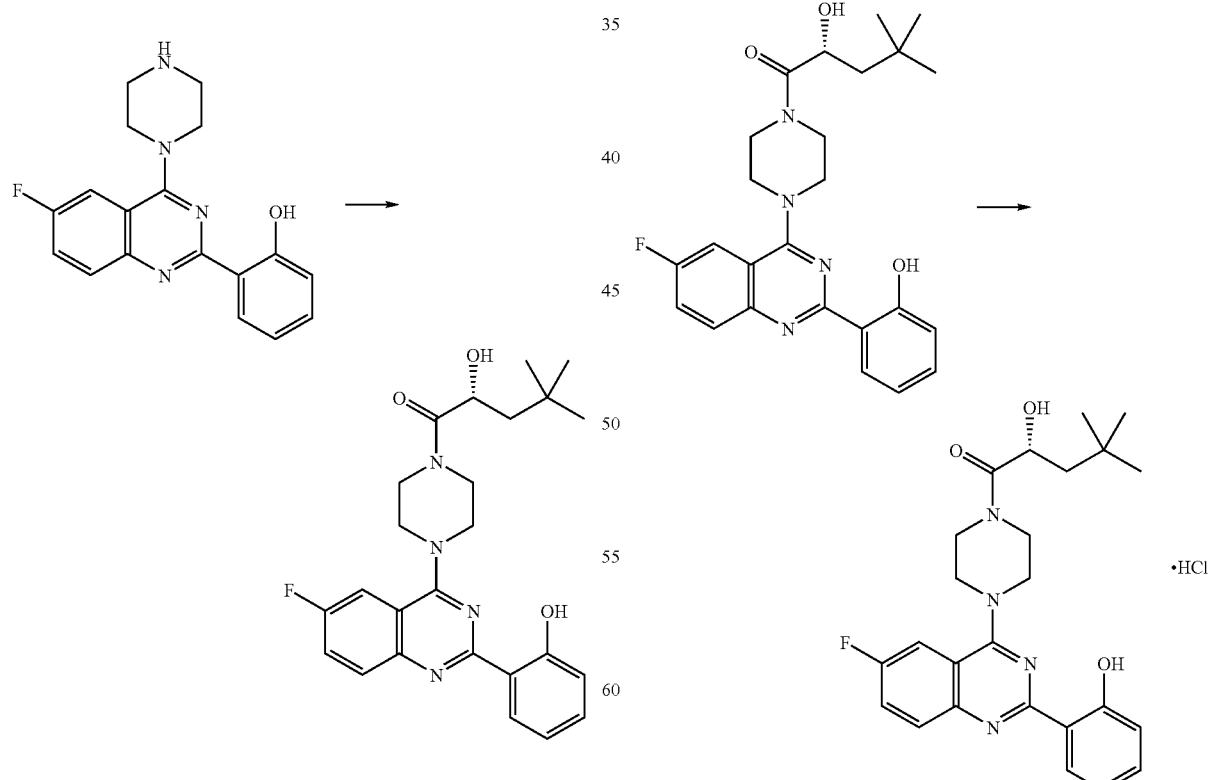

To a solution of (R)-1-(4-(6-fluoro-2-(2-hydroxyphenyl)quinazolin-4-yl)piperazin-1-yl)-2-hydroxy-4,4-dimethylpentan-1-one (230 mg, 0.51 mmol) in CH₂Cl₂ (3 mL) under an inert atmosphere was added dropwise a 2 M HCl solution in ether (02.55 mL, 0.51 mmol). To it was then added ether (15 mL) which resulted in formation of a precipitate that was allowed to stir for an hour. The product was collected by vacuum filtration and dried to afford (R)-1-(4-(6-fluoro-2-(2-hydroxyphenyl)quinazolin-4-yl)piperazin-1-yl)-2-hydroxy-4,4-dimethylpentan-1-one hydrochloride (230 mg, 92%). LCMS: m/z 453.5 (M+H)⁺ at 3.19 min (10%-99% CH₃CN (0.035% TFA)/H₂O (0.05% TFA)). ¹H NMR (400 MHz, DMSO-d6) δ 8.40 (dd, J=7.8, 1.4 Hz, 1H), 8.04 (m, 1H), 7.88 (m, 2H), 7.43 (m, 1H), 6.99 (m, 2H), 4.45 (dd, J=8.8, 3.0 Hz, 1H), 4.02 (m, 4H), 3.79 (m, 4H), 1.56 (m, 1H), 1.42 (m, 1H), 0.97 (s, 9H) ppm.

Example 112

4,4,4-Trifluoro-2-hydroxy-1-(4-(2-(2-hydroxyphenyl)-7-methylquinazolin-4-yl)piperazin-1-yl)butan-1-one

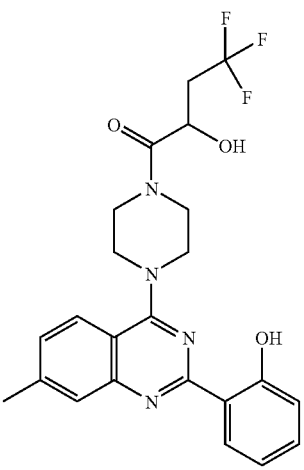

4,4,4-Trifluoro-2-hydroxy-1-(4-(2-(2-hydroxyphenyl)-7-methylquinazolin-4-yl)piperazin-1-yl)butan-1-one

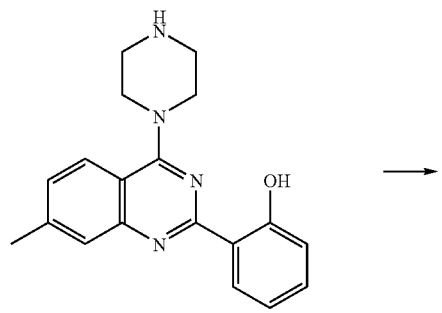

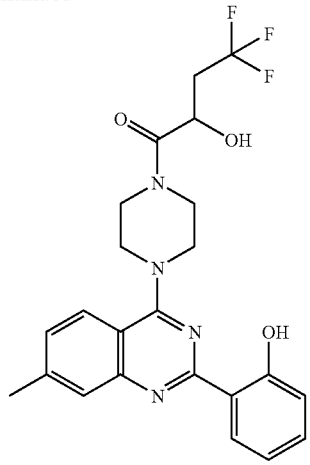

2-(7-Methyl-4-(piperazin-1-yl)quinazolin-2-yl)phenol (87 mg, 0.27 mmol), 4,4,4-trifluoro-2-hydroxybutanoic acid (43 mg, 0.27 mmol), HATU (0.12 g, 0.33 mmol) and triethylamine (45 μL, 0.33 mmol) were stirred in DMF (3 mL) at room temperature overnight. The mixture was diluted with water and extracted with EtOAc. The combined organic layers were washed with brine and water, dried over Na₂SO₄ and concentrated. Purification via silica gel chromatography using 0-20% EtOAc in 1:1 CH₂Cl₂: hexanes gave 4,4,4-trifluoro-2-hydroxy-1-(4-(2-(2-hydroxyphenyl)-7-methylquinazolin-4-yl)piperazin-1-yl)butan-1-one as an off-white solid (86 mg, 66%). ¹H NMR (400 MHz, CDCl₃) d 8.46 (dd, J=8.0, 1.7 Hz, 1H), 7.77 (d, J=8.5 Hz, 1H), 7.70 (s, 1H), 7.41-7.37 (m, 1H), 7.31 (dd, J=8.5, 1.5 Hz, 1H), 7.05-7.03 (m, 1H), 6.97-6.93 (m, 1H), 4.80-4.75 (m, 1H), 4.07-3.68 (m, 9H), 2.56 (s, 3H), 2.50-2.39 (m, 2H) ppm; LC/MS: m/z 461.3 (M+H)⁺ at 2.49 min (10%-99% CH₃CN (0.035% TFA)/H₂O (0.05% TFA)).

Example 113

2-Hydroxy-1-(4-(2-(2-hydroxyphenyl)-7-methylquinazolin-4-yl)piperazin-1-yl)-3-methylbutan-1-one 2-Hydroxy-1-(4-(2-(2-hydroxyphenyl)-7-methylquinazolin-4-yl)piperazin-1-yl)-3-methylbutan-1-one

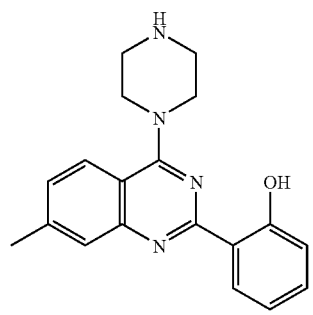

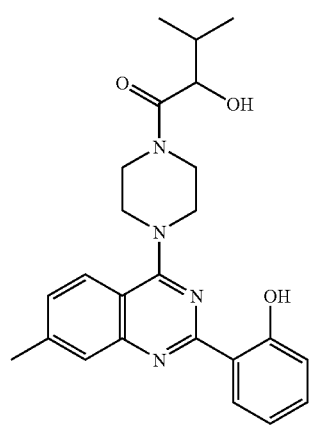

Method A

Under an N₂ atmosphere, a mixture of 2-(7-methyl-4-(piperazin-1-yl)quinazolin-2-yl)phenol (25 mg, 0.08 mmol), 2-hydroxy-3-methylbutanoic acid (9 mg, 0.08 mmol), BOP (35 mg, 0.08 mmol), triethylamine (22 μL, 0.16 mmol) and DMF (0.2 mL) was stirred at room temperature for 1 hour. The reaction mixture was then purified via preparative reverse phase HPLC using 10%-99% CH₃CN (0.035% TFA)/H₂O (0.05% TFA) to give 2-hydroxy-1-(4-(2-(2-hydroxyphenyl)-7-methylquinazolin-4-yl)piperazin-1-yl)-3-methylbutan-1-one as the TFA salt. LC/MS: m/z 421.10 (M+H)⁺ at 2.76 min (10%-99% CH₃CN (0.035% TFA)/H₂O (0.05% TFA)).

Method B

To a solution of 2-(7-methyl-4-(piperazin-1-yl)quinazolin-2-yl)phenol (250 mg, 0.78 mmol) in CH₂Cl₂ (6 mL) was added triethylamine (217 μL, 1.56 mmol) followed by the addition of 2-hydroxy-3-methylbutanoic acid (120 mg, 1.0 mmol) and HATU (380 mg, 1.00 mmol). The reaction mixture was stirred at room temperature for 3 h and then quenched with H₂O. The aqueous layer was extracted with CH₂Cl₂, dried over MgSO₄, filtered, and concentrated. Purification via silica gel chromatography using 0-10% EtOAc in 50:50 CH₂Cl₂:hexanes gave 2-hydroxy-1-(4-(2-(2-hydroxyphenyl)-7-methylquinazolin-4-yl)piperazin-1-yl)-3-methylbutan-1-one (230 mg, 70%). LC/MS: m/z 421.3 (M+H)⁺ at 2.43 min (10%-99% CH₃CN (0.035% TFA)/H₂O (0.05% TFA)). ¹H NMR (400 MHz, DMSO-d6) d 8.45 (m, 1H), 8.01 (d, J=8.5 Hz, 1H), 7.70 (s, 1H), 7.39 (m, 2H), 6.95 (m, 2H), 4.79 (d, J=7.2 Hz, 1H), 4.11 (dd, J=7.0, 5.9 Hz, 1H), 3.87 (m, 8H), 2.52 (s, 3H), 1.91 (m, 1H), 0.88 (dd, J=22.8, 6.7 Hz, 6H) ppm.

2-Hydroxy-1-(4-(2-(2-hydroxyphenyl)-7-methylquinazolin-4-yl)piperazin-1-yl)-3-methylbutan-1-one hydrochloride

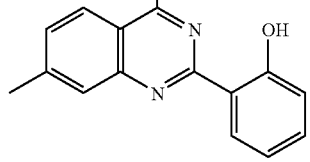

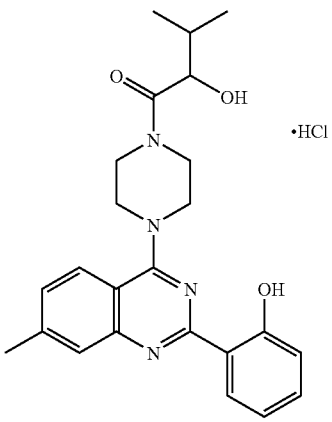

To a solution of 2-hydroxy-1-(4-(2-(2-hydroxyphenyl)-7-methylquinazolin-4-yl)piperazin-1-yl)-3-methylbutan-1-one (230 mg, 0.54 mmol) in CH₂Cl₂ (3 mL) under an inert atmosphere was added ether (12 mL) followed by the dropwise addition of 2 M HCl solution in ether (0.27 mL, 0.54 mmol) which resulted in the formation of a precipitate which was stirred for an hour and then collected by vacuum filtration and dried to afford 2-hydroxy-1-(4-(2-(2-hydroxyphenyl)-7-methylquinazolin-4-yl)piperazin-1-yl)-3-methylbutan-1-one hydrochloride (205 mg, 83%). LC/MS: m/z 421.3 (M+H)⁺ at 2.48 min (10%-99% CH₃CN (0.035% TFA)/H₂O (0.05% TFA)). ¹H NMR (400 MHz, DMSO-d6) d 8.25 (d, J=7.9 Hz, 1H), 8.08 (d, J=8.5 Hz, 1H), 7.74 (s, 1H), 7.48 (t, J=6.6 Hz, 2H), 7.04 (m, 2H), 4.10 (m, 5H), 3.79 (m, 4H), 2.53 (s, 3H), 1.90 (m, 1H), 0.87 (dd, J=16.3, 6.7 Hz, 6H) ppm.

Example 114

(Pyridin-4-yl)methyl 4-(2-(2-fluoro-6-hydroxyphenyl)-7-methylquinazolin-4-yl)piperazine-1-carboxylate

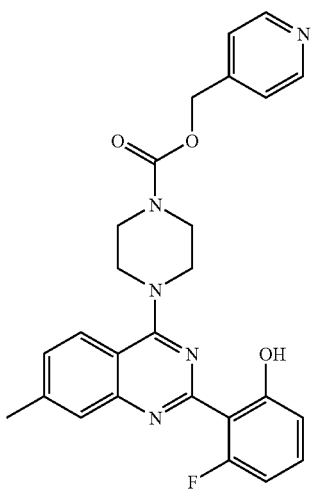

N-(2-Cyano-5-methyl-phenyl)-2-fluoro-6-methoxybenzamide

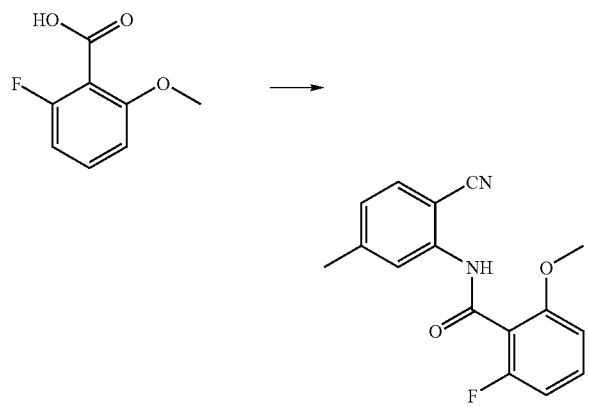

6-Fluoro-2-anisoic acid (110 g, 0.70 mol) was added in portions over 15 minutes to a mixture of thionyl chloride (230 ml, 3.2 mol), toluene (200 mL), and DMF (1 mL). The resulting mixture was stirred overnight at room temperature. The solution was evaporated to dryness and added dropwise to an ice-bath cooled solution of 2-amino-4-methylbenzonitrile (92.5 g, 0.70 mol) in pyridine (200 mL). The dropping funnel was rinsed with a minimal amount of acetonitrile. The resulting mixture was stirred overnight at room temperature under a nitrogen atmosphere and was subsequently poured into 2 L ice water. The resulting slurry was stirred vigorously for 1 hour. The formed solid was collected by filtration and was washed twice with water. The filter cake was dissolved in 2 L dichloromethane, and this solution was washed with 1 N aq. HCl (400 mL) and with saturated aq. NaCl (400 mL), dried over sodium sulfate, filtered, and evaporated to dryness to give N-(2-cyano-5-methylphenyl)-2-fluoro-6-methoxybenzamide (186 g, 93%) as a brownish solid. $^1$H-NMR (CDCl$_3$, 200 MHz): δ 9.09 (s, 1H), 8.58 (s, 1H), 7.59-7.42 (m, 2H), 7.09-7.02 (m, 1H), 6.94-6.83 (m, 2H), 4.11 (s, 3H), 2.57 (s, 3H) ppm.

2-(2-Fluoro-6-methoxy-phenyl)-7-methyl-3H-quinazolin-4-one

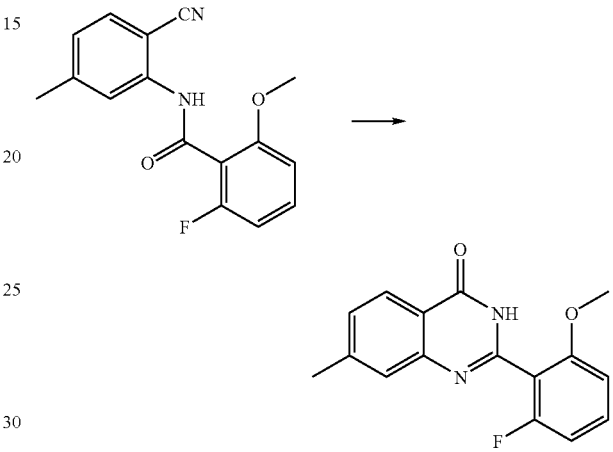

To a suspension of N-(2-cyano-5-methylphenyl)-2-fluoro-6-methoxybenzamide (31.5 g, 111 mmol) in ethanol (626 mL) was added 6 M aqueous NaOH solution (205 mL). After 10 minutes, 30% aqueous H$_2$O$_2$ (60 mL) was added, forming a slurry. The reaction was heated to reflux for 18 h and cooled to room temperature. NaOH (22.2 g, 0.56 mol) and 30% aqueous H$_2$O$_2$ (26 mL) were added, and the reaction was heated to reflux for six hours. The reaction cooled to room temperature, 30% aqueous H$_2$O$_2$ (45 mL) was added, and the reaction was heated to reflux for 18 h. The reaction was cooled to room temperature, NaOH (10 g, 0.25 mol) and 30% aqueous H$_2$O$_2$ (70 mL) were added, and the reaction was heated to reflux for six hours. The reaction was cooled to room temperature and poured over ice (800 mL). The pH was adjusted to 3-4 by addition of conc. HCl solution, and the precipitated off-white solid was filtered and washed with water (3×40 mL). The solid was dried under vacuum to provide 2-(2-fluoro-6-methoxy-phenyl)-7-methyl-3H-quinazolin-4-one (28 g, 89%).

4-Chloro-2-(2-fluoro-6-methoxyphenyl)-7-methylquinazoline

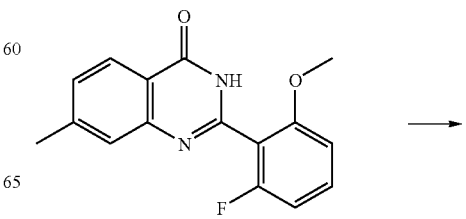

-continued

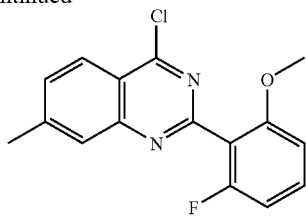

Under an N₂ atmosphere, 2-(2-fluoro-6-methoxyphenyl)-7-methylquinazolin-4(3H)-one (20 g, 70.35 mmol) was suspended in benzene (300 mL), followed by the addition of N,N-dimethylaniline (26.8 mL, 211.05 mmol), then POCl₃ (13.11 mL, 140.7 mmol). The reaction was heated at reflux, and completion of product formation was observed after 1.5 h. After cooling to room temperature, the mixture was slowly poured over 1 liter of ice. The solution was then diluted with CH₂Cl₂, and the pH was adjusted to 7 using a saturated aqueous NaHCO₃ solution. The layers were partitioned, separated and extracted with CH₂Cl₂. All organic layers were combined, dried over Na₂SO₄, filtered, and concentrated to a dark oil. The crude material was purified by silica gel chromatography using 75% CH₂Cl₂/25% hexanes to obtain 4-chloro-2-(2-fluoro-6-methoxyphenyl)-7-methylquinazoline as a yellow solid (18.82 g, 88%). LC/MS: m/z 302.9 (M+H)⁺ at 3.28 min (10%-99% CH₃CN (0.035% TFA)/H₂O (0.05% TFA)). ¹H NMR (400 MHz, CDCl₃) d 8.22 (d, J=8.5 Hz, 1H), 7.95 (s, 1H), 7.60 (dd, J=8.6, 1.5 Hz, 1H), 7.42-7.40 (m, 1H), 6.86-6.84 (m, 2H), 3.81 (s, 3H), 2.64 (s, 3H) ppm.

2-(4-Chloro-7-methylquinazolin-2-yl)-3-fluorophenol

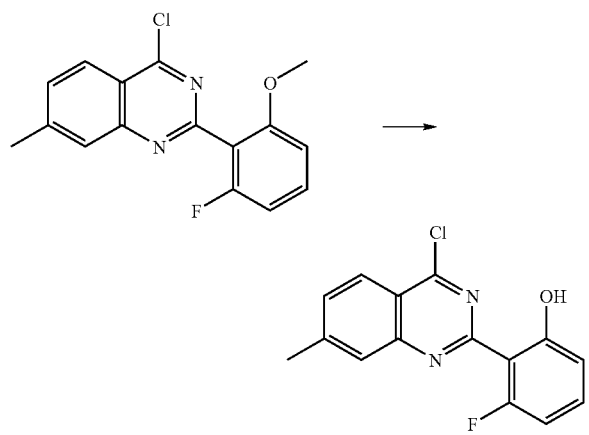

Under an N₂ atmosphere, 4-chloro-2-(2-fluoro-6-methoxyphenyl)-methylquinazolin (7.0 g, 23.12 mmol) was dissolved in CH₂Cl₂ (110 mL) and cooled to −50° C. internal temperature using a dry ice/acetone bath. A 1.0 M solution of BBr₃ in CH₂Cl₂ (115.6 mL, 115.6 mmol) was added dropwise via an addition funnel while maintaining the internal temperature at −50° C. The reaction mixture was allowed to warm to 0° C., and the reaction was complete after 1.5 h. It was then slowly quenched with saturated aqueous NaHCO₃ solution to pH 7. After partitioning between CH₂Cl₂ and H₂O, the mixture was separated and the aqueous layer was twice extracted with CH₂Cl₂. The combined organic layers were dried over Na₂SO₄, filtered, and concentrated to a brown solid. Purification via silica gel chromatography using 75% CH₂Cl₂/25% hexanes gave 2-(4-chloro-7-methylquinazolin-2-yl)-3-fluorophenol as a yellow solid (4.37 g, 66%). LC/MS: m/z 289.1 (M+H)⁺ at 3.71 min (10%-99% CH₃CN (0.035% TFA)/H₂O (0.05% TFA)). ¹H NMR (400 MHz, CDCl₃) d 8.22 (d, J=8.5 Hz, 1H), 7.95 (s, 1H), 7.60 (dd, J=8.6, 1.5 Hz, 1H), 7.42-7.36 (m, 1H), 6.86-6.82 (m, 2H), 3.81 (s, 3H), 2.64 (s, 3H) ppm.

3-Fluoro-2-(7-methyl-4-(piperazin-1-yl)quinazolin-2-yl)phenol

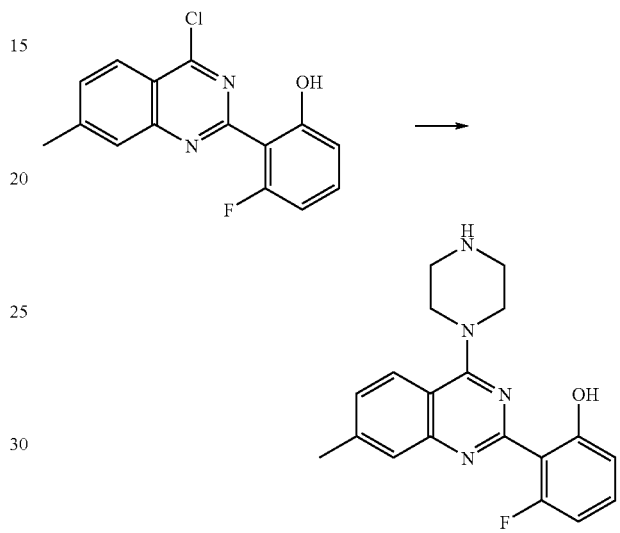

2-(4-Chloro-7-methylquinazolin-2-yl)-3-fluorophenol (4.37 g, 15.14 mmol) was suspended in CH₂Cl₂ (65 mL) under an N₂ atmosphere and placed into an ice water bath. To this solution was added a solution of piperazine (4.00 g, 45.42 mmol) and triethylamine (4.2 mL, 30.28 mmol) in CH₂Cl₂ (15 mL) in one portion. After stirring the reaction for 30 minutes, it was partitioned between CH₂Cl₂ and H₂O and separated, and the aqueous layer was extracted twice more with CH₂Cl₂. The organic phase was dried over Na₂SO₄, filtered, and concentrated to a bright yellow solid which was purified via silica gel chromatography using a 95%/5% mixture of CH₂Cl₂/MeOH to afford 3-fluoro-2-(7-methyl-4-(piperazin-1-yl)quinazolin-2-yl)phenol (4.32 g, 85%) as a bright yellow solid. LC/MS: m/z 339.3 (M+H)⁺ at 1.80 min (10%-99% CH₃CN (0.035% TFA)/H₂O (0.05% TFA)).

(Pyridin-4-yl)methyl 1H-imidazole-1-carboxylate

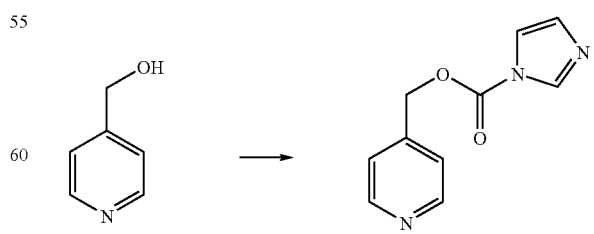

A solution of (pyridin-4-yl)methanol (2.0 g, 18.3 mmol) and di(1H-imidazol-1-yl)methanone (5.94 g, 36.6 mmol) in 20 mL CH₂Cl₂ was heated overnight at 50° C. The reaction was quenched with water, extracted with $CH_2Cl_2$, dried over $Na_2SO_4$, filtered, and concentrated. Purification via silica gel chromatography using 10-70% EtOAc in $CH_2Cl_2$ gave (pyridin-4-yl)methyl 1H-imidazole-1-carboxylate (3 g, 81%). LC/MS: m/z 204.3 (M+H)$^+$ at 0.38 min (v). $^1$H NMR (400 MHz, CDCl$_3$) d 8.69 (dd, J=4.4, 1.6 Hz, 2H), 8.20 (t, J=0.9 Hz, 1H), 7.47 (t, J=1.5 Hz, 1H), 7.34 (dd, J=4.4, 1.6 Hz, 2H), 7.11 (dd, J=1.6, 0.8 Hz, 1H), 5.45 (s, 2H) ppm.

(Pyridin-4-yl)methyl 4-(2-(2-fluoro-6-hydroxyphenyl)-7-methylquinazolin-4-yl)piperazine-1-carboxylate

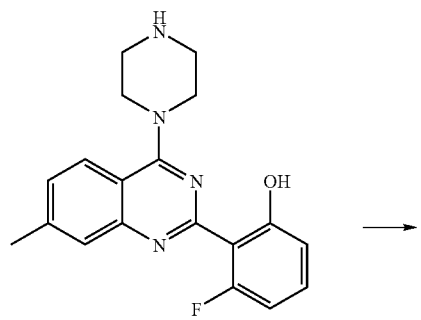

3-Fluoro-2-(7-methyl-4-(piperazin-1-yl)quinazolin-2-yl)phenol (50 mg, 0.15 mmol), (pyridin-4-yl)methyl 1H-imidazole-1-carboxylate (53 mg, 0.26 mmol) and triethylamine (30.4 mg, 0.3 mmol) were added into a tube, followed by the addition of DMSO (1 mL). The mixture was stirred at room temperature for 18 h and then filtered, and purified via preparative reverse phase HPLC (10%-99% CH$_3$CN (0.035% TFA)/H$_2$O (0.05% TFA)) giving (pyridin-4-yl)methyl 4-(2-(2-fluoro-6-hydroxyphenyl)-7-methylquinazolin-4-yl)piperazine-1-carboxylate. LC/MS: m/z 474.30 (M+H)$^+$ at 1.19 min (10%-99% CH$_3$CN (0.035% TFA)/H$_2$O (0.05% TFA)).

Example 115

2-Ethyl-2-hydroxy-1-(4-(2-(2-hydroxyphenyl)quinazolin-4-yl)piperazin-1-yl)butan-1-one

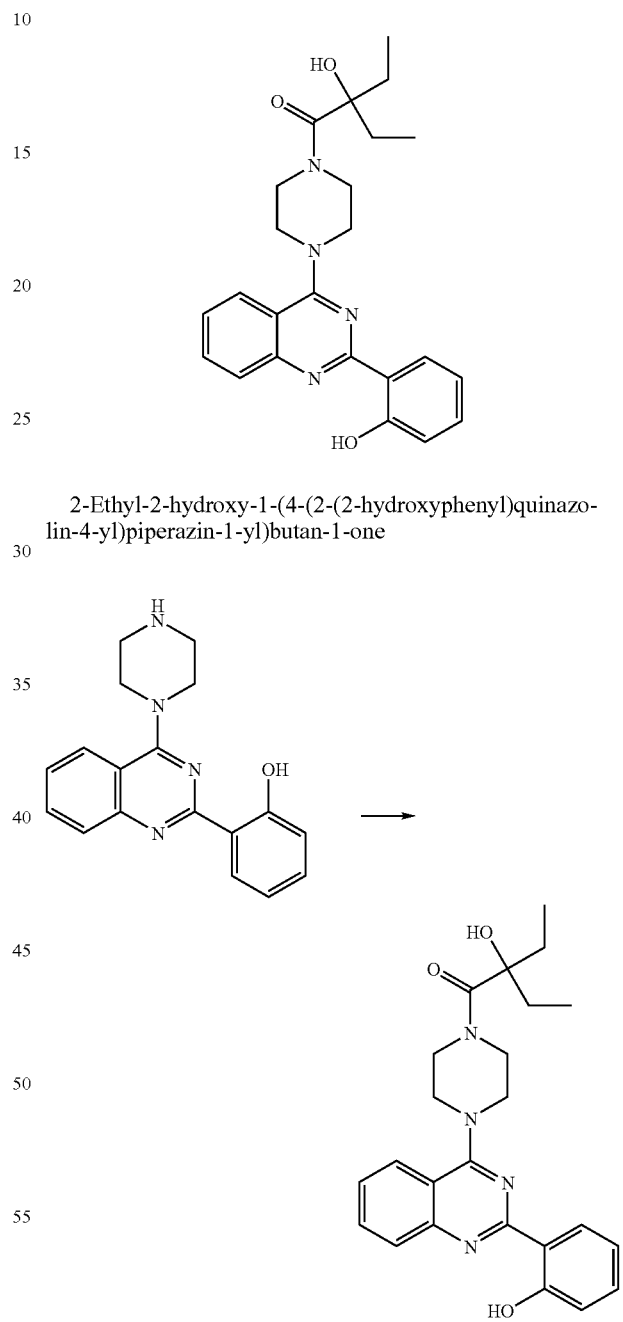

To a solution of 2-(4-(piperazin-1-yl)quinazolin-2-yl)phenol (70 mg, 0.23 mmol) in DMF (0.5 mL) was added 2-ethyl-2-hydroxybutanoic acid (39.30 mg, 0.297 mmol). It was followed by the addition of triethylamine (63 μL), then a solution of HATU (113 mg) in 0.5 mL DMF at room temperature. The reaction was stirred overnight. Purification using reverse phase HPLC (10%-99% CH$_3$CN (0.035% TFA)/H$_2$O (0.05%

TFA)) gave 2-ethyl-2-hydroxy-1-(4-(2-(2-hydroxyphenyl)quinazolin-4-yl)piperazin-1-yl)butan-1-one as the TFA salt. LC/MS: m/z 421.3 (M+H)+ at 2.51 min (10%-99% CH$_3$CN (0.035% TFA)/H$_2$O (0.05% TFA)).

Example 116

(Pyridin-4-yl)methyl 4-(2-(2-hydroxyphenyl)quinazolin-4-yl)piperazine-1-carboxylate

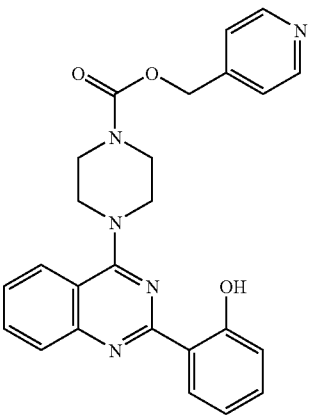

(Pyridin-4-yl)methyl 4-(2-(2-hydroxyphenyl)quinazolin-4-yl)piperazine-1-carboxylate

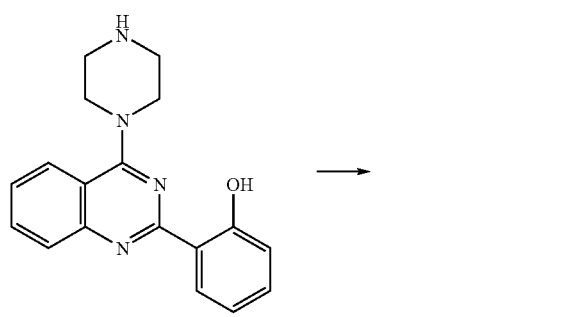

A solution of 2-(4-(piperazin-1-yl)quinazolin-2-yl)phenol (50 mg, 0.16 mmol), (pyridin-4-yl)methyl 1H-imidazole-1-carboxylate (67 mg, 0.32 mmol) and triethylamine (45 µL, 0.32 mmol) in DMSO (500 µL) was heated in a microwave synthesizer at 200° C. for 10 minutes. Purification using reverse phase HPLC (10%-99% CH$_3$CN (0.035% TFA)/H$_2$O (0.05% TFA)) gave (pyridin-4-yl)methyl 4-(2-(2-hydroxyphenyl)quinazolin-4-yl)piperazine-1-carboxylate as the TFA salt. LC/MS: m/z 442.50 (M+H)+ at 1.96 min (10%-99% CH$_3$CN (0.035% TFA)/H$_2$O (0.05% TFA)).

Example 117

(S)-Tetrahydrofuran-3-yl 4-(6-fluoro-2-(2-hydroxyphenyl)quinazolin-4-yl)piperazine-1-carboxylate

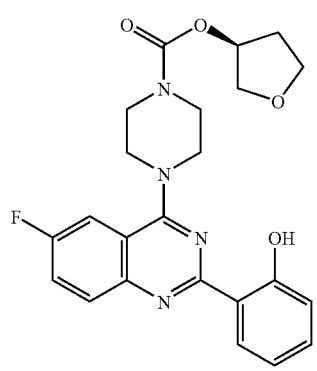

(S)-Tetrahydrofuran-3-yl chloroformate

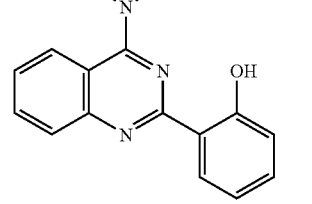

A stirred solution of (S)-tetrahydrofuran-3-ol (7.9 g, 90 mmol) in anhydrous CH$_2$Cl$_2$ (50 mL) under an N$_2$ atmosphere was cooled in an ice bath, and a 20% solution of phosgene in toluene (134 mL, 270 mmol) was slowly added. The reaction was allowed to warm to room temperature overnight, and the solvent was removed under vacuum to afford (S)-tetrahydrofuran-3-yl chloroformate (12.1 g, 85%) as a clear liquid. $^1$H NMR (400 MHz, CDCl$_3$) d 5.42-5.39 (m, 1H), 4.01-3.84 (m, 4H), 2.31-2.13 (m, 2H) ppm.

(S)-Tetrahydrofuran-3-yl 4-(6-fluoro-2-(2-hydroxyphenyl)quinazolin-4-yl)piperazine-1-carboxylate

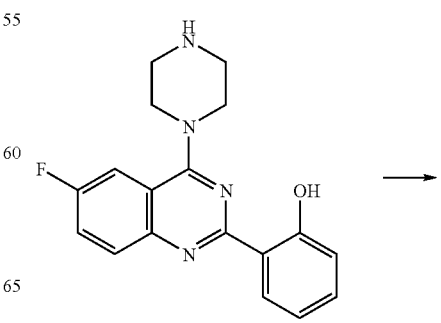

-continued

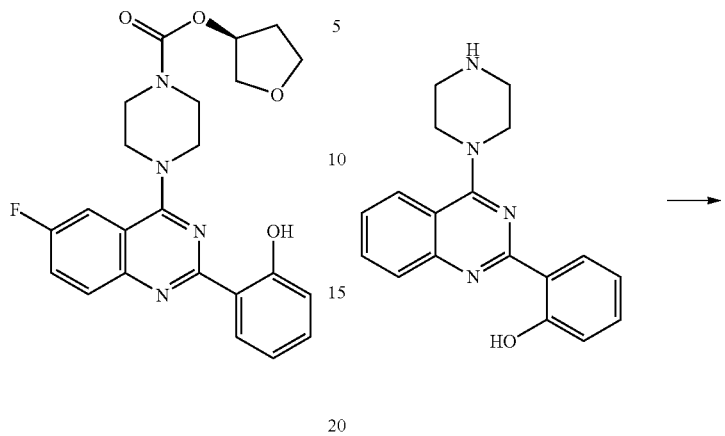

To a solution of 2-(6-fluoro-4-(piperazin-1-yl)quinazolin-2-yl)phenol (25 mg, 0.08 mmol) in DMF (1 mL) was added triethylamine (22 mL, 0.16 mmol) followed by the dropwise addition of (S)-tetrahydrofuran-3-yl chloroformate (12 mg, 0.08 mmol) at 0° C. The reaction was complete immediately after the addition of the chloroformate. Purification using reverse phase HPLC (10%-99% $CH_3CN$ (0.035% TFA)/$H_2O$ (0.05% TFA)) gave (S)-tetrahydrofuran-3-yl 4-(6-fluoro-2-(2-hydroxyphenyl)quinazolin-4-yl)piperazine-1-carboxylate as the TFA salt. LC/MS: m/z 439.5 (M+H)$^+$ at 2.79 min (10%-99% $CH_3CN$ (0.035% TFA)/$H_2O$ (0.05% TFA)).

Example 118

(R)-2-Hydroxy-1-(4-(2-(2-hydroxyphenyl)quinazolin-4-yl)piperazin-1-yl)butan-1-one

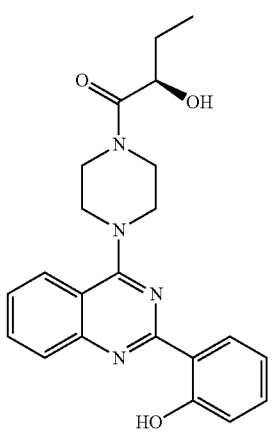

(R)-2-Hydroxy-1-(4-(2-(2-hydroxyphenyl)quinazolin-4-yl)piperazin-1-yl)butan-1-one

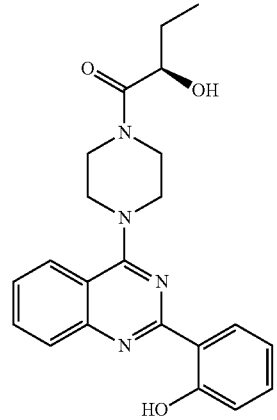

Method A

A solution of 2-(4-(piperazin-1-yl)quinazolin-2-yl)phenol (70 mg, 0.23 mmol) in DMF (0.5 mL) was added to (R)-2-hydroxybutanoic acid (31 mg, 0.297 mmol), followed by the addition of triethylamine (63 μL), then a solution of HATU (113 mg) in 0.5 mL DMF at room temperature. The reaction was stirred overnight. Purification using reverse phase HPLC (10%-99% $CH_3CN$ (0.035% TFA)/$H_2O$ (0.05% TFA)) gave (R)-2-hydroxy-1-(4-(2-(2-hydroxyphenyl)quinazolin-4-yl) piperazin-1-yl)butan-1-one as the TFA salt. LC/MS: m/z 393.30 (M+H)$^+$ at 2.22 min (10%-99% $CH_3CN$ (0.035% TFA)/$H_2O$ (0.05% TFA)).

Method B

To a solution of 2-(4-(piperazin-1-yl)quinazolin-2-yl)phenol (250 mg, 0.82 mmol) in $CH_2Cl_2$ (6 mL) was added triethylamine (227 μL, 1.63 mmol) followed by the addition of (R)-2-hydroxybutanoic acid (110 mg, 1.06 mmol) and HATU (380 mg, 1.00 mmol). The reaction mixture was stirred at room temperature for 3 h and then quenched with $H_2O$. The aqueous layer was extracted twice with $CH_2Cl_2$, dried over $MgSO_4$, filtered, and concentrated. Purification via silica gel chromatography using 0-10% EtOAc in 50:50 $CH_2Cl_2$:hexanes gave (R)-2-hydroxy-1-(4-(2-(2-hydroxyphenyl)quinazolin-4-yl)piperazin-1-yl)butan-1-one (280 mg, 88%). LC/MS: m/z 393.3 (M+H)$^+$ at 2.17 min (10%-99% $CH_3CN$ (0.035% TFA)/$H_2O$ (0.05% TFA)). $^1$H NMR (400 MHz, DMSO-d6) d 8.47 (m, 1H), 8.12 (d, J=8.3 Hz, 1H), 7.89 (m, 2H), 7.57 (m, 1H), 7.40 (m, 1H), 6.96 (m, 2H), 4.92 (d, J=7.1 Hz, 1H), 3.88 (m, 8H), 1.67 (m, 1H), 1.51 (m, 1H), 0.91 (t, J=7.4 Hz, 3H) ppm.

(R)-2-Hydroxy-1-(4-(2-(2-hydroxyphenyl)quinazolin-4-yl)piperazin-1-yl)butan-1-one hydrochloride

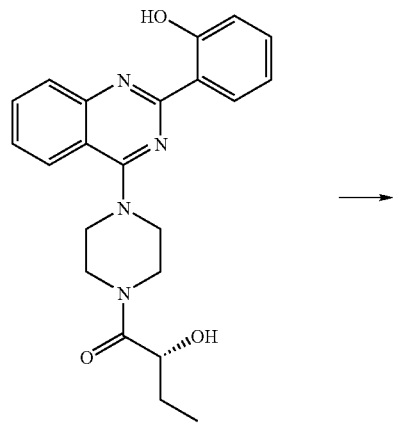

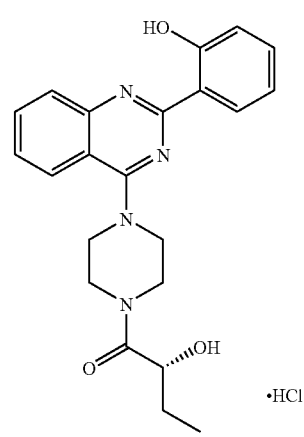

To a solution of (R)-2-hydroxy-1-(4-(2-(2-hydroxyphenyl) quinazolin-4-yl)piperazin-1-yl)butan-1-one (280 mg, 0.71 mmol) in $CH_2Cl_2$ under an $N_2$ atmosphere was added a 2 M HCl solution in ether (0.355 mL, 0.71 mmol), followed by the addition of ether which resulted in the formation of precipitate which was stirred for an hour and then filtered and dried to afford (R)-2-hydroxy-1-(4-(2-(2-hydroxyphenyl)quinazolin-4-yl)piperazin-1-yl)butan-1-one hydrochloride (272 mg, 90%). LC/MS: m/z 393.1 (M+H)$^+$ at 2.23 min (10%-99% $CH_3CN$ (0.035% TFA)/$H_2O$ (0.05% TFA)). $^1$H NMR (400 MHz, DMSO-d6) d 8.27 (dd, J=7.9, 1.6 Hz, 1H), 8.19 (d, J=8.4 Hz, 1H), 7.96 (m, 2H), 7.65 (m, 1H), 7.48 (m, 1H), 7.04 (m, 2H), 4.26 (dd, J=7.7, 4.8 Hz, 1H), 4.03 (m, 4H), 3.79 (m, 5H), 1.65 (m, 1H), 1.50 (m, 1H), 0.90 (t, J=7.4 Hz, 3H) ppm.

Example 119

(S)-3-Hydroxymethyl-4-[2-(2-hydroxyphenyl)-7-methyl-quinazolin-4-yl]-piperazine-1-carboxylic acid tetrahydro-furan-3-yl ester

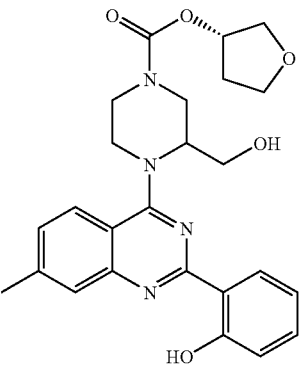

(S)-3-Hydroxymethyl-4-[2-(2-hydroxy-phenyl)-7-methyl-quinazolin-4-yl]-piperazine-1-carboxylic acid tetrahydro-furan-3-yl ester

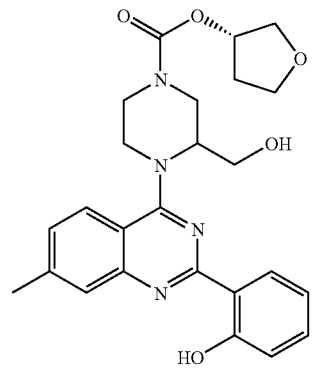

To 2-[4-(2-hydroxymethyl-piperazin-1-yl)-7-methyl-quinazolin-2-yl]-phenol (69.2 mg, 0.19 mmol) in 650 μL of $CH_2Cl_2$ at 0° C. was added (S)-tetrahydro-furan-3-ol-chloroformate (26.8 mg, 0.17 mmol), followed by triethylamine (30 μL, 0.22 mmol). The reaction mixture was stirred for an hour and then diluted with 5 mL of $CH_2Cl_2$ and 5 mL of water, and the organic layer was separated and dried over $Na_2SO_4$. The solvent was removed under reduced pressure, and the residue was subjected to purification using 30-100% EtOAc-hexanes to give the desired product. LC/MS: m/z 465.2 (M+H)$^+$ at 2.5 min (10%-99% CH$_3$CN (0.035% TFA)/H$_2$O (0.05% TFA)).

Example 121

(R)-2-Hydroxy-1-(4-(2-(2-hydroxyphenyl)quinazolin-4-yl)piperazin-1-yl)butan-1-one

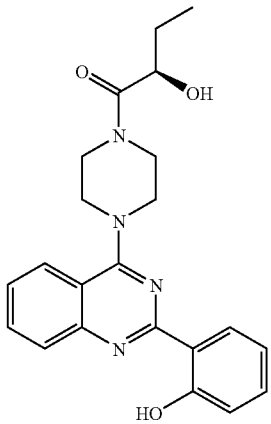

(R)-2-Hydroxy-1-(4-(2-(2-hydroxyphenyl)quinazolin-4-yl)piperazin-1-yl)butan-1-one

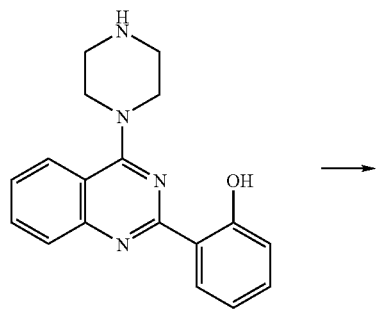

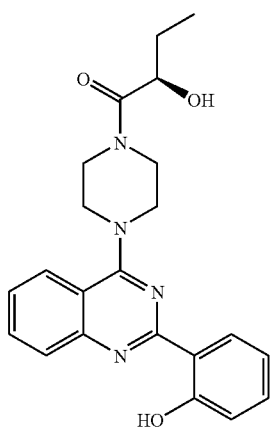

A solution of 2-(4-(piperazin-1-yl)quinazolin-2-yl)phenol (70 mg, 0.23 mmol) in DMF (0.5 mL) was added to (R)-2-hydroxybutanoic acid (31 mg, 0.297 mmol). It was followed by the addition of triethylamine (63 µL), then a solution of HATU (113 mg) in 0.5 mL DMF at room temperature. The reaction was stirred overnight. Purification using reverse phase HPLC (10-99% CH$_3$CN (0.035% TFA)/H$_2$O (0.05% TFA)) gave (R)-2-hydroxy-1-(4-(2-(2-hydroxyphenyl)quinazolin-4-yl)piperazin-1-yl)butan-1-one as the TFA salt. LC/MS: m/z 393.3 (M+H)$^+$ at 2.21 min (10%-99% CH$_3$CN (0.035% TFA)/H$_2$O (0.05% TFA)).

Example 122

2-Ethyl-2-hydroxy-1-(4-(2-(2-hydroxyphenyl)-7-methylquinazolin-4-yl)piperazin-1-yl)butan-1-one

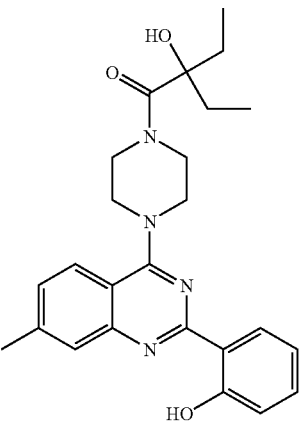

2-Ethyl-2-hydroxy-1-(4-(2-(2-hydroxyphenyl)-7-methylquinazolin-4-yl)piperazin-1-yl)butan-1-one

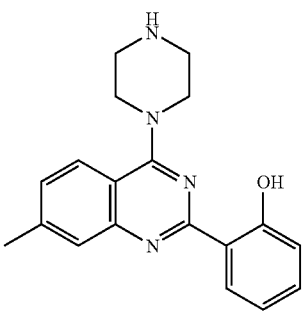

-continued

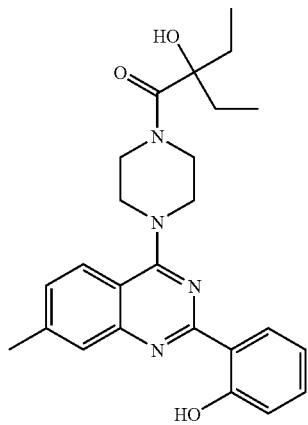

A solution of 2-(7-methyl-4-(piperazin-1-yl)quinazolin-2-yl)phenol (70 mg, 0.22 mmol) in DMF (0.5 mL) was added to 2-ethyl-2-hydroxybutanoic acid (37.5 mg, 0.284 mmol). It was followed by the addition of triethylamine (61 µL), then a solution of HATU (108 mg) in 0.5 mL DMF at room temperature. The reaction was stirred overnight. Purification using reverse phase HPLC (10-99% CH$_3$CN (0.035% TFA)/ H$_2$O (0.05% TFA)) gave 2-ethyl-2-hydroxy-1-(4-(2-(2-hydroxyphenyl)-7-methylquinazolin-4-yl)piperazin-1-yl)butan-1-one as the TFA salt. LC/MS: m/z 435.3 (M+H)$^+$ at 2.56 min (10%-99% CH$_3$CN (0.035% TFA)/H$_2$O (0.05% TFA)).

Example 123

4-[4-((R)-2-Hydroxy-4-methyl-pentanoyl)-piperazin-1-yl]-2-(2-hydroxy-phenyl)-quinazoline-7-carboxylic acid

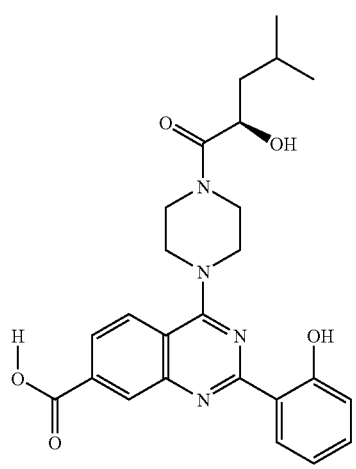

(R)-α-hydroxyisocaproic acid

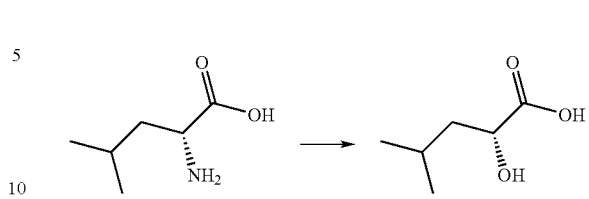

To a cooled solution (0-5° C.) of D-leucine (200 g, 1.5 mol) in sulfuric acid (3 L, 1 M) was added dropwise a solution of sodium nitrite (240 g, 3.5 mol) in water (1 L) while maintaining the temperature between 0-5° C. The reaction mixture was stirred at room temperature overnight. The solution was saturated with sodium chloride and extracted with tert-butyl methyl ether (3×). The combined organic layers were dried over Na$_2$SO$_4$ and filtered, and the solvent was removed in vacuo. (R)-α-hydroxyisocaproic acid was isolated as a white solid in a yield of 67% (132 g).

(R)-1-(4-Benzyl-piperazin-1-yl)-2-hydroxy-4-methyl-pentan-1-one

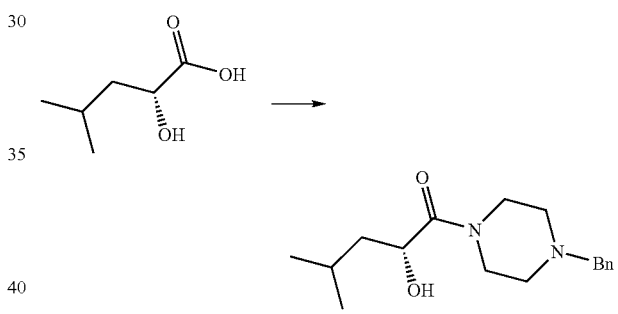

To a cooled solution (0-5° C.) of (R)-α-hydroxyisocaproic acid (64.5 g, 0.5 mol), 1-benzylpiperazine (88 g, 0.5 mol) and triethylamine (71 ml, 0.5 mol) in CH$_2$Cl$_2$ (850 ml) was added in portions HOBt (68 g, 0.5 mol) and EDCI.HCl (96 g, 0.5 mol). The reaction mixture was stirred at room temperature overnight. The organic layer was washed with water (3×) and once with brine, dried over Na$_2$SO$_4$, and filtered, and the solvent was removed in vacuo. Crude (R)-1-(4-benzyl-piperazin-1-yl)-2-hydroxy-4-methyl-pentan-1-one (132 g, 91%) was used in the next step without further purification.

(R)-2-Hydroxy-4-methyl-1-piperazin-1-yl-pentan-1-one

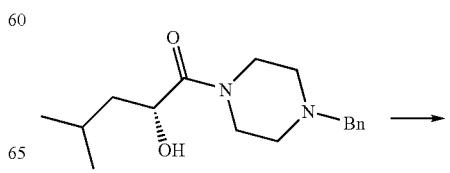

-continued

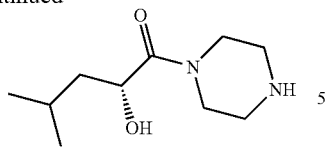

To a solution of 1-(4-benzyl-piperazin-1-yl)-2-hydroxy-4-methyl-pentan-1-one (132 g) in methanol (1 L) was added Pd/C (20 g, 10% weight Pd on carbon). The reaction mixture was stirred at room temperature overnight under an atmosphere of hydrogen. The reaction mixture was filtered through Celite, and the solvent was removed in vacuo. (R)-2-Hydroxy-4-methyl-1-piperazin-1-yl-pentan-1-one was obtained as an oil (68 g, 74%).

1,2,3,4-Tetrahydro-2,4-dioxoquinazoline-7-carboxylic acid

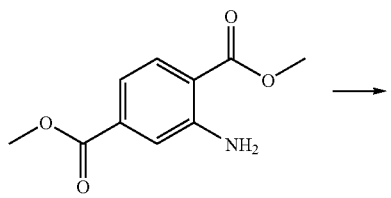

To a stirring mixture of dimethyl 2-aminobenzene-1,4-dioate (10.5 g, 50 mmol) and AcOH (3.4 mL, 60 mmol) in H$_2$O (200 mL) was added KOCN (8.1 g, 100 mmol). The reaction mixture was heated at 100° C. for 3 h. After cooling in an ice bath, NaOH (24 g, 600 mmol) was slowly added to the mixture and stirred for another 3 h at room temperature. Acidification with concentrated HCl resulted in formation of a yellow solid which was filtered, washed with water and dried under vacuum (8.3 g). NMR data showed that the solid consisted of a 3:1 mixture of the desired 1,2,3,4-tetrahydro-2,4-dioxoquinazoline-7-carboxylic acid and a side product. This mixture was used in the next step without further purification. $^1$H NMR (400 MHz, DMSO-d6) d 7.98 (d, J=8.2 Hz, 1H), 7.75 (d, J=1.2 Hz, 1H), 7.67 (dd, J=8.2, 1.4 Hz, 1H) ppm.

2,4-Dichloroquinazoline-7-carboxylic acid

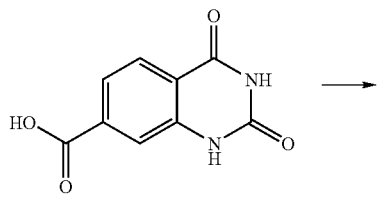

-continued

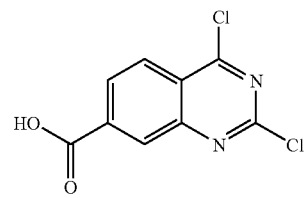

A mixture of 1,2,3,4-tetrahydro-2,4-dioxoquinazoline-7-carboxylic acid (1.0 g, 4.9 mmol), POCl$_3$ (10 mL) and dimethylaniline (0.5 mL, 3.94 mmol) was heated at 90° C. for 3 h. After cooling and pouring the reaction mixture over ice, it was extracted with EtOAc. The combined extracts were washed with water, dried over Na$_2$SO$_4$ and concentrated. Purification via silica gel chromatography using 0-10% MeOH/CH$_2$Cl$_2$ provided 2,4-dichloroquinazoline-7-carboxylic acid as a yellow solid (0.45 g, 38%). $^1$H NMR (400 MHz, DMSO-d6) d 8.46 (d, J=1.4 Hz, 1H), 8.42 (d, J=8.7 Hz, 1H), 8.30 (dd, J=8.6, 1.5 Hz, 1H); LC/MS: m/z 243.1 (M+H)$^+$ at 2.49 min (10%-99% CH$_3$CN (0.035% TFA)/H$_2$O (0.05% TFA)) ppm.

2-Chloro-4-[4-((R)-2-hydroxy-4-methyl-pentanoyl)-piperazin-1-yl]-quinazoline-7-carboxylic acid

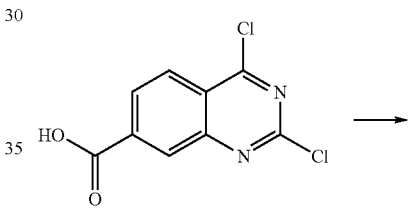

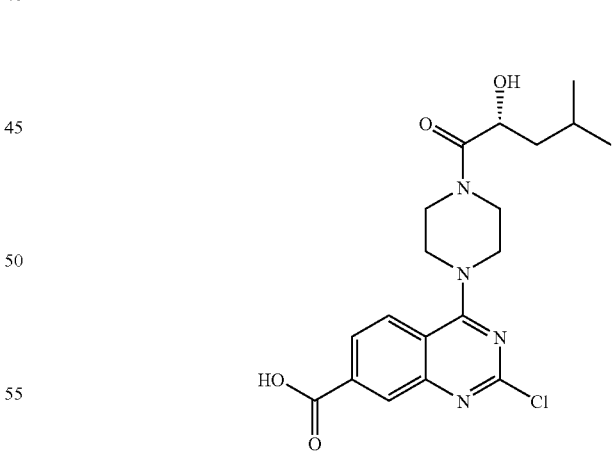

To a solution of 2,4-dichloroquinazoline-7-carboxylic acid (0.45 g, 1.9 mmol) in CH$_2$Cl$_2$ (20 mL) was added (R)-2-hydroxy-4-methyl-1-piperazin-1-yl-pentan-1-one (0.37 g, 1.9 mmol) and triethylamine (0.52 mL, 3.7 mmol). The reaction mixture was stirred overnight at room temperature and then purified via silica gel chromatography using 0-10% MeOH/CH$_2$Cl$_2$ to obtain 2-chloro-4-[4-((R)-2-hydroxy-4-methyl-pentanoyl)-piperazin-1-yl]-quinazoline-7-carboxylic acid (0.58 g, 77%). LC/MS: m/z 407.3 (M+H)+ at 2.44 min (10%-99% CH₃CN (0.035% TFA)/H₂O (0.05% TFA)).

4-[4-((R)-2-Hydroxy-4-methyl-pentanoyl)-piperazin-1-yl]-2-(2-hydroxy-phenyl)-quinazoline-7-carboxylic acid

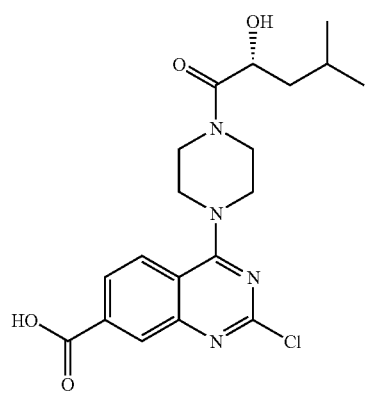

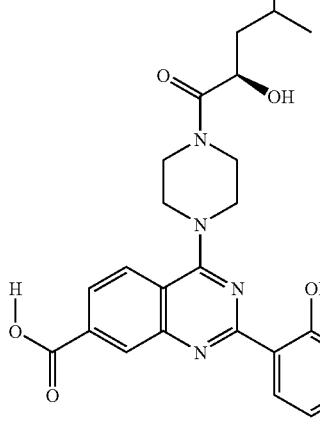

A mixture of 2'-chloro-4-[4-((R)-hydroxy-4-methyl-pentanoyl)-piperazin-1-yl]-quinazoline-7-carboxylic acid (114 mg, 0.28 mmol), 2-(4,4,5,5-tetramethyl-1,3,2-dioxaborolan-2-yl)phenol (88 µL, 0.42 mmol) Pd(dppf)Cl₂ (14 mg, 0.017 mmol) and K₂CO₃ (155 mg, 1.1 mmol) in DMF (4 mL) and H₂O (1 mL) was heated in a sealed microwave vial at 170° C. for 6 minutes. After filtration and evaporation of the solvents, the mixture was purified using preparative HPLC (10-99% CH₃CN (0.035% TFA)/H₂O (0.05% TFA)) to give 4-[4-((R)-2-hydroxy-4-methyl-pentanoyl)-piperazin-1-yl]-2-(2-hydroxy-phenyl)-quinazoline-7-carboxylic acid as the TFA salt.

LC/MS: m/z 465.3 (M+H)+ at 2.50 min (10%-99% CH₃CN (0.035% TFA)/H₂O (0.05% TFA)).

Example 124

(S)-2-Hydroxy-1-(4-(2-(2-hydroxyphenyl)-7-methylquinazolin-4-yl)piperazin-1-yl)butan-1-one

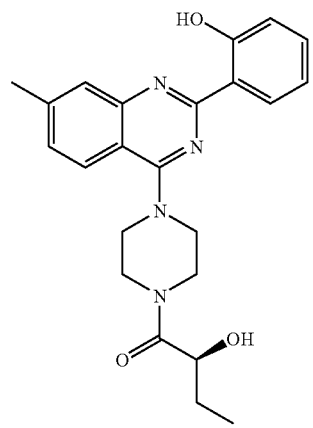

(S)-2-Hydroxy-1-(4-(2-(2-hydroxyphenyl)-7-methylquinazolin-4-yl)piperazin-1-yl)butan-1-one

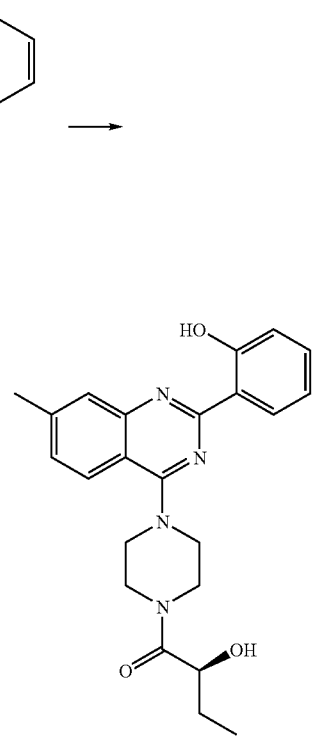

Method A: A solution of 2-(7-methyl-4-(piperazin-1-yl)quinazolin-2-yl)phenol (70 mg, 0.22 mmol) in DMF (0.5 mL) was added to (S)-2-hydroxybutanoic acid (31 mg, 0.297 mmol). It was followed by the addition of triethylamine (63 µL), then a solution of HATU (113 mg) in 0.5 mL DMF at room temperature. The reaction was stirred overnight. Purification using reverse phase HPLC (10-99% CH$_3$CN (0.035% TFA)/H$_2$O (0.05% TFA)) gave (S)-2-hydroxy-1-(4-(2-(2-hydroxyphenyl)-7-methylquinazolin-4-yl)piperazin-1-yl)butan-1-one as the TFA salt. LC/MS: m/z 407.5 (M+H)$^+$ at 2.31 min (10%-99% CH$_3$CN (0.035% TFA)/H$_2$O (0.05% TFA)).

Method B: To a solution of 2-(7-methyl-4-(piperazin-1-yl)quinazolin-2-yl)phenol (250 mg, 0.78 mmol) in CH$_2$Cl$_2$ (6 mL) was added triethylamine (217 μL, 1.56 mmol) followed by the addition of (S)-2-hydroxybutanoic acid (105 mg, 1.0 mmol) and HATU (380 mg, 1.00 mmol). The reaction mixture was stirred at room temperature for 3 h and then quenched with H$_2$O. The aqueous layer was extracted twice with CH$_2$Cl$_2$, dried over MgSO$_4$, filtered, and concentrated. Purification via silica gel chromatography using 0-10% EtOAc in 50:50 CH$_2$Cl$_2$:hexanes gave (S)-2-hydroxy-1-(4-(2-(2-hydroxyphenyl)-7-methylquinazolin-4-yl)piperazin-1-yl)butan-1-one (300 mg, 95%). LC/MS: m/z 407.5 (M+H)$^+$ at 2.31 min (10%-99% CH$_3$CN (0.035% TFA)/H$_2$O (0.05% TFA)). $^1$H NMR (400 MHz, DMSO-d6) d 8.45 (m, 1H), 8.01 (d, J=8.5 Hz, 1H), 7.70 (s, 1H), 7.39 (m, 2H), 6.95 (m, 2H), 4.92 (d, J=7.0 Hz, 1H), 4.28 (q, J=6.5 Hz, 1H), 3.89 (m, 8H), 2.52 (s, 3H), 1.67 (m, 1H), 1.51 (m, 1H), 0.91 (t, J=7.4 Hz, 3H) ppm.

(S)-2-Hydroxy-1-(4-(2-(2-hydroxyphenyl)-7-methylquinazolin-4-yl)piperazin-1-yl)butan-1-one hydrochloride

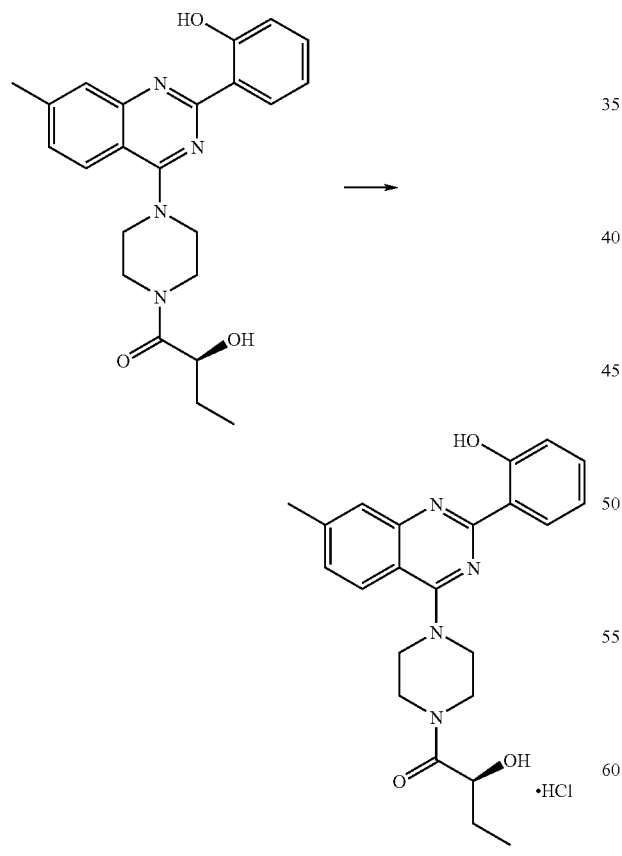

To a solution of (S)-2-hydroxy-1-(4-(2-(2-hydroxyphenyl)-7-methylquinazolin-4-yl)piperazin-1-yl)butan-1-one (300 mg, 0.73 mmol) in CH$_2$Cl$_2$ was added a 2 M HCl solution in ether (0.365 mL, 0.73 mmol), followed by the addition of ether until the salt precipitated out, which was stirred for an hour, collected by vacuum filtration and dried to afford (S)-2-hydroxy-1-(4-(2-(2-hydroxyphenyl)-7-methylquinazolin-4-yl)piperazin-1-yl)butan-1-one hydrochloride (270 mg, 84%). LC/MS: m/z 407.5 (M+H)$^+$ at 2.31 min (10%-99% CH$_3$CN (0.035% TFA)/H$_2$O (0.05% TFA)). $^1$H NMR (400 MHz, DMSO-d6) d 8.26 (dd, J=7.9, 1.6 Hz, 1H), 8.07 (d, J=8.6 Hz, 1H), 7.73 (s, 1H), 7.47 (m, 2H), 7.03 (m, 2H), 4.26 (dd, J=7.7, 4.8 Hz, 1H), 4.08 (m, 4H), 3.79 (m, 4H), 2.53 (s, 3H), 1.65 (m, 1H), 1.50 (m, 1H), 0.89 (t, J=7.4 Hz, 3H) ppm.

Example 125

(R)-4-Fluoro-2-hydroxy-1-{4-[2-(2-hydroxy-phenyl)-7-methyl-quinazolin-4-yl]-piperazin-1-yl}-4-methyl-pentan-1-one

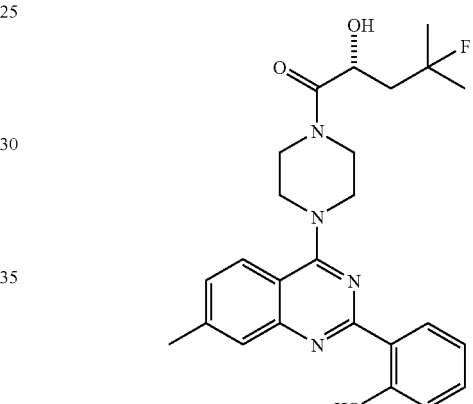

4-{4-[2-(2-Hydroxy-phenyl)-7-methyl-quinazolin-4-yl]-piperazin-1-yl}-4-oxo-but-2-enoic acid ethyl ester

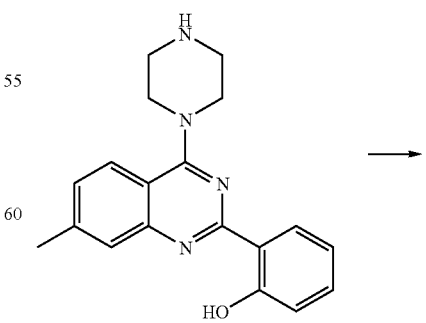

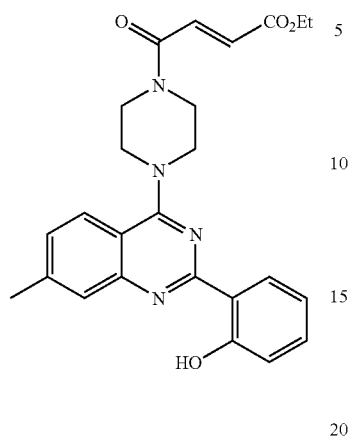

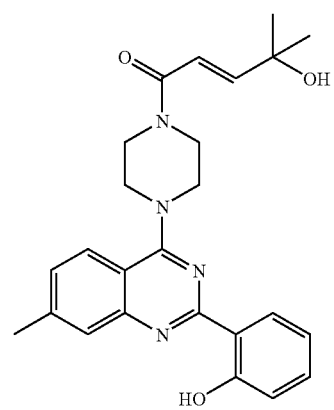

To 2-(7-methyl-4-piperazin-1-yl-quinazolin-2-yl)-phenol (787 mg, 2.46 mmol) in 8 mL of CH$_2$Cl$_2$ at room temperature was added sequentially but-2-enedioic acid monoethyl ester (531 mg, 3.69 mmol), triethylamine (686 µL, 4.92 mmol), BOP (1.63 g, 3.69 mmol). The reaction mixture was stirred for 20 min and diluted with water and CH$_2$Cl$_2$. The organic layer was separated and dried over Na$_2$SO$_4$, and the solvent was removed under reduced pressure to give an oil. The residue was subjected to purification by normal phase LC using 10-100% EtOAc-hexanes to give 4-{4-[2-(2-Hydroxy-phenyl)-7-methyl-quinazolin-4-yl]-piperazin-1-yl}-4-oxo-but-2-enoic acid ethyl ester (1.00 g, 91% yield). LC/MS: m/z 447.3 (M+H)$^+$ at 2.93 min (10%-99% CH$_3$CN (0.035% TFA)/H$_2$O (0.05% TFA)).

To 4-{4-[2-(2-hydroxy-phenyl)-7-methyl-quinazolin-4-yl]-piperazin-1-yl}-4-oxo-but-2-enoic acid ethyl ester (655 mg, 1.47 mmol) in 2 mL of diethyl ether at −20° C. was added methyl magnesium bromide (8.4 mL, 11.7 mmol, 1.4 M THF/Toluene), and the reaction mixture was allowed to warm to 0° C. over 15 minutes The mixture was diluted with 10 mL of water and 15 mL of CH$_2$Cl$_2$. The resulting emulsion was filtered, and the organic layer was separated and dried over Na$_2$SO$_4$. The solvent was removed under reduced pressure to give the alcohol. LC/MS: m/z 433.5 (M+H)$^+$ at 2.56 min (10%-99% CH$_3$CN (0.035% TFA)/H$_2$O (0.05% TFA)).

4-Hydroxy-1-{4-[2-(2-hydroxy-phenyl)-7-methyl-quinazolin-4-yl]-piperazin-1-yl}-4-methyl-pent-2-en-1-one 4-Fluoro-1-{4-[2-(2-hydroxy-phenyl)-7-methyl-quinazolin-4-yl]-piperazin-1-yl}-4-methyl-pent-2-en-1-one

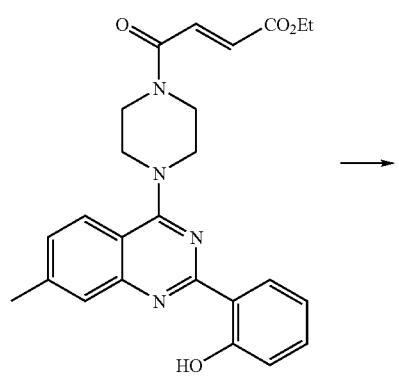

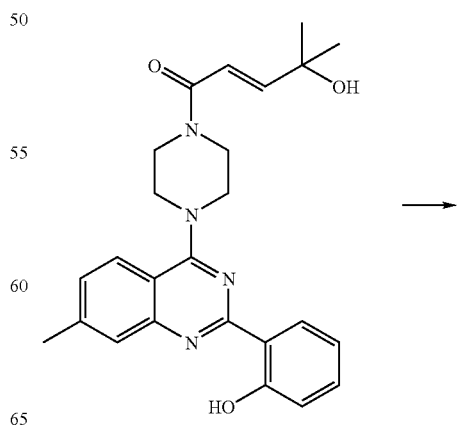

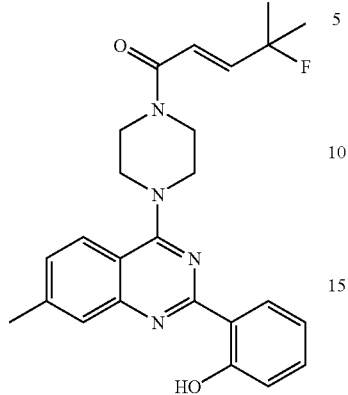

To 4-hydroxy-1-{4-[2-(2-hydroxy-phenyl)-7-methyl-quinazolin-4-yl]-piperazin-1-yl}-4-methyl-pent-2-en-1-one (330 mg, 0.76 mmol) at −78° C. in 3 mL of CH$_2$Cl$_2$ was added (diethylamino)sulfur trifluoride (185 mg, 1.15 mmol). The reaction mixture was stirred −78° C. for 2.5 h. The reaction mixture was diluted with 10 mL of water and 10 mL of CH$_2$Cl$_2$. The organic layer was separated and dried over Na$_2$SO$_4$, and the solvent was removed under reduced pressure to give an oil. The residue was subjected to purification by normal phase LC using 10-100% EtOAc-hexanes to give 4-fluoro-1-{4-[2-(2-hydroxy-phenyl)-7-methyl-quinazolin-4-yl]-piperazin-1-yl}-4-methyl-pent-2-en-1-one (133 mg, 40% yield). LC/MS: m/z 435.4.3 (M+H)$^+$ at 2.92 min (10%-99% CH$_3$CN (0.035% TFA)/H$_2$O (0.05% TFA)).

4-Fluoro-1-{4-[2-(2-hydroxy-phenyl)-7-methyl-quinazolin-4-yl]-piperazin-1-yl}-4-methyl-pentan-1-one

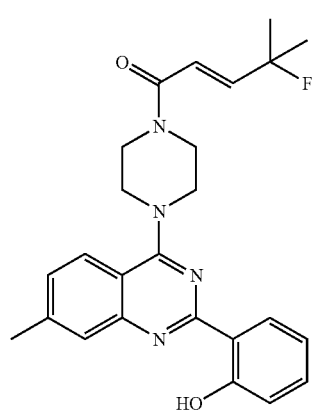

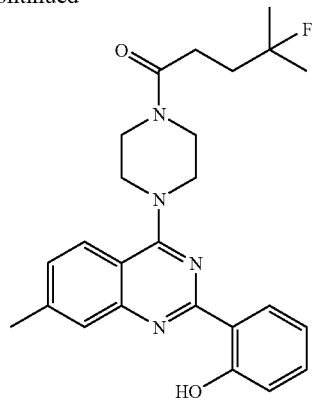

To 4-fluoro-1-{4-[2-(2-hydroxy-phenyl)-7-methyl-quinazolin-4-yl]-piperazin-1-yl}-4-methyl-pent-2-en-1-one (228 mg) in 1.5 mL of methanol was added Pd/C (34 mg, 10% weight Pd on carbon), and the reaction mixture was hydrogenated with a hydrogen balloon for 1 h. The resulting mixture was filtered through Celite, and the solvent was removed to give 4-fluoro-1-{4-[2-(2-hydroxy-phenyl)-7-methyl-quinazolin-4-yl]-piperazin-1-yl}-4-methyl-pentan-1-one. LC/MS: m/z 437.4 (M+H)$^+$ at 2.86 min (10%/99% CH$_3$CN (0.035% TFA)/H$_2$O (0.05% TFA)).

(R)-4-Fluoro-2-hydroxy-1-{4-[2-(2-hydroxy-phenyl)-7-methyl-quinazolin-4-yl]-piperazin-1-yl}-4-methyl-pentan-1-one

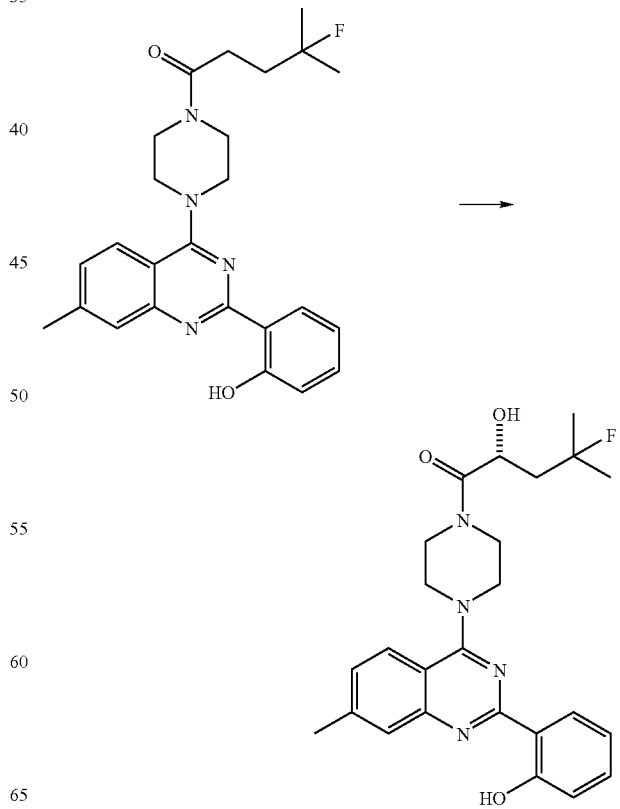

To 4-fluoro-1-{4-[2-(2-hydroxy-phenyl)-7-methyl-quinazolin-4-yl]-piperazin-1-yl}-4-methyl-pentan-1-one (225 mg, 0.53 mmol) in 500 μL of THF was added a 2.7 M LDA solution (0.8 mL, 2.1 mmol) at −78° C. The resulting solution was stirred at −78° C. for 25 min, and then (1R)-(−)-(10-camphorsulfonyl)oxaziridine (361 mg, 1.6 mmol) in 1.5 mL of THF was added slowly. The reaction mixture was allowed to warm to −45° C. over 30 min, and then diluted with water and $CH_2Cl_2$. The organic layer was separated and dried over $Na_2SO_4$, and the solvent was removed under reduced pressure. The residue was purified by preparative reverse phase HPLC using 10-99% $CH_3CN$ (0.035% TFA)/$H_2O$ (0.05% TFA) to give (R)-4-fluoro-2-hydroxy-1-{4-[2-(2-hydroxy-phenyl)-7-methyl-quinazolin-4-yl]-piperazin-1-yl}-4-methylpentan-1-one as the TFA salt. LC/MS: m/z 453.4 (M+H)$^+$ at 2.79 min (10%-99% $CH_3CN$ (0.035% TFA)/$H_2O$ (0.05% TFA)).

Example 126

3-Hydroxymethyl-4-[2-(2-hydroxy-phenyl)-7-methyl-quinazolin-4-yl]-piperazine-1-carboxylic acid phenyl ester

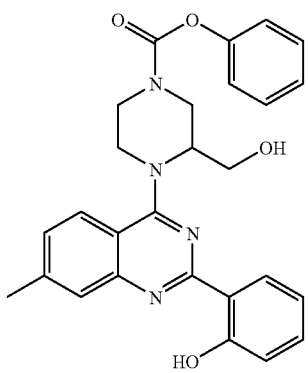

3-Hydroxymethyl-4-[2-(2-hydroxy-phenyl)-7-methyl-quinazolin-4-yl]-piperazine-1-carboxylic acid benzyl ester

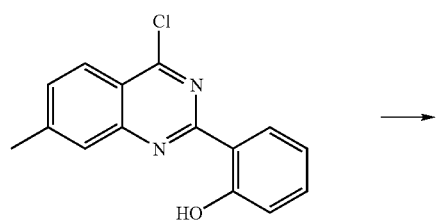

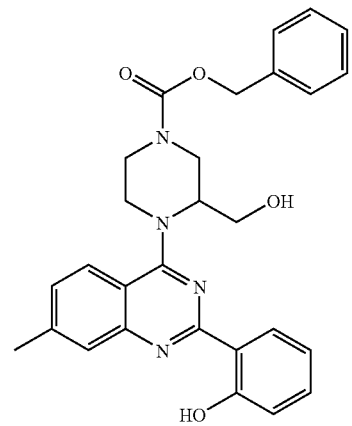

To 2-(4-chloro-7-methyl-quinazolin-2-yl)-phenol (245 mg, 0.91 mmol) in 3.0 mL of $CH_2Cl_2$ was added 3-hydroxymethyl-piperazine-1-carboxylic acid benzyl ester (226 mg, 0.58 mmol) and triethylamine (190 μL, 1.37 mmol). The reaction mixture was stirred for 12 hours at room temperature, and additional 3-hydroxymethyl-piperazine-1-carboxylic acid benzyl ester (100 mg, 0.4 mmol) and triethylamine (200 μL, 1.4 mmol) was added, and the reaction mixture was heated at 40° C. for 6 h. The reaction mixture was cooled, and diluted with 5 mL of $CH_2Cl_2$ and 5 mL of water, and the organic layer was separated and dried over $Na_2SO_4$. The solvent was removed under reduced pressure, and the residue was purified by silica gel chromatography eluting with 20-85% EtOAc/hexanes to give 3-hydroxymethyl-4-[2-(2-hydroxy-phenyl)-7-methyl-quinazolin-4-yl]-piperazine-1-carboxylic acid benzyl ester (216 mg, 65%). LCMS: m/z 485 (M+H)$^+$ at 3.03 min (10%-99% $CH_3CN/H_2O$)

2-[4-(2-Hydroxymethyl-piperazin-1-yl)-7-methyl-quinazolin-2-yl]-phenol

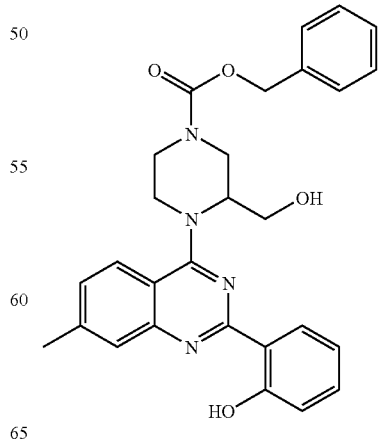

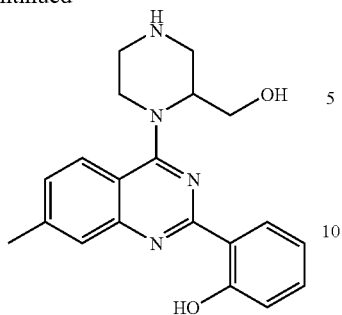

To 3-hydroxymethyl-4-[2-(2-hydroxy-phenyl)-7-methyl-quinazolin-4-yl]-piperazine-1-carboxylic acid benzyl ester (200 mg, 0.41 mmol) in 1.7 mL of methanol was added 39 mg of Pd/C (10% wt Pd on carbon). The reaction mixture was stirred under a hydrogen atmosphere for 3 h. The mixture was filtered through Celite, and the solvent was removed to give 2-[4-(2-hydroxymethyl-piperazin-1-yl)-7-methyl-quinazolin-2-yl]-phenol. LCMS: m/z 351.2 (M+H)$^+$ at 2.11 min (10%-99% CH$_3$CN/H$_2$O).

3-Hydroxymethyl-4-[2-(2-hydroxy-phenyl)-7-methyl-quinazolin-4-yl]-piperazine-1-carboxylic acid phenyl ester

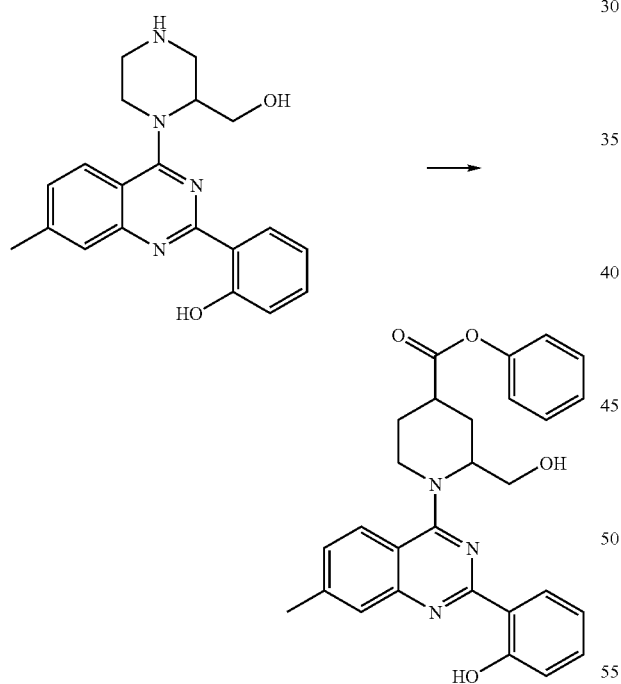

To 2-[4-(2-hydroxymethyl-piperazin-1-yl)-7-methyl-quinazolin-2-yl]-phenol (31.9 mg, 0.091 mmol) in 300 μL of CH$_2$Cl$_2$ was added at 0° C. sequentially triethylamine (13.9 μL) and phenyl chloroformate (14.3 mg, 0.091 mmol). The reaction mixture was stirred for 30 min and was warmed to room temperature and stirred for an additional 40 minutes At the end of this period, the solvent was removed, and the residue was dissolved in DMSO and purified by preparative reverse phase HPLC using 1099% CH$_3$CN (0.035% TFA)/H$_2$O (0.05% TFA) as eluent to give 3-hydroxymethyl-4-[2-(2-hydroxy-phenyl)-7-methyl-quinazolin-4-yl]-piperazine-1-carboxylic acid phenyl ester as the TFA salt. LC/MS: m/z 471.2 (M+H)$^+$ at 2.93 min (10%-99% CH$_3$CN (0.035% TFA)/H$_2$O (0.05% TFA)).

Example 127

3-Cyclopentyl-1-(4-(2-(2-hydroxyphenyl)-7-methylquinazolin-4-yl)piperazin-1-yl)propan-1-one

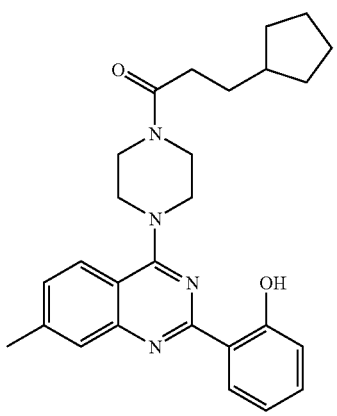

3-Cyclopentyl-1-(4-(2-(2-hydroxyphenyl)-7-methylquinazolin-4-yl)piperazin-1-yl)propan-1-one

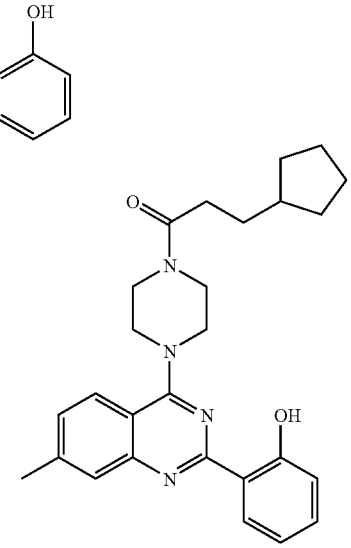

Method A

To 2-(7-methyl-4-(piperazin-1-yl)quinazolin-2-yl)phenol (53 mg, 0.17 mmol) was added sequentially 3-cyclopentylpropanoyl chloride (29 mg, 0.19 mmol) in 550 μL of CH$_2$Cl$_2$ and triethylamine (28 μL, 0.2 mmol). The mixture was stirred at 0° C. for 20 minutes. After adding H$_2$O and CH$_2$Cl$_2$, the phases were separated, and the organic layer was dried over Na₂SO₄ and concentrated under vacuum. Purification using preparative reverse phase HPLC (10-99% CH₃CN (0.035% TFA)/H₂O (0.05% TFA)) gave 3-cyclopentyl-1-(4-(2-(2-hydroxyphenyl)-7-methylquinazolin-4-yl)piperazin-1-yl)propan-1-one as the TFA salt. LC/MS: m/z 445.5 (M+H)⁺ at 2.32 min (10%-99% CH₃CN (0.035% TFA)/H₂O (0.05% TFA)).

Method B

A solution of 2-(7-methyl-4-(piperazin-1-yl)quinazolin-2-yl)phenol (200 mg, 0.62 mmol) in CH₂Cl₂ (6.0 mL) was stirred under an N₂ atmosphere. Then triethylamine (170 µL, 1.24 mmol) was added, and the reaction was cooled to −10 to −20° C. After adding 3-cyclopentylpropanoyl chloride (96 µL in 600 µL THF, 0.62 mmol), the reaction mixture was stirred for 30 minutes. CH₂Cl₂ was added, and the organic phase was washed 2× with H₂O, dried over Na₂SO₄, and concentrated. Purification via silica gel chromatography using 0-10% EtOAc in 50:50 CH₂Cl₂: hexanes gave 3-cyclopentyl-1-(4-(2-(2-hydroxyphenyl)-7-methylquinazolin-4-yl)piperazin-1-yl)propan-1-one (240 mg, 86%). LC/MS: m/z 445.50 (M+H)⁺ at 3.07 min (10%-99% CH₃CN (0.035% TFA)/H₂O (0.05% TFA)). ¹H NMR (400 MHz, DMSO-d6) d 8.45 (dd, J=8.2, 1.8 Hz, 1H), 8.00 (d, J=8.5 Hz, 1H), 7.69 (s, 1H), 7.39 (m, 2H), 6.95 (m, 2H), 3.95 (dd, J=19.9, 5.6 Hz, 4H), 3.74 (m, 4H), 2.52 (s, 3H), 2.38 (t, J=7.8 Hz, 2H), 1.76 (m, 3H), 1.55 (m, 6H), 1.16 (m, 2H) ppm.

3-Cyclopentyl-1-(4-(2-(2-hydroxyphenyl)-7-methylquinazolin-4-yl)piperazin-1-yl)propan-1-one hydrochloride

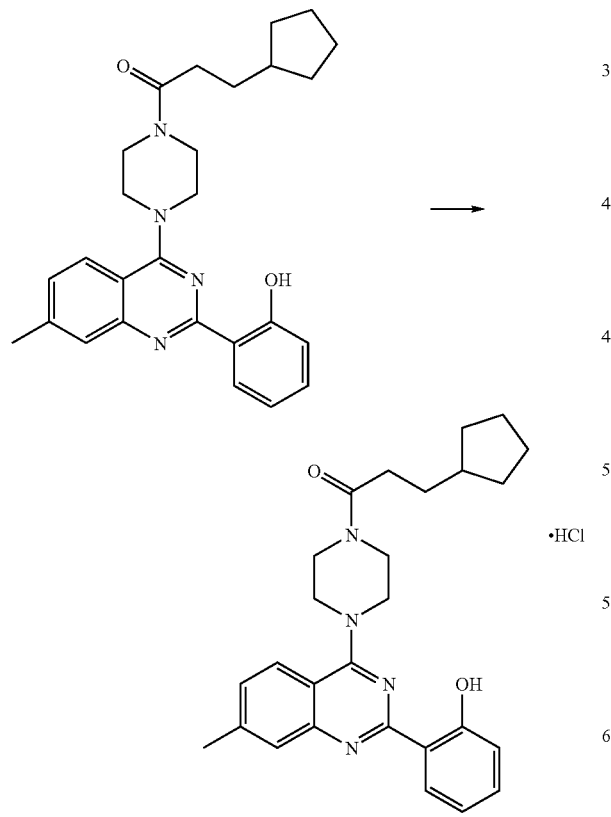

Under an N₂ atmosphere, a 1 M HCl solution in diethyl ether (0.54 mL, 0.54 mmol) was added dropwise to a stirring solution of 3-cyclopentyl-1-(4-(2-(2-hydroxyphenyl)-7-methylquinazolin-4-yl)piperazin-1-yl)propan-1-one (240 mg, 0.54 mmol) in CH₂Cl₂ (20 mL). After 10 min, ether was added until a precipitate formed. The solid was collected by filtration and dried under vacuum to give 3-cyclopentyl-1-(4-(2-(2-hydroxyphenyl)-7-methylquinazolin-4-yl)piperazin-1-yl)propan-1-one hydrochloride (230 mg, 88%). LC/MS: m/z 445.30 (M+H)⁺ at 3.08 min (10%-99% CH₃CN (0.035% TFA)4H₂O (0.05% TFA)). ¹H NMR (400 MHz, DMSO-d6) d 8.26 (d, J=8.0 Hz, 1H), 8.09 (d, J=8.5 Hz, 1H), 7.78 (s, 1H), 7.50-7.46 (m, 2H), 7.09 (d, J=8.1 Hz, 1H), 7.04-7.00 (m, 1H), 4.15-4.11 (m, 4H), 3.79-3.74 (m, 4H), 2.54 (s, 3H), 2.37 (t, J=7.7 Hz, 2H), 1.82-1.74 (m, 3H), 1.60-1.45 (m, 6H), 1.12-1.08 (m, 2H) ppm.

Example 128

1-(4-(6-Fluoro-2-(2-hydroxyphenyl)quinazolin-4-yl)piperazin-1-yl)-2-(tetrahydro-2H-pyran-4-yl)ethanone

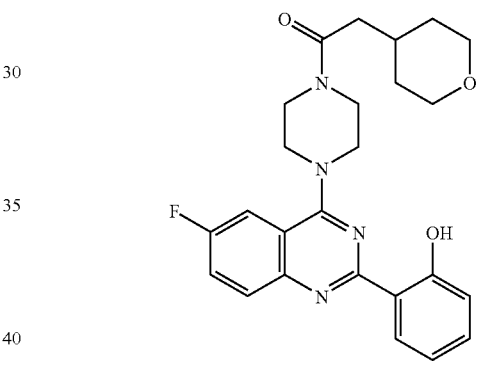

1-(4-(6-Fluoro-2-(2-hydroxyphenyl)quinazolin-4-yl)piperazin-1-yl)-2-(tetrahydro-2H-pyran-4-yl)ethanone

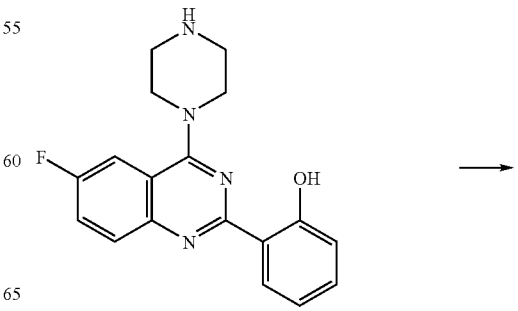

-continued

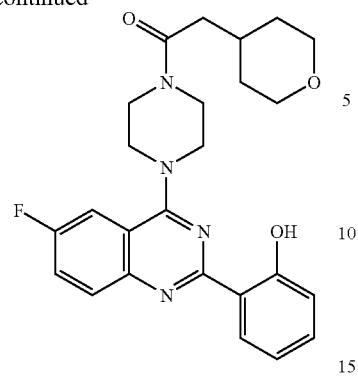

2-(6-Fluoro-4-(piperazin-1-yl)quinazolin-2-yl)phenol (25 mg, 0.077 mmol), 2-(tetrahydro-2H-pyran-4-yl)acetic acid (14.3 mg, 0.10 mmol), triethylamine (22 μL, 0.154 mmol), and HATU (38 mg, 0.10 mmol) were stirred in DMF (1 mL) overnight. Purification via reverse phase HPLC (10-99% CH$_3$CN (0.035% TFA)/H$_2$O (0.05% TFA)) gave 1-(4-(6-fluoro-2-(2-hydroxyphenyl)quinazolin-4-yl)piperazin-1-yl)-2-(tetrahydro-2H-pyran-4-yl)ethanone, TFA salt. LC/MS: m/z 451.5 (M+H)$^+$ at 2.60 min (10%-99% CH$_3$CN (0.035% TFA)/H$_2$O (0.05% TFA)).

Example 129

2-Hydroxy-1-(4-(2-(2-hydroxyphenyl)quinazolin-4-yl)piperazin-1-yl)-2-methylbutan-1-one

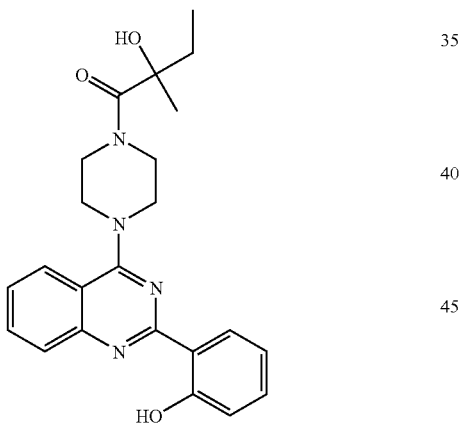

2-Hydroxy-1-(4-(2-(2-hydroxyphenyl)quinazolin-4-yl)piperazin-1-yl)-2-methylbutan-1-one

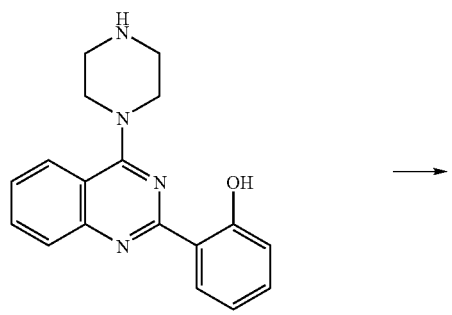

-continued

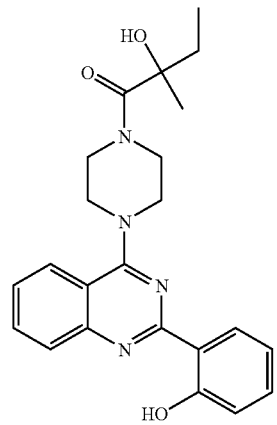

A solution of 2-(4-(piperazin-1-yl)quinazolin-2-yl)phenol (70 mg, 0.23 mmol) in DMF (0.5 mL) was added to 2-hydroxy-2-methylbutanoic acid (39.3 mg, 0.297 mmol). It was followed by the addition of triethylamine (63 μL) and a solution of HATU (113 mg) in 0.5 mL DMF at room temperature. The reaction was stirred overnight. Purification using reverse phase HPLC (10-99% CH$_3$CN (0.035% TFA)/H$_2$O (0.05% TFA)) gave 2-hydroxy-1-(4-(2-(2-hydroxyphenyl)quinazolin-4-yl)piperazin-1-yl)-2-methylbutan-1-one as the TFA salt. LC/MS: m/z 407.5 (M+H)$^+$ at 2.31 min (10%-99% CH$_3$CN (0.035% TFA)/H$_2$O (0.05% TFA)).

Example 130

(R)-2-Hydroxy-1-{4-[2-(2-hydroxy-phenyl)-7-methyl-quinazolin-4-yl]-piperazin-1-yl}-3-phenylpropan-1-one

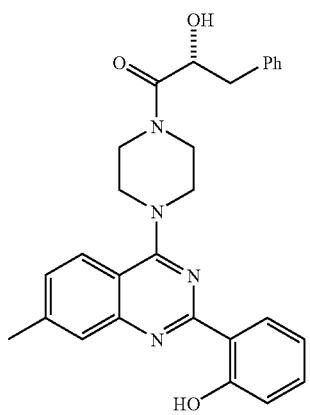

2-(7-Methyl-4-piperazin-1-yl-quinazolin-2-yl)-phenol, oxalate salt

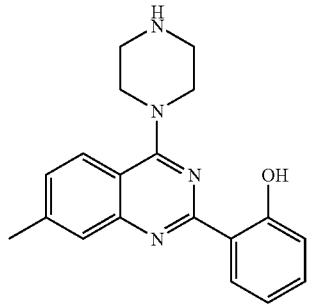

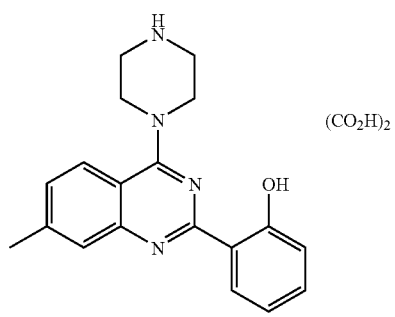

To 2-(7-Methyl-4-piperazin-1-yl-quinazolin-2-yl)-phenol (30.6 g, 95.4 mmol) in 900 mL CH$_2$Cl$_2$ was added oxalic acid (9.45 g, 105 mmol, 1.1 eq.) dissolved in 36 mL of methanol. The resulting cloudy solution was stirred for 3 h and the resulting solid was filtered, washed with hexanes, and dried to give 29.3 g (75%) the oxalate salt of 2-(7-Methyl-4-piperazin-1-yl-quinazolin-2-yl)-phenol. LC/MS: m/z 321.2 (M+H)$^+$ at 2.36 min (10%-99% CH$_3$CN (0.035% TFA)/H$_2$O (0.05% TFA)).

2-(7-Methyl-4-piperazin-1-yl-quinazolin-2-yl)-phenol

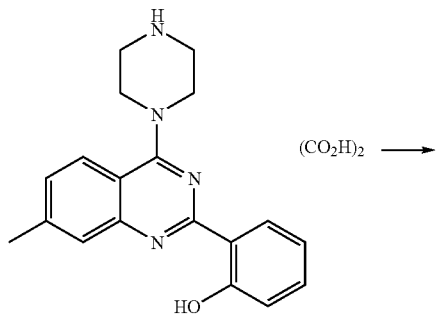

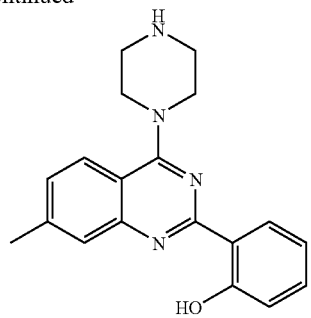

To the oxalate salt of 2-(7-methyl-4-piperazin-1-yl-quinazolin-2-yl)-phenol (1.32 g, 3.2 mmol) in 10 mL of CH$_2$Cl$_2$ was added triethylamine (2.2 mL, 16.0 mmol) at room temperature. The resulting mixture was stirred at room temperature for 30 minutes. The reaction mixture was diluted with 10 mL of water, and the organic layer was separated and dried over Na$_2$SO$_4$. The solvent was removed under reduced pressure to give 2-(7-methyl-4-piperazin-1-yl-quinazolin-2-yl)-phenol as an oil which was used without further purification.

(R)-2-Hydroxy-1-{4-[2-(2-hydroxy-phenyl)-7-methyl-quinazolin-4-yl]-piperazin-1-yl}-3-phenylpropan-1-one

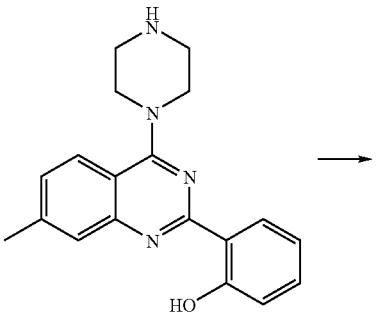

To 2-(7-methyl-4-piperazin-1-yl-quinazolin-2-yl)-phenol (64 mg, 0.19 mmol) in 600 µL of CH$_2$Cl$_2$ was added sequentially 3-(R)-phenyl lactic acid (35 mg, 0.21 mmol), BOP (93 mg, 0.21 mmol), and triethylamine (27.7 µL, 0.2 mmol) at room temperature. The reaction mixture was stirred for 1.5 h, diluted with 10 mL of methylene chloride, and washed with water (2×10 mL). The solvent was removed under reduced pressure to give an oil which was purified by normal phase LC (35%-100% EtOAc/hexanes) to give (R)-2-hydroxy-1-{4-[2-(2-hydroxy -phenyl)-7-methyl-quinazolin-4-yl]-piperazin-1-yl}-3-phenylpropan-1-one. LC/MS: m/z 469.3 (M+H)+ at 2.87 min (10%-99% CH₃CN (0.035% TFA)/H₂O (0.05% TFA)).

Example 131

(S)-2-Hydroxy-1-{4-[2-(2-hydroxy-phenyl)-7-methyl-quinazolin-4-yl]-piperazin-1-yl}-3-phenylpropan-1-one

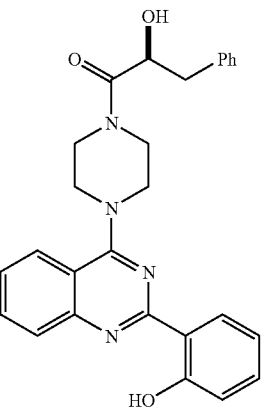

To 2-(7-methyl-4-piperazin-1-yl-quinazolin-2-yl)-phenol (79.9 mg, 0.25 mmol) in 800 μL of CH₂Cl₂ was added sequentially 3-(S)-phenyl lactic acid (41.4 mg, 0.25 mmol), BOP (110 mg, 0.25 mmol), triethylamine (34.7 μL, 0.25 mmol) at room temperature. The reaction mixture was stirred for 1.5 h, diluted with 10 mL of methylene chloride, and washed with water (2×10 mL). The solvent was removed under reduced pressure to give an oil which was purified by normal phase LC (35%-100% EtOAc/hexanes) to give (S)-2-hydroxy-1-{4-[2-(2-hydroxy-phenyl)-7-methyl-quinazolin-4-yl]-piperazin-1-yl}3-phenylpropan-1-one. LC/MS: m/z 469.4 (M+H)+ at 2.88 min (10%-99% CH₃CN (0.035% TFA)/H₂O (0.05% TFA)).

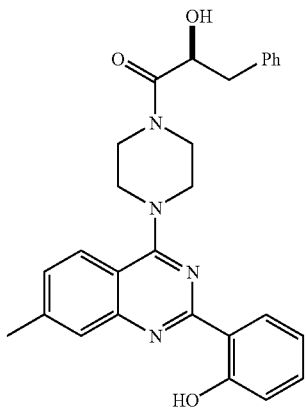

(S)-2-Hydroxy-1-{4-[2-(2-hydroxy-phenyl)-7-methyl-quinazolin-4-yl]-piperazin-1-yl}-3-phenylpropan-1-one Example 132

(Pyridin-3-yl)methyl 4-(2-(2-hydroxyphenyl)-7-methylquinazolin-4-yl)piperazine-1-carboxylate

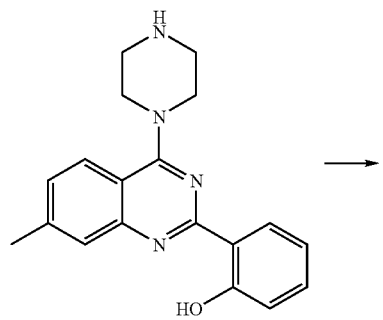

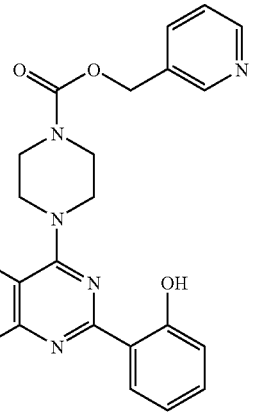

(Pyridin-3-yl)methyl 1H-imidazole-1-carboxylate

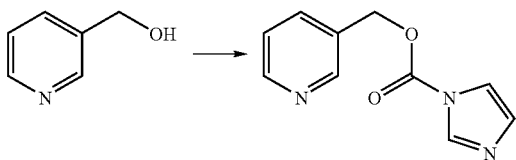

A solution of (pyridin-3-yl)methanol (2 g, 18.32 mmol) and di(1H-imidazol-1-yl)methanone (5.94 g, 36.65 mmol) in 20 mL $CH_2Cl_2$ was heated overnight at 50° C. The reaction was washed with water, dried over $MgSO_4$, filtered, and concentrated. Purification via silica gel chromatography using 10-70% EtOAc in $CH_2Cl_2$ gave (pyridin-3-yl)methyl 1H-imidazole-1-carboxylate (3 g, 81%). LC/MS: m/z 204.1 $(M+H)^+$ at 0.39 min (10%-99% $CH_3CN$ (0.035% TFA)/$H_2O$ (0.05% TFA)). $^1H$ NMR (400 MHz, $CDCl_3$) δ 8.74 (d, J=1.9 Hz, 1H), 8.68 (dd, J=4.8, 1.4 Hz, 1H), 8.16 (s, 1H), 7.81 (m, 1H), 7.44 (s, 1H), 7.38 (m, 1H), 7.09 (s, 1H), 5.46 (s, 2H) ppm.

(Pyridin-3-yl)methyl 4-(2-(2-hydroxyphenyl)-7-methylquinazolin-4-yl)piperazine-1-carboxylate

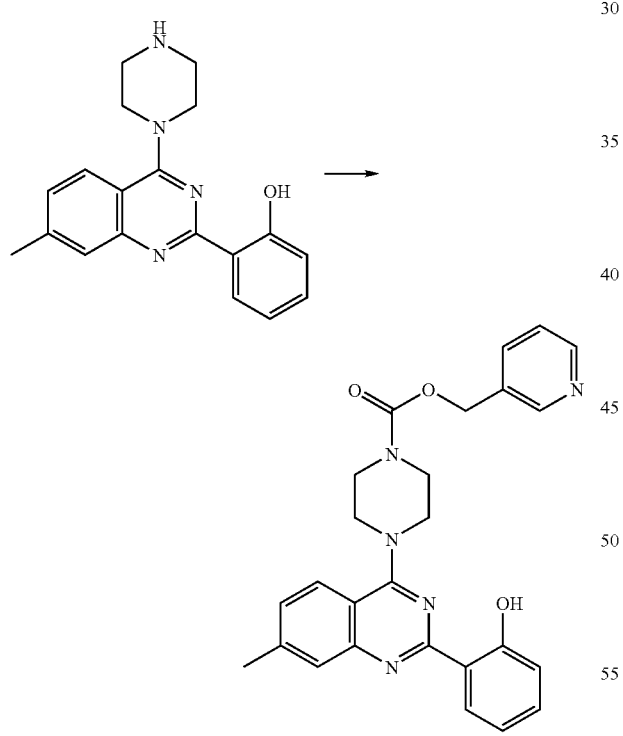

A solution of 2-(7-methyl-4-(piperazin-1-yl)quinazolin-2-yl)phenol (50 mg, 0.16 mmol), (pyridin-3-yl)methyl 1H-imidazole-1-carboxylate (67 mg, 0.32 mmol), and triethylamine (44.6 μL, 0.32 mmol) in DMSO (500 μL) was heated in a microwave synthesizer at 200° C. for 10 minutes. Purification using reverse phase HPLC (10-99% $CH_3CN$ (0.035% TFA)/$H_2O$ (0.05% TFA)) gave (pyridin-3-yl)methyl 4-(2-(2-hydroxyphenyl)-7-methylquinazolin-4-yl)piperazine-1-carboxylate as the TFA salt. LC/MS: m/z 456.5 $(M+H)^+$ at 2.04 min (10%-99% $CH_3CN$ (0.035% TFA)/$H_2O$ (0.05% TFA)).

Example 133

1-(4-(2-(2-Hydroxyphenyl)-7-methylquinazolin-4-yl)piperazin-1-yl)-3-(pyridin-2-yl)propan-1-one

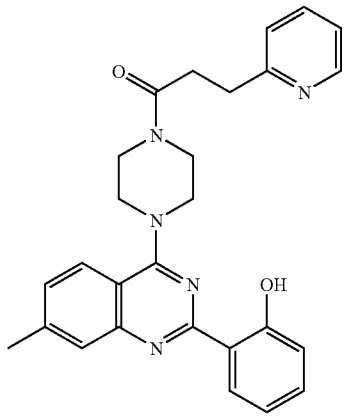

1-(4-(2-(2-Hydroxyphenyl)-7-methylquinazolin-4-yl)piperazin-1-yl)-3-(pyridin-2-yl)propan-1-one A solution of 2-(7-methyl-4-(piperazin-1-yl)quinazolin-2-yl)phenol (30 mg, 0.09 mmol) in DMF (0.5 mL) was added to 3-(pyridin-2-yl)propanoic acid (21.23 mg, 0.14 mmol). Triethylamine (25 μL) was added, followed by a solution of HATU (45 mg) in 0.5 mL DMF at room temperature. The reaction was stirred overnight. Purification using reverse phase HPLC (10-99% CH₃CN (0.035% TFA)/H₂O (0.05% TFA)) gave 1-(4-(2-(2-hydroxyphenyl)-7-methylquinazolin-4-yl)piperazin-1-yl)-3-(pyridin-2-yl)propan-1-one as the TFA salt. LC/MS: m/z 454.3 (M+H)$^+$ at 1.94 min (10%-99% CH₃CN (0.035% TFA)/H₂O (0.05% TFA)).

Example 134

2-Hydroxy-1-(4-(2-(2-hydroxyphenyl)-7-methylquinazolin-4-yl)piperazin-1-yl)pentan-1-one

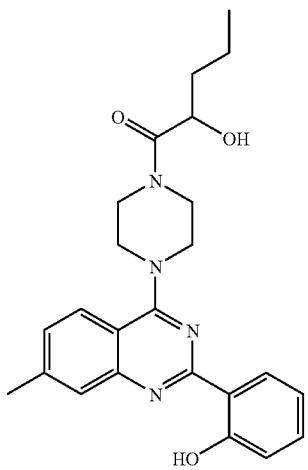

2-Hydroxy-1-(4-(2-(2-hydroxyphenyl)-7-methylquinazolin-4-yl)piperazin-1-yl)pentan-1-one

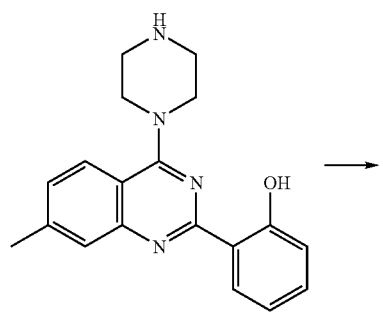

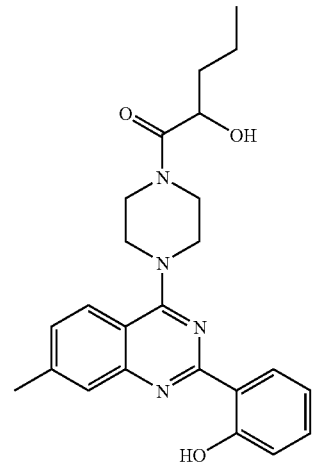

A solution of 2-(7-methyl-4-(piperazin-1-yl)quinazolin-2-yl)phenol (70 mg, 0.22 mmol) in DMF (0.5 mL) was added to 2-hydroxypentanoic acid (33.6 mg, 0.28 mmol). It was followed by the addition of triethylamine (61 µL), and a solution of HATU (108 mg) in 0.5 mL DMF at room temperature. The reaction was stirred overnight. Purification using reverse phase HPLC (10-99% CH₃CN (0.035% TFA)/H₂O (0.05% TFA)) gave 2-hydroxy-1-(4-(2-(2-hydroxyphenyl)-7-methylquinazolin-4-yl)piperazin-1-yl)pentan-1-one as the TFA salt. LC/MS: m/z 421.1 (M+H)$^+$ at 2.46 min (10%-99% CH₃CN (0.035% TFA)/H₂O (0.05% TFA)).

Example 135

(R)-1-(4-(2-(2-Fluoro-6-hydroxyphenyl)-7-methylquinazolin-4-yl)piperazin-1-yl)-2-hydroxy-4,4-dimethylpentan-1-one

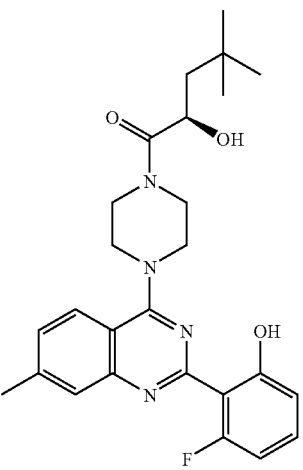

(R)-1-(4-(2-(2-Fluoro-6-hydroxyphenyl)-7-methylquinazolin-4-yl)piperazin-1-yl)-2-hydroxy-4,4-dimethylpentan-1-one

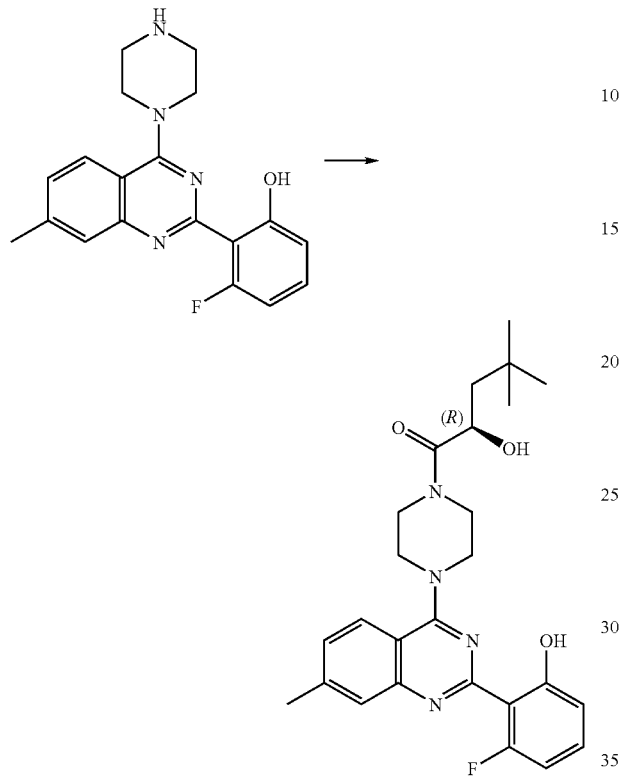

Method A

3-Fluoro-2-(7-methyl-4-(piperazin-1-yl)quinazolin-2-yl)phenol (50 mg, 0.15 mmol) was placed in a tube charged with a stir bar, (R)-2-hydroxy-4,4-dimethylpentanoic acid (26 mg, 0.18 mmol) in 1 ml of DMF, and triethylamine (30 mg, 41 µL, 0.29 mmol), and the tube was cooled to 0° C. HATU (68 mg, 0.18 mmol) was added, and the reaction was stirred at 0° C. for 10 minutes and then allowed to warm to room temperature. After 40 minutes, the reaction was filtered, and purified by reverse phase HPLC to give the TFA salt of (R)-1-(4-(2-(2-fluoro-6-hydroxyphenyl)-7-methylquinazolin-4-yl)piperazin-1-yl)-2-hydroxy-4,4-dimethylpentan-1-one. LC/MS: m/z 467.1 (M+H)$^+$ at 2.59 min (10%-99% CH$_3$CN (0.035% TFA)/H$_2$O (0.05% TFA)).

Method B

3-Fluoro-2-(7-methyl-4-(piperazin-1-yl)quinazolin-2-yl)phenol (250 mg, 0.74 mmol) was suspended in anhydrous DMF (5 mL) and cooled to 0° C. (internal temperature). Under an N$_2$ atmosphere, (R)-2-hydroxy-4,4-dimethylpentanoic acid (118.4 mg, 0.81 mmol) was added followed by triethylamine (0.207 mL, 1.48 mmol). To this stirring solution was added HATU (337 mg, 0.888 mmol). After the complete addition of HATU, the mixture was allowed to warm to 10° C. After 45 min the reaction was complete, and it was quenched with an equal portion of ice water. A yellow precipitate formed which was collected by vacuum filtration, dissolved in CH$_2$Cl$_2$, and the CH$_2$Cl$_2$ solution was desiccated with Na$_2$SO$_4$, filtered, and concentrated to a viscous yellow-orange oil. The crude material was purified via silica gel chromatography using 70% CH$_2$Cl$_2$/hexanes (1:1) and 30% EtOAc to afford (R)-1-(4-(2-(2-fluoro-6-hydroxyphenyl)-7-methylquinazolin-4-yl)piperazin-1-yl)-2-hydroxy-4,4-dimethylpentan-1-one as a yellow solid (171 mg, 50%). LC/MS: m/z 467.1 (M+H)$^+$ at 2.63 min (10%-99% CH$_3$CN (0.035% TFA)/H$_2$O (0.05% TFA)). $^1$H NMR (400 MHz, DMSO-d6) δ 8.02 (d, J=8.6 Hz, 1H), 7.69 (s, 1H), 7.43 (dd, J=8.6, 1.5 Hz, 1H), 7.37-7.32 (m, 1H), 6.80 (d, J=8.3 Hz, 1H), 6.76-6.71 (m, 1H), 4.87 (d, J=7.2 Hz, 1H), 4.47-4.43 (m, 1H), 4.01-3.75 (m, 8H), 2.52 (s, 3H), 1.55 (dd, J=14.3, 3.0 Hz, 1H), 1.40 (dd, J=14.3, 8.8 Hz, 1H), 0.96 (s, 9H) ppm.

(R)-1-(4-(2-(2-Fluoro-6-hydroxyphenyl)-7-methylquinazolin-4-yl)piperazin-1-yl)-2-hydroxy-4,4-dimethylpentan-1-one hydrochloride

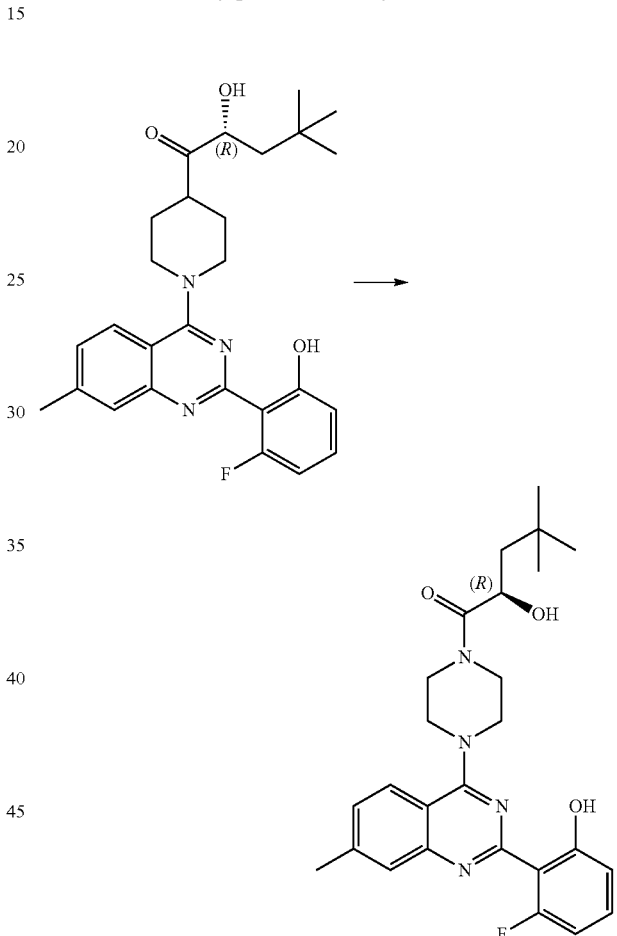

(R)-1-(4-(2-(2-Fluoro-6-hydroxyphenyl)-7-methylquinazolln-4-yl)piperazin-1-yl)-2-hydroxy-4,4-dimethylpentan-1-one (171 mg, 0.367 mmol) was dissolved in anhydrous CH$_2$Cl$_2$ (2 mL) followed by the addition of Et$_2$O (6 ml) under an N$_2$ atmosphere. A 2.0 M HCl solution in Et$_2$O (0.184 mL, 0.367 mmol) was added over a 1 minute period. The reaction solution changed from a clear yellow solution to a milky white slurry. After complete addition of the HCl solution, the reaction was allowed to stir for an additional 10 minutes. The product was collected by vacuum filtration and dried under vacuum to obtain (R)-1-(4-(2-(2-fluoro-6-hydroxyphenyl)-7-methylquinazolin-4-yl)piperazin-1-yl)-2-hydroxy-4,4-dimethylpentan-1-one hydrochloride as a light yellow solid (170 mg, 92%). LC/MS: m/z 467.3 (M+H)$^+$ at 2.60 min (10%-99% CH$_3$CN (0.035% TFA)/H$_2$O (0.05% TFA)). $^1$H NMR (400 MHz, DMSO-d6) d 8.17 (d, J=8.3 Hz, 1H), 7.66 (s, 1H), 7.56 (d, J=8.1 Hz, 1H), 7.48-7.43 (m, 1H), 6.92-6.83 (m, 2H), 4.44-4.41 (m, 1H), 3.87-3.68 (m, 8H), 2.56 (s, 3H), 1.55 (dd, J=14.3, 3.0 Hz, 1H), 1.41 (dd, J=14.3, 8.8 Hz, 1H), 0.96 (s, 9H) ppm.

Example 136

(R)-1-(4-(2-(5-Fluoro-2-hydroxyphenyl)-7-methylquinazolin-4-yl)piperazin-1-yl)-2-hydroxy-4-methylpentan-1-one

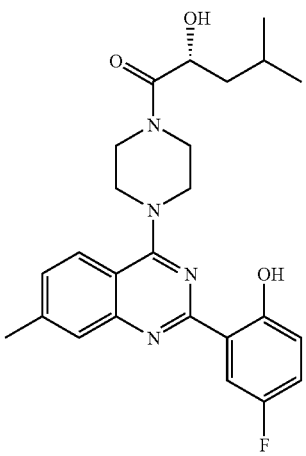

7-Methylquinazoline-2,4(1H,3H)-dione

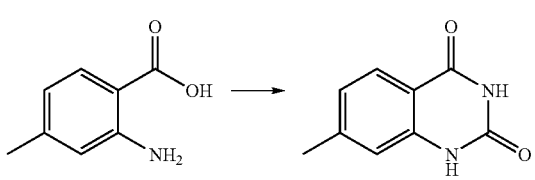

To a suspension of 2-amino-4-methylbenzoic acid (58.9 g, 390 mmol) in water (1.5 L) and glacial acetic acid (50 ml) was added dropwise a solution of potassium cyanate (80.5 g, 993 mmol) in water (300 ml). After completion of the addition and stirring at room temperature for half an hour, sodium hydroxide pellets (500 g) were added at such a rate that the temperature was kept below 50° C. (with ice cooling). During the addition the mixture became a clear solution for a short period, and upon continuation of the sodium hydroxide addition a cream precipitate started forming. The suspension was cooled to 0-5° C. and the precipitate was collected by filtration and washed twice with water (150 ml). The solid was poured in water (1 L) and was acidified with concentrated aqueous HCl (30%, 150 ml). The solid was collected by filtration and washed with water (150 ml) to yield 7-methylquinazoline-2,4(1H,3H)-dione (57.0 g, 83%) after drying at 45° C. under vacuum.

2,4-Dichloro-7-methyl-quinazoline

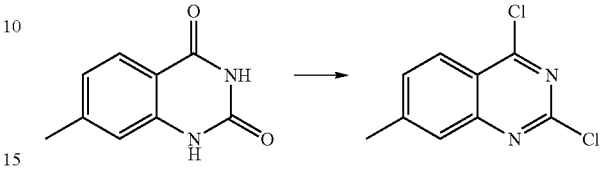

7-Methylquinazoline-2,4(1H,3H)-dione (57.0 g, 324 mmol) was refluxed overnight in phosphorus oxychloride (250 ml) in a flask equipped with a calcium chloride guard tube. The clear, dark solution was cooled in an ice bath and poured slowly into 2 L of ice water. The chocolate brown solid was collected by filtration and washed with cold water (150 ml). The solid was dissolved in dichloromethane (500 ml) and filtered. The filtrate was washed with a saturated solution of NaCl, dried over Na$_2$SO$_4$, filtered, and evaporated to dryness yielding 43.0 g of crude 2,4-dichloro-7-methyl-quinazoline. This material was dissolved in hot heptanes (0.5 L), and filtered while hot, and after cooling to room temperature, the precipitated solid was collected by filtration and washed with pentane (100 ml). The solid was purified by chromatography on silica gel with dichloromethane as the eluent to yield 2,4-dichloro-7-methylquinazoline (28.5 g, 41%) as an off-white solid.

1-(4-benzyl-piperazin-1-yl)-2-(R)-hydroxy-4-methyl-pentan-1-one

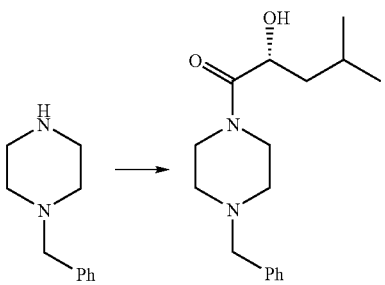

(R)-α-hydroxyisocaproic acid (52.1 g, 0.394 mol) was added to a solution of 1-benzylpiperazine (69.46 g, 0.394 mol) in CH$_2$Cl$_2$ (500 mL). The mixture was cooled in ice and Et$_3$N (57 mL, 0.5 mol) was added, followed by HOBt (53.25 g, 0.394 mol) and EDCI.HCl (76.0 g, 0.396 mol). The reaction mixture was allowed to warm to room temperature overnight. The organic layer was washed with water (3×200 mL). The combined aqueous layers were back-extracted with CH$_2$Cl$_2$ (3×25 mL). The combined organic layers were washed with water (3×20 mL), dried over Na$_2$SO$_4$ and concentrated to give 1-(4-benzyl-piperazin-1-yl)-2-(R)-hydroxy-4-methyl-pentan-1-one as a brown oil (109 g, 0.375 mol, 95%). $^1$H NMR (300 MHz, CDCl$_3$): d 7.35-7.24 (m, 5H); 4.35 (dd, J=10 Hz, 2 Hz, 1H); 3.77-3.55 (m, 4H); 3.52 (s, 2H); 3.36 (m, 2H); 4.45 (m, 4H); 1.97 (m, 1H); 1.47-1.38 (m, 1H); 1.29-1.21 (m, 1H); 0.96 (d, J=6 Hz, 3H); 0.94 (d, J=6 Hz, 3H) ppm.

2-(R)-hydroxy-4-methyl-1-piperazin-1-yl-pentan-1-one

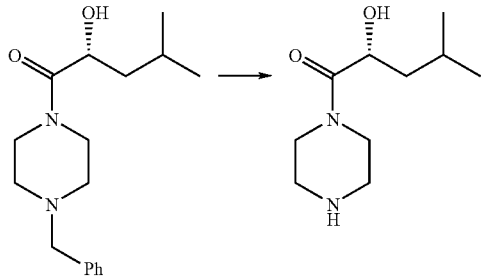

1-(4-benzyl-piperazin-1-yl)-2-(R)-hydroxy-4-methyl-pentan-1-one (109 g, 0.375 mol) was dissolved in MeOH (0.5 L). Crystals formed upon addition of 10% Pd/C (16 grams). The mixture was hydrogenated under 1-4 bar hydrogen pressure for two days. The catalyst was filtered off, the filtrate was concentrated to give 2-(R)-hydroxy-4-methyl-1-piperazin-1-yl-pentan-1-one as a brownish oil (72.7 g, 0.363 mol, 97%). $^1$H NMR (300 MHz, CDCl$_3$): d 4.36 (dd, J=10 Hz, 2 Hz, 1H); 3.76-3.66 (m, 1H); 3.62-3.52 (m, 1H); 3.37 (m, 2H); 2.99 (br. s, 2H); 2.89 (br. m, 4H); 1.96 (m, 1H); 1.48-1.38 (m, 1H); 1.29-1.21 (m, 1H); 0.96 (d, J=9 Hz, 3H); 0.94 (d, J=9 Hz, 3H) ppm.

2-(R)-hydroxy-4-methyl-1-piperazin-1-yl-pentan-1-one oxalate

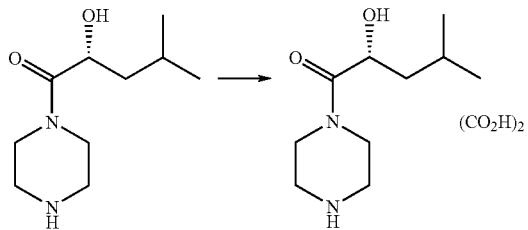

The above product was dissolved in ethanol (250 mL). Oxalic acid dihydrate (45.76 g, 0.363 mol) was added. The thick slurry was diluted with ethanol (250 mL) and stirred at room temperature for 3 hours. The salt was filtered off, washed with ethanol (2×100 mL) and dried in vacuo over drying pearls. Yield: 89.0 grams (0.307 mol, 84%) of 2-(R)-hydroxy-4-methyl-1-piperazin-1-yl-pentan-1-one oxalate as a white solid. $^1$H NMR (300 MHz, D$_2$O): d 4.68 (dd, J=3.3, 9.9 Hz, 1H); 3.95 (m, 4H); 3.35 (m, 4H); 1.80 (m, 1H); 1.59 (m, 1H); 1.41 (m, 1H); 0.96 (d, J=6.5 Hz, 3H); 0.95 (d, J=6.5 Hz, 3H) ppm.

(R)-1-(4-(2-Chloro-7-methylquinazolin-4-yl)piperazin-1-yl)-2-hydroxy-4-methylpentan-1-one

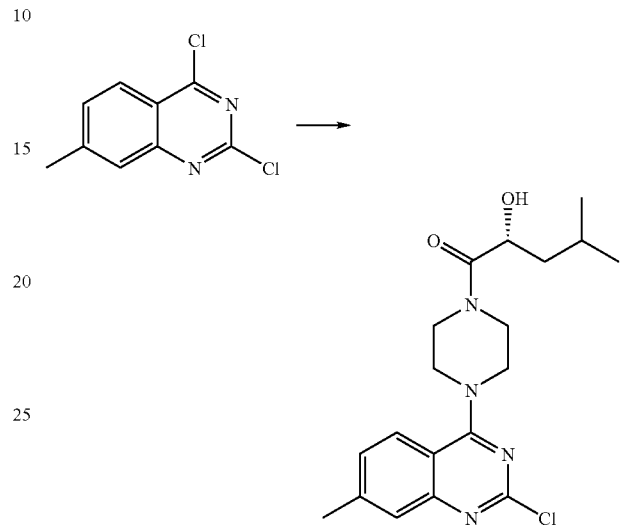

To a solution of 2,4-dichloro-7-methylquinazoline (2.09 g, 9.83 mmol) in CH$_2$Cl$_2$ (10 mL) at 0° C. was added triethylamine (2.74 mL, 19.66 mmol), followed by the addition of (R)-2-hydroxy-4-methyl-1-(piperazin-1-yl)pentan-1-one (1.97 g, 9.83 mmol). The reaction mixture was warmed to room temperature and stirred overnight. The mixture was then quenched with water and extracted twice with CH$_2$Cl$_2$. The combined organic extracts were dried over MgSO$_4$, filtered, and concentrated to obtain (R)-1-(4-(2-chloro-7-methylquinazolin-4-yl)piperazin-1-yl)-2-hydroxy-4-methylpentan-1-one (6.78 g, 95%). LC/MS: m/z 377.5 (M+H)$^+$ at 2.61 min (10%-99% CH$_3$CN (0.035% TFA)/H$_2$O (0.05% TFA)).

(R)-1-(4-(2-(5-Fluoro-2-methoxyphenyl)-7-methylquinazolin-4-yl)piperazin-1-yl)-2-hydroxy-4-methylpentan-1-one

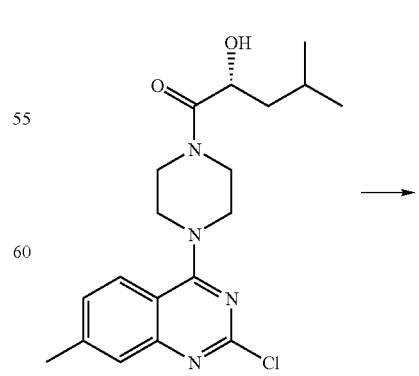

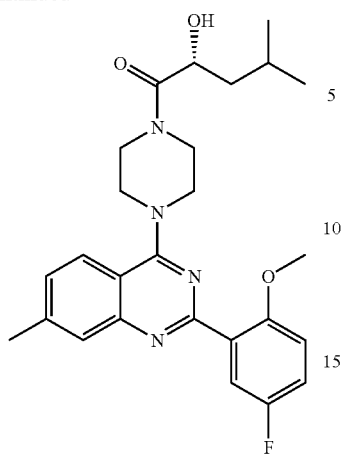

(R)-1-(4-(2-Chloro-7-methylquinazolin-4-yl)piperazin-1-yl)-2-hydroxy-4-methylpentan-1-one (50 mg, 0.13 mmol), 5-fluoro-2-methoxyphenylboronic acid (27 mg, 0.16 mmol), Pd(Ph₃P)₄ (9.2 mg, 0.008 mmol), and K₂CO₃ (37 mg, 0.27 mmol) were placed into a microwave tube charged with a stir bar. Acetonitrile (2 mL) and H₂O (400 μL) were added, and the vessel was capped and heated at 160° C. for 12 minutes in the microwave reactor. The reaction was partitioned between EtOAc and H₂O, the layers were separated, and the aqueous layer was extracted once more with EtOAc. The organic extracts were combined, dried over Na₂SO₄, filtered, and concentrated to an orange gel. The reaction was purified by silica gel chromatography using 10%-30% EtOAc in CH₂Cl₂/hexanes (2:1) to afford (R)-1-(4-(2-(5-fluoro-2-methoxyphenyl)-7-methylquinazolin-4-yl)piperazin-1-yl)-2-hydroxy-4-methylpentan-1-one as a white foam (70%). LC/MS: m/z 467.30 (M+H)⁺ at 2.38 min (10%-99% CH₃CN (0.035% TFA)/H₂O (0.05% TFA)).

(R)-1-(4-(2-(5-Fluoro-2-hydroxyphenyl)-7-methylquinazolin-4-yl)piperazin-1-yl)-2-hydroxy-4-methylpentan-1-one

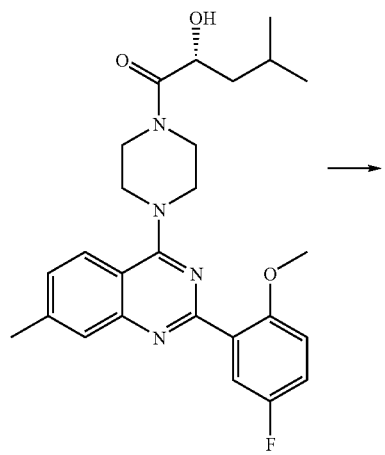

→

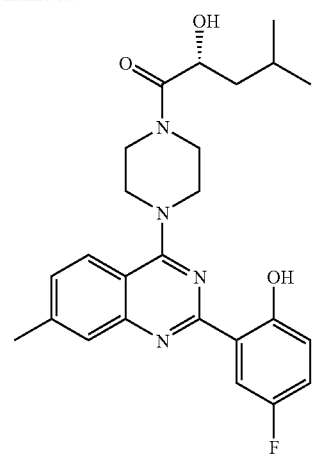

(R)-1-(4-(2-(5-Fluoro-2-methoxyphenyl)-7-methylquinazolin-4-yl)piperazin-1-yl)-2-hydroxy-4-methylpentan-1-one (30 mg, 0.064 mmol) was dissolved in 1.5 mL anhydrous CH₂Cl₂. The flask was sealed with a septum, placed under an N₂ atmosphere and cooled to −78° C., and 0.32 mL of a 1 M solution of BBr₃ in CH₂Cl₂ was added over 2 minutes. The reaction was allowed to warm to room temperature. After 5 hours, the reaction was quenched with saturated aqueous NaHCO₃, and partitioned between CH₂Cl₂ and water, and the layers were separated. The organic layer was dried over Na₂SO₄, filtered, and concentrated to a red oil. The reaction was purified by reverse phase HPLC to give (R)-1-(4-(2-(5-fluoro-2-hydroxyphenyl)-7-methylquinazolin-4-yl)piperazin-1-yl)-2-hydroxy-4-methylpentan-1-one as the TFA salt. LC/MS: m/z 453.30 (M+H)⁺ at 3.02 min (10%-99% CH₃CN (0.035% TFA)/H₂O (0.05% TFA)).

Example 137

(S)-2-Hydroxy-1-(4-(2-(2-hydroxyphenyl)-7-methylquinazolin-4-yl)piperazin-1-yl)butan-1-one

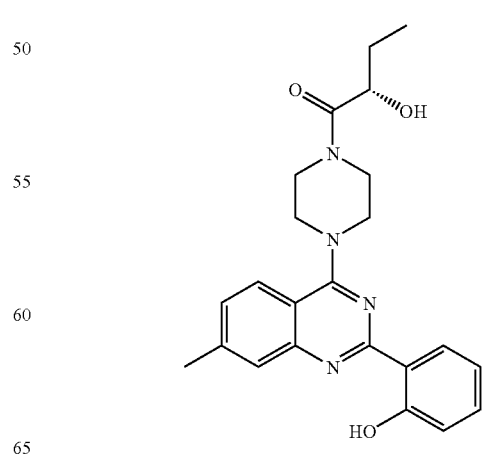

231

(S)-2-Hydroxy-1-(4-(2-(2-hydroxyphenyl)-7-methylquinazolin-4-yl)piperazin-1-yl)butan-1-one

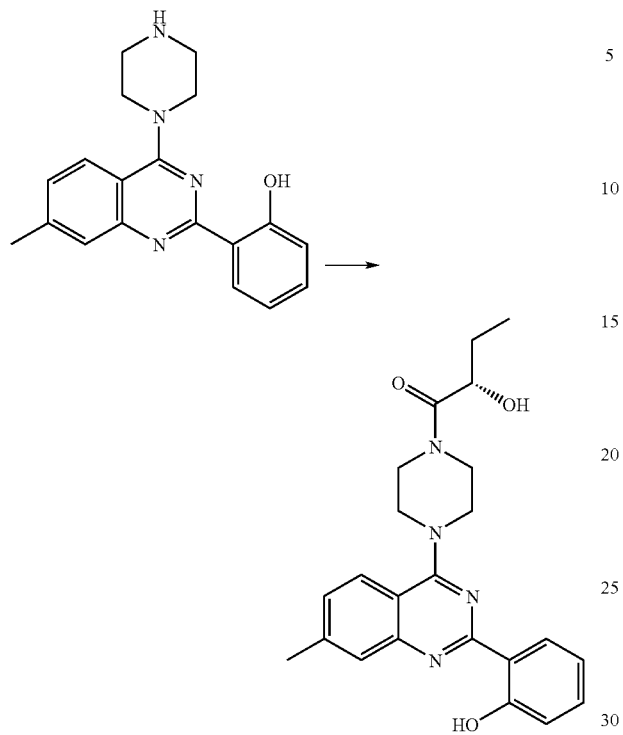

A solution of 2-(7-methyl-4-(piperazin-1-yl)quinazolin-2-yl)phenol (70 mg, 0.22 mmol) in DMF (0.5 mL) was added to (S)-2-hydroxybutanoic acid (29.6 mg, 0.284 mmol). It was followed by the addition of triethylamine (61 µL) and a solution of HATU (108 mg) in 0.5 mL DMF at room temperature. The reaction was stirred overnight. Purification using reverse phase HPLC (10-99% CH$_3$CN (0.035% TFA)/H$_2$O (0.05% TFA)) gave (S)-2-hydroxy-1-(4-(2-(2-hydroxyphenyl)-7-methylquinazolin-4-yl)piperazin-1-yl)butan-1-one as the TFA salt. LC/MS: m/z 407.3 (M+H)$^+$ at 2.28 min (10%-99% CH$_3$CN (0.035% TFA)/H$_2$O (0.05% TFA)).

Example 138

(S)-1-(4-(2-(2-Fluoro-6-hydroxyphenyl)-7-methylquinazolin-4-yl)piperazin-1-yl)-2-hydroxy-3,3-dimethylbutan-1-one

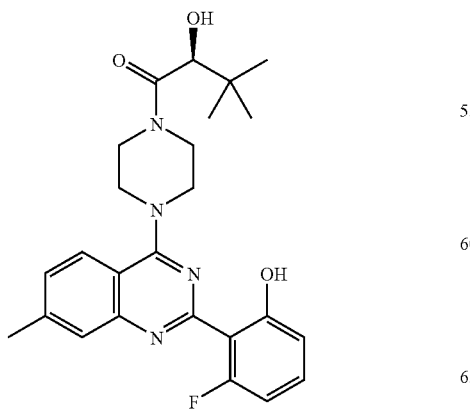

232

(S)-1-(4-(2-(2-Fluoro-6-hydroxyphenyl)-7-methylquinazolin-4-yl)piperazin-1-yl)-2-hydroxy-3,3-dimethylbutan-1-one

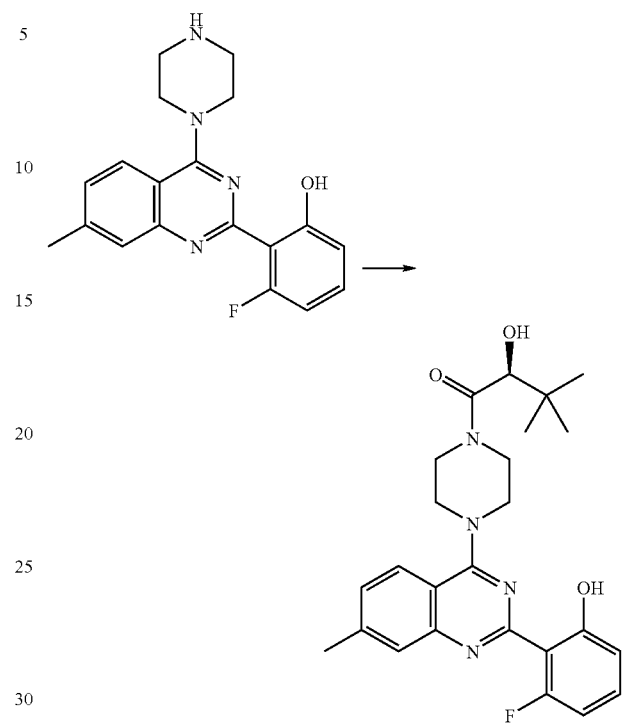

3-Fluoro-2-(7-methyl-4-(piperazin-1-yl)quinazolin-2-yl)phenol (30 mg, 0.09 mmol), (S)-2-hydroxy-3,3-dimethylbutanoic acid (15.24 mg, 0.12 mmol), triethylamine (25 µL, 0.18 mmol), and HATU (45.6 mg, 0.12 mmol) were stirred in DMF (1 mL) overnight. Purification via reverse phase HPLC (10-99% CH$_3$CN (0.035% TFA)/H$_2$O (0.05% TFA)) gave (S)-1-(4-(2-(2-fluoro-6-hydroxyphenyl)-7-methylquinazolin-4-yl)piperazin-1-yl)-2-hydroxy-3,3-dimethylbutan-1-one as the TFA salt. LC/MS: m/z 453.3 (M+H)$^+$ at 2.43 min (10%-99% CH$_3$CN (0.035% TFA)/H$_2$O (0.05% TFA)).

Example 139

(S)-1-(4-(6-Fluoro-2-(2-hydroxyphenyl)quinazolin-4-yl)piperazin-3-yl)-2-hydroxy-3,3-dimethylbutan-1-one

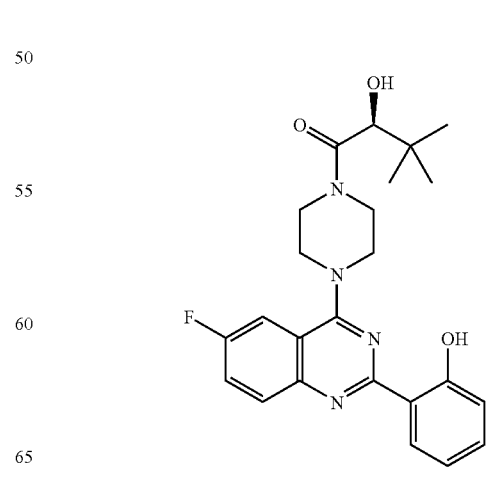

233

(S)-1-(4-(6-Fluoro-2-(2-hydroxyphenyl)quinazolin-4-yl)piperazin-1-yl)-2-hydroxy-3,3-dimethylbutan-1-one

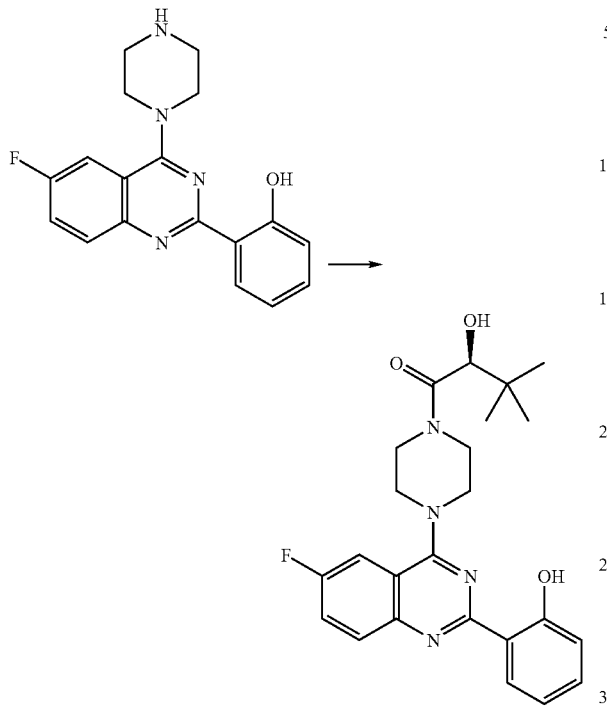

2-(6-Fluoro-4-(piperazin-1-yl)quinazolin-2-yl)phenol (30 mg, 0.09 mmol), (S)-2-hydroxy-3,3-dimethylbutanoic acid (16 mg, 0.12 mmol), triethylamine (25 mL, 0.18 mmol), and HATU (45.6 mg, 0.12 mmol) were stirred in DMF (1 mL) overnight. Purification via reverse phase HPLC (10-99% CH$_3$CN (0.035% TFA)/H$_2$O (0.05% TFA)) gave (S)-1-(4-(6-fluoro-2-(2-hydroxyphenyl)quinazolin-4-yl)piperazin-1-yl)-2-hydroxy-3,3-dimethylbutan-1-one as the TFA salt. LC/MS: m/z 439.5 (M+H)$^+$ at 2.95 min (10%-99% CH$_3$CN (0.035% TFA)/H$_2$O (0.05% TFA)).

Example 140

(Benzo[d][1,3]dioxol-7-yl)methyl 4-(2-(2-hydroxyphenyl)quinazolin-4-yl)piperazine-1-carboxylate

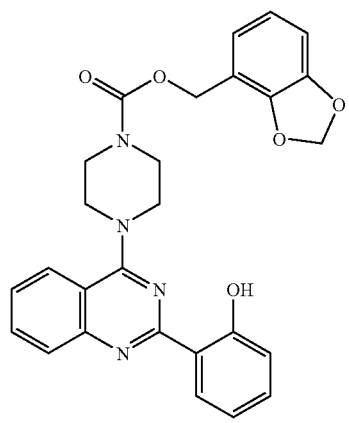

234

(Benzo[d][1,3]dioxol-7-yl)methyl 1H-imidazole-1-carboxylate

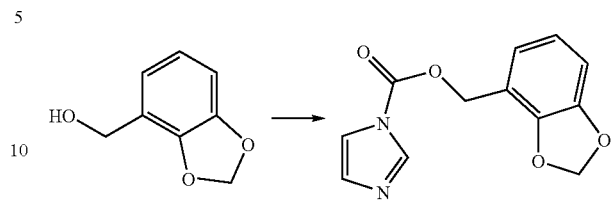

A solution of (benzo[d][1,3]dioxol-7-yl)methanol (2.0 g, 13.1 mmol) and di(1H-imidazol-1-yl)methanone (4.26 g, 26.2 mmol) in 20 mL CH$_2$Cl$_2$ was heated overnight at 50° C. The reaction was quenched with water and extracted with CH$_2$Cl$_2$, and the combined layers were dried over MgSO$_4$, filtered, and concentrated. Purification via silica gel chromatography using 10-70% EtOAc in CH$_2$Cl$_2$ gave (benzo[d][1,3]dioxol-7-yl)methyl 1H-imidazole-1-carboxylate (2.8 g, 86%). $^1$H NMR (400 MHz, CDCl$_3$) δ 8.15 (t, J=0.9 Hz, 1H), 7.44 (t, J=1.4 Hz, 1H), 7.07 (dd, J=1.6, 0.8 Hz, 1H), 6.95 (m, 2H), 6.84 (m, 1H), 6.01 (s, 2H), 5.33 (s, 2H) ppm.

(Benzo[d][1,3]dioxol-7-yl)methyl 4-(2-2-hydroxyphenyl)quinazolin-4-yl)piperazine-1-carboxylate

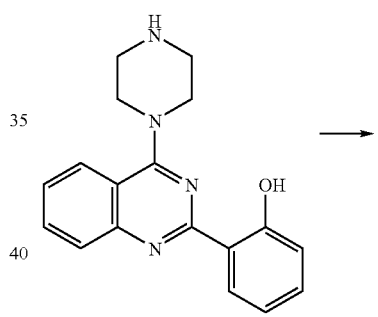

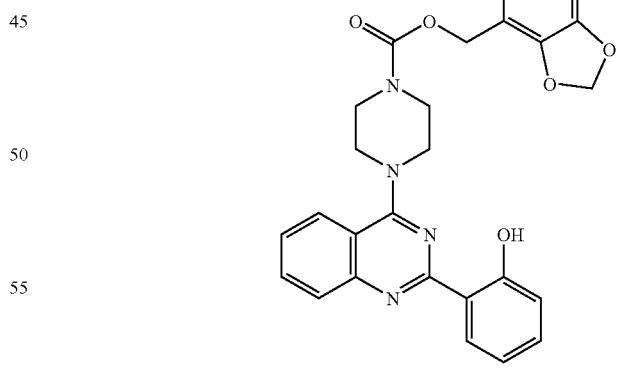

A solution of 2-(4-(piperazin-1-yl)quinazolin-2-yl)phenol (50 mg, 0.16 mmol), (benzo[d][1,3]dioxol-7-yl)methyl 1H-imidazole-1-carboxylate (78 mg, 0.32 mmol), and triethylamine (44.6 µL, 0.32 mmol) in DMSO (500 µL) was heated in a microwave synthesizer at 200° C. for 10 minutes. Purification using reverse phase HPLC (10-99% CH$_3$CN (0.035% TFA)/H$_2$O (0.05% TFA)) gave (benzo[d][1,3]dioxol-7-yl)methyl 4-(2-(2-hydroxyphenyl)quinazolin-4-yl)

piperazine-1-carboxylate as the TFA salt. LC/MS: m/z 485.5 (M+H)+ at 2.94 min (10%-99% CH₃CN (0.035% TFA)/H₂O (0.05% TFA)).

Example 141

(S)-2-Hydroxy-1-(4-(2-(2-hydroxyphenyl)-7-methylquinazolin-4-yl)piperazin-1-yl)-3-(1H-imidazol-5-yl)propan-1-one

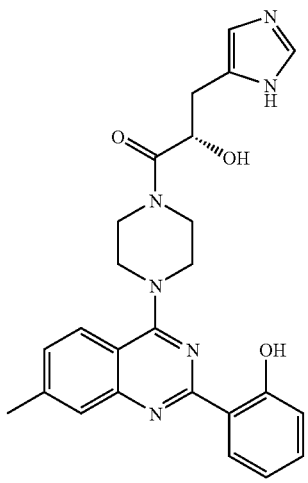

(S)-2-Hydroxy-1-(4-(2-(2-hydroxyphenyl)-7-methylquinazolin-4-yl)piperazin-1-yl)-3-(1H-imidazol-5-yl)propan-1-one

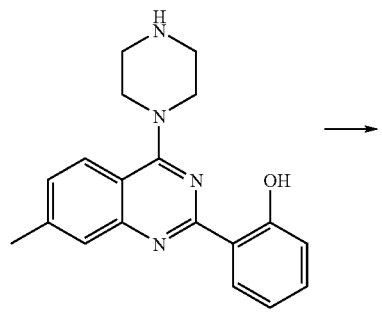

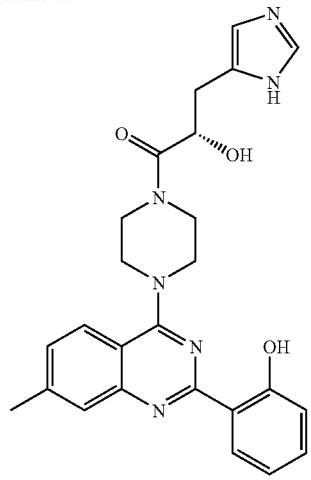

2-(7-Methyl-4-(piperazin-1-yl)quinazolin-2-yl)phenol (87 mg, 0.27 mmol), (S)-2-hydroxy-3-(1H-imidazol-5-yl) propanoic acid (64 mg, 0.41 mmol), triethylamine (76 μL, 0.54 mmol), and BOP (180 mg, 0.41 mmol) in 1 mL of CH₂Cl₂ were stirred at room temperature for 1.5 h. The reaction mixture was diluted with H₂O and CH₂Cl₂. The organic layer was dried over Na₂SO₄ and concentrated. Purification using 1-15% MeOH in CH₂Cl₂ gave (S)-2-hydroxy-1-(4-(2-(2-hydroxyphenyl)-7-methylquinazolin-4-yl)piperazin-1-yl)-3-(1H-imidazol-5-yl)propan-1-one. LC/MS: m/z 459.3 (M+H)+ at 2.13 min (10%-99% CH₃CN (0.035% TFA)/H₂O (0.05% TFA)).

Example 142

4-[4-((R)-2-Hydroxy-4-methyl-pentanoyl)-piperazin-1-yl]-2-(2-hydroxy-phenyl)-quinazoline-6-carbonitrile

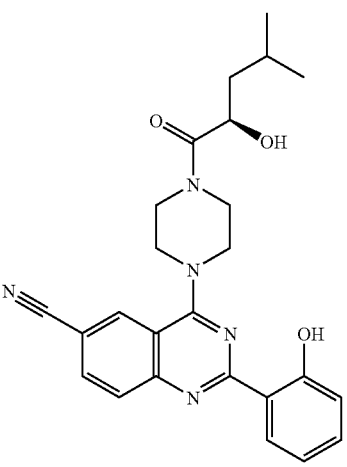

6-Bromo-1H-benzo[d][1,3]oxazine-2,4-dione

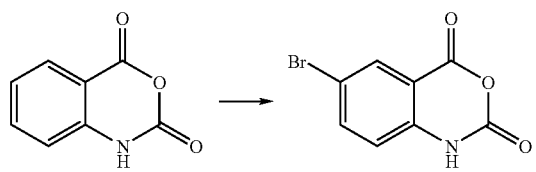

Bromine (35 mL, 660 mmol) was added dropwise to a suspension of isatoic anhydride (100 g, 610 mmol) in 1.6 L water at 50° C. This temperature was maintained for an additional 2 hours. After cooling the solution to room temperature, the solid was filtered and washed twice with water and twice with acetone, yielding 125.6 g (85%) 6-bromo-1H-benzo[d][1,3]oxazine-2,4-dione as a pink solid.

2-Amino-5-bromo-benzamide

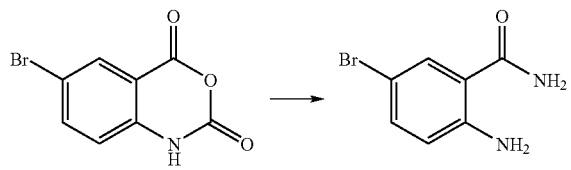

6-Bromo-1H-benzo[d][1,3]oxazine-2,4-dione (56.0 g, 230 mmol) was suspended in 1 N aq. NH$_4$OH (600 mL, 2.6 equivalents), and the suspension was stirred 3 d at room temperature. After filtration, the collected solid was washed with water and subsequently dissolved in tetrahydrofuran. This solution was filtered, evaporated to dryness, and dried by repeated azeotropic distillation with toluene. The solid was suspended in CH$_2$Cl$_2$, filtered, and washed once with CH$_2$Cl$_2$ yielding 35.4 g (71.2%) of 2-amino-5-bromo-benzamide.

2-(o-Anisoyl)-amino-5-bromo-benzamide

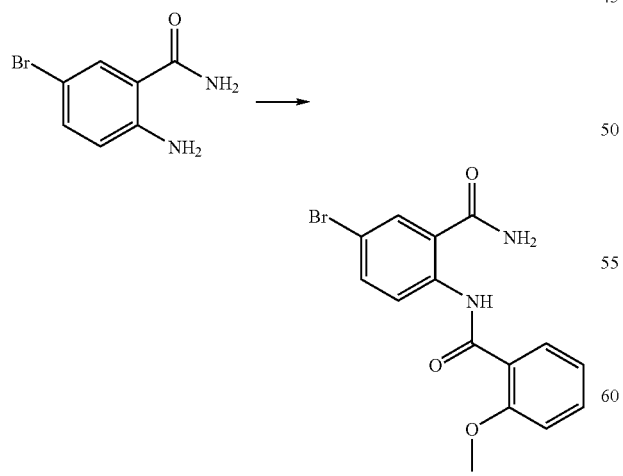

To a solution of 2-amino-5-bromo-benzamide (29.2 g, 136 mmol) and triethylamine (25.0 mL, 173 mmol) in THF (500 mL) was added dropwise o-anisoyl chloride (24.0 g, 140 mmol). Stirring at room temperature was continued for 3 h, after which the formed precipitate was filtered and washed once with THF and twice with dichloromethane yielding 2-(o-anisoyl)-amino-5-bromo-benzamide (51.4 g, 84%) with 1 equivalent of triethylamine hydrochloride.

6-Bromo-2-(2-methoxy-phenyl)-3H-quinazolin-4-one

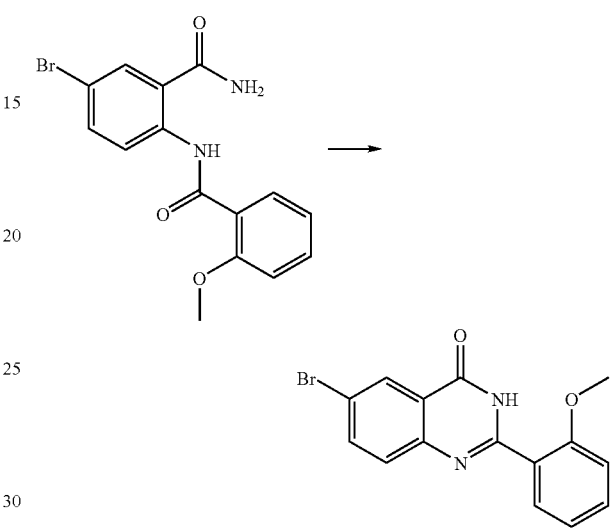

2-(o-Anisoyl)-amino-5-bromo-benzamide (50.8 g, 105 mmol) was suspended in 2 N aq. NaOH (500 mL) and heated to reflux until a clear solution was obtained (1.5 h). The solution was cooled to room temperature and filtered. The filtrate was acidified with conc. aq. HCl, and the precipitate formed was filtered and washed twice with 1 N aq. HCl and twice with water. The solid was dried by repeated azeotropic distillation with toluene yielding 6-bromo-2-(2-methoxy-phenyl)-3H-quinazolin-4-one (31.3 g, 91%).

6-Bromo-4-chloro-2-(2-methoxyphenyl)quinazoline

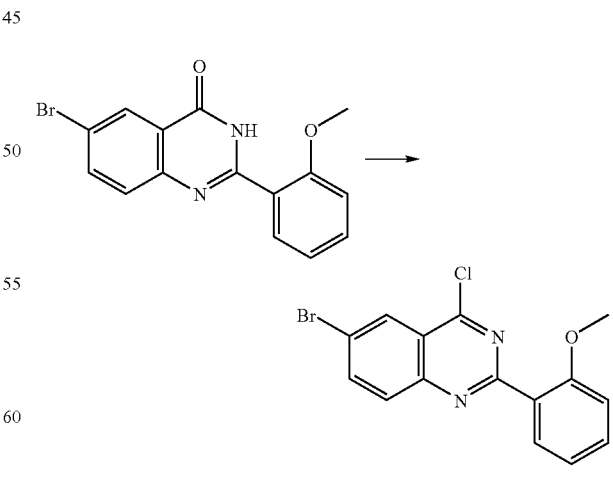

Method A

6-Bromo-2-(2-methoxyphenyl)quinazolin-4(3H)-one (674 mg, 2.0 mmol), POCl$_3$ (624 mg, 4 mmol), and N,N-dimethylaniline (740 mg, 6.1 mmol) were dissolved in benzene (12 mL) and refluxed for 3 h. The reaction mixture was diluted with EtOAc, and the organic phase was washed with aqueous saturated NaHCO$_3$ (1×) and H$_2$O (2×), dried over Na$_2$SO$_4$, and concentrated. Purification via silica gel chromatography using 0-5% EtOAc in CH$_2$Cl$_2$/hexanes (1:1) gave 6-bromo-4-chloro-2-(2-methoxyphenyl)quinazoline. LC/MS: m/z 348.9 (M+H)$^+$ at 3.66 min (10%-99% CH$_3$CN (0.035% TFA)/H$_2$O (0.05% TFA)).

Method B

6-Bromo-2-(2-methoxyphenyl)quinazolin-4(3H)-one (0.31 g, 0.94 mmol), POCl$_3$ (86 µL, 0.94 mmol), and N,N-dimethylaniline (180 µL, 1.4 mmol) were refluxed in dry toluene for 3 h. Additional POCl$_3$ (0.94 mmol) was added, and the reaction was refluxed for one additional hour. The reaction mixture was diluted with EtOAc and water. The aqueous layer was made basic with NaHCO$_3$, and the layers were separated. After the organic phase was washed with water, dried over Na$_2$SO$_4$ and concentrated, purification via silica gel chromatography using 0-50% EtOAc in 1:1 hexanes:CH$_2$Cl$_2$ gave 6-bromo-4-chloro-2-(2-methoxyphenyl)quinazoline as a yellow solid (144 mg, 44%). $^1$H NMR (400 MHz, CDCl$_3$) d 8.45-8.45 (m, 1H), 8.04-7.99 (m, 2H), 7.82 (dd, J=7.6, 1.7 Hz, 1H), 7.49-7.45 (m, 1H), 7.12-7.08 (m, 1H), 7.06 (d, J=8.4 Hz, 1H), 3.90 (s, 3H) ppm; LC/MS: m/z 350.9 (M+H)$^+$ at 3.56 min (10%-99% CH$_3$CN (0.035% TFA)/H$_2$O (0.05% TFA)).

2-(6-Bromo-4-chloroquinazolin-2-yl)phenol

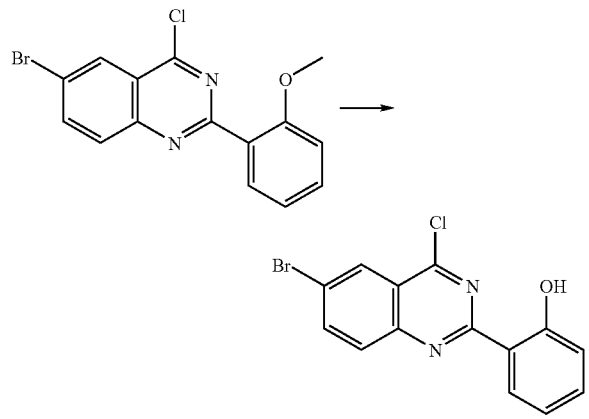

Method A

6-Bromo-4-chloro-2-(2-methoxyphenyl)quinazoline (393 mg, 1.12 mmol) was dissolved in CH$_2$Cl$_2$ (3 mL), and the flask was flushed with N$_2$. After cooling the reaction mixture to −78° C., 1 M BBr$_3$ in CH$_2$Cl$_2$ (3.37 mL, 3.37 mmol) was added dropwise, then the reaction was slowly warmed to room temperature and stirred for 2 h. After quenching the mixture with saturated aqueous NaHCO$_3$ (1×), it was transferred into a separatory funnel with CH$_2$Cl$_2$. The organic layer was washed with H$_2$O (2×), dried over Na$_2$SO$_4$, and concentrated. Purification via silica gel chromatography using 0-5% EtOAc and CH$_2$Cl$_2$:hexanes (1:1) gave 2-(6-bromo-4-chloroquinazolin-2-yl)phenol (229 mg, 61%). LC/MS: m/z 335.30 (M+H)$^+$ at 4.18 min (10%-99% CH$_3$CN (0.035% TFA)/H$_2$O (0.05% TFA)).

Method B

A solution of 6-bromo-4-chloro-2-(2-methoxyphenyl)quinazoline (0.14 g, 0.4 mmol) in CH$_2$Cl$_2$ (mL) was cooled in a dry ice/acetone bath. A solution of 1.0 M BBr$_3$ in CH$_2$Cl$_2$ (1.2 mL, 1.2 mmol) was slowly added. The cooling bath was removed, and the reaction was stirred at room temperature for 2 h. The reaction was diluted with CH$_2$Cl$_2$ and made basic with a saturated NaHCO$_3$ solution. The organic layer was separated, washed with water, dried over Na$_2$SO$_4$, and evaporated to give 6-bromo-4-chloro-2-(2-hydroxyphenyl)quinazoline (0.15 g).

(R)-1-(4-(6-Bromo-2-(2-hydroxyphenyl)quinazolin-4-yl)piperazin-1-yl)-2-hydroxy-4-methylpentan-1-one

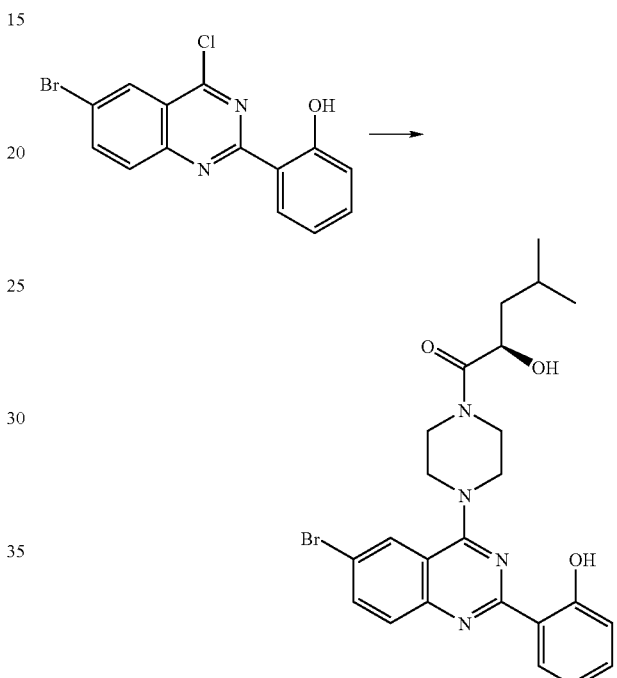

Method A

To a solution of 2-(6-bromo-4-chloroquinazolin-2-yl)phenol (228 mg, 0.68 mmol), triethylamine (129 µL, 0.92 mmol), and CH$_2$Cl$_2$ (6 mL) was added (R)-2-hydroxy-4-methyl-1-(piperazin-1-yl)pentan-1-one (185 mg, 0.92 mmol) dissolved in CH$_2$Cl$_2$ (3 mL). The flask was flushed with N$_2$ and stirred for 3 hours. The reaction mixture was then transferred into a separatory funnel with CH$_2$Cl$_2$, and the organic phase was washed with H$_2$O (2×), dried over Na$_2$SO$_4$, and concentrated. Purification via silica gel chromatography using 0 to 20% EtOAc and CH$_2$Cl$_2$:hexanes (1:1) gave (R)-1-(4-(6-bromo-2-(2-hydroxyphenyl)quinazolin-4-yl)piperazin-1-yl)-2-hydroxy-4-methylpentan-1-one (285 mg, 84%). LC/MS: m/z 500.30 (M+H)$^+$ at 3.29 min (10%-99% CH$_3$CN (0.035% TFA)/H$_2$O (0.05% TFA)).

Method B

A solution of 6-bromo-4-chloro-2-(2-hydroxyphenyl)quinazoline (75 mg, 0.22 mmol), (R)-2-hydroxy-4-methyl-1-piperazin-1-yl-pentan-1-one (60 mg, 0.3 mmol), triethylamine (42 µL, 0.3 mmol), and CH$_2$Cl$_2$ (2 mL) was stirred at room temperature overnight. After diluting with CH$_2$Cl$_2$, the reaction mixture was washed with H$_2$O, dried over Na$_2$SO$_4$, and concentrated. The crude material was purified by silica gel chromatography using 0-10% MeOH/CH$_2$Cl$_2$ to give (R)-

1-{4-[6-bromo-2-(2-hydroxyphenyl)-quinazolin-4-yl]-piperazin-1-yl}-2-hydroxy-4-methyl-pentan-1-one (40 mg, 36%).

4-[4-((R)-2-Hydroxy-4-methyl-pentanoyl)-piperazin-1-yl]-2-(2-hydroxy-phenyl)-quinazoline-6-carbonitrile

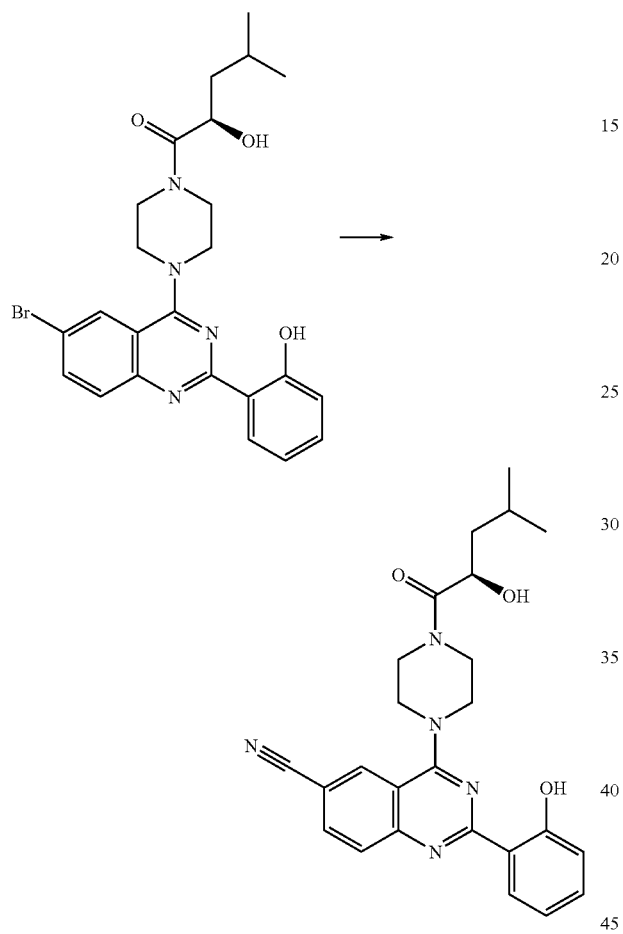

Method A

A mixture of (R)-1-{4-[6-bromo-2-(2-hydroxyphenyl)-quinazolin-4-yl]-piperazin-1-yl}-2-hydroxy-4-methyl-pentan-1-one (20 mg, 0.04 mmol), Zn(CN)$_2$ (4.7 mg, 0.04 mmol), and Pd(PPh$_3$)$_4$ (1.4 mg, 1.4 µmol) in DMF (0.5 mL) was heated in a microwave synthesizer at 200° C. for 15 minutes. Purification via preparative HPLC gave 4-[4-((R)-2-hydroxy-4-methyl-pentanoyl)-piperazin-1-yl]-2-(2-hydroxy-phenyl)-quinazoline-6-carbonitrile as the TFA salt. LC/MS: m/z 446.3 (M+H)$^+$ at 3.17 min (10%-99% CH$_3$CN (0.035% TFA)/H$_2$O (0.05% TFA)).

Method B (R)-1-(4-(6-Bromo-2-(2-hydroxyphenyl)quinazolin-4-yl)piperazin-1-yl)-2-hydroxy-4-methylpentan-1-one (188 mg, 0.38 mmol), Zn(CN)$_2$ (44 mg, 0.38 mmol), and Pd(Ph$_3$)$_4$ (6.5 mg, 0.0112 mmol) were dissolved in DMF (4 mL) and the reaction mixture was heated in a microwave synthesizer at 200° C. for 15 minutes. EtOAc (50 mL) was added and the mixture was washed twice with H$_2$O. The organic layer was dried over Na$_2$SO$_4$, filtered, and concentrated. Purification via silica gel chromatography using 0-40% EtOAc in CH$_2$Cl$_2$:hexanes (1:1) gave 4-[4-((R)-2-hydroxy-4-methyl-pentanoyl)-piperazin-1-yl]-2-(2-hydroxy-phenyl)-quinazoline-6-carbonitrile (127 mg, 75%). LC/MS: m/z 446 (M+H)$^+$ at 3.24 min (10%-99% CH$_3$CN (0.035% TFA)/H$_2$O (0.05% TFA)). $^1$H NMR (400 MHz, DMSO-d6) δ 8.60 (d, J=1.5 Hz, 1H), 8.46 (dd, J=8.4, 1.8 Hz, 1H), 8.15 (dd, J=8.7, 1.7 Hz, 1H), 8.00 (d, J=8.7 Hz, 1H), 7.45-7.41 (m, 1H), 6.99-6.95 (m, 2H), 4.94 (d, J=7.0 Hz, 1H), 4.39-4.36 (m, 1H), 4.14-4.04 (m, 4H), 3.89-3.67 (m, 4H), 1.82-1.76 (m, 1H), 1.47-1.37 (m, 2H), 0.93-0.91 (m, 6H) ppm.

4-[4-((R)-2-Hydroxy-4-methyl-pentanoyl)-piperazin-1-yl]-2-(2-hydroxy-phenyl)-quinazoline-6-carbonitrile hydrochloride

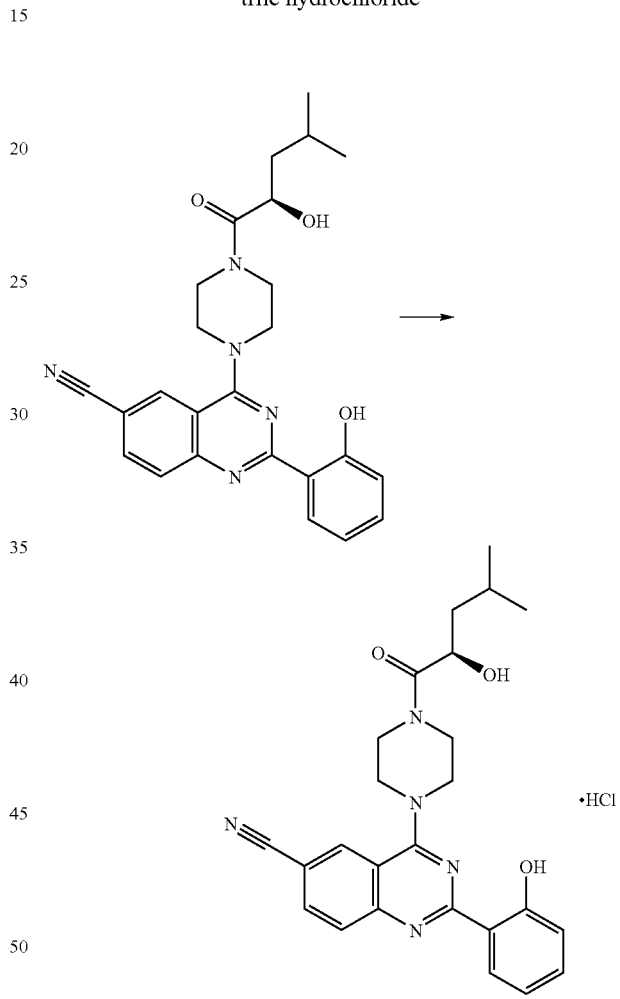

4-[4-((R)-2-Hydroxy-4-methyl-pentanoyl)-piperazin-1-yl]-2-(2-hydroxy-phenyl)-quinazoline-6-carbonitrile (137 mg, 0.31 mmol) was dissolved in the minimum amount of CH$_2$Cl$_2$. After stirring the solution under an N$_2$ atmosphere for 30 minutes, 1 M HCl in ether (0.31 mL, 0.31 mmol) was added dropwise to the solution and stirred for 10 minutes. Ether was added to precipitate the hydrochloride salt of 4-[4-((R)-2-hydroxy-4-methyl-pentanoyl)-piperazin-1-yl]-2-(2-hydroxy-phenyl)-quinazoline-6-carbonitrile, which was filtered and dried to obtain 136 mg of solid (91%). LC/MS: m/z 446 (M+H)$^+$ at 3.21 min (10%-99% CH$_3$CN (0.035% TFA)/H$_2$O (0.05% TFA)). $^1$H NMR (400 MHz, DMSO-d6) δ 8.62 (s, 1H), 8.43-8.41 (m, 1H), 8.17 (dd, J=8.7, 1.5 Hz, 1H), 8.02 (d, J=8.7 Hz, 1H), 7.47-7.43 (m, 1H), 7.00-6.96 (m, 2H), 4.39-4.36 (m, 1H), 4.18-4.00 (m, 4H), 3.91-3.68 (m, 4H), 1.85-1.75 (m, 1H), 1.51-1.35 (m, 2H), 0.94-0.91 (m, 6H) ppm; $^{13}$C NMR (100 MHz, DMSO-d6) δ 172.5, 161.7, 160.6, 135.1, 133.6, 132.4, 129.7, 126.9, 118.8, 118.4, 118.2, 117.4, 113.3, 107.3, 66.9, 48.7, 48.1, 43.5, 42.8, 41.1, 24.0, 23.4, 21.6.

Example 143

(R)-1-(4-(6-Fluoro-2-(2-hydroxyphenyl)quinazolin-4-yl)piperazin-1-yl)-2-hydroxy-4-methylpentan-1-one

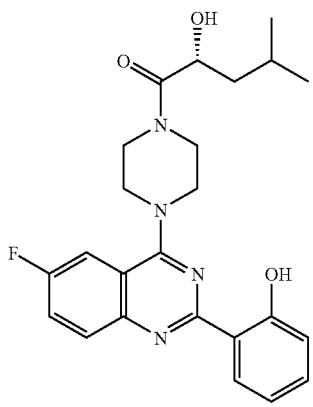

(R)-1-(4-(6-Fluoro-2-(2-hydroxyphenyl)quinazolin-4-yl)piperazin-1-yl)-2-hydroxy-4-methylpentan-1-one

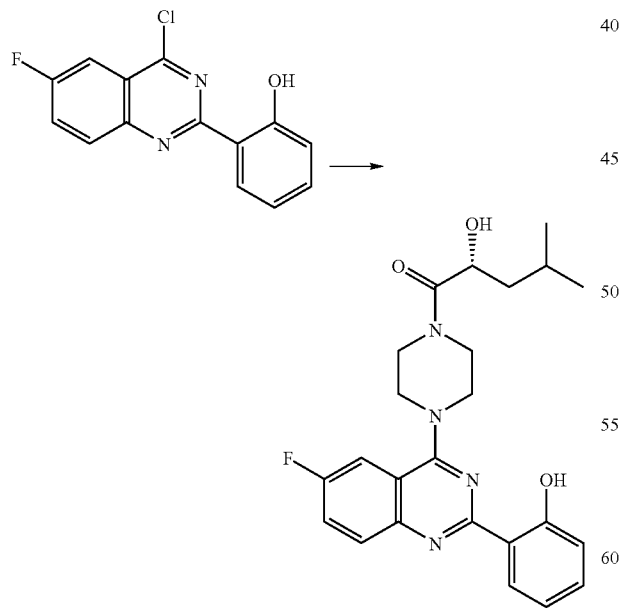

Method A

To a solution of 2-(4-chloro-6-fluoroquinazolin-2-yl)phenol (25 mg, 0.09 mmol) in DMF (1 mL) was added triethylamine (25 μL, 0.18 mmol) followed by the addition of (R)-2-hydroxy-4-methyl-1-(piperazin-1-yl)pentan-1-one oxalate (52 mg, 0.18 mmol) at 0° C. The reaction was stirred for 2 hours, and purification using reverse phase HPLC (10-99% CH$_3$CN (0.035% TFA)/H$_2$O (0.05% TFA)) gave (R)-1-(4-(6-fluoro-2-(2-hydroxyphenyl)quinazolin-4-yl)piperazin-1-yl)-2-hydroxy-4-methylpentan-1-one as the TFA salt. LC/MS: m/z 439.5 (M+H)$^+$ at 2.99 min (10%-99% CH$_3$CN (0.035% TFA)/H$_2$O (0.05% TFA)).

Method B

To a mixture of 2-(4-chloro-6-fluoroquinazolin-2-yl)phenol (200 mg, 0.72 mmol) and CH$_2$Cl$_2$ (7 mL) was added (R)-2-hydroxy-4-methyl-1-(piperazin-1-yl)pentan-1-one oxalate (275 mg, 0.95 mmol). The reaction was complete after two hours. Purification via silica gel chromatography using 0-10% EtOAc in 50:50 mixture of CH$_2$Cl$_2$:hexanes gave (R)-1-(4-(6-fluoro-2-(2-hydroxyphenyl)quinazolin-4-yl)piperazin-1-yl)-2-hydroxy-4-methylpentan-1-one (289 mg, 91%). LC/MS: m/z 439.30 (M+H)$^+$ at 3.00 min (10%-99% CH$_3$CN (0.035% TFA)/H$_2$O (0.05% TFA)). $^1$H NMR (400 MHz, DMSO-d6) d 8.46 (m, 1H), 8.02 (m, 1H), 7.84 (m, 2H), 7.40 (m, 1H), 6.97 (m, 2H), 4.92 (d, J=7.2 Hz, 1H), 4.38 (m, 1H), 3.98 (m, 4H), 3.76 (m, 4H), 1.80 (m, 1H), 1.42 (m, 2H), 0.92 (q, J=3.8 Hz, 6H) ppm.

(R)-1-(4-(6-Fluoro-2-(2-hydroxyphenyl)quinazolin-4-yl)piperazin-1-yl)-2-hydroxy-4-methylpentan-1-one hydrochloride

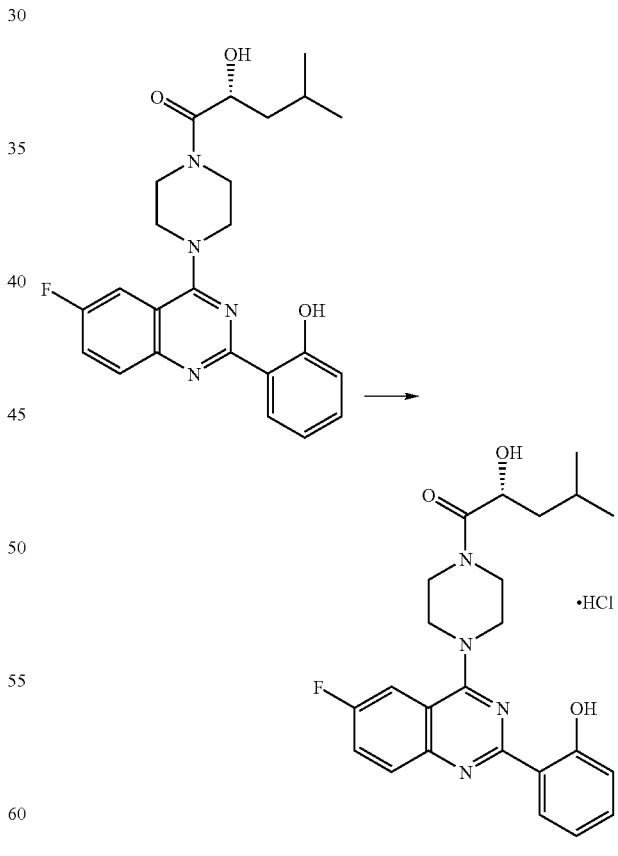

To a solution of (R)-1-(4-(6-fluoro-2-(2-hydroxyphenyl)quinazolin-4-yl)piperazin-1-yl)-2-hydroxy-4-methylpentan-1-one (285 mg, 0.65 mmol) in CH$_2$Cl$_2$ (2 mL) under an N$_2$ atmosphere was added ether (10 mL), followed by the dropwise addition of a 2 M HCl solution in ether (0.325 mL, 0.65 mmol). A precipitate was formed which was stirred for 30 min, collected by vacuum filtration, and dried to afford (R)-1-(4-(6-fluoro-2-(2-hydroxyphenyl)quinazolin-4-yl)piperazin-1-yl)-2-hydroxy-4-methylpentan-1-one hydrochloride (284 mg, 92%). LC/MS: m/z 439.30 (M+H)+ at 3.00 min (10%-99% CH$_3$CN (0.035% TFA)/H$_2$O (0.05% TFA)): $^1$H NMR (400 MHz, DMSO-d6) d 8.32 (dd, J=8.1, 1.5 Hz, 1H), 8.02 (m, 1H), 7.92 (dd, J=9.7, 2.7 Hz, 1H), 7.85 (m, 1H), 7.45 (m, 1H), 7.01 (m, 2H), 4.37 (dd, J=9.2, 4.1 Hz, 1H), 4.04 (m, 4H), 3.83 (m, 4H), 1.76 (m, 1H), 1.41 (m, 2H), 0.90 (dd, J=6.6, 3.7 Hz, 6H) ppm.

Example 144

(S)-2-Hydroxy-1-(4-(2-(2-hydroxyphenyl)-7-methylquinazolin-4-yl)piperazin-1-yl)-4-methylpentan-1-one

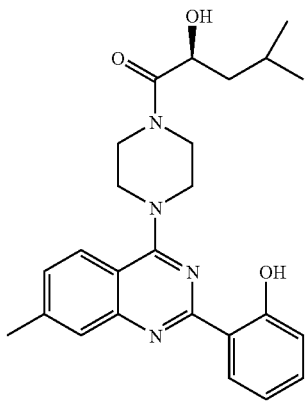

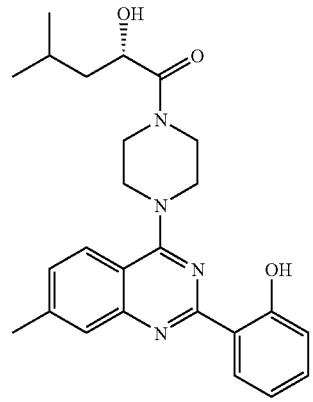

Under an N$_2$ atmosphere, BOP (137 mg, 0.31 mmol) was added in a single portion to a stirring solution of 2-(7-methyl-4-(piperazin-1-yl)quinazolin-2-yl)phenol (100 mg, 0.31 mmol), (S)-2-hydroxy-4-methylpentanoic acid (41 mg, 0.31 mmol), and triethylamine (43 μL, 0.31 mmol) in DMF (0.5 ml). After stirring the mixture for 1 h at room temperature, it was partitioned between H$_2$O and ether. The organic phase was washed with H$_2$O (3×20 mL), dried over MgSO$_4$, filtered, and concentrated. Purification via silica gel chromatography using 1:1 ethyl acetate/hexane gave (S)-2-hydroxy-1-(4-(2-(2-hydroxyphenyl)-7-methylquinazolin-4-yl)piperazin-1-yl)-4-methylpentan-1-one as a white solid. LC/MS: m/z 435.3 (M+H)+ at 2.62 min (10%-99% CH$_3$CN (0.035% TFA)/H$_2$O (0.05% TFA)). $^1$H NMR (400 MHz, DMSO-d6) d 8.44 (dd, J=8.2, 1.7 Hz, 1H), 7.99 (d, J=8.5 Hz, 1H), 7.67 (s, 1H), 7.40-7.36 (m, 2H), 6.96-6.93 (m, 2H), 4.92 (d, J=7.2 Hz, 1H) 4.41-4.36 (m, 1H), 4.06-3.67 (m, 8H), 2.51 (s, 3H), 1.85-1.73 (m, 1H), 1.49-1.35 (m, 2H), 0.93-0.91 (m, 6H) ppm.

(S)-2-Hydroxy-1-(4-(2-(2-hydroxyphenyl)-7-methylquinazolin-4-yl)piperazin-1-yl)-4-methylpentan-1-one hydrochloride (S)-2-Hydroxy-1-(4-(2-(2-hydroxyphenyl)-7-methylquinazolin-4-yl)piperazin-1-yl)-4-methylpentan-1-one

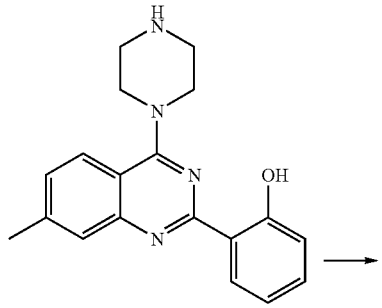

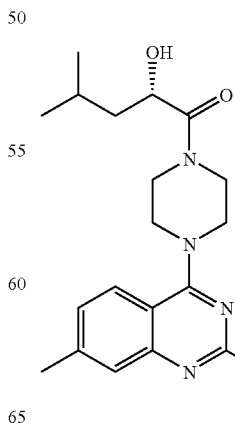

247
-continued

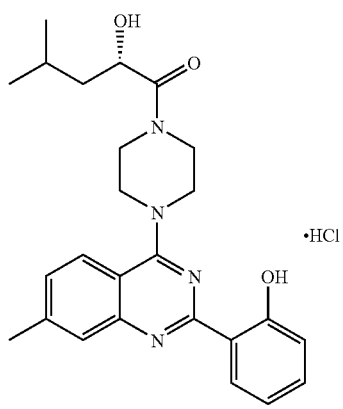

·HCl (S)-2-hydroxy-1-(4-(2-(2-hydroxyphenyl)-7-methylquinazolin-4-yl)piperazin-1-yl)-4-methylpentan-1-one (90 mg, 0.20 mmol) was dissolved in 1 mL $CH_2Cl_2$ and treated with 1 equivalent of 2.0 M HCl in ether (100 μL, 0.20 mmol). The formed precipitate was filtered and vacuum dried to obtain (S)-2-hydroxy-1-(4-(2-(2-hydroxyphenyl)-7-methylquinazolin-4-yl)piperazin-1-yl)-4-methylpentan-1-one hydrochloride. LC/MS: m/z 435.5 (M+H)$^+$ at 2.62 min (10%-99% $CH_3CN$ (0.035% TFA)/$H_2O$ (0.05% TFA)). $^1$H NMR (400 MHz, DMSO-d6) δ 8.27 (d, J=6.8 Hz, 1H), 8.09 (d, J=8.6 Hz, 1H), 7.78 (s, 1H), 7.50-7.45 (m, 2H), 7.09 (d, J=8.2 Hz, 1H), 7.03-6.99 (m, 1H), 4.39-4.35 (m, 1H), 4.16-3.68 (m, 8H), 2.54 (s, 3H), 1.84-1.72 (m, 1H), 1.49-1.35 (m, 2H), 0.93 (d, J=2.8 Hz, 6H) ppm.

Example 145

(R)-3-Hydroxy-4-(4-(2-(2-hydroxyphenyl)-7-methylquinazolin-4-yl)piperazin-1-yl)-4-oxobutanoic acid

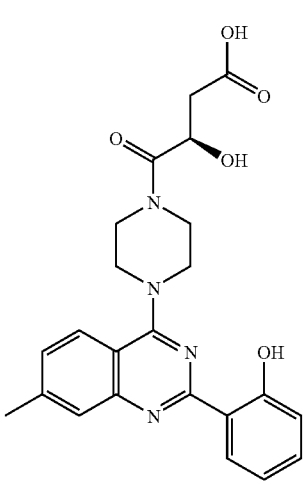

248

(R)-3-hydroxy-4-(4-(2-(2-hydroxyphenyl)-7-methylquinazolin-4-yl)piperazin-1-yl)-4-oxobutanoic acid

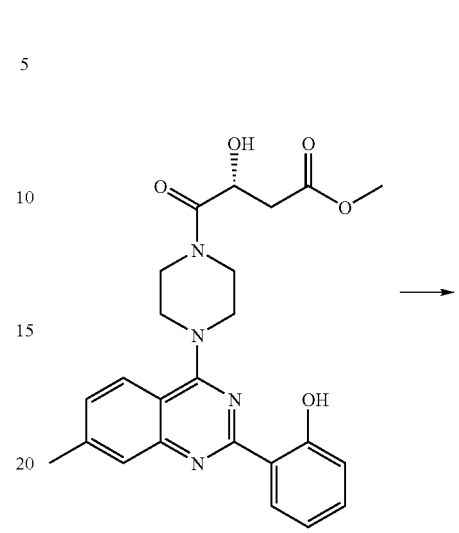

→

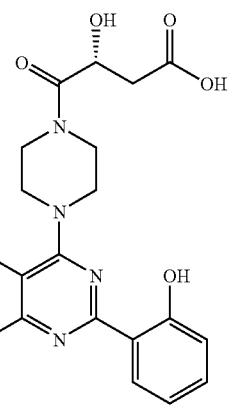

(R)-Methyl 3-hydroxy-4-(4-(2-(2-hydroxyphenyl)-7-methylquinazolin-4-yl)piperazin-1-yl)-4-oxobutanoate (88 mg, 0.20 mmol) and LiOH.H$_2$O (33 mg, 0.78 mmol) were stirred in THF:H$_2$O 1:1 at room temperature for 3 h. After acidification with 1 M HCl and extraction with EtOAc, the organic extracts were washed with water, dried over Na$_2$SO$_4$, and concentrated. The crude material was then purified via silica gel chromatography using 0-10% MeOH/CH$_2$Cl$_2$ to obtain (R)-3-hydroxy-4-(4-(2-(2-hydroxyphenyl)-7-methylquinazolin-4-yl)piperazin-1-yl)-4-oxobutanoic acid (75 mg, 88%). LC/MS: m/z 437.3 (M+H)+ at 2.04 min (10%-99% CH$_3$CN (0.035% TFA)/H$_2$O (0.05% TFA)).

Example 146

(R)-1-(4-(2-(2-Chloro-6-hydroxyphenyl)quinazolin-4-yl)piperazin-1-yl)-2-hydroxy-4-methylpentan-1-one

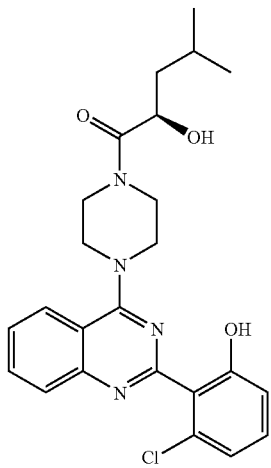

2-Amino-benzamide

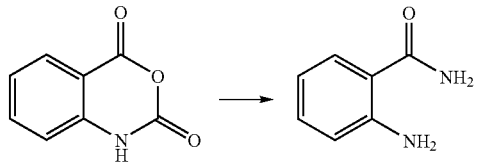

Isatoic anhydride (40 g, 245 mmol) was suspended in 650 mL 1 N NH$_4$OH (2.5 equiv) and stirred at room temperature for 3 days. The precipitate was filtered and washed with water. The product was then dissolved in THF, filtered, and concentrated to dryness. The product was dried by azeotropic distillation with toluene and washed with CH$_2$Cl$_2$ to yield 10.9 g (32.7%) of 2-amino-benzamide.

N-(2-carbamoylphenyl)-2-chloro-6-methoxybenzamide

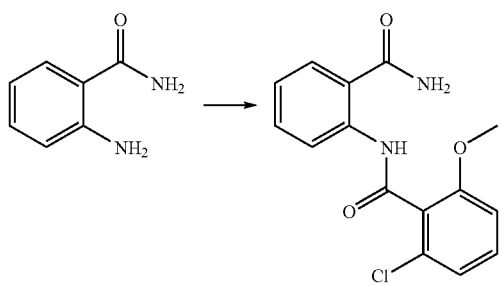

2-Amino-benzamide (6.9 g, 50.8 mmol) was dissolved in 50 mL of pyridine and cooled to 0° C. 2-Chloro-6-methoxy-benzoyl chloride was added dropwise to the solution. After complete addition, the reaction was left to stir at room temperature for three days, which resulted in formation of a brown, cloudy solution. The reaction mixture was then poured into 150 mL of ice water. The precipitate was filtered and washed twice with water, twice with THF and finally twice with CH$_2$Cl$_2$ to obtain N-(2-carbamoylphenyl)-2-chloro-6-methoxybenzamide (13.3 g, 43.7 mmol, 86%).

2-(2-Chloro-6-methoxy-phenyl)-3H-quinazolin-4-one

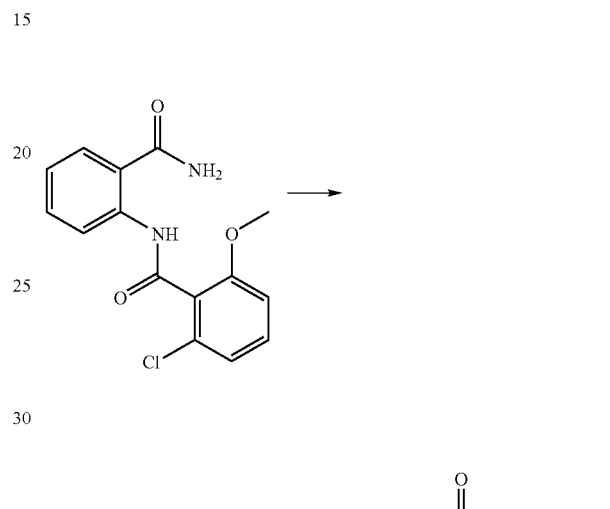

N-(2-carbamoylphenyl)-2-chloro-6-methoxybenzamide (13 g, 42.7 mmol) was suspended in 100 mL of a 2 N NaOH solution and heated to reflux. After refluxing for 3 hours, another 25 mL of a 2 N NaOH solution was added, and the reaction was refluxed for another hour. The mixture was cooled to room temperature and acidified with acetic acid to pH 5. The formed precipitate was collected by filtration. The product was purified over alumina using EtOAc as an eluent giving 1.7 g (5.9 mmol, 14%) of 2-(2-chloro-6-methoxy-phenyl)-3H-quinazolin-4-one.

4-Chloro-2-(2-chloro-6-methoxy-phenyl)-quinazoline

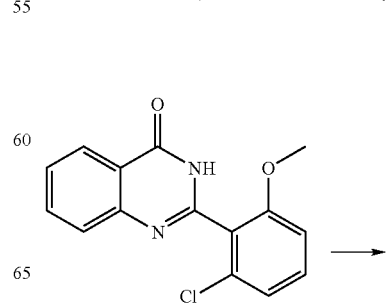

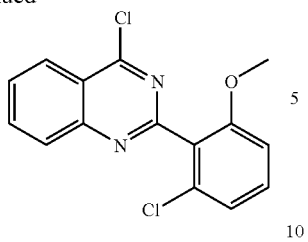

2-(2-Chloro-6-methoxy-phenyl)-3H-quinazolin-4-one (1.7 g, 5.9 mmol) was dissolved in 25 mL benzene. Then, N,N-dimethylaniline (1.15 mL, 9 mmol) and POCl$_3$ (1.65 mL, 17.7 mmol) were added. The reaction mixture was refluxed for 3 hours during which the yellow suspension changed to a dark red color. The mixture was cooled and diluted with 50 mL toluene. The solution was poured onto ice. Saturated aq. NaHCO$_3$ was added while stirring and cooling the mixture until the pH remained constant at 7. The layers were separated, and the aqueous layer was extracted with 100 mL toluene. The toluene layers were combined and washed with 100 mL saturated aqueous NaCl solution, 150 mL 0.5 N HCl, 150 mL 5% aq. NaHCO$_3$ and saturated aqueous NaCl solution. The toluene layer was dried over Na$_2$SO$_4$, filtered, and concentrated to dryness to yield 1.87 g impure product. The product was purified over silica gel with heptane/CH$_2$Cl$_2$ (2:1) as an eluent to yield 4-chloro-2-(2-chloro-6-methoxy-phenyl)-quinazoline (1.22 g, 64%).

3-Chloro-2-(4-chloroquinazolin-2-yl)phenol

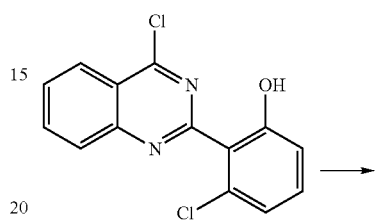

To a solution of 4-chloro-2-(2-chloro-6-methoxyphenyl)quinazoline (300 mg, 0.98 mmol) in 10 mL CH$_2$Cl$_2$ was added dropwise 5 equivalents of a 1 M BBr$_3$ solution in CH$_2$Cl$_2$ at −78° C. The reaction was warmed to room temperature and was complete in 30 minutes. The reaction was quenched with a saturated aqueous NaHCO$_3$ solution to pH 7. The aqueous layer was extracted with CH$_2$Cl$_2$, and the combined extracts were dried over Na$_2$SO$_4$, filtered, and concentrated to obtain 3-chloro-2-(4-chloroquinazolin-2-yl)phenol.

LC/MS: m/z 291.3 (M+H)$^+$ at 3.16 min (10%-99% CH$_3$CN (0.035% TFA)/H$_2$O (0.05% TFA)).

(R)-1-(4-(2-(2-Chloro-6-hydroxyphenyl)quinazolin-4-yl)piperazin-1-yl)-2-hydroxy-4-methylpentan-1-one

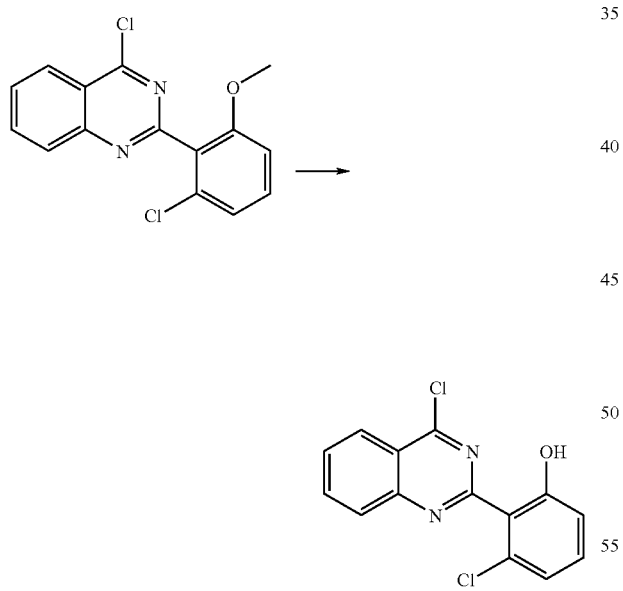

To a solution of 3-chloro-2-(4-chloroquinazolin-2-yl)phenol (42 mg, 0.14 mmol) in 2 mL CH$_2$Cl$_2$ was added triethylamine (40 µL) followed by the addition of (R)-2-hydroxy-4-methyl-1-(piperazin-1-yl)pentan-1-one (37.5 mg, 0.187 mmol). The reaction was complete after 1 hour. Purification using reverse phase HPLC (10-99% CH$_3$CN (0.035% TFA)/H$_2$O (0.05% TFA)) gave (R)-1-(4-(2-(2-chloro-6-hydroxyphenyl)quinazolin-4-yl)piperazin-1-yl)-2-hydroxy-4-methylpentan-1-one as the TFA salt. LC/MS: m/z 455.5 (M+H)+ at 2.45 min (10%-99% CH3CN (0.035% TFA)/H2O (0.05% TFA)).

Example 147

(R)-1-(4-(2-(2-Fluoro-6-hydroxyphenyl)-7-methylquinazolin-4-yl)piperazin-1-yl)-2-hydroxy-4-methylpentan-1-one

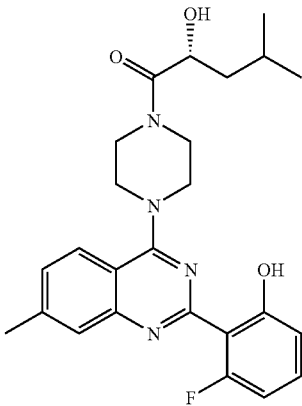

(R)-1-(4-(2-(2-Fluoro-6-hydroxyphenyl)-7-methylquinazolin-4-yl)piperazin-1-yl)-2-hydroxy-4-methylpentan-1-one

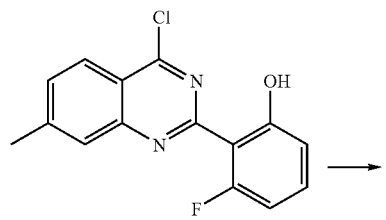

Method A

To a solution of 2-(4-chloro-7-methylquinazolin-2-yl)-3-fluorophenol (50 mg, 0.174 mmol) in 1 mL DMF was added triethylamine (35.2 mg, 0.348 mmol), followed by the addition of (R)-2-hydroxy-4-methyl-1-(piperazin-1-yl)pentan-1-one (42.1 mg, 0.21 mmol). After stirring the reaction for 1 hour, it was filtered, and purified via preparative reverse phase HPLC (10-99% CH3CN (0.035% TFA)/H2O (0.05% TFA)) to obtain (R)-1-(4-(2-(2-fluoro-6-hydroxyphenyl)-7-methylquinazolin-4-yl)piperazin-1-yl)-2-hydroxy-4-methylpentan-1-one as the TFA salt. LC/MS: m/z 453.3 (M+H)+ at 2.40 min (10%-99% CH3CN (0.035% TFA)/H2O (0.05% TFA)).

Method B 2-(4-Chloro-7-methylquinazolin-2-yl)-3-fluorophenol (300 mg, 1.04 mmol) in CH2Cl2 (5 mL) was cooled using an ice water batch. To this stirring solution was added (R)-2-hydroxy-4-methyl-1-(piperazin-1-yl)pentan-1-one (312 mg, 1.56 mmol), followed by triethylamine (210 mg, 291 µL, 2.08 mmol). After letting the reaction warm to room temperature, it was stirred overnight. The mixture was partitioned between water and CH2Cl2 and separated, and the aqueous layer was extracted with CH2Cl2. The combined organic layers were dried over Na2SO4, filtered, and concentrated to a viscous yellow oil. Purification via silica gel chromatography using 0-30% EtOAc in CH2Cl2/hexanes (2:1) gave (R)-1-(4-(2-(2-fluoro-6-hydroxyphenyl)-7-methylquinazolin-4-yl)piperazin-1-yl)-2-hydroxy-4-methylpentan-1-one as a bright yellow foam/solid. (413 mg, 88%). LC/MS: m/z 453.1 (M+H)+ at 2.44 min (10%-99% CH3CN (0.035% TFA)/H2O (0.05% TFA)). 1H NMR (400 MHz, DMSO-d6) d 8.01 (d, J=8.5 Hz, 1H), 7.68 (s, 1H), 7.42 (d, J=8.5 Hz, 1H), 7.37-7.32 (m, 1H), 6.80 (d, J=8.3 Hz, 1H), 6.76-6.71 (m, 1H), 4.91 (d, J=7.2 Hz, 1H), 4.40-4.35 (m, 1H), 4.02-3.65 (m, 8H), 2.52 (s, 3H), 1.82-1.73 (m, 1H), 1.47-1.34 (m, 2H), 0.91 (dd, J=6.5, 4.1 Hz, 6H) ppm.

(R)-1-(4-(2-(2-Fluoro-6-hydroxyphenyl)-7-methylquinazolin-4-yl)piperazin-1-yl)-2-hydroxy-4-methylpentan-1-one hydrochloride

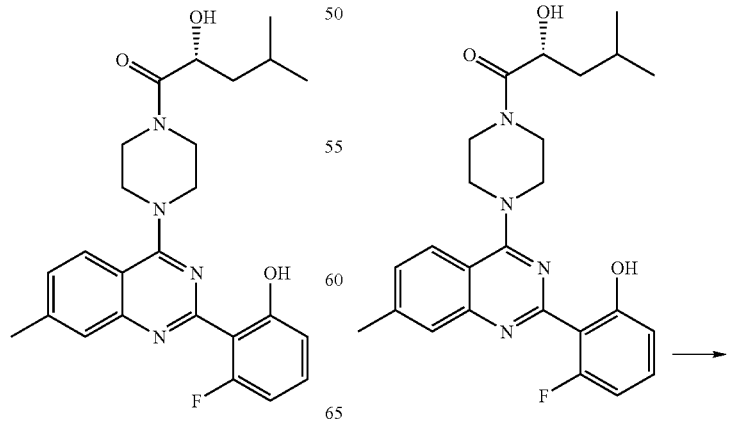

-continued

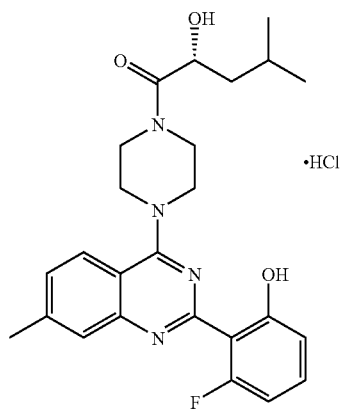

(R)-1-(4-(2-(2-Fluoro-6-hydroxyphenyl)-7-methylquinazolin-4-yl)piperazin-1-yl)-2-hydroxy-4-methylpentan-1-one (406 mg, 0.898 mmol) was dissolved in anhydrous CH$_2$Cl$_2$ (3 mL) followed by the addition of Et$_2$O (6 mL) under an N$_2$ atmosphere. A 2.0 M HCl solution in Et$_2$O (0.449 mL, 0.898 mmol) was added over a 2-minute period. The reaction solution changed from a clear yellow solution to a turbid white slurry. After complete addition of the HCl solution, the reaction was allowed to stir for an additional 15 minutes. The product was collected by vacuum filtration and dried under vacuum to obtain (R)-1-(4-(2-(2-fluoro-6-hydroxyphenyl)-7-methylquinazolin-4-yl)piperazin-1-yl)-2-hydroxy-4-methylpentan-1-one hydrochloride as a white solid (403 mg, 92%). LC/MS: m/z 453.5 (M+H)$^+$ at 2.44 min (10%-99% CH$_3$CN (0.035% TFA)/H$_2$O (0.05% TFA)). $^1$H NMR (400 MHz, DMSO-d6) d 8.20 (d, J=8.7 Hz, 1H), 7.71 (s, 1H), 7.60-7.60 (m, 1H), 7.50-7.44 (m, 1H), 6.99 (d, J=8.4 Hz, 1H), 6.87 (t, J=9.1 Hz, 1H), 4.36-4.33 (m, 1H), 4.25-3.67 (m, 8H), 2.57 (s, 3H), 1.83-1.71 (m, 1H), 1.49-1.35 (m, 2H), 0.91 (d, J=6.7 Hz, 6H) ppm.

Example 148

(R)-Tetrahydrofuran-3-yl 4-(6-fluoro-2-(2-hydroxyphenyl)quinazolin-4-yl)piperazine-1-carboxylate

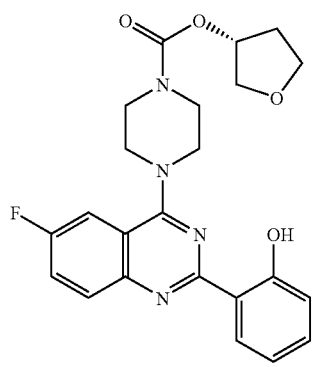

(R)-Tetrahydrofuran-3-yl chloroformate

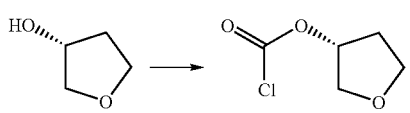

A stirred solution of (R)-tetrahydrofuran-3-ol (7.9 g, 90 mmol) in anhydrous CH$_2$Cl$_2$ (50 mL) under an N$_2$ atmosphere was cooled in an ice bath, and a 20% solution of phosgene in toluene (134 mL, 270 mmol) was slowly added. The reaction was allowed to warm to room temperature overnight, and the solvent was removed under vacuum to afford (R)-tetrahydrofuran-3-yl chloroformate (12.1 g, 85%) as a clear liquid.

(R)-Tetrahydrofuran-3-yl 4-(6-fluoro-2-(2-hydroxyphenyl)quinazolin-4-yl)piperazine-1-carboxylate

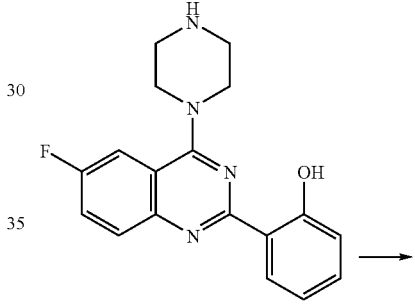

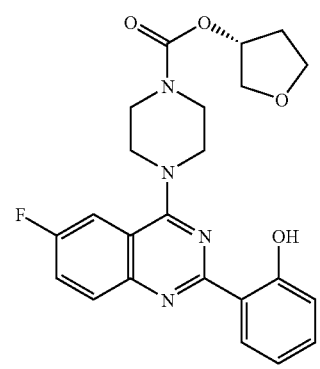

2-(6-Fluoro-4-(piperazin-1-yl)quinazolin-2-yl)phenol (25 mg, 0.08 mmol), (R)-tetrahydrofuran-3-yl chloroformate (12 mg, 0.08 mmol), triethylamine (22 µL, 0.154 mmol) were stirred in DMF (1 mL) overnight. Purification via reverse phase HPLC (10-99% CH$_3$CN (0.035% TFA)/H$_2$O (0.05% TFA)) gave (R)-tetrahydrofuran-3-yl 4-(6-fluoro-2-(2-hydroxyphenyl)quinazolin-4-yl)piperazine-1-carboxylate as the TFA salt. LC/MS: m/z 439.5 (M+H)+ at 2.80 min (10%-99% CH₃CN (0.035% TFA)/H₂O (0.05% TFA)).

Example 149

(2R)-(R)-Tetrahydrofuran-3-yl 2-(hydroxymethyl)-4-(2-(2-hydroxyphenyl)-7-methylquinazolin-4-yl)piperazine-1-carboxylate

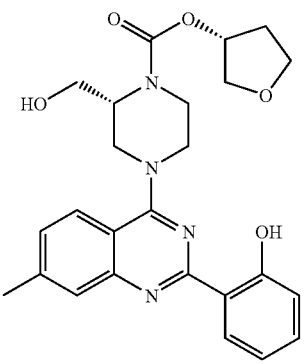

(2R)-(R)-Tetrahydrofuran-3-yl 2-((benzyloxy)methyl)-4-(2-(2-hydroxyphenyl)-7-methylquinazolin-4-yl)piperazine-1-carboxylate

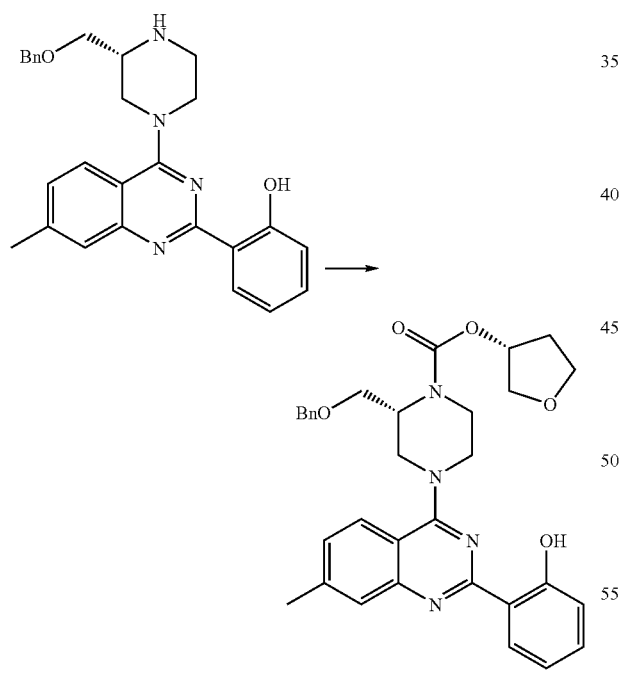

To a solution of 2-(4-((R)-3-((benzyloxy)methyl)piperazin-1-yl)-7-methylquinazolin-2-yl)phenol (75 mg, 0.17 mmol) in DMF (1 mL) was added triethylamine (47 μL) followed by the dropwise addition of (R)-tetrahydrofuran-3-yl chloroformate (25 mg, 0.17 mmol) at 0° C. The reaction was warmed to room temperature and stirred for 10 minutes. Purification using reverse phase HPLC (10-99% CH₃CN (0.035% TFA)/H₂O (0.05% TFA)) gave (2R)-(R)-tetrahydrofuran-3-yl 2-((benzyloxy)methyl)-4-(2-(2-hydroxyphenyl)-7-methylquinazolin-4-yl)piperazine-1-carboxylate as the TFA salt.

(2R)-(R)-Tetrahydrofuran-3-yl 2-(hydroxymethyl)-4-(2-(2-hydroxyphenyl)-7-methylquinazolin-4-yl)piperazine-1-carboxylate

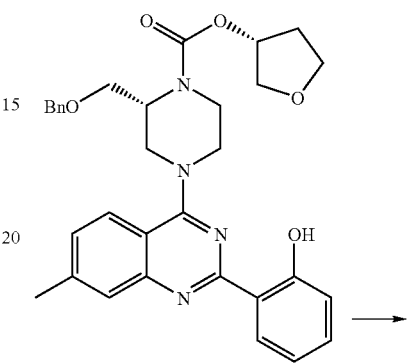

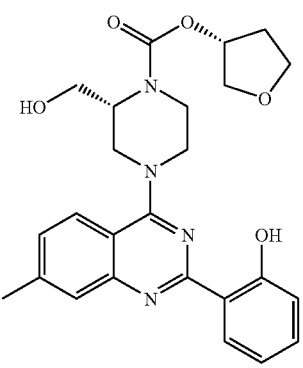

To a solution of (2R)-(R)-tetrahydrofuran-3-yl 2-((benzyloxy)methyl)-4-(2-(2-hydroxyphenyl)-7-methylquinazolin-4-yl)piperazine-1-carboxylate TFA salt (94 mg, 0.17 mmol) in ethanol was added Pd(OH)₂ (78 mg), and the reaction was heated at 50° C. under an H₂ atmosphere at ambient pressure. The reaction was filtered, and purification using reverse phase HPLC (10-99% CH₃CN (0.035% TFA)/H₂O (0.05% TFA)) gave (2R)-(R)-tetrahydrofuran-3-yl 2-(hydroxymethyl)-4-(2-(2-hydroxyphenyl)-7-methylquinazolin-4-yl)piperazine- 1-carboxylate trifluoroacetate. LC/MS: m/z 465.5 (M+H)+ at 2.23 min (10%-99% CH$_3$CN (0.035% TFA)/H$_2$O (0.05% TFA)).

Example 150

(R)-2-Hydroxy-1-(4-(2-(2-hydroxy-6-methylphenyl)-7-methylquinazolin-4-yl)piperazin-1-yl)-4-methylpentan-1-one

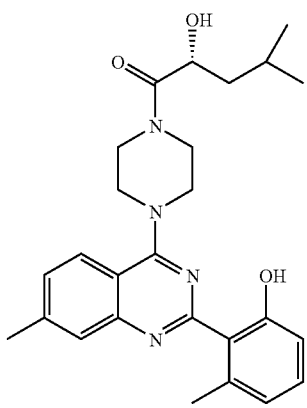

2-Methoxy-6-methyl-benzoic acid

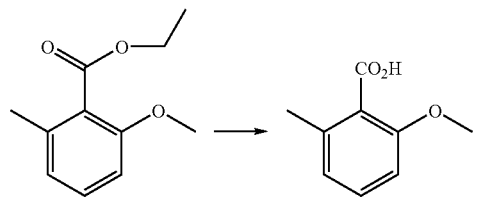

Ethyl-2-methoxy-6-methylbenzoate (30.4 g, 0.157 mol) was added to 100 mL 3.2 M NaOH (2 equiv) and 150 mL hot EtOH. The mixture was refluxed overnight after which EtOH was removed in vacuo. The aqueous mixture was acidified with 5 M HCl to pH 3. CH$_2$Cl$_2$ (200 mL) was added, and the layers were separated. The water layer was extracted two times with 200 mL CH$_2$Cl$_2$, and the organic layers were combined and dried over Na$_2$SO$_4$. Filtering the Na$_2$SO$_4$ and concentrating the CH$_2$Cl$_2$ to dryness yielded 21.4 g (0.129 mol, 82.3%) of 2-methoxy-6-methyl-benzoic acid.

2-Methoxy-6-methyl-benzoyl chloride

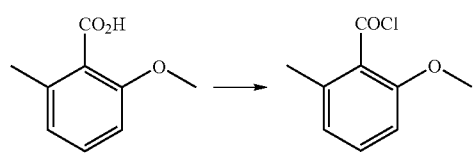

2-Methoxy-6-methyl-benzoic acid (21.4 g, 0.129 mol) was refluxed for 3 hours in 230 mL thionyl chloride. Excess thionyl chloride was removed under reduced pressure. Co-evaporation of the residue with toluene gave 23.8 g of 2-methoxy-6-methyl-benzoyl chloride.

N-(2-Cyano-5-methyl-phenyl)-2-methoxy-6-methyl-benzamide

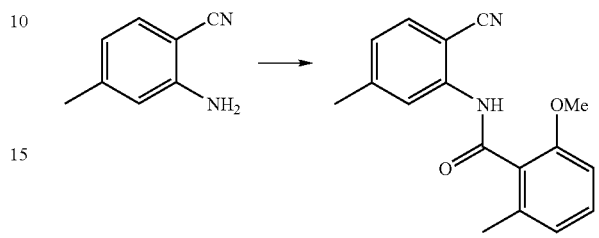

2-Amino-4-methyl-benzonitrile (15.4 g, 0.117 mol) was dissolved in 100 mL pyridine and cooled to 0° C. To this mixture was added dropwise 2-methoxy-6-methylbenzoyl chloride (24 g, 0.13 mol, 1.1 equiv). During the addition the temperature did not exceed 2° C. The reaction was stirred at room temperature for 48 hours. The mixture was poured into 400 mL ice water, and the precipitate was collected by filtration and washed with water. The crude product was dissolved in 600 mL CH$_2$Cl$_2$, and the solution was washed twice with 500 mL of a 1 N HCl solution and once with 400 mL of a saturated aq. NaCl solution. The CH$_2$Cl$_2$ layer was dried over Na$_2$SO$_4$, filtered, and concentrated to dryness to yield 25.44 g (0.09 mol, 77.6%) of N-(2-cyano-5-methyl-phenyl)-2-methoxy-6-methyl-benzamide.

2-(2-Methoxy-6-methyl-phenyl)-7-methyl-3H-quinazolin-4-one

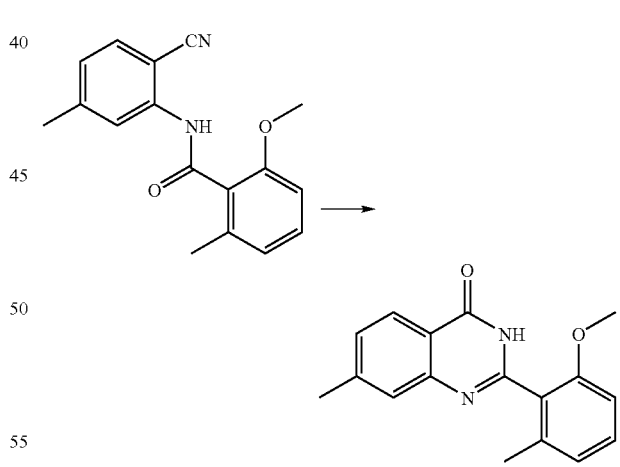

N-(2-Cyano-5-methyl-phenyl)-2-methoxy-6-methyl-benzamide (25 g, 0.09 mol) was suspended in 500 mL EtOH, and 121.3 g of 33% aq. NaOH (1 mol, 11 equiv) was added. To this was added a 35% H$_2$O$_2$ solution (50 mL, 0.58 mol), and the reaction was heated to reflux. Additional H$_2$O$_2$ was added dropwise until the reaction mixture became clear. EtOH was removed under reduced pressure, and the precipitate formed was removed by filtration. The solution was acidified with acetic acid to pH 5, and the precipitate formed was collected by filtration. The precipitate was washed twice with water and once with diethyl ether. The product was purified over alumina using EtOAc/heptane (1:1) as an eluent. Another purification was performed, over silica gel with the same eluent to yield 2-(2-methoxy-6-methyl-phenyl)-7-methyl-3H-quinazolin-4-one (1.61 g).

4-Chloro-2-(2-methoxy-6-methyl-phenyl)-7-methyl-quinazoline

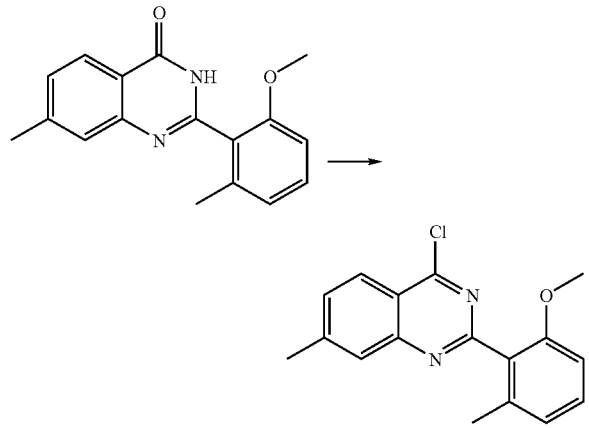

2-(2-Methoxy-6-methyl-phenyl)-7-methyl-3H-quinazolin-4-one (1.61 g, 5.74 mmol) was suspended in benzene after which was added N,N-dimethylaniline (1.1 mL, 8.62 mmol) and POCl$_3$ (1.61 mL, 17.27 mmol). The reaction mixture was refluxed for 3 hours during which the color changed from yellow to dark red. The reaction mixture was cooled to room temperature, diluted with 40 mL toluene and poured onto ice. Saturated aq. NaHCO$_3$ was carefully added until the pH remained constant at 7 and no more gas formed. The layers were separated, and the water layer was extracted with toluene. The organic layers were combined and washed with respectively 50 mL saturated aq. NaCl, 60 mL 0.5 N HCl, 40 mL 5% NaHCO$_3$ and 50 mL saturated aq. NaCl. The solution was dried over Na$_2$SO$_4$ and evaporated to dryness to yield 1.7 g of the impure product. The product was filtered through silica gel and washed with CH$_2$Cl$_2$:heptane (2:1) to yield of 4-chloro-2-(2-methoxy-6-methyl-phenyl)-7-methyl-quinazoline (1.22 g, 71%).

2-(4-Chloro-7-methylquinazolin-2-yl)-3-methylphenol

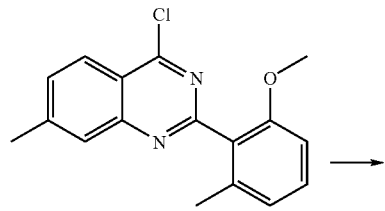

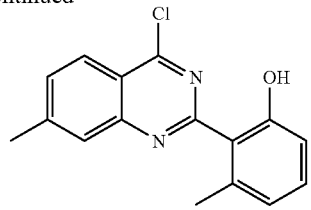

To a solution of 4-chloro-2-(2-methoxy-6-methylphenyl)-7-methylquinazoline (669 mg, 2.24 mmol) in 7 mL CH$_2$Cl$_2$ was added dropwise 5 equivalents of a 1 M solution of BBr$_3$ in CH$_2$Cl$_2$ at −78° C. The reaction was warmed to room temperature and was complete in 30 minutes. The reaction was quenched with a saturated aqueous NaHCO$_3$ solution until the pH was neutral. The aqueous layer was extracted with CH$_2$Cl$_2$, dried over MgSO$_4$, filtered, and concentrated to obtain 2-(4-chloro-7-methylquinazolin-2-yl)-3-methylphenol. LC/MS: m/z 285.1 (M+H)$^+$ at 3.94 min (10%-99% CH$_3$CN (0.035% TFA)/H$_2$O (0.05% TFA)).

(R)-2-Hydroxy-1-(4-(2-(2-hydroxy-6-methylphenyl)-7-methylquinazolin-4-yl)piperazin-1-yl)-4-methylpentan-1-one

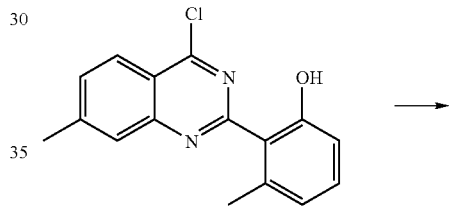

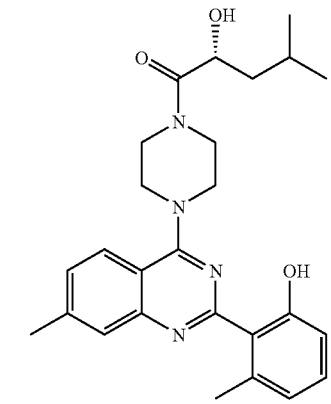

To a solution of 2-(4-chloro-7-methylquinazolin-2-yl)-1-methylphenol (60 mg, 2.1 mmol) in 2 mL CH$_2$Cl$_2$ was added triethylamine followed by the addition of (R)-2-hydroxy-4-methyl-1-(piperazin-1-yl)pentan-1-one (54.8 mg, 2.73 mmol). The reaction was complete after 1 hour. Purification using reverse phase HPLC (10-99% CH$_3$CN (0.035% TFA)/H$_2$O (0.05% TFA)) gave (R)-2-hydroxy-1-(4-(2-(2-hydroxy-6-methylphenyl)-7-methylquinazolin-4-yl)piperazin-1-yl)-

4-methylpentan-1-one as the TFA salt. LC/MS: m/z 449.3 (M+H)⁺ at 2.22 min (10%-99% CH₃CN (0.035% TFA)/H₂O (0.05% TFA)).

Example 151

(R)-2-Hydroxy-1-(4-(2-(2-hydroxyphenyl)-7-methylquinazolin-4-yl)piperazin-1-yl)pentan-1,4-dione

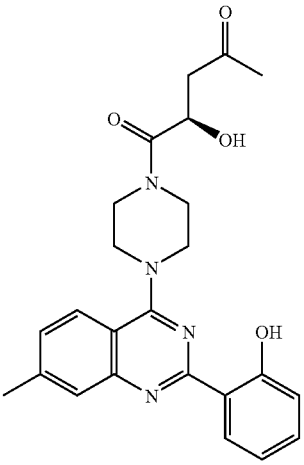

Methyl 2-((R)-2,2-dimethyl-5-oxo-1,3-dioxolan-4-yl)acetate

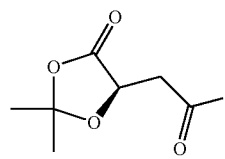

2-((R)-2,2-Dimethyl-5-oxo-1,3-dioxolan-4-yl)acetic acid (15.8 g, 90.9 mmol) in a 3:1 mixture of THF:MeOH (100 mL) was cooled in an ice bath. After adding 2.0 M TMSCHN₂ (50 mL, 100 mmol) the bath was removed, and the mixture was stirred at room temperature for 3 h. The solvent was evaporated, and the crude material was purified via silica gel chromatography using 0-50% EtOAc/hexanes to give methyl 2-((R)-2,2-dimethyl-5-oxo-1,3-dioxolan-4-yl)acetate. ¹H NMR (400 MHz, CDCl₃) d 4.73 (dd, J=6.6, 3.8 Hz, 1H), 3.74 (s, 3H), 2.95 (dd, J=17.0, 3.9 Hz, 1H), 2.81 (dd, J=17.0, 6.6 Hz, 1H), 1.63 (s, 3H), 1.57 (s, 3H) ppm.

4-((R)-2-Hydroxy-3-methoxycarbonyl-propionyl)-piperazine-1-carboxylic acid benzyl ester

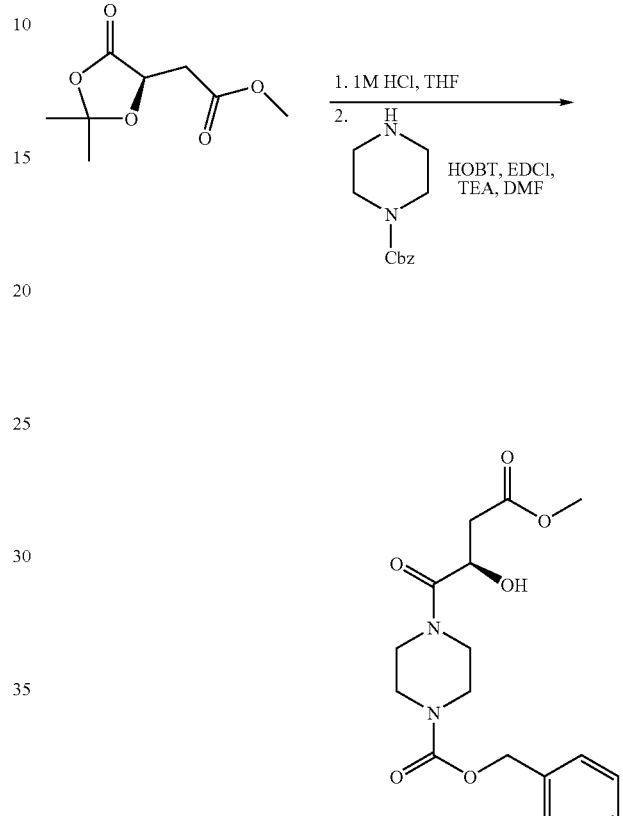

Methyl 2-((R)-2,2-dimethyl-5-oxo-1,3-dioxolan-4-yl)acetate (17.1 g, 90.9 mmol) was stirred in a 1:1 mixture of THF:1 M HCl (200 mL) for 1 h at room temperature. After addition of NaCl to nearly saturate the aqueous layer, the mixture was extracted with EtOAc, and the extracts were dried over Na₂SO₄ and concentrated. To the resulting oil dissolved in dry DMF (500 mL) was added HOBt (13.5 g, 100 mmol) and EDCI (19.2 g, 100 mmol). After stirring for 5 min, benzyl piperazine-1-carboxylate (19.3 mL, 100 mmol) and triethylamine (13.9 mL, 100 mmol) were added to the reaction mixture, which was left stirring at room temperature overnight. Purification via silica gel chromatography using 0-10% MeOH/CH₂Cl₂ provided a colorless oil 4-((R)-2-hydroxy-3-methoxycarbonyl-propionyl)-piperazine-1-carboxylic acid benzyl ester (6.71 g, 21%). LC/MS: m/z 351.5 (M+H)⁺ at 2.67 min (10%-99% CH₃CN (0.035% TFA)/H₂O (0.05% TFA)).

4-((R)-2-Hydroxy-4-oxo-pentanoyl)-piperazine-1-carboxylic acid benzyl ester

To a solution of 4-((R)-2-hydroxy-3-methoxycarbonyl-propionyl)-piperazine-1-carboxylic acid benzyl ester (8.5 g, 24.0 mmol) in THF (240 mL) cooled in a dry ice acetone

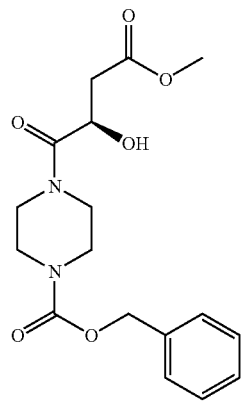

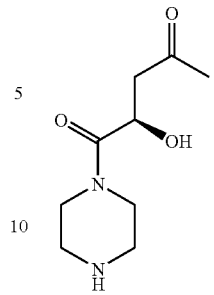

→

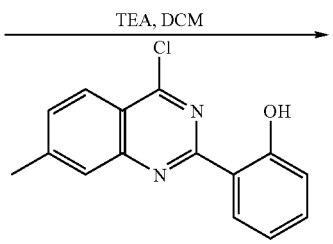

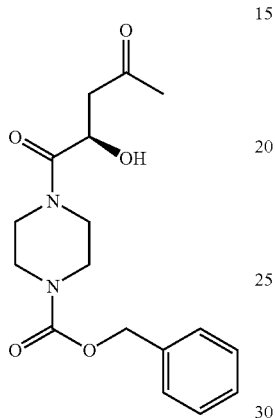

bath, was added 1.4 M MeMgBr (61 mL, 85 mmol). The reaction was allowed to slowly warm to room temperature overnight. After quenching the mixture with saturated NH$_4$Cl and extracting with EtOAc, the combined organic extracts were washed with water, dried over Na$_2$SO$_4$, and concentrated. Purification via silica gel chromatography using 0-10% MeOH/CH$_2$Cl$_2$ gave 4-((R)-2-hydroxy-4-oxo-pentanoyl)-piperazine-1-carboxylic acid benzyl ester as a colorless oil (0.9 g, 11%). $^1$H NMR (400 MHz, CDCl$_3$) δ 7.39-7.31 (m, 5H), 5.15 (s, 2H), 4.79-4.74 (m, 1H), 4.00 (d, J=7.8 Hz, 1H), 3.75-3.45 (m, 8H), 2.85 (dd, J=16.6, 7.3 Hz, 1H), 2.63 (dd, J=16.6, 3.4 Hz, 1H), 2.26 (s, 3H) ppm; LC/MS: m/z 335.1 (M+H)$^+$ at 2.17 min (10%-99% CH$_3$CN (0.035% TFA)/H$_2$O (0.05% TFA)).

(R)-2-hydroxy-1-(4-(2-(2-hydroxyphenyl)-7-methylquinazolin-4-yl)piperazin-1-yl)pentan-1,4-dione

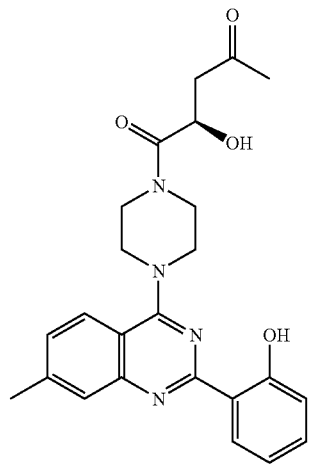

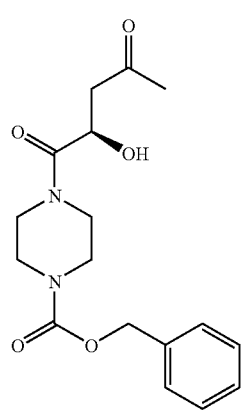

H$_2$, 10% Pd/C →

A mixture of 4-((R)-2-hydroxy-4-oxo-pentanoyl)-piperazine-1-carboxylic acid benzyl ester (0.13 g, 0.39 mmol) and MeOH (4 mL) was stirred with 10 mg of Pd/C (10% wt Pd on carbon) under H$_2$ atmosphere at ambient pressure overnight. After filtration and evaporation of the solvent, the residue was taken up in CH$_2$Cl$_2$, and 2-(4-chloro-7-methylquinazolin-2-yl)phenol (0.11 g, 0.39 mmol) and triethylamine (0.11 mL, 0.78 mmol) were added. The reaction mixture was stirred at room temperature overnight, washed with water, dried over Na$_2$SO$_4$, and concentrated. Purification via silica gel chromatography using 0-10% MeOH/CH$_2$Cl$_2$ provided (R)-2-hydroxy-1-(4-(2-(2-hydroxyphenyl)-7-methylquinazolin-4-yl) piperazin-1-yl)pentan-1,4-dione as a yellow solid (91 mg, 54%). LC/MS: m/z 435.5 (M+H)$^+$ at 2.13 min (10%-99% CH$_3$CN (0.035% TFA)/H$_2$O (0.05% TFA))yl)piperazin-1-yl)

pentan-1,4-dione as a yellow solid (91 mg, 54%). LC/MS: m/z 435.5 (M+H)+ at 2.13 min (10%-99% CH3CN (0.035% TFA)/H2O (0.05% TFA)).

Example 152

(Pyridin-4-yl)methyl 4-(2-(2-hydroxyphenyl)-7-methylquinazolin-4-yl)piperazine-1-carboxylate

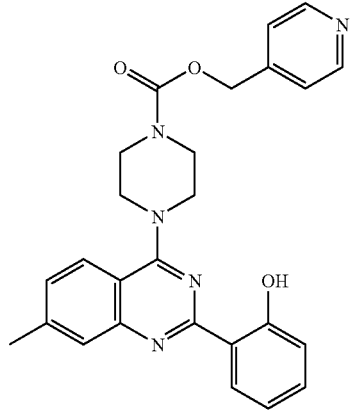

(Pyridin-4-yl)methyl 4-(2-(2-hydroxyphenyl)-7-methylquinazolin-4-yl)piperazine-1-carboxylate

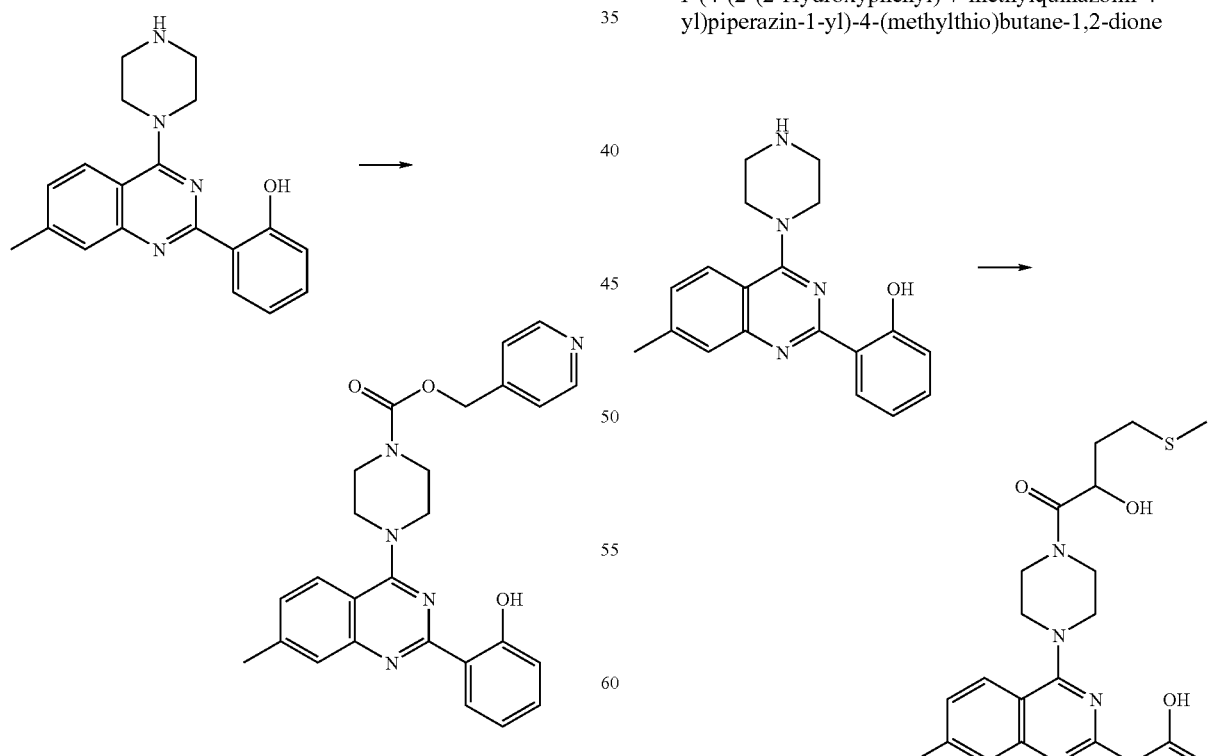

A solution of 2-(7-methyl-4-(piperazin-1-yl)quinazolin-2-yl)phenol (50 mg, 0.16 mmol), (pyridin-4-yl)methyl 1H-imidazole-1-carboxylate (67 mg, 0.32 mmol), and triethylamine (44.6 μL, 0.32 mmol) in DMSO (500 μL) was heated in a microwave synthesizer at 200° C. for 10 minutes. Purification using reverse phase HPLC (10-99% CH3CN (0.035% TFA)/H2O (0.05% TFA)) gave (pyridin-4-yl)methyl 4-(2-(2-hydroxyphenyl)-7-methylquinazolin-4-yl)piperazine-1-carboxylate as the TFA salt. LC/MS: m/z 456.5 (M+H)+ at 2.02 min (10%99% CH3CN (0.035% TFA)/H2O (0.05% TFA)).

Example 153

2-Hydroxy-1-(4-(2-(2-hydroxyphenyl)-7-methylquinazolin-4-yl)piperazin-1-yl)-4-(methylthio)butan-1-one

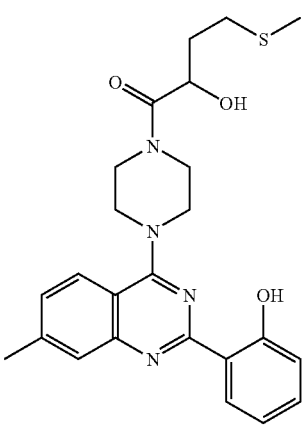

1-(4-(2-(2-Hydroxyphenyl)-7-methylquinazolin-4-yl)piperazin-1-yl)-4-(methylthio)butane-1,2-dione A mixture of 2-(7-methyl-4-(piperazin-1-yl)quinazolin-2-yl)phenol (200 mg, 0.63 mmol), sodium 4-methylsulfanyl-2-oxo-butyrate (160 mg, 0.94 mmol), BOP (414 mg, 0.94 mmol), and triethylamine (348 µL, 2.5 mmol) in 2.1 mL of $CH_2Cl_2$ was stirred at room temperature for 1 h. After adding saturated $NaHCO_3$ solution, the mixture was extracted with $CH_2Cl_2$. The organic extracts were dried over $Na_2SO_4$ and concentrated to give 1-(4-(2-(2-hydroxyphenyl)-7-methylquinazolin-4-yl)piperazin-1-yl)-4-(methylthio)butane-1,2-dione. LC/MS: m/z 451.2 $(M+H)^+$ at 3.10 min (10%-99% $CH_3CN$ (0.035% TFA)/$H_2O$ (0.05% TFA)).

2-Hydroxy-1-(4-(2-(2-hydroxyphenyl)-7-methylquinazolin-4-yl)piperazin-1-yl)-4-(methylthio)butan-1-one

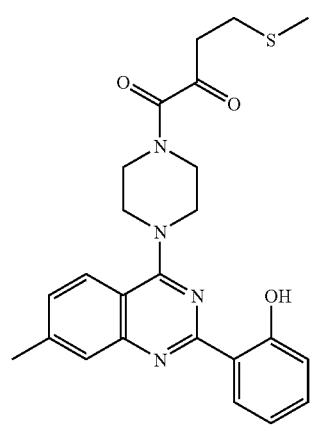

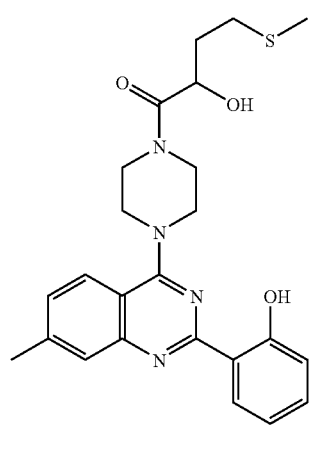

NaBH$_4$ (34 mg, 0.88 mmol) was added to 1-(4-(2-(2-hydroxyphenyl)-7-methylquinazolin-4-yl)piperazin-1-yl)-4-(methylthio)butane-1,2-dione (200 mg, 0.44 mmol) in 1.5 mL of MeOH, and the reaction mixture was stirred at 0° C. for 20 minutes The reaction mixture was allowed to warm to room temperature, saturated $NaHCO_3$ was added, and the aqueous layer was extracted with $CH_2Cl_2$. The organic layer was dried over $Na_2SO_4$ and concentrated. Purification using preparative reverse phase HPLC with 10-99% $CH_3CN$ (0.035% TFA)/$H_2O$ (0.05% TFA) gave 2-hydroxy-1-(4-(2-(2-hydroxyphenyl)-7-methylquinazolin-1-yl)piperazin-1-yl)-4-(methylthio)butan-1-one as the TFA salt. (LC/MS: m/z 453.4 $(M+H)^+$ at 2.73 min (10%-99% $CH_3CN$ (0.035% TFA)/$H_2O$ (0.05% TFA)).

Example 154

(R)-3-Hydroxy-4-(4-(2-(2-hydroxyphenyl)-7-methylquinazolin-4-yl)piperazin-1-yl)-4-oxobutanamide

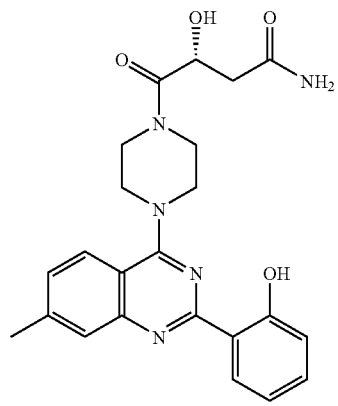

(R)-3-Hydroxy-4-(4-(2-(2-hydroxyphenyl)-7-methylquinazolin-4-yl)piperazin-1-yl)-4-oxobutanamide

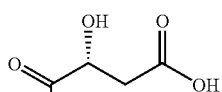

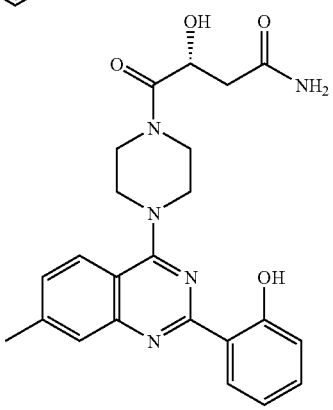

(R)-3-Hydroxy-4-{4-[2-(2-hydroxy-phenyl)-7-methyl-quinazolin-4-yl]-piperazin-1-yl}-4-oxo-butyric acid (17 mg, 0.039 mmol) and HATU (16 mg, 0.043 mmol) were stirred in DMF (0.5 mL). After adding 0.5 M NH₃ in dioxane (0.38 mL, 0.19 mmol), the reaction mixture was stirred at room temperature for 5 h. Purification via preparative reverse phase HPLC (10-99% CH₃CN (0.035% TFA)/H₂O (0.05% TFA)) gave (R)-3-hydroxy-4-(4-(2-(2-hydroxyphenyl)-7-methylquinazolin-4-yl)piperazin-1-yl)-4-oxobutanamide as the TFA salt. LC/MS: m/z 436.3 (M+H)⁺ at 1.94 min (10%-99% CH₃CN (0.035% TFA)/H₂O (0.05% TFA)).

Example 155

(R)-2-Hydroxy-1-((S)-4-(2-(2-hydroxyphenyl)-7-methylquinazolin-4-yl)-3-isopropylpiperazin-1-yl)-4-methylpentan-1-one To a solution of 2-(4-chloro-7-methylquinazolin-2-yl)phenol (200 mg, 0.74 mmol) in 10 mL DMF was added (S)-1-benzyl-3-isopropylpiperazine followed by the addition of triethylamine (206 µL). The reaction was heated at 85° C. for two hours. The reaction was quenched with water after cooling it to room temperature. The aqueous layer was extracted twice with CH₂Cl₂, and the combined extracts were dried over MgSO₄, filtered, and concentrated. The reaction was purified via silica gel chromatography using 1:1 hexanes: CH₂Cl₂ solvent system to yield 2-(4-((S)-4-benzyl-2-isopropylpiperazin-1-yl)-7-methylquinazolin-2-yl)phenol (230 mg, 64%). LC/MS: m/z 453.5 (M+H)⁺ at 2.61 min (10%-99% CH₃CN (0.035% TFA)/H₂O (0.05% TFA)).

2-(4-((S)-2-Isopropylpiperazin-1-yl)-7-methylquinazolin-2-yl)phenol

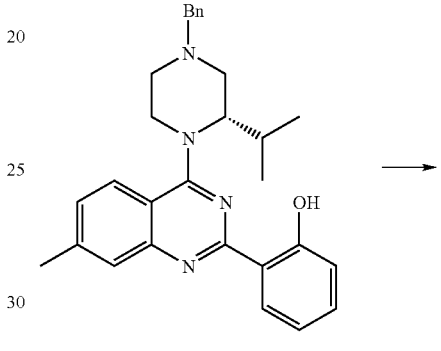

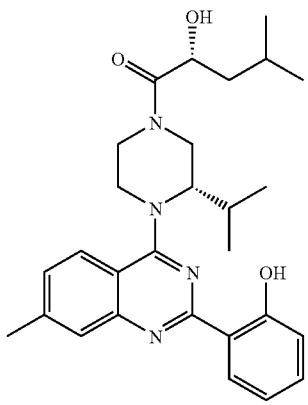

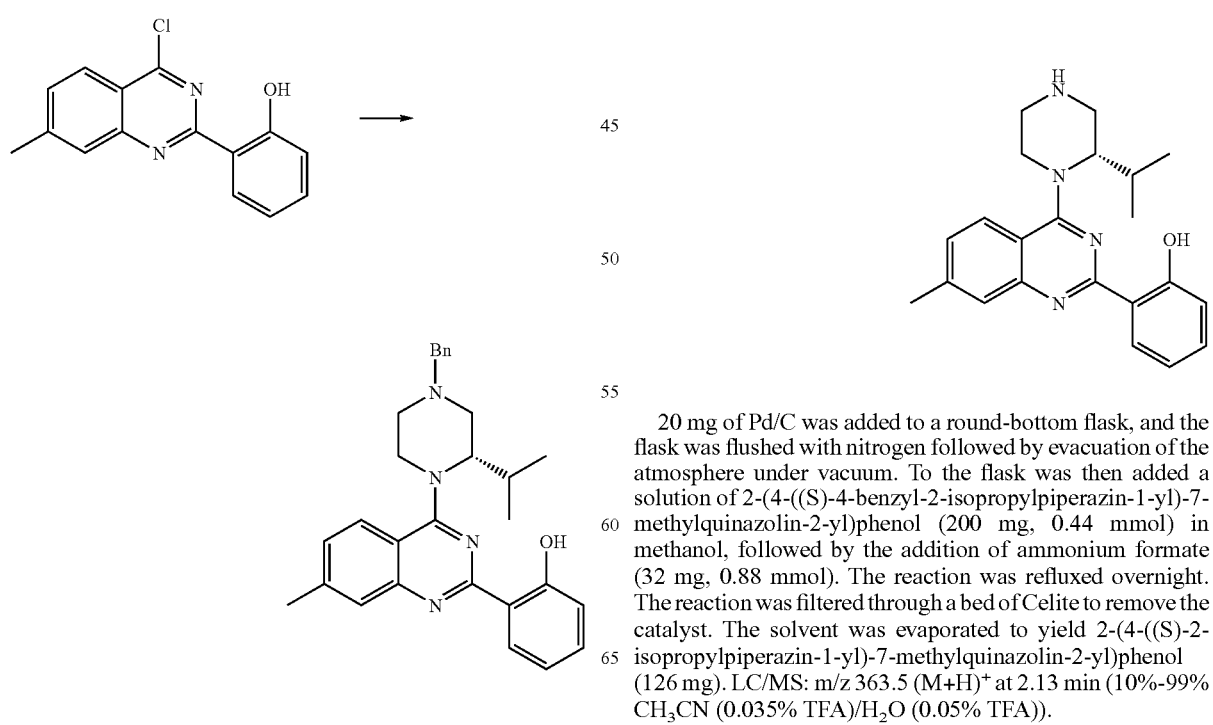

20 mg of Pd/C was added to a round-bottom flask, and the flask was flushed with nitrogen followed by evacuation of the atmosphere under vacuum. To the flask was then added a solution of 2-(4-((S)-4-benzyl-2-isopropylpiperazin-1-yl)-7-methylquinazolin-2-yl)phenol (200 mg, 0.44 mmol) in methanol, followed by the addition of ammonium formate (32 mg, 0.88 mmol). The reaction was refluxed overnight. The reaction was filtered through a bed of Celite to remove the catalyst. The solvent was evaporated to yield 2-(4-((S)-2-isopropylpiperazin-1-yl)-7-methylquinazolin-2-yl)phenol (126 mg). LC/MS: m/z 363.5 (M+H)⁺ at 2.13 min (10%-99% CH₃CN (0.035% TFA)/H₂O (0.05% TFA)).

273

(R)-2-Hydroxy-1-((S)-4-(2-(2-hydroxyphenyl)-7-methylquinazolin-4-yl)-3-isopropylpiperazin-1-yl)-4-methylpentan-1-one

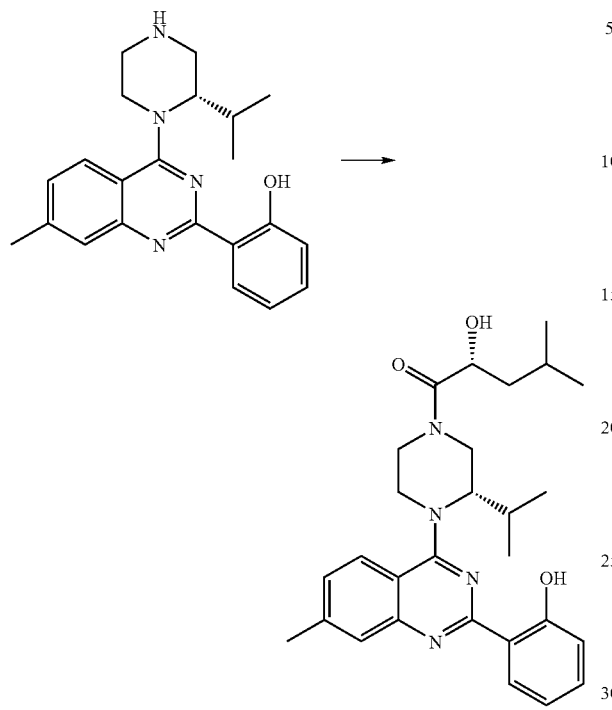

To a solution of 2-(4-((S)-2-isopropylpiperazin-1-yl)-7-methylquinazolin-2-yl)phenol (70 mg, 0.19 mmol) in DMF (0.5 mL) was added (R)-2-hydroxy-4-methylpentanoic acid (32.6 mg, 0.247 mmol). It was followed by the addition of triethylamine (52 µL) and a solution of HATU (94 mg) in 0.5 mL DMF at room temperature. The reaction was complete in an hour. Purification using reverse phase HPLC (10-99% $CH_3CN$ (0.035% TFA)/$H_2O$ (0.05% TFA)) gave (R)-2-hydroxy-1-((S)-4-(2-(2-hydroxyphenyl)-7-methylquinazolin-4-yl)-3-isopropylpiperazin-1-yl)-4-methylpentan-1-one as the TFA salt. LC/MS: m/z 477.5 (M+H)$^+$ at 2.96 min (10%-99% $CH_3CN$ (0.035% TFA)/$H_2O$ (0.05% TFA)).

Example 156

(Pyridin-3-yl)methyl 4-(2-(2-fluoro-6-hydroxyphenyl)-7-methylquinazolin-4-yl)piperazine-1-carboxylate

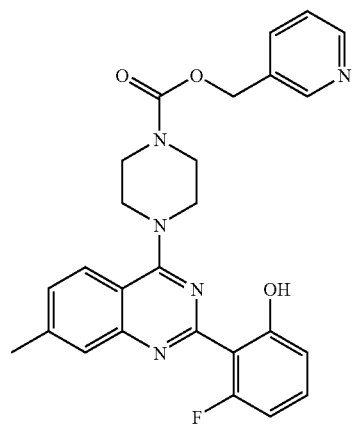

274

(Pyridin-3-yl)methyl 4-(2-(2-fluoro-6-hydroxyphenyl)-7-methylquinazolin-4-yl)piperazine-1-carboxylate

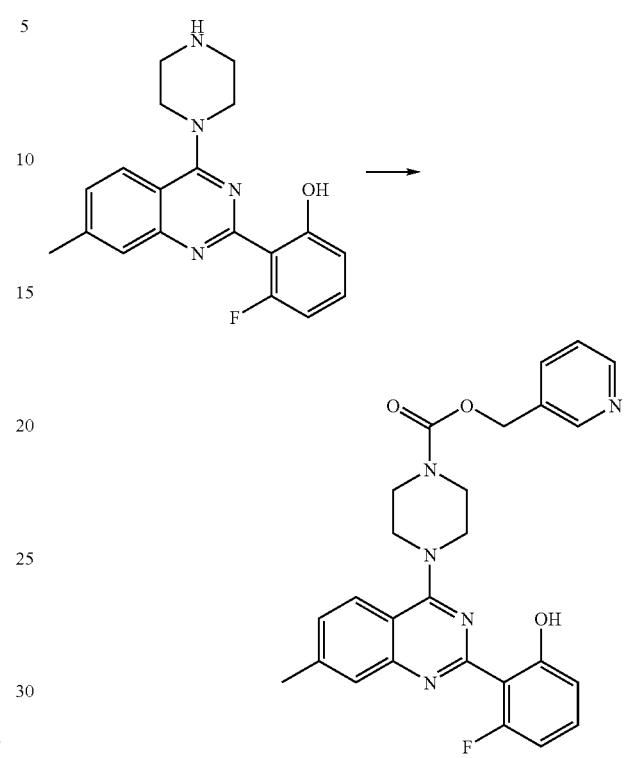

3-Fluoro-2-(7-methyl-4-(piperazin-1-yl)quinazolin-2-yl)phenol (50 mg, 0.15 mmol), (pyridin-3-yl)methyl 1H-imidazole-1-carboxylate (53 mg, 0.26 mmol), triethylamine (30.4 mg, 0.3 mmol) and DMSO (1 mL) were stirred for 18 hours at room temperature. The reaction was purified by preparative reverse phase HPLC to give (pyridin-3-yl)methyl 4-(2-(2-fluoro-6-hydroxyphenyl)-7-methylquinazolin-4-yl)piperazine-1-carboxylate as the TFA salt. LC/MS: m/z 474.30 (M+H)$^+$ at 1.19 min (10%-99% $CH_3CN$ (0.035% TFA)/$H_2O$ (0.05% TFA)).

Example 157

3-Hydroxymethyl-4-[2-(2-hydroxy-phenyl)-7-methyl-quinazolin-4-yl]-piperazine-1-carboxylic acid benzyl ester

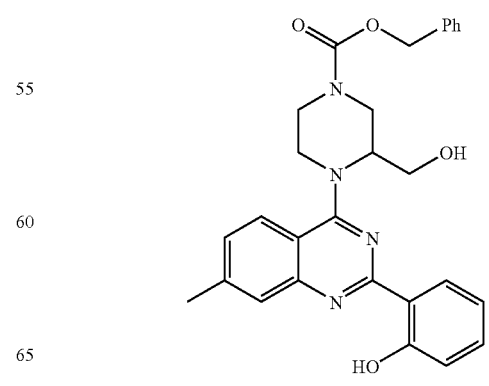

3-Hydroxymethyl-4-[2-(2-hydroxy-phenyl)-7-methyl-quinazolin-4-yl]-piperazine-1-carboxylic acid benzyl ester

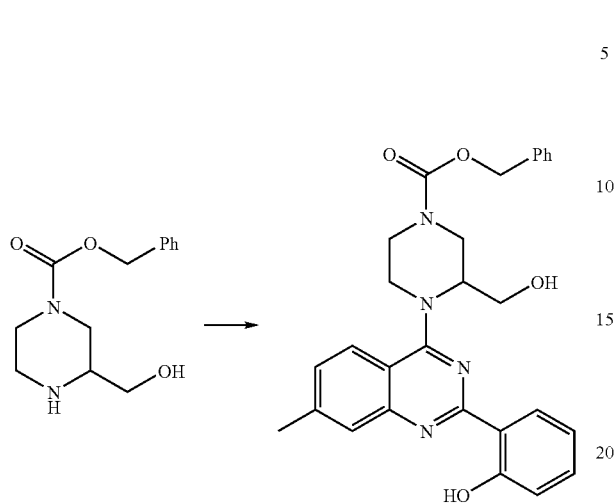

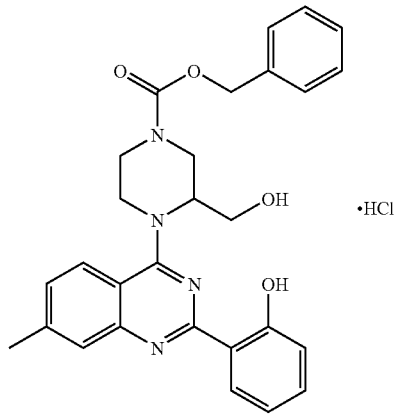

To 2-(4-chloro-7-methyl-quinazolin-2-yl)-phenol (245 mg, 0.91 mmol) in 3.0 mL of $CH_2Cl_2$ was added sequentially 3-hydroxymethyl-piperazine-1-carboxylic acid benzyl ester (336.3 mg, 1.34 mmol) and triethylamine (190 mL, 1.37 mmol), and the reaction mixture was heated at 40° C. for 6 h. The reaction mixture was cooled and extracted with water (2×10 mL) and the organic layer was separated and dried over $Na_2SO_4$. The solvent was removed under reduced pressure to give an oil. The residue was purified by normal phase LC (20-85% EtOAc-hexanes) to give 3-hydroxymethyl-4-[2-(2-hydroxy-phenyl)-7-methyl-quinazolin-4-yl]-piperazine-1-carboxylic acid benzyl ester (216 mg, 64% yield). LC/MS: m/z 485.4 (M+H)$^+$ at 3.02 min (10%-99% $CH_3CN$ (0.035% TFA)/$H_2O$ (0.05% TFA)).

Benzyl 3-(hydroxymethyl)-4-(2-(2-hydroxyphenyl)-7-methylquinazolin-4-yl)piperazine-1-carboxylate hydrochloride

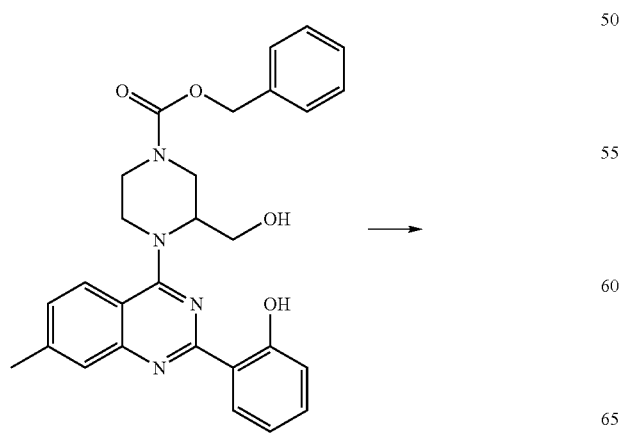

A 2.0 M HCl solution in $Et_2O$ (212 µL, 0.42 mmol) was slowly added at room temperature to a stirring solution of 3-hydroxymethyl-4-[2-(2-hydroxy-phenyl)-7-methyl-quinazolin-4-yl]-piperazine-1-carboxylic acid benzyl ester (206 mg, 0.42 mmol) in 500 µL of $CH_2Cl_2$. The reaction was stirred for 1 hour. Solvents were removed under reduced pressure, and the residue was triturated with $Et_2O$ and filtered to give benzyl 3-(hydroxymethyl)-4-(2-(2-hydroxyphenyl)-7-methylquinazolin-4-yl)piperazine-1-carboxylate hydrochloride. LC/MS: m/z 485.5 (M+H)+ at 3.07 min (10%-99% $CH_3CN$ (0.035% TFA)/$H_2O$ (0.05% TFA))

Example 158

2-Hydroxy-1-(4-(2-(2-hydroxyphenyl)-7-methylquinazolin-4-yl)piperazin-1-yl)but-3-yn-1-one

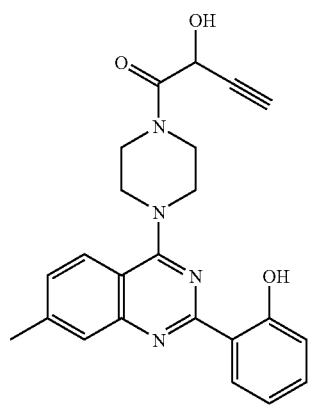

277

2-Hydroxy-1-(4-(2-(2-hydroxyphenyl)-7-methylquinazolin-4-yl)piperazin-1-yl)but-3-yn-1-one

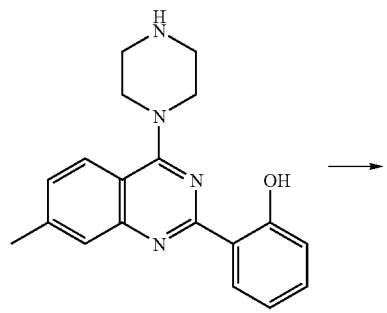

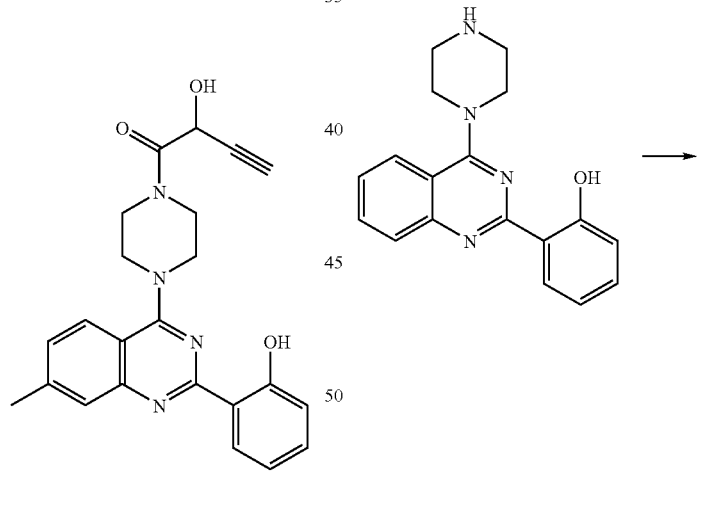

To a mixture of 2-(7-methyl-4-(piperazin-1-yl)quinazolin-2-yl)phenol (75 mg, 0.23 mmol) in 0.78 ml CH$_2$Cl$_2$ were added successively 2-hydroxybut-3-ynoic acid (30 mg, 0.30 mmol), BOP (134 mg, 0.30 mmol), and triethylamine (36 mg, 49 µL, 0.35 mmol). The mixture was stirred at 0° C. for 30 minutes. Purification via silica gel chromatography using 0-100% ethyl acetate/hexanes gave 2-hydroxy-1-(4-(2-(2-hydroxyphenyl)-7-methylquinazolin-4-yl)piperazin-1-yl)but-3-yn-1-one. (LC/MS: m/z 403.5 (M+H)$^+$ at 2.34 min (10%-99% CH$_3$CN (0.035% TFA)/H$_2$O (0.05% TFA)).

278

Example 159

2-Hydroxy-1-(4-(2-(2-hydroxyphenyl)quinazolin-4-yl)piperazin-1-yl)hexan-1-one

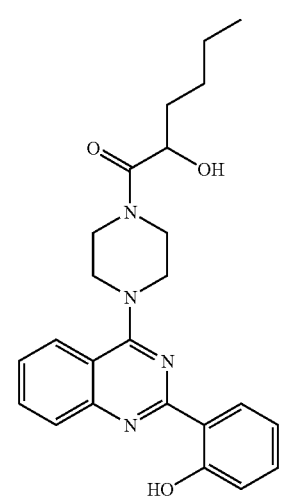

2-Hydroxy-1-(4-(2-(2-hydroxyphenyl)quinazolin-4-yl)piperazin-1-yl)hexan-1-one

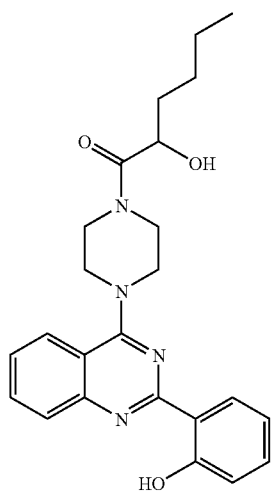

A solution of 2-(4-(piperazin-1-yl)quinazolin-2-yl)phenol (70 mg, 0.23 mmol) in DMF (0.5 mL) was added to 2-hydroxyhexanoic acid (39.3 mg, 0.297 mmol). Triethylamine (63 µL) was added at room temperature, then a solution of HATU (113 mg) in 0.5 mL DMF. The reaction was stirred overnight. Purification using reverse phase HPLC (10-99% $CH_3CN$ (0.035% TFA)/$H_2O$ (0.05% TFA)) gave 2-hydroxy-1-(4-(2-(2-hydroxyphenyl)quinazolin-4-yl)piperazin-1-yl)-2-methylbutan-1-one. LC/MS: m/z 421.3 $(M+H)^+$ at 2.60 min (10%-99% $CH_3CN$ (0:035% TFA)/$H_2O$ (0.05% TFA)).

Example 160

(Tetrahydro-2H-pyran-2-yl)methyl 4-(6-fluoro-2-(2-hydroxyphenyl)quinazolin-4-yl)piperazine-1-carboxylate

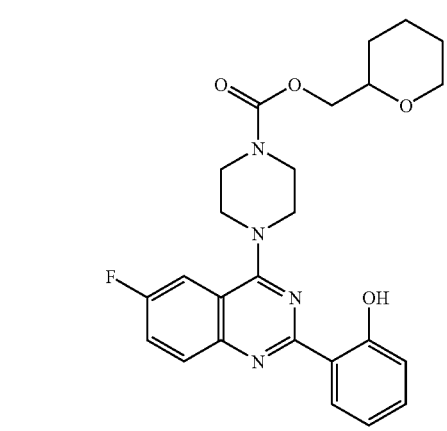

(Tetrahydro-2H-pyran-2-yl)methyl 1H-imidazole-1-carboxylate

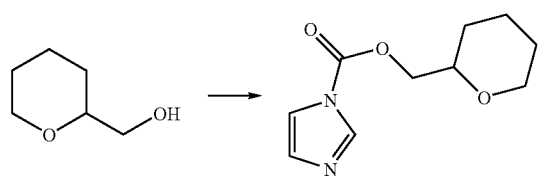

A solution of (tetrahydro-2H-pyran-2-yl)methanol (1 g, 8.60 mmol) and di(1H-imidazol-1-yl)methanone (2.8 g, 17.2 mmol) in 17 mL $CH_2Cl_2$ was heated overnight at 50° C. The reaction was quenched with water, extracted with $CH_2Cl_2$, dried over $MgSO_4$, filtered, and concentrated.

(Tetrahydro-2H-pyran-2-yl)methyl 4-(6-fluoro-2-(2-hydroxyphenyl) quinazolin-4-yl)piperazine-1-carboxylate 2-(6-Fluoro-4-(piperazin-1-yl)quinazolin-2-yl)phenol (25 mg, 0.077 mmol), (tetrahydro-2H-pyran-2-yl)methyl 1H-imidazole-1-carboxylate (48.5 mg, 0.23 mmol), triethylamine (22 µL, 0.154 mmol) were stirred in DMF (1 mL) overnight. Purification via reverse phase HPLC (10-99% $CH_3CN$ (0.035% TFA)/$H_2O$ (0.05% TFA)) gave (tetrahydro-2H-pyran-2-yl)methyl 4-(6-fluoro-2-(2-hydroxyphenyl) quinazolin-4-yl)piperazine-1-carboxylate as the TFA salt.

LC/MS: m/z 467.3 (M+H)⁺ at 3.13 min (10%-99% CH₃CN (0.035% TFA)/H₂O (0.05% TFA)).

Example 162

(Tetrahydrofuran-3-yl)methyl 4-(2-(2-fluoro-6-hydroxyphenyl)-7-methylquinazolin-4-yl)piperazine-1-carboxylate

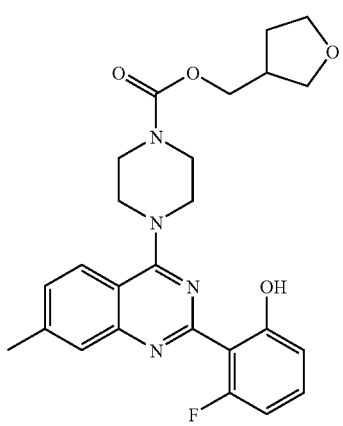

4-Benzyl-piperazine-1-carboxylic acid tetrahydro-furan-3-ylmethyl ester

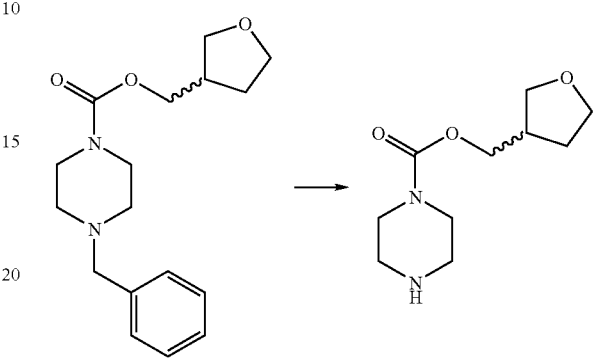

To a cooled (0° C.) solution of triphosgene (5.0 g, 17 mmol) in 50 ml dichloromethane under a nitrogen atmosphere was added dropwise a solution of tetrahydro-3-furanmethanol (5.4 g, 53 mmol) in 10 ml dichloromethane. Pyridine (4.3 ml, 53 mmol) was added dropwise, and the solution was warmed to room temperature. After 2 hours at room temperature a mixture of triethylamine (7.5 ml, 52 mmol) and N-benzylpiperazine (9.5 ml, 54 mmol) was added dropwise with cooling. The resulting mixture was refluxed for 1 hour. The solution was stirred at room temperature overnight under a nitrogen atmosphere. The mixture was washed with aqueous sodium bicarbonate solution (5%, 2×50 ml), and with a solution of saturated aqueous NaCl (50 ml). The organic layer was dried over sodium sulfate, filtered, and evaporated to dryness. The residue was co-evaporated three times with toluene (50 ml) to yield 4-benzyl-piperazine-1-carboxylic acid tetrahydro-furan-3-ylmethyl ester (13.0 g, 81%) as a brownish oil.

Piperazine-1-carboxylic acid tetrahydro-furan-3-ylmethyl ester

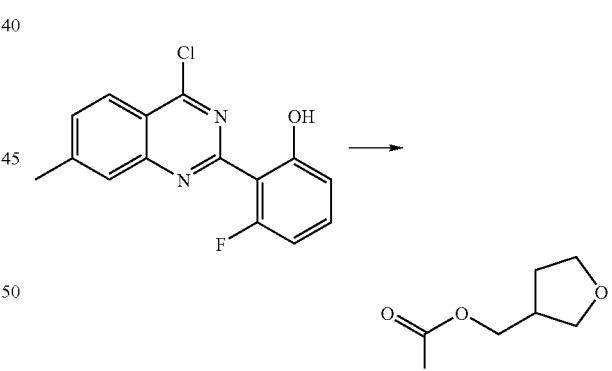

4-Benzyl-piperazine-1-carboxylic acid tetrahydro-furan-3-ylmethyl ester (11.0 g) was dissolved in 100 ml ethanol. Palladium on carbon (10% Pd/C, 0.5 g) was added, and a hydrogen atmosphere was applied overnight at room temperature. The solution was filtered through Celite to remove the catalyst, and the Celite cake was rinsed with 50 ml ethanol. The combined filtrates were evaporated to dryness to yield piperazine-1-carboxylic acid tetrahydro-furan-3-ylmethyl ester (8.0 g) as a colorless oil.

(Tetrahydrofuran-3-yl)methyl 4-(2-(2-fluoro-6-hydroxyphenyl)-7-methylquinazolin-4-yl)piperazine-1-carboxylate

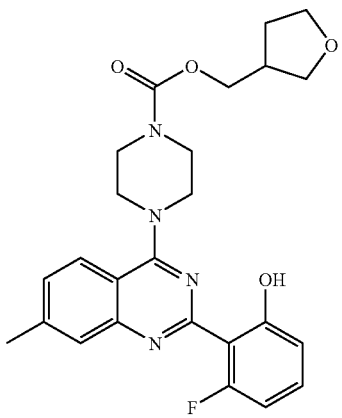

2-(4-Chloro-7-methylquinazolin-2-yl)-3-fluorophenol (50 mg, 0.174 mmol) was dissolved in 1 mL DMF, followed by the addition of triethylamine (35.2 mg, 0.348 mmol). (Tetrahydrofuran-3-yl)methyl piperazine-1-carboxylate (45 mg, 0.21 mmol) was then added. After 1 hour at room temperature, the reaction was complete. It was filtered and purified by reverse phase preparative HPLC to give (tetrahydrofuran-3-yl)methyl 4-(2-(2-fluoro-6-hydroxyphenyl)-7-methylquinazolin-4-yl)piperazine-1-carboxylate as the TFA salt. LC/MS: m/z 467.3 (M+H)$^+$ at 2.33 min (10%-99% CH$_3$CN (0.035% TFA)/H$_2$O (0.05% TFA)).

Example 163

(S)-Tetrahydrofuran-3-yl 4-(2-(2-fluoro-6-hydroxyphenyl)-7-methylquinazolin-4-yl)piperazine-1-carboxylate

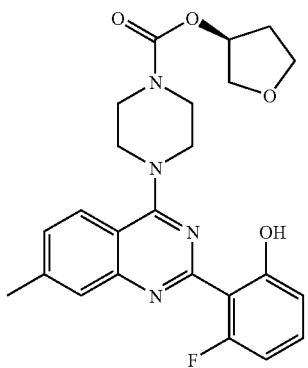

(S)-Tetrahydrofuran-3-yl 4-(2-(2-fluoro-6-hydroxyphenyl)-7-methylquinazolin-4-yl)piperazine-1-carboxylate

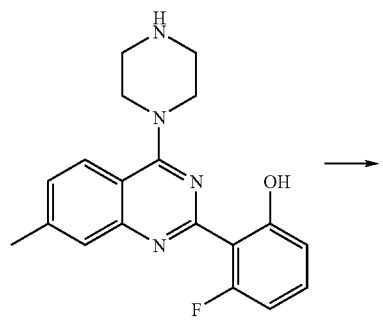

3-Fluoro-2-(7-methyl-4-(piperazin-1-yl)quinazolin-2-yl)phenol (70 mg, 0.21 mmol) was dissolved in 1 mL anhydrous DMF under an N$_2$ atmosphere and cooled to 0° C. (S)-Tetrahydrofuran-3-yl chloroformate (34.3 mg, 0.228 mmol) was dissolved in 150 µL anhydrous DMF and added dropwise to the reaction, followed by triethylamine (42 mg, 0.41 mmol). After 1 hour the reaction was complete, and it was filtered and purified by reverse phase HPLC to give (S)-tetrahydrofuran-3-yl 4-(2-(2-fluoro-6-hydroxyphenyl)-7-methylquinazolin-4-yl)piperazine-1-carboxylate as the TFA salt. LC/MS: m/z 453.3 (M+H)$^+$ at 2.25 min (10%-99% CH$_3$CN (0.035% TFA)/H$_2$O (0.05% TFA)).

Example 164

(R)-2,4-Dihydroxy-1-(4-(2-(2-hydroxyphenyl)-7-methylquinazolin-4-yl)piperazin-1-yl)-4-methylpentan-1-one

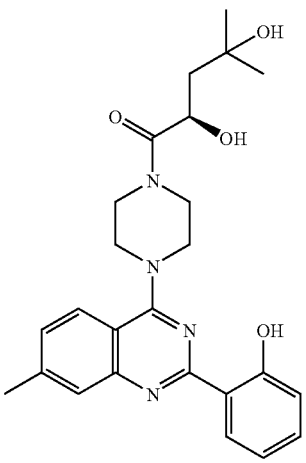

(R)-Benzyl-4-(2-hydroxy-4-methoxy-4-oxobutanoyl)piperazine-1-carboxylate

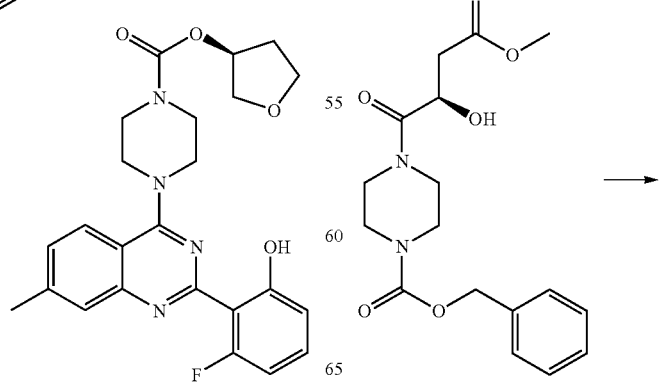

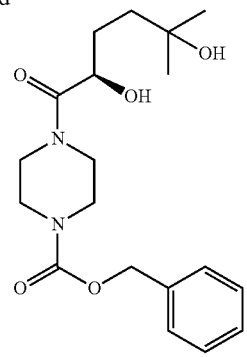

To a solution of 4-((R)-2-hydroxy-3-methoxycarbonyl-propionyl)-piperazine-1-carboxylic acid benzyl ester (5.26 g, 15.0 mmol) in THF (150 mL) cooled in a dry ice acetone bath was added 1.4 M MeMgBr (32 mL, 45 mmol). The reaction was allowed to slowly warm to room temperature overnight. After quenching the mixture with saturated NH$_4$Cl and extracting with EtOAc, the combined organic extracts were washed with water, dried over Na$_2$SO$_4$, and concentrated. Purification via silica gel chromatography using 0-10% MeOH/CH$_2$Cl$_2$ gave (R)-benzyl-4-(2-hydroxy-4-methoxy-4-oxobutanoyl)piperazine-1-carboxylate as a colorless oil (0.79 g, 15%). $^1$H NMR (400 MHz, CDCl$_3$) δ 7.40-7.31 (m, 5H), 5.15 (s, 2H), 4.71-4.68 (m, 1H), 4.05 (d, J=6.8 Hz, 1H), 3.80-3.73 (m, 1H), 3.62-3.42 (m, 6H), 3.31-3.23 (m, 1H), 1.72-1.61 (m, 2H), 1.35 (s, 3H), 1.30 (s, 3H) ppm; LC/MS: m/z 351.3 (M+H)$^+$ at 2.22 min (10%-99% CH$_3$CN (0.035% TFA)/H$_2$O (0.05% TFA)).

(R)-2,4-Dihydroxy-1-(4-(2-(2-hydroxyphenyl)-7-methylquinazolin-4-yl)piperazin-1-yl)-4-methylpentan-1-one

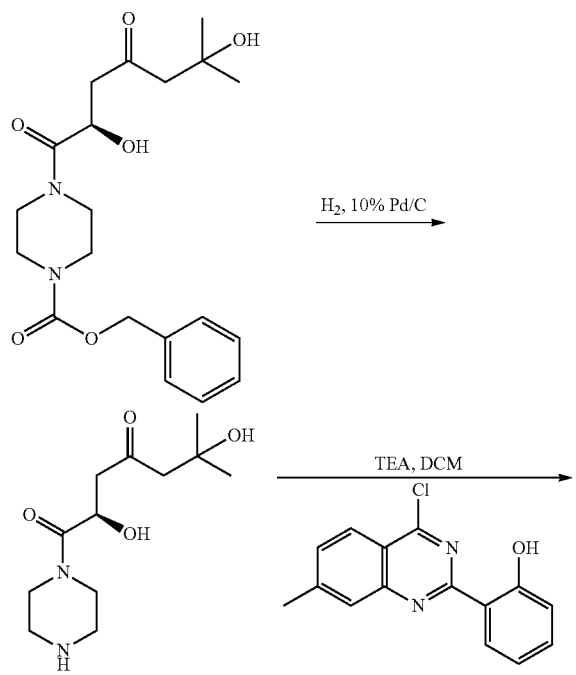

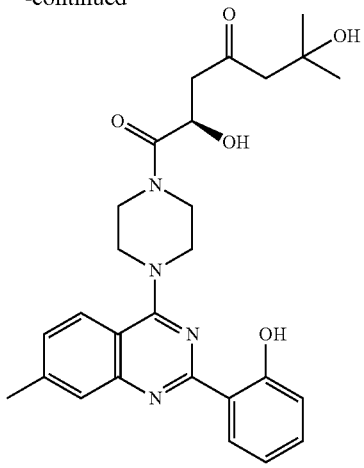

A mixture of (R)-Benzyl-4-(2-hydroxy-4-methoxy-4-oxobutanoyl)piperazine-1-carboxylate (0.79 g, 2.20 mmol) and MeOH (25 mL) was stirred with 40 mg of Pd/C (10% wt Pd on carbon) under H$_2$ atmosphere at ambient pressure overnight. After filtration and evaporation of the solvent, the residue was taken up in CH$_2$Cl$_2$, and 2-(4-chloro-7-methylquinazolin-2-yl)phenol (0.61 g, 2.20 mmol) and triethylamine (0.63 mL, 4.50 mmol) were added. The reaction mixture was stirred at room temperature overnight and then diluted with CH$_2$Cl$_2$, washed with water, dried over Na$_2$SO$_4$, and concentrated. Purification via silica gel chromatography using 0-10% MeOH/CH$_2$Cl$_2$ gave (R)-2,6-dihydroxy-1-(4-(2-(2-hydroxyphenyl)-7-methylquinazolin-4-yl)piperazin-1-yl) 4-methylpentan-1-one as a yellow solid (372 mg, 37%). $^1$H NMR (400 MHz, CDCl$_3$) δ 8.45 (dd, J 8.5 Hz, 1H), 7.67 (s, 1H), 7.40-7.36 (m, 1H), 7.29 (dd, J=8.5, 1.4 Hz, 1H), 7.03 (d, J=8.2 Hz, 1H), 6.96-6.92 (m, 1H), 4.81-4.76 (m, 1H), 4.09 (d, J=6.8 Hz, 1H), 4.03-3.77 (m, 6H), 3.75-3.67 (m, 2H), 3.28 (s, 1H), 2.55 (s, 3H), 1.78-1.69 (m, 2H), 1.40 (s, 3H), 1.33 (s, 3H) ppm; $^{13}$C NMR (100 MHz, CDCl$_3$) δ 173.1, 164.0, 161.3, 160.5, 150.1, 144.5, 132.7, 129.2, 127.7, 126.8, 124.4, 119.3, 118.5, 117.7, 112.7, 70.6, 66.4, 49.9, 49.0, 46.1, 44.5, 42.4, 30.6, 29.2, 21.9; LC/MS: m/z 451.1 (M+H)$^+$ at 2.12 min (10%-99% CH$_3$CN (0.035% TFA)/H$_2$O (0.05% TFA)).

Example 165

2-Hydroxy-1-(4-(2-(2-hydroxyphenyl)-7-methylquinazolin-4-yl)piperazin-1-yl)-2-methylbutan-1-one

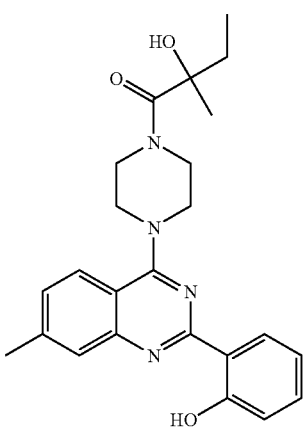

287

2-Hydroxy-1-(4-(2-(2-hydroxyphenyl)-7-methylquinazolin-4-yl)piperazin-1-yl)-2-methylbutan-1-one

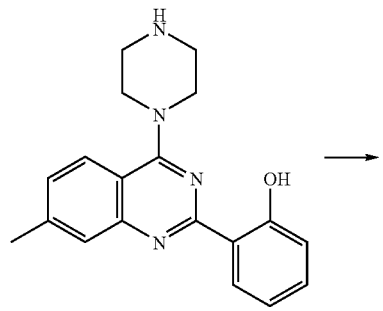

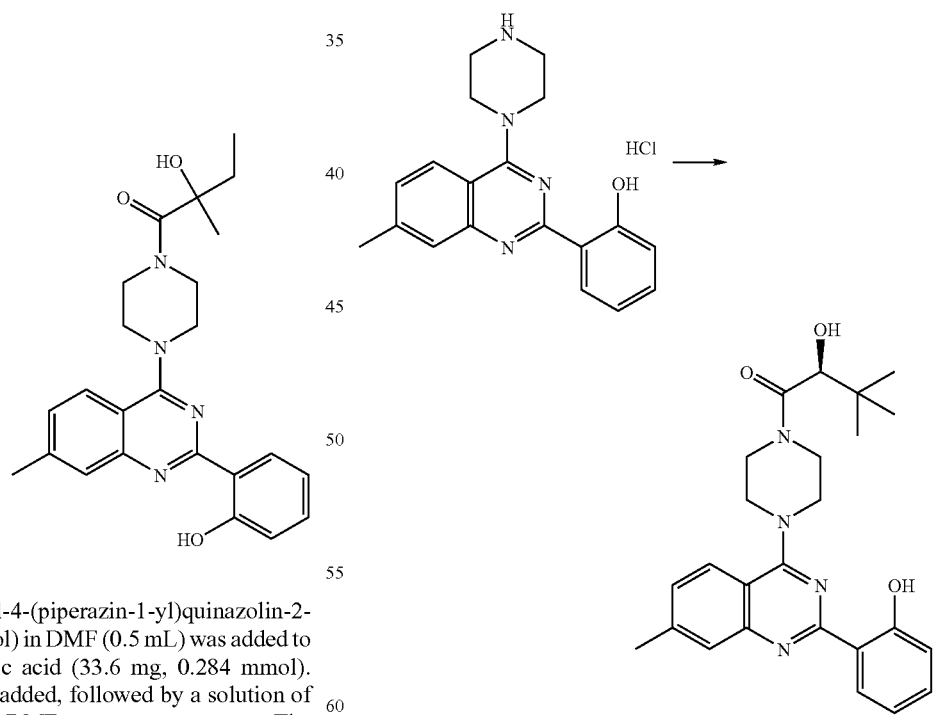

A solution of 2-(7-methyl-4-(piperazin-1-yl)quinazolin-2-yl)phenol (70 mg, 0.22 mmol) in DMF (0.5 mL) was added to 2-hydroxy-2-methylbutanoic acid (33.6 mg, 0.284 mmol). Triethylamine (61 µL) was added, followed by a solution of HATU (108 mg) in 0.5 mL DMF at room temperature. The reaction was stirred overnight. Purification using reverse phase HPLC (10-99% CH₃CN (0.035% TFA)/H₂O (0.05% TFA)) gave 2-hydroxy-1-(4-(2-(2-hydroxyphenyl)-7-methylquinazolin-4-yl)piperazin-1-yl)-2-methylbutan-1-one as the TFA salt. LC/MS: m/z 421.3 (M+H)⁺ at 2.40 min (10%-99% CH₃CN (0.035% TFA)/H₂O (0.05% TFA)).

288

Example 166

(S)-2-Hydroxy-1-(4-(2-(2-hydroxyphenyl)-7-methylquinazolin-4-yl)piperazin-1-yl)-3,3-dimethylbutan-1-one

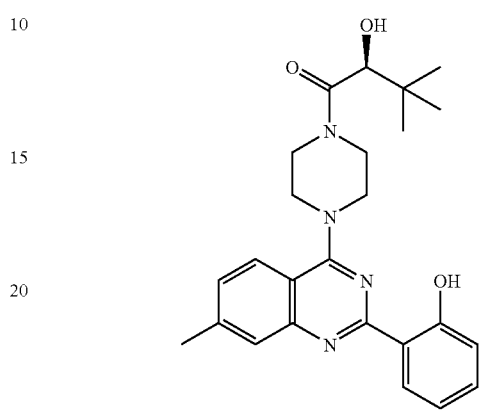

(S)-2-Hydroxy-1-(4-(2-(2-hydroxyphenyl)-7-methylquinazolin-4-yl)piperazin-1-yl)-3,3-dimethylbutan-1-one 2-(7-Methyl-4-(piperazin-1-yl)quinazolin-2-yl)phenol hydrochloride (30 mg, 0.09 mmol), (S)-2-hydroxy-3,3-dimethylbutanoic acid (16 mg, 0.12 mmol), triethylamine (37.5 µL, 0.27 mmol), and HATU (45.6 mg, 0.12 mmol) were stirred in DMF (1 mL) overnight. Purification via reverse phase HPLC (10-99% CH₃CN (0.035% TFA)/H₂O (0.05% TFA)) gave (S)-2-hydroxy-1-(4-(2-(2-hydroxyphenyl)-7-methylquinazolin-4-yl)piperazin-1-yl)-3,3-dimethylbutan-1-one as the TFA salt. LC/MS: m/z 434.53 (M+H)⁺ at 2.61 min (10%-99% CH₃CN (0.035% TFA)/H₂O (0.05% TFA)).

Example 167

1-(4-(2-(2-Fluoro-6-hydroxyphenyl)-7-methylquinazolin-4-yl)piperazin-1-yl)-2-(4-fluorophenyl)-2-hydroxyethanone

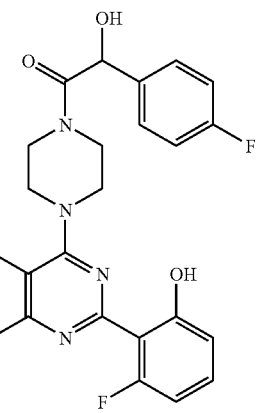

1-(4-(2-(2-Fluoro-6-hydroxyphenyl)-7-methylquinazolin-4-yl)piperazin-1-yl)-2-(4-fluorophenyl)-2-hydroxyethanone

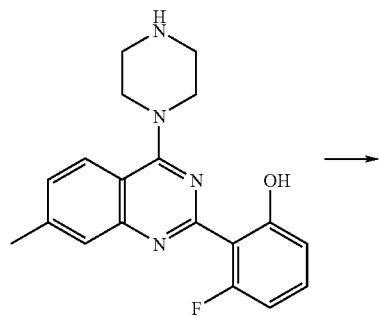
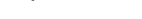
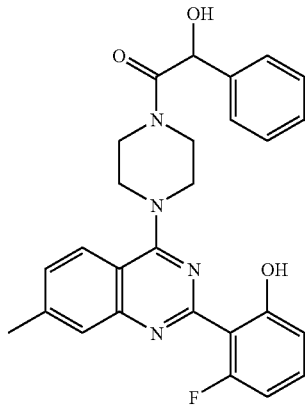

3-Fluoro-2-(7-methyl-4-(piperazin-1-yl)quinazolin-2-yl)phenol (30 mg, 0.09 mmol), 2-(4-fluorophenyl)-2-hydroxy-acetic acid (19.62 mg, 0.12 mmol), triethylamine (25 μL, 0.18 mmol) and HATU (45.6 mg, 0.12 mmol) were stirred in DMF (1 mL) overnight. Purification via reverse phase HPLC (10-99% CH₃CN (0.035% TFA)/H₂O (0.05% TFA)) gave 1-(4-(2-(2-fluoro-6-hydroxyphenyl)-7-methylquinazolin-4-yl)piperazin-1-yl)-2-(4-fluorophenyl)-2-hydroxyethanone as the TFA salt. LC/MS: m/z 491.3 (M+H)⁺ at 2.46 min (10%-99% CH₃CN (0.035% TFA)/H₂O (0.05% TFA)).

Example 168

(R)-2-Hydroxy-1-(4-(2-(2-hydroxyphenyl)-7-methylquinazolin-4-yl)piperazin-1-yl)-4-methylpentan-1-one

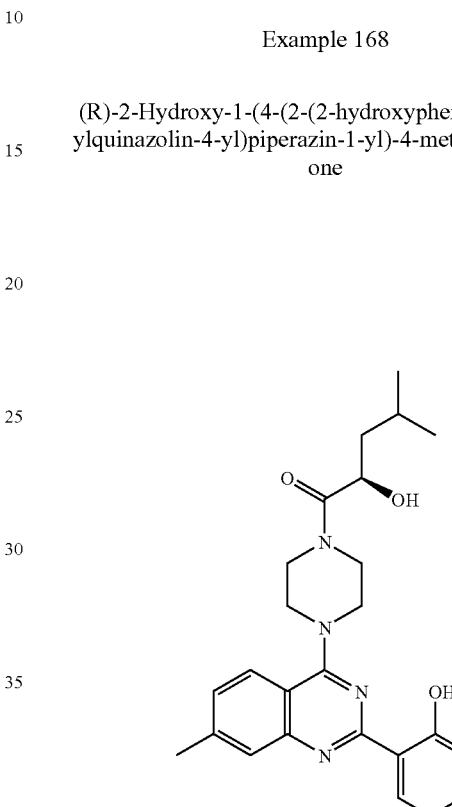

(R)-2-Hydroxy-1-(4-(2-(2-hydroxyphenyl)-7-methylquinazolin-4-yl)piperazin-1-yl)-4-methylpentan-1-one

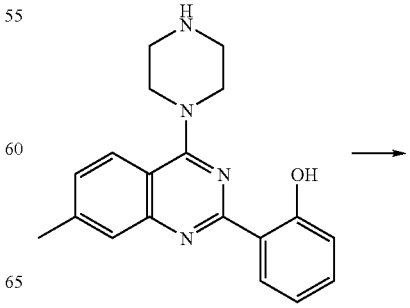

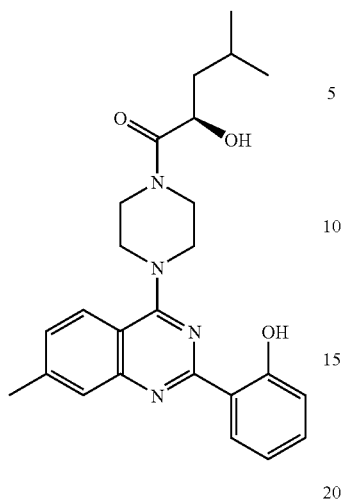

Under an N₂ atmosphere, BOP (138 mg, 0.31 mmol) was added in a single portion to a stirring solution of 2-(7-methyl-4-(piperazin-1-yl)quinazolin-2-yl)phenol (100 mg, 0.31 mmol), (R)-2-hydroxy-4-methylpentanoic acid (41 mg, 0.31 mmol), and triethylamine (43 μL, 0.31 mmol) in DMF (0.5 ml). After stirring the mixture for 1 h at room temperature, it was partitioned between H₂O and ether. The organic phase was washed with H₂O (3×20 mL), dried over MgSO₄, filtered, and concentrated. Purification via silica gel chromatography using 20% EtOAc and 80% CH₂Cl₂ gave (R)-2-hydroxy-1-(4-(2-(2-hydroxyphenyl)-7-methylquinazolin-4-yl)piperazin-1-yl)-4-methylpentan-1-one as a light yellow solid (89 mg, 60%). LC/MS: m/z 435.1 (M+H)⁺ at 2.93 min (10%-99% CH₃CN (0.035% TFA)/H₂O (0.05% TFA)). ¹H NMR (400 MHz, CDCl₃) δ 8.46 (dd, J=7.9, 1.7 Hz, 1H), 7.76 (d, J=8.5 Hz, 1H), 7.66 (s, 1H), 7.41-7.37 (m, 1H), 7.30 (dd, J=8.5, 1.5 Hz, 1H), 7.06-7.04 (m, 1H), 6.98-6.94 (m, 1H), 4.51-4.45 (m, 1H), 4.04-3.80 (m, 6H), 3.72-3.62 (m, 3H), 2.56 (s, 3H), 2.12-1.99 (m, 1H), 1.57-1.49 (m, 1H), 1.38-1.32 (m, 1H), 1.05 (d, J=6.6 Hz, 3H), 1.00 (d, J=6.7 Hz, 3H) ppm.

(R)-2-Hydroxy-1-(4-(2-(2-hydroxyphenyl)-7-methylquinazolin-4-yl)piperazin-1-yl)-4-methylpentan-1-one hydrochloride

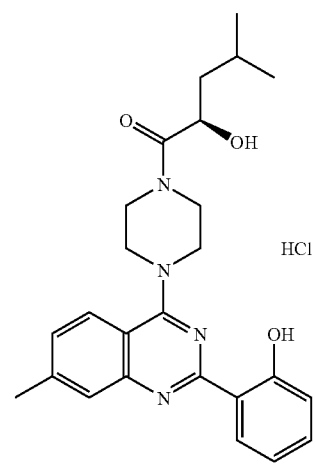

(R)-2-hydroxy-1-(4-(2-(2-hydroxyphenyl)-7-methylquinazolin-4-yl)piperazin-1-yl)-4-methylpentan-1-one (90 mg, 0.20 mmol) was dissolved in 1 mL CH₂Cl₂ and treated with 1 equivalent of 2.0 M HCl in ether (100 μL, 0.20 mmol). The formed precipitate was filtered and vacuum dried to obtain (R)-2-hydroxy-1-(4-(2-(2-hydroxyphenyl)-7-methylquinazolin-4-yl)piperazin-1-yl)-4-methylpentan-1-one hydrochloride. LC/MS: m/z 435.1 (M+H)⁺ at 2.84 min (10%-99% CH₃CN (0.035% TFA)/H₂O (0.05% TFA)). ¹H NMR (400 MHz, CD 30D) δ 8.39-8.37 (m, 1H), 8.18 (d, J=8.6 Hz, 1H), 7.78 (s, 1H), 7.61-7.55 (m, 2H), 7.15-7.11 (m, 2H), 4.57 (dd, J=9.5, 3.5 Hz, 1H), 4.49-4.32 (m, 4H), 4.07-3.79 (m, 4H), 2.62 (s, 3H), 1.97-1.87 (m, 1H), 1.65-1.58 (m, 1H), 1.53-1.47 (m, 1H), 1.03-1.00 (m, 6H) ppm.

(R)-2-Hydroxy-1-(4-(2-(2-hydroxyphenyl)-7-methylquinazolin-4-yl)piperazin-1-yl)-4-methylpentan-1-one sulfate

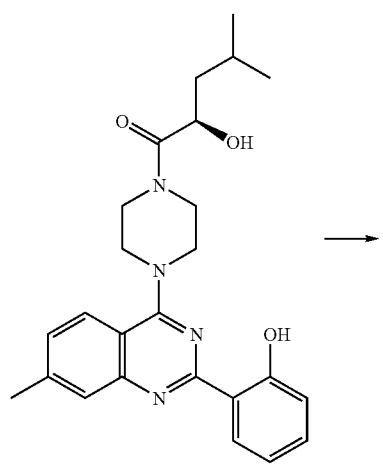 → 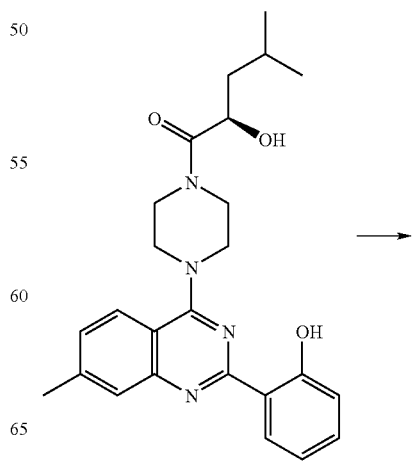 →

293

-continued

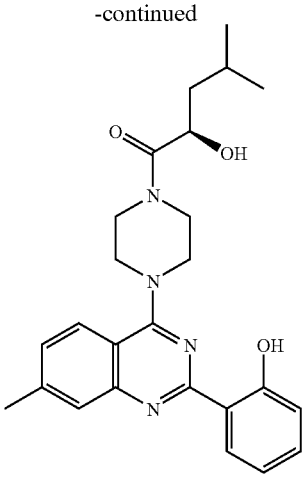

To a stirring yellow solution of (R)-2-hydroxy-1-(4-(2-(2-hydroxyphenyl)-7-methylquinazolin-4-yl)piperazin-1-yl)-4-methylpentan-1-one (200 mg, 0.46 mmol) and THF (0.9 mL) under an $N_2$ atmosphere was added a solution of concentrated $H_2SO_4$ solution (95.9%) (26 µL, 0.46 mmol) and $CH_3CN$ (0.75 mL) in a single portion. A white precipitate formed slowly over a period of 1 h. The solid was filtered and vacuum dried to obtain (R)-2-hydroxy-1-(4-(2-(2-hydroxyphenyl)-7-methylquinazolin-4-yl)piperazin-1-yl)-4-methylpentan-1-one sulfate as a white solid (229 mg, 94%). LC/MS: m/z 435.3 $(M+H)^+$ at 2.81 min (10%-99% $CH_3CN$ (0.035% TFA)/$H_2O$ (0.05% TFA)). $^1H$ NMR (400 MHz, DMSO-d6) δ 8.20 (dd, J=7.9, 1.5 Hz, 1H), 8.12 (d, J=8.6 Hz, 1H), 7.77 (s, 1H), 7.53-7.49 (m, 2H), 7.10-7.03 (m, 2H), 4.39-4.35 (m, 1H), 4.30-4.04 (m, 4H), 3.93-3.69 (m, 4H), 2.55 (s, 3H), 1.86-1.73 (m, 1H), 1.52-1.33 (m, 2H), 0.93-0.91 (m, 6H) ppm.

Example 169

(R)-[Methyl-(2-methylamino-acetyl)-amino]-acetic acid 1-{4-[2-(2-hydroxy-phenyl)-7-methyl-quinazolin-4-yl]-piperazine-1-carbonyl}-3-methyl-butyl ester

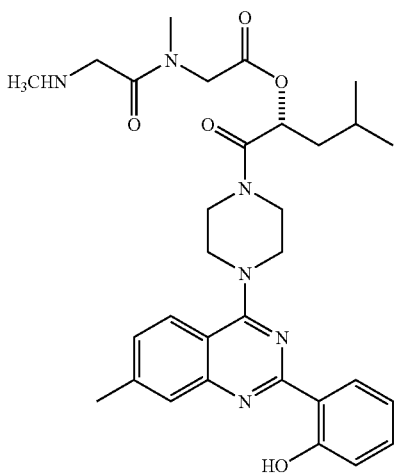

294

{[2-(tert-Butoxycarbonyl-methyl-amino)-acetyl]-methyl-amino}-acetic acid

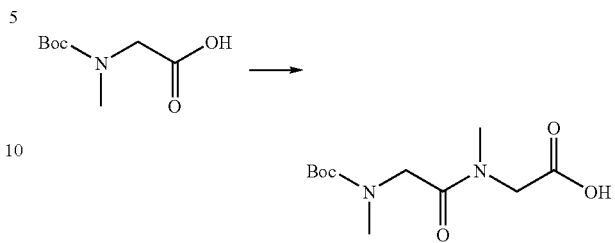

To (tert-butoxycarbonyl-methyl-amino)-acetic acid (2.73 g, 14.4 mmol) in 70 mL of THF was added sequentially diisopropyl ethylamine (7.5 mL, 14.4 mmol) and HBTU (5.47 g, 14.4 mmol), and the reaction mixture was stirred at room temperature for one hour. To this reaction mixture was added methylamino-acetic acid ethyl ester (2.22 g, 14.4 mmol) in one portion, and the reaction mixture was heated at 65° C. for 12 h. The reaction mixture was cooled, diluted with a solution of saturated $NaHCO_3$, and extracted with EtOAc. The organic layer was separated and dried over $Na_2SO_4$, and the solvent was removed under reduced pressure to give {[2-(tert-butoxycarbonyl-methyl-amino)-acetyl]-methyl-amino}-acetic acid ethyl ester.

The ester was taken up in 49 mL of methanol, and to this was added a 1 M NaOH solution (25.1 mL, 25 mmol). The reaction mixture was heated at 65° C. for 3 h. The reaction mixture was cooled, and methanol was removed under reduced pressure. The residue was diluted with 50 mL of water and acidified with glacial acetic acid until the pH was 5. This solution was extracted with EtOAc (50 mL), and the organic layer was separated and dried over $Na_2SO_4$, and the solvent was removed under reduced pressure to give {[2-(tert-Butoxycarbonyl-methyl-amino)-acetyl]-methyl-amino}-acetic acid as an oil.

4-(2(R)-Hydroxy-4-methyl-pentanoyl)-piperazine-1-carboxylic acid benzyl ester

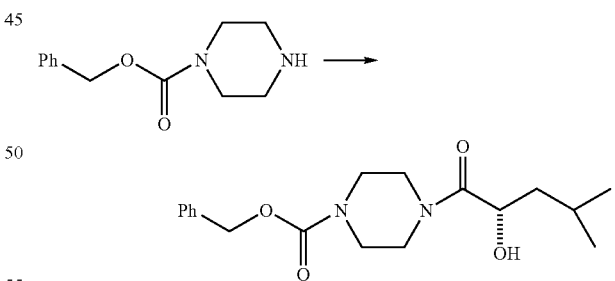

To (R)-2-hydroxy-4-methyl-pentanoic acid (1.71 g, 12.9 mmol) in 48 mL of DMF was added sequentially triethylamine (4.9 mL, 35 mmol), HOBt (1.75 g, 12.9 mmol), EDCI-.HCl (2.48 g, 12.9 mmol) and piperazine-1-carboxylic acid benzyl ester (2.59 g, 11.8 mmol) at room temperature. The reaction mixture was stirred for 4 h and then diluted with EtOAc (50 mL) and extracted with 50 mL of water. The organic layer was separated and dried over $Na_2SO_4$, and the solvent was removed under reduced pressure to give an oil. The residue was subjected to purification by normal phase LC using 40-85% EtOAc-hexanes to give (1.92 g, 49% yield) of 4-(2(R)-hydroxy-4-methyl-pentanoyl)-piperazine-1-carboxylic acid benzyl ester the desired product. LC/MS: m/z 335.4 (M+H)+ at 2.96 min (10%-99% CH3CN (0.035% TFA)/H2O (0.05% TFA)).

4-[2-(2-{[2-(tert-Butoxycarbonyl-methyl-amino)-acetyl]-methyl-amino}-acetoxy)-4-methyl-pentanoyl]-piperazine-1-carboxylic acid benzyl ester

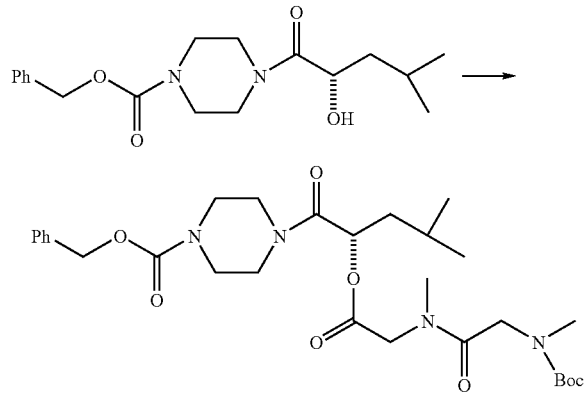

To {[2-(tert-butoxycarbonyl-methyl-amino)-acetyl]-methyl-amino}-acetic acid (427 mg, 1.57 mmol) in 2 mL of THF was added sequentially HBTU (624 mg, 1.2 mmol), diisopropyl ethylamine (860 µL, 4.71 mmol) at room temperature. After 5 min, 4-(2-hydroxy-4-methyl-pentanoyl)-piperazine-1-carboxylic acid benzyl ester (403 mg 1.2 mmol) in 2 mL of THF was added to the reaction mixture, and the solution was heated at 65° C. for 12 h. The reaction mixture was cooled and diluted with 20 mL of CH2Cl2 and 10 mL of water. The organic layer was separated and dried over Na2SO4, and the solvent was removed under reduced pressure to give an oil. The residue was subjected to purification by normal phase LC using 30-100% EtOAc-hexanes to give 4-[2-(2-{[2-(tert-butoxycarbonyl-methyl-amino)-acetyl]-methyl-amino}-acetoxy)-4-methyl-pentanoyl]-piperazine-1-carboxylic acid benzyl ester (283 mg, 41% yield). LC/MS: m/z 577 (M+H)+ at 3.43 min (10%-99% CH3CN (0.035% TFA)/H2O (0.05% TFA)).

{[2-(tert-Butoxycarbonyl-methyl-amino)-acetyl]-methyl-amino}-acetic acid 1-{4-[2-(2-hydroxy-phenyl)-7-methyl-quinazolin-4-yl]-piperazine-1-carbonyl}-3-methyl-butyl ester

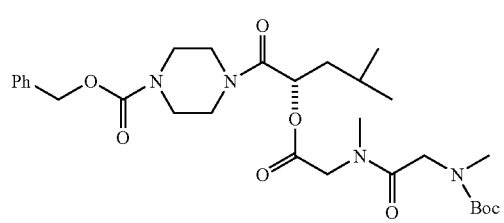

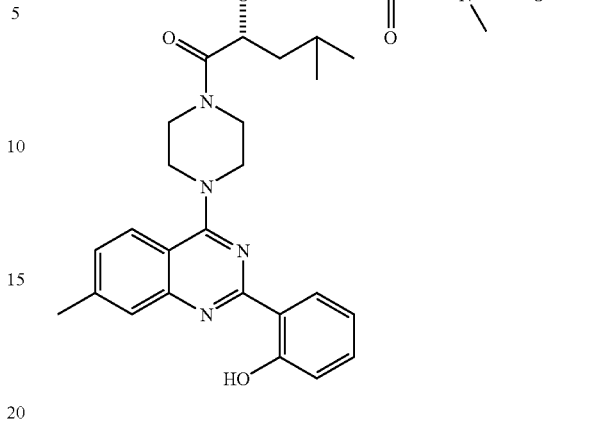

To 4-[2-(2-{[2-(tert-butoxycarbonyl-methyl-amino)-acetyl]-methyl-amino}-acetoxy)-4-methyl-pentanoyl]-piperazine-1-carboxylic acid benzyl ester (208 mg, 0.49 mmol) in 1.6 mL of methanol was added 70 mg of Pd/C (10% wt Pd on carbon). The reaction mixture was hydrogenated using a balloon of H2 for 4 h at room temperature. The mixture was then filtered through Celite, and the solvent removed to give {[2-(tert-butoxycarbonyl-methyl-amino)-acetyl]-methyl-amino}-acetic acid 3-methyl-1-(piperazine-1-carbonyl)-butyl ester.

The amine was taken up in 1 mL CH2Cl2 and treated with 2-(4-chloro-7-methyl-quinazolin-2-yl)-phenol (53 mg, 0.19 mmol) and 49 µL of triethylamine, and stirred at room temperature for 3 h. The reaction mixture was diluted with 10 mL of CH2Cl2 and 10 mL of water. The organic layer was separated and dried over Na2SO4, and the solvent was removed under reduced pressure to give {[2-(tert-butoxycarbonyl-methyl-amino)-acetyl]-methyl-amino}-acetic acid 1-{4-[2-(2-hydroxy-phenyl)-7-methyl-quinazolin-4-yl]-piperazine-1-carbonyl}-3-methyl-butyl ester. LC/MS: m/z 677.4 (M+H)+ at 3.25 min (10%-99% CH3CN (0.035% TFA)/H2O (0.05% TFA)).

[Methyl-(2-methylamino-acetyl)-amino]-acetic acid 1-{4-[2-(2-hydroxy-phenyl)-7-methyl-quinazolin-4-yl]-piperazine-1-carbonyl}-3-methyl-butyl ester

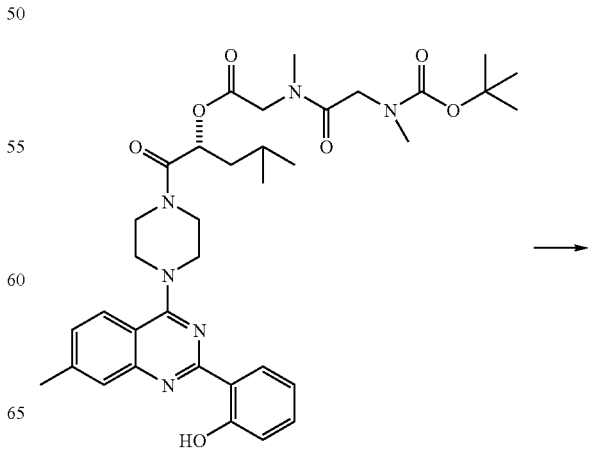

297
-continued

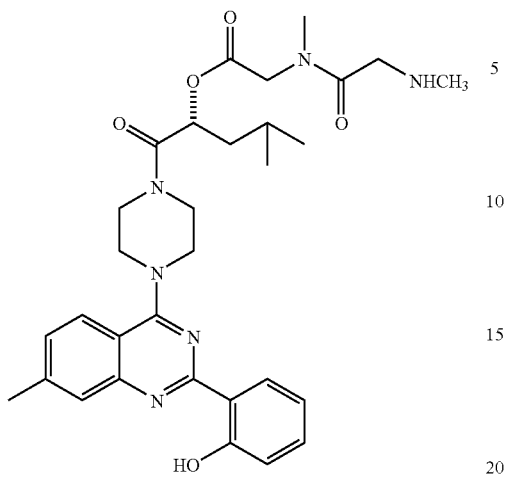

To {[2-(tert-butoxycarbonyl-methyl-amino)-acetyl]-methyl-amino}-acetic acid 1-{4-[2-(2-hydroxy-phenyl)-7-methyl-quinazolin-4-yl]-piperazine-1-carbonyl}-3-methyl-butyl ester (42 mg, 0.062 mmol) was added 300 µL of 1.25 M HCl in methanol at room temperature, and the reaction mixture was stirred for 12 h. The solvent was removed, and the residue was purified with reverse phase LC using 10-99% CH$_3$CN (0.035% TFA)/H$_2$O (0.05% TFA) as eluent to give [methyl-(2-methylamino-acetyl)-amino]-acetic acid 1-{4-[2-(2-hydroxy-phenyl)-7-methyl-quinazolin-4-yl]-piperazine-1-carbonyl}-3-methyl-butyl ester as the TFA salt. LC/MS: m/z 577.4 (M+H)$^+$ at 2.50 min (10%-99% CH$_3$CN (0.035% TFA)/H$_2$O (0.05% TFA)).

Example 170

2-(4-Fluorophenyl)-2-hydroxy-1-(4-(2-(2-hydroxyphenyl)-7-methylquinazolin-4-yl)piperazin-1-yl)ethanone

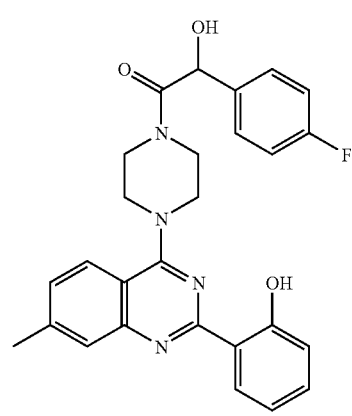

298

2-(4-Fluorophenyl)-2-hydroxy-1-(4-(2-(2-hydroxyphenyl)-7-methylquinazolin-4-yl)piperazin-1-yl)ethanone

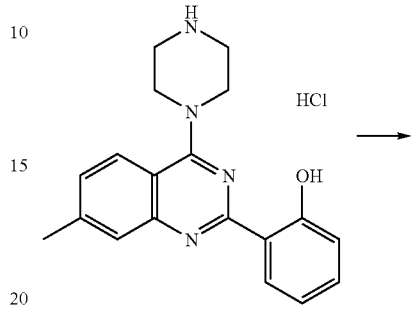

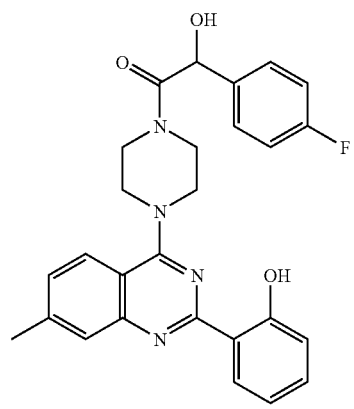

2-(7-Methyl-4-(piperazin-1-yl)quinazolin-2-yl)phenol hydrochloride (prepared analogously to 2-(7-Methyl-4-piperazin-1-yl-quinazolin-2-yl)-phenol, oxalate salt, see Example 130; 30 mg, 0.09 mmol), 2-(4-fluorophenyl)-2-hydroxyacetic acid (20 mg, 0.12 mmol), triethylamine (37.5 µL, 0.27 mmol) and HATU (45 mg, 0.12 mmol) were stirred in DMF (1 mL) overnight. Purification via preparative reverse phase HPLC (10-99% CH$_3$CN (0.035% TFA)/H$_2$O (0.05% TFA)) gave 2-(4-fluorophenyl)-2-hydroxy-1-(4-(2-(2-hydroxyphenyl)-7-methylquinazolin-4-yl)piperazin-1-yl)ethanone as the TFA salt. LC/MS: m/z 473.1 (M+H)$^+$ at 2.63 min (10%-99% CH$_3$CN (0.035% TFA)/H$_2$O (0.05% TFA)).

Example 171

2-(2-Isopropyl-5-methylcyclohexyloxy)-1-(4-(2-(2-hydroxyphenyl)-7-methylquinazolin-4-yl)piperazin-1-yl)ethanone

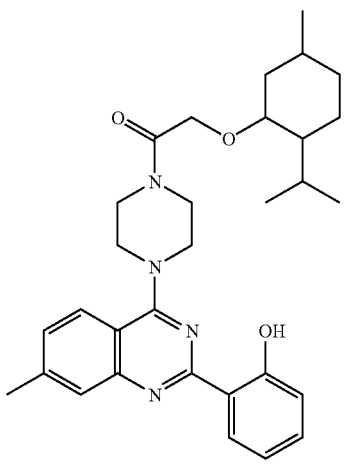

2-(2-Isopropyl-5-methylcyclohexyloxy)-1-(4-(2-(2-hydroxyphenyl)-7-methylquinazolin-4-yl)piperazin-1-yl)ethanone

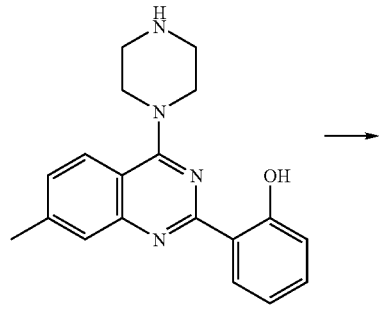

→

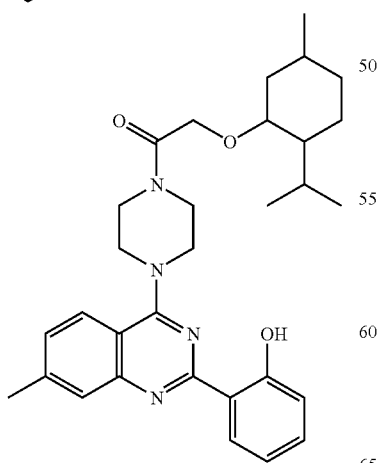

To a solution of 2-(7-methyl-4-(piperazin-1-yl)quinazolin-2-yl)phenol (30 mg, 0.09 mmol) in DMF (1 mL) was added of triethylamine (25 µL) followed by the dropwise addition of 2-(2-isopropyl-5-methylcyclohexyloxy)acetyl chloride (21 µL, 0.09 mmol) at 0° C. The reaction was warmed to room temperature, and purification using reverse phase HPLC (10-99% CH₃CN (0.035% TFA)/H₂O (0.05% TFA)) gave 2-(2-isopropyl-5-methylcyclohexyloxy)-1-(4-(2-(2-hydroxyphenyl)-7-methylquinazolin-4-yl)piperazin-1-yl)ethanone as the TFA salt. LC/MS: m/z 517.5 (M+H)$^+$ at 3.49 min (10%-99% CH₃CN (0.035% TFA)/H₂O (0.05% TFA)).

Example 172

(R)-2-Hydroxy-1-{3-hydroxymethyl-4-[2-(2-hydroxy-phenyl)-7-methyl-quinazolin-4-yl]-piperazin-1-yl}-4-methyl-pentan-1-one

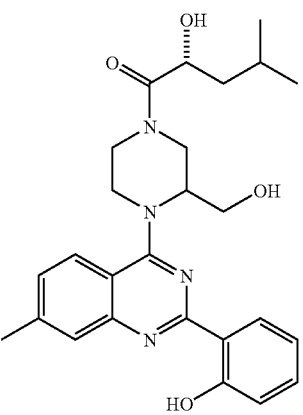

(R)-2-Hydroxy-1-{3-hydroxymethyl-4-[2-(2-hydroxy-phenyl)-7-methyl-quinazolin-4-yl]-piperazin-1-yl}-4-methyl-pentan-1-one

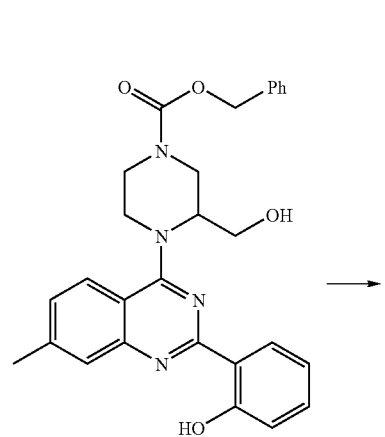

→

301
-continued

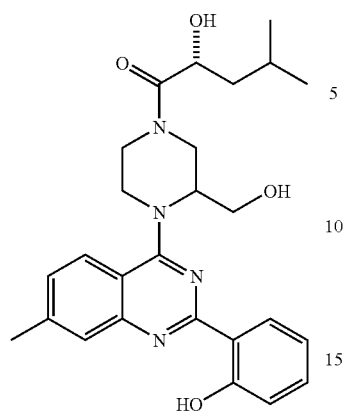

To 3-hydroxymethyl-4-[2-(2-hydroxy-phenyl)-7-methyl-quinazolin-4-yl]-piperazine-1-carboxylic acid benzyl ester (200 mg, 0.41 mmol) in 1.7 mL of methanol was added 39 mg of Pd/C (10% weight Pd on carbon). The reaction mixture was subjected to hydrogenation using a $H_2$ balloon for 3 h. The reaction mixture was filtered through Celite and the solvent was removed to give 2-[4-(2-hydroxymethyl-piperazin-1-yl)-7-methyl-quinazolin-2-yl]-phenol. This amine was treated with (R)-2-hydroxy-4-methyl-pentanoic acid (60 mg, 0.45 mmol), BOP (200 mg, 0.45 mmol) and 115 μL of triethylamine in 1.6 mL of DMF at room temperature for 12 h. The reaction mixture was diluted with 20 mL of $CH_2Cl_2$ and 20 mL of water, and the organic layer was separated and dried over $Na_2SO_4$. The solvent was removed under reduced pressure, and the residue was subjected to purification using 60-100% EtOAc-hexanes to give (R)-2-hydroxy-1-{3-hydroxymethyl-4-[2-(2-hydroxy-phenyl)-7-methyl-quinazolin-4-yl]-piperazin-1-yl}-4-methyl-pentan-1-one. LC/MS: m/z 465 (M+H)$^+$ at 2.77 min (10%-99% $CH_3CN$ (0.035% TFA)/$H_2O$ (0.05% TFA)).

Example 173

(R)-3-Hydroxy-1-(4-(2-(2-hydroxyphenyl)quinazolin-4-yl)piperazin-1-yl)butan-1-one

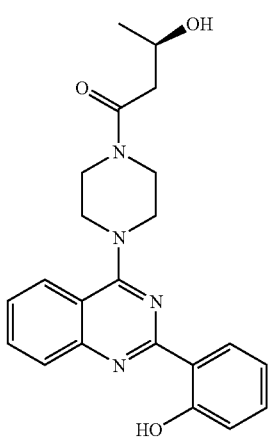

302

(R)-3-Hydroxy-1-(4-(2-(2-hydroxyphenyl)quinazolin-4-yl)piperazin-1-yl)butan-1-one

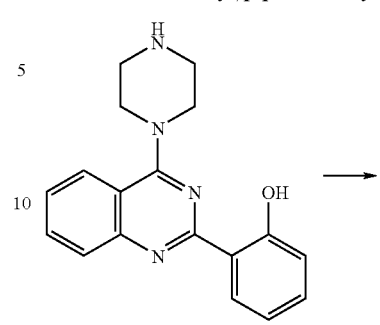

A solution of 2-(4-(piperazin-1-yl)quinazolin-2-yl)phenol (70 mg, 0.23 mmol) in DMF (0.5 mL) was added to (R)-3-hydroxybutanoic acid (31 mg, 0.30 mmol). Then, triethylamine (63 μL) was added, followed by a solution of HATU (113 mg) in 0.5 mL DMF at room temperature. The reaction was stirred overnight. Purification using reverse phase HPLC (10-99% $CH_3CN$ (0.035% TFA)/$H_2O$ (0.05% TFA)) gave (R)-3-hydroxy-1-(4-(2-(2-hydroxyphenyl)quinazolin-4-yl)piperazin-1-yl)butan-1-one as the TFA salt. LC/MS: m/z 393.1 (M+H)$^+$ at 2.03 min (10%-99% $CH_3CN$ (0.035% TFA)/$H_2O$ (0.05% TFA)).

Example 174

2-Hydroxy-1-(4-(2-(2-hydroxyphenyl)quinazolin-4-yl)piperazin-1-yl)pentan-1-one

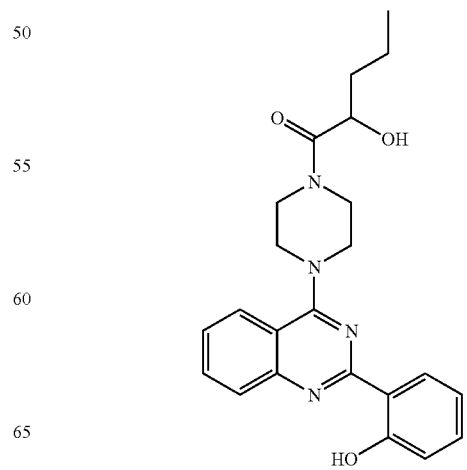

303

2-Hydroxy-1-(4-(2-(2-hydroxyphenyl)quinazolin-4-yl)piperazin-1-yl)pentan-1-one

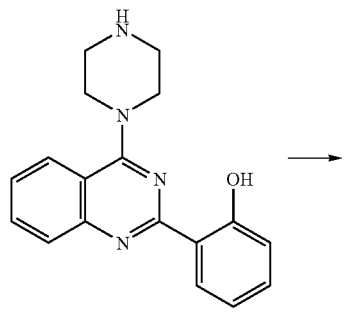

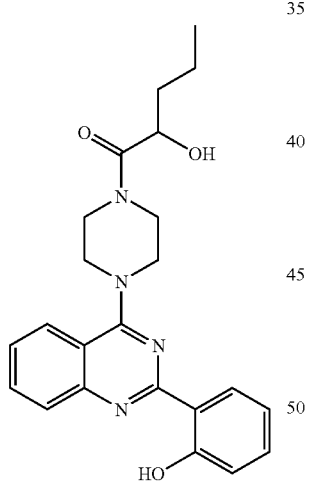

A solution of 2-(4-(piperazin-1-yl)quinazolin-2-yl)phenol (70 mg, 0.23 mmol) in DMF (0.5 mL) was added to 2-hydroxypentanoic acid (35 mg, 0.30 mmol). This was followed by the addition of triethylamine (63 μL) and a solution of HATU (113 mg) in 0.5 mL DMF at room temperature. The reaction was stirred overnight. Purification using reverse phase HPLC (10-99% CH$_3$CN (0.035% TFA)/H$_2$O (0.05% TFA)) gave 2-hydroxy-1-(4-(2-(2-hydroxyphenyl)quinazolin-4-yl)piperazin-1-yl)-2-methylbutan-1-one as the TFA salt. LC/MS: m/z 407.5 (M+H)$^+$ at 2.41 min (10%-99% CH$_3$CN (0.035% TFA)/H$_2$O (0.05% TFA)).

Example 175

1-(4-(2-(2-Hydroxyphenyl)-7-methylquinazolin-4-yl)piperazin-1-yl)-3-(piperidin-1-yl)propan-1-one

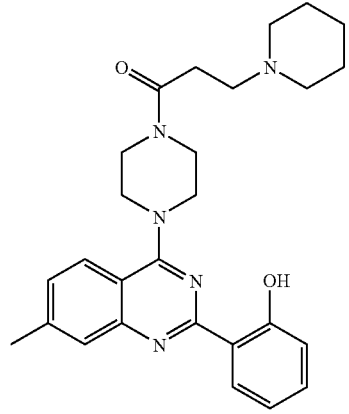

1-(4-(2-(2-Hydroxyphenyl)-7-methylquinazolin-4-yl)piperazin-1-yl)-3-(piperidin-1-yl)propan-1-one

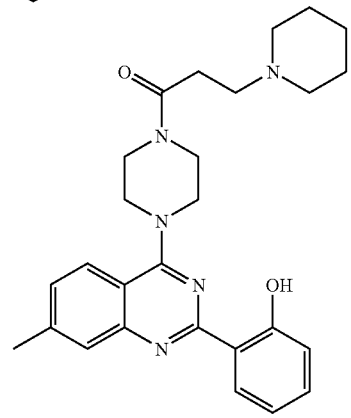

To 2-(7-methyl-4-(piperazin-1-yl)quinazolin-2-yl)phenol (53 mg, 0.17 mmol) was added sequentially 3-(piperidin-1-yl)propanoyl chloride (33 mg, 0.19 mmol) in 28 μL of CH$_2$Cl$_2$ and triethylamine (28 μL, 0.2 mmol). The mixture was stirred at 0° C. for 20 minutes After adding H$_2$O and CH$_2$Cl$_2$, the phases were separated, and the organic layer was dried over Na$_2$SO$_4$ and concentrated under vacuum. Purification using preparative reverse phase HPLC with 10-99% CH$_3$CN (0.035% TFA)/H$_2$O (0.05% TFA) gave 1-(4-(2-(2-hydroxyphenyl)-7-methylquinazolin-4yl)piperazin-1-yl)-3-(piperdin-1-yl)propan-1-one as the bis TFA salt. LC/MS: m/z 460.5 (M+H)$^+$ at 2.33 min (10%-99% CH$_3$CN (0.035% TFA)/H$_2$O (0.05% TFA)).

Example 176

(2R,3R)-2-Hydroxy-1-(4-(2-(2-hydroxyphenyl)-7-methylquinazolin-4-yl)piperazin-1-yl)-3-methylpentan-1-one

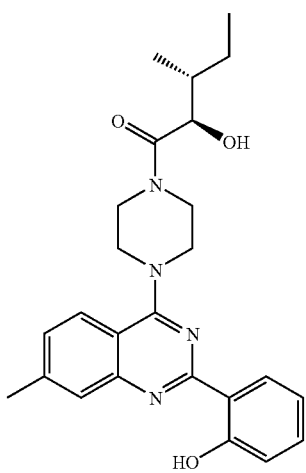

(2R,3R)-2-Hydroxy-1-(4-(2-(2-hydroxyphenyl)-7-methylquinazolin-4-yl)piperazin-1-yl)-3-methylpentan-1-one

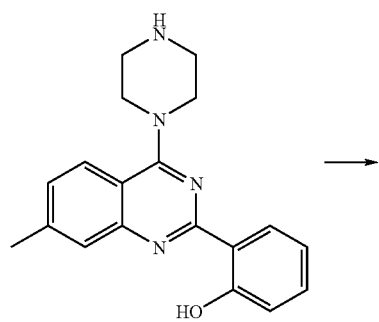

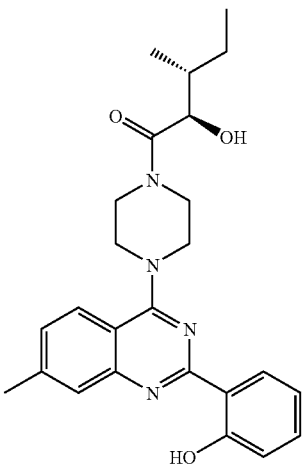

To 2-(7-methyl-4-(piperazin-1-yl)quinazolin-2-yl)phenol (su mg, 0.25 mmol) in 800 μL of CH$_2$Cl$_2$ was added sodium of (2R,3R)-2-hydroxy-3-methyl-pentanoate (50 mg, 0.33 mmol), BOP (144 mg, 0.33 mmol), and triethylamine (52 μL, 0.38 mmol). The reaction mixture was stirred at room temperature for 2 h. After adding H$_2$O and CH$_2$Cl$_2$, the layers were separated, and the organic layer was dried over Na$_2$SO$_4$ and concentrated. Purification via preparative reverse phase HPLC using 10-99% CH$_3$CN (0.035% TFA)/H$_2$O (0.05% TFA) gave (2R,3R)-2-hydroxy-1-(4-(2-(2-hydroxyphenyl)-7-methylquinazolin-4-yl)piperazin-1-yl)-3-methylpentan-1-one as the TFA salt. LC/MS: m/z 435.5 (M+H)$^+$ at 2.62 min (10%-99% CH$_3$CN (0.035% TFA)/H$_2$O (0.05% TFA)).

Example 177

(S)-3,3,3-Trifluoro-2-hydroxy-1-(4-(2-(2-hydroxyphenyl)-7-methylquinazolin-4-yl)piperazin-1-yl)propan-1-one

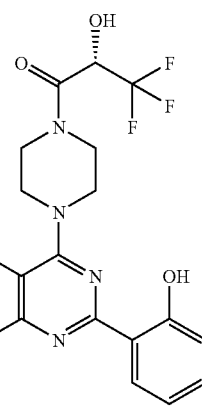

307

(S)-3,3,3-Trifluoro-2-hydroxy-1-(4-(2-(2-hydroxyphenyl)-7-methylquinazolin-4-yl)piperazin-1-yl)propan-1-one

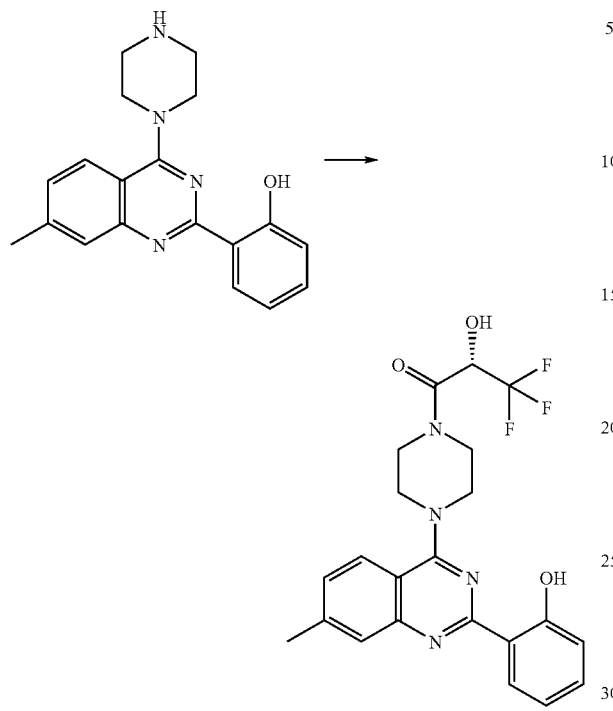

A mixture of 2-(7-methyl-4-(piperazin-1-yl)quinazolin-2-yl)phenol (64 mg, 0.2 mmol), (S)-3,3,3-trifluoro-2-hydroxypropanoic acid (29 mg, 0.2 mmol), HATU (76 mg, 0.2 mmol) and triethylamine (28 μL, 0.2 mmol) in DMF (1 mL) was stirred at room temperature overnight. Purification via preparative HPLC (10-99% CH$_3$CN (0.035% TFA)/H$_2$O (0.05% TFA)) gave (S)-3,3,3-trifluoro-2-hydroxy-1-(4-(2-(2-hydroxyphenyl)-7-methylquinazolin-4-yl)piperazin-1-yl)propan-1-one as the TFA salt. LC/MS: m/z 447.1 (M+H)$^+$ at 2.53 min (10%-99% CH$_3$CN (0.035% TFA)/H$_2$O (0.05% TFA)).

Example 178

2-(Trifluoromethyl)-2-hydroxy-1-(4-(2-(2-hydroxyphenyl)quinazolin-4-yl)piperazin-1-yl)propan-1-one

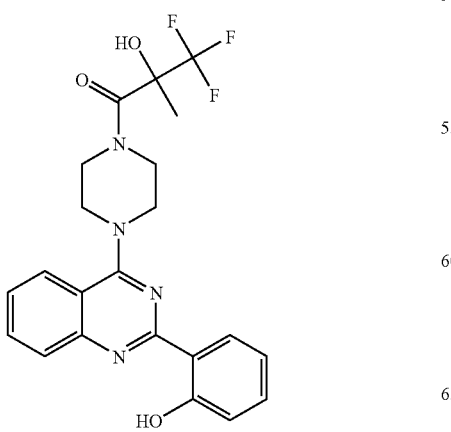

308

2-(Trifluoromethyl)-2-hydroxy-1-(4-(2-(2-hydroxyphenyl)quinazolin-4-yl)piperazin-1-yl)propan-1-one

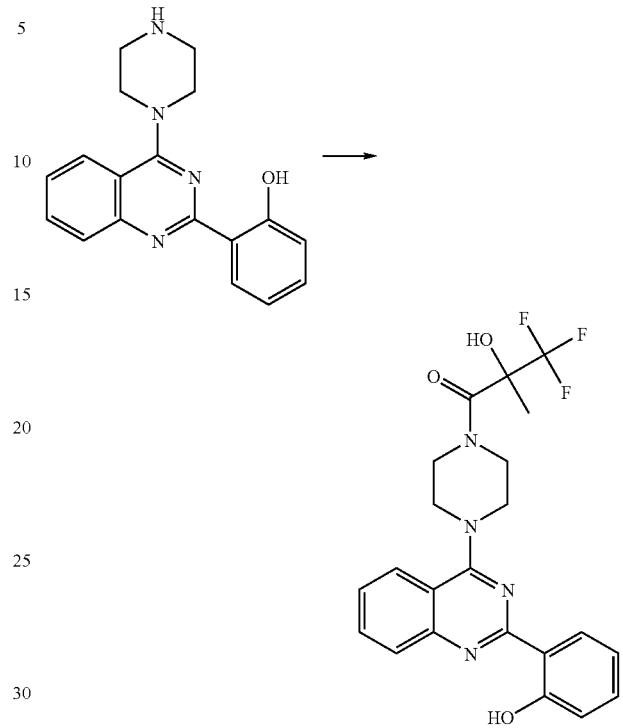

A solution of 2-(4-(piperazin-1-yl)quinazolin-2-yl)phenol (70 mg, 0.23 mmol) in DMF (0.5 mL) was added to 2-(trifluoromethyl)-2-hydroxypropanoic acid (47.0 mg, 0.297 mmol). Then, triethylamine (63 μL) was added, followed by a solution of HATU (113 mg) in 0.5 mL DMF at room temperature. The reaction was stirred overnight. Purification using reverse phase HPLC (10-99% CH$_3$CN (0.035% TFA)/H$_2$O (0.05% TFA)) gave 2-(trifluoromethyl)-2-hydroxy-1-(4-(2-(2-hydroxyphenyl)quinazolin-4-yl)piperazin-1-yl)propan-1-one as the TFA salt. LC/MS: m/z 447.3 (M+H)$^+$ at 2.50 min (10%-99% CH$_3$CN (0.035% TFA)/H$_2$O (0.05% TFA)).

Example 179

3-Chloro-2-hydroxy-1-(4-(2-(2-hydroxyphenyl)-7-methylquinazolin-4-yl)piperazin-1-yl)propan-1-one

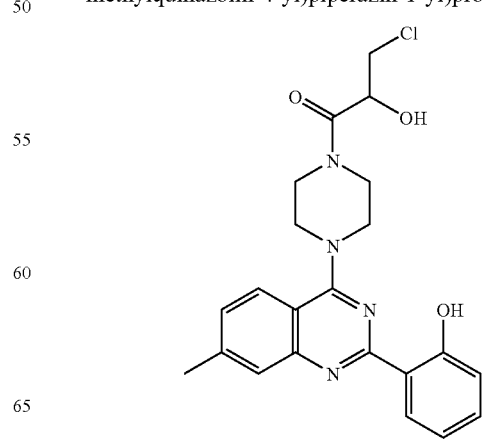

3-Chloro-2-hydroxy-1-(4-(2-(2-hydroxyphenyl)-7-methylquinazolin-4-yl)piperazin-1-yl)propan-1-one

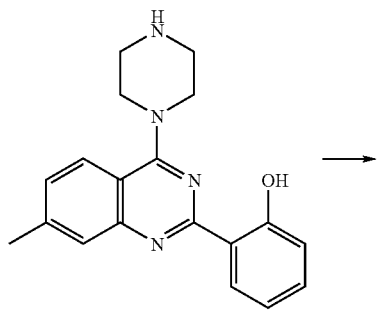

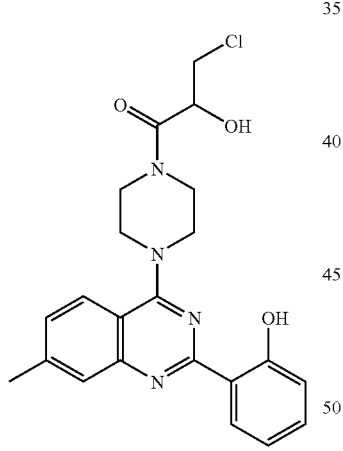

A mixture of 2-(7-methyl-4-(piperazin-1-yl)quinazolin-2-yl)phenol (121 mg, 0.38 mmol), 3-chloro-2-hydroxypropanoic acid (61 mg, 0.49 mmol), BOP (217 mg, 0.49 mmol), and triethylamine (79 µL, 0.56 mmol) in 1.2 mL of CH₂Cl₂ was stirred at room temperature for 1 h. The reaction was washed with water and the organic layer was dried over Na₂SO₄ and concentrated. Purification via preparative reverse phase HPLC using 10-99% CH₃CN (0.035% TFA)/H₂O (0.05% TFA) gave 3-chloro-2-hydroxy-1-(4-(2-(2-hydroxyphenyl)-7-methylquinazolin-4-yl)piperazin-1-yl)pro-pan-1-one as the TFA salt. LC/MS: m/z 427.2 (M+H)⁺ at 2.59 min (10%-99% CH₃CN (0.035% TFA)/H₂O (0.05% TFA)).

Example 201

1-(2-(2-Hydroxyphenyl)-7-methylquinazolin-4-yl)-N-((pyridin-3-yl)methyl)piperidine-3-carboxamide

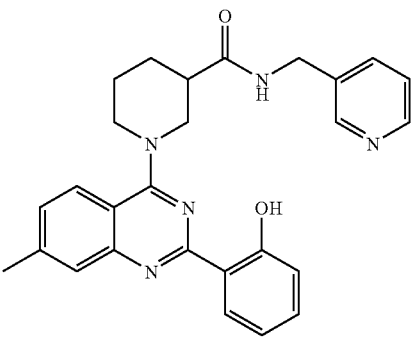

Piperidine-3-carboxylic acid

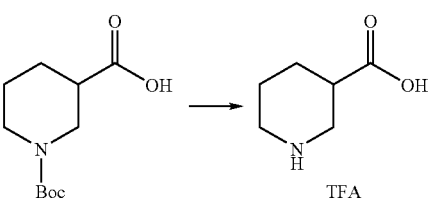

To a solution of 1-(tert-butoxycarbonyl)piperidine-3-carboxylic acid (500 mg, 2.18 mmol) in CH₂Cl₂ (10 mL) was added TFA (5 ml). The reaction mixture was stirred for an hour. Excess TFA was removed under reduced pressure, and the piperidine-3-carboxylic acid was used without neutralization for the next step. LC/MS: m/z 1303 (M+H)⁺ at 0.35 min (10%-99% CH₃CN (0.035% TFA)/H₂O (0.05% TFA)).

1-(2-(2-Hydroxyphenyl)-7-methylquinazolin-4-yl)piperidine-3-carboxylic acid

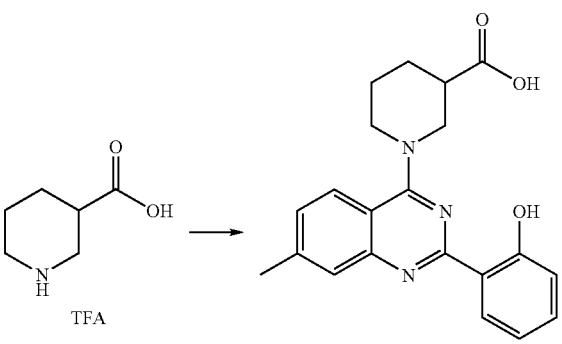

To a solution of 2-(4-chloro-7-methylquinazolin-2-yl)phenol (0.449 mg, 1.66 mmol) in CH₂Cl₂ was added 5 equivalents of triethylamine followed by the addition of piperidine-3-carboxylic acid as a TFA salt. The reaction was stirred for 2 hours and quenched with water. The layers were separated, and the organic extracts were dried over MgSO₄, filtered, and concentrated to give 1-(2-(2-hydroxyphenyl)-7-methylquinazolin-4-yl)piperidine-3-carboxylic acid which was used without further purification. LC/MS: m/z 364.3 (M+H)⁺ at 2.22 min (10%-99% CH₃CN (0.035% TFA)/H₂O (0.05% TFA)).

1-(2-(2-Hydroxyphenyl)-7-methylquinazolin-4-yl)-N-((pyridin-3-yl)methyl)piperidine-3-carboxamide

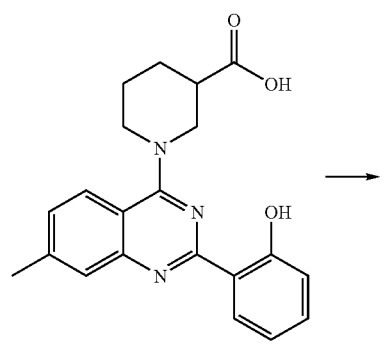

A solution of 1-(2-(2-hydroxyphenyl)-7-methylquinazolln-4-yl)piperidine-3-carboxylic acid (45 mg, 0.12 mmol), (pyridin-3-yl)methanamine (14 µL, 0.136 mmol) and triethylamine (25 mg, 35 µL, 0.25 mmol) in 500 µL DMF was cooled to 0° C., and HATU (57 mg, 0.15 mmol) was added. The reaction was warmed to room temperature, stirred overnight and purified by reverse phase HPLC (10-99% CH₃CN (0.035% TFA)/H₂O (0.05% TFA)) giving 1-(2-(2-hydroxyphenyl)-7-methylquinazolin-4-yl)-N-((pyridin-3-yl)methyl)piperidine-3-carboxamide as the TFA salt. LC/MS: m/z 454.5 (M+H)⁺ at 1.87 min (10%-99% CH₃CN (0.035% TFA)/H₂O (0.05% TFA)).

Example 203

(R)-Tetrahydrofuran-3-yl (S)-1-(2-(2-hydroxyphenyl)-7-methylquinazolin-4-yl)piperidin-3-ylcarbamate

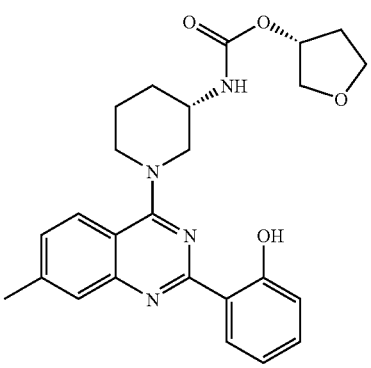

Benzyl (S)-1-(2-(2-hydroxyphenyl)-7-methylquinazolin-4-yl)piperidin-3-ylcarbamate

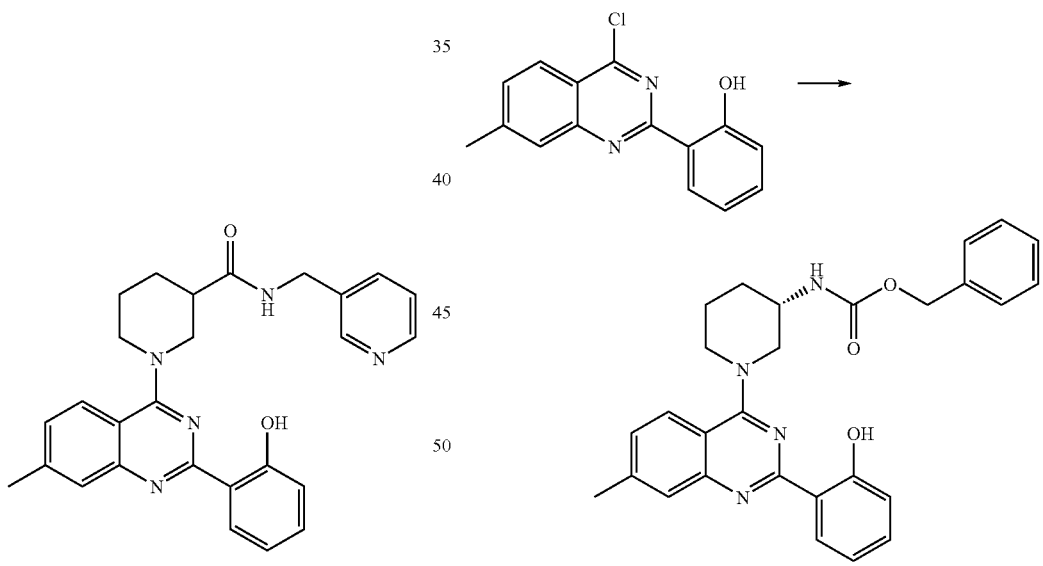

To a solution of 2-(4-chloro-7-methylquinazolin-2-yl)phenol (1.15 g, 4.26 mmol) in CH₂Cl₂ (25 mL) at 0° C. under inert atmosphere was slowly added a solution of benzyl (S)-piperidin-3-ylcarbamate (1.0 g, 4.26 mmol) and triethylamine (1.18 mL, 8.52 mmol) in CH₂Cl₂ (10 mL). The reaction was allowed to warm to room temperature and was then quenched with water. The mixture was extracted with CH₂Cl₂ and the organic layers were combined, dried over MgSO₄, and concentrated to obtain benzyl (S)-1-(2-(2-hydroxyphenyl)-7-methylquinazolin-4-yl)piperidin-3-ylcarbamate (2.03 g). This material was used without further purification.

LC/MS: m/z 469.1 (M+H)+ at 2.86 min (10%-99% CH3CN (0.035% TFA)/H2O (0.05% TFA))

2-(4-((S)-3-Aminopiperidin-1-yl)-7-methylquinazo-lin-2-yl)phenol

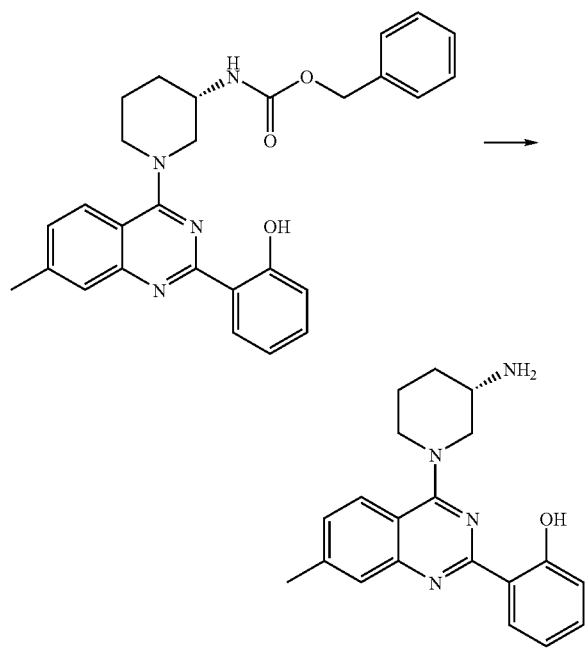

Pd/C (175 mg, 10% weight Pd on carbon) was added to a round bottom flask and the flask was flushed with N2. To this flask was then added MeOH (10 mL). After purging the flask again with N2, (S)-1-(2-(2-hydroxyphenyl)-7-methylquinazolin-4-yl)piperidin-3-ylcarbamate (1.75 g, 3.74 mmol) dissolved in EtOAc (60 mL) and MeOH (50 mL) was added. After flushing the flask 3 times with N2, and evacuating it under vacuum, H2 was passed through the vigorously stirring mixture for 4 h until hydrogenation was complete. The mixture was filtered through a pad of Celite. The filtrate was concentrated to afford 2-(4-((S)-3-aminopiperidin-1-yl)-7-methylquinazolin-2-yl)phenol (0.62 g, 50%). LC/MS: m/z 335.5 (M+H)+ at 1.50 min (10%-99% CH3CN (0.035% TFA)/H2O (0.05% TFA)).

(R)-Tetrahydrofuran-3-yl (S)-1-(2-(2-hydroxyphenyl)-7-methylquinazolin-4-yl)piperidin-3-ylcarbamate

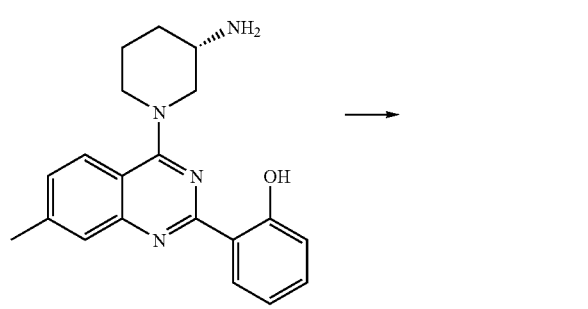

-continued

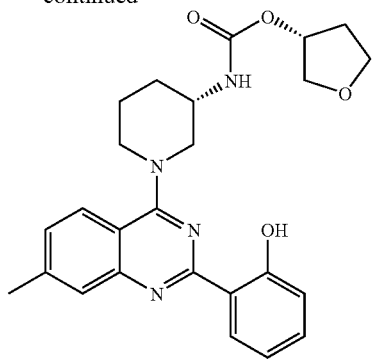

2-(4-((S)-3-Aminopiperidin-1-yl)-7-methylquinazolin-2-yl)phenol (50 mg, 0.15 mmol), (R)-tetrahydrofuran-3-yl chloroformate (22.6 mg, 0.15 mmol) and triethylamine (30 mg, 0.3 mmol) were stirred in DMF (1 mL) at 0° C. After allowing the reaction to warm to room temperature, it was purified via reverse phase HPLC (10-99% CH3CN (0.035% TFA)/H2O (0.05% TFA)) to give (R)-tetrahydrofuran-3-yl (S)-1-(2-(2-hydroxyphenyl)-7-methylquinazolin-4-yl)piperidin-3-ylcarbamate as the TFA salt. LC/MS: m/z 449.3.5 (M+H)+ at 1.52 min (10%-99% CH3CN (0.035% TFA)/H2O (0.05% TFA)).

Example 204

(S)-Tetrahydrofuran-3-yl (S)-1-(2-(2-hydroxyphenyl)-7-methylquinazolin-4-yl)piperidin-3-ylcarbamate

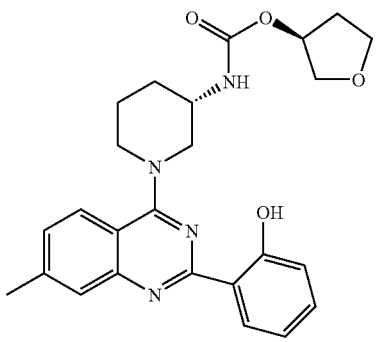

(S)-Tetrahydrofuran-3-yl (S)-1-(2-(2-hydroxyphenyl)-7-methylquinazolin-4-yl)piperidin-3-ylcarbamate

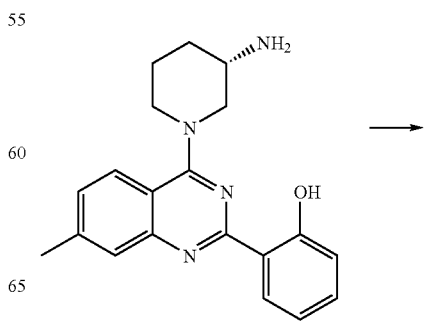

315
-continued

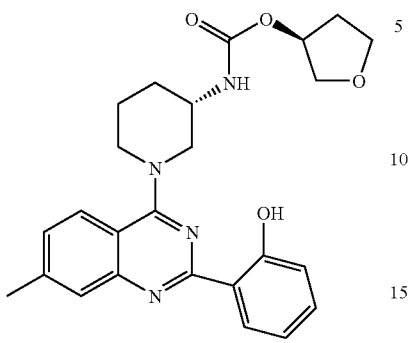

2-(4-((S)-3-Aminopiperidin-1-yl)-7-methylquinazolin-2-yl)phenol (50 mg, 0.15 mmol), (S)-tetrahydrofuran-3-yl chloroformate (22.6 mg, 0.15 mmol), and triethylamine (30 mg, 0.3 mmol) were stirred in DMF (1 mL) at 0° C. After allowing the reaction to warm to room temperature it was purified via reverse phase HPLC (10-99% CH₃CN (0.035% TFA)/H₂O (0.05% TFA)) to afford (S)-tetrahydrofuran-3-yl (S)-1-(2-(2-hydroxyphenyl)-7-methylquinazolin-4-yl)piperidin-3-ylcarbamate as the TFA salt. LC/MS: m/z 449.3 (M+H)⁺ at 2.33 min (10%-99% CH₃CN (0.035% TFA)/H₂O (0.05% TFA))

Example 205

(2R)-Tetrahydro-N—((S)-1-(2-(2-hydroxyphenyl)-7-methylquinazolin-4-yl)piperidin-3-yl)furan-2-carboxamide

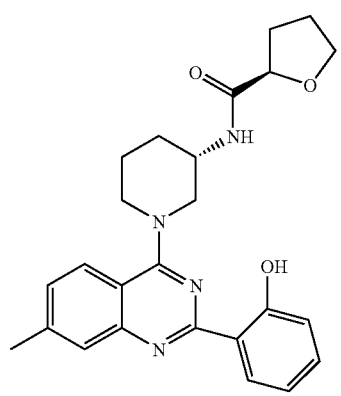

316

(2R)-Tetrahydro-N—((S)-1-(2-(2-hydroxyphenyl)-7-methylquinazolin-4-yl)piperidin-3-yl)furan-2-carboxamide

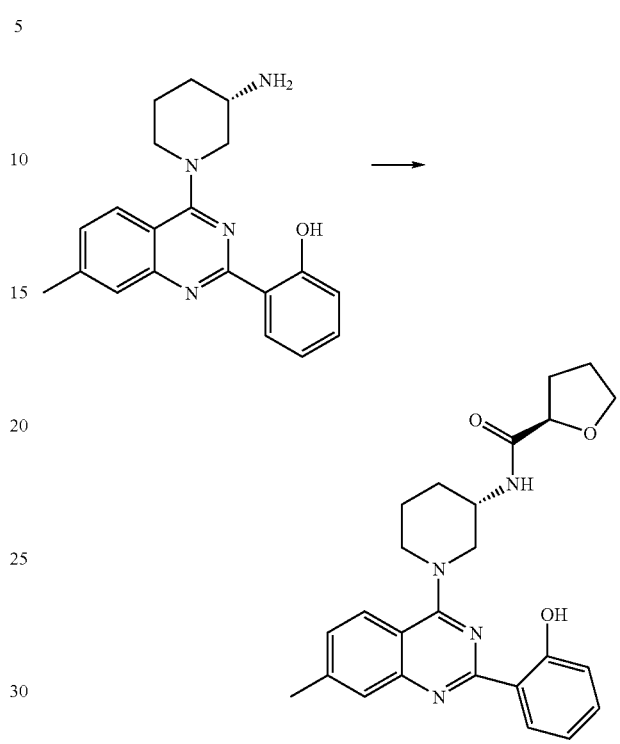

2-(4-((S)-3-Aminopiperidin-1-yl)-7-methylquinazolin-2-yl)phenol (50 mg, 0.15 mmol), (R)-tetrahydrofuran-2-carboxylic acid (22.6 mg, 0.195 mmol), triethylamine (30 mg, 0.3 mmol), and HATU (74.14 mg, 0.195 mmol) were stirred at room temperature in DMF for 1 h. Purification via reverse phase HPLC (10-99% CH₃CN (0.035% TFA)/H₂O (0.05% TFA)) gave (2R)-tetrahydro-N—((S)-1-(2-(2-hydroxyphenyl)-7-methylquinazolin-4-yl)piperidin-3-yl)furan-2-carboxamide as the TFA salt. LC/MS: m/z 433.3 (M+H)⁺ at 2.33 min (10%-99% CH₃CN (0.035% TFA)/H₂O (0.05% TFA)).

Example 206

(2R)-Tetrahydro-N—((R)-1-(2-(2-hydroxyphenyl)-7-methylquinazolin-4-yl)piperidin-3-yl)furan-2-carboxamide

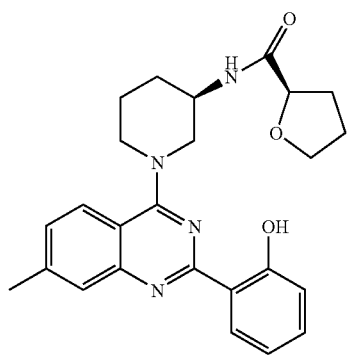

317 tert-Butyl (R)-1-(2-(2-hydroxyphenyl)-7-methylquinazolin-4-yl)piperidin-3-ylcarbamate

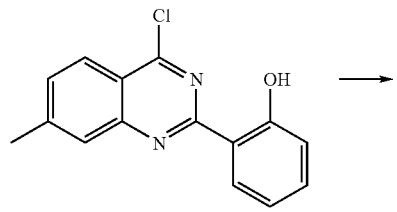

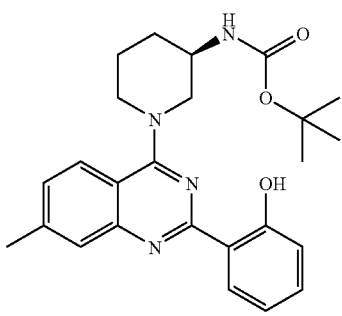

To a solution of 2-(4-chloro-7-methylquinazolin-2-yl)phenol (0.5 g, 1.84 mmol) in CH$_2$Cl$_2$ (10 mL) at 0° C. was added dropwise a solution of tert-butyl (R)-piperidin-3-ylcarbamate (0.37 g, 1.84 mmol) in CH$_2$Cl$_2$ (5 mL), then triethylamine (0.51 µL, 3.68 mmol). The mixture was allowed to warm to room temperature and was stirred for 3 h. After quenching with water, it was extracted with CH$_2$Cl$_2$. The organic layers were combined, dried over MgSO$_4$, and concentrated. Purification via silica gel chromatography using 5:1 CH$_2$Cl$_2$:hexanes gave tert-butyl (R)-1-(2-(2-hydroxyphenyl)-7-methylquinazolin-4-yl)piperidin-3-ylcarbamate (0.54 g, 68%). LC/MS: m/z 435.5 (M+H)$^+$ at 2.80 min (10%-99% CH$_3$CN (0.035% TFA)/H$_2$O (0.05% TFA)).

2-(4-((R)-3-Aminopiperidin-1-yl)-7-methylquinazolin-2-yl)phenol

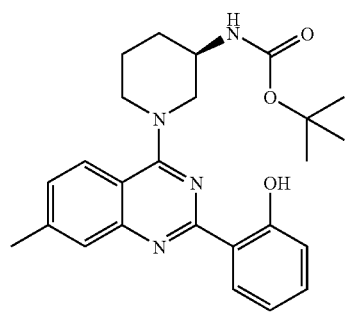

318

-continued

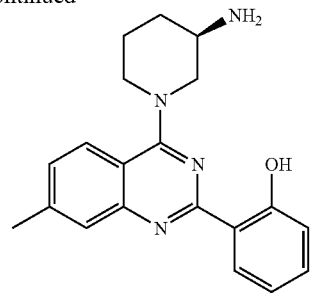

tert-Butyl (R)-1-(2-(2-hydroxyphenyl)-7-methylquinazolin-4-yl)piperidin-3-ylcarbamate (0.54 g, 1.24 mmol) was dissolved in CH$_2$Cl$_2$ (15 mL) followed by the addition of TFA (8 mL). The reaction was stirred for 1.5 h, and the solvents were evaporated to an oily liquid which was diluted with CH$_2$Cl$_2$ and neutralized with a 1 M aqueous NaOH solution. The organic layer was separated, and the aqueous layer was washed two times with CH$_2$Cl$_2$. After drying the combined organic phases over MgSO$_4$, they were filtered, and concentrated to afford 2-(4-((R)-3-aminopiperidin-1-yl)-7-methylquinazolin-2-yl)phenol as a solid (0.354 g, 85%). LC/MS: m/z 335.7 (M+H)$^+$ at 1.42 min (10%-99% CH$_3$CN (0.035% TFA)/H$_2$O (0.05% TFA)).

(2R)-Tetrahydro-N—((R)-1-(2-(2-hydroxyphenyl)-7-methylquinazolin-4-yl)piperidin-3-yl)furan-2-carboxamide

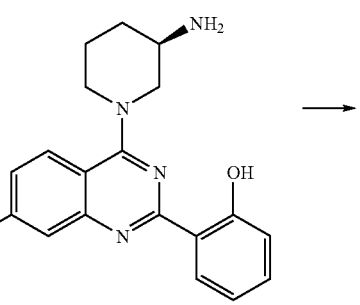

2-(4-((R)-3-Aminopiperidin-1-yl)-7-methylquinazolin-2-yl)phenol (50 mg, 0.15 mmol), (R)-tetrahydrofuran-2-carboxylic acid (22.6 mg, 0.15 mmol), triethylamine (30 mg, 0.3 mmol), and HATU (74.14 mg, 0.195 mmol) were stirred at room temperature in DMF for 1 h. Purification via reverse phase HPLC (10-99% CH$_3$CN (0.035% TFA)/H$_2$O (0.05% TFA)) gave (2R)-tetrahydro-N—((R)-1-(2-(2-hydroxyphenyl)-7-methylquinazolin-4-yl)piperidin-3-yl)furan-2-carboxamide as the TFA salt. LC/MS: m/z 433.3 (M+H)+ at 2.34 min (10%-99% CH₃CN (0.035% TFA)/H₂O (0.05% TFA)).

Example 207

(R)-Tetrahydrofuran-3-yl (R)-1-(2-(2-hydroxyphenyl)-7-methylquinazolin-4-yl)piperidin-3-ylcarbamate

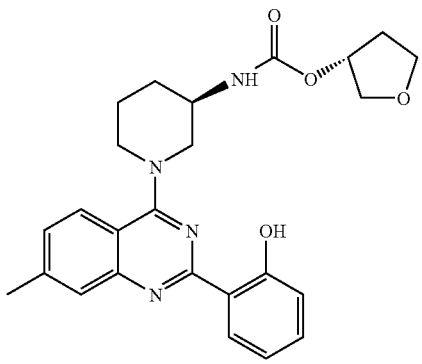

(R)-Tetrahydrofuran-3-yl (R)-1-(2-(2-hydroxyphenyl)-7-methylquinazolin-4-yl)piperidin-3-ylcarbamate

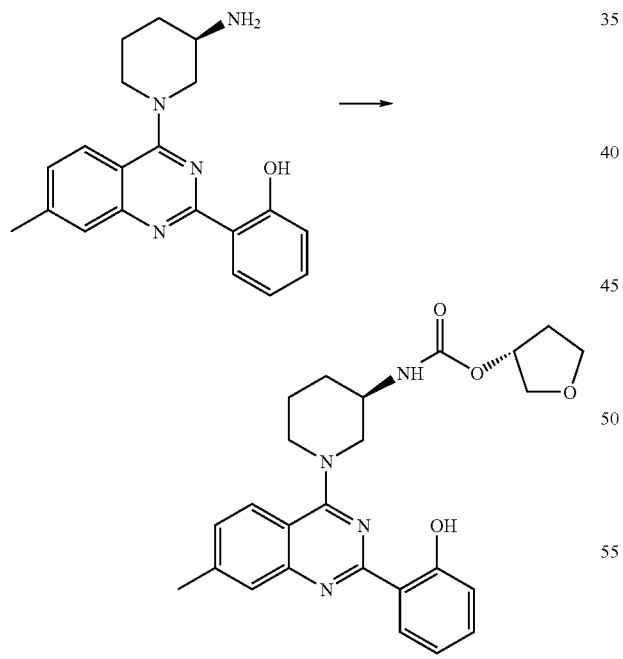

A solution of 2-(4-((R)-3-aminopiperidin-1-yl)-7-methylquinazolin-2-yl)phenol (50 mg, 0.15 mmol) in DMF (0.5 mL) was cooled to 0° C. Then, a solution of triethylamine (30 mg, 0.3 mmol) and (R)-tetrahydrofuran-3-yl chloroformate (22.6 mg, 0.15 mmol) in DMF (0.5 mL) was added dropwise. The mixture was allowed to warm to room temperature over a period of 30 min before it was purified using reverse phase HPLC (10-99% CH₃CN (0.035% TFA)/H₂O (0.05% TFA)) to obtain (R)-tetrahydrofuran-3-yl (R)-1-(2-(2-hydroxyphenyl)-7-methylquinazolin-4-yl)piperidin-3-ylcarbamate as the TFA salt. LC/MS: m/z 449.5 (M+H)+ at 2.34 min (10%-99% CH₃CN (0.035% TFA)/H₂O (0.05% TFA)).

Example 208

(S)-Tetrahydrofuran-3-yl (R)-1-(2-(2-hydroxyphenyl)-7-methylquinazolin-4-yl)piperidin-3-ylcarbamate

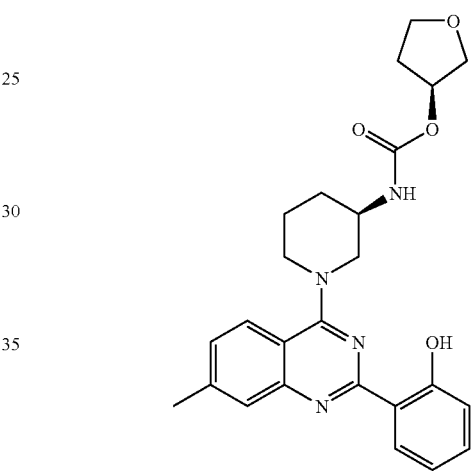

(S)-Tetrahydrofuran-1-yl (R)-1-(2-(2-hydroxyphenyl)-7-methylquinazolin-4-yl)piperidin-3-ylcarbamate

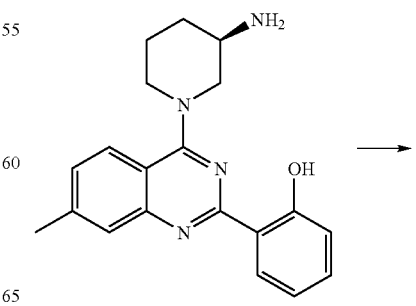

322

3-(Benzyloxycarbonylamino-methyl)-piperidine-1-carboxylic acid tert-butyl ester

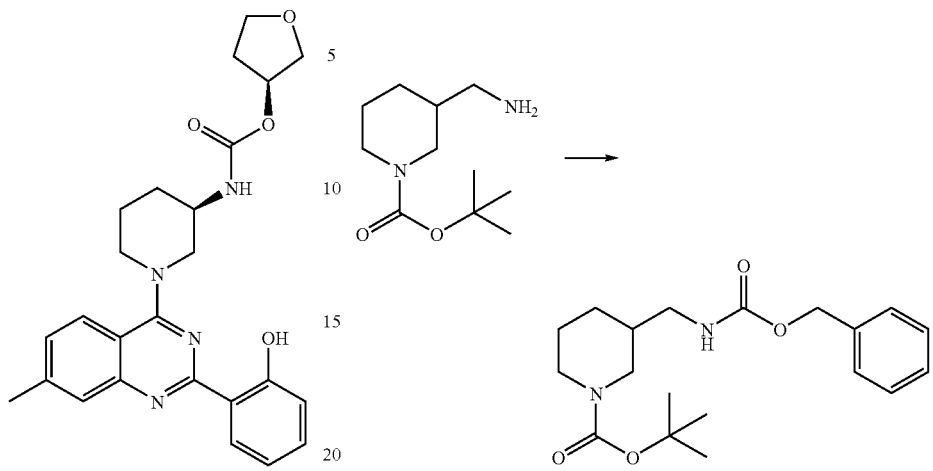

3-Aminomethyl-piperidine-1-carboxylic acid tert-butyl ester (3.6 g, 16.8 mmol) was dissolved in 42 mL anhydrous $CH_2Cl_2$ under an $N_2$ atmosphere and cooled in an ice water bath. Triethylamine (4.7 mL, 33.6 mmol) was added followed by the dropwise addition of benzyl chloroformate (3.55 mL, 25.2 mmol). After 16 hours, the reaction mixture was partitioned between $CH_2Cl_2/H_2O$, and separated, and the aqueous layer was extracted twice with $CH_2Cl_2$. All of the organic extracts were combined, dried over $Na_2SO_4$, filtered, and concentrated to a light yellow oil. Purification by silica gel chromatography using 97% $CH_2Cl_2$/3% MeOH gave the product as a clear, colorless oil (55%). LC/MS: m/z 349.3 $(M+H)^+$ at 3.22 min (10%-99% $CH_3CN$ (0.035% TFA)/$H_2O$ (0.05% TFA)).

Benzyl (piperidin-3-yl)methylcarbamate hydrochloride

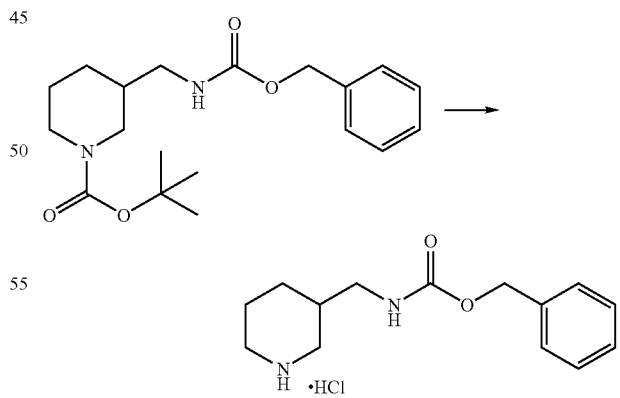

Benzyl (1-(tert-butoxycarbonyl)piperidin-3-yl)methylcarbamate (3.22 g, 9.25 mmol) was treated with a 4.0 M HCl solution in dioxane (11.3 mL, 46.25 mmol). Formation of a white precipitate was observed. After 3 h, the reaction was complete. The solvent and excess HCl were removed under reduced pressure to obtain benzyl (piperidin-3-yl)methylcar-

321
-continued

To a solution of 2-(4-((R)-3-aminopiperidine-1-yl)-7-methylquinazolin-2-yl)phenol (50 mg, 0.15 mmol) in DMF (0.5 mL) was cooled to 0° C. A solution of (S)-tetrahydrofuran-3-yl chloroformate (22.6 mg, 0.15 mmol) in DMF (0.5 mL) was then added, followed by triethylamine (30 mg, 0.3 mmol). The mixture was allowed to warm to room temperature over a period of 30 min before it was purified using reverse phase HPLC (10-99% $CH_3CN$ (0.035% TFA)/$H_2O$ (0.05% TFA)) to obtain (S)-tetrahydrofuran-3-yl (R)-1-(2-(2-hydroxyphenyl)-7-methylquinazolin-4-yl)piperidin-3-ylcarbamate as the TFA salt. LC/MS: m/z 449.5 $(M+H)^+$ at 2.33 min (10%-99% $CH_3CN$ (0.035% TFA)/$H_2O$ (0.05% TFA)).

Example 209

(2S)-Tetrahydro-N-((1-(2-(2-hydroxyphenyl)-7-methylquinazolin-4-yl)piperidin-3-yl)methyl)furan-2-carboxamide

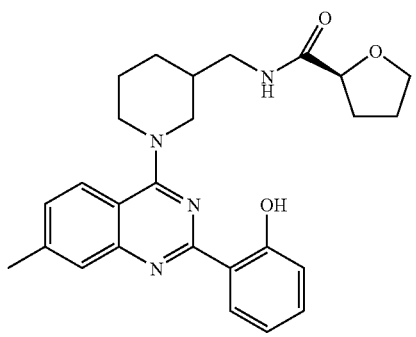

bamate hydrochloride as a white solid. LC/MS: m/z 249.3 (M+H)+ at 1.28 min (10%-99% CH₃CN (0.035% TFA)/H₂O (0.05% TFA)).

Benzyl (1-(2-(2-hydroxyphenyl)-7-methylquinazolin-4-yl)piperidin-3-yl)methylcarbamate

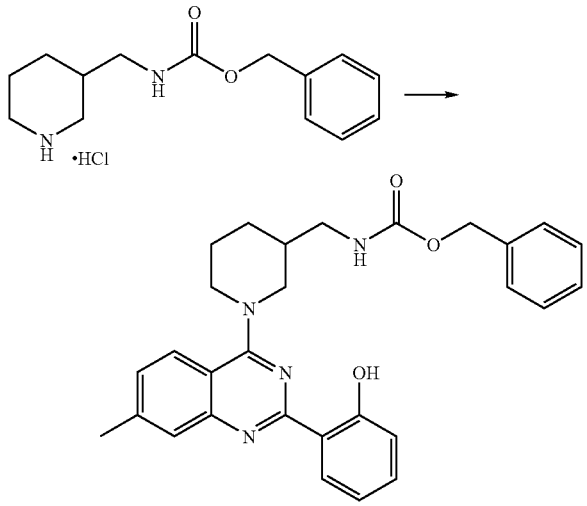

2-(4-Chloro-7-methylquinazolin-2-yl)phenol (1.5 g, 5.54 mmol) was suspended in anhydrous CH₂Cl₂ (15 μL) and cooled to 0° C. under an N₂ atmosphere. A mixture of benzyl (piperidin-3-yl)methylcarbamate hydrochloride (1.73 g, 6.09 mmol) in CH₂Cl₂ (20 mL), and triethylamine (23 mL, 16.67 mmol) was added dropwise. The reaction mixture was allowed to warm to room temperature, and the reaction was complete after one hour. It was then partitioned between CH₂Cl₂/H₂O, and separated, and the organic phase was dried over Na₂SO₄, filtered, and concentrated to an orange solid. Purification by silica gel chromatography using 98% CH₂Cl₂/ 2% EtOAc gave benzyl (1-(2-(2-hydroxyphenyl)-7-methylquinazolin-4-yl)piperidin-3-yl)methylcarbamate as a bright yellow solid (1.75 g, 66%). LC/MS: m/z 483.5 (M+H)+ at 2.81 min (10%-99% CH₃CN (0.035% TFA)/H₂O (0.05% TFA)).

2-(4-(3-(Aminomethyl)piperidin-1-yl)-7-methylquinazolin-2-yl)phenol

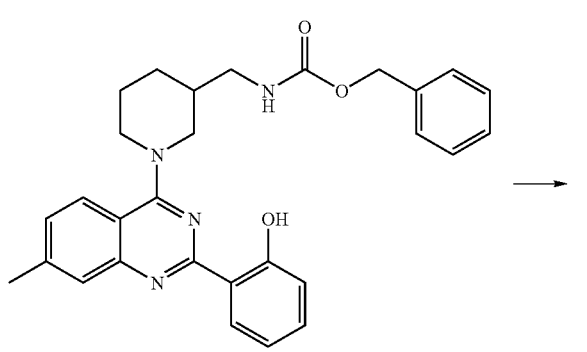

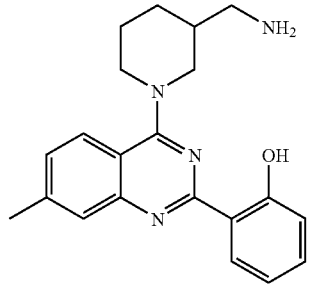

A mixture of benzyl (1-(2-(2-hydroxyphenyl)-7-methylquinazolin-4-yl)piperidin-3-yl)methylcarbamate (1.75 g, 3.63 mmol) and EtOH/EtOAc (50 mL/20 mL) was heated to obtain a homogeneous solution. After cooling to room temperature, Pd/C (175 mg, 10% wt Pd on carbon) was added and the flask was sealed with a septum. The same flask was 3 times charged with N₂ and evacuated under vacuum. The mixture was then stirred under an H₂ atmosphere at ambient pressure for 1 h. The product was collected by filtration through a plug of Celite, eluting with MeOH. The filtrate was concentrated to a yellow solid (1.26 g) to give 2-(4-(3-(aminomethyl)piperidin-1-yl)-7-methylquinazolin-2-yl)phenol. LC/MS: m/z 349.3 (M+H)+ at 1.80 min (10%-99% CH₃CN (0.035% TFA)/H₂O (0.05% TFA)).

(2S)-Tetrahydro-N-((1-(2-(2-hydroxyphenyl)-7-methylquinazolin-4-yl)piperidin-3-yl)methyl)furan-2-carboxamide

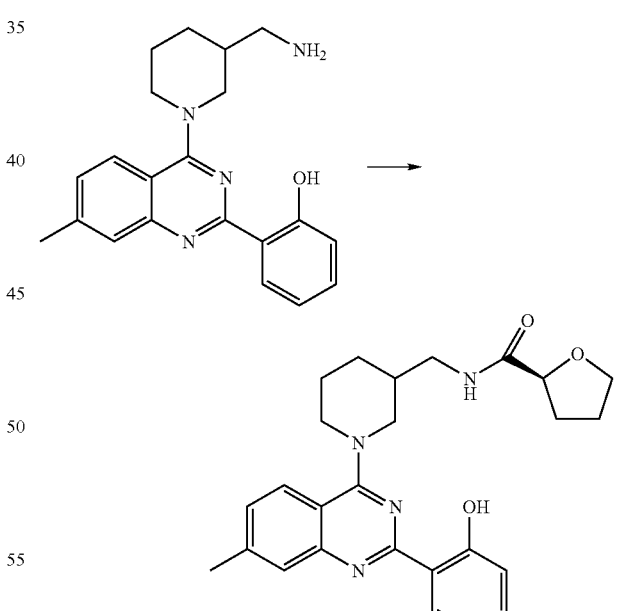

2-(4-(3-(Aminomethyl)piperidin-1-yl)-7-methylquinazolin-2-yl)phenol (60 mg, 0.17 mmol) was dissolved in anhydrous DMF (1 mL) and cooled in an ice water bath. To this was added (S)-tetrahydrofuran-2-carboxylic acid (24.0 mg, 19.8 μL, 0.2 mmol), and triethylamine (50 μL, 0.34 mmol). After 5 minutes, HATU (78.3 mg, 0.2 mmol) was added in one portion, and the reaction was allowed to warm to room temperature overnight. Purification by reverse phase HPLC (10-99% CH₃CN (0.035% TFA)/H₂O (0.05% TFA)) gave (2S)-1-tetrahydro-N-((1-(2-(2-hydroxyphenyl)-7-methylquinazolin-4-yl)piperidin-3-yl)methyl)furan-2-carboxamide as the TFA salt. LC/MS: m/z 447.5 (M+H)⁺ at 2.27 min (10%-99% CH₃CN (0.035% TFA)/H₂O (0.05% TFA)).

Example 210

(R)-Tetrahydrofuran-3-yl (1-(2-(2-hydroxyphenyl)-7-methylquinazolin-4-yl)piperidin-3-yl)methylcarbamate

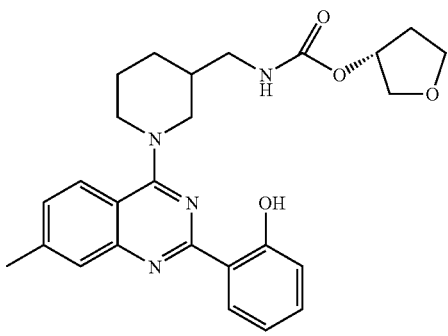

(R)-Tetrahydrofuran-3-yl (1-(2-(2-hydroxyphenyl)-7-methylquinazolin-4-yl)piperidin-3-yl)methylcarbamate

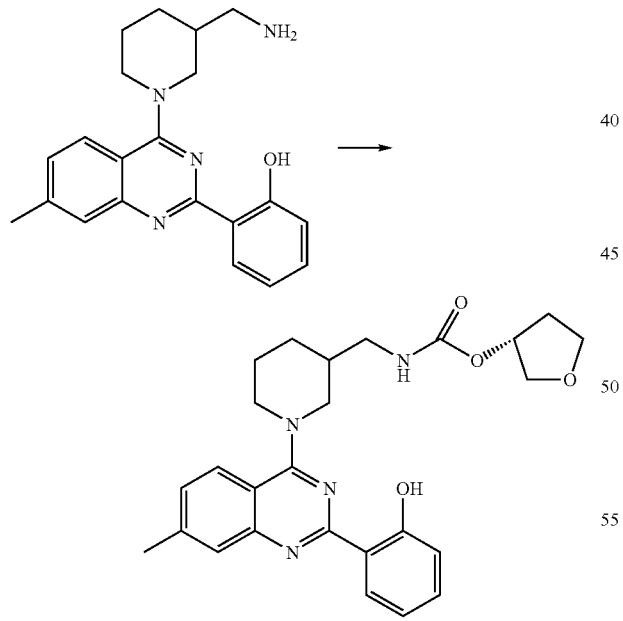

2-(4-(3-(Aminomethyl)piperidin-1-yl)-7-methylquinazolin-2-yl)phenol (60 mg, 0.17 mmol) was dissolved in DMF (0.5 mL) and placed into an ice water bath. (R)-tetrahydrofuran-3-yl chloroformate (31 mg, 0.2 mmol) was dissolved in DMF (0.1 mL) and added dropwise, followed by the addition of triethylamine (50 µL, 0.34 mmol). The reaction was allowed to warm to room temperature and was stirred overnight. Purification using reverse phase HPLC (10-99% CH₃CN (0.035% TFA)/H₂O (0.05% TFA)) gave (R)-tetrahydrofuran-3-yl (1-(2-(2-hydroxyphenyl)-7-methylquinazolin-4-yl)piperidin-3-yl)methylcarbamate as the TFA salt. LC/MS: m/z 463.5 (M+H)⁺ at 2.34 min (10%-99% CH₃CN (0.035% TFA)/H₂O (0.05% TFA)).

Example 211

(S)-Tetrahydrofuran-3-yl (1-(2-(2-hydroxyphenyl)-7-methylquinazolin-4-yl)piperidin-3-yl)methylcarbamate

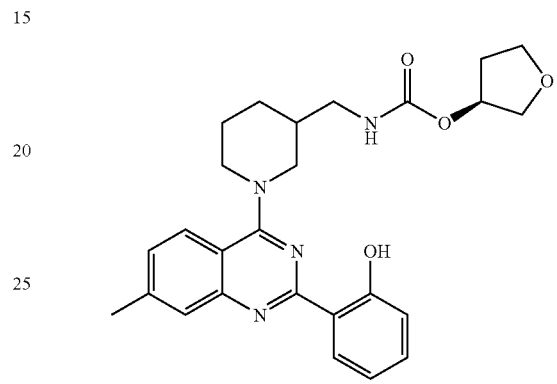

(S)-Tetrahydrofuran-3-yl (1-(2-(2-hydroxyphenyl)-7-methylquinazolin-4-yl)piperidin-3-yl)methylcarbamate

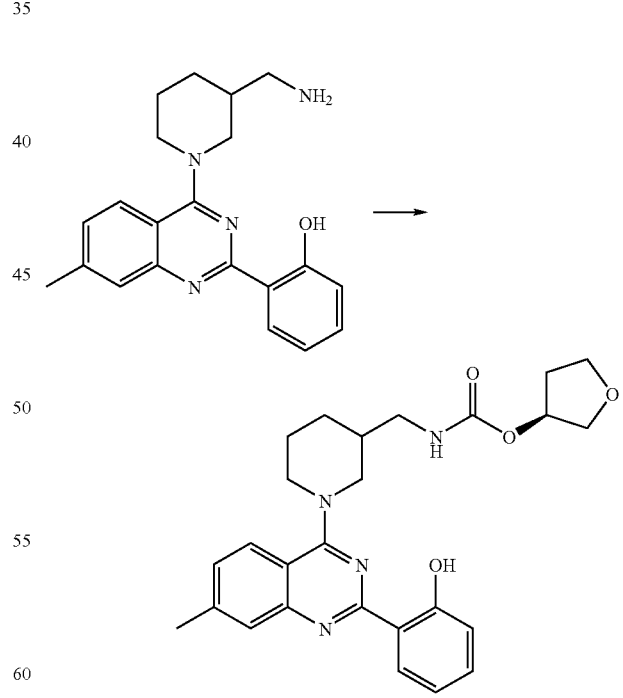

2-(4-(3-(Aminomethyl)piperidin-1-yl)-7-methylquinazolin-2-yl)phenol (60 mg, 0.17 mmol) dissolved in DMF (0.5 mL) was cooled to 0° C. (S)-Tetrahydrofuran-3-yl chloroformate (31 mg, 0.2 mmol) was dissolved in DMF (0.1 mL) and added dropwise to the reaction mixture, followed by the addition of triethylamine (50 µL, 0.34 mmol). The reaction was allowed to warm to room temperature and was stirred overnight. The reaction was purified by reverse phase HPLC (10-99% CH₃CN (0.035% TFA)/H₂O (0.05% TFA)) to obtain (S)-tetrahydrofuran-3-yl (1-(2-(2-hydroxyphenyl)-7-methylquinazolin-4-yl)piperidin-3-yl)methylcarbamate as the TFA salt. LC/MS: m/z 463.5 (M+H)⁺ at 2.34 min (10%-99% CH₃CN (0.035% TFA)/H₂O (0.05% TFA)).

Example 212

N—((1-(2-(2-Hydroxyphenyl)-7-methylquinazolin-4-yl)piperidin-3-yl)methyl)cyclopropanecarboxamide

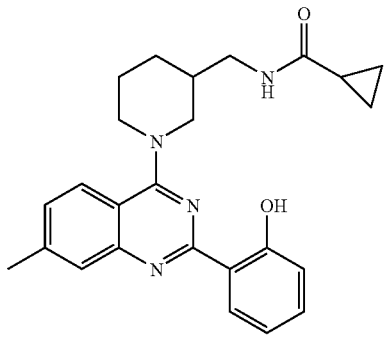

N—((1-(2-(2-Hydroxyphenyl)-7-methylquinazolin-4-yl)piperidin-3-yl)methyl)cyclopropanecarboxamide

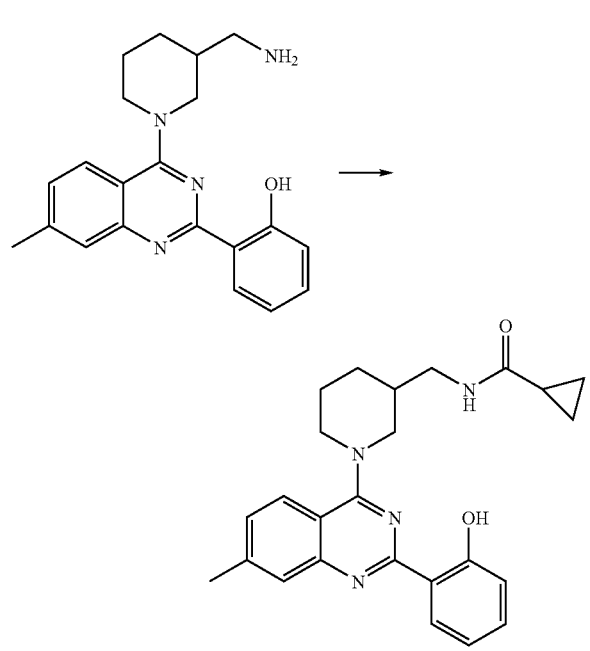

2-(4-(3-(Aminomethyl)piperidin-1-yl)-7-methylquinazolin-2-yl)phenol (60 mg, 0.17 mmol) was dissolved in DMF (0.5 mL) and cooled to 0° C. Cyclopropanecarbonyl chloride (15.7 mg, 0.2 mmol) was dissolved in DMF (0.1 mL) and added dropwise, followed by the addition of triethylamine (50 µL, 0.34 mmol). The reaction was allowed to warm to room temperature and was stirred overnight. Purification using reverse phase HPLC (10-99% CH₃CN (0.035% TFA)/H₂O (0.05% TFA)) gave N-((1-(2-(2-hydroxyphenyl)-7-methylquinazolin-4-yl)piperidin-3-yl)methyl)cyclopropanecarboxamide as the TFA salt. LC/MS: m/z 417.0 (M+H)⁺ at 2.30 min (10%-99% CH₃CN (0.035% TFA)/H₂O (0.05% TFA)).

Example 213

(2R)—N—(1-(2-(2-Chloro-6-hydroxyphenyl)quinazolin-4-yl)piperidin-4-yl)-tetrahydrofuran-2-carboxamide

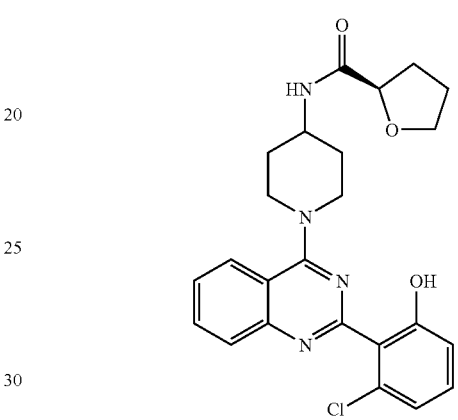

3-Chloro-2-(4-chloroquinazolin-2-yl)phenol

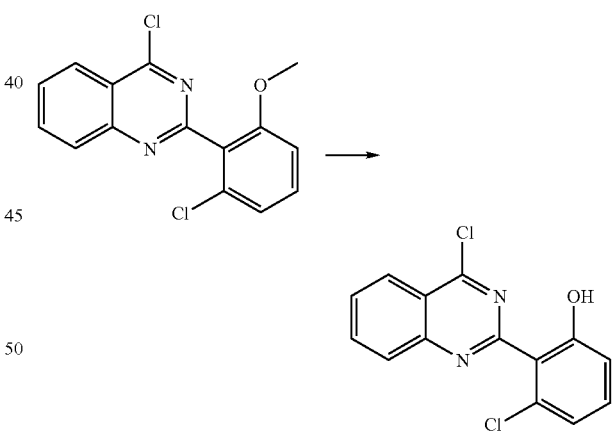

To a solution of 4-chloro-2-(2-chloro-6-methoxyphenyl)quinazoline (0.3 g, 0.98 mmol) in CH₂Cl₂ at −78° C. was added 5 equivalents of 1 M BBr₃ solution (4.9 mL, 4.9 mmol) in CH₂Cl₂. The reaction was complete after 30 minutes After allowing it to warm to room temperature, the reaction mixture was quenched with aqueous NaHCO₃ to pH 7, the layers were separated and the aqueous layer was extracted with CH₂Cl₂. The combined organic extracts were dried over MgSO₄, filtered, and concentrated. Purification via silica gel chromatography using 2:1 CH₂Cl₂:hexanes yielded 3-chloro-2-(4-chloroquinazolin-2-yl)phenol (0.17 g, 60%). LC/MS: m/z 291.1 (M+H)⁺ at 3.16 min (10%-99% CH₃CN (0.035% TFA)/H₂O (0.05% TFA)).

(2R)—N-(1-(2-(2-Chloro-6-hydroxyphenyl)quinazolin-4-yl)piperidin-4-yl)-tetrahydrofuran-2-carboxamide

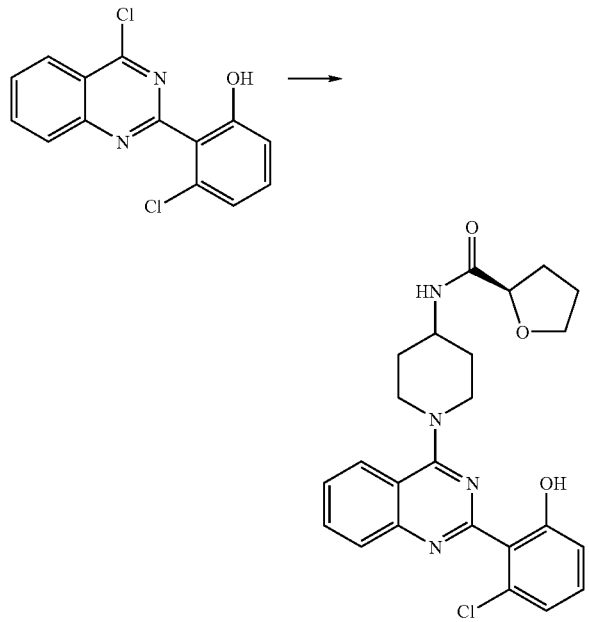

At 0° C., to a solution of 3-chloro-2-(4-chloroquinazolin-2-yl)phenol (42 mg, 0.144 mmol) in CH$_2$Cl$_2$ was added triethylamine (80 µL, 0.58 mmol) followed by the addition of (R)-tetrahydro-N-(piperidin-4-yl)furan-2-carboxamide a oxalate. After allowing the reaction to warm to room temperature it was purified via reverse phase HPLC (10-99% CH$_3$CN (0.035% TFA)/H$_2$O (0.05% TFA)) to afford (2R)—N-(1-(2-(2-chloro-6-hydroxyphenyl)quinazolin-4-yl)piperidin-4-yl)-tetrahydrofuran-2-carboxamide as the TFA salt. LC/MS: m/z 453.5 (M+H)$^+$ at 1.98 min (10%-99% CH$_3$CN (0.035% TFA)/H$_2$O (0.05% TFA)).

Example 214

(R)-Tetrahydrofuran-3-yl ((S)-1-(2-(2-hydroxyphenyl)-7-methylquinazolin-4-yl)piperidin-3-yl)methylcarbamate

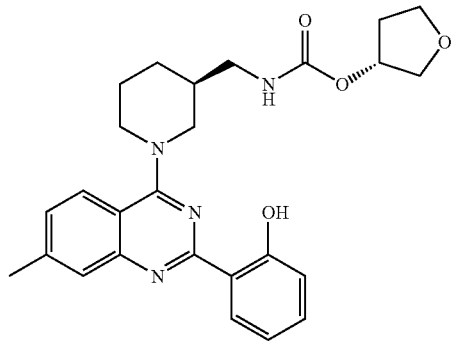

Method 1

Benzyl ((S)-1-(tert-butoxycarbonyl)piperidin-3-yl)methylcarbamate

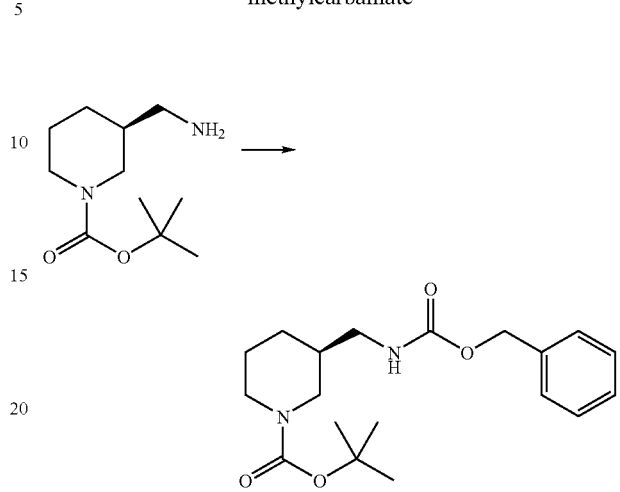

(S)-tert-Butyl 3-(aminomethyl)piperidine-1-carboxylate (1.00 g, 4.67 mmol) was dissolved in 14 mL anhydrous CH$_2$Cl$_2$ under an N$_2$ atmosphere and cooled to 0° C. Triethylamine (1.30 mL, 945 mg, 9.34 mmol) was added followed by the dropwise addition of benzyl chloroformate (0.99 mL, 1.20 g, 7.00 mmol). After 16 h, the reaction mixture was partitioned between H$_2$O and CH$_2$Cl$_2$, and separated, and the aqueous layer was extracted twice with CH$_2$Cl$_2$. The organic layers were combined, dried over Na$_2$SO$_4$, filtered, and concentrated to a light yellow oil. Purification via silica gel chromatography using 97% CH$_2$Cl$_2$/3% MeOH gave benzyl ((S)-1-(tert-butoxycarbonyl)piperidin-3-yl)methylcarbamate as a clear, colorless oil (895 mg, 55%). LC/MS: m/z 349.5 (M+H)$^+$ at 3.21 min (10%-99% CH$_3$CN (0.035% TFA)/H$_2$O (0.05% TFA)).

Benzyl ((S)-1-(2-(2-hydroxyphenyl)-7-methylquinazolin-4-yl)piperidin-3-yl)methylcarbamate

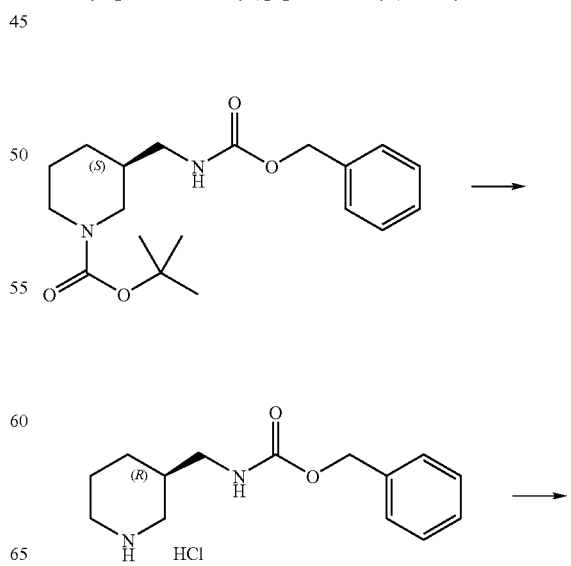

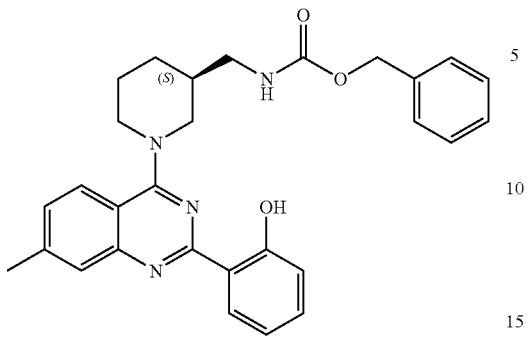

Benzyl ((S)-1-(tert-butoxycarbonyl)piperidin-3-yl)methylcarbamate(895 mg, 2.57 mmol) was treated with a 4.0 M HCl solution in dioxane (3.2 mL, 12.85 mmol) Formation of a white precipitate was observed. After 3 h, complete conversion of starting material was seen by TLC. The solvent and excess HCl were removed under reduced pressure to obtain benzyl ((R)-piperidin-3-yl)methylcarbamate hydrochloride as a white solid. This solid was suspended in DMF/CH$_2$Cl$_2$ (3 mL/3 mL), followed by the addition of 2-(4-chloro-7-methylquinazolin-2-yl)phenol (696 mg, 2.57 mmol), and triethylamine (1.8 mL, 1.3 g, 12.85 mmol). The mixture was stirred at room temperature under an N$_2$ atmosphere for 16 h. The reaction was then partitioned between H$_2$O/CH$_2$Cl$_2$, and separated and the aqueous layer was extracted twice with CH$_2$Cl$_2$. The combined organic layers were dried over Na$_2$SO$_4$, filtered, and concentrated under reduced pressure. Purification via silica gel chromatography using 0-5% MeOH in CH$_2$Cl$_2$ gave benzyl ((S)-1-(2-(2-hydroxyphenyl)-7-methylquinazolin-4-yl)piperidin-3-yl)methylcarbamate as a thick yellow oil (610 mg, 49%). LC/MS: m/z 483.3 (M+H)$^+$ at 2.83 min (10%-99% CH$_3$CN (0.035% TFA)/H$_2$O (0.05% TFA)).

2-(4-((S)-3-(Aminomethyl)piperidin-1-yl)-7-methylquinazolin-2-yl)phenol

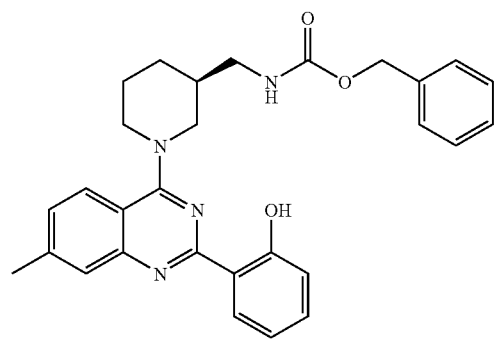

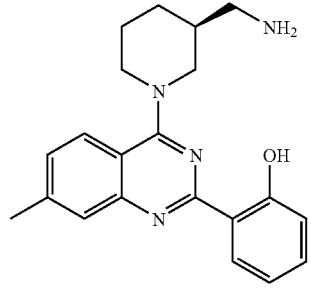

To a mixture of benzyl ((S)-1-(2-(2-hydroxyphenyl)-7-methylquinazolin-4-yl)piperidin-3-yl)methylcarbamate (610 mg, 1.26 mmol) and EtOH (15 mL) in a round bottom flask was added Pd/C (61 mg, 10% wt Pd on carbon) and the flask was sealed with a septum. The atmosphere in the flask was evacuated, purged with N$_2$, and equipped with a balloon charged with H$_2$. The mixture was then stirred under an H$_2$ atmosphere at ambient pressure for 3 h. After filtration through a plug of Celite, using MeOH as the eluting solvent, the reaction mixture was concentrated to a yellow solid 2-(4-((S)-3-(aminomethyl)piperidin-1-yl)-7-methylquinazolin-2-yl)phenol (441 mg). LC/MS: nm/z 349.3 (M+H)$^+$ at 1.52 min (10%-99% CH$_3$CN (0.035% TFA)/H$_2$O (0.05% TFA)). $^1$H NMR (400 MHz, DMSO-d6) δ 8.43-8.45 (m, 1H), 7.95 (d, J=8.5 Hz, 1H), 7.64 (s, 1H), 7.35-7.39 (m, 2H), 6.92-6.96 (m, 2H), 4.52 (d, J=12.5 Hz, 1H), 4.41 (d, J=13.2 Hz, 1H), 3.26-3.29 (m, 2H), 3.02-3.08 (m, 1H), 2.55-2.61 (m, 1H), 2.45-2.48 (m, 1H), 1.84-1.91 (m, 2H), 1.65-1.77 (m, 3H), 1.24-1.36 (m, 1H) ppm.

(R)-Tetrahydrofuran-3-yl ((S)-1-(2-(2-hydroxyphenyl)-7-methylquinazolin-4-yl)piperidin-3-yl)methylcarbamate

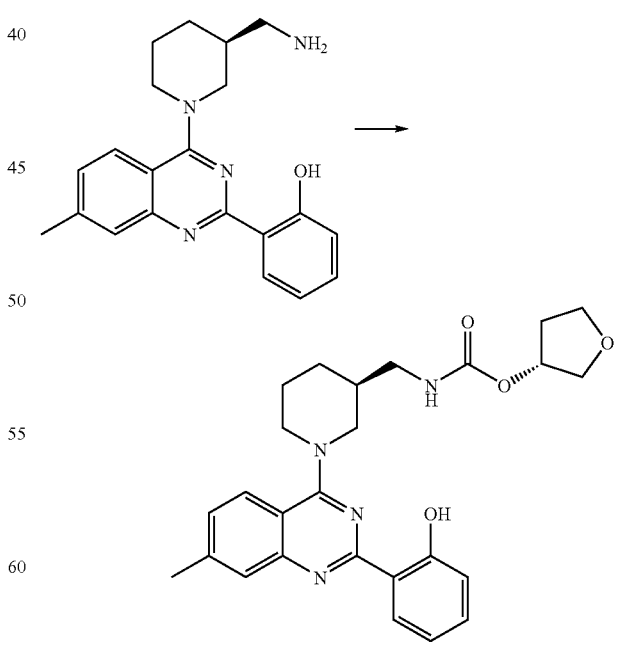

Method A
2-(4-((S)-3-(Aminomethyl)piperidin-1-yl)-7-methylquinazolin-2-yl)phenol (60 mg, 0.17 mmol) was dissolved in anhydrous DMF (1 mL) and cooled to 0° C., and (R)-tetrahydrofuran-3-yl chloroformate (31 mg, 0.2 mmol) dissolved in DMF (100 μL) was added dropwise followed by triethylamine (35 mg, 48 μL, 0.34 mmol). The reaction was allowed to warm to room temperature. The reaction was complete after two hours. Purification using reverse phase HPLC (10-99% CH$_3$CN (0.035% TFA)/H$_2$O (0.05% TFA)) gave (R)-tetrahydrofuran-3-yl ((S)-1-(2-(2-hydroxyphenyl)-7-methylquinazolin-4-yl)piperidin-3-yl)methylcarbamate as the TFA salt. LC/MS: m/z 463.5 (M+H)$^+$ at 2.32 min (10%-99% CH$_3$CN (0.035% TFA)/H$_2$O (0.05% TFA)).

Method B 2-(4-((S)-3-(Aminomethyl)piperidin-1-yl)-7-methylquinazolin-2-yl)phenol (127 mg, 0.364 mmol) was dissolved in 5 mL anhydrous DMF and cooled to 0° C., and a solution of (R)-tetrahydrofuran-3-yl chloroformate (65.4 mg, 0.436 mmol) in 200 μL DMF was added dropwise followed by the addition of triethylamine (74 mg, 0.10 mL, 0.73 mmol). The reaction was allowed to warm to room temperature. The reaction was complete after two hours. The mixture was partitioned between H$_2$O and CH$_2$Cl$_2$, and separated, and the aqueous layer was extracted twice with CH$_2$Cl$_2$. The combined organic phases were dried over Na$_2$SO$_4$, filtered, and concentrated to a yellow solid. Purification via silica gel chromatography using 98% CH$_2$Cl$_2$/2% MeOH gave (R)-tetrahydrofuran-3-yl ((S)-1-(2-(2-hydroxyphenyl)-7-methylquinazolin-4-yl)piperidin-3-yl)methylcarbamate as an off white solid (116 mg, 69%). LC/MS: m/z 463.5 (M+H)$^+$ at 2.37 min (10%-99% CH$_3$CN (0.035% TFA)/H$_2$O (0.05% TFA)).

$^1$H NMR (400 MHz, DMSO-d6) δ 8.41-8.43 (m, 1H), 7.86 (d, J=8.5 Hz, 1H), 7.65 (s, 1H), 7.33-7.44 (m, 3H), 6.90-6.95 (m, 2H), 5.11 (dd, J=6.2, 4.6 Hz, 1H), 4.38 (t, J=14.5 Hz, 2H), 3.68-3.79 (m, 3H), 3.60-3.63 (m, 1H), 3.28-3.31 (m, 1H), 2.98-3.07 (m, 3H), 2.50 (s, 3H), 2.06-2.15 (m, 1H), 1.85-1.91 (m, 4H), 1.70 (d, J=12.9 Hz, 1H), 1.24-1.37 (m, 1H) ppm.

(R)-Tetrahydrofuran-3-yl ((S)-1-(2-(2-hydroxyphenyl)-7-methylquinazolin-4-yl)piperidin-3-yl)methylcarbamate hydrochloride

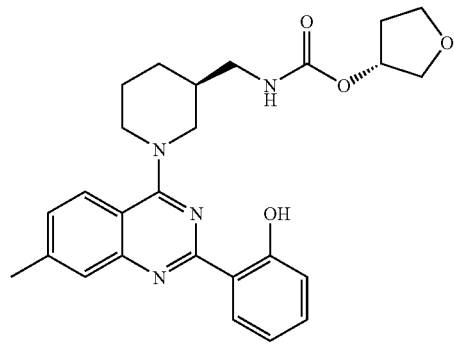

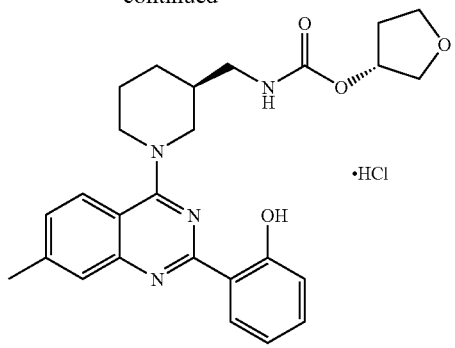

(R)-Tetrahydrofuran-3-yl ((S)-1-(2-(2-hydroxyphenyl)-7-methylquinazolin-4-yl)piperidin-3-yl)methylcarbamate (116 mg, 0.251 mmol) was suspended in 8 mL anhydrous CH$_2$Cl$_2$ and gently heated until an homogenous solution was formed. After the reaction was cooled to room temperature, a 2.0 M solution of HCl in Et$_2$O (0.126 mL, 0.251 mmol) was added in one portion. The reaction mixture was diluted with 25 mL Et$_2$O, and the product precipitated from solution. The reaction was stirred for an additional 30 minutes before the solid was filtered and dried to obtain (R)-tetrahydrofuran-3-yl ((S)-1-(2-(2-hydroxyphenyl)-7-methylquinazolin-4-yl)piperidin-3-yl)methylcarbamate hydrochloride as a light yellow solid (99 mg, 70%). LC/MS: m/z 463.5 (M+H)$^+$ at 2.37 min (10%-99% CH$_3$CN (0.035% TFA)/H$_2$O (0.05% TFA)). $^1$H NMR (400 MHz, DMSO-d6) δ 8.22 (d, J=7.7 Hz, 1H), 7.95 (d, J=8.5 Hz, 1H), 7.75 (s, 1H), 7.42-7.49 (m, 3H), 6.97-7.08 (m, 2H), 5.08 (dd, J=6.1, 4.6 Hz, 1H), 4.52-4.54 (m, 2H), 3.66-3.78 (m, 3H), 3.58-3.60 (m, 1H), 3.48 (t, J=10.7 Hz, 1H), 3.23 (t, J=11.5 Hz, 1H), 3.00 (t, J=6.3 Hz, 2H), 2.53 (s, 3H), 2.05-2.14 (m, 1H), 1.80-1.91 (m, 4H), 1.72 (d, J=9.0 Hz, 1H), 1.34-1.43 (m, 1H) ppm.

Method 2 tert-Butyl ((S)-1-(2-(2-hydroxyphenyl)-7-methylquinazolin-4-yl)piperidin-3-yl)methylcarbamate

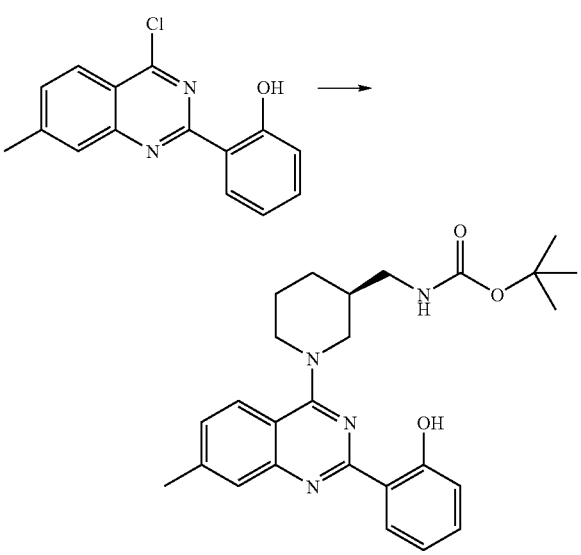

To a solution of 2-(4-chloro-7-methylquinazolin-2-yl)phenol (0.478 g, 1.76 mmol) in CH$_2$Cl$_2$ was added triethylamine (0.98 mL, 0.712 g, 7.04 mmol), and the mixture was cooled to 0° C. To the reaction mixture was added tert-butyl ((R)-piperidin-3-yl)methylcarbamate oxalate (prepared analogously to 2-(7-Methyl-4-piperazin-1-yl-quinazolin-2-yl)-phenol, oxalate salt, see Example 130; 700 mg, 2.3 mmol). The reaction was allowed to warm to room temperature and was stirred overnight. The reaction was quenched with water, and the aqueous layer was extracted with $CH_2Cl_2$. The combined organic layers were dried over $MgSO_4$, filtered, and concentrated. Purification via silica gel chromatography using 0-2% EtOAc in $CH_2Cl_2$ gave tert-butyl ((S)-1-(2-(2-hydroxyphenyl)-7-methylquinazolin-4-yl)piperidin-3-yl)methylcarbamate (700 mg, 88%). LC/MS: nm/z 449.5 $(M+H)^+$ at 2.77 min (10%-99% $CH_3CN$ (0.035% TFA)/$H_2O$ (0.05% TFA)).

2-(4-((S)-3-(Aminomethyl)piperidin-1-yl)-7-methylquinazolin-2-yl)phenol

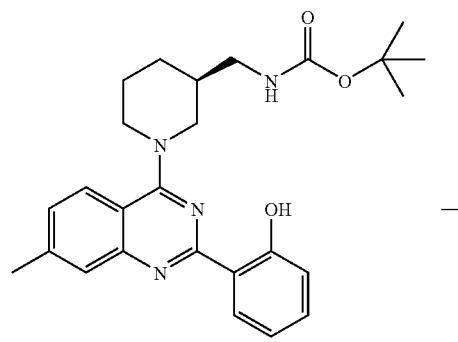

To tert-Butyl-((S)-1-(2-(2-hydroxyphenyl)-7-methylquinazolin-4-yl)piperidin-3-yl)methylcarbamate (700 mg, 1.56 mmol) was added 20 mL $CH_2Cl_2$ followed by addition of 7 mL of TFA. After the reaction was stirred for 1 hour it was neutralized with a 1.0 M aqueous NaOH solution. The mixture was partitioned between $H_2O$ and $CH_2Cl_2$, and separated, and the aqueous layer was extracted with $CH_2Cl_2$. The combined organic layers were dried over $MgSO_4$, filtered, and concentrated to yield 2-(4-((S)-3-(aminomethyl)piperidin-1-yl)-7-methylquinazolin-2-yl)phenol (400 mg, 74%).

LC/MS: m/z 349.3 $(M+H)^+$ at 1.52 min (10%-99% $CH_3CN$ (0.035% TFA)/$H_2O$ (0.05% TFA)).

(R)-Tetrahydrofuran-3-yl ((S)-1-(2-(2-hydroxyphenyl)-7-methylquinazolin-4-yl)piperidin-3-yl)methylcarbamate

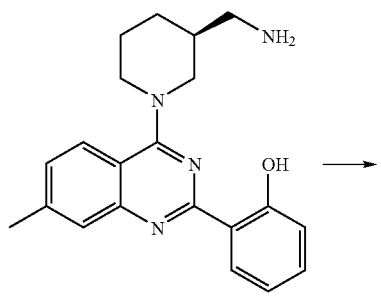

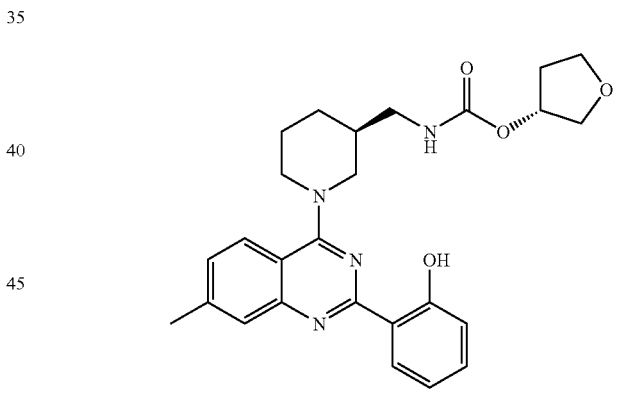

To a solution of 2-(4-((S)-3-(aminomethyl)piperidin-1-yl)-7-methylquinazolin-2-yl)phenol (210 mg, 0.6 mmol) in DMF at 0° C. were added (R)-tetrahydrofuran-3-yl chloroformate (0.09 g, 0.6 mmol) and triethylamine (167 µL, 1.2 mmol) simultaneously. Ten to fifteen minutes after addition, the reaction was complete, and quenched with water, extracted with $CH_2Cl_2$. The combined organic layers were dried over $MgSO_4$, filtered, and concentrated to give (R)-tetrahydrofuran-3-yl ((S)-1-(2-(2-hydroxyphenyl)-7-methylquinazolin-4-yl)piperidin-3-yl)methylcarbamate (150 mg, 54%). LC/MS: m/z 463.5 $(M+H)^+$ at 2.37 min (10%-99% $CH_3CN$ (0.035% TFA)/$H_2O$ (0.05% TFA)). $^1H$ NMR (400 MHz, DMSO-d6) δ 8.41-8.43 (m, 1H), 7.86 (d, J=8.5 Hz, 1H), 7.65 (s, 1H), 7.33-7.44 (m, 3H), 6.90-6.95 (m, 2H), 5.11 (dd, J=6.2, 4.6 Hz, 1H), 4.38 (t, J=14.5 Hz, 2H), 3.68-3.79 (m, 3H), 3.60-3.63 (m, 1H), 3.28-3.31 (m, 1H), 2.98-3.07 (m, 3H), 2.50 (s, 3H), 2.06-2.15 (m, 1H), 1.85-1.91 (m, 4H), 1.70 (d, J=12.9 Hz, 1H), 1.24-1.37 (m, 1H) ppm.

Example 215

(S)-Tetrahydrofuran-3-yl ((S)-1-(2-(2-hydroxyphenyl)-7-methylquinazolin-4-yl)piperidin-3-yl)methylcarbamate

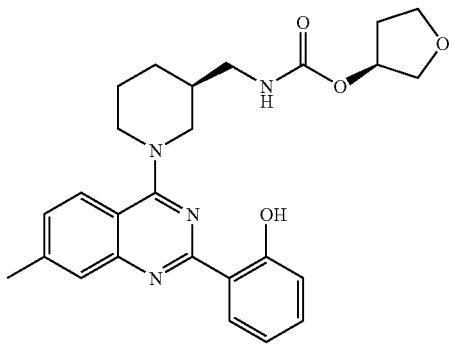

(S)-Tetrahydrofuran-3-yl ((S)-1-(2-(2-hydroxyphenyl)-7-methylquinazolin-4-yl)piperidin-3-yl)methylcarbamate

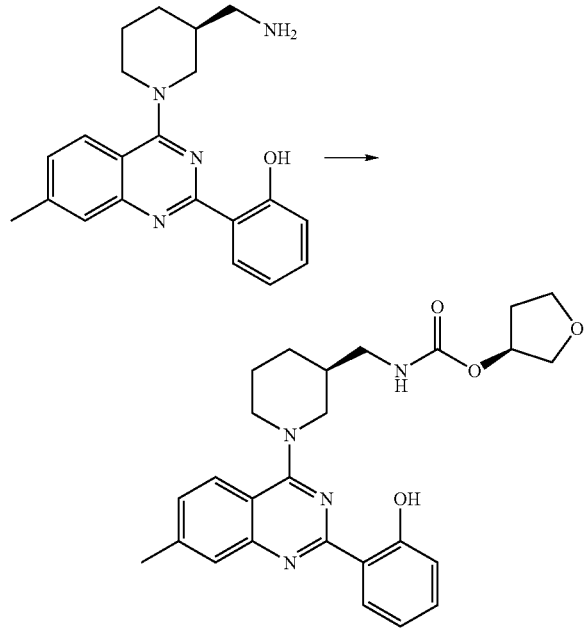

Method A 2-(4-((S)-3-(Aminomethyl)piperidin-1-yl)-7-methylquinazolin-2-yl)phenol (60 mg, 0.17 mmol) was dissolved in anhydrous DMF (1 mL) and cooled to 0° C., and (S)-tetrahydrofuran-3-yl chloroformate (31 mg, 0.2 mmol) in DMF (100 µL) was added dropwise followed by triethylamine (35 mg, 48 µL, 0.34 mmol). The reaction was allowed to warm to room temperature. The reaction was complete after two hours. Purification using preparative HPLC (10-99% $CH_3CN$ (0.035% TFA)/$H_2O$ (0.05% TFA)) gave (S)-tetrahydrofuran-3-yl ((S)-1-(2-(2-hydroxyphenyl)-7-methylquinazolin-4-yl)piperidin-3-yl)methylcarbamate as the TFA salt. LC/MS: m/z 463.5 (M+H)$^+$ at 2.37 min (10%-99% $CH_3CN$ (0.035% TFA)/$H_2O$ (0.05% TFA)).

Method B 2-(4-((S)-3-(Aminomethyl)piperidin-1-yl)-7-methylquinazolin-2-yl)phenol (126.8 mg, 0.364 mmol) was dissolved in 5 mL anhydrous DMF and cooled to 0° C., and a solution of (S)-tetrahydrofuran-3-yl chloroformate (65.4 mg, 0.436 mmol) in 200 µl of DMF was added dropwise followed by the addition of triethylamine (74 mg, 0.102 mL, 0.728 mmol). The reaction was allowed to warm to room temperature and was complete after two hours. The mixture was partitioned between $H_2O$ and $CH_2Cl_2$, separated, and the aqueous layer was extracted twice with $CH_2Cl_2$. The combined organic phases were dried over $Na_2SO_4$, filtered, and concentrated to a yellow solid. Purification via silica gel chromatography using 98% $CH_2Cl_2$/2% MeOH gave (S)-tetrahydrofuran-3-yl ((S)-1-(2-(2-hydroxyphenyl)-7-methylquinazolin-4-yl)piperidin-3-yl)methylcarbamate as an off white solid (116 mg, 69%). LC/MS: m/z 463.5 (M+H)$^+$ at 2.37 min (10%-99% $CH_3CN$ (0.035% TFA)/$H_2O$ (0.05% TFA)).

Method C

To a solution of 2-(4-((S)-3-(aminomethyl)piperidin-1-yl)-7-methylquinazolin-2-yl)phenol (175 mg, 0.5 mmol) in DMF at 0° C. were added (S)-tetrahydrofuran-3-yl chloroformate (75 mg, 0.5 mmol) and triethylamine (137 µL, 1.0 mmol) simultaneously. Ten to fifteen minutes after addition, the reaction was complete, and it was quenched with water and extracted with $CH_2Cl_2$ The combined organic layers were dried over $MgSO_4$, filtered, and concentrated. Purification via silica gel chromatography using 98% $CH_2Cl_2$/2% MeOH gave (S)-tetrahydrofuran-3-yl ((S) -1-(2-(2-hydroxyphenyl)-7-methylquinazolin-4-yl)piperidin-3-yl)methylcarbamate (150 mg, 54%). LC/MS: m/z 463.5 (M+H)$^+$ at 2.37 min (10%-99% $CH_3CN$ (0.035% TFA)/$H_2O$ (0.05% TFA)).

(S)-Tetrahydrofuran-3-yl ((S)-1-(2-(2-hydroxyphenyl)-7-methylquinazolin-4-yl)piperidin-3-yl)methylcarbamate hydrochloride

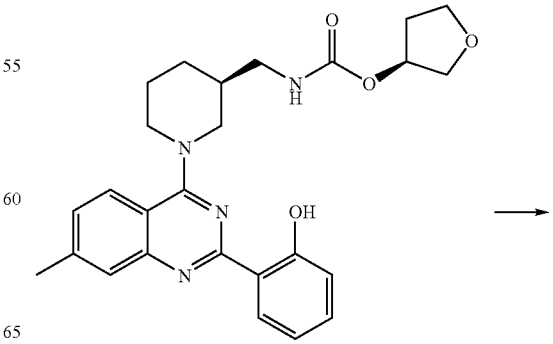

-continued

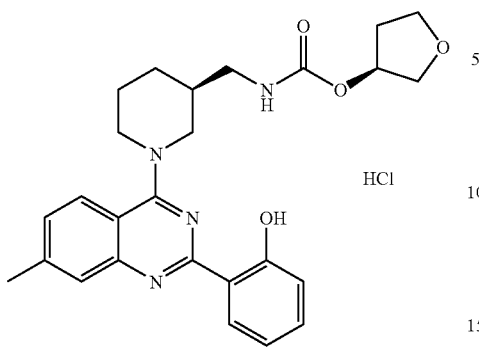

(S)-Tetrahydrofuran-3-yl ((S)-1-(2-(2-hydroxyphenyl)-7-methylquinazolin-4-yl)piperidin-3-yl)methylcarbamate (115 mg, 0.251 mmol) was suspended in 8 mL of anhydrous $CH_2Cl_2$ and gently heated until an homogenous solution was formed. After cooling to room temperature, a 2.0 M solution of HCl in $Et_2O$ (0.126 mL, 0.251 mmol) was added in one portion. The reaction mixture was diluted with 25 mL $Et_2O$, and the product precipitated from the solution. The reaction was stirred for an additional 30 minutes before the solid was filtered and dried to obtain (S)-tetrahydrofuran-3-yl ((S)-1-(2-(2-hydroxyphenyl)-7-methylquinazolin-4-yl)piperidin-3-yl)methylcarbamate hydrochloride (108 mg, 86%) as a light yellow solid. LC/MS: m/z 463.5 (M+H)$^+$ at 2.37 min (10%-99% $CH_3CN$ (0.035% TFA)/$H_2O$ (0.05% TFA)). $^1$H NMR (400 MHz, DMSO-d6) δ 8.18 (d, J=6.6 Hz, 1H), 7.94 (d, J=8.6 Hz, 1H), 7.73 (s, 1H), 7.44-7.51 (m, 2H), 7.00-7.07 (m, 2H), 5.06-5.09 (m, 1H), 4.52-4.62 (m, 2H), 3.62-3.74 (m, 4H), 3.23-3.29 (m, 1H), 3.00 (d, J=6.8 Hz, 2H), 2.52 (s, 3H), 2.02-2.11 (m, 1H), 1.61-2.01 (m, 4H), 1.24-1.43 (m, 2H), 0.84-0.89 (m, 1H) ppm.

Example 216

(R)-Tetrahydrofuran-3-yl ((R)-1-(2-(2-hydroxyphenyl)-7-methylquinazolin-4-yl)piperidin-3-yl)methylcarbamate

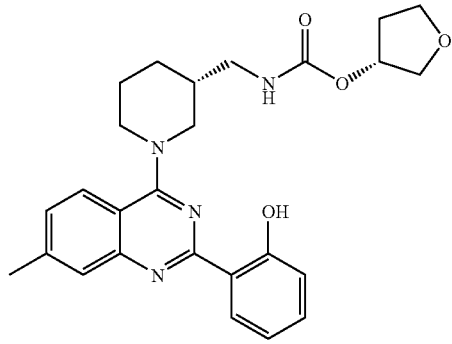

Benzyl ((R)-1-(tert-butoxycarbonyl)piperidin-3-yl)methylcarbamate

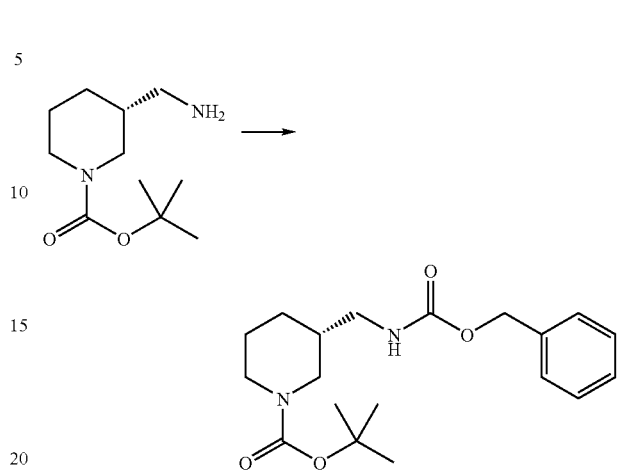

(R)-tert-Butyl 3-(aminomethyl)piperidine-1-carboxylate (1.00 g, 4.67 mmol) was dissolved in 14 mL anhydrous $CH_2Cl_2$ under an $N_2$ atmosphere and cooled to 0° C. Triethylamine (1.30 mL, 945 mg, 9.34 mmol) was added followed by the dropwise addition of benzyl chloroformate (0.99 mL, 1.20 g, 7.00 mmol). After 16 h, the reaction was complete. The mixture was partitioned between $H_2O$ and $CH_2Cl_2$, and separated, and the aqueous layer was extracted twice with $CH_2Cl_2$. The organic layers were combined, dried over $Na_2SO_4$, filtered, and concentrated to a light, yellow oil. Purification via silica gel chromatography using 97% $CH_2Cl_2$/3% MeOH gave, benzyl ((R)-1-(tert-butoxycarbonyl)piperidin-3-yl)methylcarbamate as a clear colorless oil (1.2 g, 74%). LC/MS: m/z 349.5 (M+H)$^+$ at 3.21 min (10%-99% $CH_3CN$ (0.035% TFA)/$H_2O$ (0.05% TFA)).

Benzyl ((R)-1-(2-(2-hydroxyphenyl)-7-methylquinazolin-4-yl)piperidin-3-yl)methylcarbamate

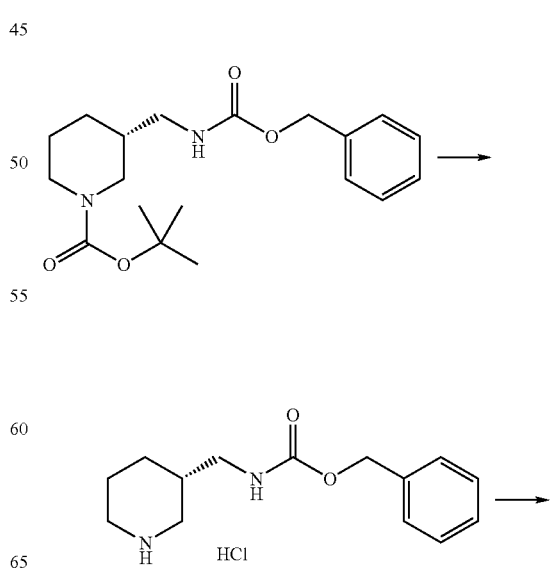

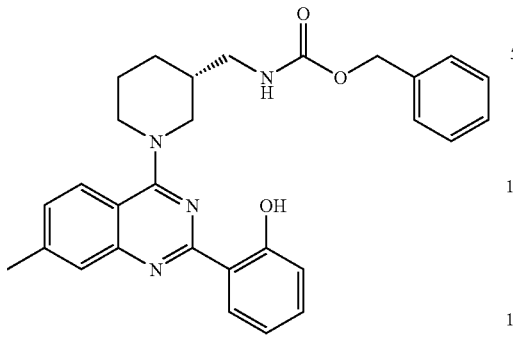

Benzyl ((S)-1(tert-butoxycarbonyl)piperdin-3-yl)methylcarbamate(1.2 g, 3.54 mmol) was treated with 4.0 M HCl solution in dioxane (4.3 mL, 17.2 mmol). Formation of a white precipitate was observed. The reaction was complete after three hours. The solvent and excess HCl were removed under reduced pressure to obtain benzyl ((S)-piperidin-3-yl)methylcarbamate hydrochloride as a white solid. This solid was suspended in DMF/CH$_2$Cl$_2$ (3 mL/3 mL), followed by the addition of 2-(4-chloro-7-methylquinazolin-2-yl)phenol (958 mg, 3.54 mmol) and then triethylamine (1.8 mL, 1.3 g, 12.85 mmol). The mixture was stirred at room temperature under an N$_2$ atmosphere for 16 h. The reaction was then partitioned between H$_2$O and CH$_2$Cl$_2$, separated, and the aqueous layer was extracted twice with CH$_2$Cl$_2$. The combined organic layers were dried over Na$_2$SO$_4$, filtered, and concentrated under reduced pressure. Purification via silica gel chromatography using 0-5% MeOH in CH$_2$Cl$_2$ gave benzyl ((R)-1-(2-(2-hydroxyphenyl)-7-methylquinazolin-4-yl)piperidin-3-yl)methylcarbamate as a thick yellow oil (855 mg, 51%). LC/MS: m/z 483.5 (M+H)$^+$ at 2.81 min (10%-99% CH$_3$CN (0.035% TFA)/H$_2$O (0.05% TFA)).

2-(4-((R)-3-(Aminomethyl)piperidin-1-yl)-7-methylquinazolin-2-yl)phenol

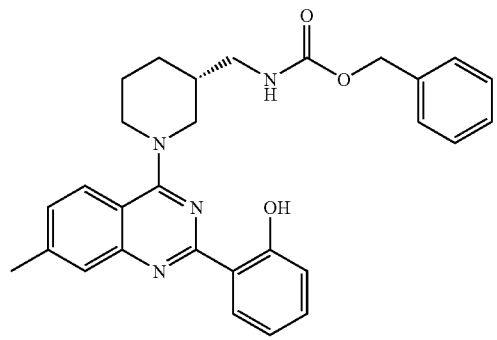

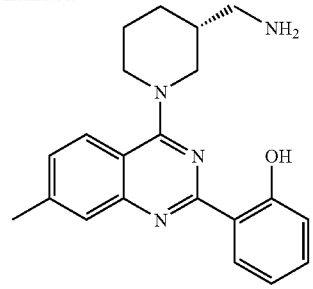

To a mixture of benzyl ((R)-1-(2-(2-hydroxyphenyl)-7-methylquinazolin-4-yl)piperidin-3-yl)methylcarbamate (855 mg, 1.77 mmol) and EtOH (15 mL) in a round bottom flask was added Pd/C (86 mg, 10% wt Pd on carbon) and the flask was sealed with a septum. The atmosphere in the flask was evacuated, purged with N$_2$, and equipped with a balloon charged with H$_2$. The mixture was stirred under an H$_2$ atmosphere at ambient pressure for 3 h. After filtration through a plug of Celite using MeOH as the eluting solvent, the reaction mixture was concentrated to 2-(4-((R)-3-(aminomethyl)piperidin-1-yl)-7-methylquinazolin-2-yl)phenol (625 mg) as a yellow solid. LC/MS: m/z 349.3 (M+H)$^+$ at 1.82 min (10%-99% CH$_3$CN (0.035% TFA)/H$_2$O (0.05% TFA)).

(R)-Tetrahydrofuran-3-yl ((R)-1-(2-(2-hydroxyphenyl)-7-methylquinazolin-4-yl)piperidin-3-yl)methylcarbamate

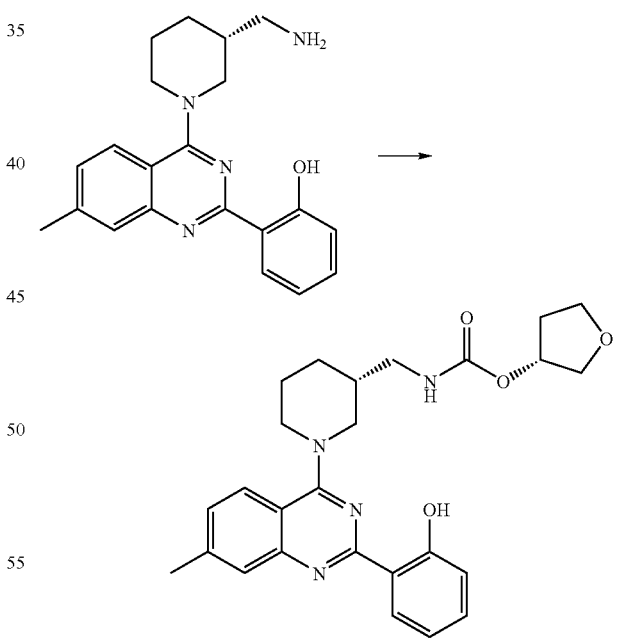

Method A 2-(4-((R)-3-(Aminomethyl)piperidin-1-yl)-7-methylquinazolin-2-yl)phenol (60 mg, 0.17 mmol) was dissolved in anhydrous DMF (1 mL) and cooled to 0° C., upon which (R)-tetrahydrofuran-3-yl chloroformate (31 mg, 0.2 mmol) dissolved in DMF (100 µL) was added dropwise followed by the addition of triethylamine (35 mg, 48 µL, 0.34 mmol). The reaction was allowed to warm to room temperature, and was complete after two hours. Purification using reverse phase HPLC (10%-99% CH₃CN (0.035% TFA)/H₂O (0.05% TFA)) gave (R)-tetrahydrofuran-3-yl ((R)-1-(2-(2-hydroxyphenyl)-7-methylquinazolin-4-yl)piperidin-3-yl)methylcarbamate as the TFA salt. LC/MS: m/z 463.5 (M+H)⁺ at 2.35 min (10%-99% CH₃CN (0.035% TFA)/H₂O (0.05% TFA)).

Method B

To a stirred solution of 2-(4-((R)-3-(aminomethyl)piperidin-1-yl)-7-methylquinazolin-2-yl)phenol (150 mg, 0.43 mmol) under an N₂ atmosphere at 0° C. was added triethylamine (87 mg, 0.86 mmol) followed by the dropwise addition of (R)-tetrahydrofuran-3-yl chloroformate (65 mg, 0.43 mmol). The reaction was allowed to warm to room temperature and was stirred for 2 h. The mixture was partitioned between H₂O and CH₂Cl₂ and separated, and the aqueous layer was extracted twice with CH₂Cl₂. The organic layers were combined, dried over Na₂SO₄, filtered, and concentrated. Purification via silica gel chromatography using 4:1 CH₂Cl₂:EtOAc afforded (R)-tetrahydrofuran-3-yl ((R)-1-(2-(2-hydroxyphenyl)-7-methylquinazolin-4-yl)piperidin-3-yl)methylcarbamate. LC/MS: m/z 463.5 (M+H)⁺ at 2.34 min (10%-99%.CH₃CN (0.035% TFA)/H₂O (0.05% TFA)).

(R)-Tetrahydrofuran-3-yl ((R)-1-(2-(2-hydroxyphenyl)-7-methylquinazolin-4-yl)piperidin-3-yl)methylcarbamate hydrochloride To a solution of (R)-tetrahydrofuran-3-yl ((R)-1-(2-(2-hydroxyphenyl)-7-methylquinazolin-4-yl)piperidin-3-yl)methylcarbamate (0.085 g, 0.18 mmol) in 9 mL CH₂Cl₂ was added dropwise a 2.0 M HCl solution in ether (0.09 mL, 0.18 mmol). Ether (20 mL) was then added, leading to the precipitation of (R)-tetrahydrofuran-3-yl ((R)-1-(2-(2-hydroxyphenyl)-7-methylquinazolin-4-yl)piperidin-3-yl)methylcarbamate hydrochloride which was filtered and dried (85 mg, 95%). LC/MS: m/z 463.5 (M+H)⁺ at 2.33 min (10%-99% CH₃CN (0.035% TFA)/H₂O (0.05% TFA)).

Example 217

(S)-Tetrahydrofuran-3-yl ((R)-1-(2-(2-hydroxyphenyl)-7-methylquinazolin-4-yl)piperidin-3-yl)methylcarbamate

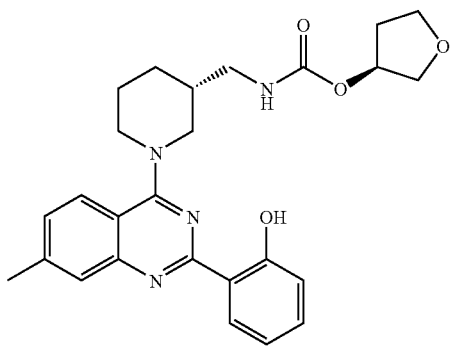

(S)-Tetrahydrofuran-3-yl ((R)-1-(2-(2-hydroxyphenyl)-7-methylquinazolin-4-yl)piperidin-3-yl)methylcarbamate

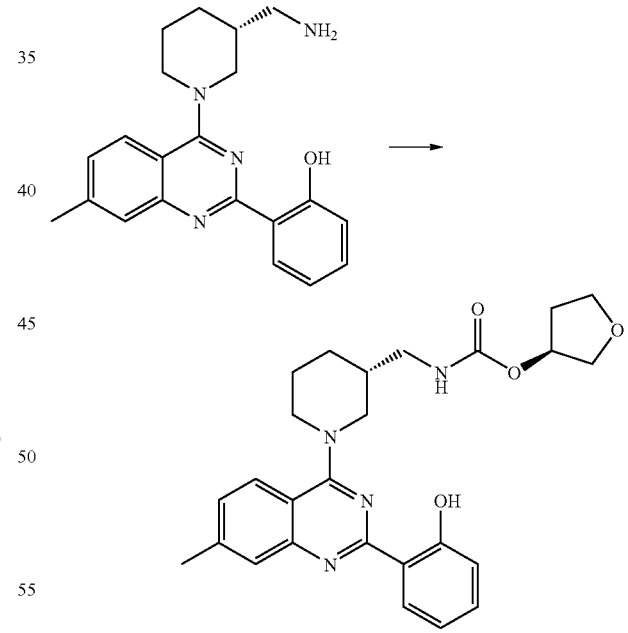

Method A 2-(4-((R)-3-(Aminomethyl)piperidin-1-yl)-7-methylquinazolin-2-yl)phenol (60 mg, 0.17 mmol) was dissolved in anhydrous DMF (1 mL) and cooled to 0° C., upon which (S)-tetrahydrofuran-3-yl chloroformate (31 mg, 0.2 mmol) dissolved in DMF (100 µL) was added dropwise followed by triethylamine (35 mg, 48 µL, 0.34 mmol). The reaction was allowed to warm to room temperature and was complete after 2 h. Purification by reverse phase HPLC (10%-99% CH₃CN

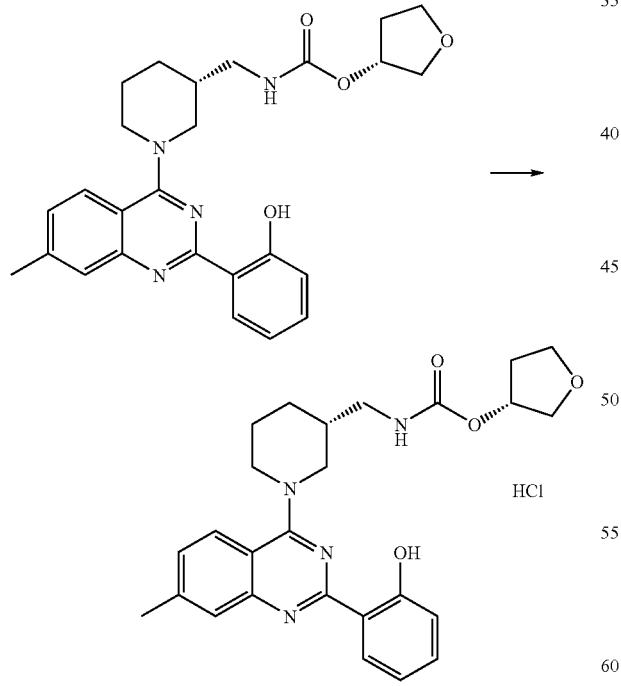

(0.035% TFA)/H₂O (0.05% TFA)) gave (S)-tetrahydrofuran-3-yl ((R)-1-(2-(2-hydroxyphenyl)-7-methylquinazolin-4-yl)piperidin-3-yl)methylcarbamate as the TFA salt. LC/MS: m/z 463.5 (M+H)⁺ at 2.35 min (10%-99% CH₃CN (0.035% TFA)/H₂O (0.05% TFA)).

Method B

To a stirred solution of 2-(4-((R)-3-(aminomethyl)piperidin-1-yl)-7-methylquinazolin-2-yl)phenol (200 mg, 0.57 mmol) in DMF under an N₂ atmosphere at 0° C. was added triethylamine (115 mg, 1.14 mmol) followed by the dropwise addition of (S)-tetrahydrofuran-3-yl chloroformate (86 mg, 0.57 mmol). The reaction was allowed to warm to room temperature and was stirred for 2 h. The mixture was partitioned between H₂O and CH₂Cl₂ and separated, and the aqueous layer was extracted twice with CH₂Cl₂. The organic layers were combined, dried over Na₂SO₄, filtered, and concentrated. Purification via silica gel chromatography using 4:1 CH₂Cl₂:EtOAc afforded (S)-tetrahydrofuran-3-yl ((R)-1-(2-(2-hydroxyphenyl)-7-methylquinazolin-4-yl)piperidin-3-yl)methylcarbamate. LC/MS: m/z 463.5 (M+H)⁺ at 2.34 min (10%-99% CH₃CN (0.035% TFA)/H₂O (0.05% TFA)).

((S)-Tetrahydrofuran-3-yl ((R)-1-(2-(2-hydroxyphenyl)-7-methylquinazolin-4-yl)piperidin-3-yl)methylcarbamate hydrochloride

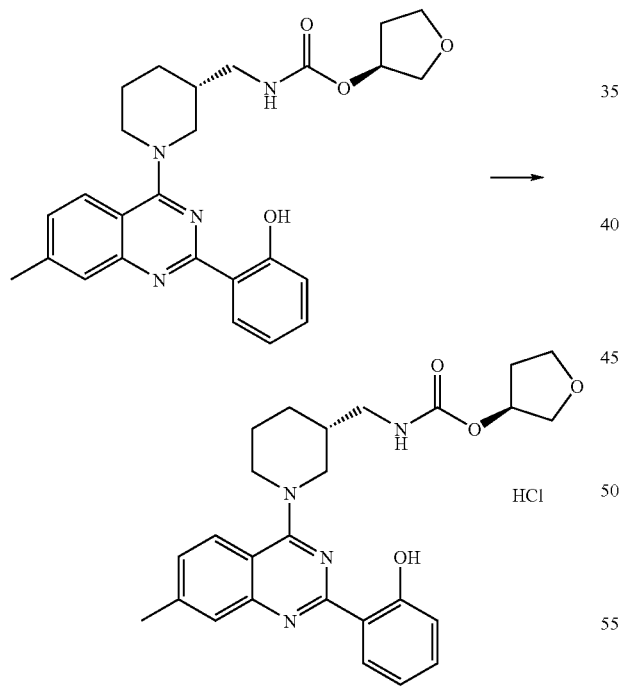

To a solution of (S)-tetrahydrofuran-3-yl ((R)-1-(2-(2-hydroxyphenyl)-7-methylquinazolin-4-yl)piperidin-3-yl)methylcarbamate in 12 mL CH₂Cl₂ was added dropwise 2.0 M HCl solution in ether (0.13 mL, 0.25 mmol). To the solution was then added 20 mL ether leading to the precipitation of ((S)-tetrahydrofuran-3-yl ((R)-1-(2-(2-hydroxyphenyl)-7-methylquinazolin-4-yl)piperidin-3-yl)methylcarbamate hydrochloride which was filtered and dried (116 mg, 92%).

LC/MS: m/z 463.5 (M+H)⁺ at 2.33 min (10%-99% CH₃CN (0.035% TFA)/H₂O (0.05% TFA)).

Example 218

(2R)-Tetrahydro-N-(1-(2-(2-hydroxy-6-methylphenyl)-7-methylquinazolin-4-yl)piperidin-4-yl)furan-2-carboxamide

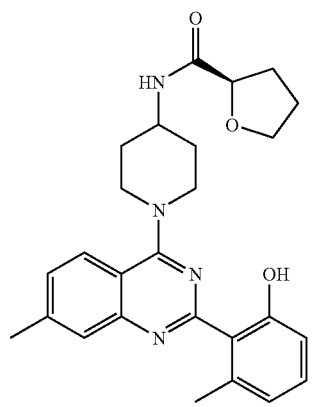

(R)-Tetrahydrofuran-2-carboxylic acid (1-benzylpiperidin-4-yl)-amide

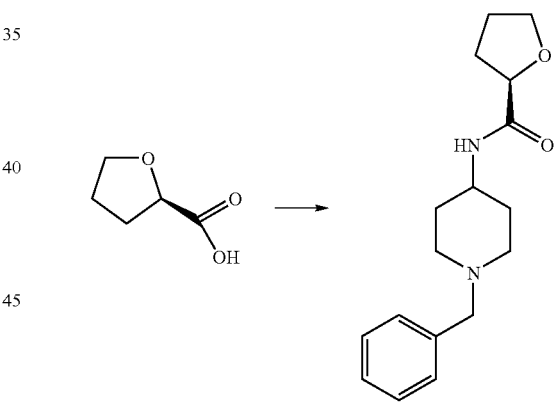

A solution of (R)-tetrahydro-2-furoic acid (58.5 g, 504 mmol) and oxalyl chloride (86 mL, 1.0 mol) in 100 mL CH₂Cl₂ were refluxed for 2 hours in a flask equipped with a CaCl₂ guard tube. After the solution was cooled to room temperature the solvents and excess oxalyl chloride were removed by evaporation under reduced pressure. The resulting acid chloride was dissolved in 200 mL CH₂Cl₂ and added dropwise to a solution of 1-benzyl-4-amino piperidine dihydrochloride (142 g, 539 mmol) and triethylamine (240 mL, 1.7 mol) in 300 mL CH₂Cl₂ cooled in an ice bath. The resulting mixture was stirred for 2 hours at room temperature and subsequently washed twice with 300 mL portions of 5% aq. NaHCO₃ and 300 mL saturated aq. NaCl solution, dried over Na₂SO₄, filtered, and evaporated to dryness under reduced pressure. The solid residue was triturated with 500 mL heptanes, collected by filtration, and washed twice with 200 mL portions of heptanes. The solid was air-dried at 45° C. to yield

347

(R)-tetrahydrofuran-2-carboxylic acid (1-benzyl-piperidin-4-yl)-amide (128 g, 88%) as an off-white solid. ¹H-NMR (300 MHz, CDCl₃): δ 7.35-7.20 (m, 5H), 6.58 (bs, 1H), 4.29 (dd, J=5.9, 8.4 Hz, 1H), 3.92-3.77 (m, 2H), 3.48 (s, 2H), 2.82-2.74 (m, 2H), 2.32-2.21 (m, 1H), 2.19-1.95 (m, 3H), 1.94-1.78 (m, 4H), 1.58-1.40 (m, 2H) ppm.

(R)-Tetrahydro-furan-2-carboxylic acid piperidin-4-ylamide as an oxalate salt

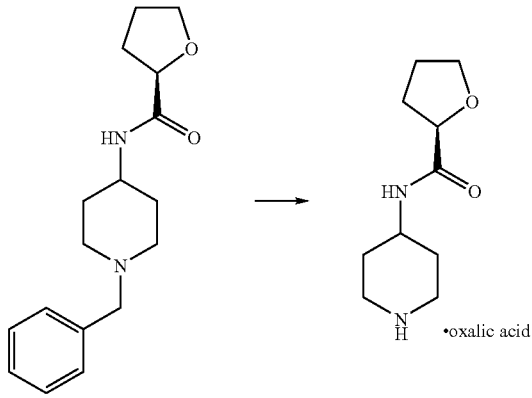

(R)-Tetrahydro-furan-2-carboxylic acid (1-benzyl-piperidin-4-yl)-amide (128 g, 444 mmol) was dissolved in 300 mL ethanol and 50 mL acetic acid. Palladium on activated carbon (5 g) was added. A hydrogen pressure of 5 bars was applied, and hydrogenation was continued until no more hydrogen was consumed (about 5 days). The suspension was filtered through Celite, and the filtrate was evaporated to dryness under reduced pressure. The residue and oxalic acid (50 g, 555 mmol) were suspended in 500 mL 2-propanol and heated to dissolve the solids. Upon cooling, the oxalate salt of R-tetrahydro-furan-2-carboxylic acid piperidin-4-ylamide crystallized and was collected by filtration to yield (R)-Tetrahydro-furan-2-carboxylic acid piperidin-4-ylamide as an oxalate salt (99.0 g, 77%) as an off-white solid. ¹H-NMR (300 MHz, DMSO-d₆): δ 7.84 (d, J=7.8 Hz, 1H), 5.90 (bs, 2H), 4.18-4.14 (m, 1H), 3.89-3.67 (m, 3H), 3.25-3.20 (m, 2H), 2.94-2.71 (m, 2H), 2.13-2.00 (m, 1H), 1.56-1.58 (m, 6H) ppm.

(2R)-Tetrahydro-N-(1-(2-(2-hydroxy-6-methylphenyl)-7-methylquinazolin-4-yl)piperidin-4-yl)furan-2-carboxamide

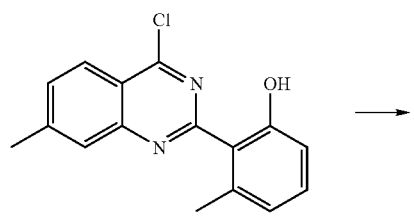

348

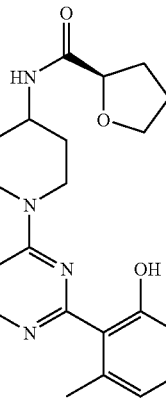

To a solution of 2-(4-chloro-7-methylquinazolin-2-yl)-3-methylphenol (60 mg, 2.1 mmol) in DMF (1 mL) was added triethylamine (1.17 mL, 8.4 mmol) and (R)-tetrahydro-N-(piperidin-4-yl)furan-2-carboxamide as an oxalate salt (80 mg, 2.73 mmol). This mixture was stirred for 2 h at room temperature before it was purified via reverse phase HPLC using 10%-99% CH₃CN (0.035% TFA)/H₂O (0.05% TFA) to afford (2R)-tetrahydro-N-(1-(2-(2-hydroxy-6-methylphenyl)-7-methylquinazolin-4-yl)piperidin-4-yl)furan-2-carboxamide as the TFA salt. LC/MS: m/z 447.5 (M+H)⁺ at 2.19 min (10%-99% CH₃CN (0.035% TFA)/H₂O (0.05% TFA)).

Example 219

{1-[2-(2-Hydroxy-phenyl)-7-methyl-quinazolin-4-yl]-piperidin-4-yl}-carbamic acid tetrahydro-pyran-2-ylmethyl ester

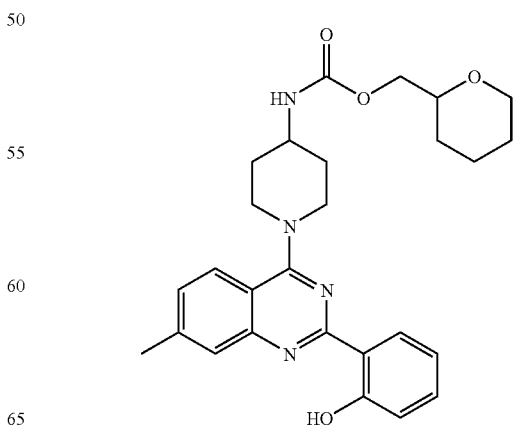

(Tetrahydro-2H-pyran-2-yl)methyl 1H-imidazole-1-carboxylate

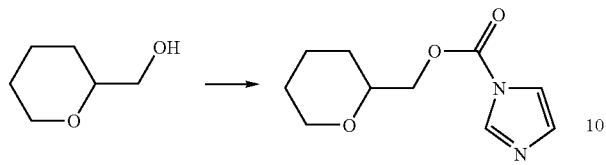

A mixture of (tetrahydro-2H-pyran-2-yl)methanol (369 mg, 3.18 mmol) and di(1H-imidazol-1-yl)methanone (1.0 g, 6.36 mmol) in 0.3 M CH$_3$Cl (10 mL) was stirred at 50° C. for 3 h. After allowing the reaction to cool to room temperature, the solvent was evaporated under reduced pressure giving (tetrahydro-2H-pyran-2-yl)methyl 1H-imidazole-1-carboxylate (412 mg) which was used without further purification. LC/MS: m/z 211.1 (M+H)$^+$ at 0.94 min (10%-99% CH$_3$CN (0.035% TFA)/H$_2$O (0.05% TFA)).

{1-[2-(2-Hydroxy-phenyl)-7-methyl-quinazolin-4-yl]-piperidin-4-yl}-carbamic acid tetrahydro-pyran-2-ylmethyl ester

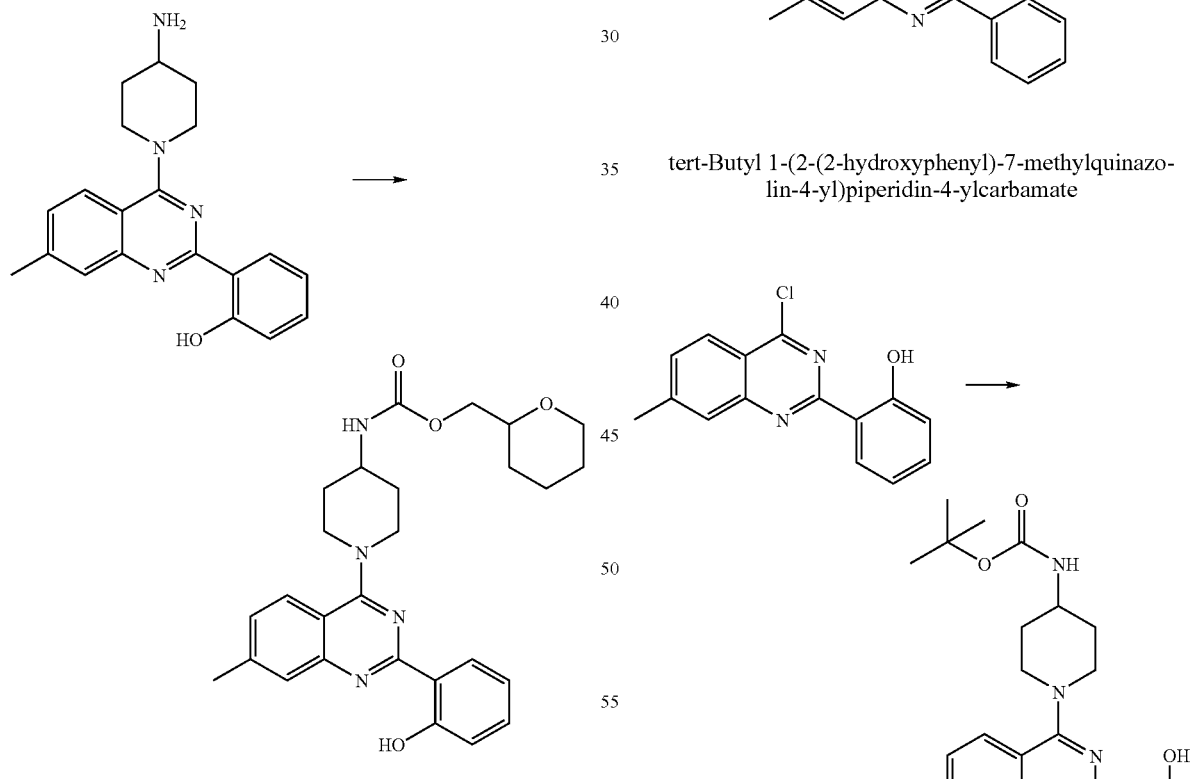

To 2-[4-(4-amino-piperidin-1-yl)-7-methyl-quinazolin-2-yl]-phenol (100 mg, 0.3 mmol) in 1 mL CH$_2$Cl$_2$ was added sequentially triethylamine (62.5 µL, 0.45 mmol) and imidazole-1-carboxylic acid tetrahydro-pyran-2-ylmethyl ester (94 mg, 0.45 mmol). The reaction mixture was stirred at room temperature for 12 h and at 45° C. for 3 h. The reaction mixture was cooled and diluted with water and CH$_2$Cl$_2$. The organic layer was separated and dried over Na$_2$SO$_4$, and the solvent was removed under reduced pressure to give an oil. The residue was purified by reverse phase HPLC using 10%-99% CH$_3$CN (0.035% TFA)/H$_2$O (0.05% TFA) as eluent to give the desired product {1-[2-(2-hydroxy-phenyl)-7-methyl-quinazolin-4-yl]-piperidin-4-yl}-carbamic acid tetrahydro-pyran-2-ylmethyl ester as the TFA salt. LC/MS: m/z 477.4 (M+H)$^+$ at 2.84 min (10%-99% CH$_3$CN (0.035% TFA)/H$_2$O (0.05% TFA)).

Example 220

Tetrahydro-N-(1-(2-(2-hydroxyphenyl)-7-methylquinazolin-4-yl)piperidin-4-yl)-2H-pyran-4-carboxamide

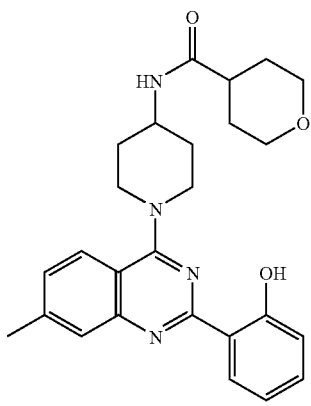

tert-Butyl 1-(2-(2-hydroxyphenyl)-7-methylquinazolin-4-yl)piperidin-4-ylcarbamate

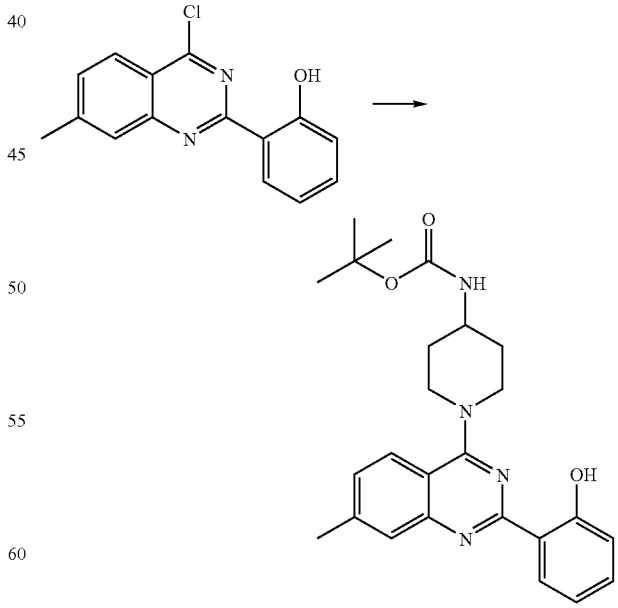

To a cooled (0-5° C.) suspension of 2-(4-chloro-7-methylquinazolin-2-yl)phenol (50.2 g, 186 mmol) in dichloromethane (200 mL) was slowly added a solution of tert-butyl piperidin-4-ylcarbamate (39.0 g, 195 mmol) and triethylamine (56 mL, 390 mmol) in dichloromethane (200 mL). The resulting mixture was stirred overnight at room temperature. Water (400 ml) was added, and the layers were separated. The aqueous layer was extracted with dichloromethane (2×200 mL), and the combined organic layers were dried over sodium sulfate, filtered, and evaporated to dryness under reduced pressure. The residue was purified by column chromatography (SiO$_2$, eluent: dichloromethane/heptanes 4:6-1:0). Two fractions were obtained: 38.7 g of tert-butyl 1-(2-(2-hydroxyphenyl)-7-methylquinazolin-4-yl)piperidin-4-ylcarbamate as a yellow solid, and a less pure fraction (26.1 g) that was purified by recrystallization from methanol to yield tert-butyl 1-(2-(2-hydroxyphenyl)-7-methylquinazolin-4-yl)piperidin-4-ylcarbamate. Both fractions were combined (17.0 g, 69%).

2-(4-(4-Aminopiperidin-1-yl)-7-methylquinazolin-2-yl)phenol

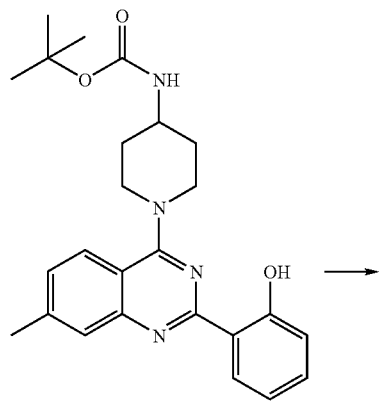

tert-Butyl 1-(2-(2-hydroxyphenyl)-7-methylquinazolin-4-yl)piperidin-4-ylcarbamate (55.7 g, 128 mmol) was dissolved in dichloromethane (200 mL) and trifluoroacetic acid (215 ml) was slowly added (careful: immediate gas evolution!). The resulting solution was stirred overnight at room temperature under a nitrogen atmosphere and evaporated to dryness. To the residue were added equal amounts of water and dichloromethane (300 mL). The obtained emulsion was basified to pH 9 with 33% aq. NaOH. The emulsion was cleared by the addition of methanol, and the layers were separated. The aqueous layer was extracted with dichloromethane (200 mL), and the combined organic extracts were dried over sodium sulfate, filtered, and evaporated to dryness to yield crude 2-(4-(4-aminopiperidin-1-yl)-7-methylquinazolin-2-yl)phenol. The crude material was purified by column chromatography (SiO$_2$, 2% methanol in dichloromethane) to yield 2-(4-(4-aminopiperidin-1-yl)-7-methylquinazolin-2-yl)phenol (44 g, 97%) as a yellow solid. $^1$H-NMR (300 MHz, CDCl$_3$): δ 8.52 (dd, J=2.1, 8.1 Hz, 1H), 7.77 (d, J=8.4 Hz, 1H), 7.62 (s, 1H), 7.37 (dt, J=1.5, 7.2 Hz, 1H), 7.22 (dd, J=1.5, 9.0 Hz, 1H), 7.04 (dd, J=1.2, 6.9 Hz, 1H), 6.92 (dt, J=1.2, 7.2 Hz, 1H), 4.49-4.39 (m, 2H), 3.34 (dt, J=2.4, 12.2 Hz, 2H), 3.12-3.02 (m, 1H), 2.54 (s, 3H), 2.09-2.00 (m, 2H), 1.68-1.55 (m, 2H), 1.40-1.25 (m, 2H) ppm.

Tetrahydro-N-(1-(2-(2-hydroxyphenyl)-7-methylquinazolin-4-yl)piperidin-4-yl)-2H-pyran-4-carboxamide

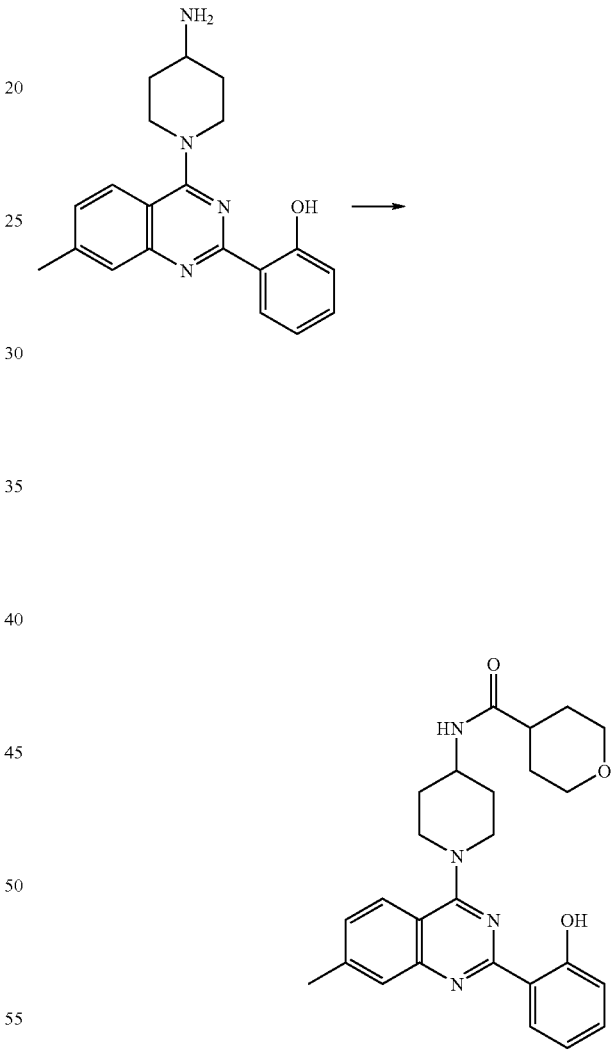

To a solution of 2-(4-(4-aminopiperidin-1-yl)-7-methylquinazolin-2-yl)phenol (30 mg, 0.09 mmol) in DMF (1 mL) was added tetrahydro-2H-pyran-4-carboxylic acid (17.5 mg, 0.13 mmol) followed by the addition of triethylamine (25 μL, 0.18 mmol) and HATU (44 mg, 0.117 mmol). The reaction was stirred for 16 h, filtered, and purified by reverse phase HPLC (10%-99% CH$_3$CN (0.035% TFA)/H$_2$O (0.05% TFA)) to afford tetrahydro-N-(1-(2-(2-hydroxyphenyl)-7-methylquinazolin-4-yl)piperidin-4-yl)-2H-pyran-4-carboxamide as the TFA salt. LC/MS: m/z 447.5 (M+H)+ at 2.19 min (10%-99% CH₃CN (0.035% TFA)/H₂O (0.05% TFA)).

Example 221

2-(Tetrahydro-2H-pyran-4-yl)-N-(1-(2-(2-hydroxyphenyl)-7-methylquinazolin-4-yl)piperidin-4-yl)acetamide

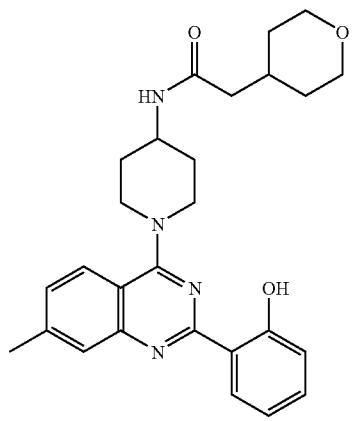

2-(Tetrahydro-2H-pyran-4-yl)-N-(1-(2-(2-hydroxyphenyl)-7-methylquinazolin-4-yl)piperidin-4-yl)acetamide

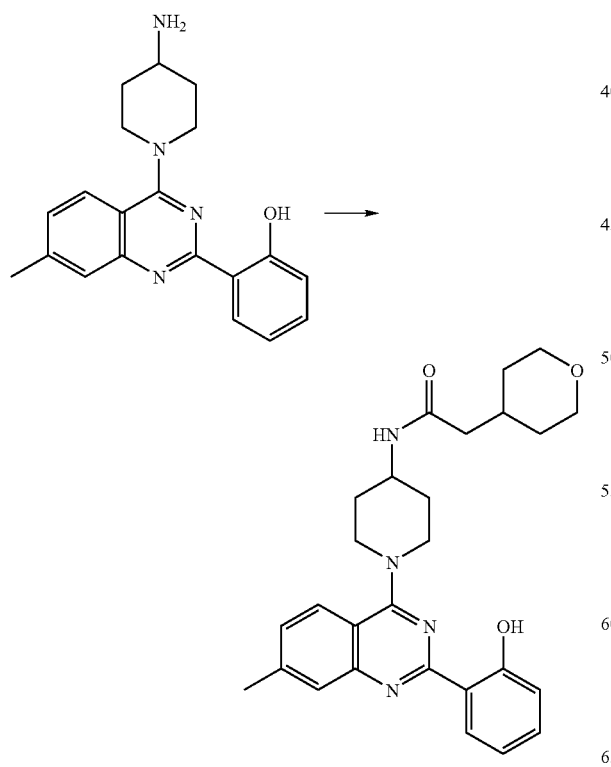

To a solution of 2-(4-(4-aminopiperidin-1-yl)-7-methylquinazolin-2-yl)phenol (30 mg, 0.09 mmol) in DMF (1 mL) was added 2-(tetrahydro-2H-pyran-4-yl)acetic acid (13 mg, 0.09 mmol) followed by the addition of triethylamine (25 μL, 0.18 mmol) and HATU (44 mg, 0.117 mmol). The reaction was stirred for 16 h, filtered, and purified by reverse phase HPLC (10%-99% CH₃CN (0.035% TFA)/H₂O (0.05% TFA)) to afford 2-(tetrahydro-2H-pyran-4-yl)-N-(1-(2-(2-hydroxyphenyl)-7-methylquinazolin-4-yl)piperidin-4-yl)acetamide as the TFA salt. LC/MS: m/z 461.5 (M+H)+ at 2.22 min (10%-99% CH₃CN (0.035% TFA)/H₂O (0.05% TFA)).

Example 222

2-(2-Isopropyl-5-methylcyclohexyloxy)-N-(1-(2-(2-hydroxyphenyl)-7-methylquinazolin-4-yl)piperidin-4-yl)acetamide

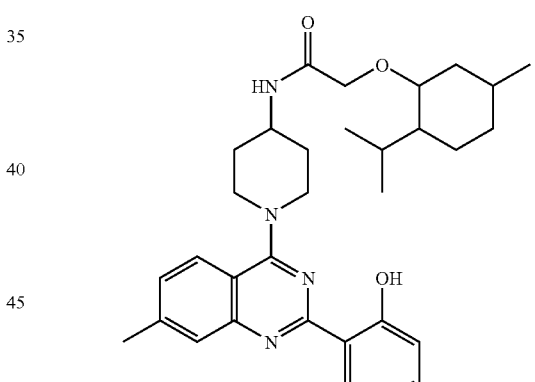

To a solution of 2-(4-(4-aminopiperidin-1-yl)-7-methylquinazolin-2-yl)phenol (30 mg, 0.09 mmol) in DMF (1 mL) at 0° C. was added triethylamine (25 μL, 0.18 mmol) followed by the addition of 2-(2-isopropyl-5-methylcyclohexyloxy)acetyl chloride (21 mg, 0.09 mmol). The reaction was stirred for 16 h, filtered, and purified by reverse phase HPLC (10%-99% CH₃CN (0.035% TFA)/H₂O (0.05% TFA)) to afford 2-(2-isopropyl-5-methylcyclohexyloxy)-N-(1-(2-(2-hydroxyphenyl)-7-methylquinazolin-4-yl)piperidin-4-yl)acetamide as the TFA salt. LC/MS: m/z 531.3 (M+H)$^+$ at 3.08 min (10%-99% CH$_3$CN (0.035% TFA)/H$_2$O (0.05% TFA)).

Example 223

N-(1-(2-(2-Hydroxyphenyl)-7-methylquinazolin-4-yl)piperidin-4-yl)-3-(pyridin-2-yl)propanamide

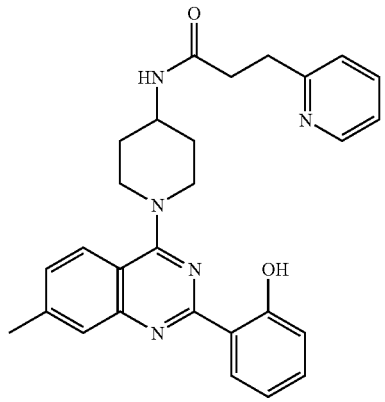

N-(1-(2-(2-Hydroxyphenyl)-7-methylquinazolin-4-yl)piperidin-4-yl)-3-(pyridin-2-yl)propanamide

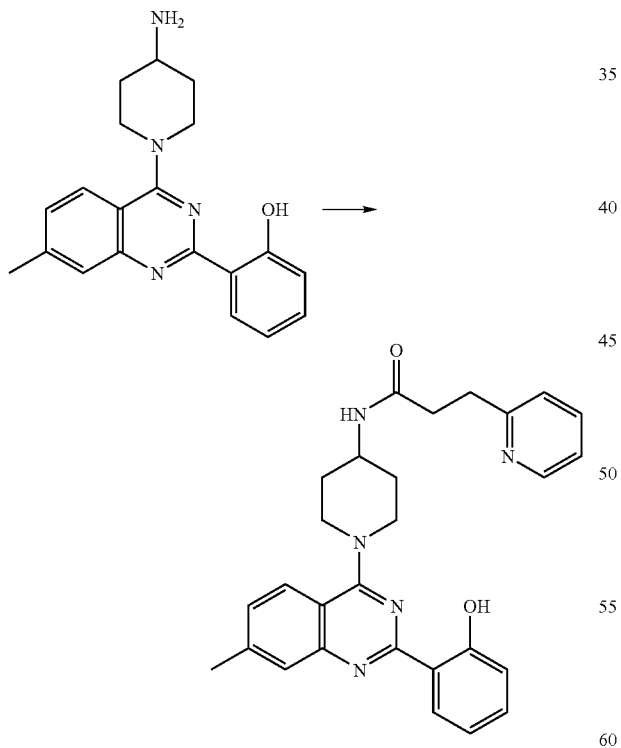

To a solution of 2-(4-(4-aminopiperidin-1-yl)-7-methylquinazolin-2-yl)phenol (30 mg, 0.09 mmol) in DMF (1 mL) was added 3-(pyridin-2-yl)propanoic acid (20 mg, 0.13 mmol) followed by the addition of triethylamine (25 μL, 0.18 mmol) and HATU (44 mg, 0.117 mmol). The reaction was stirred for 16 h, filtered, and purified by reverse phase HPLC (10%-99% CH$_3$CN (0.035% TFA)/H$_2$O (0.05% TFA)) to afford N-(1-(2-(2-hydroxyphenyl)-7-methylquinazolin-4-yl)piperidin-4-yl)-3-(pyridin-2-yl)propanamide as the TFA salt. LC/MS: m/z 468.3 (M+H)$^+$ at 1.86 min (10%-99% CH$_3$CN (0.035% TFA)/H$_2$O (0.05% TFA)).

Example 224

(2R)—N-(1-(6-Fluoro-2-(2-hydroxyphenyl)quinazolin-4-yl)piperidin-4-yl)-tetrahydrofuran-2-carboxamide

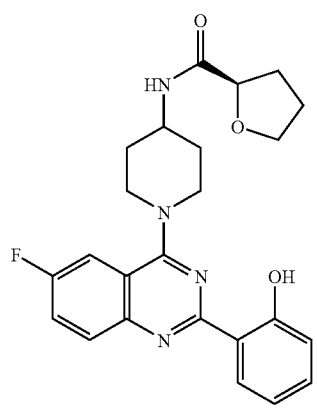

(2R)—N-(1-(6-Fluoro-2-(2-hydroxyphenyl)quinazolin-4-yl)piperidin-4-yl)-tetrahydrofuran-2-carboxamide

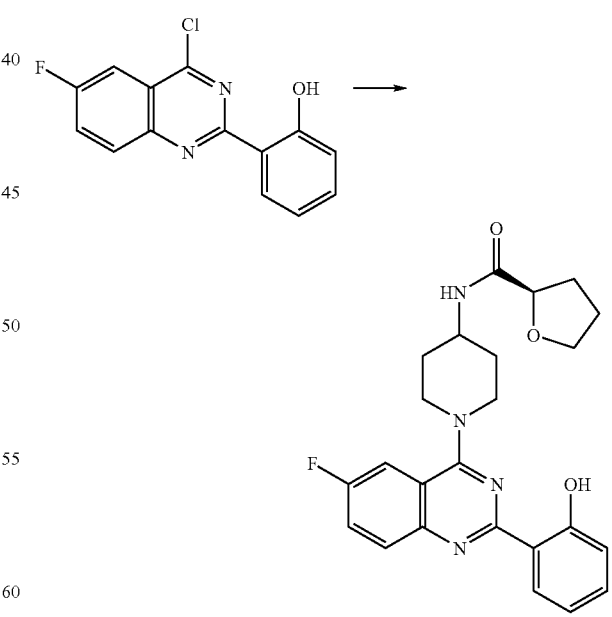

To a solution of 2-(4-chloro-6-fluoroquinazolin-2-yl)phenol (25 mg, 0.09 mmol) in CH$_2$Cl$_2$ (1 mL) was added (R)-tetrahydro-N-(piperidin-4-yl)furan-2-carboxamide oxalate (33 mg, 0.117 mmol), followed by the addition of triethylamine (50 μL, 0.36 mmol). The reaction was stirred for 2 h before it was filtered, and purified by reverse phase HPLC (10%-99% CH₃CN (0.035% TFA)/H₂O (0.05% TFA)) to afford (2R)—N-(1-(6-fluoro-2-(2-hydroxyphenyl)quinazolin-4-yl)piperidin-4-yl)-tetrahydrofuran-2-carboxamide as the TFA salt. LC/MS: m/z 437.1 (M+H)⁺ at 2.54 min (10%-99% CH₃CN (0.035% TFA)/H₂O (0.05% TFA)).

Example 225

N-{1-[2-(2-Hydroxy-phenyl)-7-methyl-quinazolin-4-yl]-piperidin-4-yl}-3-pyridin-3-yl-propionamide

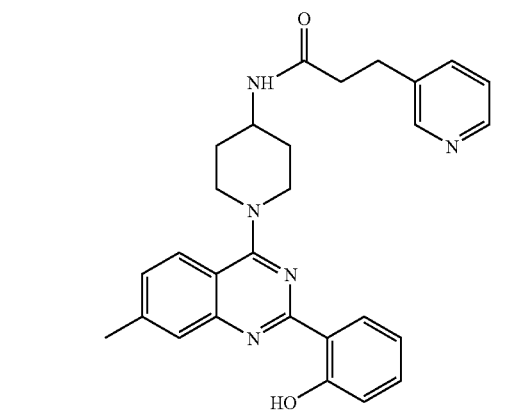

N-{1-[2-(2-Hydroxy-phenyl)-7-methyl-quinazolin-4-yl]-piperidin-4-yl}-3-pyridin-3-yl-propionamide

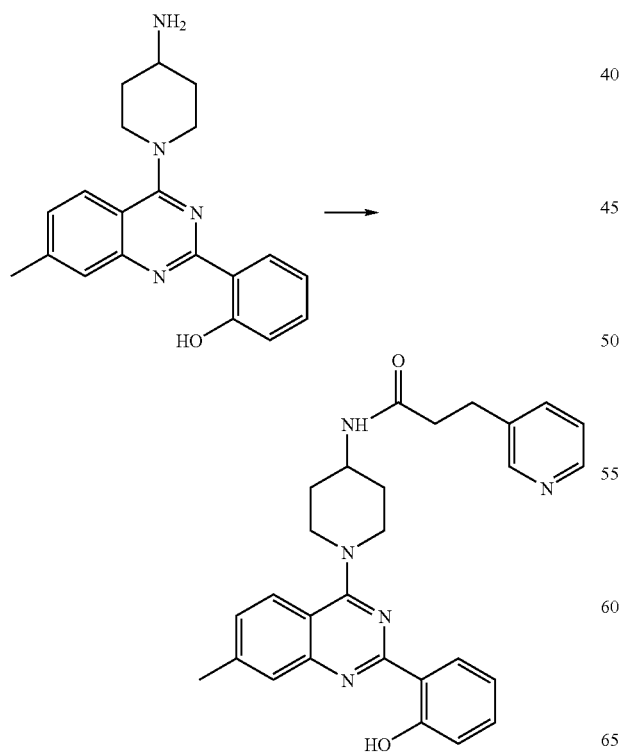

To 2-[4-(4-amino-piperidin-1-yl)-7-methyl-quinazolin-2-yl]-phenol (238 mg, 0.71 mmol) in 2.4 mL of CH₂Cl₂ was added sequentially 3-pyridin-3-yl-propionic acid (118.3 mg, 0.78 mmol), triethylamine (129 µL, 0.92 mmol), and BOP (346 mg, 0.78 mmol) at room temperature. The reaction mixture was stirred for 40 min and diluted with water and CH₂Cl₂. The organic layer was separated and dried over Na₂SO₄, and the solvent was removed under reduced pressure to give an oil. The residue was purified by reverse phase LC using 10%-99% CH₃CN (0.035% TFA)/H₂O (0.05% TFA) as eluent to give the desired product as the TFA salt. LC/MS: m/z 468.6 (M+H)⁺ at 2.19 min (10%-99% CH₃CN (0.035% TFA)/H₂O (0.05% TFA)).

Example 226

N—(((S)-1-(2-(2-Hydroxyphenyl)-7-methylquinazolin-4-yl)piperidin-3-yl)methyl)cyclopropanecarboxamide

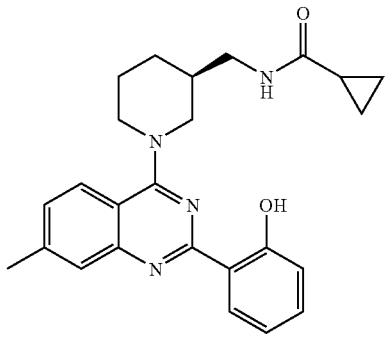

N—(((S)-1-(2-(2-Hydroxyphenyl)-7-methylquinazolin-4-yl)piperidin-3-yl)methyl)cyclopropanecarboxamide

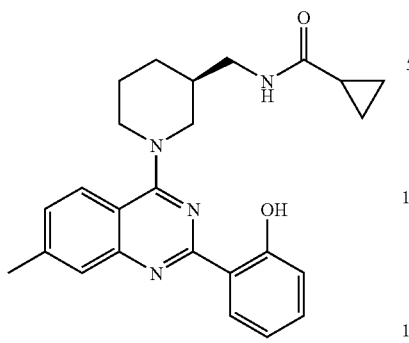

2-(4-((S)-3-(Aminomethyl)piperidin-1-yl)-7-methylquinazolin-2-yl)phenol (35 mg, 0.10 mmol) was dissolved in DMF (1 mL). Cyclopropanecarboxylic acid (9.7 mg, 0.11 mmol) was added, followed by the addition of triethylamine (28 μL, 0.2 mmol), and the mixture was cooled in an ice water bath. HATU (42 mg, 0.11 mmol) was added in one portion, and the reaction was allowed to warm to room temperature while stirring for 16 h. The reaction mixture was filtered, and purified by reverse phase HPLC (10%-99% CH$_3$CN (0.035% TFA)/H$_2$O (0.05% TFA)) to give N—(((S)-1-(2-(2-hydroxyphenyl)-7-methylquinazolin-4-yl)piperidin-3-yl)methyl) cyclopropanecarboxamide as the TFA salt. LC/MS: m/z 417.5 (M+H)$^+$ at 2.30 min (10%-99% CH$_3$CN (0.035% TFA)/H$_2$O (0.05% TFA)).

Example 227

(Pyridin-3-yl)methyl 1-(2-(2-hydroxyphenyl)-7-methylquinazolin-4-yl)piperidin-4-ylcarbamate tert-Butyl 1-(2-(2-hydroxyphenyl)-7-methylquinazolin-4-yl)piperidin-4-ylcarbamate

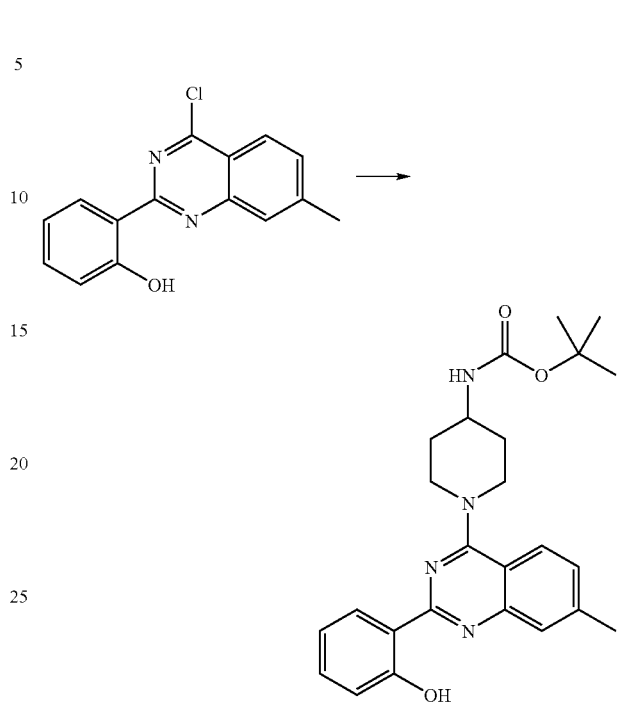

To a suspension of 2-(4-chloro-7-methylquinazolin-2-yl) phenol (2.0 g, 7.38 mmol) in CH$_2$Cl$_2$ (25 ml) at 0° C. under an N$_2$ atmosphere was added dropwise a solution of tert-butyl piperidin-4-ylcarbamate (1.92 g, 9.6 mmol) in CH$_2$Cl$_2$ (10 ml) and triethylamine (2.0 ml, 14.76 mmol). The reaction was stirred for 6 hours, then it was quenched with water (25 ml), and the layers were separated. The aqueous phase was extracted twice with CH$_2$Cl$_2$ (10 ml), and the combined organic layers were dried over MgSO$_4$, filtered, and concentrated to give tert-butyl 1-(2-(2-hydroxyphenyl)-7-methylquinazolin-4-yl)piperidin-4-ylcarbamate as a yellow solid (3.24 g, 100%). LC/MS: m/z 435.3 (M+H)$^+$ at 2.79 min (10%-99% CH$_3$CN (0.035% TFA)/H$_2$O (0.05% TFA)).

2-(4-(4-Aminopiperidin-1-yl)-7-methylquinazolin-2-yl)phenol

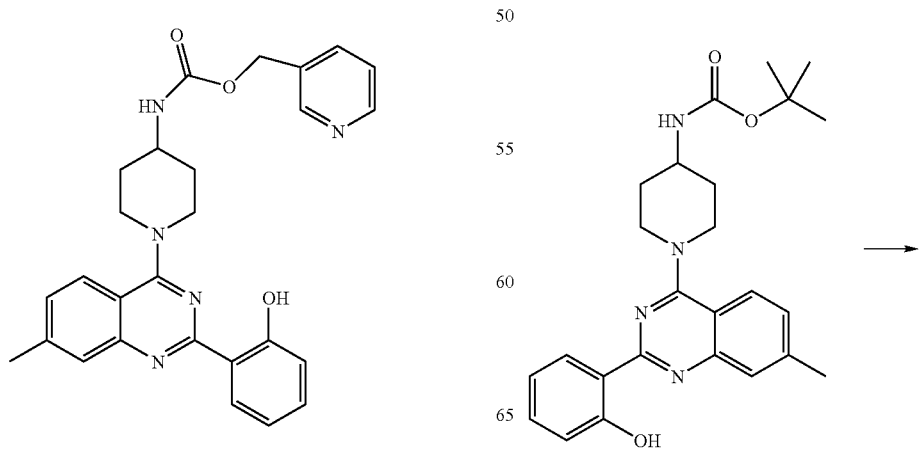

-continued

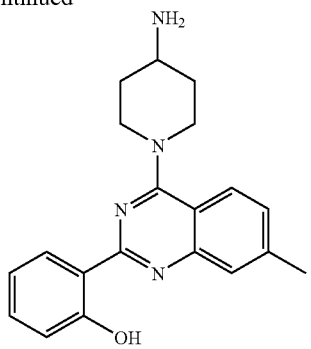

tert-Butyl 1-(2-(2-hydroxyphenyl)-7-methylquinazolin-4-yl)piperidin-4-ylcarbamate (3.21 g, 7.39 mmol) was dissolved in CH$_2$Cl$_2$ (55 ml). TFA (50 ml) was added and the reaction was stirred for 1 hour. After evaporating the solvents in vacuo, the crude material was diluted with CH$_2$Cl$_2$ and neutralized with a 1 N NaOH solution. The layers were separated, and the aqueous layer was extracted three times with CH$_2$Cl$_2$ (30 ml). The combined organic layers were dried over MgSO$_4$, filtered, and concentrated to give 2-(4-(4-aminopiperidin-1-yl)-7-methylquinazolin-2-yl)phenol as a yellow solid (2.06 g, 83%). LC/MS: m/z 335.3 (M+H)$^+$ at 1.42 min (10%-99% CH$_3$CN (0.035% TFA)/H$_2$O (0.05% TFA)).

(Pyridin-3-yl)methyl 1-(2-(2-hydroxyphenyl)-7-methylquinazolin-4-yl)piperidin-4-ylcarbamate

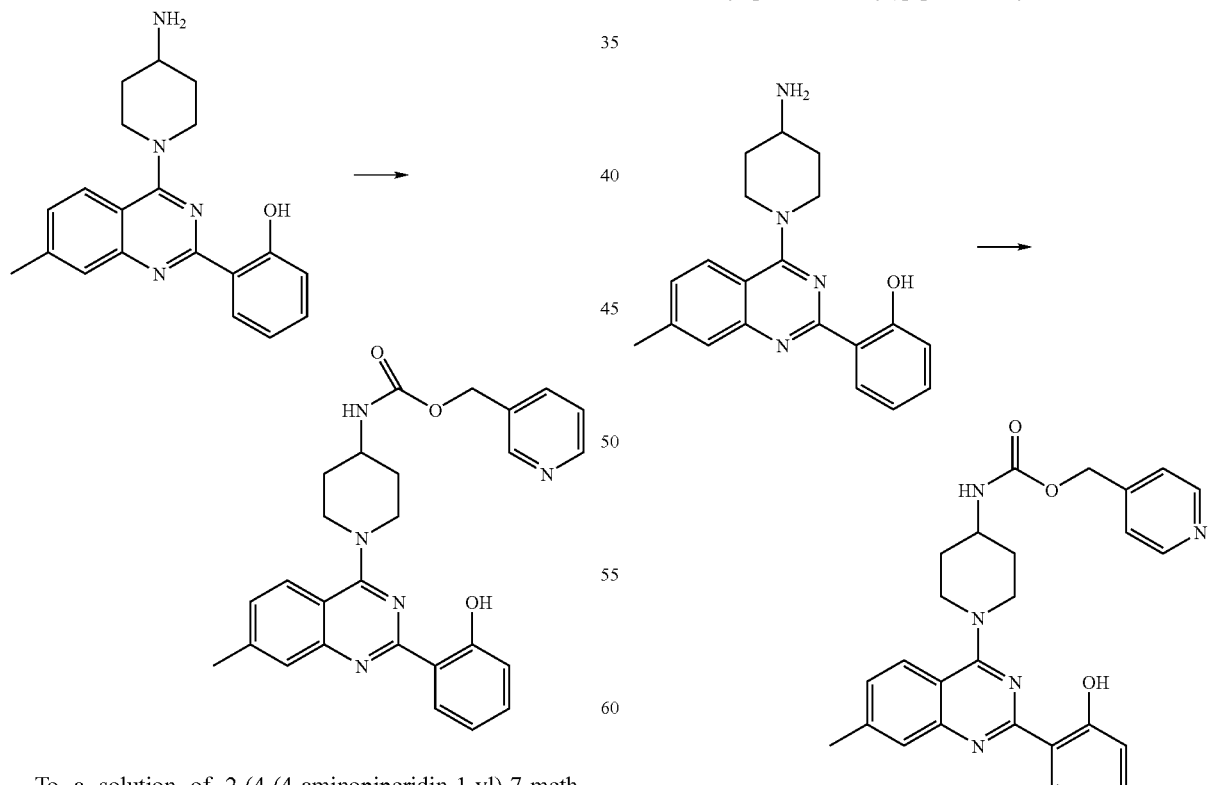

To a solution of 2-(4-(4-aminopiperidin-1-yl)-7-methylquinazolin-2-yl)phenol (50 mg, 0.15 mmol) in DMSO (1 mL) was added (pyridin-3-yl)methyl 1H-imidazole-1-carboxylate (53 mg, 0.263 mmol) and triethylamine (30.4 mg, 42 µL, 0.3 mmol). The reaction was stirred overnight at room temperature and then purified by reverse phase HPLC (10%-99% CH$_3$CN (0.035% TFA)/H$_2$O (0.05% TFA)) to give (pyridin-3-yl)methyl 1-(2-(2-hydroxyphenyl)-7-methylquinazolin-4-yl)piperidin-4-ylcarbamate as the TFA salt. LC/MS: m/z 470.5 (M+H)$^+$ at 1.98 min (10%-99% CH$_3$CN (0.035% TFA)/H$_2$O (0.05% TFA)).

Example 228

(Pyridin-4-yl)methyl 1-(2-(2-hydroxyphenyl)-7-methylquinazolin-4-yl)piperidin-4-ylcarbamate

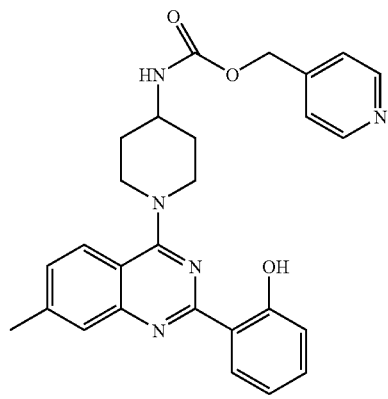

(Pyridin-4-yl)methyl 1-(2-(2-hydroxyphenyl)-7-methylquinazolin-4-yl)piperidin-4-ylcarbamate To a solution of 2-(4-(4-aminopiperidin-1-yl)-7-methylquinazolin-2-yl)phenol (50 mg, 0.15 mmol) in DMSO (1 mL) was added (pyridin-4-yl)methyl 1H-imidazole-1-carboxylate (53 mg, 0.263 mmol) and triethylamine (30.4 mg, 42 μL, 0.3 mmol). The reaction was stirred overnight at room temperature and purified by reverse phase HPLC (10%-99% CH₃CN (0.035% TFA)/H₂O (0.05% TFA)) to give (pyridin-4-yl)methyl 1-(2-(2-hydroxyphenyl)-7-methylquinazolin-4-yl)piperidin-4-ylcarbamate as the TFA salt. LC/MS: m/z 470.5 (M+H)⁺ at 1.98 min (10%-99% CH₃CN (0.035% TFA)/H₂O (0.05% TFA)).

Example 229

(Benzo[d][1,3]dioxol-7-yl)methyl 1-(2-(2-hydroxyphenyl)-7-methylquinazolin-4-yl)piperidin-4-ylcarbamate

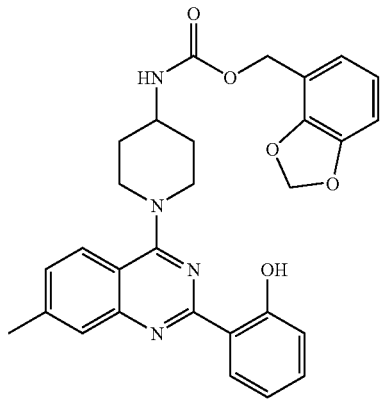

To a solution of 2-(4-(4-aminopiperidin-1-yl)-7-methylquinazolin-2-yl)phenol (50 mg, 0.15 mmol) in DMSO (1 mL), was added (benzo[d][1,3]dioxol-4-yl)methyl 1H-imidazole-1-carboxylate (65 mg, 0.263 mmol), followed by the addition of triethylamine (30.4 mg, 42 μL, 0.3 mmol). The reaction was stirred overnight at room temperature and then purified by reverse phase HPLC (10%-99% CH₃CN (0.035% TFA)/H₂O (0.05% TFA)) to give (benzo[d][1,3]dioxol-7-yl)methyl 1-(2-(2-hydroxyphenyl)-7-methylquinazolin-4-yl)piperidin-4-ylcarbamate as the TFA salt. LC/MS: m/z 513.3 (M+H)⁺ at 2.82 min (10%-99% CH₃CN (0.035% TFA)/H₂O (0.05% TFA)).

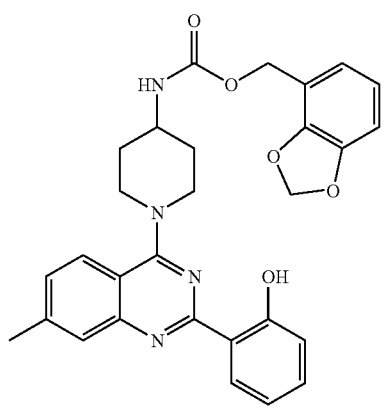

(Benzo[d][1,3]dioxol-7-yl)methyl 1-(2-(2-hydroxyphenyl)-7-methylquinazolin-4-yl)piperidin-4-ylcarbamate Example 230

N-((Tetrahydrofuran-2-yl)methyl)-1-(2-(2-hydroxyphenyl)-7-methylquinazolin-4-yl)piperidine-3-carboxamide

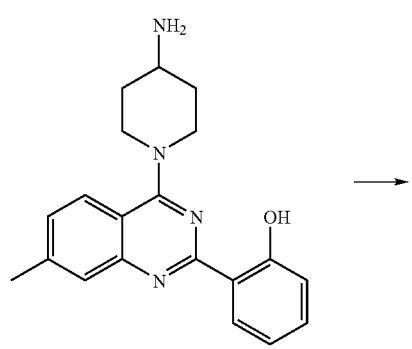

→

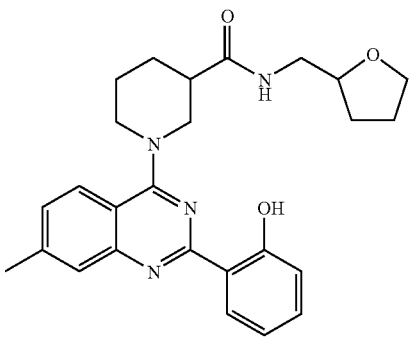

N-((Tetrahydrofuran-2-yl)methyl)-1-(2-(2-hydroxyphenyl)-7-methylquinazolin-4-yl)piperidine-3-carboxamide

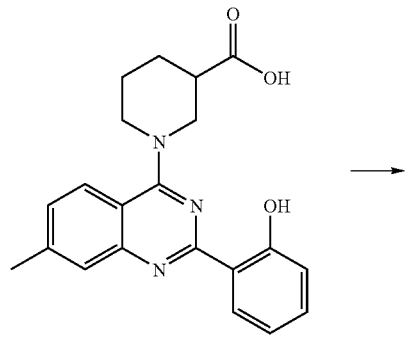

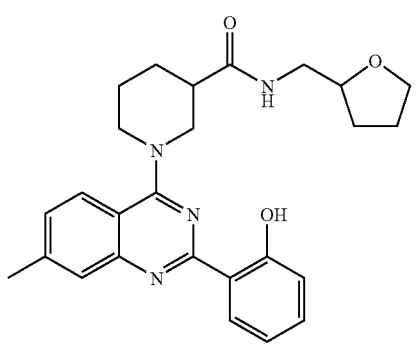

A solution of 1-(2-(2-hydroxyphenyl)-7-methylquinazolin-4-yl)piperidine-3-carboxylic acid (45 mg, 0.12 mmol) in 500 μL DMF was cooled to 0° C., and (tetrahydrofuran-2-yl)methanamine (13.2 mg, 0.13 mmol) and triethylamine (25 mg, 35 μL, 0.25 mmol) were added. After ten minutes HATU (57 mg, 0.15 mmol) was added to the reaction mixture in one portion. The reaction was allowed to warm to room temperature, stirred overnight, and purified by reverse phase HPLC (10%-99% CH₃CN (0.035% TFA)/H₂O (0.05% TFA)) yielding N-((tetrahydrofuran-2-yl)methyl)-1-(2-(2-hydroxyphenyl)-7-methylquinazolin-4-yl)piperidine-3-carboxamide as the TFA salt. LC/MS: m/z 447.3 (M+H)⁺ at 2.21 min (10%-99% CH₃CN (0.035% TFA)/H₂O (0.05% TFA)).

Example 231

(S)-Tetrahydrofuran-3-yl ((S)-1-(2-(2-fluoro-6-hydroxyphenyl)-7-methylquinazolin-4-yl)piperidin-3-yl)methylcarbamate

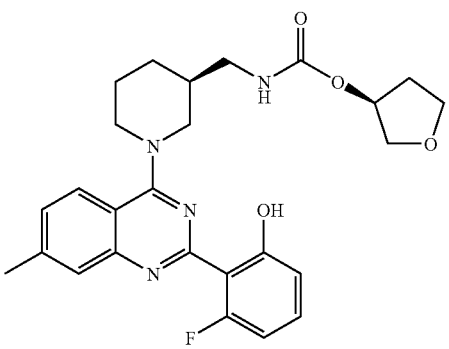

tert-butyl piperidin-3-ylmethylcarbamate

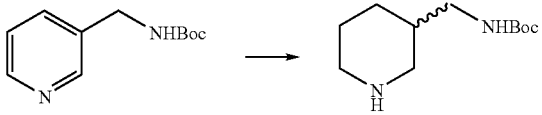

A cold solution of HCl in MeOH (prepared by adding acetyl chloride (13.5 mL, 14.9 g, 0.19 mol) to 1 L of MeOH) was added to a cold solution of tert-butyl pyridin-3-ylmethylcarbamate (41.0 grams, 0.20 mol) in MeOH (100 mL). The solution was transferred to a Parr hydrogenation apparatus at 12° C. PtO₂ (3 g) was added, and 12 bar pressure of H₂ was applied. After 16 hours ¹H NMR of a concentrated sample indicated the reaction to be complete. The catalyst was filtered, and conc. aq. NaOH (20 mL) was added to neutralize the HCl. The solution was concentrated to remove the bulk of the MeOH and extracted with tert-butyl methyl ether (4×200 mL). The combined organic layers were washed with saturated aqueous NaCl solution, dried over Na₂SO₄, and concentrated to give the product (40.16 g, 0.187 mol, 95%) as a yellow oil that crystallized upon standing. ¹H NMR (300 MHz, CDCl₃): δ 4.62 (bs. s, 1H), 3.06-2.94 (m, 4H), 2.52 (dt, J=12 Hz, 3 Hz, 1H), 2.28 (dd, J=12 Hz, 10 Hz, 1H), 1.82-1.72 (m, 1H), 1.70-1.51 (m, 3H), 1.49-1.34 (m, 1H), 1.42 (s, 9H), 1.06 (dq, J=12 Hz, 4 Hz, 1H) ppm.

(R)-tert-Butyl piperidin-3-ylmethylcarbamate

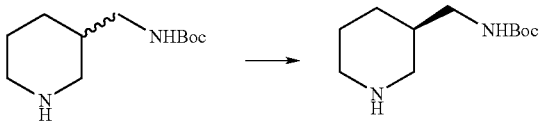

To a solution of tert-butyl piperidin-3-ylmethylcarbamate (162 g, 0.758 mol) in EtOH was added (+)-dianisoyltartaric acid (316 g, 0.756 mol). The suspension was heated until clear and allowed to cool to room temperature overnight. The precipitated salt was recrystallized three times from EtOH. The salt was washed with EtOH (2×200 mL) and air-dried. Residual solvent was removed in vacuo. The salt was taken up in tert-butyl methyl ether and 10% aq. NaOH. The organic layer was separated, and the aqueous layer was extracted with tert-butyl methyl ether (3×200 mL). More product was extracted after addition of 30% aq. NaOH to the aqueous layer. The combined organic layers were washed with water and saturated aqueous NaCl solution, dried over $Na_2SO_4$, and concentrated to give (R)-tert-butyl piperidin-3-ylmethylcarbamate as a white crystalline solid (41.3 g, 0.192 mol, 25%). For ee determinations, samples of the salt were taken up in $CH_2Cl_2$ and 1 N aq. NaOH. The organic layer was washed with water, dried over $Na_2SO_4$, and filtered. A drop of 1-naphthyl isocyanate was added, and after 15 minutes a drop of morpholine was added to quench excess isocyanate. Volatiles were evaporated after another 15 minutes. The sample was dissolved in EtOH for chiral HPLC (Chiralcel OD-H; heptane/EtOH/$Et_2NH$ 90/10/0.2; 0.5 mL/min; Rt (R): 46 min, Rt (S): 57 min, Rt (N-(naphthalen-1-yl)morpholine-4-carboxamide): 64 min.

2-(4-((S)-3-(Aminomethyl)piperidin-1-yl)-7-methylquinazolin-2-yl)-3-fluorophenol 2-(4-Chloro-7-methylquinazolin-2-yl)-3-fluorophenol (1.0 g, 3.46 mmol) was dissolved in 15 mL anhydrous $CH_2Cl_2$ under an $N_2$ atmosphere and cooled using an ice bath and (S)-piperidin-3-ylmethyl-carbamic acid tert-butyl ester/oxalic acid (1.16 g, 3.81 mmol) was added in portions, followed by triethylamine (1.05 g, 1.45 mL, 10.4 mmol). The reaction was allowed to warm to room temperature and was complete after 1.5 hour. The mixture was partitioned between $CH_2Cl_2$ and $H_2O$ and separated, and the aqueous layer was extracted once more with $CH_2Cl_2$. The organic extracts were combined, dried over $Na_2SO_4$, filtered, and concentrated to a yellow solid. This solid was suspended in 40 mL $CH_2Cl_2$ and 20 mL of TFA were added. The reaction was complete after 1 hour. The solvent and the excess TFA were removed in vacuo, the residue was re-dissolved in $CH_2Cl_2$, and the pH was adjusted to 7 using an aqueous 1 M solution of NaOH. The reaction was partitioned between $CH_2Cl_2$ and $H_2O$ and separated, and the aqueous layer was extracted once more with $CH_2Cl_2$. The organic extracts were combined, dried over $Na_2SO_4$, filtered, and concentrated to yield of 2-(4-((S)-3-(aminomethyl) piperidin-1-yl)-7-methylquinazolin-2-yl)-3-fluorophenol (900 mg, 71% overall yield) as a yellow solid. LC/MS: m/z 367.3 (M+H)$^+$ at 1.35 min (10%-99% $CH_3CN$ (0.035% TFA)/$H_2O$ (0.05% TFA)).

(S)-Tetrahydrofuran-3-yl ((S)-1-(2-(2-fluoro-6-hydroxyphenyl)-7-methylquinazolin-4-yl)piperidin-3-yl)methylcarbamate

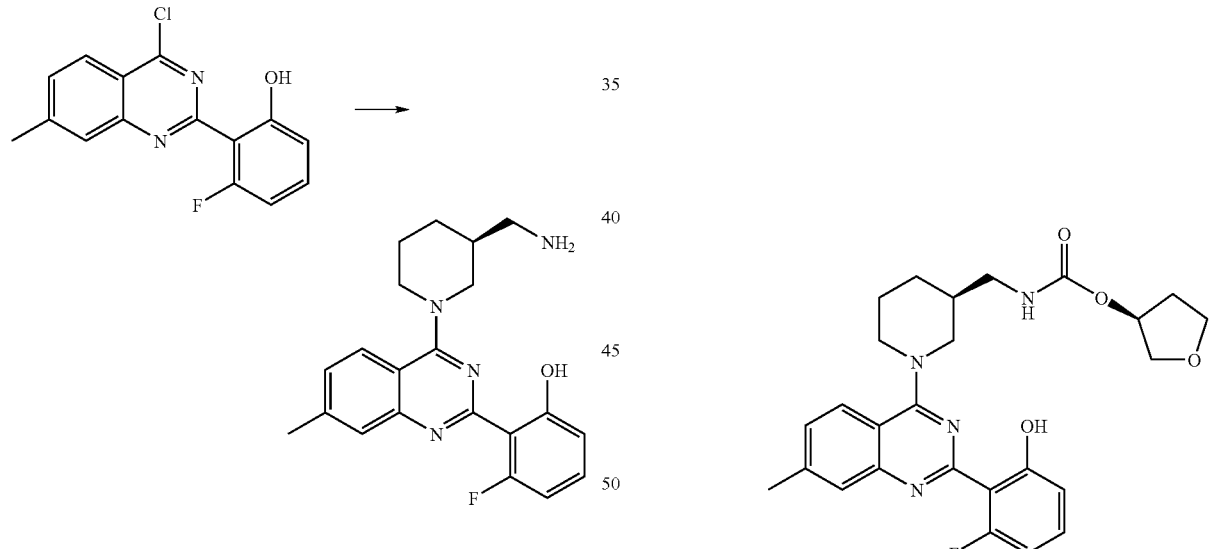

2-(4-((S)-3-(Aminomethyl)piperidin-1-yl)-7-methylquinazolin-2-yl)-3-fluorophenol (40 mg, 0.11 mmol) was dissolved in anhydrous DMF (800 μL) and cooled to 0° C., upon which (S)-tetrahydrofuran-3-yl chloroformate (16.3 mg, 0.12 mmol) dissolved in DMF (100 μL) was added dropwise followed by triethylamine (22 mg, 30.3 μL, 0.218 mmol). The reaction was allowed to warm to room temperature, and after 2 h the reaction was complete. The mixture was purified using reverse phase HPLC (10%-99% $CH_3CN$ (0.035% TFA)/$H_2O$ (0.05% TFA)) to yield (S)-tetrahydrofuran-3-yl ((S)-1-(2-(2-fluoro-6-hydroxyphenyl)-7-methylquinazolin-4-yl)piperidin-3-yl)methylcarbamate as the TFA salt. LC/MS: m/z 481.1 (M+H)+ at 2.17 min (10%-99% CH₃CN (0.035% TFA)/H₂O (0.05% TFA)).

Example 232

(2R)-2-Hydroxy-N-(1-(2-(2-hydroxyphenyl)-7-methylquinazolin-4-yl)piperidin-4-yl)-4,4-dimethylpentanamide

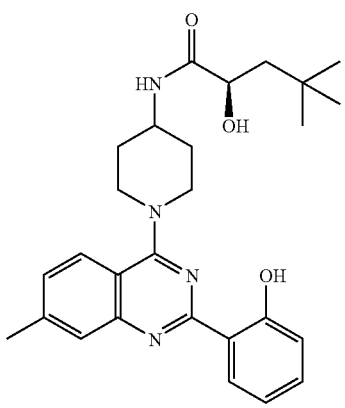

(2R)-2-Hydroxy-N-(1-(2-(2-hydroxyphenyl)-7-methylquinazolin-4-yl)piperidin-4-yl)-4,4-dimethylpentanamide

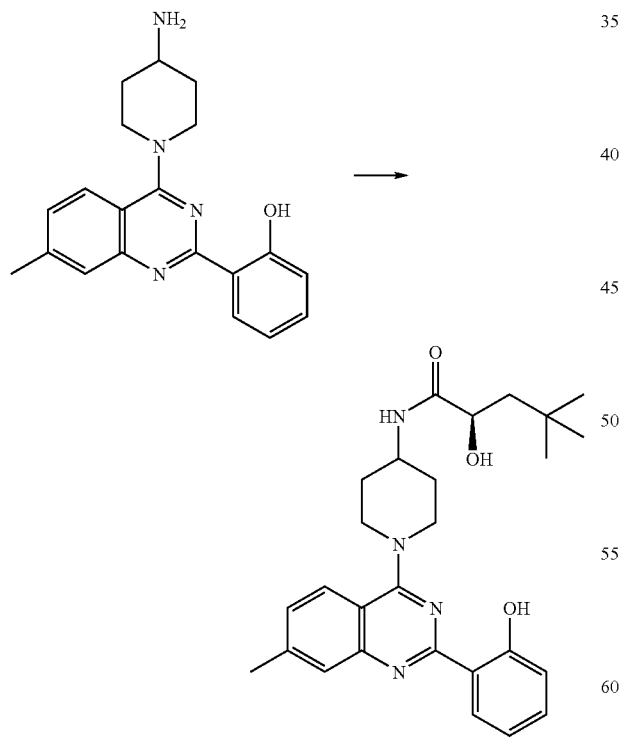

2-(4-(4-Aminopiperidin-1-yl)-7-methylquinazolin-2-yl)phenol (50 mg, 0.15 mmol) was dissolved in DMF (1 mL) and cooled to 0° C. (2R)-Hydroxy-4,4-dimethyl-pentanoic acid (26.3 mg, 0.18 mmol) was added followed by the addition of triethylamine (42 µL, 0.3 mmol). After ten minutes, HATU (68 mg, 0.18 mmol) was added in one portion. The reaction was stirred at 0° C. for 10 minutes, and then allowed to warm to room temperature. The reaction was complete after 40 minutes, then filtered, and purified by reverse phase HPLC (10%-99% CH₃CN (0.035% TFA)/H₂O (0.05% TFA)) to give (2R)-2-hydroxy-N-(1-(2-(2-hydroxyphenyl)-7-methylquinazolin-4-yl)piperidin-4-yl)-4,4-dimethylpentanamide as the TFA salt. LC/MS: m/z 463.3 (M+H)+ at 2.58 min (10%-99% CH₃CN (0.035% TFA)/H₂O (0.05% TFA)).

Example 233

2-Hydroxy-N-(1-(2-(2-hydroxyphenyl)-7-methylquinazolin-4-yl)piperidin-4-yl)-2-methylpropanamide

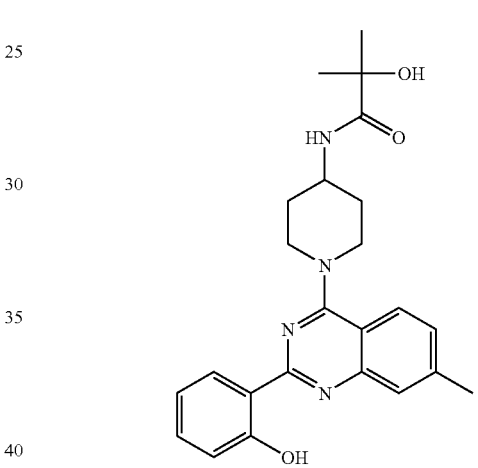

2-Hydroxy-N-(1-(2-(2-hydroxyphenyl)-7-methylquinazolin-4-yl)piperidin-4-yl)-2-methylpropanamide

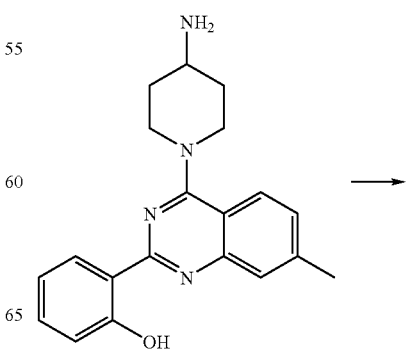

371
-continued 372
2-Ethyl-2-hydroxy-N-(1-(2-(2-hydroxyphenyl)-7-methylquinazolin-4-yl)piperidin-4-yl)butanamide

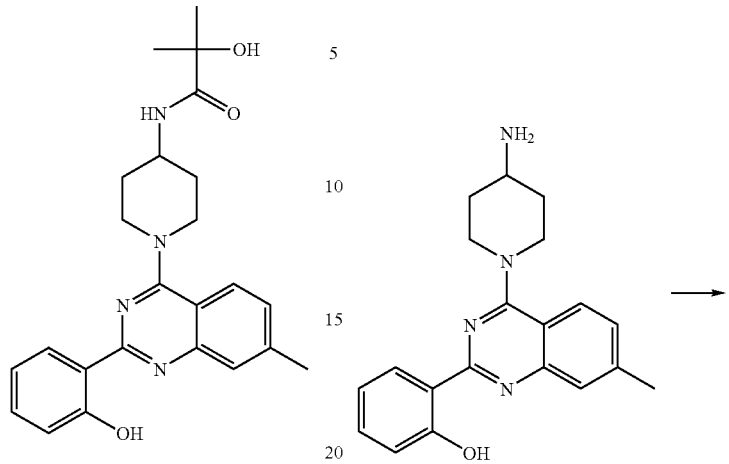

To 2-hydroxy-2-methylpropanoic acid (28 mg, 0.27 mmol) was added a solution of 2-(4-(4-aminopiperidin-1-yl)-7-methylquinazolin-2-yl)phenol (0.07 g, 0.21 mmol) in DMF (0.5 mL), followed by the addition of triethylamine (0.058 mL, 0.42 mmol) and a solution of HATU (0.103 g, 0.273 mmol) in DMF (0.5 mL). The reaction was stirred overnight, filtered, and purified using reverse phase HPLC (10%-99% CH$_3$CN (0.035% TFA)/H$_2$O (0.05% TFA)) to afford 2-hydroxy-N-(1-(2-(2-hydroxyphenyl)-7-methylquinazolin-4-yl)piperidin-4-yl)-2-methylpropanamide as the TFA salt. LC/MS: m/z 421.2 (M+H)$^+$ at 2.17 min (10%-99% CH$_3$CN (0.035% TFA)/H$_2$O (0.05% TFA)).

Example 234

2-Ethyl-2-hydroxy-N-(1-(2-(2-hydroxyphenyl)-7-methylquinazolin-4-yl)piperidin-4-yl)butanamide

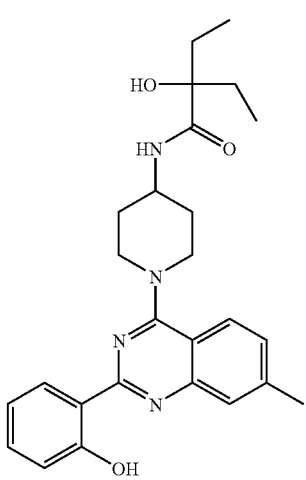

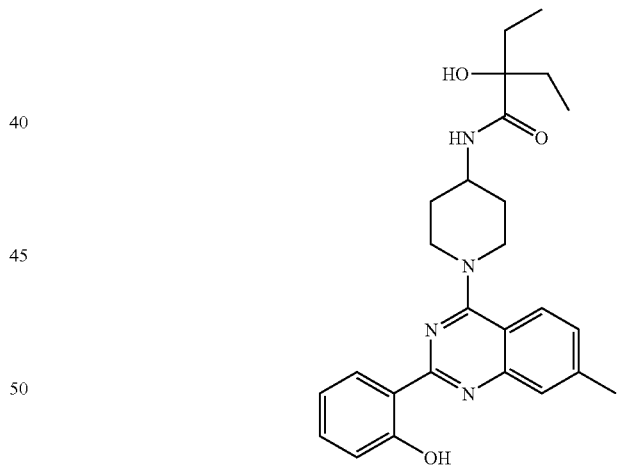

To 2-ethyl-2-hydroxybutanoic acid (36 mg, 0.27 mmol) was added a solution of 2-(4-(4-aminopiperidin-1-yl)-7-methylquinazolin-2-yl)phenol (0.07 g, 0.21 mmol) in DMF (0.5 mL) followed by the addition of triethylamine (0.058 mL, 0.42 mmol) and a solution HATU (0.103 g, 0.273 mmol) in DMF (0.5 mL). The reaction was stirred overnight, filtered, and purified using reverse phase HPLC (10%-99% CH$_3$CN (0.035% TFA)/H$_2$O (0.05% TFA)) to afford 2-ethyl-2-hydroxy-N-(1-(2-(2-hydroxyphenyl)-7-methylquinazolin-4- yl)piperidin-4-yl)butanamide as the TFA salt. LC/MS: m/z 449.2 (M+H)+ at 2.42 min (10%-99% CH₃CN (0.035% TFA)/H₂O (0.05% TFA)).

Example 235

2-Hydroxy-N-(1-(2-(2-hydroxyphenyl)quinazolin-4-yl)piperidin-4-yl)-2-methylpropanamide

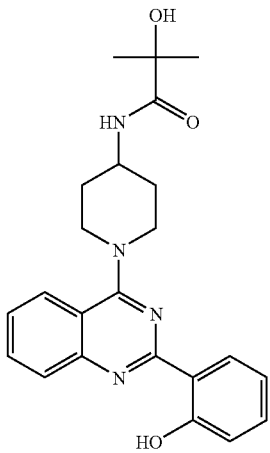

tert-Butyl 1-(2-(2-hydroxyphenyl)quinazolin-4-yl)piperidin-4-ylcarbamate

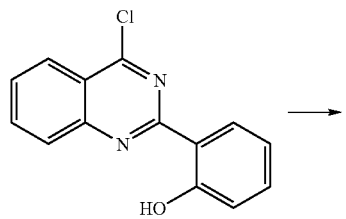

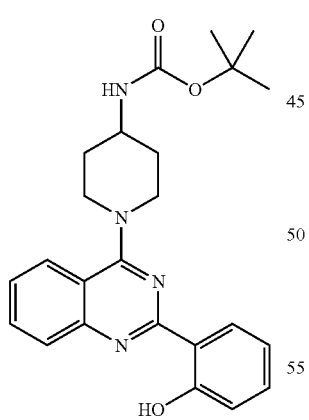

To a suspension of 2-(4-chloroquinazolin-2-yl)phenol (2.0 g, 7.79 mmol) in CH₂Cl₂ (25 mL) at 0° C. under an N₂ atmosphere, was added dropwise tert-butyl piperidin-4-ylcarbamate (2.08 g, 10.13 mmol) and triethylamine (2.20 mL, 15.8 mmol) in CH₂Cl₂ (10 mL). The reaction was stirred overnight, quenched with water and extracted with CH₂Cl₂, and the combined organic layers were dried over MgSO₄, filtered, and concentrated to afford tert-butyl 1-(2-(2-hydroxyphenyl)quinazolin-4-yl)piperidin-4-ylcarbamate (3.27 g, 100%-solvent residue). LC/MS: m/z 421.3 (M+H)+ at 2.70 min (10%-99% CH₃CN (0.035% TFA)/H₂O (0.05% TFA)).

2-(4-(4-Aminopiperidin-1-yl)quinazolin-2-yl)phenol

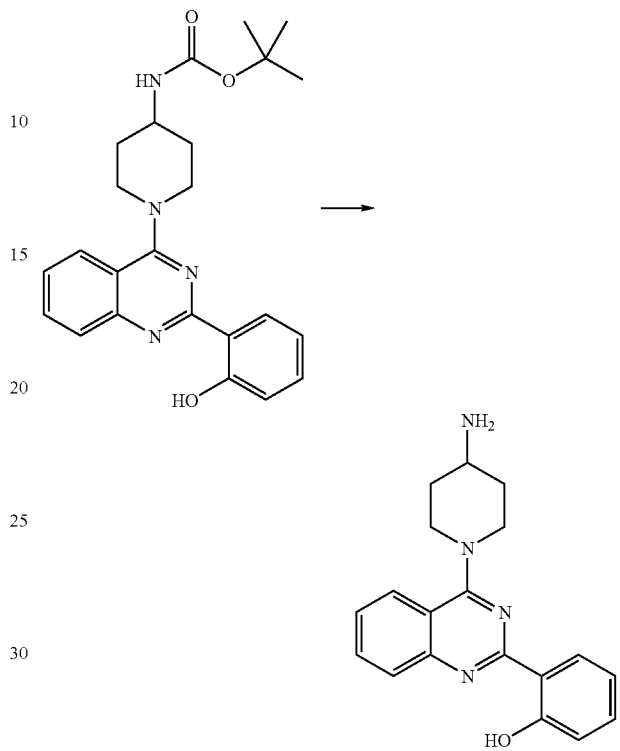

To a solution of tert-butyl 1-(2-(2-hydroxyphenyl)quinazolin-4-yl)piperidin-4-ylcarbamate (3.27 g, 8.09 mmol) in CH₂Cl₂ (75 mL) was added TFA (50 mL). The reaction was complete after 45 minutes After evaporating the solvents in vacuo, the crude material was diluted with CH₂Cl₂ and neutralized by adding a 1 N aqueous NaOH solution. The layers were separated, and the aqueous layer was extracted with CH₂Cl₂ (2×15 mL). The combined organic layers were dried over MgSO₄, filtered, and concentrated to afford 2-(4-(4-aminopiperidin-1-yl)quinazolin-2-yl)phenol as a solid (2.09 g, 84%). LC/MS: m/z 321.3 (M+H)+ at 1.28 min (10%-99% CH₃CN (0.035% TFA)/H₂O (0.05% TFA)).

2-Hydroxy-N-(1-(2-(2-hydroxyphenyl)quinazolin-4-yl)piperidin-4-yl)-2-methylpropanamide

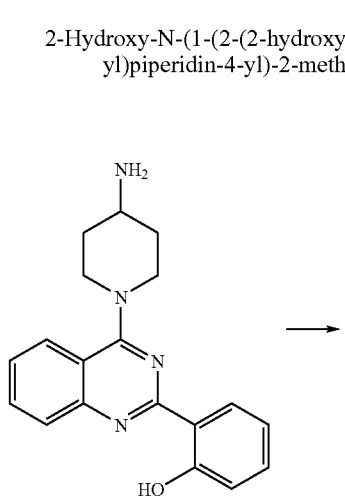

375
-continued 376
(2R)-2-Hydroxy-N-(1-(2-(2-hydroxyphenyl)quinazo-
lin-4-yl)piperidin-4-yl)butanamide

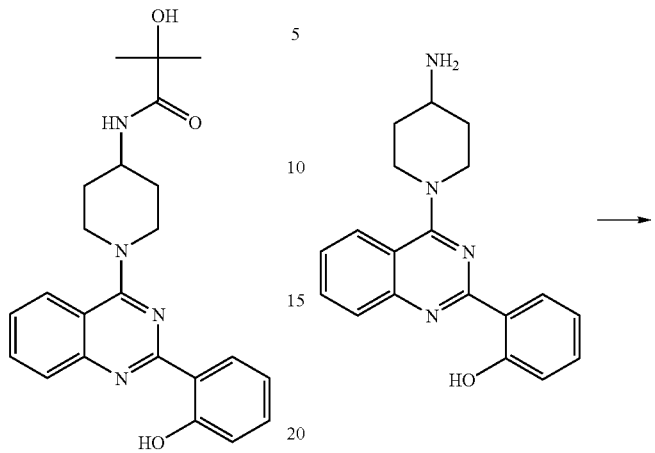

To 2-hydroxy-2-methylpropanoic acid (27 mg, 0.28 mmol) was added a solution of 2-(4-(4-aminopiperidin-1-yl)quinazolin-2-yl)phenol (0.07 g, 0.22 mmol) in DMF (0.5 mL) followed by the addition of triethylamine (0.061 mL, 0.44 mmol) and a solution of HATU (0.107 g, 0.284 mmol) in DMF (0.5 mL). The reaction was stirred overnight, filtered, and purified using reverse phase HPLC (10%-99% CH$_3$CN (0.035% TFA)/H$_2$O (0.05% TFA)) to afford 2-hydroxy-N-(1-(2-(2-hydroxyphenyl)quinazolin-4-yl)piperidin-4-yl)-2-methylpropanamide as the TFA salt. LC/MS: m/z 407.5 (M+H)$^+$ at 2.04 min (10%-99% CH$_3$CN (0.035% TFA)/H$_2$O (0.05% TFA)).

Example 236

(2R)-2-Hydroxy-N-(1-(2-(2-hydroxyphenyl)quinazo-
lin-4-yl)piperidin-4-yl)butanamide

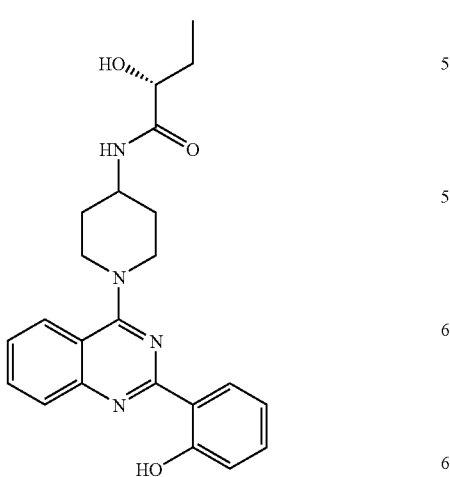

To (R)-2-hydroxybutanoic acid (30 mg, 0.28 mmol) was added a solution of 2-(4-(4-aminopiperidin-1-yl)quinazolin-2-yl)phenol (0.07 g, 0.22 mmol) in DMF (0.5 mL) followed by the addition of triethylamine (0.061 mL, 0.44 mmol) and a solution of HATU (0.107 g, 0.284 mmol) dissolved in DMF (0.5 mL). The reaction was stirred overnight, filtered, and purified using reverse phase HPLC (10%-99% CH$_3$CN (0.035% TFA)/H$_2$O (0.05% TFA)) to afford (2R)-2-hydroxy-N-(1-(2-(2-hydroxyphenyl)quinazolin-4-yl)piperidin-4-yl)butanamide as the TFA salt. LC/MS: m/z 407.3 (M+H)$^+$ at 2.08 min (10%-99% CH$_3$CN (0.035% TFA)/H$_2$O (0.05% TFA)).

Example 237

(2S)-2-Hydroxy-N-(1-(2-(2-hydroxyphenyl)quinazolin-4-yl)piperidin-4-yl)butanamide

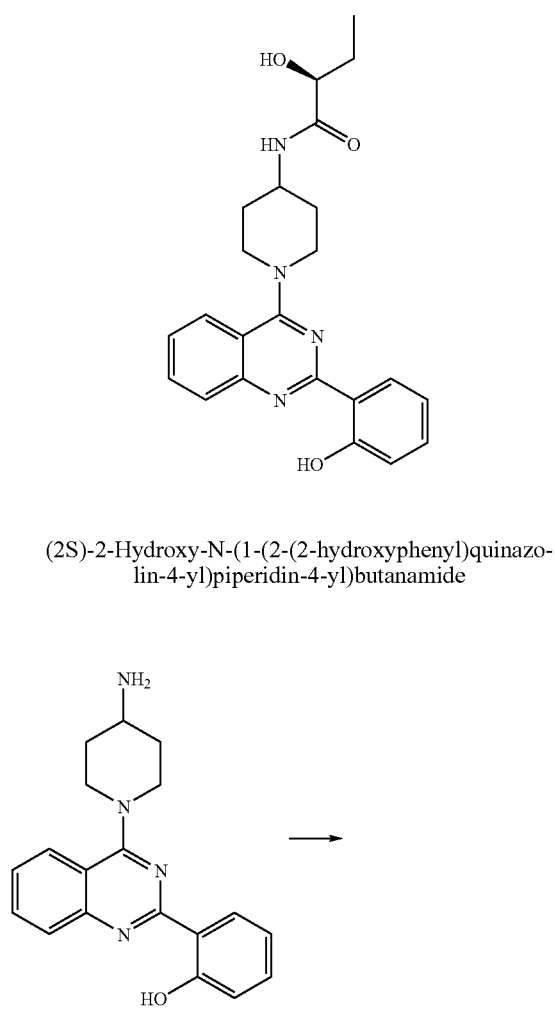

(2S)-2-Hydroxy-N-(1-(2-(2-hydroxyphenyl)quinazolin-4-yl)piperidin-4-yl)butanamide To (S)-2-hydroxybutanoic acid (30 mg, 0.28 mmol) was added a solution of 2-(4-(4-aminopiperidin-1-yl)quinazolin-2-yl)phenol (0.07 g, 0.22 mmol) in DMF (0.5 mL) followed by the addition of triethylamine (0.061 mL, 0.44 mmol) and a solution of HATU (0.107 g, 0.284 mmol) in DMF (0.5 mL). The reaction was stirred overnight, filtered, and purified using reverse phase HPLC (10%-99% CH$_3$CN (0.035% TFA)/H$_2$O (0.05% TFA)) to afford (2S)-2-hydroxy-N-(1-(2-(2-hydroxyphenyl)quinazolin-4-yl)piperidin-4-yl)butanamide as the TFA salt. LC/MS: m/z 407.3 (M+H)$^+$ at 2.09 min (10%-99% CH$_3$CN (0.035% TFA)/H$_2$O (0.05% TFA)).

Example 238

2-Hydroxy-N-(1-(2-(2-hydroxyphenyl)quinazolin-4-yl)piperidin-4-yl)hexanamide

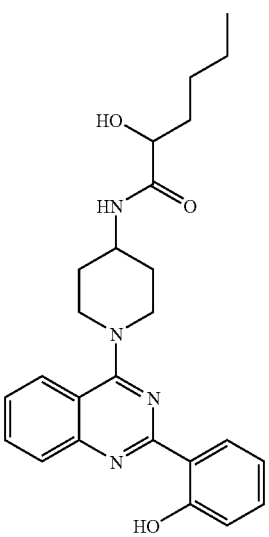

2-Hydroxy-N-(1-(2-(2-hydroxyphenyl)quinazolin-4-yl)piperidin-4-yl)hexanamide

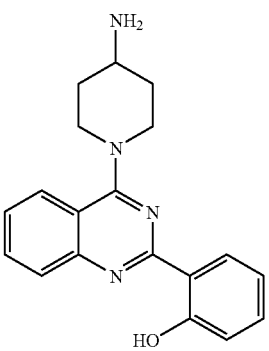

379
-continued

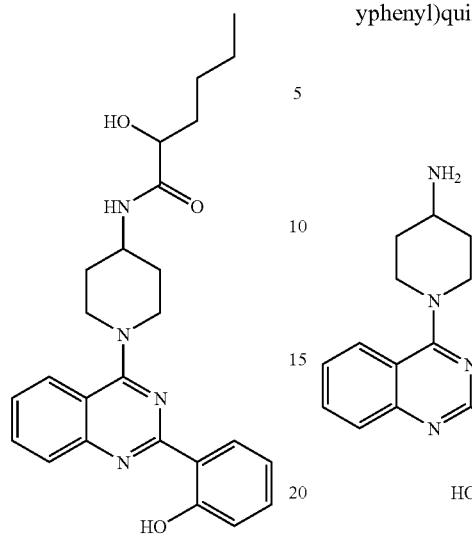

To 2-hydroxyhexanoic acid (38 mg, 0.28 mmol) was added a solution of 2-(4-(4-aminopiperidin-1-yl)quinazolin-2-yl)phenol (0.07 g, 0.22 mmol) in DMF (0.5 mL) followed by the addition of triethylamine (0.061 mL, 0.44 mmol) and a solution of HATU (0.107 g, 0.284 mmol) in DMF (0.5 mL). The reaction was stirred overnight, filtered, and purified using reverse phase HPLC (10%-99% CH$_3$CN (0.035% TFA)/H$_2$O (0.05% TFA)) to afford 2-hydroxy-N-(1-(2-(2-hydroxyphenyl)quinazolin-4-yl)piperidin-4-yl)hexanamide as the TFA salt. LC/MS: m/z 435.3 (M+H)$^+$ at 2.4 min (10%-99% CH$_3$CN (0.035% TFA)/H$_2$O (0.05% TFA)).

Example 239

2-(Trifluoromethyl)-2-hydroxy-N-(1-(2-(2-hydroxyphenyl)quinazolin-4-yl)piperidin-4-yl)propanamide

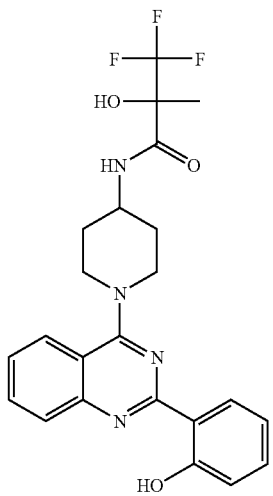

380

2-(Trifluoromethyl)-2-hydroxy-N-(1-(2-(2-hydroxyphenyl)quinazolin-4-yl)piperidin-4-yl)propanamide

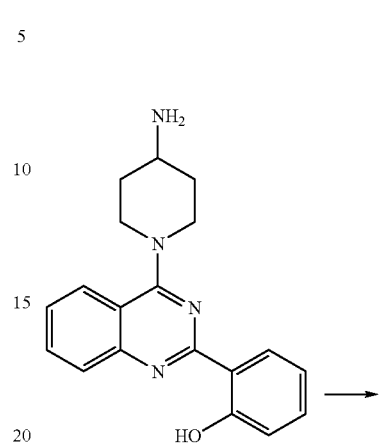

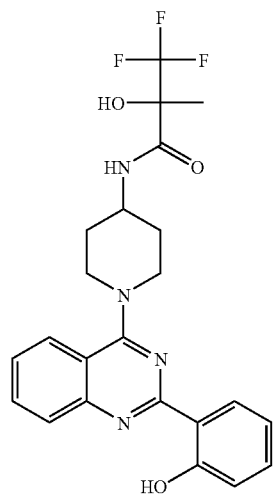

To 2-(trifluoromethyl)-2-hydroxypropanoic acid (45 mg, 0.28 mmol) was added a solution of 2-(4-(4-aminopiperidin-1-yl)quinazolin-2-yl)phenol (0.07 g, 0.22 mmol) dissolved in DMF (0.5 mL) followed by the addition of triethylamine (0.061 mL, 0.44 mmol) and a solution of HATU (0.107 g, 0.284 mmol) in DMF (0.5 mL). The reaction was stirred overnight, filtered, and purified using reverse phase HPLC (10%-99% CH$_3$CN (0.035% TFA)/H$_2$O (0.05% TFA)) to afford 2-(trifluoromethyl)-2-hydroxy-N-(1-(2-(2-hydroxyphenyl)quinazolin-4-yl)piperidin-4-yl)propanamide as the TFA salt. LC/MS: m/z 461.1 (M+H)+ at 2.4 min (10%-99% CH₃CN (0.035% TFA)/H₂O (0.05% TFA)).

Example 240

2-Ethyl-2-hydroxy-N-(1-(2-(2-hydroxyphenyl)quinazolin-4-yl)piperidin-4-yl)butanamide

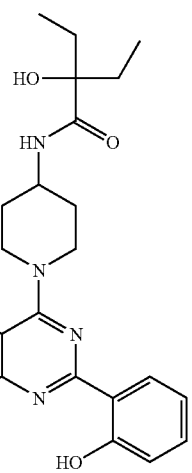

2-Ethyl-2-hydroxy-N-(1-(2-(2-hydroxyphenyl)quinazolin-4-yl)piperidin-4-yl)butanamide

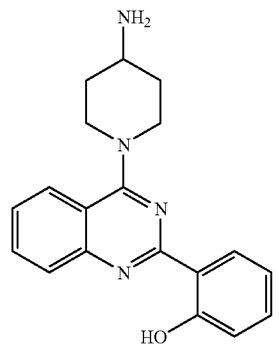

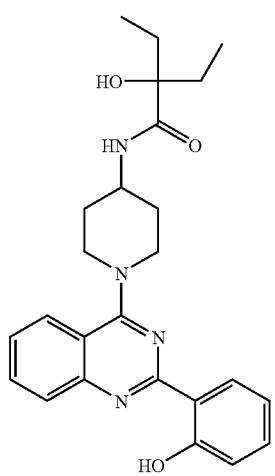

To 2-ethyl-2-hydroxybutanoic acid (38 mg, 0.28 mmol) was added a solution of 2-(4-(4-aminopiperidin-1-yl)quinazolin-2-yl)phenol (0.07 g, 0.22 mmol) in DMF (0.5 mL) followed by the addition of triethylamine (0.061 mL, 0.44 mmol) and a solution of HATU (0.107 g, 0.284 mmol) in DMF (0.5 mL). The reaction was stirred overnight, filtered, and purified using reverse phase HPLC (10%-99% CH₃CN (0.035% TFA)/H₂O (0.05% TFA)) to afford 2-ethyl-2-hydroxy-N-(1-(2-(2-hydroxyphenyl)quinazolin-4-yl)piperidin-4-yl)butanamide as the TFA salt. LC/MS: m/z 435.5 (M+H)+ at 2.29 min (10%-99% CH₃CN (0.035% TFA)/H₂O (0.05% TFA)).

Example 241

2-Hydroxy-N-(1-(2-(2-hydroxyphenyl)quinazolin-4-yl)piperidin-4-yl)pentanamide

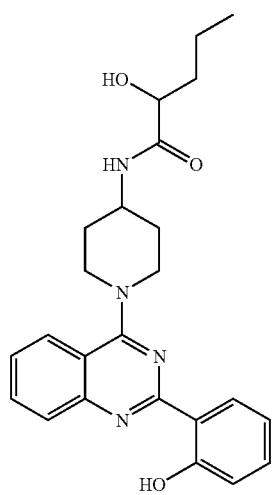

2-Hydroxy-N-(1-(z-(2-hydroxyphenyl)quinazolin-4-yl)piperidin-4-yl)pentanamide

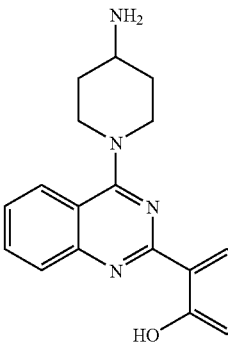

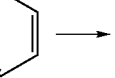

384

2-Hydroxy-N-(1-(2-(2-hydroxyphenyl)quinazolin-4-yl)piperidin-4-yl)-2-methylbutanamide

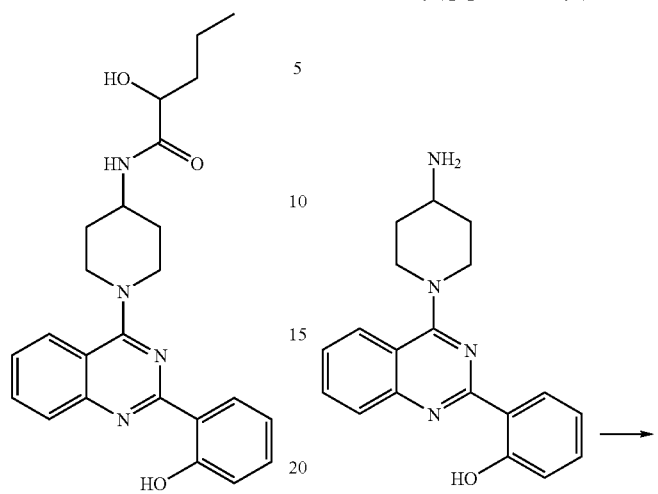

To 2-hydroxypentanoic acid (34 mg, 0.28 mmol) was added a solution of 2-(4-(4-aminopiperidin-1-yl)quinazolin-2-yl)phenol (0.07 g, 0.22 mmol) in DMF (0.5 mL) followed by the addition of triethylamine (0.061 mL, 0.44 mmol) and a solution of HATU (0.107 g, 0.284 mmol) in DMF (0.5 mL). The reaction was stirred overnight, filtered, and purified using reverse phase HPLC (10%-99% CH$_3$CN (0.035% TFA)/H$_2$O (0.05% TFA)) to afford 2-hydroxy-N-(1-(2-(2-hydroxyphenyl)quinazolin-4-yl)piperidin-4-yl)pentanamide as the TFA salt. LC/MS: m/z 421.1 (M+H)$^+$ at 2.24 min (10%-99% CH$_3$CN (0.035% TFA)/H$_2$O (0.05% TFA)).

Example 242

2-Hydroxy-N-(1-(2-(2-hydroxyphenyl)quinazolin-4-yl)piperidin-4-yl)-2-methylbutanamide

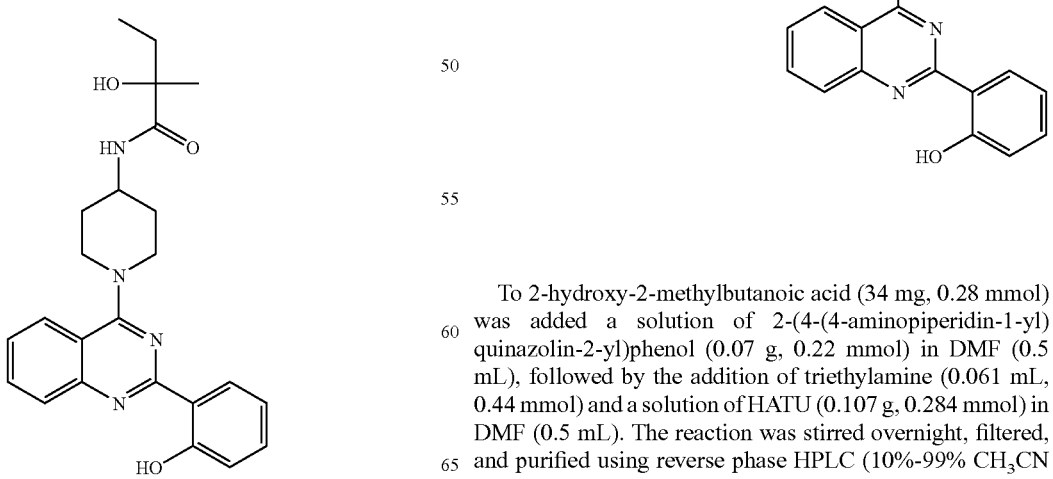

To 2-hydroxy-2-methylbutanoic acid (34 mg, 0.28 mmol) was added a solution of 2-(4-(4-aminopiperidin-1-yl)quinazolin-2-yl)phenol (0.07 g, 0.22 mmol) in DMF (0.5 mL), followed by the addition of triethylamine (0.061 mL, 0.44 mmol) and a solution of HATU (0.107 g, 0.284 mmol) in DMF (0.5 mL). The reaction was stirred overnight, filtered, and purified using reverse phase HPLC (10%-99% CH$_3$CN (0.035% TFA)/H$_2$O (0.05% TFA)) to afford 2-hydroxy-N-(1-(2-(2-hydroxyphenyl)quinazolin-4-yl)piperidin-4-yl)-2-methylbutanamide as the TFA salt. LC/MS: m/z 421.3 (M+H)+ at 2.18 min (10%-99% CH3CN (0.035% TFA)/H2O (0.05% TFA)).

Example 243

(2R)-2-Hydroxy-N-(1-(2-(2-hydroxyphenyl)-7-methylquinazolin-4-yl)piperidin-4-yl)butanamide

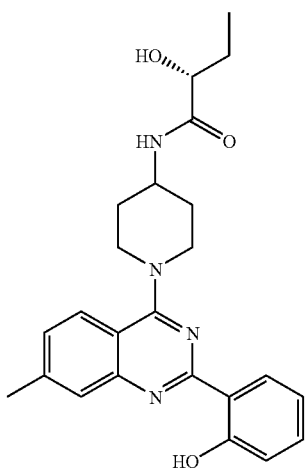

(2R)-2-Hydroxy-N-(1-(2-(2-hydroxyphenyl)-7-methylquinazolin-4-yl)piperidin-4-yl)butanamide

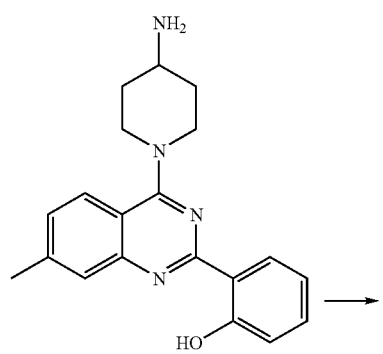

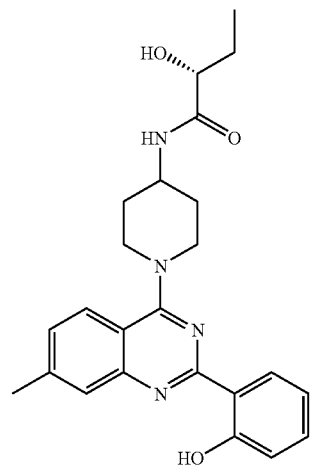

To (R)-2-hydroxybutanoic acid (28 mg, 0.27 mmol) was added a solution of 2-(4-(4-aminopiperidin-1-yl)-7-methylquinazolin-2-yl)phenol (0.07 g, 0.21 mmol) in DMF (0.5 mL) followed by the addition of triethylamine (0.058 mL, 0.42 mmol) and a solution of HATU (0.103 g, 0.273 mmol) in DMF (0.5 mL). The reaction was stirred overnight, filtered, and purified using reverse phase HPLC (10%-99% CH3CN (0.035% TFA)/H2O (0.05% TFA)) to afford (2R)-2-hydroxy-N-(1-(2-(2-hydroxyphenyl)-7-methylquinazolin-4-yl)piperidin-4-yl)butanamide as the TFA salt. LC/MS: m/z 421.3 (M+H)+ at 2.18 min (10%-99% CH3CN (0.035% TFA)/H2O (0.05% TFA)).

Example 244

(2S)-2-Hydroxy-N-(1-(2-(2-hydroxyphenyl)-7-methylquinazolin-4-yl)piperidin-4-yl)butanamide

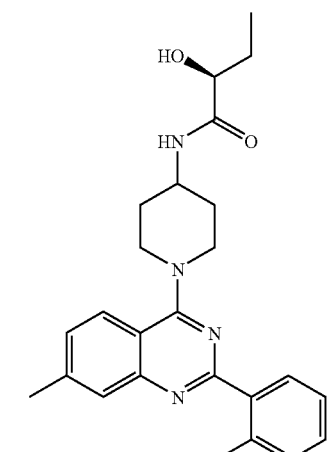

387

(2S)-2-Hydroxy-N-(1-(2-(2-hydroxyphenyl)-7-methylquinazolin-4-yl)piperidin-4-yl)butanamide

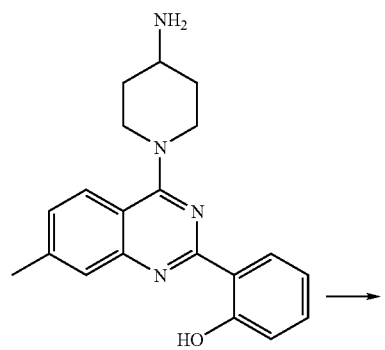

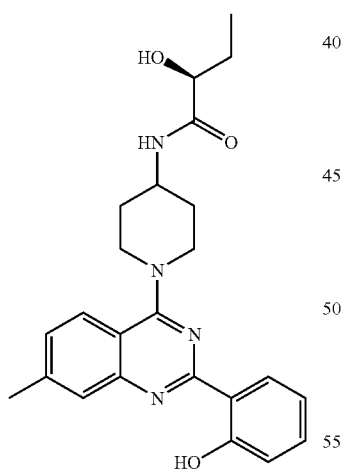

To (S)-2-hydroxybutanoic acid (28 mg, 0.27 mmol) was added a solution of 2-(4-(4-aminopiperidin-1-yl)-7-methylquinazolin-2-yl)phenol (0.07 g, 0.21 mmol) in DMF (0.5 mL), followed by the addition of triethylamine (0.058 mL, 0.42 mmol) and a solution of HATU (0.103 g, 0.273 mmol) in DMF (0.5 mL). The reaction was stirred overnight, then filtered, and purified using reverse phase HPLC (10%-99% CH₃CN (0.035% TFA)/H₂O (0.05% TFA)) to afford (2S)-2-hydroxy-N-(1-(2-(2-hydroxyphenyl)-7-methylquinazolin-4-

388 yl)piperidin-4-yl)butanamide as the TFA salt. LC/MS: m/z 421.3 (M+H)⁺ at 2.18 min (10%-99% CH₃CN (0.035% TFA)/H₂O (0.05% TFA)).

Example 245

2-Hydroxy-N-(1-(2-(2-hydroxyphenyl)-7-methylquinazolin-4-yl)piperidin-4-yl)hexanamide

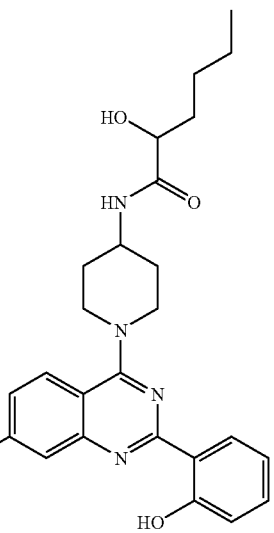

2-Hydroxy-N-(1-(2-(2-hydroxyphenyl)-7-methylquinazolin-4-yl)piperidin-4-yl)hexanamide

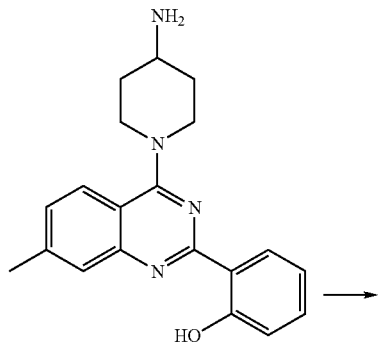

389
-continued

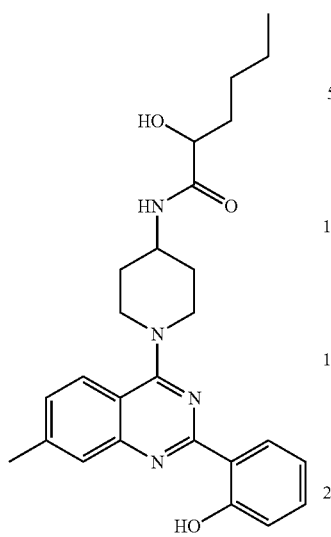

To 2-hydroxyhexanoic acid (36 mg, 0.27 mmol) was added a solution of 2-(4-(4-aminopiperidin-1-yl)-7-methylquinazolin-2-yl)phenol (0.07 g, 0.21 mmol) in DMF (0.5 mL) followed by the addition of triethylamine (0.058 mL, 0.42 mmol) and a solution of HATU (0.103 g, 0.273 mmol) in DMF (0.5 mL). The reaction was stirred overnight, filtered, and purified using reverse phase HPLC (10%-99% CH$_3$CN (0.035% TFA)/H$_2$O (0.05% TFA)) to afford 2-hydroxy-N-(1-(2-(2-hydroxyphenyl)-7-methylquinazolin-4-yl)piperidin-4-yl)hexanamide as the TFA salt. LC/MS: m/z 449.3 (M+H)$^+$ at 2.45 min (10%-99% CH$_3$CN (0.035% TFA)/H$_2$O (0.05% TFA)).

Example 246

2-(Trifluoromethyl)-2-hydroxy-N-(1-(2-(2-hydroxyphenyl)-7-methylquinazolin-4-yl)piperidin-4-yl)propanamide

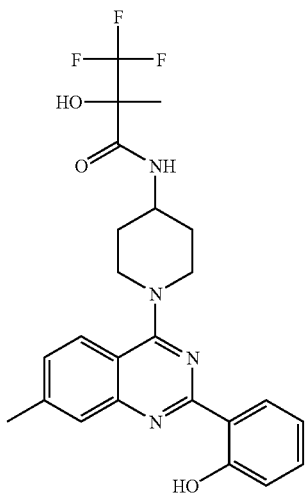

390

2-(Trifluoromethyl)-2-hydroxy-N-(1-(2-(2-hydroxyphenyl)-7-methylquinazolin-4-yl)piperidin-4-yl)propanamide

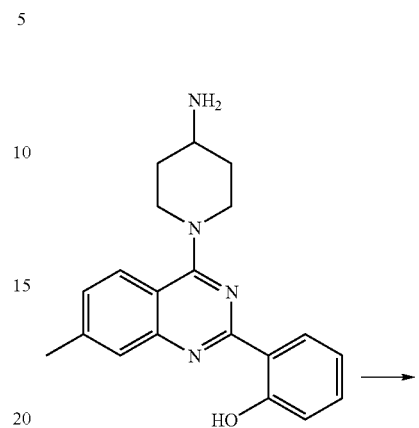

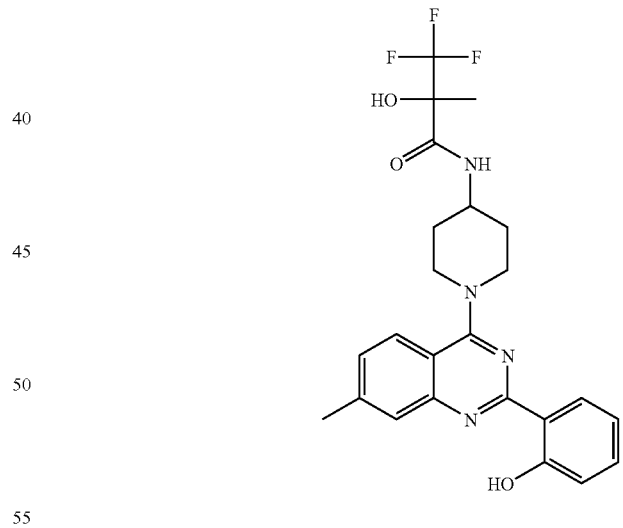

To 2-(trifluoromethyl)-2-hydroxypropanoic acid (43 mg, 0.27 mmol) was added a solution of 2-(4-(4-aminopiperidin-1-yl)-7-methylquinazolin-2-yl)phenol (0.07 g, 0.21 mmol) in DMF (0.5 mL) followed by the addition of triethylamine (0.058 mL, 0.42 mmol) and a solution of HATU (0.103 g, 0.273 mmol) in DMF (0.5 mL). The reaction was stirred overnight, filtered, and purified using reverse phase HPLC (10%-99% CH$_3$CN (0.035% TFA)/H$_2$O (0.05% TFA)) to afford 2-(trifluoromethyl)-2-hydroxy-N-(1-(2-(2-hydroxyphenyl)-7-methylquinazolin-4-yl)piperidin-4-yl)propanamide as the TFA salt. LC/MS: m/z 475.1 (M+H)+ at 2.46 min (10%-99% CH₃CN (0.035% TFA)/H₂O (0.05% TFA)).

Example 247

2-Hydroxy-N-(1-(2-(2-hydroxyphenyl)-7-methylquinazolin-4-yl)piperidin-4-yl)pentanamide

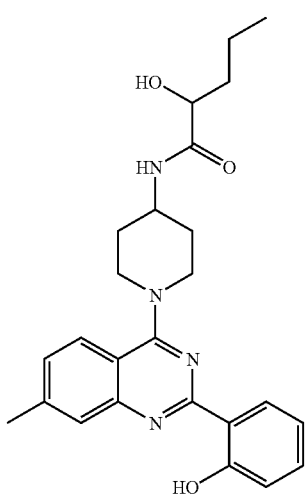

2-Hydroxy-N-(1-(2-(2-hydroxyphenyl)-7-methylquinazolin-4-yl)piperidin-4-yl)pentanamide

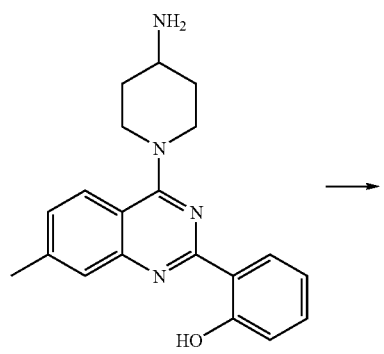 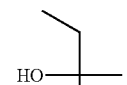

-continued

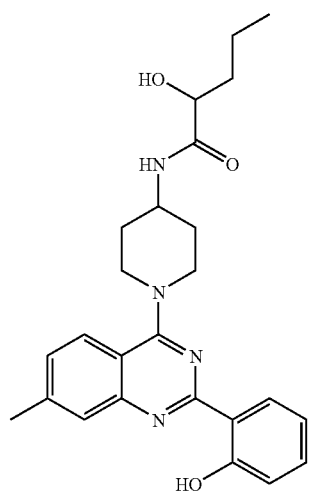

To 2-hydroxypentanoic acid (32 mg, 0.27 mmol) was added a solution of 2-(4-(4-aminopiperidin-1-yl)-7-methylquinazolin-2-yl)phenol (0.07 g, 0.21 mmol) in DMF (0.5 mL), followed by the addition of triethylamine (0.058 mL, 0.42 mmol) and a solution of HATU (0.103 g, 0.273 mmol) in DMF (0.5 mL). The reaction was stirred overnight, filtered, and purified using reverse phase HPLC (10%-99% CH₃CN (0.035% TFA)/H₂O (0.05% TFA)) to afford 2-hydroxy-N-(1-(2-(2-hydroxyphenyl)-7-methylquinazolin-4-yl)piperidin-4-yl)pentanamide as the TFA salt. LC/MS: m/z 435.3 (M+H)+ at 2.31 min (10%-99% CH₃CN (0.035% TFA)/H₂O (0.05% TFA)).

Example 248

2-Hydroxy-N-(1-(2-(2-hydroxyphenyl)-7-methylquinazolin-4-yl)piperidin-4-yl)-2-methylbutanamide

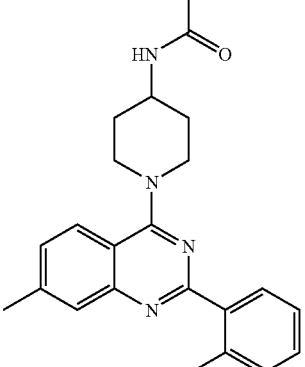

393

2-Hydroxy-N-(1-(2-(2-hydroxyphenyl)-7-methylquinazolin-4-yl)piperidin-4-yl)-2-methylbutanamide

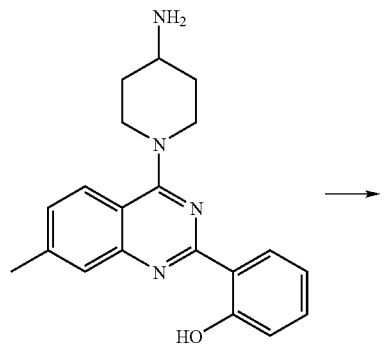

394 yl)-2-methylbutanamide as the TFA salt. LC/MS: m/z 435.3 (M+H)$^+$ at 2.24 min (10%-99% CH$_3$CN (0.035% TFA)/H$_2$O (0.05% TFA)).

Example 249

(2R)—N-(1-(2-(2-Fluoro-6-hydroxyphenyl)-7-methylquinazolin-4-yl)piperidin-4-yl)-2-hydroxy-4,4-dimethylpentanamide

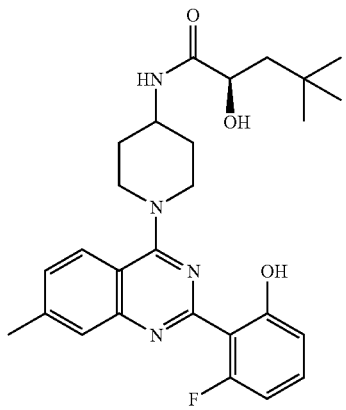

tert-Butyl 1-(2-(2-fluoro-6-hydroxyphenyl)-7-methylquinazolin-4-yl)piperidin-4-ylcarbamate

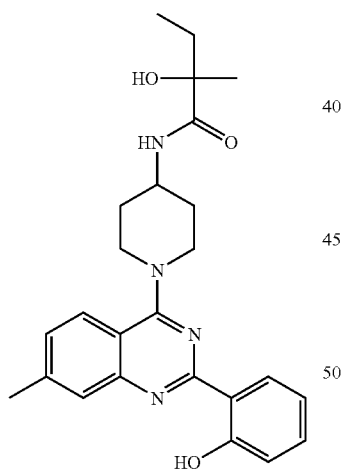

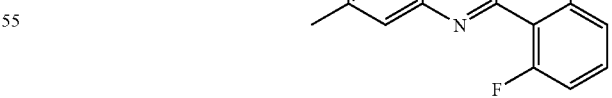

To 2-hydroxy-2-methylbutanoic acid (32 mg, 0.27 mmol) was added a solution of 2-(4-(4-aminopiperidin-1-yl)-7-methylquinazolin-2-yl)phenol (0.07 g, 0.21 mmol) in DMF (0.5 mL) followed by the addition of triethylamine (0.058 mL, 0.42 mmol) and a solution of HATU (0.103 g, 0.273 mmol) in DMF (0.5 mL). The reaction was stirred overnight, filtered, and purified using reverse phase HPLC (10%-99% CH$_3$CN (0.035% TFA)/H$_2$O (0.05% TFA)) to afford 2-hydroxy-N-(1-(2-(2-hydroxyphenyl)-7-methylquinazolin-4-yl)piperidin-4-

To a solution of 2-(4-chloro-7-methylquinazolin-2-yl)-3-fluorophenol (700 mg, 2.42 mmol) in 10 ml CH$_2$Cl$_2$ at 0° C. was added triethylamine (0.67 mL, 4.8 mmol) followed by the addition of tert-butyl piperidin-4-ylcarbamate (630 mg, 3.14 mmol) under an N$_2$ atmosphere. The reaction was gradually warmed to room temperature and stirred overnight. The reaction mixture was then quenched with water, and the layers were separated. The aqueous layer was extracted twice with CH$_2$Cl$_2$, and the combined organic layers were dried over MgSO$_4$, filtered, and concentrated to obtain tert-butyl 1-(2-(2-fluoro-6-hydroxyphenyl)-7-methylquinazolin-4-yl)piperidin-4-ylcarbamate (1.05 g, 96%) LC/MS: m/z 453.3 (M+H)$^+$ at 2.60 min (10%-99% CH$_3$CN (0.035% TFA)/H$_2$O (0.05% TFA)).

2-(4-(4-Aminopiperidin-1-yl)-7-methylquinazolin-2-yl)-3-fluorophenol

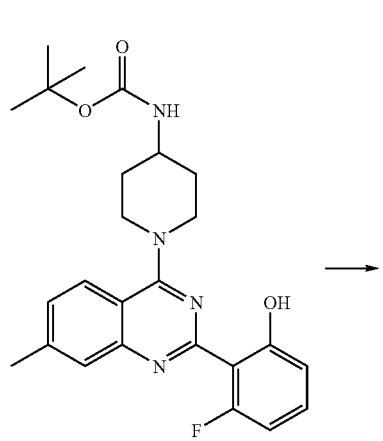

To a solution of tert-butyl 1-(2-(2-fluoro-6-hydroxyphenyl)-7-methylquinazolin-4-yl)piperidin-4-ylcarbamate (1.05 g, 2.3 mmol) in 20 ml CH$_2$Cl$_2$ was slowly added TFA (5 mL). The reaction was stirred for one hour before it was evaporated to dryness. To the residue was added CH$_2$Cl$_2$, and the reaction was neutralized using an aqueous 1 M NaOH solution. The aqueous layer was extracted twice with CH$_2$Cl$_2$, and the combined organic layers were dried over MgSO4, filtered, and concentrated to obtain 2-(4-(4-aminopiperidin-1-yl)-7-methylquinazolin-2-yl)-3-fluorophenol (0.75 g, 92%). LC/MS: m/z 353.3 (M+H)$^+$ at 1.35 min (10%-99% CH$_3$CN (0.035% TFA)/H$_2$O (0.05% TFA)).

(2R)—N-(1-(2-(2-Fluoro-6-hydroxyphenyl)-7-methylquinazolin-4-yl)piperidin-4-yl)-2-hydroxy-4,4-dimethylpentanamide

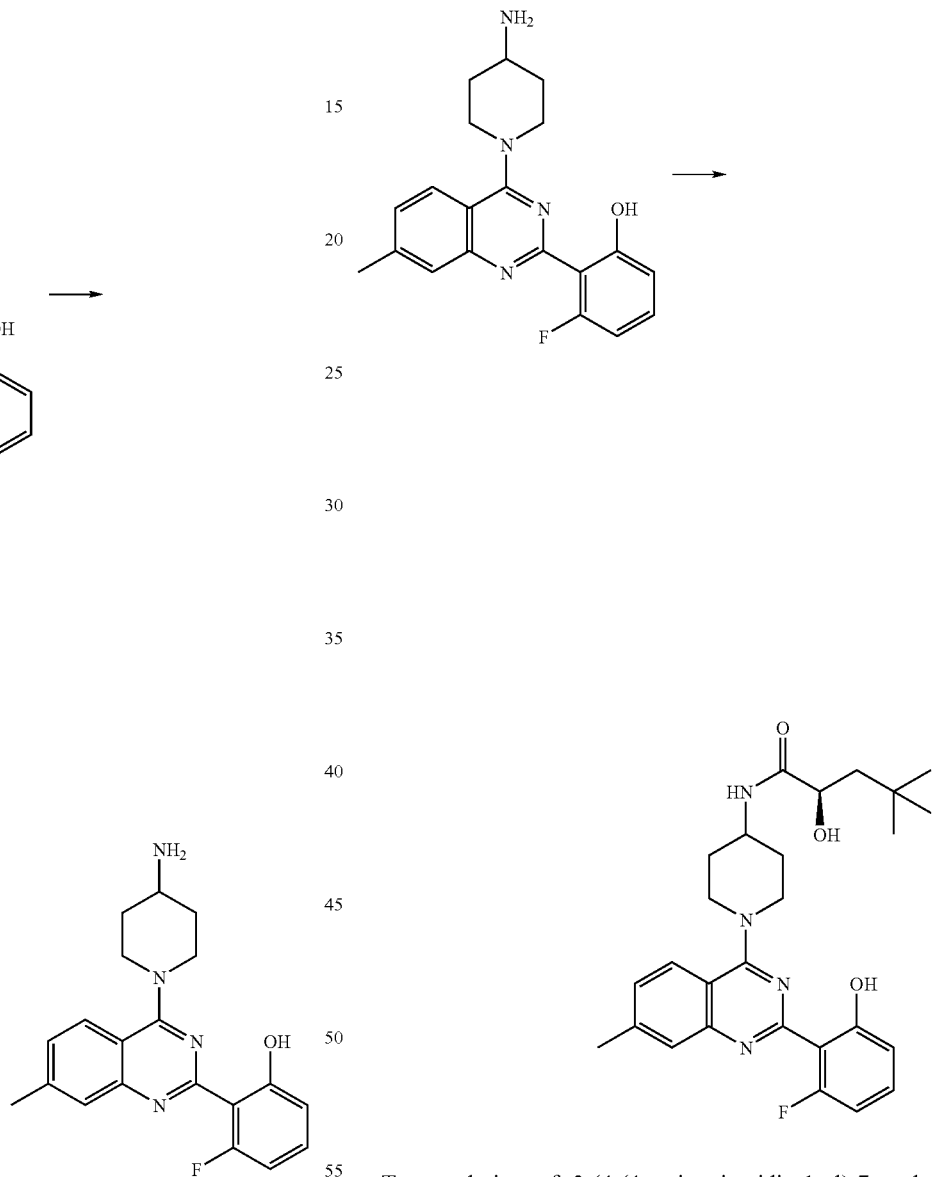

To a solution of 2-(4-(4-aminopiperidin-1-yl)-7-methylquinazolin-2-yl)-3-fluorophenol (50 mg, 0.14 mmol) in 1 mL DMF at 0° C. was added (R)-2-hydroxy-4,4-dimethylpentanoic acid (25 mg, 0.17 mmol), followed by the addition of triethylamine (29 mg, 0.28 mmol). HATU (65 mg, 0.17 mmol) was then added, and the reaction was stirred at 0° C. for an additional 10 minutes and then warmed to room temperature. The reaction was complete after 40 minutes, filtered, and purified by reverse phase HPLC (10%-99% CH$_3$CN (0.035% TFA)/H$_2$O (0.05% TFA)) to give (2R)—N-(1-(2-(2-fluoro-6-hydroxyphenyl)-7-methylquinazolin-4-yl)piperidin-4-yl)-2-hydroxy-4,4-dimethylpentanamide as the TFA salt. LC/MS: m/z 481.3 (M+H)+ at 2.42 min (10%-99% CH₃CN (0.035% TFA)/H₂O (0.05% TFA)).

TFA salt. LC/MS: m/z 449.5 (M+H)+ at 2.77 min (10%-99% CH₃CN (0.035% TFA)/H₂O (0.05% TFA)).

Example 250

Isobutyl (1-(2-(2-hydroxyphenyl)-7-methylquinazolin-4-yl)piperidin-3-yl)methylcarbamate

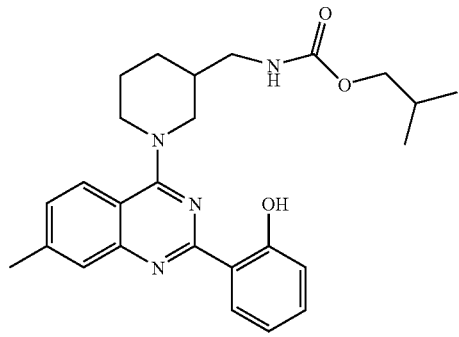

Example 251

Ethyl (1-(2-(2-hydroxyphenyl)-7-methylquinazolin-4-yl)piperidin-3-yl)methylcarbamate

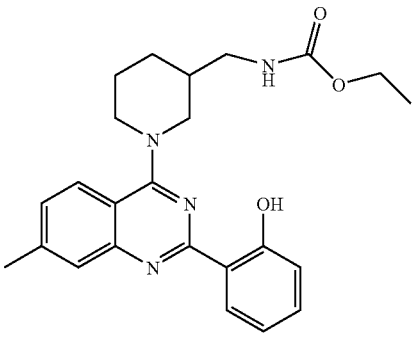

Isobutyl (1-(2-(2-hydroxyphenyl)-7-methylquinazolin-4-yl)piperidin-3-yl)methylcarbamate

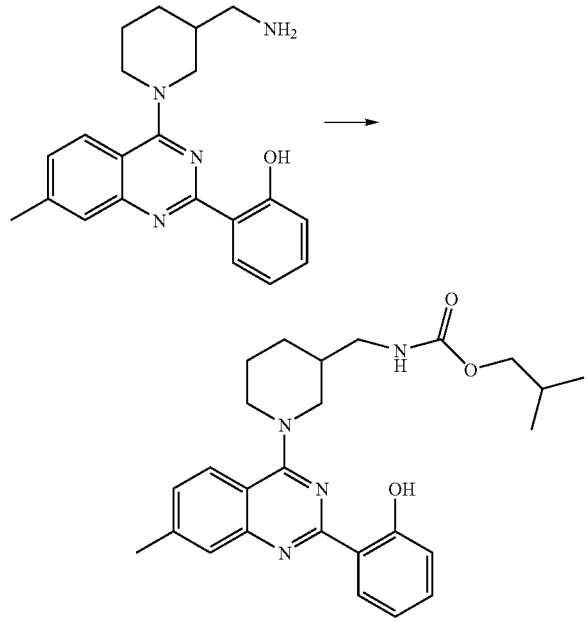

Ethyl (1-(2-(2-hydroxyphenyl)-7-methylquinazolin-4-yl)piperidin-3-yl)methylcarbamate

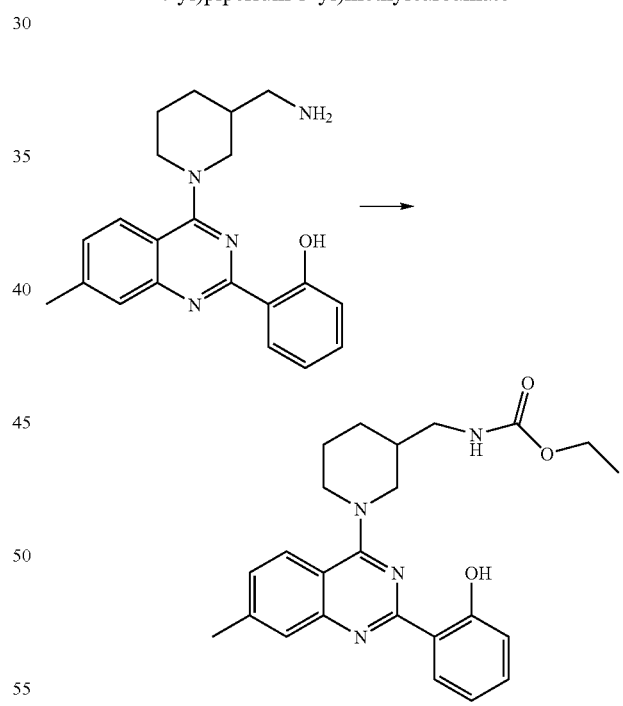

2-(4-(3-(Aminomethyl)piperidin-1-yl)-7-methylquinazolin-2-yl)phenol (60 mg, 0.17 mmol) was dissolved in anhydrous DMF (1 mL) and cooled to 0° C., upon which isobutyl chloroformate (27 μL, 0.2 mmol) dissolved in DMF (100 L) was added dropwise followed by triethylamine (35 mg, 48 μL, 0.34 mmol). The reaction was allowed to warm to room temperature, and was complete after 2 h. Purification by reverse phase HPLC (10%-99% CH₃CN (0.035% TFA)/H₂O (0.05% TFA)) gave isobutyl (1-(2-(2-hydroxyphenyl)-7-methylquinazolin-4-yl)piperidin-3-yl)methylcarbamate as the 2-(4-(3-(Aminomethyl)piperidin-1-yl)-7-methylquinazolin-2-yl)phenol (60 mg, 0.17 mmol) was dissolved in anhydrous DMF (1 mL) and cooled to 0° C., upon which ethyl chloroformate (20 μL, 0.2 mmol) dissolved in DMF (100 μL) was added dropwise followed by the addition of triethylamine (35 mg, 48 μL, 0.34 mmol). The reaction was allowed to warm to room temperature and was complete after 2 h. Purification by reverse phase HPLC (10%-99% CH₃CN (0.035% TFA)/H₂O (0.05% TFA)) gave ethyl (1-(2-(2-hydroxyphenyl)-7-methylquinazolin-4-yl)piperidin-3-yl)methylcarbamate as the TFA salt. LC/MS: m/z 421.0 (M+H)+ at 2.48 min (10%-99% CH$_3$CN (0.035% TFA)/H$_2$O (0.05% TFA)).

Example 252

Isobutyl ((S)-1-(2-(2-hydroxyphenyl)-7-methylquinazolin-4-yl)piperidin-3-yl)methylcarbamate

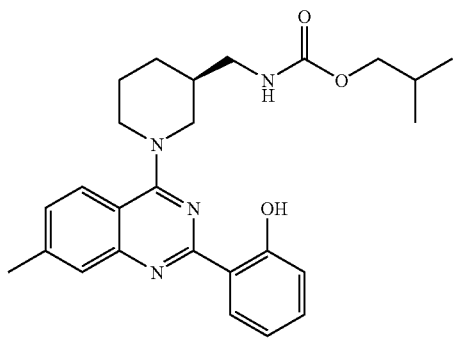

Isobutyl ((S)-1-(2-(2-hydroxyphenyl)-7-methylquinazolin-4-yl)piperidin-3-yl)methylcarbamate

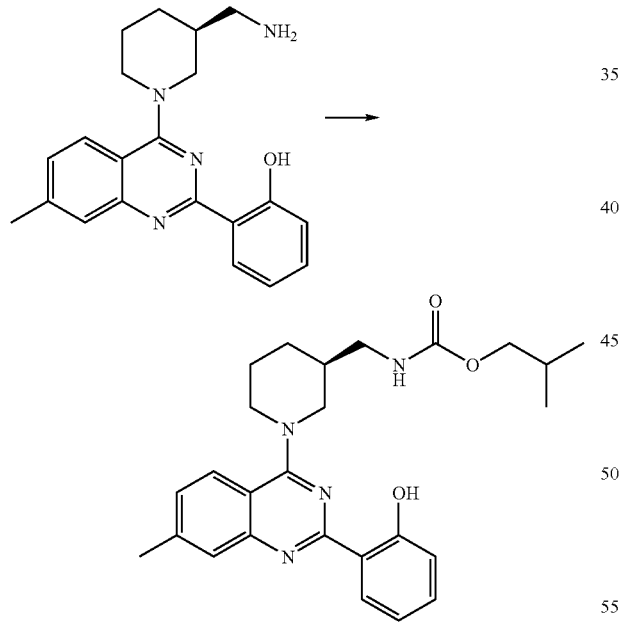

2-(4-((S)-3-(Aminomethyl)piperidin-1-yl)-7-methylquinazolin-2-yl)phenol (60 mg, 0.17 mmol) was dissolved in anhydrous DMF (1 mL) and cooled to 0° C., upon which isobutyl chloroformate (27 µL, 0.2 mmol) dissolved in DMF (100 µL) was added dropwise followed by the addition of triethylamine (35 mg, 48 µL, 0.34 mmol). The reaction was allowed to warm to room temperature and was complete after 2 h. Purification by reverse phase HPLC (10%-99% CH$_3$CN (0.035% TFA)/H$_2$O (0.05% TFA)) gave isobutyl ((S)-1-(2-(2-hydroxyphenyl)-7-methylquinazolin-4-yl)piperidin-3-yl)

methylcarbamate as the TFA salt. LC/MS: m/z 449.3 (M+H)+ at 2.80 min (10%-99% CH$_3$CN (0.035% TFA)/H$_2$O (0.05% TFA)).

Example 253

Isobutyl ((R)-1-(2-(2-hydroxyphenyl)-7-methylquinazolin-4-yl)piperidin-3-yl)methylcarbamate

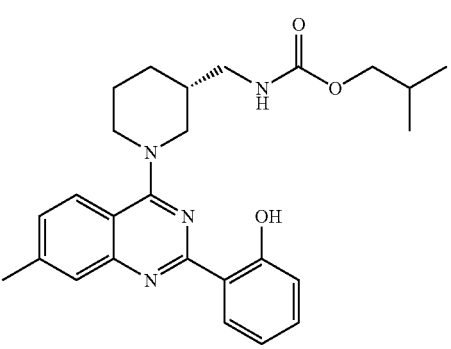

Isobutyl ((R)-1-(2-(2-hydroxyphenyl)-7-methylquinazolin-4-yl)piperidin-3-yl)methylcarbamate

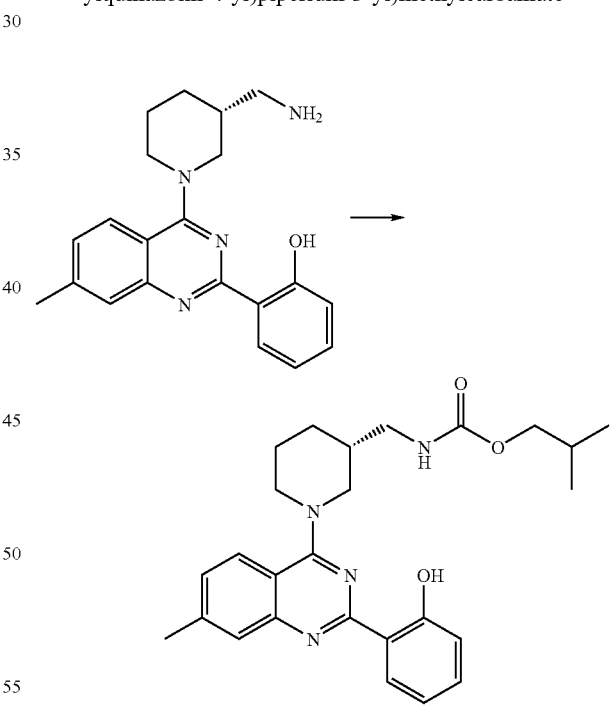

2-(4-((R)-3-(Aminomethyl)piperidin-1-yl)-7-methylquinazolin-2-yl)phenol (60 mg, 0.172 mmol) was dissolved in anhydrous DMF (1 mL) and cooled to 0° C., upon which isobutyl chloroformate (27 µL, 0.21 mmol) dissolved in DMF (100 µL) was added dropwise followed by the addition of triethylamine (35 mg, 48 µL, 0.34 mmol). The reaction was allowed to warm to room temperature, and it was complete after 2 h. Purification by reverse phase HPLC (10%-99% CH$_3$CN (0.035% TFA)/H$_2$O (0.05% TFA)) gave isobutyl ((R)-1-(2-(2-hydroxyphenyl)-7-methylquinazolin-4-yl)piperidin-3-yl)methylcarbamate as the TFA salt. LC/MS: m/z 449.3 (M+H)+ at 2.78 min (10%-99% CH$_3$CN (0.035% TFA)/H$_2$O (0.05% TFA)).

Example 254

Ethyl((S)-1-(2-(2-hydroxyphenyl)-7-methylquinazolin-4-yl)piperidin-3-yl)methylcarbamate

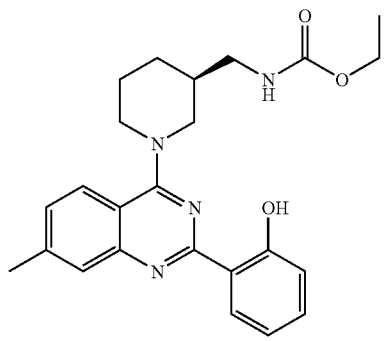

Ethyl ((S)-1-(2-(2-hydroxyphenyl)-7-methylquinazolin-4-yl)piperidin-3-yl)methylcarbamate

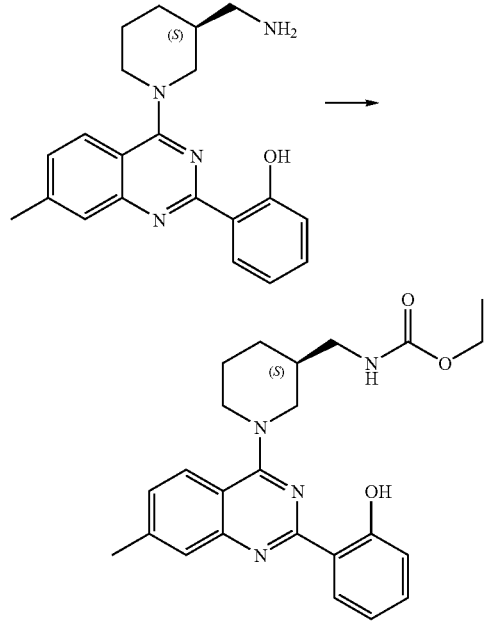

2-(4-((S)-3-(Aminomethyl)piperidin-1-yl)-7-methylquinazolin-2-yl)phenol (35 mg, 0.10 mmol) was dissolved in anhydrous DMF (1 mL) and cooled to 0° C., upon which ethyl chloroformate (10.5 μL, 0.11 mmol) dissolved in DMF (100 μL) was added dropwise followed by triethylamine (20.2 mg, 27.8 μL, 0.2 mmol). The reaction was allowed to warm to room temperature, and it was complete after 2 h. Purification by reverse phase HPLC (10%-99% CH$_3$CN (0.035% TFA)/H$_2$O (0.05% TFA)) gave ethyl ((S)-1-(2-(2-hydroxyphenyl)-7-methylquinazolin-4-yl)piperidin-3-yl)methylcarbamate as the TFA salt. LC/MS: m/z 421.1 (M+H)+ at 2.50 min (10%-99% CH$_3$CN (0.035% TFA)/H$_2$O (0.05% TFA)).

Example 255

Isopropyl ((S)-1-(2-(2-hydroxyphenyl)-7-methylquinazolin-4-yl)piperidin-3-yl)methylcarbamate

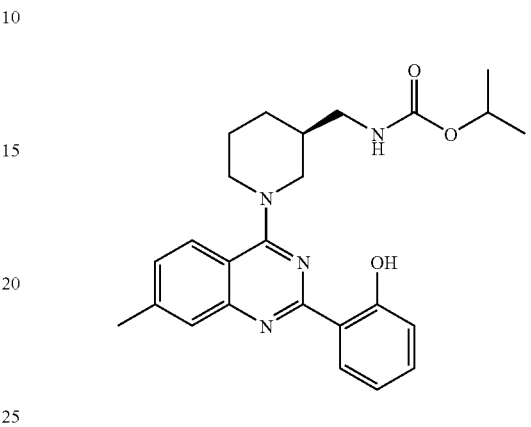

Isopropyl ((S)-1-(2-(2-hydroxyphenyl)-7-methylquinazolin-4-yl)piperidin-3-yl)methylcarbamate

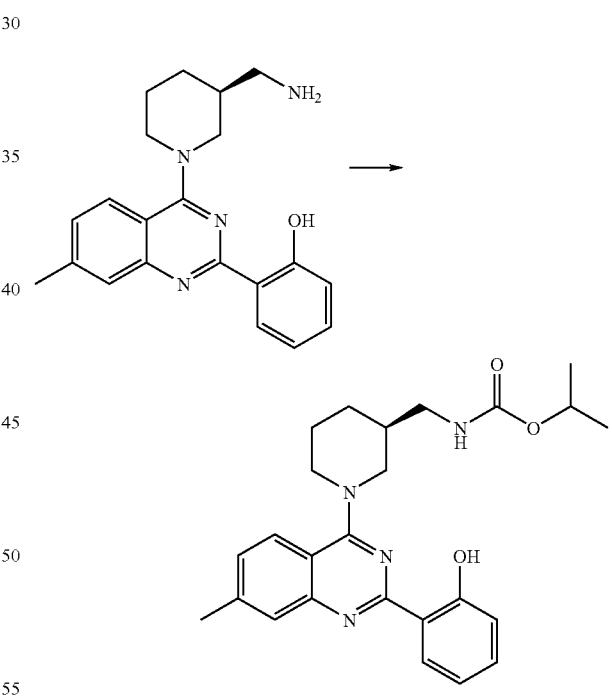

2-(4-((S)-3-(Aminomethyl)piperidin-1-yl)-7-methylquinazolin-2-yl)phenol (35 mg, 0.10 mmol) was dissolved in anhydrous DMF (1 mL) and cooled to 0° C., upon which isopropyl chloroformate (1 M solution in toluene, 98.1 mg, 110 μL, 0.11 mmol) was dissolved in DMF (100 μL) and added dropwise, followed by triethylamine (20.2 mg, 27.8 μL, 0.2 mmol). The reaction was allowed to warm to room temperature, and it was complete after 2 h. Purification by reverse phase HPLC (10%-99% CH$_3$CN (0.035% TFA)/H$_2$O (0.05% TFA)) gave isopropyl ((S)-1-(2-(2-hydroxyphenyl)-7-methylquinazolin-4-yl)piperidin-3-yl)methylcarbamate as the TFA salt. LC/MS: m/z 435.5 (M+H)+ at 2.61 min (10%-99% CH₃CN (0.035% TFA)/H₂O (0.05% TFA)).

Example 256

Propyl ((S)-1-(2-(2-hydroxyphenyl)-7-methylquinazolin-4-yl)piperidin-3-yl)methylcarbamate

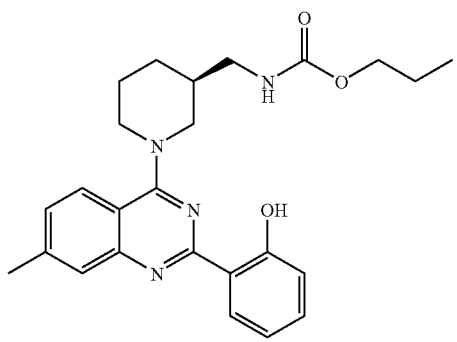

Propyl ((S)-1-(2-(2-hydroxyphenyl)-7-methylquinazolin-4-yl)piperidin-3-yl)methylcarbamate

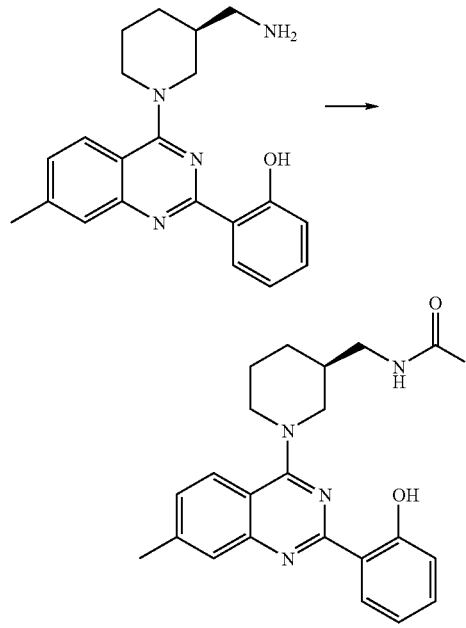

2-(4-((S)-3-(Aminomethyl)piperidin-1-yl)-7-methylquinazolin-2-yl)phenol (35 mg, 0.10 mmol) was dissolved in anhydrous DMF (1 mL) and cooled to 0° C., upon which propyl chloroformate (12.4 µL, 0.11 mmol) dissolved in DMF (100 µL) was added dropwise followed by triethylamine (20.2 mg, 27.8 µL, 0.2 mmol). The reaction was allowed to warm to room temperature and was complete after 2 h. Purification by reverse phase HPLC (10%-99% CH₃CN (0.035% TFA)/H₂O (0.05% TFA)) gave propyl ((S)-1-(2-(2-hydroxyphenyl)-7-methylquinazolin-4-yl)piperidin-3-yl)

methylcarbamate as the TFA salt. LC/MS: m/z 435.5 (M+H)+ at 2.61 min (10%-99% CH₃CN (0.035% TFA)/H₂O (0.05% TFA)).

Example 257

2-Methoxyethyl ((S)-1-(2-(2-hydroxyphenyl)-7-methylquinazolin-4-yl)piperidin-3-yl)methylcarbamate

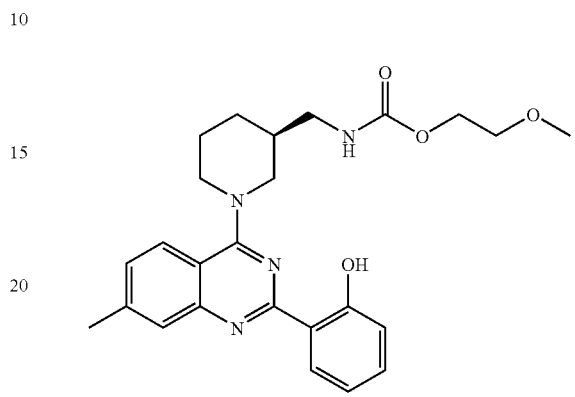

2-Methoxyethyl-((S)-1-(2-(2-hydroxyphenyl)-7-methylquinazolin-4-yl)piperidin-3-yl)methylcarbamate

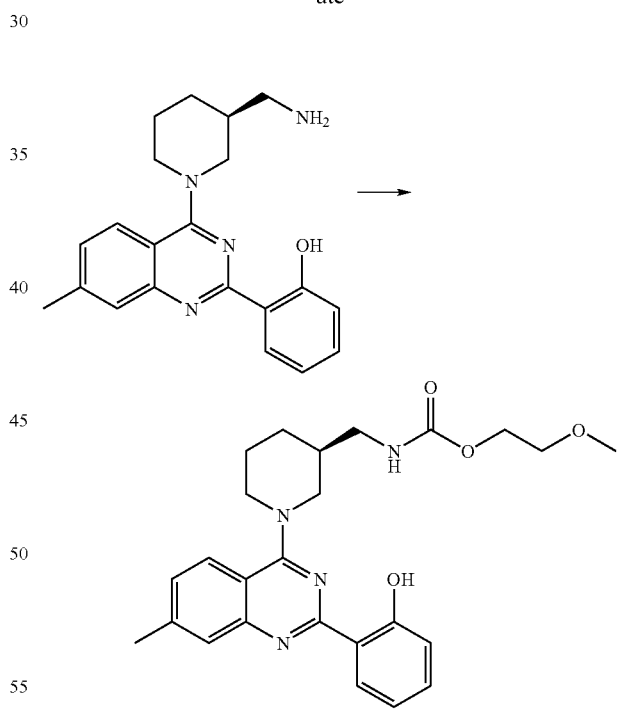

2-(4-((S)-3-(Aminomethyl)piperidin-1-yl)-7-methylquinazolin-2-yl)phenol (35 mg, 0.1 mmol) was dissolved in anhydrous DMF (1 mL) and cooled to 0° C., upon which 2-methoxyethyl chloroformate (11.6 µL, 0.1 mmol) dissolved in DMF (100 µL) was added dropwise followed by triethylamine (20.2 mg, 27.8 µL, 0.2 mmol). The reaction was allowed to warm to room temperature, and was complete after 2 h. Purification by reverse phase HPLC (10%-99% CH₃CN (0.035% TFA)/H₂O (0.05% TFA)) gave 2-methoxyethyl ((S)-1-(2-(2-hydroxyphenyl)-7-methylquinazolin-4-yl)piperidin- 3-yl)methylcarbamate as the TFA salt. LC/MS: m/z 451.1 (M+H)+ at 2.34 min (10%-99% CH₃CN (0.035% TFA)/H₂O (0.05% TFA)).

Example 258

2-Methoxyethyl 1-(6-fluoro-2-(2-hydroxyphenyl)quinazolin-4-yl)piperidin-4-ylcarbamate

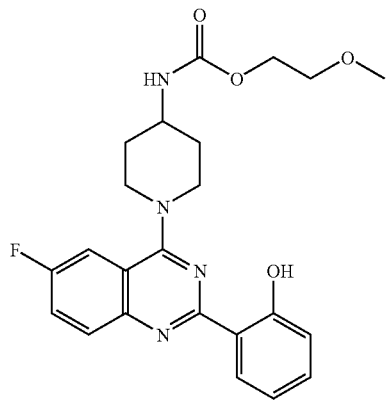

2-(4-(4-Aminopiperidin-1-yl)-6-fluoroquinazolin-2-yl)phenol

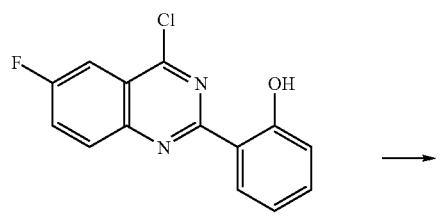

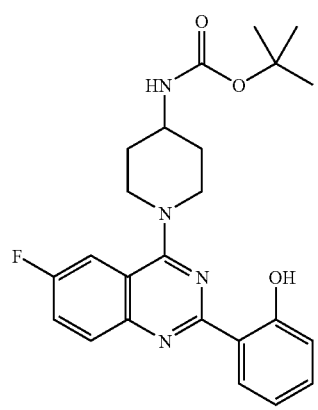

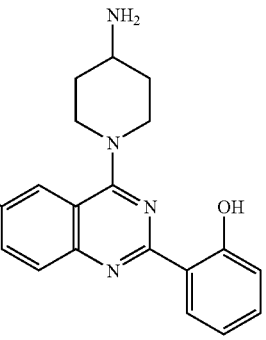

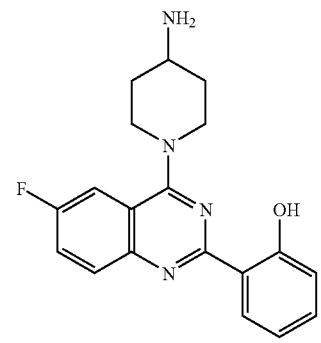

To a stirred solution of 2-(4-chloro-6-fluoroquinazolin-2-yl)phenol (0.20 g, 0.73 mmol) in CH₂Cl₂ (5 mL) was added dropwise a solution of tert-butyl piperidin-4-ylcarbamate (0.19 g, 0.95 mmol) and triethylamine (203 μL, 147 mg, 1.46 mmol) in CH₂Cl₂. The reaction was stirred for 3 h and then quenched with water. The aqueous layer was extracted with CH₂Cl₂. The combined organic layers were dried over MgSO₄, filtered, and concentrated to obtain tert-butyl 1-(6-fluoro-2-(2-hydroxyphenyl)quinazolin-4-yl)piperidin-4-yl-carbamate. The residue was dissolved in 10 mL CH₂Cl₂ and 3 mL TFA. The reaction was stirred for 2 hours and neutralized with a 1.0 M aqueous NaOH solution. The mixture was partitioned between H₂O/CH₂Cl₂ and separated, and the aqueous layer was extracted with CH₂Cl₂. The combined organic layers were dried over MgSO₄, filtered, and concentrated to obtain 2-(4-(4-aminopiperidin-1-yl)-6-fluoroquinazolin-2-yl)phenol. LC/MS: m/z 339.3 (M+H)+ at 1.87 min (10%-99% CH₃CN (0.035% TFA)/H₂O (0.05% TFA)).

2-Methoxyethyl 1-(6-fluoro-2-(2-hydroxyphenyl)quinazolin-4-yl)piperidin-4-ylcarbamate 407
-continued

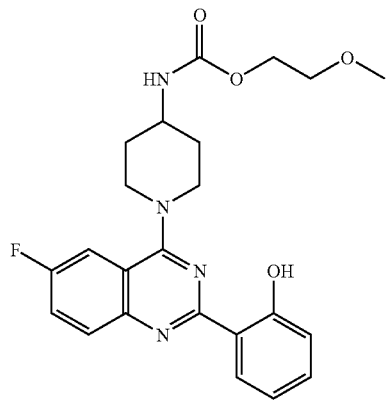

A solution of 2-(4-(4-aminopiperidin-1-yl)-6-fluoro-quinazolin-2-yl)phenol (50 mg, 0.15 mmol) in DMF (1 mL) was cooled to −40° C. (external temp). To it was added triethylamine (41 μL, 30 mg, 0.29 mmol) and a solution of 2-methoxyethyl chloroformate (17 μL, 20 mg, 0.15 mmol) in 100 μL DMF dropwise. The reaction was allowed to warm to room temperature and was stirred for 2 h. Purification via reverse phase HPLC (10%-99% CH$_3$CN (0.035% TFA)/H$_2$O (0.05% TFA)) gave 2-methoxyethyl 1-(6-fluoro-2-(2-hydroxyphenyl)quinazolin-4-yl)piperidin-4-ylcarbamate as the TFA salt. LC/MS: m/z 441.5 (M+H)$^+$ at 2.6 min (10%-99% CH$_3$CN (0.035% TFA)/H$_2$O (0.05% TFA)).

Example 259

{1-[2-(2-Hydroxy-phenyl)-7-methyl-quinazolin-4-yl]-piperidin-4-yl}-carbamic acid tert-butyl ester

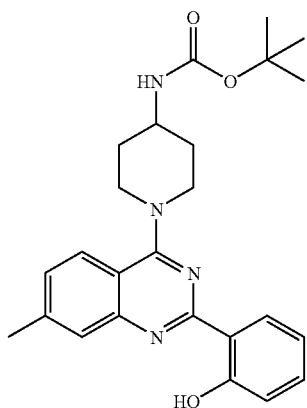

408

{1-[2-(2-Hydroxy-phenyl)-7-methyl-quinazolin-4-yl]-piperidin-4-yl}-carbamic acid tert-butyl ester

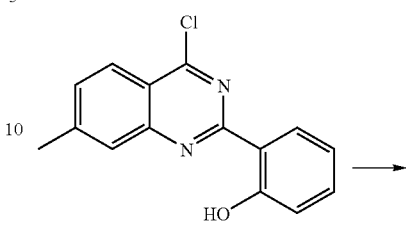

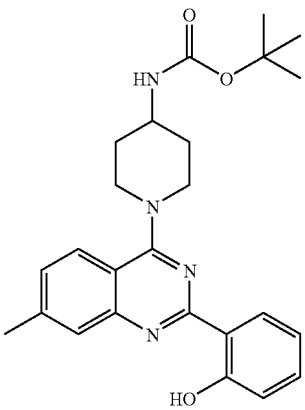

To piperidin-4-yl-carbamic acid tert-butyl ester (887 mg, 4.4 mmol) in 10 mL of was CH$_2$Cl$_2$ was added sequentially triethylamine (720 μL, 5.2 mmol) and 2-(4-chloro-7-methyl-quinazolin-2-yl)-phenol (1.0 g, 3.7 mmol). The reaction mixture was stirred at room temperature for 2 h and then diluted with water and CH$_2$Cl$_2$. The organic layer was separated and dried over Na$_2$SO$_4$, and the solvent was removed under reduced pressure. The residue was subjected to purification via reverse phase HPLC (10%-99% CH$_3$CN (0.035% TFA)/H$_2$O (0.05% TFA)) to give {1-[2-(2-hydroxy-phenyl)-7-methyl-quinazolin-4-yl]-piperidin-4-yl}-carbamic acid tert-butyl ester as the TFA salt. LC/MS: m/z 435.2 (M+H)$^+$ at 3.03 min (10%-99% CH$_3$CN (0.035% TFA)/H$_2$O (0.05% TFA)).

Example 260

Isobutyl ((S)-1-(2-(2-fluoro-6-hydroxyphenyl)-7-methylquinazolin-4-yl)piperidin-3-yl)methylcarbamate

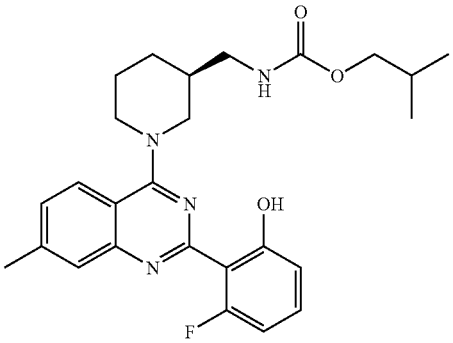

409

Isobutyl ((S)-1-(2-(2-fluoro-6-hydroxyphenyl)-7-methylquinazolin-4-yl)piperidin-3-yl)methylcarbamate

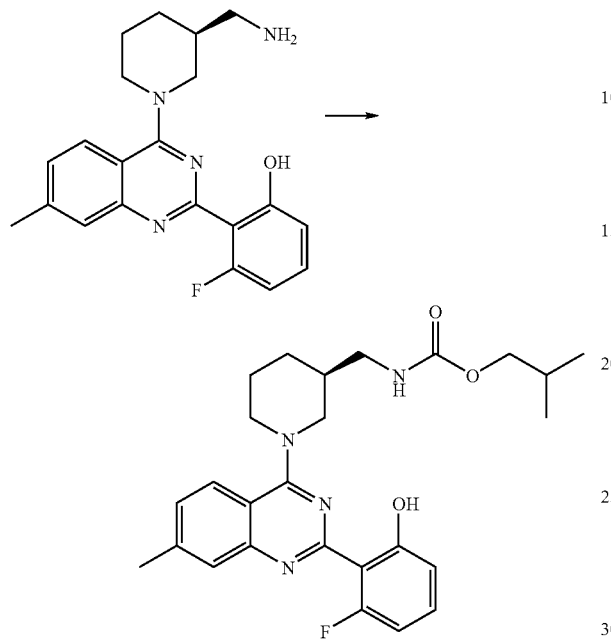

To a solution of 2-(4-((S)-3-(aminomethyl)piperidin-1-yl)-7-methylquinazolin-2-yl)-3-fluorophenol (40 mg, 0.11 mmol) in DMF (400 μL) at 0° C. was added dropwise isobutyl chloroformate (15.7 μL, 0.12 mmol) in DMF (400 μL), followed by the addition of triethylamine (30 mL, 0.22 mmol). The reaction was allowed to warm to room temperature and was complete after 2 h. Purification by reverse phase HPLC (10%-99% CH$_3$CN (0.035% TFA)/H$_2$O (0.05% TFA)) gave isobutyl ((S)-1-(2-(2-fluoro-6-hydroxyphenyl)-7-methylquinazolin-4-yl)piperidin-3-yl)methylcarbamate as the TFA salt. LC/MS: m/z 467.1 (M+H)$^+$ at 2.56 min (10%-99% CH$_3$CN (0.035% TFA)/H$_2$O (0.05% TFA)).

Example 261

2-Methoxyethyl ((S)-1-(2-(2-fluoro-6-hydroxyphenyl)-7-methylquinazolin-4-yl)piperidin-3-yl)methylcarbamate

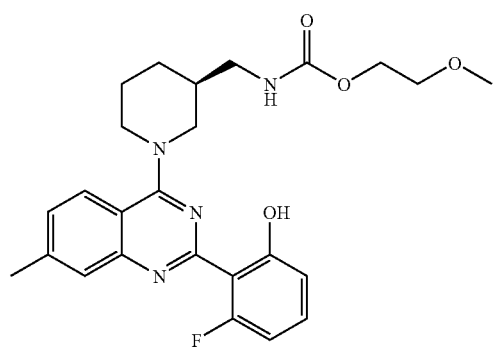

410

Method A

2-Methoxyethyl ((S)-1-(2-(2-fluoro-6-hydroxyphenyl)-7-methylquinazolin-4-yl)piperidin-3-yl)methylcarbamate

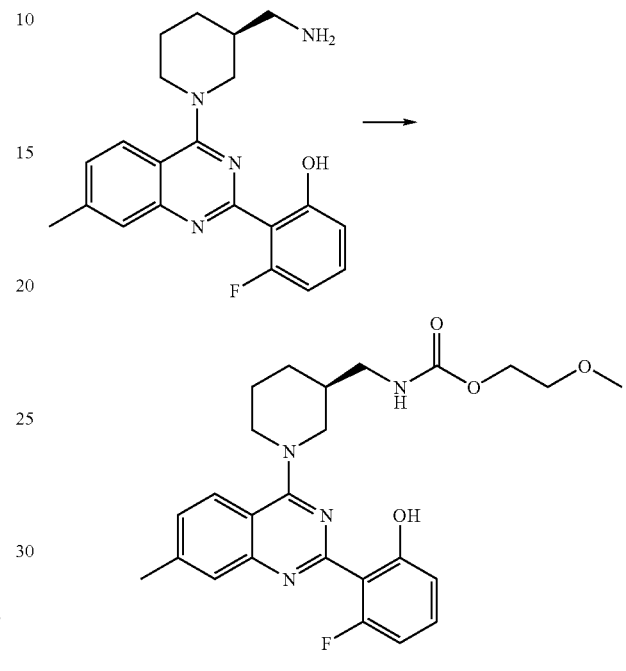

To a solution of 2-(4-((S)-3-(aminomethyl)piperidin-1-yl)-7-methylquinazolin-2-yl)-3-fluorophenol (40 mg, 0.11 mmol) in DMF (400 mL) at 0° C. was added dropwise 2-methoxyethyl chloroformate (12.6 mL, 0.11 mmol) in DMF (400 mL), followed by the addition of triethylamine (30 mL, 0.22 mmol). The reaction was allowed to warm to room temperature and was complete after 2 h. Purification by reverse phase HPLC (10%-99% CH$_3$CN (0.035% TFA)/H$_2$O (0.05% TFA)) gave 2-methoxyethyl ((S)-1-(2-(2-fluoro-6-hydroxyphenyl)-7-methylquinazolin-4-yl)piperidin-3-yl)methylcarbamate as the TFA salt. LC/MS: m/z 469.1 (M+H)$^+$ at 2.20 min (10%-99% CH$_3$CN (0.035% TFA)/H$_2$O (0.05% TFA)).

Method B

2-Methoxyethyl ((S)-1-(tert-butoxycarbonyl)piperidin-3-yl)methylcarbamate

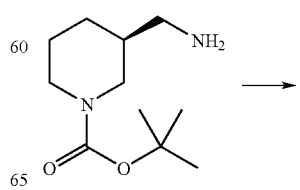

-continued

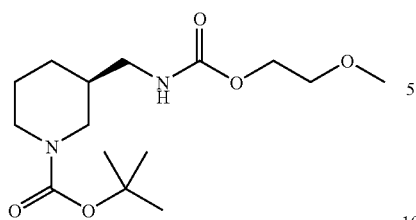

To a solution of (S)-tert-butyl 3-(aminomethyl)piperidine-1-carboxylate (500 mg, 2.33 mmol) in CH$_2$Cl$_2$ at −10° C. was added triethylamine (650 μL, 4.66 mmol) followed by the dropwise addition of 2-methoxyethyl chloroformate (325 μL, 2.79 mmol). The reaction was warmed to room temperature and quenched with water. The aqueous layer was extracted with CH$_2$Cl$_2$, and the combined extracts were dried over MgSO$_4$, filtered, and evaporated. Purification via silica gel chromatography using 0 to 10% EtOAc in CH$_2$Cl$_2$ afforded 2-methoxyethyl ((S)-1-(tert-butoxycarbonyl)piperidin-3-yl)methylcarbamate (496 mg, 67%). LC/MS: m/z 317.3 (M+H)$^+$ at 2.56 min (10%-99% CH$_3$CN (0.035% TFA)/H$_2$O (0.05% TFA)).

2-Methoxyethyl ((R)-piperidin-3-yl)methylcarbamate

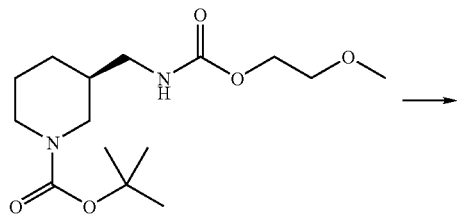

To 2-methoxyethyl ((S)-1-(tert-butoxycarbonyl)piperidin-3-yl)methylcarbamate (496 mg, 1.6 mmol) dissolved in 10 mL CH$_2$Cl$_2$ was added 5 mL TFA, and the reaction was stirred for 1 hour. After neutralizing the mixture with a 1 N NaOH solution it was extracted with CH$_2$Cl$_2$, and the combined organic layers were dried over MgSO$_4$, filtered, and concentrated to give 2-methoxyethyl ((R)-piperidin-3-yl)methylcarbamate (300 mg, 87%) which was used without further purification. LC/MS: m/z 217.5 (M+H)$^+$ at 0.49 min (10%-99% CH$_3$CN (0.035% TFA)/H$_2$O (0.05% TFA)).

2-Methoxyethyl ((S)-1-(2-(2-fluoro-6-hydroxyphenyl)-7-methylquinazolin-4-yl)piperidin-3-yl)methylcarbamate

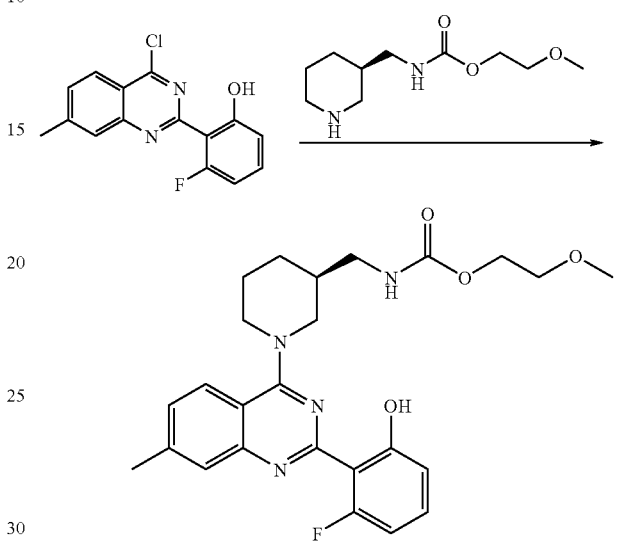

To a solution of 2-methoxyethyl ((R)-piperidin-3-yl)methylcarbamate (0.24 g, 1.1 mmol) and 2-(4-chloro-7-methylquinazolin-2-yl)-3-fluorophenol (250 mg, 0.865 mmol) in CH$_2$Cl$_2$ was added triethylamine (2.41 mL, 1.73 mmol). After stirring the reaction at room temperature for 2 h, it was quenched with water and then extracted with CH$_2$Cl$_2$. The combined organic layers were dried over MgSO$_4$, filtered, and concentrated. Purification via silica gel chromatography using 0%-10% EtOAc in CH$_2$Cl$_2$ yielded 2-methoxyethyl ((S)-1-(2-(2-fluoro-6-hydroxyphenyl)-7-methylquinazolin-4-yl)piperidin-3-yl)methylcarbamate (357 mg, 88%). LC/MS: m/z 469.5 (M+H)$^+$ at 2.30 min (10%-99% CH$_3$CN (0.035% TFA)/H$_2$O (0.05% TFA)).

2-Methoxyethyl ((S)-1-(2-(2-fluoro-6-hydroxyphenyl)-7-methylquinazolin-4-yl)piperidin-3-yl)methylcarbamate hydrochloride

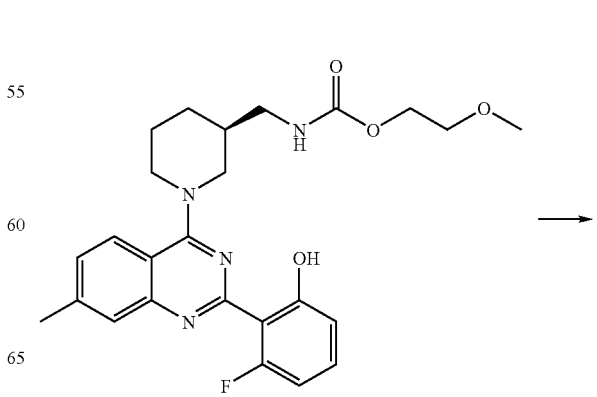

413
-continued

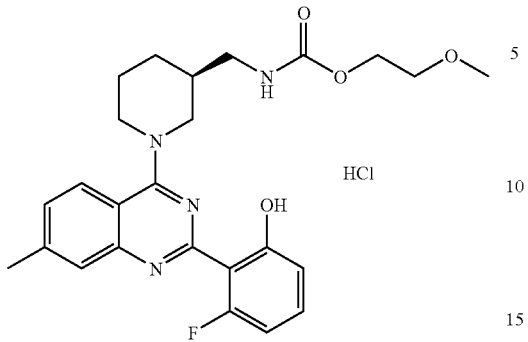

HCl

To a solution of ((S)-1-(2-(2-fluoro-6-hydroxyphenyl)-7-methylquinazolin-4-yl)piperidin-3-yl)methylcarbamate (352 mg, 0.75 mmol) in $CH_2Cl_2$ (3 mL) was added dropwise a 2.0 M HCl solution in ether (0.375 mL, 0.75 mmol) under an $N_2$ atmosphere. It was followed by the addition of 20 mL ether which lead to the precipitation of 2-methoxyethyl ((S)-1-(2-(2-fluoro-6-hydroxyphenyl)-7-methylquinazolin-4-yl)piperidin-3-yl)methylcarbamate hydrochloride (350 mg, 92%) which was then filtered and dried. LC/MS: m/z 469.5 (M+H)$^+$ at 2.29 min (10%-99% $CH_3CN$ (0.035% TFA)/$H_2O$ (0.05% TFA)). $^1$H NMR (400 MHz, DMSO-d6) δ 7.97 (d, J=7.9 Hz, 1H), 7.63 (s, 1H), 7.45 (m, 3H), 6.89 (d, J=8.3 Hz, 1H), 6.82 (t, J=9.5 Hz, 1H), 4.54 (s, 1H), 4.03 (d, J=2.7 Hz, 2H), 3.47 (t, J=4.6 Hz, 4H), 3.24 (s, 3H), 2.99 (m, 2H), 2.54 (s, 3H), 1.89 (m, 3H), 1.70 (m, 1H), 1.38 (m, 1H) ppm.

Example 262

Ethyl ((S)-1-(2-(2-fluoro-6-hydroxyphenyl)-7-methylquinazolin-4-yl)piperidin-3-yl)methylcarbamate

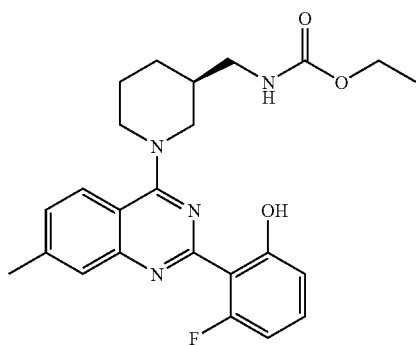

414

Ethyl ((S)-1-(2-(2-fluoro-6-hydroxyphenyl)-7-methylquinazolin-4-yl)piperidin-3-yl)methylcarbamate

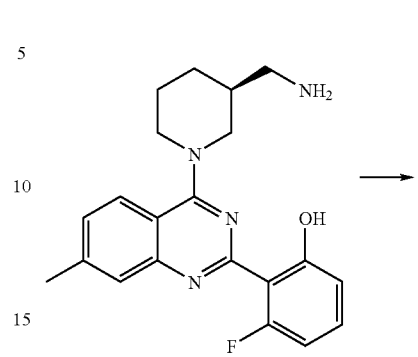

Method A

To a solution of 2-(4-((S)-3-(aminomethyl)piperidin-1-yl)-7-methylquinazolin-2-yl)-3-fluorophenol (40 mg, 0.11 mmol) in DMF (400 µL) at 0° C. was added dropwise ethyl chloroformate (10.4 µl, 0.10 mmol) in DMF (400 µL), followed by the addition of triethylamine (30 µL, 0.22 mmol). The reaction was allowed to warm to room temperature and was complete after 2 h. Purification by reverse phase HPLC (10%-99% $CH_3CN$ (0.035% TFA)/$H_2O$ (0.05% TFA)) gave 2-methoxyethyl ethyl ((S)-1-(2-(2-fluoro-6-hydroxyphenyl)-7-methylquinazolin-4-yl)piperidin-3-yl)methylcarbamate as the TFA salt. LC/MS: m/z 439.5 (M+H)$^+$ at 2.31 min (10%-99% $CH_3CN$ (0.035% TFA)/$H_2O$ (0.05% TFA)).

Method B

To a stirred solution of 2-(4-((S)-3-(aminomethyl)piperidin-1-yl)-7-methylquinazolin-2-yl)-3-fluorophenol (200 mg, 0.54 mmol) in 12 mL THF was added diisopropyl ethylamine (188 µL, 1.08 mmol) at room temperature. The mixture was cooled to −60° C., and a solution of ethyl chloroformate (52 µL, 0.54 mmol) in 0.6 mL THF was added dropwise. After allowing the reaction to warm to room temperature, the mixture was partitioned between $H_2O$ and $CH_2Cl_2$. The layers were separated, and the aqueous layer was extracted twice more with $CH_2Cl_2$. The organic layers were combined, dried over $Na_2SO_4$, filtered, and concentrated. Purification via silica gel chromatography using 0-10% EtOAc in 50:50 hexanes:$CH_2Cl_2$ gave ethyl ((S)-1-(2-(2-fluoro-6-hydroxyphenyl)-7-methylquinazolin-4-yl)piperidin-3-yl)methylcarbamate (92 mg, 38%). LC/MS: m/z 439.5 (M+H)$^+$ at 2.40 min (10%-99% $CH_3CN$ (0.035% TFA)/$H_2O$ (0.05% TFA)).

415

Ethyl ((S)-1-(2-(2-fluoro-6-hydroxyphenyl)-7-methylquinazolin-4-yl)piperidin-3-yl)methylcarbamate hydrochloride

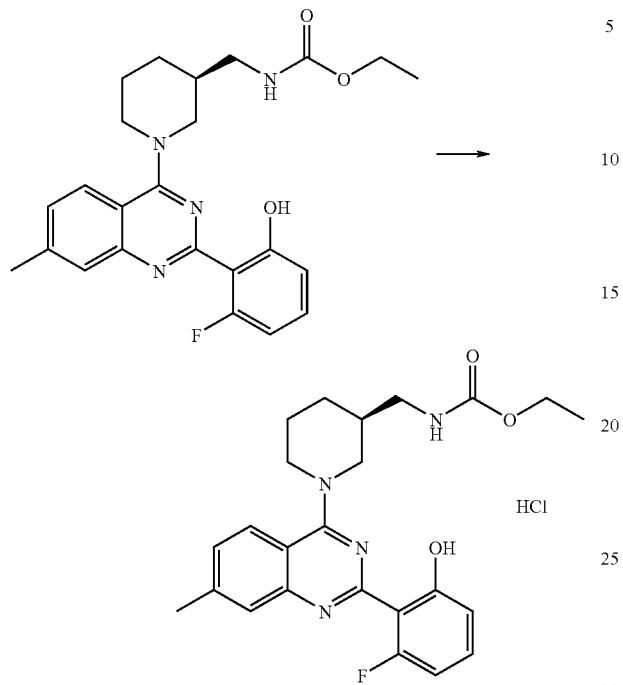

To a solution of ethyl ((S)-1-(2-(2-fluoro-6-hydroxyphenyl)-7-methylquinazolin-4-yl)piperidin-3-yl)methylcarbamate (89 mg, 0.2 mmol) in 2 mL CH$_2$Cl$_2$ under an N$_2$ atmosphere was added ether (10 mL) followed by the dropwise addition of a 2.0 M solution of HCl in ether (0.1 mL, 0.2 mmol) which resulted in precipitation of ethyl ((S)-1-(2-(2-fluoro-6-hydroxyphenyl)-7-methylquinazolin-4-yl)piperidin-3-yl)methylcarbamate hydrochloride which was then filtered and dried (85 mg, 90%). LC/MS: m/z 439.5 (M+H)$^+$ at 2.37 min (10%-99% CH$_3$CN (0.035% TFA)/H$_2$O (0.05% TFA)). $^1$H NMR (400 MHz, DMSO-d6) δ 8.26 (d, J=8.5 Hz, 1H), 7.57 (s, 1H), 7.45 (m, 2H), 6.81 (m, 2H), 4.57 (m, 2H), 3.89 (m, 2H), 3.52 (m, 1H), 3.36 (m, 1H), 2.95 (s, 2H), 2.52 (s, 3H), 1.86 (m, 3H), 1.66 (m, 1H), 1.39 (m, 1H), 1.07 (t, J=6.6 Hz, 3H) ppm.

Example 276

(R)-Tetrahydro-furan-2-carboxylic acid {1-[2-(2-hydroxy-phenyl)-7-methyl-quinazolin-4-yl]-piperidin-4-yl}-amide

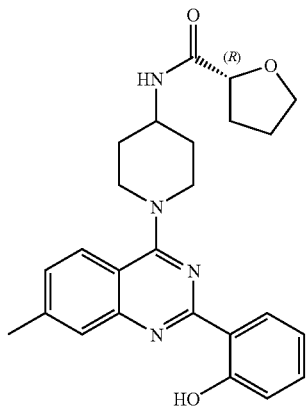

416

(R)-Tetrahydro-furan-2-carboxylic acid {1-[2-(2-hydroxy-phenyl)-7-methyl-quinazolin-4-yl]-piperidin-4-yl}-amide

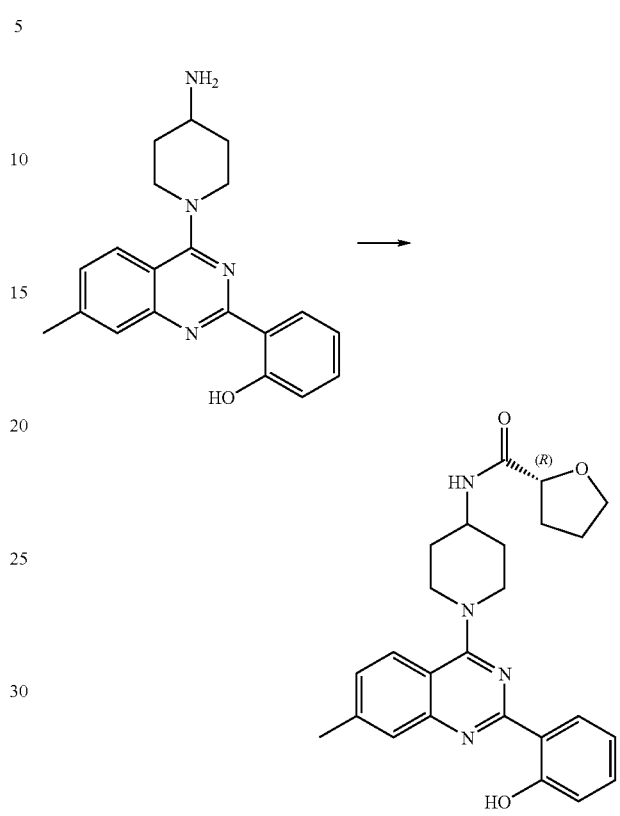

Method A: (R)-Tetrahydrofuran-2-carboxylic acid (23 mg, 0.20 mmol) and HATU (84 mg, 0.22 mmol) were dissolved in 0.75 mL DMF, then triethylamine (40 mg, 55 μL, 0.40 mmol) was added, followed immediately by 2-[4-(4-Amino-piperidin-1-yl)-7-methyl-quinazolin-2-yl]-phenol (67 mg, 0.20 mmol). The reaction was then stirred for 30 min at room temperature, diluted with 0.75 mL 1:1 methanol/DMSO, filtered, and purified by reverse phase HPLC (2-99% CH$_3$CN (0.035% TFA)/H$_2$O (0.05% TFA)) to give (R)-Tetrahydro-furan-2-carboxylic acid {1-[2-(2-hydroxy-phenyl)-7-methyl-quinazolin-4-yl]-piperidin-4-yl}-amide as the TFA salt. LC/MS: m/z 433.2 (M+H)$^+$ at 2.33 min (10%-99% CH$_3$CN (0.035% TFA)/H$_2$O (0.05% TFA)).

Method B: (R)-Tetrahydrofuran-2-carboxylic acid (193 mg, 1.66 mmol) was dissolved in DMF (6 mL), followed by the addition of HATU (696 mg, 1.83 mmol). The mixture was then stirred for 15 min at room temperature under an N$_2$ atmosphere. The 2-[4-(4-Amino-piperidin-1-yl)-7-methyl-quinazolin-2-yl]-phenol (556 mg, 1.66 mmol) was dissolved in DMF (8 mL) and added to the mixture, followed by triethylamine (336 mg, 0.463 mL, 3.32 mmol). After 30 min, theDMF was removed in vacuo and the crude product partitioned between water and ethyl acetate. The aqueous layer was separated, washed with ethyl acetate, and the combined organic layers dried over MgSO$_4$, filtered, and concentrated to give crude product as an orange oil. Purification via silica gel chromatography (20% ethyl acetate/80% 1:1 CH$_2$Cl$_2$: hexane) gave pure (R)-Tetrahydro-furan-2-carboxylic acid {1-[2-(2-hydroxy-phenyl)-7-methyl-quinazolin-4-yl]-piperidin-4-yl}-amide (303 mg, 42%). $^1$H NMR (400 MHz, DMSO-d6) δ 8.44 (dd, J=8.2, 1.5 Hz, 1H), 7.90 (d, J=8.5 Hz, 1H), 7.75 (d, J=8.3 Hz, 1H), 7.67 (s, 1H), 7.40-7.36 (m, 2H), 6.97-6.93 (m, 2H), 4.48-4.45 (m, 2H), 4.20 (dd, J=8.2, 5.3 Hz, 1H), 4.06-3.96 (m, 1H), 3.88 (dd, J=14.3, 6.6 Hz, 1H), 3.74 (dd, J=14.5, 6.7 Hz, 1H), 3.43-3.32 (m, 2H), 2.51 (s, 3H), 2.16-2.07 (m, 1H), (R)-Tetrahydro-furan-2-carboxylic acid {1-[2-(2-hydroxy-phenyl)-7-methyl-quinazolin-4-yl]-piperidin-4-yl}-amide hydrochloride

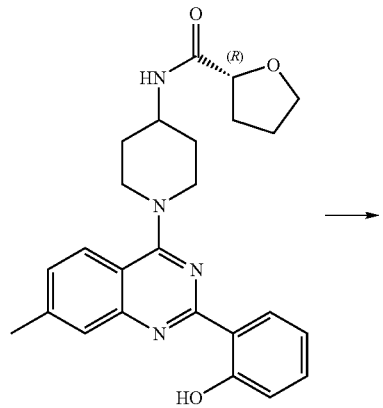

(R)-Tetrahydro-furan-2-carboxylic acid {1-[2-(2-hydroxy-phenyl)-7-methyl-quinazolin-4-yl]-piperidin-4-yl}-amide (303 mg, 0.701 mmol) was dissolved in 9 mL 2:1 dry ether/dry CH$_2$Cl$_2$ and 2.0 M HCl in ether added dropwise (0.35 mL, 0.70 mmol), producing a white precipitate which was collected by filtration to give (R)-Tetrahydro-furan-2-carboxylic acid {1-[2-(2-hydroxy-phenyl)-7-methyl-quinazolin-4-yl]-piperidin-4-yl}-amide hydrochloride (268 mg, 82%). LC/MS: m/z 433.5 (M+H)$^+$ at 2.26 min (10%-99% CH$_3$CN (0.035% TFA)/H$_2$O (0.05% TFA)). $^1$H NMR (400 MHz, DMSO-d6) δ 8.20 (dd, J=7.8, 1.2 Hz, 1H), 8.00 (d, J=8.6 Hz, 1H), 7.80-7.79 (m, 2H), 7.51-7.47 (m, 2H), 7.15 (d, J=8.2 Hz, 1H), 7.05-7.01 (m, 1H), 4.66-4.63 (m, 2H), 4.21 (dd, J=8.2, 5.2 Hz, 1H), 4.12-4.03 (m, 1H), 3.91-3.84 (m, 1H), 3.78-3.70 (m, 1H), 3.59 (t, J=12.3 Hz, 2H), 2.54 (s, 3H), 2.16-2.05 (m, 1H), 1.97-1.94 (m, 2H), 1.89-1.72 (m, 5H) ppm.

Example 301

(S)-Tetrahydrofuran-3-yl (R)-1-(2-(2-hydroxyphenyl)-7-methylquinazolin-4-yl)pyrrolidin-3-ylcarbamate

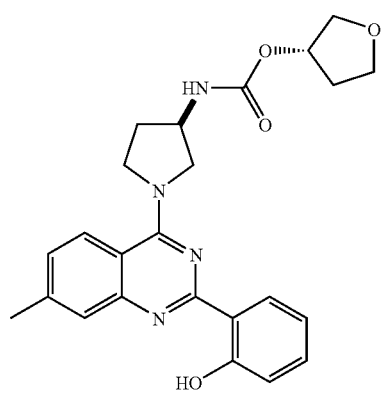

tert-Butyl (R)-1-(2-(2-hydroxyphenyl)-7-methylquinazolin-4-yl)pyrrolidin-3-ylcarbamate

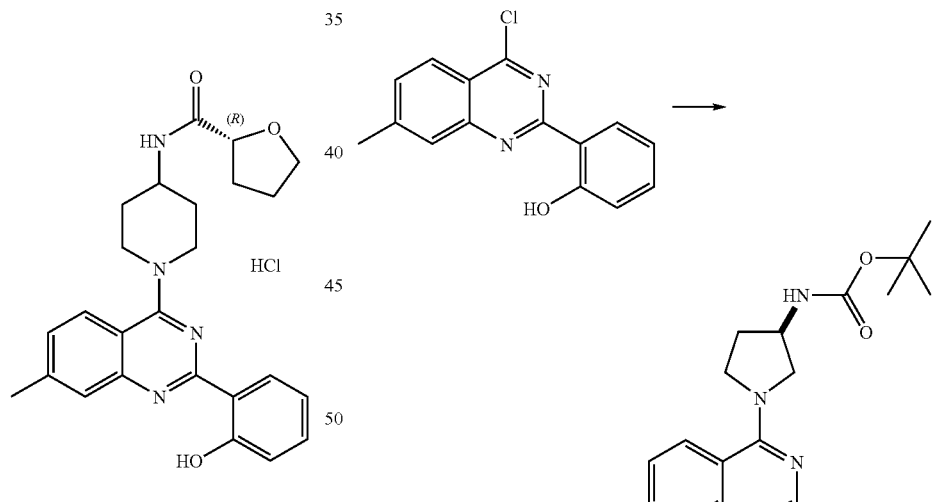

To 2-(4-chloro-7-methyl-quinazolin-2-yl)-phenol (644 mg, 2.4 mmol) in 2.9 mL of DMF at room temperature was added sequentially (R)-pyrrolidin-3-yl-carbamic acid tert-butyl ester (857 mg, 4.6 mmol) and triethylamine (662 μL, 4.8 mmol), and the reaction mixture was stirred for 12 h. The reaction mixture was diluted with water (10 mL) and CH$_2$Cl$_2$ (10 mL). The organic layer was separated and dried (Na$_2$SO$_4$), and the residue was purified by silica gel chromatography with 25-85% ethyl acetate/hexanes to give tert-butyl (R)-1-(2-(2-hydroxyphenyl)-7-methylquinazolin-4-yl)pyrrolidin-3-ylcarbamate (856 mg, 86%). LC/MS: m/z 421 (M+H)+ at 2.82 min (10%-99% CH₃CN (0.035% TFA)/H₂O (0.05% TFA)).

(S)-Tetrahydrofuran-3-yl (R)-1-(2-(2-hydroxyphenyl)-7-methylquinazolin-4-yl)pyrrolidin-3-ylcarbamate

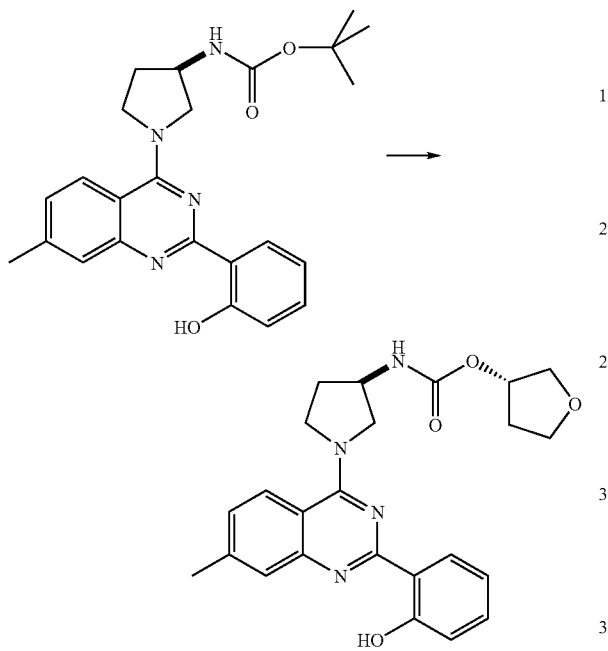

Method A

To tert-butyl (R)-1-(2-(2-hydroxyphenyl)-7-methylquinazolin-4-yl)pyrrolidin-3-ylcarbamate (850 mg, 2.02 mmol) was added at room temperature 4 mL of 1:1 TFA:CH₂Cl₂. The reaction mixture was stirred for 50 min, diluted with 20 mL of CH₂Cl₂, and washed with 15 mL of satd. NaHCO₃ solution. The organic layer was separated and dried over Na₂SO₄, and the solvent was removed under reduced pressure to give (R)-2-[4-(3-amino-pyrrolidin-1-yl)-7-methyl-quinazolin-2-yl]-phenol as an oil which was used without further purification.

To 45.9 mg (0.14 mmol) of the amine from above procedure was added 570 μL of CH₂Cl₂ and the solution was cooled to 0° C. To this solution was added sequentially 24 μL (0.17 mmol) of triethylamine and 19.4 mg (0.13 mmol) of (S)-tetrahydro-furan-3-ol chloroformate. The reaction mixture was stirred at 0° C. for 45 min, diluted with water and CH₂Cl₂ (10 mL). The organic layer was separated and dried over Na₂SO₄, and the solvent was removed under reduced pressure. The residue was purified via preparative reverse phase HPLC using 10%-99% CH₃CN (0.035% TFA)/H₂O (0.05% TFA) to give (S)-tetrahydrofuran-3-yl (R)-1-(2-(2-hydroxyphenyl)-7-methylquinazolin-4-yl)pyrrolidin-3-ylcarbamate as the TFA salt. LC/MS: m/z 435 (M+H)+ at 2.41 min (10%-99% CH₃CN (0.035% TFA)/H₂O (0.05% TFA)).

Method B

To tert-butyl (R)-1-(2-(2-hydroxyphenyl)-7-methylquinazolin-4-yl)pyrrolidin-3-ylcarbamate (907.2 mg, 2.16 mmol) was added 4 mL of 1:1 TFA:CH₂Cl₂. The mixture was stirred at room temperature for 5 hours. The reaction was diluted with a solution of saturated aqueous NaHCO₃ and CH₂Cl₂. The organic layer was separated, dried over Na₂SO₄, and concentrated under reduced pressure to give 2-(4-((R)-3-aminopyrrolidin-1-yl)-7-methylquinazolin-2-yl)phenol. To this free amine (640 mg, 2 mmol) was added 8 ml of CH₂Cl₂ and triethylamine (335 μL, 2.4 mmol). After cooling the mixture to 0° C., (S)-tetrahydrofuran-3-yl chloroformate (271 mg, 1.8 mmol) was added, and the reaction was allowed to stir for 30 minutes. Purification on silica gel using 30-100% ethyl acetate/hexanes gave (S)-tetrahydrofuran-3-yl (R)-1-(2-(2-hydroxyphenyl)-7-methylquinazolin-4-yl)pyrrolidin-3-ylcarbamate. ¹H NMR (400 MHz, CDCl₃) δ 14.8 (bs, 1H), 8.34 (d, J=6.4 Hz, 1H), 7.83 (d, J=4.0 Hz, 1H), 7.48 (bs, 1H), 7.27 (m, 1H), 7.08 (d, J=8.1 Hz, 1H), 6.93 (d, J=8.1 Hz, 1H), 6.82 (t, J=7.5 Hz, 1H), 5.21 (s, 1H), 5.06 (s, 1H), 4.37 (s, 1H), 4.15 (m, 1H), 4.02 (s, 1H), 3.97 (d, J=5.6 Hz, 1H), 3.87-3.77 (m, 5H), 2.42 (s, 3H), 2.24 (t, J=6.0 Hz, 1H), 2.15-2.06 (m, 1H), 1.98 (q, J=9.3 Hz, 2H) ppm.

(S)-Tetrahydrofuran-3-yl (R)-1-(2-(2-hydroxyphenyl)-7-methylquinazolin-4-yl)pyrrolidin-3-ylcarbamate hydrochloride

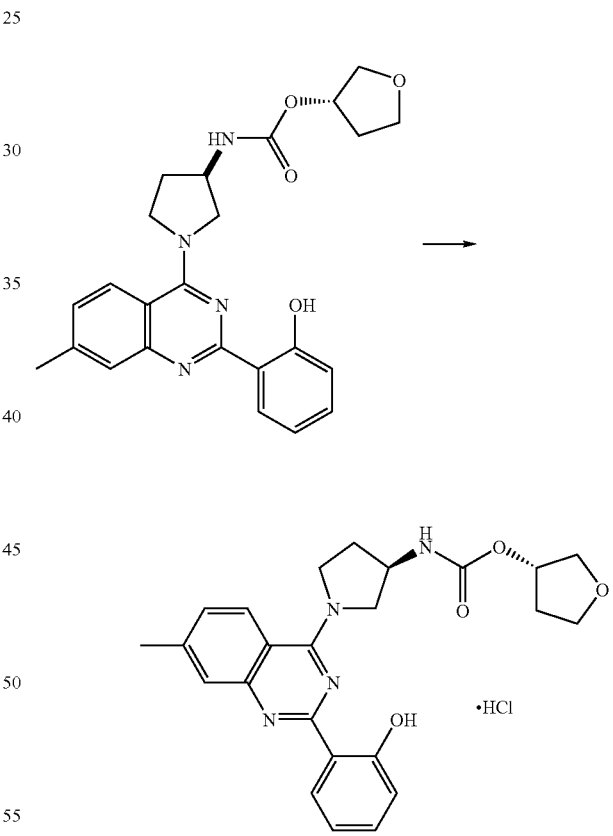

A 2.0 M HCl solution in Et₂O (192 μL, 0.38 mmol) was slowly added at −20° C. to a stirring solution of (S)-tetrahydrofuran-3-yl (R)-1-(2-(2-hydroxyphenyl)-7-methylquinazolin-4-yl)pyrrolidin-3-ylcarbamate (167 mg, 0.38 mmol) in 700 μL of CH₂Cl₂. The reaction was allowed to warm to room temperature and was stirred for 25 minutes. Solvents were removed under reduced pressure, and the residue was triturated with Et₂O and filtered to give (S)-tetrahydrofuran-3-yl (R)-1-(2-(2-hydroxyphenyl)-7-methylquinazolin-4-yl)pyrrolidin-3-ylcarbamate hydrochloride.

LC/MS: m/z 435.2 (M+H)+ at 2.41 min (10%-99% CH3CN (0.035% TFA)/H2O (0.05% TFA)).

Example 302

(R,R)-Tetrahydro-furan-2-carboxylic acid {1-[2-(2-hydroxy-phenyl)-7-methyl-quinazolin-4-yl]-pyrrolidin-3-yl}-amide

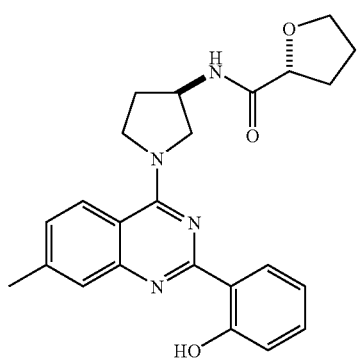

(R,R)-Tetrahydro-furan-2-carboxylic acid {1-[2-(2-hydroxy-phenyl)-7-methyl-quinazolin-4-yl]-pyrrolidin-3-yl}-amide

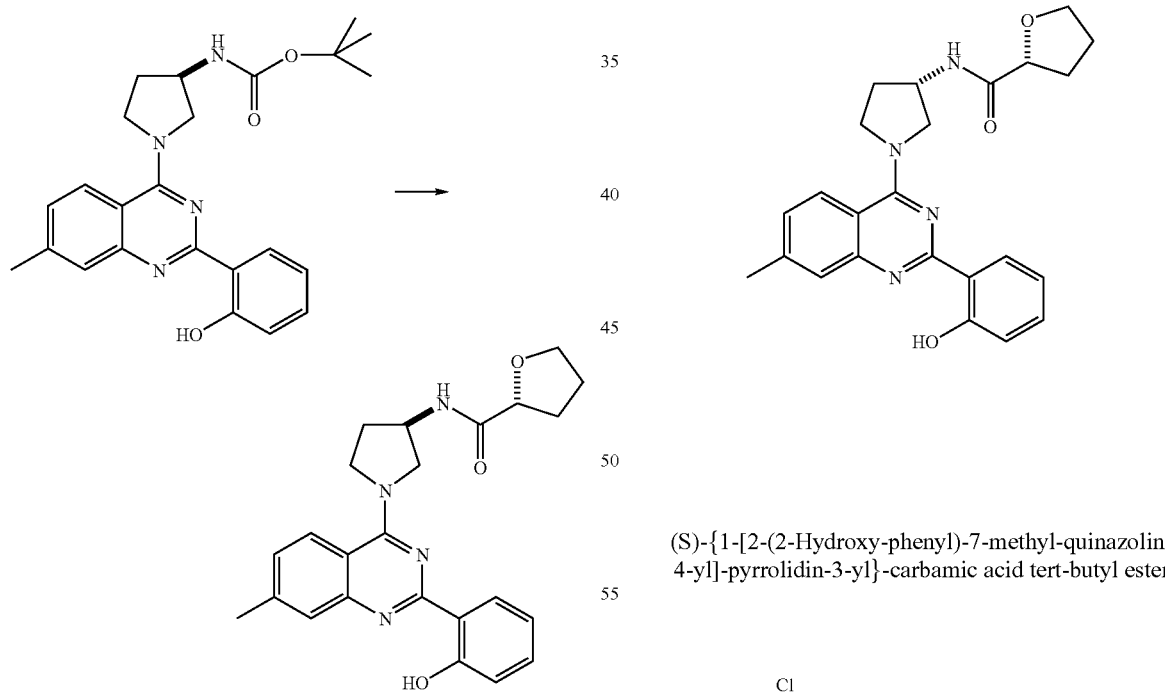

To 850 mg (2.02 mmol) of (R)-{1-[2-(2-hydroxy-phenyl)-7-methyl-quinazolin-4-yl]-pyrrolidin-3-yl}-carbamic acid tert-butyl ester was added at room temperature 4 mL of 1:1 TFA:CH2Cl2. The reaction mixture was stirred for 50 min and diluted with 20 mL of CH2Cl2 and extracted with 15 mL of satd. NaHCO3 solution. The organic layer was separated and dried over Na2SO4, and the solvent was removed under reduced pressure to give (R)-2-[4-(3-amino-pyrrolidin-1-yl)-7-methyl-quinazolin-2-yl]-phenol as an oil which was used without further purification.

To 52.6 mg (0.16 mmol) of the amine from above procedure was added 600 µL of CH2Cl2. To this solution was added sequentially 27.4 µL (0.19 mmol) of triethylamine and 20.9 mg (0.18 mmol) of (R)—tetrahydro-furan-2-carboxylic acid, 24.2 mg (0.18 mmol) of HOBt, 34.6 mg (0.18 mmol) of EDCI at room temperature. The reaction mixture was stirred for 12 h, then diluted with water and CH2Cl2 (10 mL). The organic layer was separated and dried over Na2SO4, and the solvent was removed under reduced pressure. The residue was purified via preparative reverse phase HPLC using 10%-99% CH3CN (0.035% TFA)/H2O (0.05% TFA) to give (R,R)-tetrahydro-furan-2-carboxylic acid {1-[2-(2-hydroxy-phenyl)-7-methyl-quinazolin-4-yl]-pyrrolidin-3-yl}-amide as the TFA salt. LC/MS: m/z 419 (M+H)+ at 2.35 min (10%-99% CH3CN (0.035% TFA)/H2O (0.05% TFA)).

Example 303

(2R)-Tetrahydro-N—((S)-1-(2-(2-hydroxyphenyl)-7-methylquinazolin-4-yl)pyrrolidin-3-yl)furan-2-carboxamide

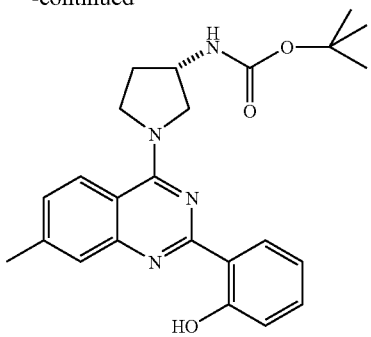

To 2-(4-chloro-7-methyl-quinazolin-2-yl)-phenol (551 mg, 2.03 mmol) in 2.5 mL of DMF at room temperature was added sequentially (S)-pyrrolidin-3-yl-carbamic acid tert-butyl ester (740 mg, 3.9 mmol) and triethylamine (567 µL, 4.0 mmol), and the reaction mixture was stirred for 12 h. The reaction mixture was diluted with water (10 mL) and CH$_2$Cl$_2$ (10 mL). The organic layer was separated and dried (Na$_2$SO$_4$), and the residue was purified via silica gel chromatography with 25-85% ethyl acetate/hexanes to give of (S)-{1-[2-(2-hydroxy-phenyl)-7-methyl-quinazolin-4-yl]-pyrrolidin-3-yl}-carbamic acid tert-butyl ester (694 mg, 81%). LC/MS: m/z 421 (M+H)$^+$ at 2.79 min (10%-99% CH$_3$CN (0.035% TFA)/H$_2$O (0.05% TFA)).

(2R)-Tetrahydro-N—((S)-1-(2-(2-hydroxyphenyl)-7-methylquinazolin-4-yl)pyrrolidin-3-yl)furan-2-carboxamide NaHCO$_3$ solution. The organic layer was separated and dried over Na$_2$SO$_4$, and the solvent was removed under reduced pressure to give (S)-2-[4-(3-amino-pyrrolidin-1-yl)-7-methyl-quinazolin-2-yl]-phenol as an oil which was used without further purification.

To the amine from above procedure (133.3 mg, 0.42 mmol) was added 1.6 mL of CH$_2$Cl$_2$. To this solution was added sequentially triethylamine (174 µL, 1.25 mmol) and (R)-tetrahydro-furan-2-carboxylic acid (57.9 mg, 0.5 mmol), HOBt (67.5 mg 0.5 mmol), EDCI (95.8 mg 0.5 mmol) at room temperature. The reaction mixture was stirred for 12 h and diluted with water and CH$_2$Cl$_2$ (10 mL). The organic layer was separated and dried over Na$_2$SO$_4$, and the solvent was removed under reduced pressure. The residue was purified via preparative reverse phase HPLC using 10%-99% CH$_3$CN (0.035% TFA)/H$_2$O (0.05% TFA) to give (2R)-tetrahydro-N—((S)-1-(2-(2-hydroxyphenyl)-7-methylquinazolin-4-yl)pyrrolidin-3-yl)furan-2-carboxamide as the TFA salt. LC/MS: m/z 419 (M+H)$^+$ at 2.34 min (10%-99% CH$_3$CN (0.035% TFA)/H$_2$O (0.05% TFA)).

Example 304

(S,S)-{1-[2-(2-Hydroxy-phenyl)-7-methyl-quinazolin-4-yl]-pyrrolidin-3-yl}-carbamic acid tetrahydro-furan-3-yl ester

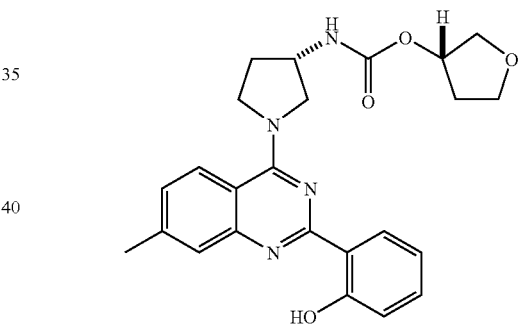

(S,S)-{1-[2-(2-Hydroxy-phenyl)-7-methyl-quinazolin-4-yl]-pyrrolidin-3-yl}-carbamic acid tetrahydro-furan-3-yl ester

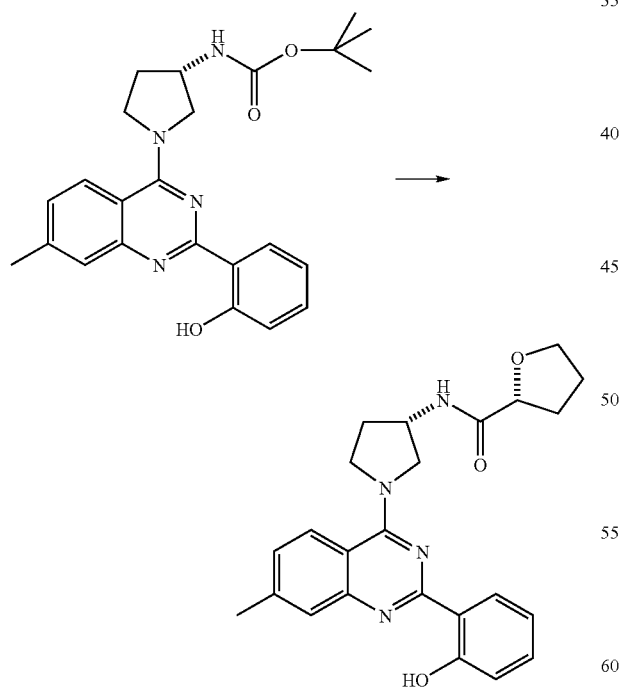

To (S)-{1-[2-(2-hydroxy-phenyl)-7-methyl-quinazolin-4-yl]-pyrrolidin-3-yl}-carbamic acid tert-butyl ester (690 mg, 1.64 mmol) was added at room temperature 3 mL of 1:1 TFA:CH$_2$Cl$_2$. The reaction mixture was stirred for 55 min, diluted with 20 mL of CH$_2$Cl$_2$ and washed with 15 mL of satd.

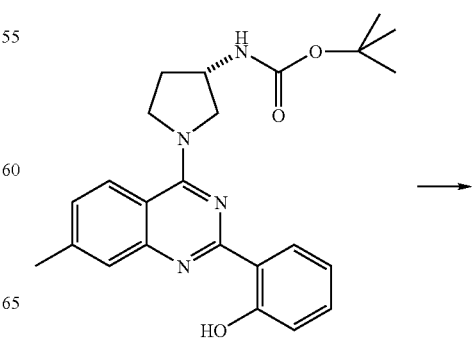

425

-continued

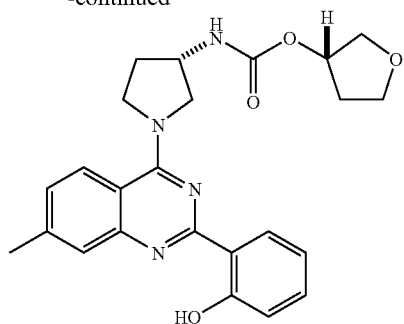

To (S)-{1-[2-(2-hydroxy-phenyl)-7-methyl-quinazolin-4-yl]-pyrrolidin-3-yl}-carbamic acid tert-butyl ester (690 mg, 1.64 mmol) was added at room temperature, 3 mL of 1:1 TFA:CH$_2$Cl$_2$. The reaction mixture was stirred for 55 min, diluted with 20 mL of CH$_2$Cl$_2$, and washed with 15 mL of satd. NaHCO$_3$ solution. The organic layer was separated and dried over Na$_2$SO$_4$, and the solvent was removed under reduced pressure to give (S)-2-[4-(3-amino-pyrrolidin-1-yl)-7-methyl-quinazolin-2-yl]-phenol as an oil which was used without further purification.

To the amine from above procedure (134.7 mg, 0.42 mmol) was added 1.6 mL of CH$_2$Cl$_2$, and the solution was cooled to 0° C. To this solution was added sequentially triethylamine (88 μL, 0.63 mmol) and (S)-tetrahydro-furan-3-ol chloroformate (82.3 mg, 0.55 mmol). The reaction mixture was stirred and allowed to warm from 0° C. to room temperature over 12 h and was diluted with water and CH$_2$Cl$_2$ (10 mL). The organic layer was separated and dried over Na$_2$SO$_4$, and the solvent was removed under reduced pressure. The residue was purified via preparative reverse phase HPLC using 10%-99% CH$_3$CN (0.035% TFA)/H$_2$O (0.05% TFA) to give (S,S)-{1-[2-(2-hydroxy-phenyl)-7-methyl-quinazolin-4-yl]-pyrrolidin-3-yl}-carbamic acid tetrahydro-furan-3-yl ester as the TFA salt. LC/MS: m/z 435 (M+H)$^+$ at 2.39 min (10%-99% CH$_3$CN (0.035% TFA)/H$_2$O (0.05% TFA)).

Example 305

(S)-Tetrahydrofuran-3-yl ((S)-1-(2-(2-hydroxyphenyl)-7-methylquinazolin-4-yl)pyrrolidin-3-yl)methylcarbamate

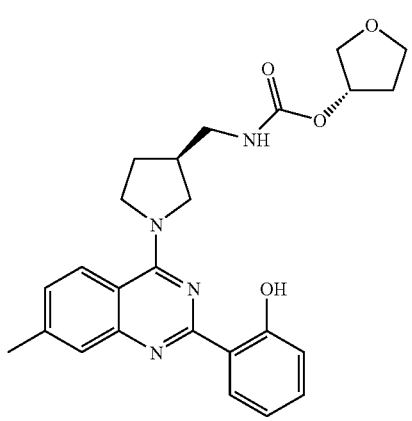

426

Benzyl ((S)-1-(tert-butoxycarbonyl)pyrrolidin-3-yl)methylcarbamate

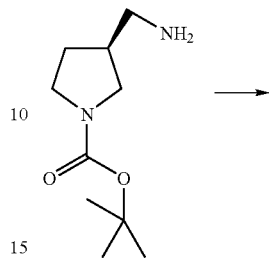

A mixture of (S)-tert-butyl 3-(aminomethyl)pyrrolidine-1-carboxylate (1.0 g, 5.0 mmol) and 50 mL THF was cooled in an ice bath. To this was added benzyl chloroformate (0.77 mL, 5.5 mmol), followed by triethylamine (1.39 mL, 10 mmol). After removing the ice bath, the reaction was stirred for 4 h. The mixture was poured into ice water and extracted with EtOAc. The organic extracts were washed with water, dried over Na$_2$SO$_4$, filtered, and concentrated. Purification via silica gel chromatography using EtOAc in hexanes (0-40%) gave benzyl ((S)-1-(tert-butoxycarbonyl)pyrrolidin-3-yl)methylcarbamate (1.29 g, 77%) as a colorless oil. $^1$H NMR (400 MHz, CDCl$_3$) δ 7.39-7.28 (m, 5H), 5.10 (s, 2H), 4.87 (s, 1H), 3.52-2.95 (m, 6H), 2.41-2.35 (m, 1H), 2.10-1.79 (m, 2H), 1.45 (s, 9H) ppm.

Benzyl ((S)-1-(2-(2-hydroxyphenyl)-7-methylquinazolin-4-yl)pyrrolidin-3-yl)methylcarbamate

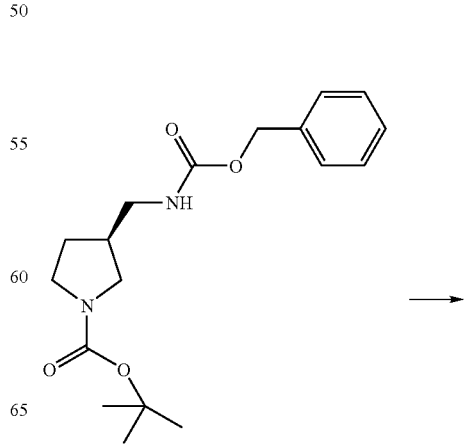

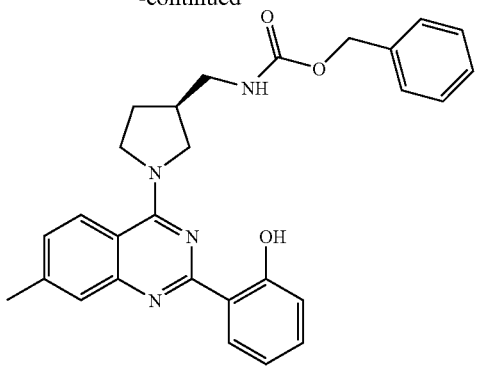

A solution of benzyl ((S)-1-(tert-butoxycarbonyl)pyrrolidin-3-yl)methylcarbamate (0.20 g, 0.60 mmol) and 4 M HCl in dioxane (10 mL) was stirred for 3 h at room temperature. After evaporating the solvent under reduced pressure, the solid was triturated with Et₂O and dried under vacuum, then taken up in CH₂Cl₂ (10 mL). To this solution was added 2-(4-chloro-7-methylquinazolin-2-yl)phenol (0.16 g, 0.60 mmol) and triethylamine (0.25 mL, 1.8 mmol). The reaction mixture was stirred at room temperature overnight, then diluted with CH₂Cl₂ and washed with water. The organic extracts were dried over Na₂SO₄, filtered, and concentrated. Purification via silica gel chromatography using 0-40% EtOAc in hexanes gave benzyl ((S)-1-(2-(2-hydroxyphenyl)-7-methylquinazolin-4-yl)pyrrolidin-3-yl)methylcarbamate as a colorless oil (0.19 g, 68%). LC/MS: m/z 469.1 (M+H)⁺ at 2.58 min (10%-99% CH₃CN (0.035% TFA)/H₂O (0.05% TFA)).

2-(4-((S)-3-(Aminomethyl)pyrrolidin-1-yl)-7-methylquinazolin-2-yl)phenol

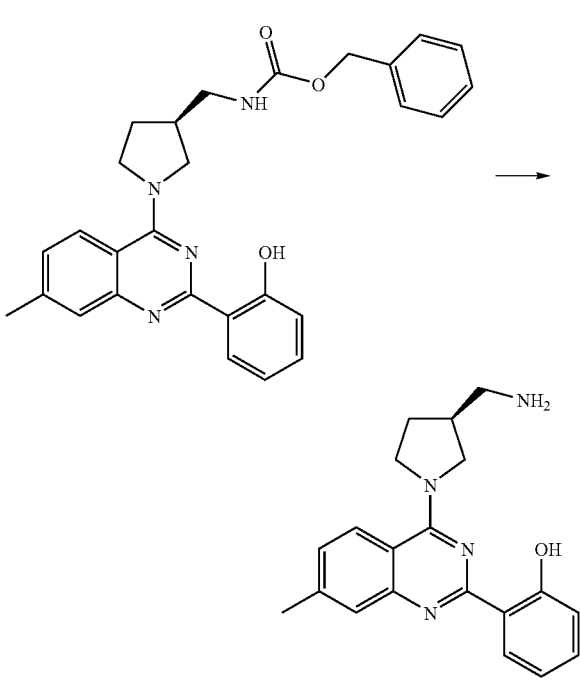

A solution of benzyl ((S)-1-(2-(2-hydroxyphenyl)-7-methylquinazolin-4-yl)pyrrolidin-3-yl)methylcarbamate (0.19 g, 0.41 mmol) and MeOH (5 mL) was stirred with Pd/C (20 mg, 10% weight of Pd on carbon) under an H₂ atmosphere at ambient pressure at ambient pressure overnight. Purification via silica gel chromatography using MeOH in CH₂Cl₂ (0-10%) gave 2-(4-((S)-3-(aminomethyl)pyrrolidin-1-yl)-7-methylquinazolin-2-yl)phenol (27 mg, 19%). LC/MS: m/z 335.5 (M+H)⁺ at 1.28 min (10%-99% CH₃CN (0.035% TFA)/H₂O (0.05% TFA)).

(S)-Tetrahydrofuran-3-yl ((S)-1-(2-(2-hydroxyphenyl)-7-methylquinazolin-4-yl)pyrrolidin-3-yl)methylcarbamate

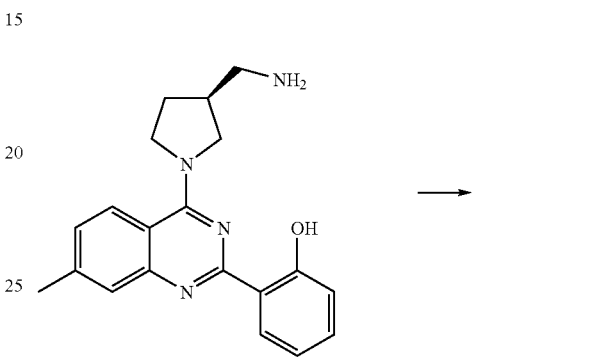

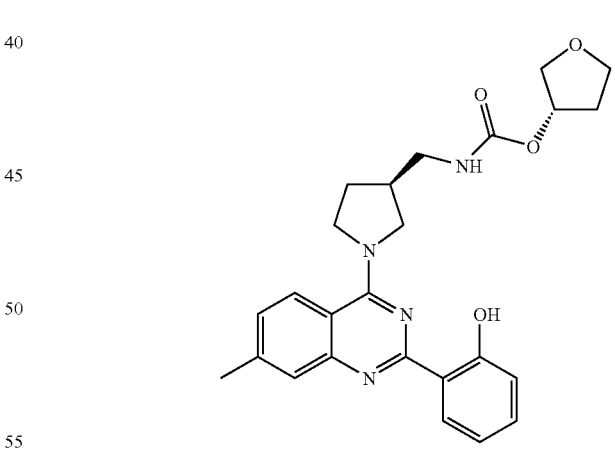

A solution of 2-(4-((S)-3-(aminomethyl)pyrrolidin-1-yl)-7-methylquinazolin-2-yl)phenol (13 mg, 0.04 mmol) and CH₂Cl₂ (0.5 mL) was cooled in an ice bath. To this mixture was added (S)-tetrahydrofuran-3-yl chloroformate (6 μL, 0.04 mmol), followed by triethylamine (11 μL, 0.08 mmol). After removing the ice bath, the reaction was stirred for 3 h at room temperature. Purification via preparative reverse phase HPLC (10%-99% CH₃CN (0.035% TFA)/H₂O (0.05% TFA)) gave (S)-tetrahydrofuran-3-yl ((S)-1-(2-(2-hydroxyphenyl)-7-methylquinazolin-4-yl)pyrrolidin-3-yl)methylcarbamate

Example 306

(R)-Tetrahydrofuran-3-yl ((R)-1-(2-(2-hydroxyphenyl)-7-methylquinazolin-4-yl)pyrrolidin-3-yl)methylcarbamate

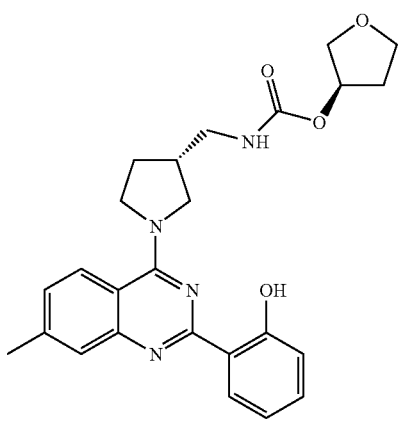

Benzyl ((R)-1-(tert-butoxycarbonyl)pyrrolidin-3-yl)methylcarbamate

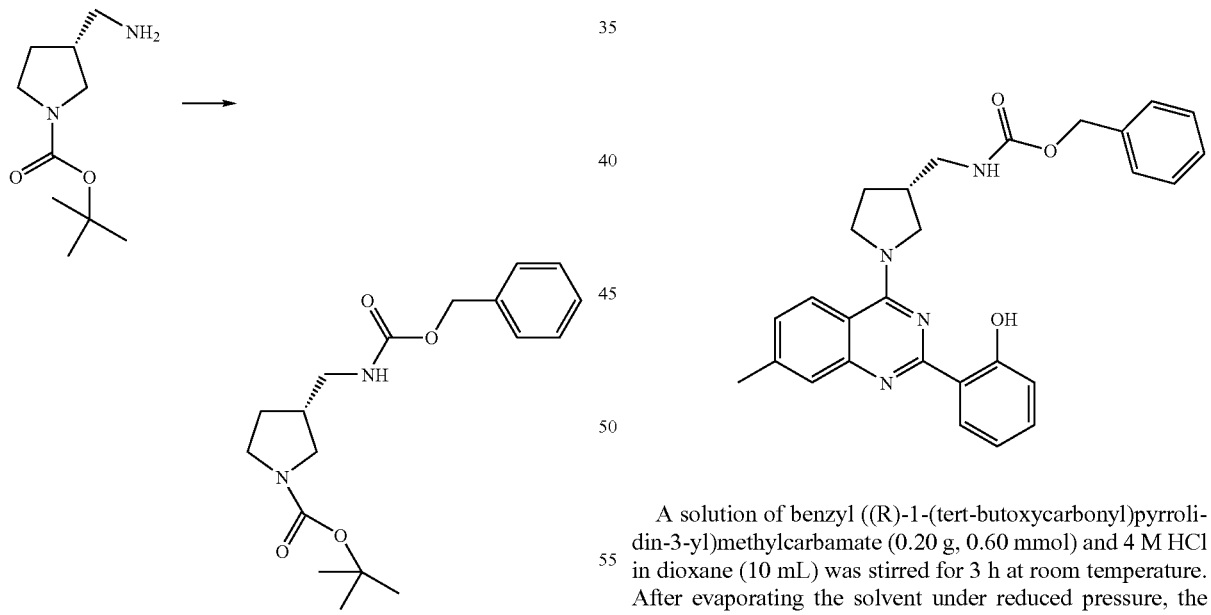

A solution of (R)-tert-butyl 3-(aminomethyl)pyrrolidine-1-carboxylate (1.0 g, 5.0 mmol) and 50 mL THF was cooled in an ice bath. To this mixture was added benzyl chloroformate (0.77 mL, 5.5 mmol), followed by triethylamine (1.39 mL, 10 mmol). After removing the ice bath, the reaction was stirred for 4 h. The mixture was poured into ice water and extracted with EtOAc. The organic extracts were washed with water, dried over $Na_2SO_4$, filtered, and concentrated. Purification via silica gel chromatography using EtOAc in hexanes as the TFA salt. LC/MS: m/z 449.3 (M+H)$^+$ at 2.18 min (10%-99% $CH_3CN$ (0.035% TFA)/$H_2O$ (0.05% TFA)).

(0-40%) gave benzyl ((R)-1-(tert-butoxycarbonyl)pyrrolidin-3-yl)methylcarbamate (1.29 g, 77%) as a colorless oil. $^1$H NMR (400 MHz, $CDCl_3$) δ 7.39-7.28 (m, 5H), 5.10 (s, 2H), 4.87 (s, 1H), 3.52-2.95 (m, 6H), 2.41-2.35 (m, 1H), 2.10-1.79 (m, 2H), 1.45 (s, 9H) ppm.

Benzyl ((R)-1-(2-(2-hydroxyphenyl)-7-methylquinazolin-4-yl)pyrrolidin-3-yl)methylcarbamate

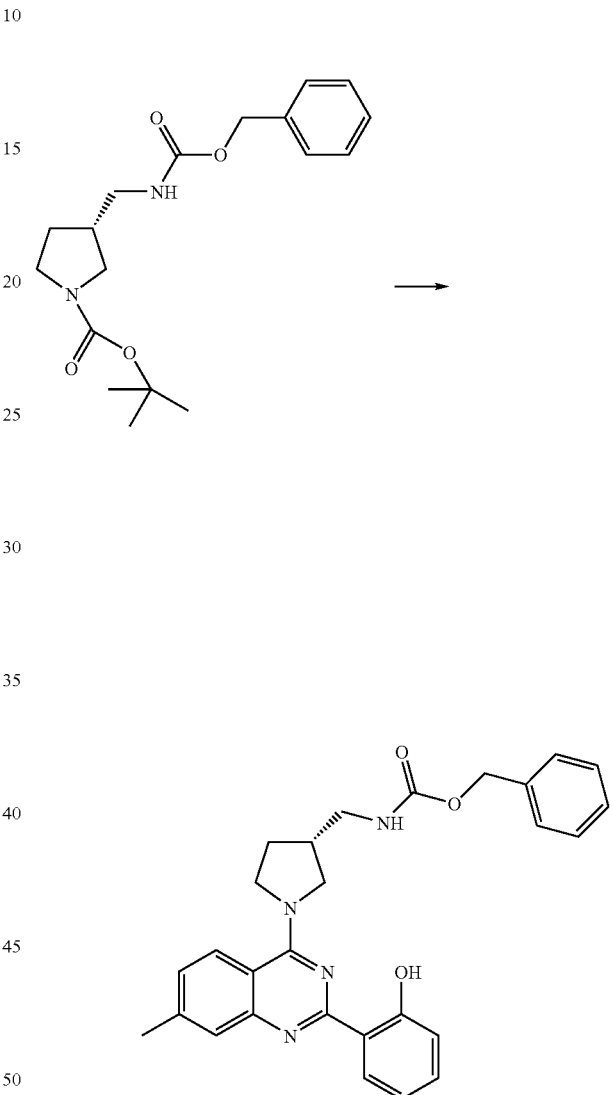

A solution of benzyl ((R)-1-(tert-butoxycarbonyl)pyrrolidin-3-yl)methylcarbamate (0.20 g, 0.60 mmol) and 4 M HCl in dioxane (10 mL) was stirred for 3 h at room temperature. After evaporating the solvent under reduced pressure, the resulting solid was triturated with $Et_2O$ and dried under vacuum, then taken up in $CH_2Cl_2$ (10 mL). To this solution was added 2-(4-chloro-7-methylquinazolin-2-yl)phenol (0.16 g, 0.60 mmol) and triethylamine (0.25 mL, 1.8 mmol). The reaction mixture was stirred at room temperature overnight, then diluted with $CH_2Cl_2$ and washed with water. The $CH_2Cl_2$ solution was dried over $Na_2SO_4$, filtered, and concentrated. Purification via silica gel chromatography using 0-40% EtOAc in hexanes gave benzyl ((R)-1-(2-(2-hydroxyphenyl)-7-methylquinazolin-4-yl)pyrrolidin-3-yl)methylcarbamate as a colorless oil (0.19 g, 68%). LC/MS: m/z 469.1 (M+H)⁺ at 2.58 min (10%-99% CH₃CN (0.035% TFA)/H₂O (0.05% TFA)).

2-(4-((R)-3-(Aminomethyl)pyrrolidin-1-yl)-7-methylquinazolin-2-yl)phenol

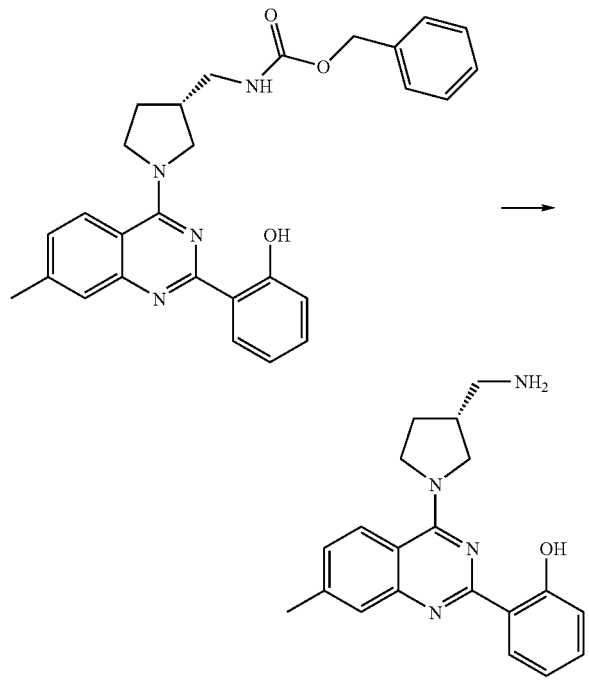

A solution of benzyl ((K)-1-(2-(2-hydroxyphenyl)-7-methylquinazolin-4-yl)pyrrolidin-3-yl)methylcarbamate (0.19 g, 0.41 mmol) and MeOH (5 mL) was stirred with Pd/C (20 mg, 10% weight of Pd on carbon) under an H₂ atmosphere at ambient pressure overnight. Purification via silica gel chromatography using MeOH in CH₂Cl₂ (0-10%) gave 2-(4-((R)-3-(aminomethyl)pyrrolidin-1-yl)-7-methylquinazolin-2-yl)phenol (63 mg, 45%). LC/MS: m/z 335.7 (M+H)⁺ at 1.23 min (10%-99% CH₃CN (0.035% TFA)/H₂O (0.05% TFA)).

(R)-Tetrahydrofuran-3-yl ((R)-1-(2-(2-hydroxyphenyl)-7-methylquinazolin-4-yl)pyrrolidin-3-yl)methylcarbamate

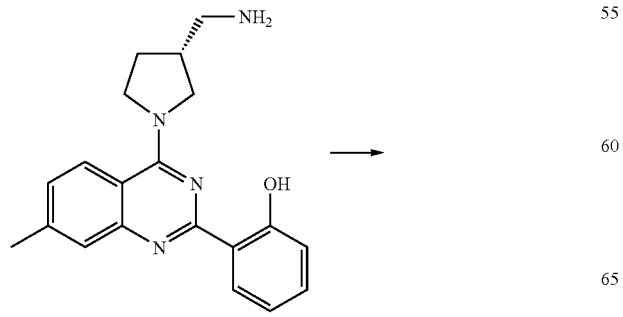

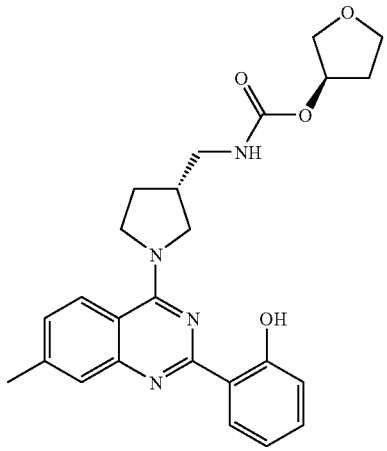

A solution of 2-(4-((R)-3-(aminomethyl)pyrrolidin-1-yl)-7-methylquinazolin-2-yl)phenol (15 mg, 0.045 mmol) and CH₂Cl₂ (0.5 mL) was cooled in an ice bath. To this mixture was added (R)-tetrahydrofuran-3-yl chloroformate (7 μL, 0.045 mmol), followed by triethylamine (13 μL, 0.090 mmol). After removing the ice bath, the reaction was stirred at room temperature for 3 h. Purification via preparative reverse phase HPLC (10%-99% CH₃CN (0.035% TFA)/H₂O (0.05% TFA)) gave (R)-tetrahydrofuran-3-yl ((R)-1-(2-(2-hydroxyphenyl)-7-methylquinazolin-4-yl)pyrrolidin-3-yl)methylcarbamate as the TFA salt. LC/MS: m/z 449.3 (M+H)⁺ at 2.17 min (10%-99% CH₃CN (0.035% TFA)/H₂O (0.05% TFA)).

Example 307

(S)-Tetrahydrofuran-3-yl ((R)-1-(2-(2-hydroxyphenyl)-7-methylquinazolin-4-yl)pyrrolidin-3-yl)methylcarbamate

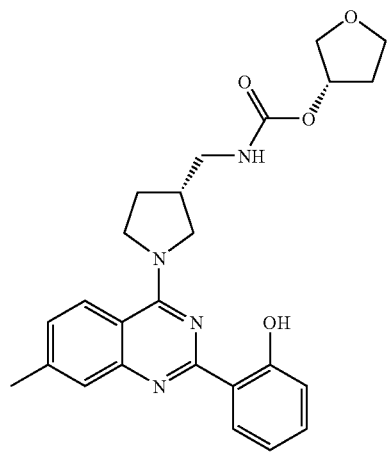

433

(S)-Tetrahydrofuran-3-yl ((R)-1-(2-(2-hydroxyphenyl)-7-methylquinazolin-4-yl)pyrrolidin-3-yl)methylcarbamate

434

(2R)-Tetrahydro-N—(((R)-1-(2-(2-hydroxyphenyl)-7-methylquinazolin-4-yl)pyrrolidin-3-yl)methyl)furan-2-carboxamide

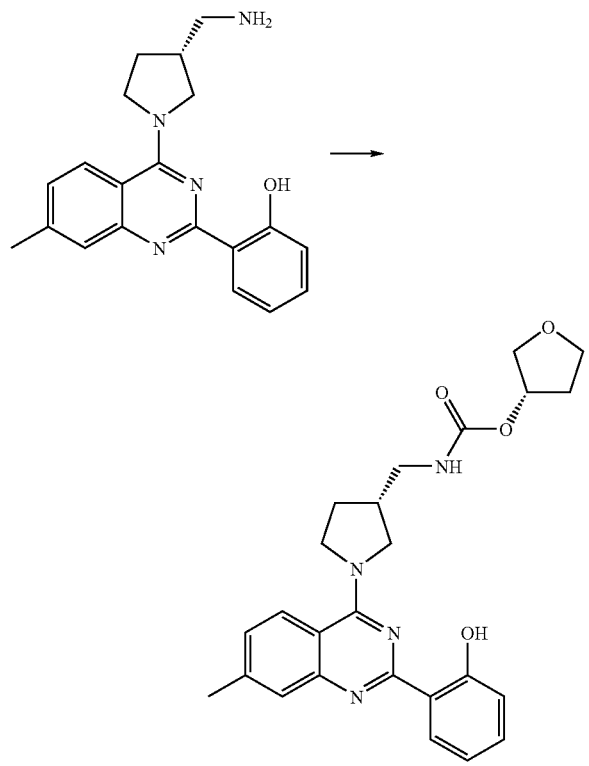

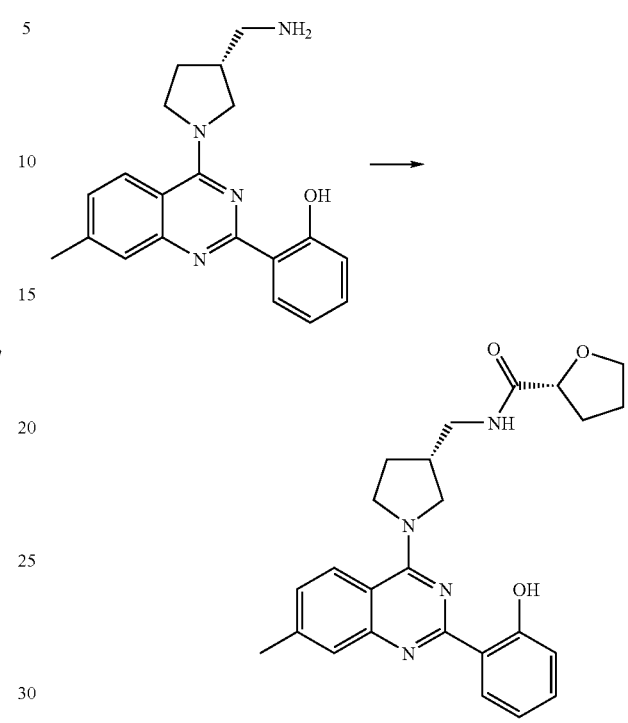

A mixture of 2-(4-((R)-3-(aminomethyl)pyrrolidin-1-yl)-7-methylquinazolin-2-yl)phenol (15 mg, 0.045 mmol) and CH$_2$Cl$_2$ (0.5 mL) was cooled in an ice bath. To this was added (S)-tetrahydrofuran-3-yl chloroformate (7 µL, 0.045 mmol), followed by triethylamine (13 µL, 0.090 mmol). After removing the ice bath, the reaction was stirred at room temperature for 3 h. Purification via preparative reverse phase HPLC (10%-99% CH$_3$CN (0.035% TFA)/H$_2$O (0.05% TFA)) gave (S)-tetrahydrofuran-3-yl ((R)-1-(2-(2-hydroxyphenyl)-7-methylquinazolin-4-yl)pyrrolidin-3-yl)methylcarbamate as the TFA salt. LC/MS: m/z 449.3 (M+H)$^+$ at 2.18 min (10%-99% CH$_3$CN (0.035% TFA)/H$_2$O (0.05% TFA)).

To a solution of 2-(4-((R)-3-(aminomethyl)pyrrolidin-1-yl)-7-methylquinazolin-2-yl)phenol (15 mg, 0.045 mmol) and DMF (0.5 mL) was added (R)-tetrahydrofuran-2-carboxylic acid (6 µL, 0.062 mmol), followed by the addition of HATU (26 mg, 67 mmol) and triethylamine (13 µL, 0.090 mmol). The reaction was stirred at room temperature for 3 h. Purification via preparative reverse phase HPLC (10%-99% CH$_3$CN (0.035% TFA)/H$_2$O (0.05% TFA)) gave (2R)-tetrahydro-N-(((R)-1-(2-(2-hydroxyphenyl)-7-methylquinazolin-4-yl)pyrrolidin-3-yl)methyl)furan-2-carboxamide as the TFA salt. LC/MS: m/z 433.5 (M+H)$^+$ at 2.11 min (10%-99% CH$_3$CN (0.035% TFA)/H$_2$O (0.05% TFA)).

Example 308

(2R)-Tetrahydro-N—(((R)-1-(2-(2-hydroxyphenyl)-7-methylquinazolin-4-yl)pyrrolidin-3-yl)methyl)furan-2-carboxamide Example 309

(R)-{1-[2-(2-Hydroxy-phenyl)-7-methyl-quinazolin-4-yl]-pyrrolidin-3-yl}-carbamic acid benzyl ester

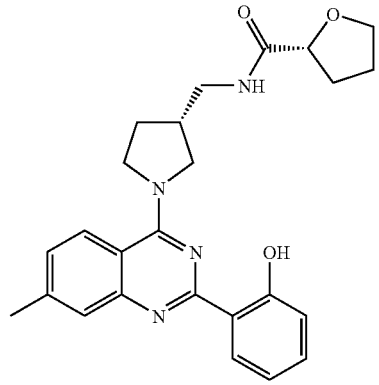

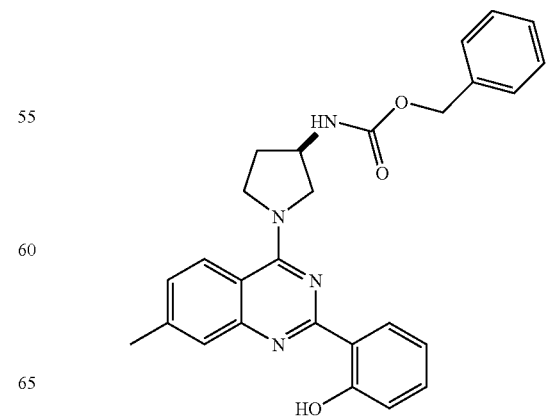

435

{1-[2-(2-Hydroxy-phenyl)-7-methyl-quinazolin-4-yl]-pyrrolidin-3R-yl}-carbamic acid tert-butyl ester

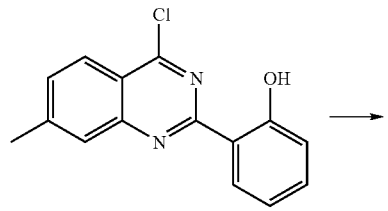

To a cooled (−15° C.) solution of 2-(4-chloro-7-methylquinazolin-2-yl)phenol (43.8 g, 0.15 mol) in CH$_2$Cl$_2$ (125 mL) was added dropwise a solution of (3R)-(+)-3-(tert-butoxycarbonylamino)pyrrolidine (30 g, 0.16 mol) and triethylamine (38 mL, 0.27 mol) in CH$_2$Cl$_2$ (170 mL). The addition, during which the temperature stayed below 30° C., was completed in 20 minutes. The external cooling was removed and the reaction mixture was stirred at room temperature overnight. Water (1 L) and CH$_2$Cl$_2$ (1 L) were added. The resulting precipitate was collected by filtration, washed with water and CH$_2$Cl$_2$, and air-dried to yield 33 g of pure {1-[2-(2-hydroxy-phenyl)-7-methyl-quinazolin-4-yl]-pyrrolidin-3R-yl}-carbamic acid tert-butyl ester. The filtrates were evaporated to give another batch of crude {1-[2-(2-hydroxy-phenyl)-7-methyl-quinazolin-4-yl]-pyrrolidin-3R-yl}-carbamic acid tert-butyl ester which was purified by trituration with CH$_2$Cl$_2$. Total yield: 43.5 g (70%). $^1$H-NMR (300 MHz, CDCl$_3$): δ 8.45 (dd, J=8 Hz, 1.7 Hz, 1H), 7.95 (d, J=8.8 Hz, 1H), 7.57 (s, 1H), 7.37-7.31 (m, 1H), 7.18 (dd, J=8.5 Hz, 1.7, 1H), 7.0 (dd, J=8.3 Hz, 1.1 Hz, 1H), 6.9 (dt, J=8.9 Hz, 1.4 Hz, 1H), 4.77 (bs, 1H), 4.40 (bs, 1H), 4.27-4.21 (m, 1H), 4.14-4.03 (m, 2H), 3.86 (dd, J=11.8 Hz, 4.4 Hz, 1H), 2.50 (s, 3H), 2.34-2.28 (m, 1H), 2.08-2.02 (m, 1H), 1.46 (s, 9H) ppm.

2-(4-(3R-Aminopyrrolidin-1-yl)-7-methylquinazolin-2-yl)phenol

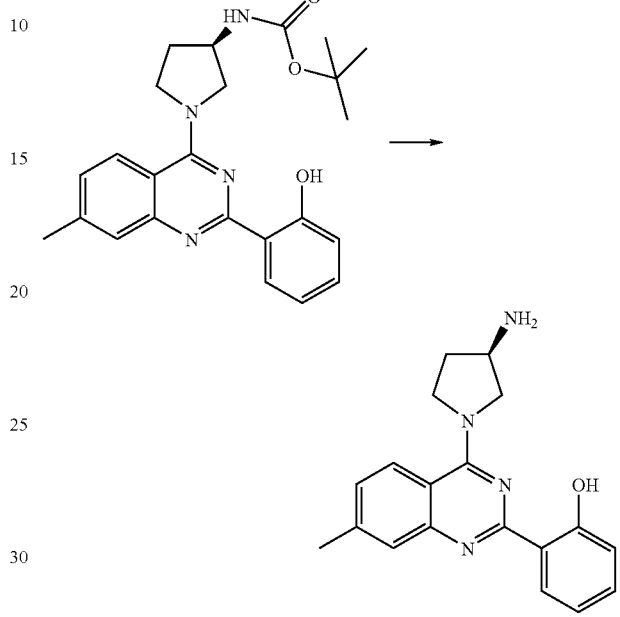

{1-[2-(2-Hydroxy-phenyl)-7-methyl-quinazolin-4-yl]-pyrrolidin-3R-yl}-carbamic acid tert-butyl ester (43.5 g, 100 mmol) was stirred with CF$_3$CO$_2$H (142 mL) in CH$_2$Cl$_2$ (300 mL) at room temperature overnight. The solution was concentrated to dryness, and the residue was suspended in 10% aq. Na$_2$CO$_3$ (900 mL) and stirred for 2 hours. The suspension was filtered, and the yellow solid was washed with water several times. The product was air-dried at 45° C. to yield 2-(4-(3R-aminopyrrolidin-1-yl)-7-methylquinazolin-2-yl)phenol (34.2 g) as a light-yellow solid. $^1$H-NMR (300 MHz, CD$_3$OD): δ 8.41 (dd, J=7.4 Hz, 1.4 Hz, 1H), 8.09 (d, J=8.5 Hz, 1H), 7.46 (s, 1H), 7.34-7.28 (m, 1H), 7.23 (dd, J=8.8 Hz, 1.9 Hz, 1H), 6.91-6.85 (m, 2H), 4.16-4.09 (m, 2H), 4.00-3.94 (m, 1H), 3.73-3.64 (m, 2H), 2.48 (s, 3H), 2.26-2.20 (m, 1H), 1.92-1.86 (m, 1H) ppm.

(R)-{1-[2-(2-Hydroxy-phenyl)-7-methyl-quinazolin-4-yl]-pyrrolidin-3-yl}-carbamic acid benzyl ester

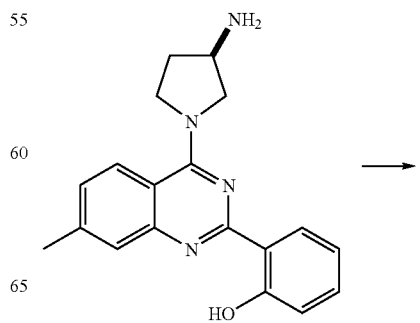

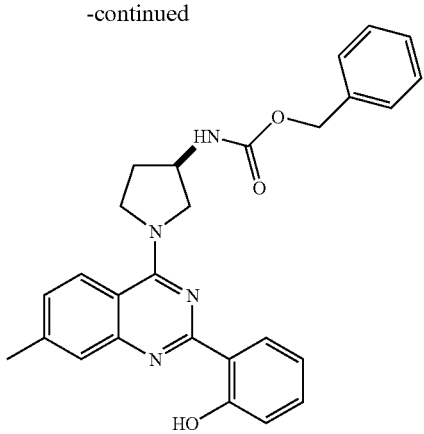

Method A

To (R)-2-[4-(3-amino-pyrrolidin-1-yl)-7-methyl-quinazolin-2-yl]-phenol (50.8 mg, 0.16 mmol) was added 500 μL of CH$_2$Cl$_2$ and the solution was cooled to 0° C. To this solution was added sequentially triethylamine (33.2 μL, 0.24 mmol) and benzyl chloroformate (29.2 mg, 0.17 mmol). The reaction mixture was stirred from 0° C. to 5° C. over 45 min, then diluted with water and CH$_2$Cl$_2$ (10 mL). The organic layer was separated and dried over Na$_2$SO$_4$, and the solvent was removed under reduced pressure to give (R)-{1-[2-(2-hydroxy-phenyl)-7-methyl-quinazolin-4-yl]-pyrrolidin-3-yl}-carbamic acid benzyl ester. LC/MS: m/z 455.2 (M+H)$^+$ at 2.81 min (10%-99% CH$_3$CN (0.035% TFA)/H$_2$O (0.05% TFA)).

Method B

Benzyl (R)-1-(2-(2-hydroxyphenyl)-7-methylquinazolin-4-yl)pyrrolidin-3-ylcarbamate

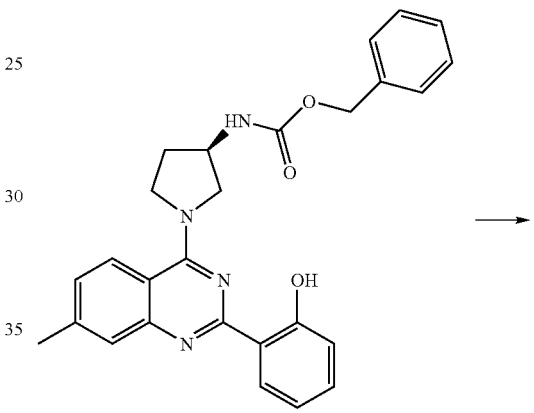

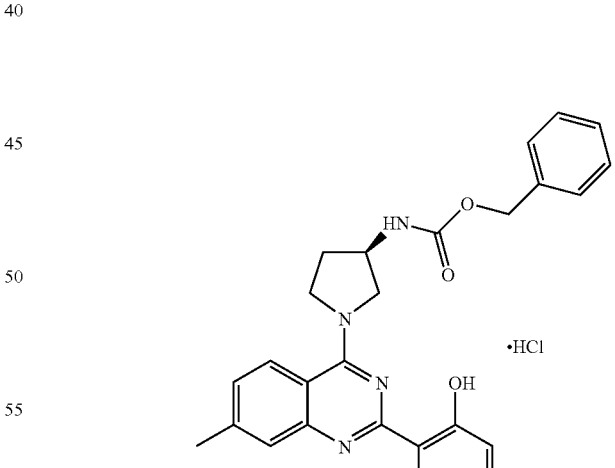

To tert-butyl (R)-1-(2-(2-hydroxyphenyl)-7-methylquinazolin-4-yl)pyrrolidin-3-ylcarbamate (398 mg, 0.94 mmol) was added 3 mL of 1:1 TFA: CH$_2$Cl$_2$. The mixture was then stirred at room temperature for 30 minutes. The reaction mixture was diluted with a solution of saturated NaHCO$_3$ and CH$_2$Cl$_2$. The organic layer was separated, washed with a solution of extracted 1 N NaOH, dried over Na$_2$SO$_4$ and evaporated under reduced pressure to give the intermediate amine. To this amine (300 mg, 0.94 mmol) were added 3 ml of CH$_2$Cl$_2$ and triethylamine (145 μL, 1.04 mmol). After cooling the mixture to 0° C., benzyl chloroformate (161.6 mg, 0.94 mmol) was added, and the reaction was stirred for 30 minutes. Purification via silica gel chromatography using 20-100% ethyl acetate/hexanes gave benzyl (R)-1-(2-(2-hydroxyphenyl)-7-methylquinazolin-4-yl)pyrrolidin-3-ylcarbamate. LC/MS: m/z 455.2 (M+H)$^+$ at 2.81 min (10%-99% CH$_3$CN (0.035% TFA)/H$_2$O (0.05% TFA)).

Benzyl (R)-1-(2-(2-hydroxyphenyl)-7-methylquinazolin-4-yl)pyrrolidin-3-ylcarbamate hydrochloride

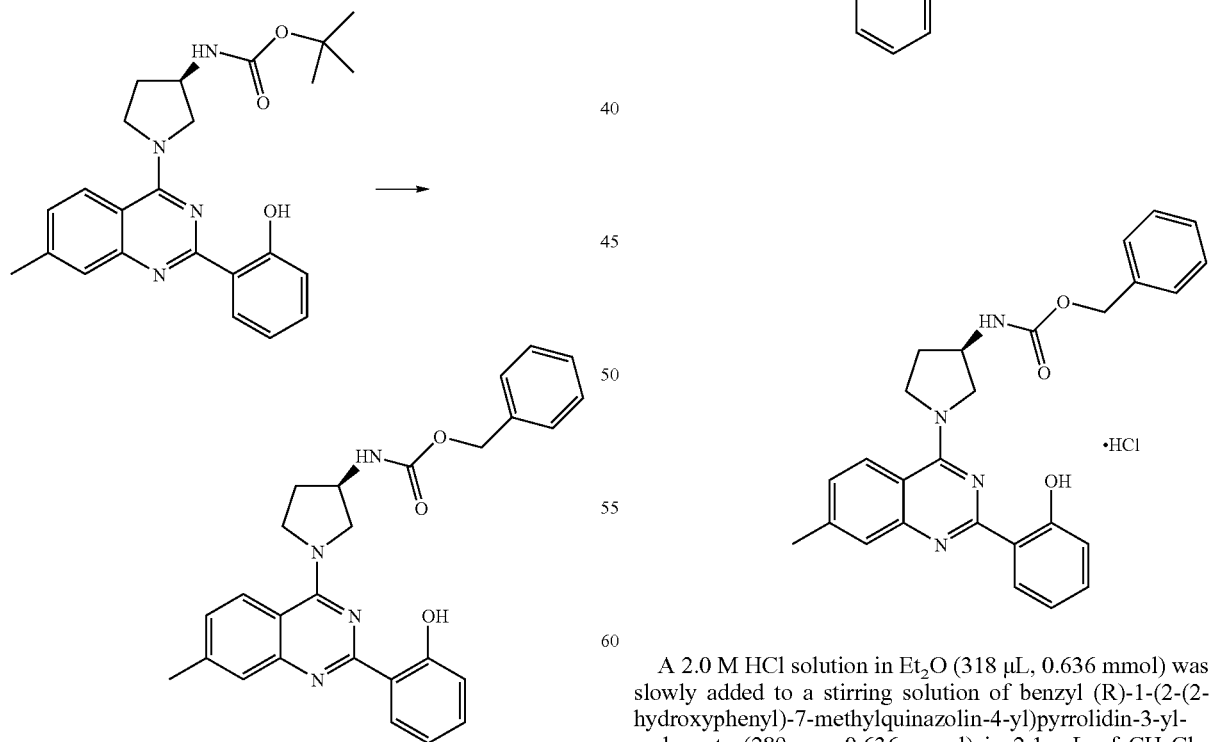

A 2.0 M HCl solution in Et$_2$O (318 μL, 0.636 mmol) was slowly added to a stirring solution of benzyl (R)-1-(2-(2-hydroxyphenyl)-7-methylquinazolin-4-yl)pyrrolidin-3-ylcarbamate (289 mg, 0.636 mmol) in 2.1 mL of CH$_2$Cl$_2$. Solvents were removed under reduced pressure and the residue was triturated with Et$_2$O and filtered to give benzyl (R)-1-(2-(2-hydroxyphenyl)-7-methylquinazolin-4-yl)pyrrolidin-3-ylcarbamate hydrochloride. LC/MS: m/z 455.2 (M+H)+ at 2.80 min (10%-99% CH₃CN (0.035% TFA)/H₂O (0.05% TFA)).

Example 310

(2R)-Tetrahydro-N—(((S)-1-(2-(2-hydroxyphenyl)-7-methylquinazolin-4-yl)pyrrolidin-3-yl)methyl)furan-2-carboxamide

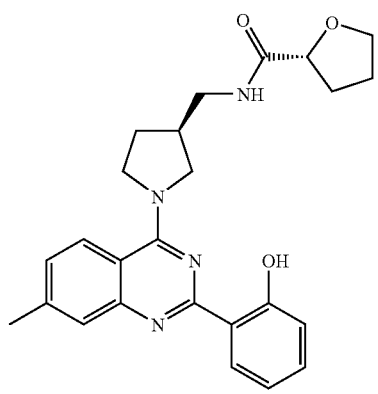

(2R)-Tetrahydro-N—(((S)-1-(2-(2-hydroxyphenyl)-7-methylquinazolin-4-yl)pyrrolidin-3-yl)methyl)furan-2-carboxamide

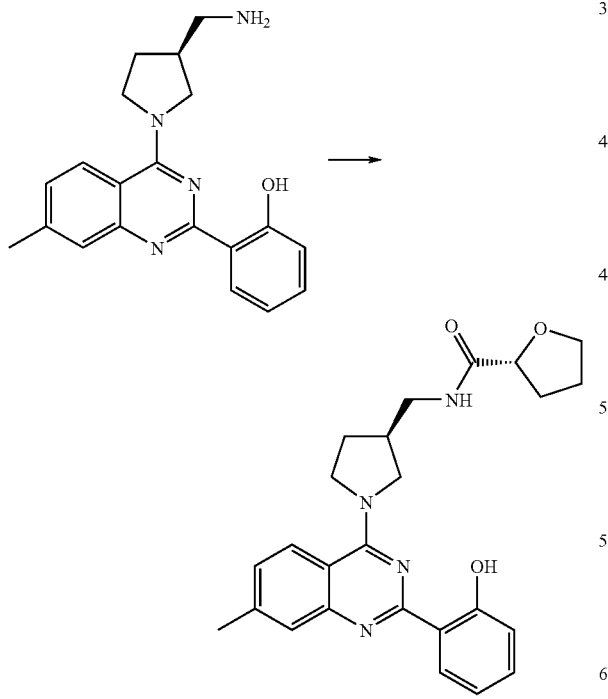

To a solution of 2-(4-((S)-3-(aminomethyl)pyrrolidin-1-yl)-7-methylquinazolin-2-yl)phenol (25 mg, 0.075 mmol) and DMF (0.5 mL) was added (R)-tetrahydrofuran-2-carboxylic acid (8.6 µL, 0.09 mmol), followed by the addition of HATU (34 mg, 0.09 mmol) and triethylamine (21 µL, 0.15 mmol). The reaction was stirred at room temperature for 3 h. Purification via preparative reverse phase HPLC (10%-99% CH₃CN (0.035% TFA)/H₂O (0.05% TFA)) gave (2R)-tetrahydro-N—(((S)-1-(2-(2-hydroxyphenyl)-7-methylquinazolin-4-yl)pyrrolidin-3-yl)methyl)furan-2-carboxamide as the TFA salt. LC/MS: m/z 433.5 (M+H)+ at 2.13 min (10%-99% CH₃CN (0.035% TFA)/H₂O (0.05% TFA)).

Example 311

N—(((S)-1-(2-(2-Hydroxyphenyl)-7-methylquinazolin-4-yl)pyrrolidin-3-yl)methyl)cyclopropanecarboxamide

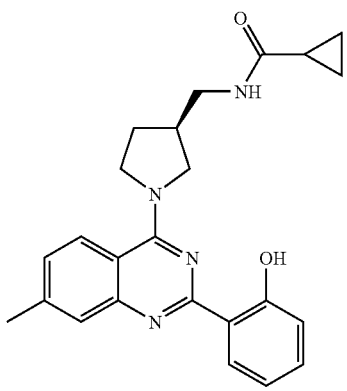

N—(((S)-1-(2-(2-Hydroxyphenyl)-7-methylquinazolin-4-yl)pyrrolidin-3-yl)methyl)cyclopropanecarboxamide

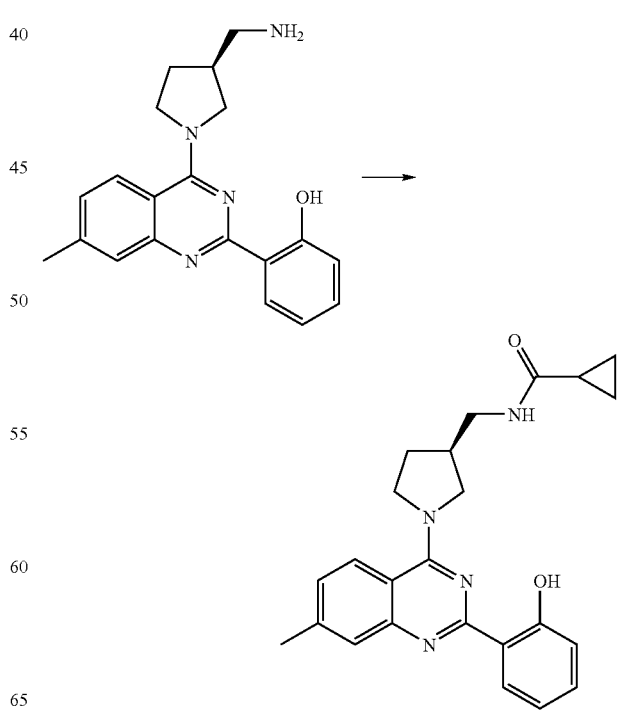

A solution of 2-(4-((S)-3-(aminomethyl)pyrrolidin-1-yl)-7-methylquinazolin-2-yl)phenol (25 mg, 0.075 mmol) and CH₂Cl₂ (0.5 mL) was cooled in an ice bath. To this mixture was added cyclopropanecarbonyl chloride (7.5 μL, 82 mmol), followed by triethylamine (21 μL, 0.15 mmol). After removing the ice bath, the reaction was stirred at room temperature for 3 h. Purification via preparative reverse phase HPLC (10%-99% CH₃CN (0.035% TFA)/H₂O (0.05% TFA)) gave N—(((S)-1-(2-(2-hydroxyphenyl)-7-methylquinazolin-4-yl)pyrrolidin-3-yl)methyl)cyclopropanecarboxamide as the TFA salt. LC/MS: m/z 403.7 (M+H)⁺ at 2.17 min (10%-99% CH₃CN (0.035% TFA)/H₂O (0.05% TFA)).

Example 312

(R)-Cyclopropanecarboxylic acid {1-[2-(2-hydroxy-phenyl)-7-methyl-quinazolin-4-yl]-pyrrolidin-3-yl}-amide

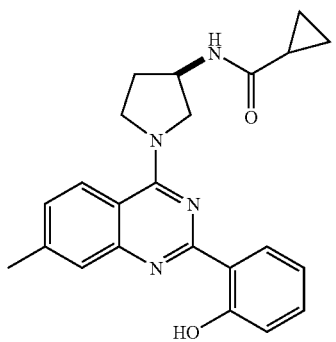

(R)-Cyclopropanecarboxylic acid {1-[2-(2-hydroxy-phenyl)-7-methyl-quinazolin-4-yl]-pyrrolidin-3-yl}-amide

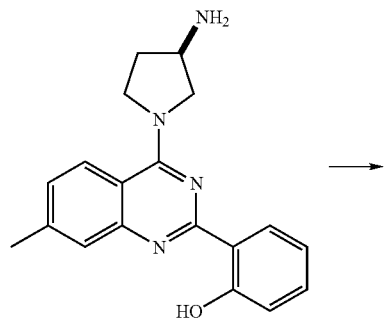

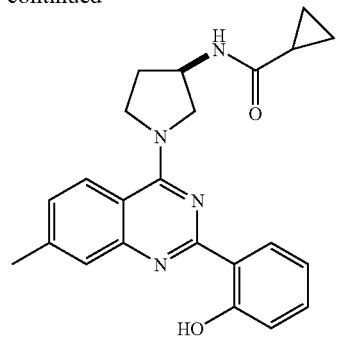

To (R)-2-[4-(3-amino-pyrrolidin-1-yl)-7-methyl-quinazolin-2-yl]-phenol (49.3 mg, 0.15 mmol) was added 500 μL of CH₂Cl₂ and the solution was cooled to 0° C. To this solution was added sequentially triethylamine (21.5 μL, 0.15 mmol) and cyclopropanecarbonyl chloride (16.1 mg, 0.15 mmol). The reaction mixture was stirred from 0° C. to 5° C. over 40 min and diluted with water and CH₂Cl₂ (10 mL). The organic layer was separated and dried over Na₂SO₄, and the solvent was removed under reduced pressure. The residue was purified via preparative reverse phase HPLC using 10%-99% CH₃CN (0.035% TFA)/H₂O (0.05% TFA) to give (R)-cyclopropanecarboxylic acid {1-[2-(2-hydroxy-phenyl)-7-methyl-quinazolin-4-yl]-pyrrolidin-3-yl}-amide as the TFA salt. LC/MS: m/z 389 (M+H)⁺ at 2.38 min (10%-99% CH₃CN (0.035% TFA)/H₂O (0.05% TFA)).

Example 313

(R)-{1-[2-(2-Hydroxy-phenyl)-7-methyl-quinazolin-4-yl]-pyrrolidin-3-yl}-carbamic acid phenyl ester

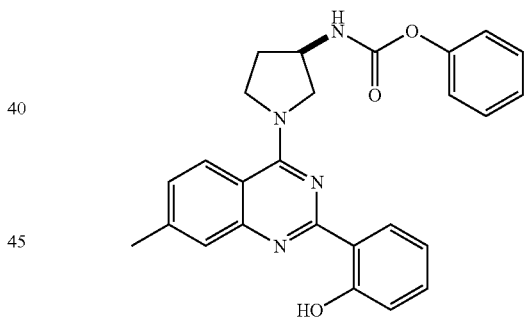

(R)-{1-[2-(2-Hydroxy-phenyl)-7-methyl-quinazolin-4-yl]-pyrrolidin-3-yl}-carbamic acid phenyl ester

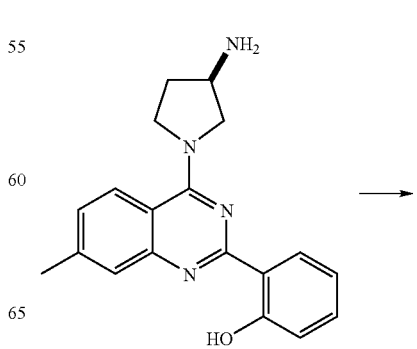

443

-continued

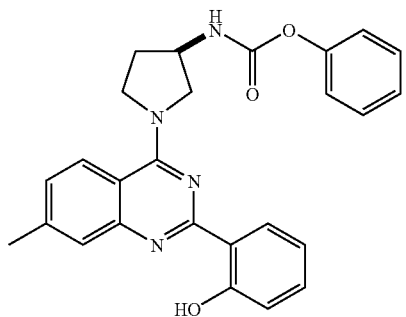

To (R)-2-[4-(3-amino-pyrrolidin-1-yl)-7-methyl-quinazolin-2-yl]-phenol (48 mg, 0.15 mmol) was added 500 μL of CH$_2$Cl$_2$, and the solution was cooled to 0° C. To this solution was added sequentially triethylamine (21 μL, 0.15 mmol) and phenyl chloroformate (22.8 mg, 0.15 mmol). The reaction mixture was stirred from 0° C. to 5° C. over 40 min, diluted with water and CH$_2$Cl$_2$ (10 mL). The organic layer was separated and dried over Na$_2$SO$_4$, and the solvent was removed under reduced pressure. The residue was purified via preparative reverse phase HPLC using 10%-99% CH$_3$CN (0.035% TFA)/H$_2$O (0.05% TFA) to give (R)-{1-[2-(2-hydroxy-phenyl)-7-methyl-quinazolin-4-yl]-pyrrolidin-3-yl}-carbamic acid phenyl ester as the TFA salt. LC/MS: m/z 441 (M+H)$^+$ at 2.78 min (10%-99% CH$_3$CN (0.035% TFA)/H$_2$O (0.05% TFA)).

Example 314

(Tetrahydro-2H-pyran-2-yl)methyl (R)-1-(2-(2-hydroxyphenyl)-7-methylquinazolin-4-yl)pyrrolidin-3-ylcarbamate

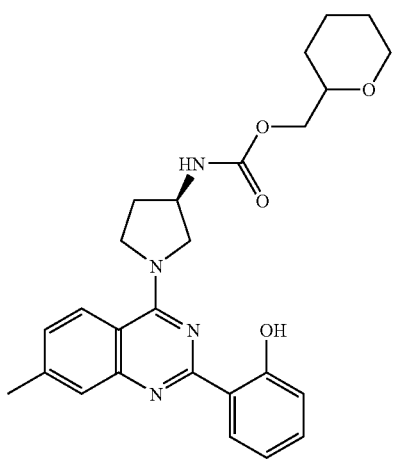

444

(Tetrahydro-2H-pyran-2-yl)methyl 1H-imidazole-1-carboxylate

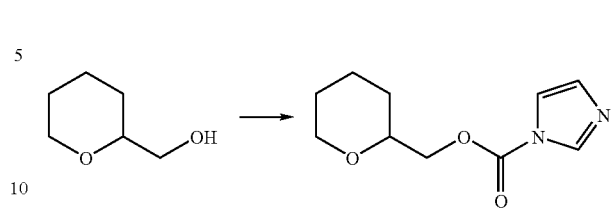

To a mixture of (tetrahydro-2H-pyran-2-yl)methanol (369 mg, 3.17 mmol) and di(1H-imidazol-1-yl)methanone (1.03 g, 6.35 mmol) was added 10.5 mL of CH$_2$Cl$_2$. The reaction was stirred at 50° C. for 3 hours. The reaction mixture was used without further purification. LC/MS: m/z 211.1 (M+H)$^+$ at 0.94 min (10%-99% CH$_3$CN (0.035% TFA)/H$_2$O (0.05% TFA)).

(Tetrahydro-2H-pyran-2-yl)methyl (R)-1-(2-(2-hydroxyphenyl)-7-methylquinazolin-4-yl)pyrrolidin-3-ylcarbamate

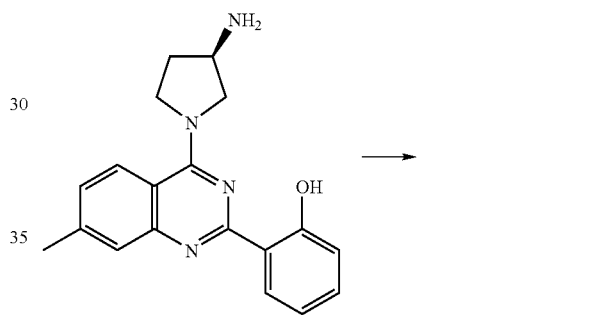

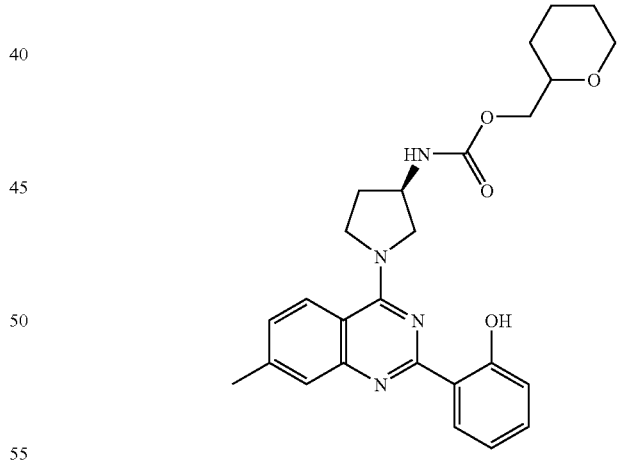

To a mixture of 2-(4-((R)-3-aminopyrrolidin-1-yl)-7-methylquinazolin-2-yl)phenol (100 mg, 0.31 mmol) and (tetrahydro-2H-pyran-2-yl)methyl 1H-imidazole-1-carboxylate (98 mg, 0.47 mmol) was added 1.04 mL CH$_2$Cl$_2$ and triethylamine (65 μL, 47 mg, 0.46 mmol). The mixture was stirred at room temperature overnight. An additional equivalent of (tetrahydro-2H-pyran-2-yl)methyl 1H-imidazole-1-carboxylate (100 mg, 0.47 mmol) was added to the mixture, and the reaction was heated at 45° C. for 4 hours. Purification via silica gel chromatography using 10%-100% ethyl acetate/hexanes gave (tetrahydro-2H-pyran-2-yl)methyl (R)-1-(2-(2- hydroxyphenyl)-7-methylquinazolin-4-yl)pyrrolidin-3-yl-carbamate. LC/MS: m/z 463.4 (M+H)+ at 2.66 min (10%-99% CH₃CN (0.035% TFA)/H₂O (0.05% TFA)).

Example 315

(R)-5-Oxo-pyrrolidine-2-carboxylic acid {1-[2-(2-hydroxy-phenyl)-7-methyl-quinazolin-4-yl]-pyrrolidin-3-yl}-amide

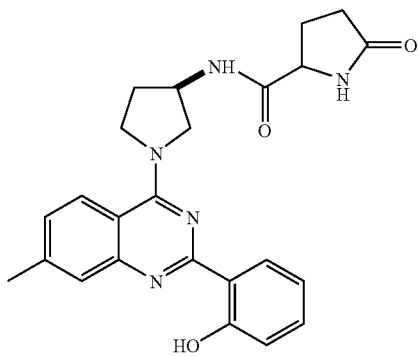

(R)-5-Oxo-pyrrolidine-2-carboxylic acid {1-[2-(2-hydroxy-phenyl)-7-methyl-quinazolin-4-yl]-pyrrolidin-3-yl}-amide

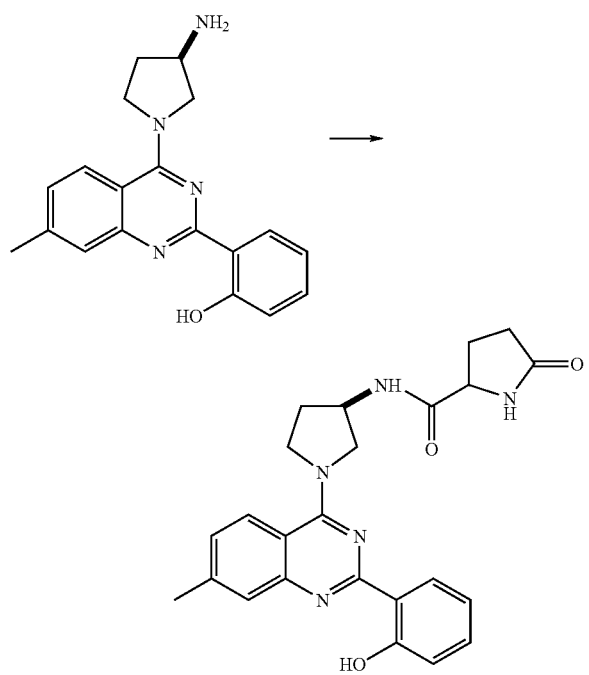

To (R)-2-[4-(3-amino-pyrrolidin-1-yl)-7-methyl-quinazolin-2-yl]-phenol (71 mg, 0.22 mmol) was added 890 μL of CH₂Cl₂. To this solution was added sequentially triethylamine (47 μL, 0.34 mmol) and 5-oxo-pyrrolidine-2-carboxylic acid (34.8 mg, 0.27 mmol) and BOP (119 mg, 0.27 mmol). The reaction mixture was stirred at room temperature for 2 h and diluted with water and CH₂Cl₂ (10 mL). The organic layer was separated and dried over Na₂SO₄, and the solvent was removed under reduced pressure to give (R)-5-oxo-pyrrolidine-2-carboxylic acid {1-[2-(2-hydroxy-phenyl)-7-methyl-quinazolin-4-yl]-pyrrolidin-3-yl}-amide. LC/MS: m/z 432.5 (M+H)+ at 2.24 min (10%-99% CH₃CN (0.035% TFA)/H₂O (0.05% TFA)).

Example 316

Tetrahydro-N—((R)-1-(2-(2-hydroxyphenyl)-7-methylquinazolin-4-yl)pyrrolidin-3-yl)-2H-pyran-4-carboxamide

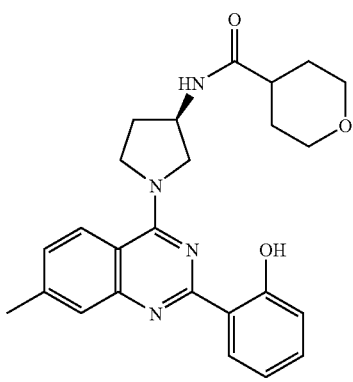

Tetrahydro-N—((R)-1-(2-(2-hydroxyphenyl)-7-methylquinazolin-4-yl)pyrrolidin-3-yl)-2H-pyran-4-carboxamide

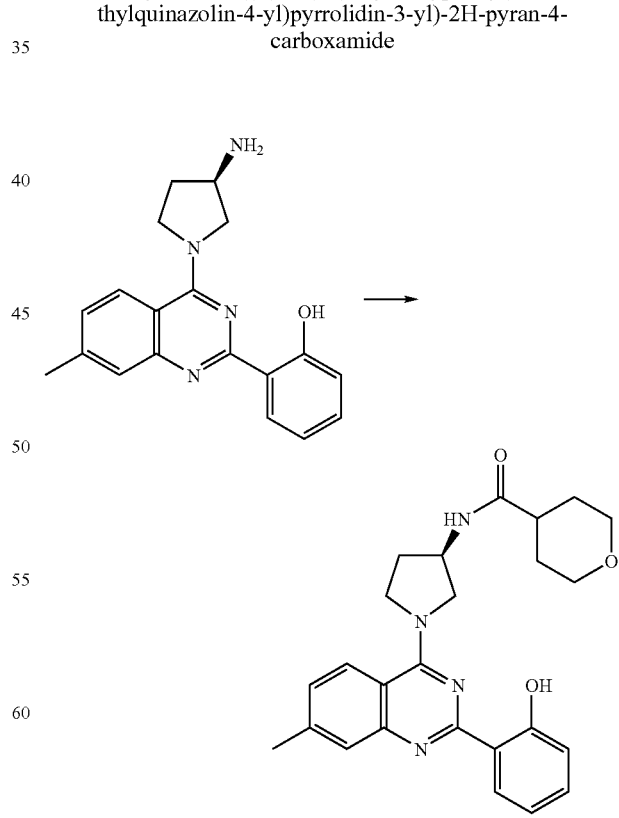

To a stirred solution of 2-(4-((R)-3-aminopyrrolidin-1-yl)-7-methylquinazolin-2-yl)phenol (50 mg, 0.16 mmol) in 1 mL of DMF was cooled to 0° C. and tetrahydro-2H-pyran-4-carboxylic acid (24 mg, 0.19 mmol) was added, followed by the addition of triethylamine (32 mg, 44 μL, 0.31 mmol) and HATU (71.1 mg, 0.187 mmol). The reaction was stirred at 0° C. for 10 minutes, then gradually warmed to room temperature, then filtered. Purification via reverse phase HPLC (10%-99% CH$_3$CN (0.035% TFA)/H$_2$O (0.05% TFA)) gave tetrahydro-N—((R)-1-(2-(2-hydroxyphenyl)-7-methylquinazolin-4-yl)pyrrolidin-3-yl)-2H-pyran-4-carboxamide as the TFA salt. LC/MS: m/z 433.5 (M+H)$^+$ at 2.05 min (10%-99% CH$_3$CN (0.035% TFA)/H$_2$O (0.05% TFA)).

Example 317

2-(Tetrahydro-2H-pyran-4-yl)-N—((R)-1-(2-(2-hydroxyphenyl)-7-methylquinazolin-4-yl)pyrrolidin-3-yl)acetamide

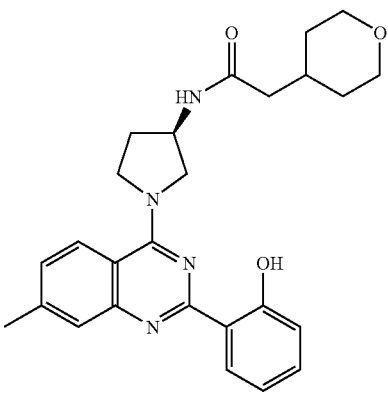

2-(Tetrahydro-2H-pyran-4-yl)-N—((R)-1-(2-(2-hydroxyphenyl)-7-methylquinazolin-4-yl)pyrrolidin-3-yl)acetamide

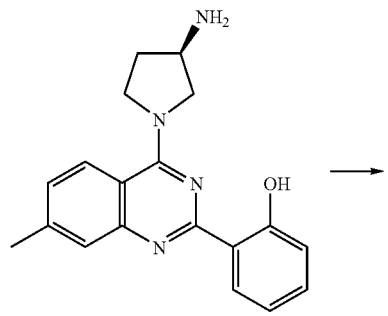

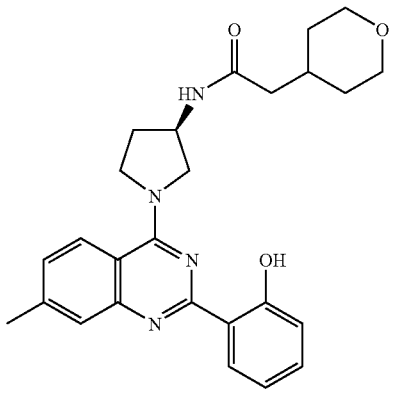

To a stirred solution of 2-(4-((R)-3-aminopyrrolidin-1-yl)-7-methylquinazolin-2-yl)phenol (50 mg, 0.16 mmol) in 1 mL of DMF cooled to 0° C. was added 2-(tetrahydro-2H-pyran-4-yl)acetic acid (27 mg, 0.19 mmol), followed by the addition of triethylamine (32 mg, 44 μL, 0.31 mmol) and HATU (71.1 mg, 0.187 mmol). The reaction was stirred at 0° C. for 10 minutes, then gradually warmed to room temperature. Filtered, and purified via reverse phase HPLC (10%-99% CH$_3$CN (0.035% TFA)/H$_2$O (0.05% TFA)) to give 2-(tetrahydro-2H-pyran-4-yl)-N—((R)-1-(2-(2-hydroxyphenyl)-7-methylquinazolin-4-yl)pyrrolidin-3-yl)acetamide as the TFA salt. LC/MS: m/z 477.3 (M+H)$^+$ at 2.07 min (10%-99% CH$_3$CN (0.035% TFA)/H$_2$O (0.05% TFA)).

Example 318

N—((R)-1-(2-(2-Hydroxyphenyl)-7-methylquinazolin-4-yl)pyrrolidin-3-yl)-3-(pyridin-2-yl)propanamide

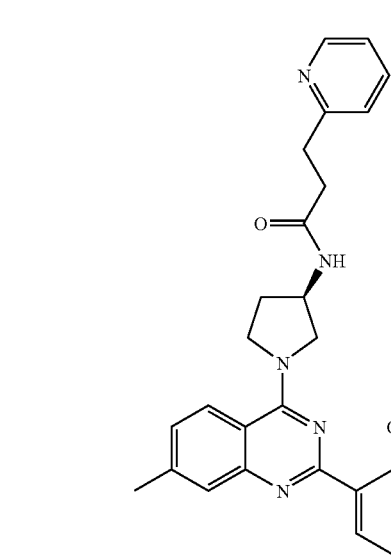

449

N—((R)-1-(2-(2-Hydroxyphenyl)-7-methylquinazolin-4-yl)pyrrolidin-3-yl)-3-(pyridin-2-yl)propanamide

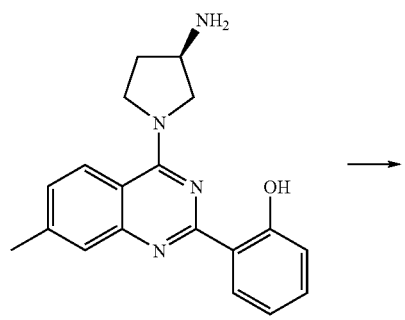

450

Example 319

(Pyridin-3-yl)methyl (R)-1-(2-(2-hydroxyphenyl)-7-methylquinazolin-4-yl)pyrrolidin-3-ylcarbamate

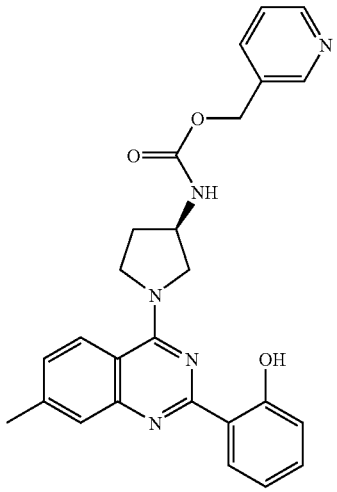

(Pyridin-3-yl)methyl (R)-1-(2-(2-hydroxyphenyl)-7-methylquinazolin-4-yl)pyrrolidin-3-ylcarbamate

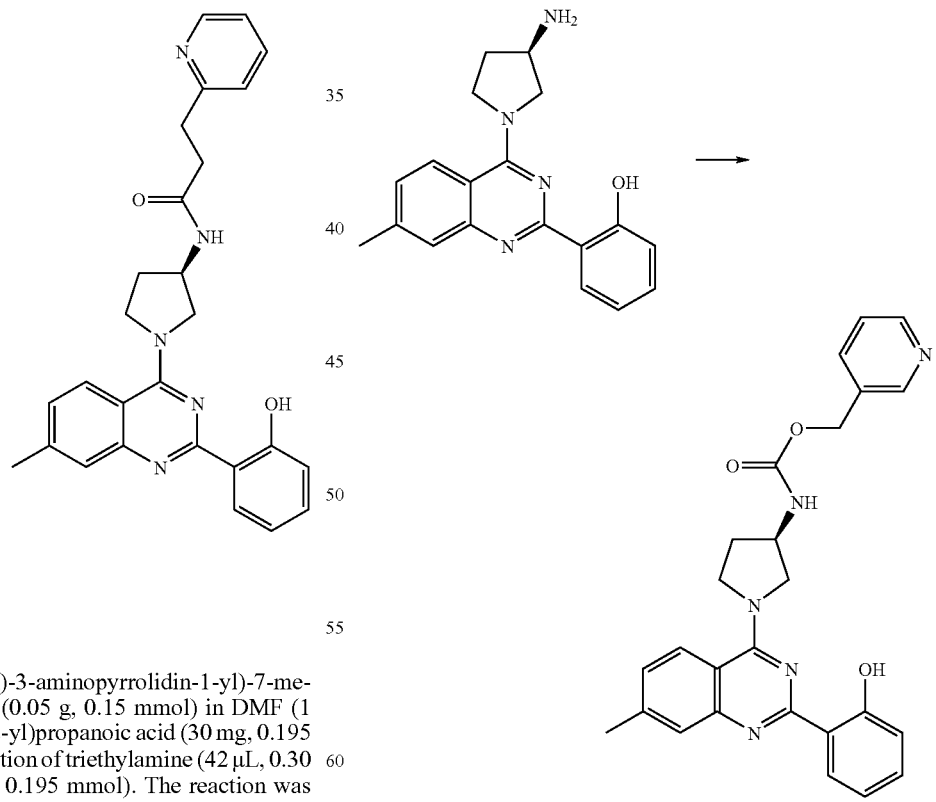

To a solution of 2-(4-((R)-3-aminopyrrolidin-1-yl)-7-methylquinazolin-2-yl)phenol (0.05 g, 0.15 mmol) in DMF (1 mL) was added 3-(pyridin-2-yl)propanoic acid (30 mg, 0.195 mmol), followed by the addition of triethylamine (42 µL, 0.30 mmol) and HATU (74 mg, 0.195 mmol). The reaction was stirred at room temperature for 2 h and then purified via reverse phase HPLC (10%-99% CH$_3$CN (0.035% TFA)/H$_2$O (0.05% TFA)) to obtain N—((R)-1-(2-(2-hydroxyphenyl)-7-methylquinazolin-4-yl)pyrrolidin-3-yl)-3-(pyridin-2-yl)propanamide as the TFA salt. LC/MS: m/z 454.3 (M+H)$^+$ at 1.79 min (10%-99% CH$_3$CN (0.035% TFA)/H$_2$O (0.05% TFA)).

To a solution of 2-(4-((R)-3-aminopyrrolidin-1-yl)-7-methylquinazolin-2-yl)phenol (50 mg, 0.16 mmol) in DMSO (0.5 mL) at room temperature was added triethylamine (43 µL, 0.31 mmol), followed by the addition of (pyridin-3-yl)

methyl 1H-imidazole-1-carboxylate (63 mg, 0.31 mmol). The reaction was stirred at room temperature overnight, filtered, and purified using reverse phase HPLC (10%-99% CH$_3$CN (0.035% TFA)/H$_2$O (0.05% TFA)) to afford (pyridin-3-yl)methyl (R)-1-(2-(2-hydroxyphenyl)-7-methylquinazolin-4-yl)pyrrolidin-3-ylcarbamate as the TFA salt. LC/MS: m/z 456.5 (M+H)$^+$ at 1.85 min (10%-99% CH$_3$CN (0.035% TFA)/H$_2$O (0.05% TFA)).

Example 320

(Pyridin-4-yl)methyl (R)-1-(2-(2-hydroxyphenyl)-7-methylquinazolin-4-yl)pyrrolidin-3-ylcarbamate

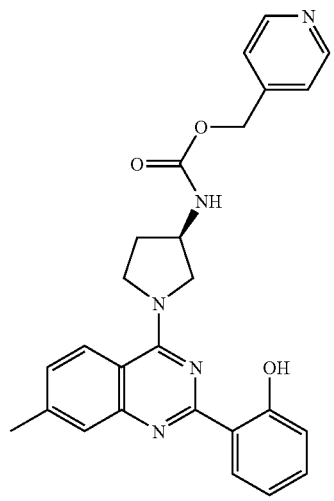

To a solution of 2-(4-((R)-3-aminopyrrolidin-1-yl)-7-methylquinazolin-2-yl)phenol (50 mg, 0.16 mmol) in DMSO (0.5 mL) at room temperature was added triethylamine (43 µL, 0.31 mmol), followed by the addition of (pyridin-4-yl)methyl 1H-imidazole-1-carboxylate (63 mg, 0.31 mmol). The reaction was stirred at room temperature overnight, filtered, and purified using reverse phase HPLC (10%-99% CH$_3$CN (0.035% TFA)/H$_2$O (0.05% TFA)) to afford (pyridin-4-yl)methyl (R)-1-(2-(2-hydroxyphenyl)-7-methylquinazolin-4-yl)pyrrolidin-3-ylcarbamate as the TFA salt. LC/MS: m/z 456.5 (M+H)$^+$ at 1.84 min (10%-99% CH$_3$CN (0.035% TFA)/H$_2$O (0.05% TFA)).

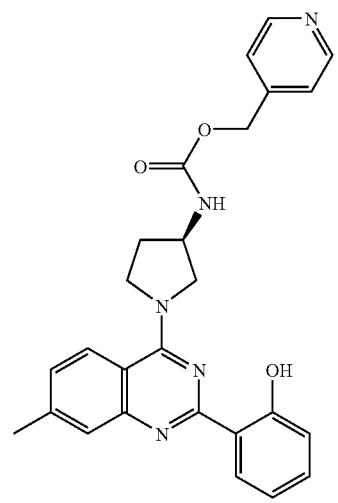

(Pyridin-4-yl)methyl (R)-1-(2-(2-hydroxyphenyl)-7-methylquinazolin-4-yl)pyrrolidin-3-ylcarbamate Example 321

(Benzo[d][1,3]dioxol-7-yl)methyl (R)-1-(2-(2-hydroxyphenyl)-7-methylquinazolin-4-yl)pyrrolidin-3-ylcarbamate

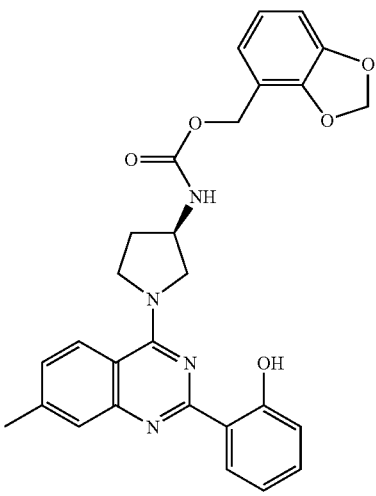

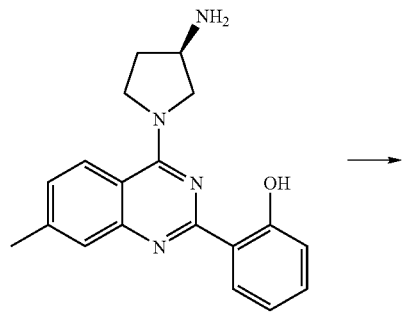

453

(Benzo[d][1,3]dioxol-7-yl)methyl (R)-1-(2-(2-hydroxyphenyl)-7-methylquinazolin-4-yl)pyrrolidin-3-ylcarbamate

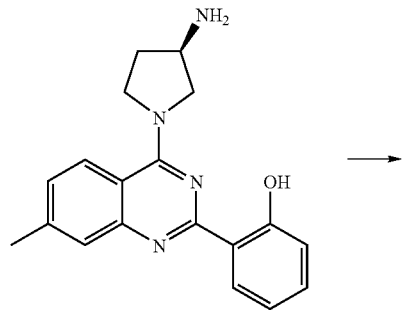

→

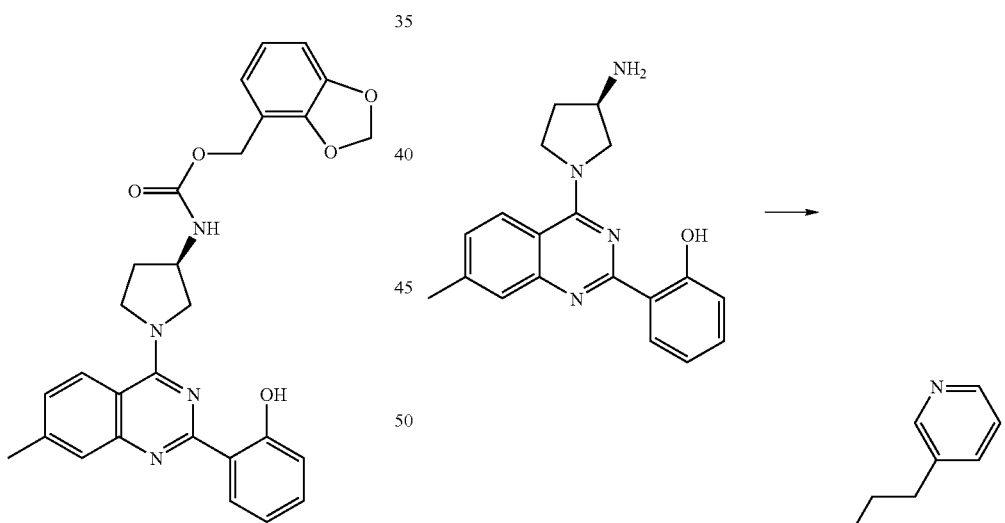

To a solution of 2-(4-((R)-3-aminopyrrolidin-1-yl)-7-methylquinazolin-2-yl)phenol (50 mg, 0.16 mmol) in DMSO (0.5 mL) was added triethylamine (43 µL, 0.31 mmol), followed by the addition of (benzo[d][1,3]dioxol-4-yl)methyl 1H-imidazole-1-carboxylate (77 mg, 0.31 mmol). The reaction was stirred at room temperature overnight, filtered, and purified using reverse phase HPLC (10%-99% CH₃CN (0.035% TFA)/H₂O (0.05% TFA)) to afford (benzo[d][1,3]dioxol-7-yl)methyl (R)-1-(2-(2-hydroxyphenyl)-7-methylquinazolin-4-yl)pyrrolidin-3-ylcarbamate as the TFA salt. LC/MS: m/z 499.3 (M+H)⁺ at 2.57 min (10%-99% CH₃CN (0.035% TFA)/H₂O (0.05% TFA)).

454

Example 322

N—((R)-1-(2-(2-Hydroxyphenyl)-7-methylquinazolin-4-yl)pyrrolidin-3-yl)-3-(pyridin-3-yl)propanamide

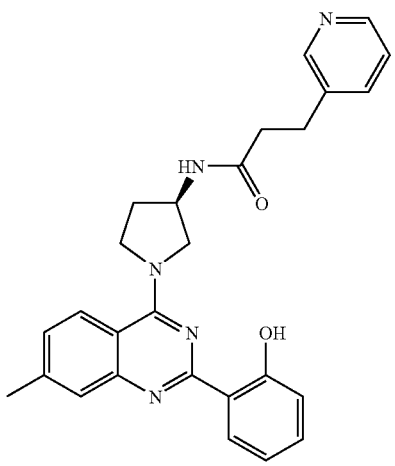

N—((R)-1-(2-(2-Hydroxyphenyl)-7-methylquinazolin-4-yl)pyrrolidin-3-yl)-3-(pyridin-3-yl)propanamide

→

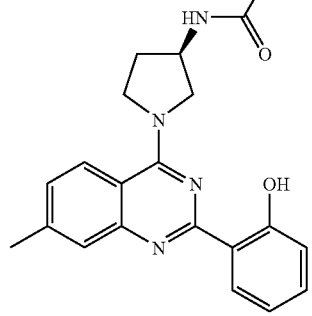

2-(4-((R)-3-Aminopyrrolidin-1-yl)-7-methylquinazolin-2-yl)phenol (249 mg, 0.778 mmol) was dissolved in 2.6 mL of CH$_2$Cl$_2$. 3-(Pyridin-3-yl)propanoic acid (129 mg, 0.85 mmol) was added followed by triethylamine (102 mg, 141 μL, 1.01 mmol) and BOP (378 mg, 0.85 mmol). After stirring the reaction for 35 minutes at room temperature, it was filtered, and purified by reverse phase HPLC (10%-99% CH$_3$CN (0.035% TFA)/H$_2$O (0.05% TFA)) to give N—((R)—-1-(2-(2-hydroxyphenyl)-7-methylquinazolin-4-yl)pyrrolidin-3-yl)-3-(pyridin-3-yl)propanamide as the TFA salt. LC/MS: m/z 454.4 (M+H)$^+$ at 2.08 min (10%-99% CH$_3$CN (0.035% TFA)/H$_2$O (0.05% TFA)).

Example 323

(R)-3-Cyclopentyl-N-{1-[2-(2-hydroxy-phenyl)-7-methyl-quinazolin-4-yl]-pyrrolidin-3-yl}-propionamide (R)-3-Cyclopentyl-N-{1-[2-(2-hydroxy-phenyl)-7-methyl-quinazolin-4-yl]-pyrrolidin-3-yl}-propionamide

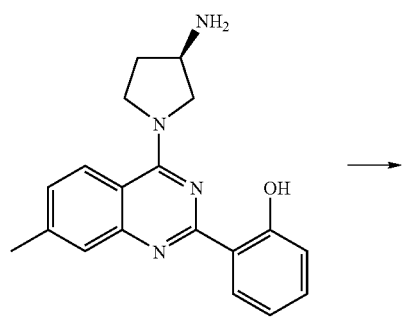

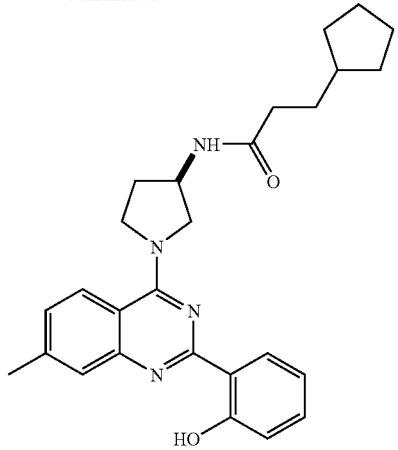

To (R)-2-[4-(3-amino-pyrrolidin-1-yl)-7-methyl-quinazolin-2-yl]-phenol (100 mg, 0.31 mmol) was added 1 mL of CH$_2$Cl$_2$, and the solution was cooled to 0° C. To this solution was added sequentially triethylamine (56.6 μL, 0.41 mmol) and 3-cyclopentyl-propionyl chloride (57 mg, 0.35 mmol). The reaction mixture was stirred at room temperature for 2 h, then diluted with water and CH$_2$Cl$_2$ (10 mL). The organic layer was separated and dried over Na$_2$SO$_4$, and the solvent was removed under reduced pressure. The residue was purified via preparative reverse phase HPLC using 10%-99% CH$_3$CN (0.035% TFA)/H$_2$O (0.05% TFA) to give ((R)-3-cyclopentyl-N-{1-[2-(2-hydroxy-phenyl)-7-methyl-quinazolin-4-yl]-pyrrolidin-3-yl}-propionamide as the TFA salt. LC/MS: m/z 445.4 (M+H)$^+$ at 2.85 min (10%-99% CH$_3$CN (0.035% TFA)/H$_2$O (0.05% TFA)).

Example 324

(R)—N-{1-[2-(2-Hydroxy-phenyl)-7-methyl-quinazolin-4-ylPpyrrolidin-3-yl}-3-piperidin-1-yl-propionamide

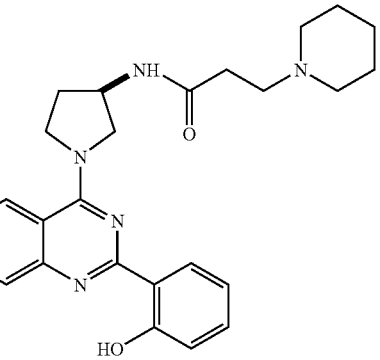

(R)—N-{1-[2-(2-Hydroxy-phenyl)-7-methyl-quinazolin-4-ylPpyrrolidin-3-yl}-3-piperidin-1-yl-propionamide To (R)-2-[4-(3-amino-pyrrolidin-1-yl)-7-methyl-quinazolin-2-yl]-phenol (58.6 mg, 0.18 mmol) was added 700 μL of CH$_2$Cl$_2$. To this solution was added sequentially triethylamine (38.3 μL, 0.27 mmol), 3-piperidin-1-yl-propionic acid (37.4 mg, 0.24 mmol) and BOP (119 mg, 0.27 mmol). The reaction mixture was stirred at room temperature for 2 h and diluted with water and CH₂Cl₂ (10 mL). The organic layer was separated and dried over Na₂SO₄, and the solvent was removed under reduced pressure. The residue was purified via preparative reverse phase HPLC using 10%-99% CH₃CN (0.035% TFA)/H₂O (0.05% TFA) to give (R)—N-{1-[2-(2-hydroxy-phenyl)-7-methyl-quinazolin-4-yl]-pyrrolidin-3-yl}-3-piperidin-1-yl-propionamide as the TFA salt. LC/MS: m/z 460.4 (M+H)⁺ at 2.1 min (10%-99% CH₃CN (0.035% TFA)/H₂O (0.05% TFA)).

Example 325

N—((R)-1-(2-(2-Hydroxyphenyl)-7-methylquinazolin-4-yl)pyrrolidin-3-yl)-3-(trifluoromethoxy)benzamide

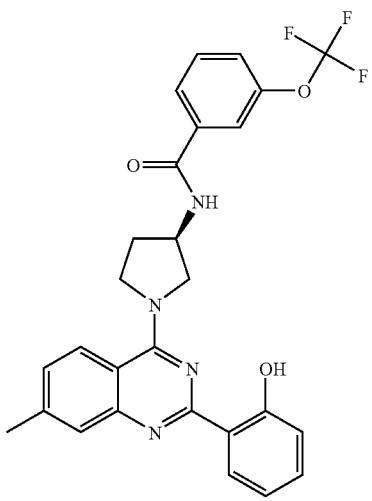

N—((R)-1-(2-(2-Hydroxyphenyl)-7-methylquinazolin-4-yl)pyrrolidin-3-yl)-3-(trifluoromethoxy)benzamide

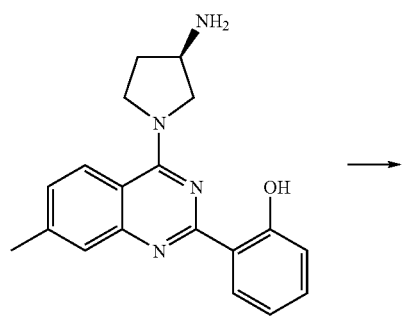

To a stirring solution of 2-(4-((R)-3-aminopyrrolidin-1-yl)-7-methylquinazolin-2-yl)phenol (32 mg, 0.10 mmol) and DMF (1.0 mL) was added 3-(trifluoromethoxy)benzoyl chloride (19 μL, 0.10 mmol), followed by the addition of triethylamine (28 μL, 0.2 mmol). The reaction was stirred at room temperature overnight, filtered, and purified via preparative reverse phase HPLC (10%-99% CH₃CN (0.035% TFA)/H₂O (0.05% TFA)) to give N—((R)-1-(2-(2-hydroxyphenyl)-7-methylquinazolin-4-yl)pyrrolidin-3-yl)-3-(trifluoromethoxy)benzamide as the TFA salt. LC/MS: m/z 509.5 (M+H)⁺ at 2.71 min (10%-99% CH₃CN (0.035% TFA)/H₂O (0.05% TFA)).

Example 326

N—((R)-1-(2-(2-Hydroxyphenyl)-7-methylquinazolin-4-yl)pyrrolidin-3-yl)-3-methoxybenzamide

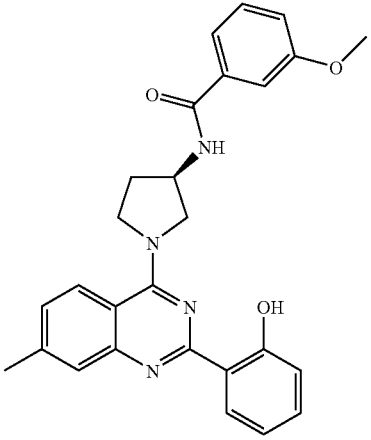

459
N—((R)-1-(2-(2-Hydroxyphenyl)-7-methylquinazolin-4-yl)pyrrolidin-3-yl)-3-methoxybenzamide

460
3-Cyano-N—((R)-1-(2-(2-hydroxyphenyl)-7-methylquinazolin-4-yl)pyrrolidin-3-yl)benzamide

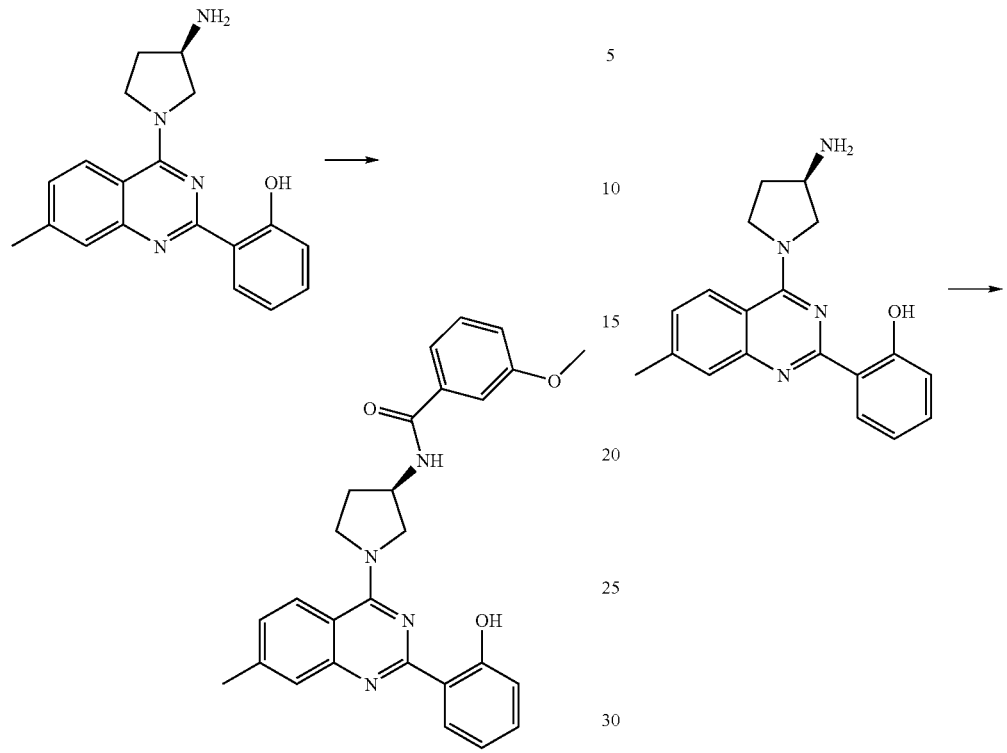

To a stirring solution of 2-(4-((R)-3-aminopyrrolidin-1-yl)-7-methylquinazolin-2-yl)phenol (32 mg, 0.10 mmol) and DMF (1.0 mL) was added 3-methoxybenzoyl chloride (14 μL, 0.1 mmol), followed by the addition of triethylamine (28 μL, 0.2 mmol). The reaction was stirred at room temperature overnight, then filtered, and purified via preparative reverse phase HPLC (10%-99% CH$_3$CN (0.035% TFA)/H$_2$O (0.05% TFA)) to give N—((R)-1-(2-(2-hydroxyphenyl)-7-methylquinazolin-4-yl)pyrrolidin-3-yl)-3-methoxybenzamide as the TFA salt. LC/MS: m/z 455.3 (M+H)$^+$ at 2.43 min (10%-99% CH$_3$CN (0.035% TFA)/H$_2$O (0.05% TFA)).

Example 327

3-Cyano-N—((R)-1-(2-(2-hydroxyphenyl)-7-methylquinazolin-4-yl)pyrrolidin-3-yl)benzamide

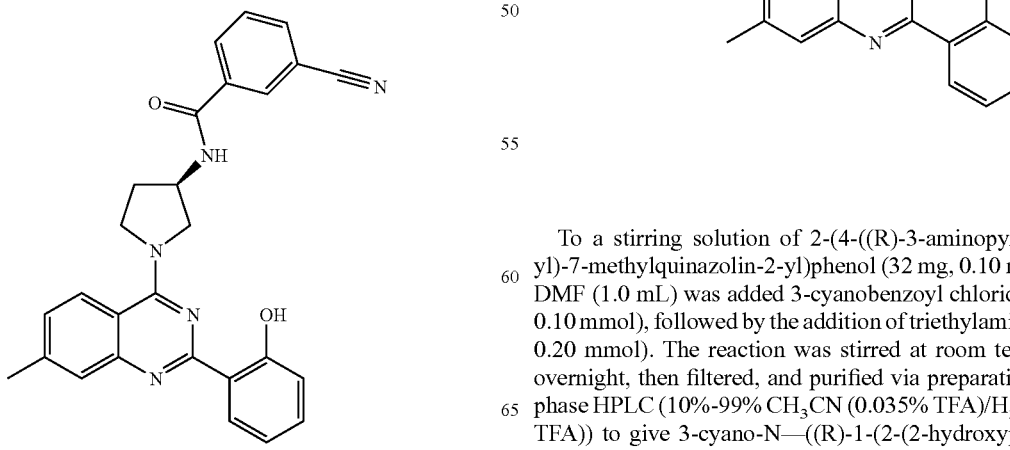

To a stirring solution of 2-(4-((R)-3-aminopyrrolidin-1-yl)-7-methylquinazolin-2-yl)phenol (32 mg, 0.10 mmol) and DMF (1.0 mL) was added 3-cyanobenzoyl chloride (17 mg, 0.10 mmol), followed by the addition of triethylamine (28 μL, 0.20 mmol). The reaction was stirred at room temperature overnight, then filtered, and purified via preparative reverse phase HPLC (10%-99% CH$_3$CN (0.035% TFA)/H$_2$O (0.05% TFA)) to give 3-cyano-N—((R)-1-(2-(2-hydroxyphenyl)-7-methylquinazolin-4-yl)pyrrolidin-3-yl)benzamide as the TFA salt. LC/MS: m/z 450.3 (M+H)+ at 2.39 min (10%-99% CH₃CN (0.035% TFA)/H₂O (0.05% TFA)).

Example 328

N—((R)-1-(2-(2-Hydroxyphenyl)-7-methylquinazolin-4-yl)pyrrolidin-3-yl)nicotinamide

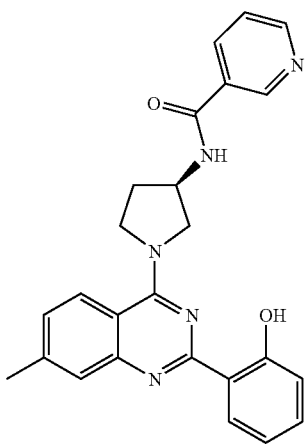

N—((R)-1-(2-(2-Hydroxyphenyl)-7-methylquinazolin-4-yl)pyrrolidin-3-yl)nicotinamide

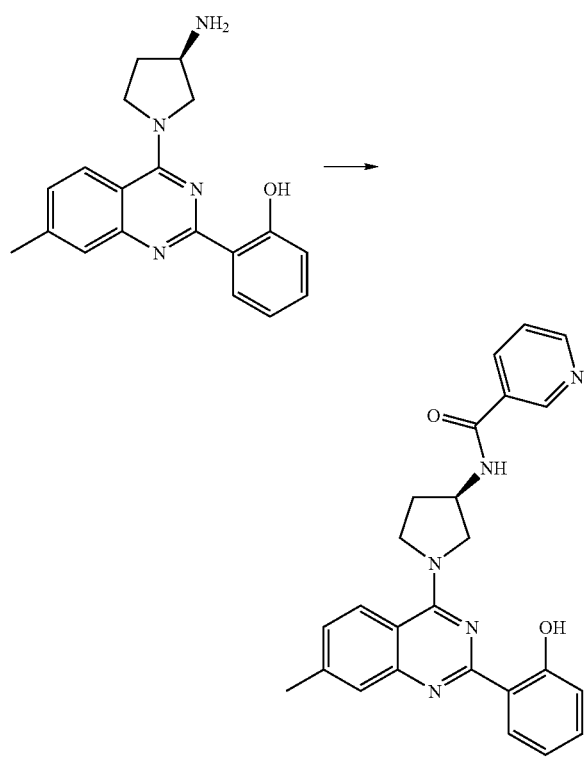

To a stirring solution of 2-(4-((R)-3-aminopyrrolidin-1-yl)-7-methylquinazolin-2-yl)phenol (32 mg, 0.1 mmol) and DMF (1.0 mL) was added nicotinoyl chloride (18 mg, 0.1 mmol), followed by the addition of triethylamine (28 µL, 0.2 mmol). The reaction was stirred at room temperature overnight, then filtered, and purified via preparative reverse phase HPLC (10%-99% CH₃CN (0.035% TFA)/H₂O (0.05% TFA)) to give N—((R)-1-(2-(2-hydroxyphenyl)-7-methylquinazolin-4-yl)pyrrolidin-3-yl)nicotinamide as the TFA salt. LC/MS: m/z 426.3 (M+H)+ at 1.91 min (10%-99% CH₃CN (0.035% TFA)/H₂O (0.05% TFA)).

Example 329

N—((R)-1-(6-Fluoro-2-(2-hydroxyphenyl)quinazolin-4-yl)pyrrolidin-3-yl)cyclopropanecarboxamide

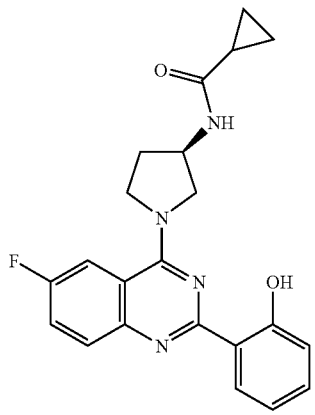

Method A 2-(4-Chloro-6-fluoroquinazolin-2-yl)phenol

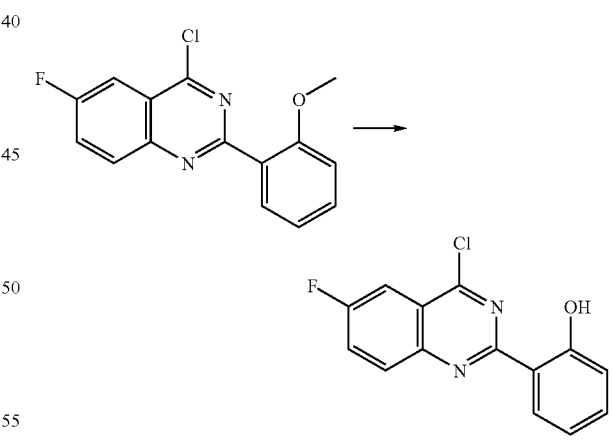

A solution of 4-chloro-6-fluoro-2-(2-methoxyphenyl)quinazoline (3.0 g, 10.39 mmol) in CH₂Cl₂ (15 mL) was cooled to −78° C. To it was added a 1.0 M BBr₃ solution in CH₂Cl₂ (52 mL, 52 mmol) dropwise. The reaction was allowed to warm to room temperature. It was neutralized with a saturated aqueous NaHCO₃ solution, and the aqueous layer was extracted twice with CH₂Cl₂. The combined organic layers were dried over MgSO₄, filtered, and concentrated. Purification via silica gel chromatography using 5-20% CH₂Cl₂/hexanes gave 2-(4-chloro-6-fluoroquinazolin-2-yl)

phenol (1.68 g, 60%). LC/MS: m/z 275.3 (M+H)+ at 3.39 min (10%-99% CH₃CN (0.035% TFA)/H₂O (0.05% TFA)).

tert-Butyl (R)-1-(6-fluoro-2-(2-hydroxyphenyl) quinazolin-4-yl)pyrrolidin-3-ylcarbamate

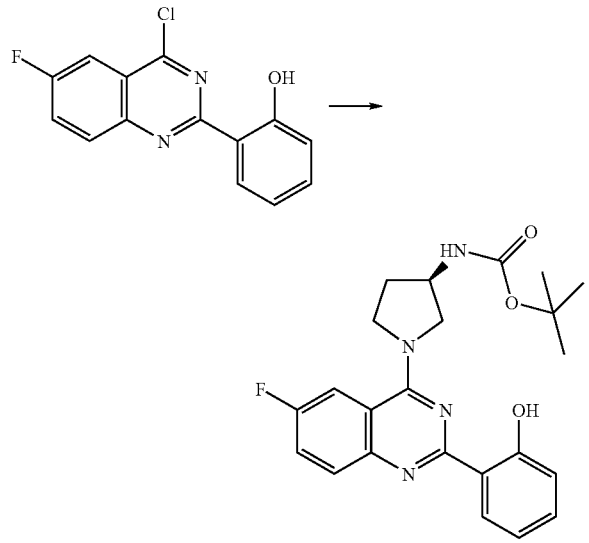

At 0° C. under an N₂ atmosphere, a solution of tert-butyl (R)-pyrrolidin-3-ylcarbamate (264 mg, 1.42 mmol) and triethylamine (0.33 mL, 2.36 mmol) in CH₂Cl₂ was rapidly added to a stirring solution of 2-(4-chloro-6-fluoroquinazolin-2-yl)phenol (325 mg, 1.18 mmol) in 15 mL CH₂Cl₂. The reaction mixture was stirred for 1 h before it was quenched with water, and the aqueous layer was extracted twice with CH₂Cl₂. The combined organic extracts were dried over MgSO₄, filtered, and concentrated. Purification via silica gel chromatography using 0-10% EtOAc/CH₂Cl₂ yielded tert-butyl (R)-1-(6-fluoro-2-(2-hydroxyphenyl)quinazolin-4-yl) pyrrolidin-3-ylcarbamate. LC/MS: m/z 425.5 (M+H)+ at 2.74 min (10%-99% CH₃CN (0.035% TFA)/H₂O (0.05% TFA)).

2-(4-((R)-3-Aminopyrrolidin-1-yl)-6-fluoroquinazolin-2-yl)phenol

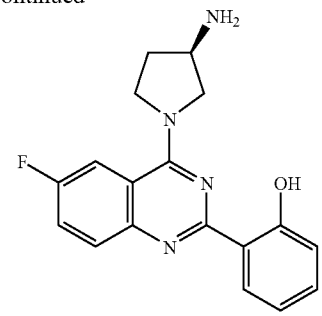

To a solution of tert-butyl (R)-1-(6-fluoro-2-(2-hydroxyphenyl)quinazolin-4-yl)pyrrolidin-3-ylcarbamate (480 mg, 1.11 mmol) in CH₂Cl₂ (10 mL) was added TFA (4 mL). The reaction was stirred for an hour, diluted with 10 mL CH₂Cl₂, and neutralized with a saturated aqueous NaHCO₃ solution. The aqueous layer was extracted twice with CH₂Cl₂. The combined organic layers were dried over MgSO₄, filtered, and concentrated. Purification via silica gel chromatography using 3-20% EtOAc/CH₂Cl₂ gave 2-(4-((R)-3-aminopyrrolidin-1-yl)-6-fluoroquinazolin-2-yl)phenol. LC/MS: m/z 325.5 (M+H)+ at 1.26 min (10%-99% CH₃CN (0.035% TFA)/H₂O (0.05% TFA)).

N—((R)-1-(6-Fluoro-2-(2-hydroxyphenyl)quinazolin-4-yl)pyrrolidin-3-yl)cyclopropanecarboxamide

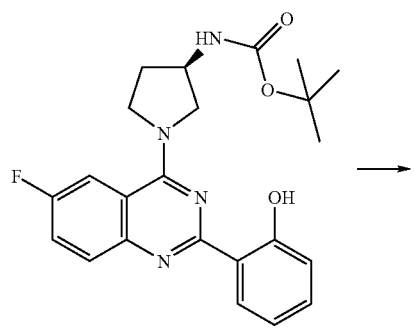

To a solution of 2-(4-((R)-3-aminopyrrolidin-1-yl)-6-fluoroquinazolin-2-yl)phenol (0.025 g, 0.08 mmol) in DMF (1.0 mL) was added cyclopropanecarboxylic acid (10 mg, 0.12 mmol), followed by the addition of triethylamine (22 µL, 0.16 mmol) and HATU (40 mg, 0.1 mmol). The reaction was stirred at room temperature for 2 h, filtered, and purified using reverse phase HPLC (10%-99% CH₃CN (0.035% TFA)/H₂O (0.05% TFA)) to obtain N—((R)-1-(6-fluoro-2-(2-hydroxyphenyl)quinazolin-4-yl)pyrrolidin-3-yl)cyclopropanecarboxamide as the TFA salt. LC/MS: m/z 393.3 (M+H)$^+$ at 2.23 min (10%-99% CH₃CN (0.035% TFA)/H₂O (0.05% TFA)).
Method B Benzyl (R)-1-(tert-butoxycarbonyl)pyrrolidin-3-yl-carbamate

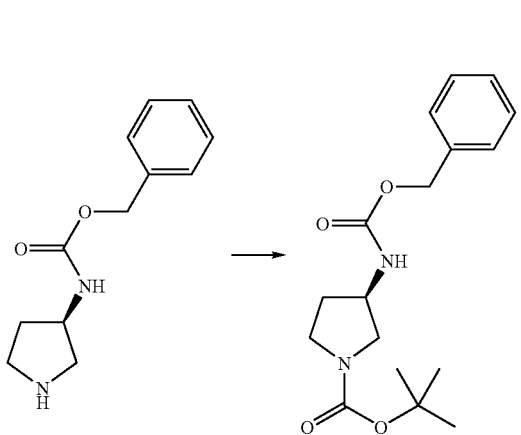

At −10° C., triethylamine (2.3 mL, 16.6 mmol) was added to a solution of benzyl (R)-pyrrolidin-3-ylcarbamate oxalate (2.0 g, 6.4 mmol) in MeOH, followed by the slow addition of Boc₂O (1.92 mL, 8.3 mmol). The reaction was allowed to warm to room temperature and was stirred overnight. The mixture was quenched with water and extracted twice with CH₂Cl₂. The combined organic layers were dried over MgSO₄, filtered, and concentrated. Purification via silica gel chromatography using 0-10% EtOAc in CH₂Cl₂ gave benzyl (R)-1-(tert-butoxycarbonyl)pyrrolidin-3-ylcarbamate (1.85 g, 90%). LC/MS: m/z 321.3 (M+H)$^+$ at 3.01 min (10%-99% CH₃CN (0.035% TFA)/H₂O (0.05% TFA)).

(R)-tert-Butyl 3-aminopyrrolidine-1-carboxylate

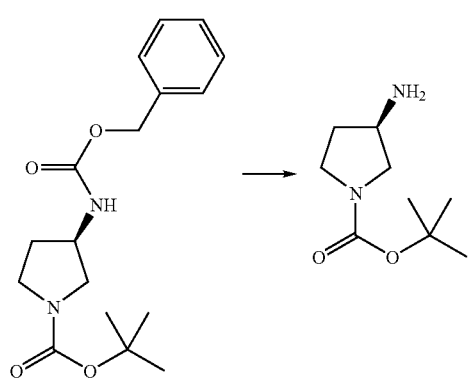

Under an N₂ atmosphere, a solution of benzyl (R)-1-(tert-butoxycarbonyl)pyrrolidin-3-ylcarbamate (1.85 g, 5.75 mmol) in 10 mL MeOH was added to a flask containing Pd/C (185 mg, 10% weight Pd on carbon). After evacuating the flask under vacuum and purging it twice with N₂, the reaction was stirred for 3 h under an H₂ atmosphere at ambient pressure. The reaction was filtered through a bed of Celite, and the solvent was evaporated under reduced pressure to obtain (R)-tert-butyl 3-aminopyrrolidine-1-carboxylate which was used without further purification. LC/MS: m/z 187.3 (M+H)$^+$ at 1.07 min (10%-99% CH₃CN (0.035% TFA)/H₂O (0.05% TFA)).

(R)-tert-Butyl 3-(cyclopropanecarboxamido)pyrrolidine-1-carboxylate

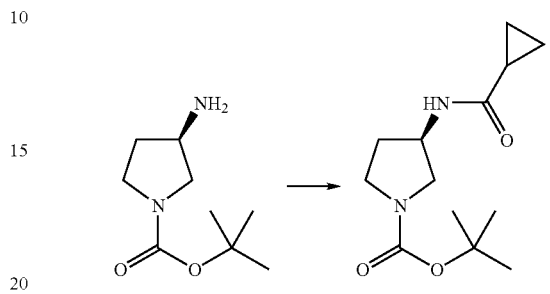

To a mixture of (R)-tert-butyl 3-aminopyrrolidine-1-carboxylate (500 mg, 2.68 mmol) in CH₂Cl₂ (101 mL) was added cyclopropanecarboxylic acid (276 μL, 3.48 mmol), followed by the addition of HATU (1.3 g, 3.48 mmol) and triethylamine (725 μL, 5.2 mmol). The reaction was complete after stirring for 1 h. After quenching with water, the aqueous layer was extracted twice with CH₂Cl₂, and the combined organic extracts were dried over MgSO₄, filtered, and concentrated. The crude material was purified via silica gel chromatography 0-20% EtOAc/CH₂Cl₂ to afford (R)-tert-butyl 3-(cyclopropanecarboxamido)pyrrolidine-1-carboxylate (500 mg, 73%). LC/MS: m/z 255.3 (M+H)$^+$ at 2.33 min (10%-99% CH₃CN (0.035% TFA)/H₂O (0.05% TFA)).

N—((R)-Pyrrolidin-3-yl)cyclopropanecarboxamide

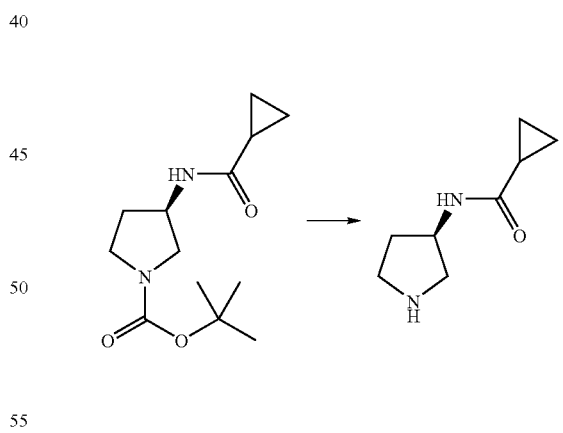

TFA (1 mL) was added to a solution of (R)-tert-butyl 3-(cyclopropanecarboxamido)pyrrolidine-1-carboxylate (500 mg, 1.96 mmol) in 5 mL CH₂Cl₂. After stirring for 30 min, the reaction was quenched with 1M NaOH solution till neutral and extracted twice with EtOAc. The organic extracts were combined, dried over MgSO₄, filtered, and concentrated to yield N—((R)-pyrrolidin-3-yl)cyclopropanecarboxamide (250 mg) which was used without further purification. LC/MS: m/z 155.3 (M+H)$^+$ at 0.6 min (10%-99% CH₃CN (0.035% TFA)/H₂O (0.05% TFA)).

467

N—((R)-1-(6-Fluoro-2-(2-hydroxyphenyl)quinazo-lin-4-yl)pyrrolidin-3-yl)cyclopropanecarboxamide

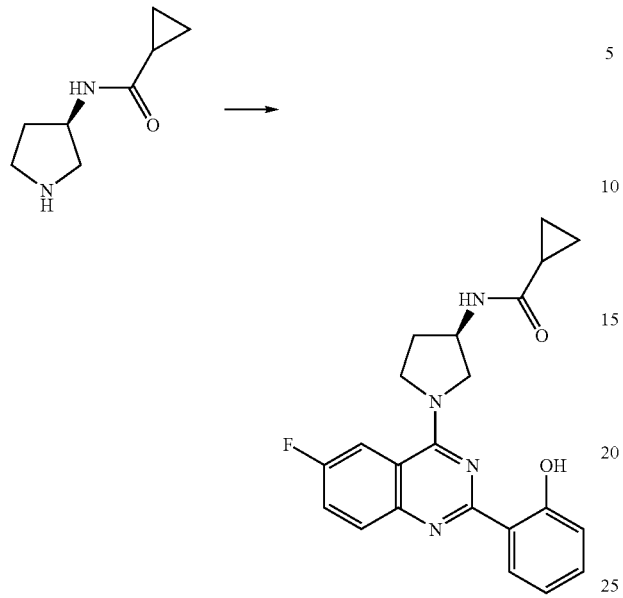

A mixture of N—((R)-pyrrolidin-3-yl)cyclopropanecarboxamide (250 mg, 0.86 mmol), 2-(4-chloro-6-fluoroquinazolin-2-yl)phenol (250 mg, 0.86 mmol) and triethylamine (0.240 mL, 1.72 mmol) in CH$_2$Cl$_2$ (10 mL) was stirred at room temperature. The reaction was complete after one hour. The reaction was quenched with water, the aqueous layer was extracted twice with CH$_2$Cl$_2$, and the combined organic extracts were dried-over MgSO$_4$, filtered, and concentrated. Purification via silica gel chromatography using 0-10% EtOAc/CH$_2$Cl$_2$ gave N—((R)-1-(6-fluoro-2-(2-hydroxyphenyl)quinazolin-4-yl)pyrrolidin-3-yl)cyclopropanecarboxamide (230 mg, 68%). LC/MS: m/z 393.3 (M+H)$^+$ at 2.35 min (10%-99% CH$_3$CN (0.035% TFA)/H$_2$O (0.05% TFA)). $^1$H NMR (400 MHz, DMSO-d6) δ 8.42-8.46 (m, 2H), 8.03 (dd, J=10.5, 2.6 Hz, 1H), 7.88-7.92 (m, 1H), 7.74-7.79 (m, 1H), 7.35-7.39 (m, 1H), 6.92-6.96 (m, 2H), 4.44-4.47 (m, 1H), 4.01-4.28 (m, 3H), 3.83-3.87 (m, 1H), 2.20-2.28 (m, 1H), 1.99-2.06 (m, 1H), 1.51-1.57 (m, 1H), 0.63-0.73 (m, 4H) ppm.

N—((R)-1-(6-Fluoro-2-(2-hydroxyphenyl)quinazo-lin-4-yl)pyrrolidin-3-yl)cyclopropanecarboxamide hydrochloride

468

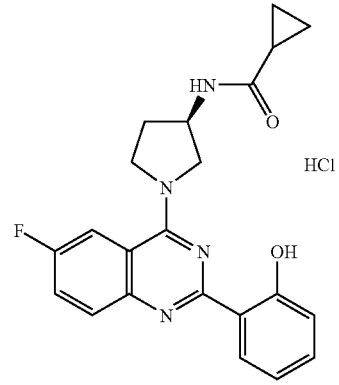

To a solution of N—((R)-1-(6-fluoro-2-(2-hydroxyphenyl)quinazolin-4-yl)pyrrolidin-3-yl)cyclopropanecarboxamide (225 mg, 0.57 mmol) in 5 mL CH$_2$Cl$_2$ was added a 2 M HCl solution in ether (0.28 mL, 0.57 mmol), which resulted in the precipitation of a solid. After the addition of 20 mL ether, the reaction mixture was stirred for 1 h. The solvents were evaporated under reduced pressure to afford N—((R)-1-(6-fluoro-2-(2-hydroxyphenyl)quinazolin-4-yl)pyrrolidin-3-yl)cyclopropanecarboxamide hydrochloride (225 mg, 91%). LC/MS: m/z 393.3 (M+H)$^+$ at 2.43 min (10%-99% CH$_3$CN (0.035% TFA)/H$_2$O (0.05% TFA)). $^1$H NMR (400 MHz, DMSO-d6) δ 8.23 (d, J=8.3 Hz, 1H), 8.04 (d, J=10.6 Hz, 1H), 7.91-7.94 (m, 1H), 7.79-7.83 (m, 1H), 7.44-7.48 (m, 1H), 7.00-7.03 (m, 2H), 4.44 (t, J=4.9 Hz, 1H), 4.09-4.23 (m, 3H), 3.87-3.90 (m, 1H), 2.25-2.34 (m, 1H), 2.02-2.09 (m, 1H), 1.49-1.55 (m, 1H), 0.68-0.71 (m, 4H) ppm.

Example 330

(2S)—N—((R)-1-(2-(2-Hydroxyphenyl)-7-methylquinazolin-4-yl)pyrrolidin-3-yl)-2-phenylcyclopropanecarboxamide

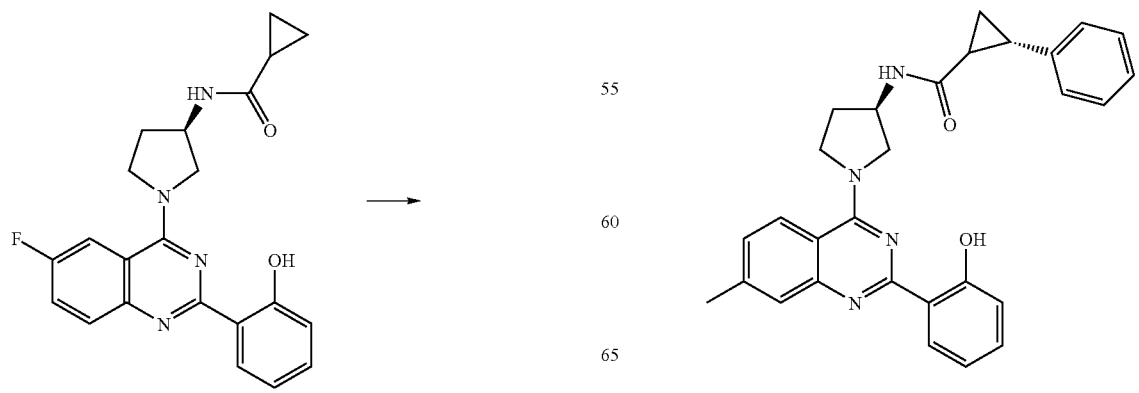

469

(2S)—N—((R)-1-(2-(2-Hydroxyphenyl)-7-methylquinazolin-4-yl)pyrrolidin-3-yl)-2-phenylcyclopropanecarboxamide

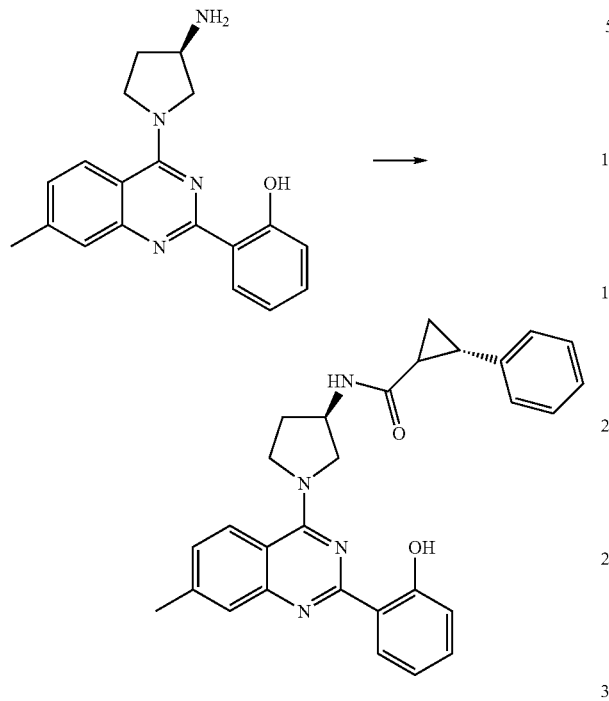

2-(4-((R)-3-Aminopyrrolidin-1-yl)-7-methylquinazolin-2-yl)phenol (50 mg, 0.16 mmol) was dissolved in 260 μL of anhydrous CH$_2$Cl$_2$ and cooled to 0° C. (2R)-2-Phenylcyclopropanecarbonyl chloride (31 mg, 0.17 mmol) dissolved in 260 μL of anhydrous CH$_2$Cl$_2$ was added dropwise to the mixture followed by triethylamine (21 mg, 28 μL, 0.20 mmol). The reaction was stirred for 20 minutes at 0° C. and purified via reverse phase HPLC (10%-99% CH$_3$CN (0.035% TFA)/H$_2$O (0.05% TFA)) to give (2S)—N—((R)-1-(2-(2-hydroxyphenyl)-7-methylquinazolin-4-yl)pyrrolidin-3-yl)-2-phenylcyclopropanecarboxamide as the TFA salt. LC/MS (10%-99% CH$_3$CN (0.035% TFA)/H$_2$O (0.05% TFA)), LC/MS: m/z 465.4 (M+H)$^+$ at 2.88 min (10%-99% CH$_3$CN (0.035% TFA)/H$_2$O (0.05% TFA)).

Example 331

2-Chloro-6-fluoro-N—((R)-1-(2-(2-hydroxyphenyl)-7-methylquinazolin-4-yl)pyrrolidin-3-yl)benzamide

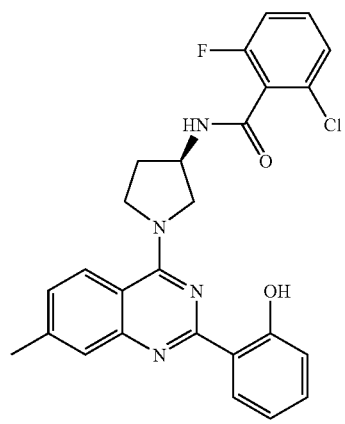

470

2-Chloro-6-fluoro-N—((R)-1-(2-(2-hydroxyphenyl)-7-methylquinazolin-4-yl)pyrrolidin-3-yl)benzamide

2-(4-((R)-3-Aminopyrrolidin-1-yl)-7-methylquinazolin-2-yl)phenol (50 mg, 0.16 mmol) was dissolved in 260 μL of anhydrous CH$_2$Cl$_2$ and cooled to 0° C. 2-Chloro-6-fluorobenzoyl chloride (36 mg, 0.18 mmol) dissolved in 260 μL of anhydrous CH$_2$Cl$_2$ was added dropwise to the mixture followed by triethylamine (21 mg, 28 μL, 0.20 mmol). The reaction was stirred for 20 minutes at 0° C. and purified via reverse phase HPLC (10%-99% CH$_3$CN (0.035% TFA)/H$_2$O (0.05% TFA)) to give 2-chloro-6-fluoro-N—((R)-1-(2-(2-hydroxyphenyl)-7-methylquinazolin-4-yl)pyrrolidin-3-yl)benzamide as the TFA salt. LC/MS: m/z 477.3 (M+H)$^+$ at 2.81 min (10%-99% CH$_3$CN (0.035% TFA)/H$_2$O (0.05% TFA)).

Example 332

4-Fluoro-3-(trifluoromethyl)-N—((R)-1-(2-(2-hydroxyphenyl)-7-methylquinazolin-4-yl)pyrrolidin-3-yl)benzamide

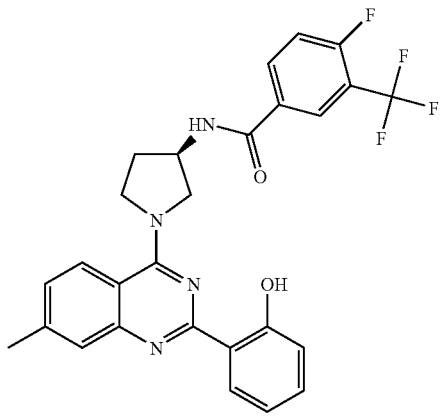

4-Fluoro-3-(trifluoromethyl)-N—((R)-1-(2-(2-hydroxyphenyl)-7-methylquinazolin-4-yl)pyrrolidin-3-yl)benzamide

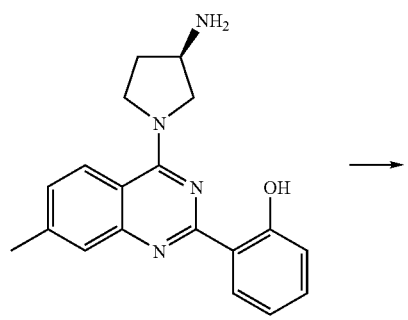

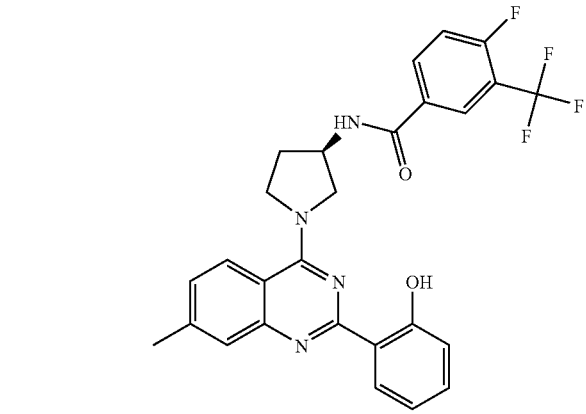

2-(4-((R)-3-Aminopyrrolidin-1-yl)-7-methylquinazolin-2-yl)phenol (50 mg, 0.16 mmol) was dissolved in 260 μL of anhydrous CH$_2$Cl$_2$ and cooled to 0° C. 4-Fluoro-3-(trifluoromethyl)benzoyl chloride (42 mg, 0.18 mmol) dissolved in 260 μL of anhydrous CH$_2$Cl$_2$ was added dropwise to the mixture followed by triethylamine (21 mg, 28 μL, 0.20 mmol). The reaction was stirred for 20 minutes at 0° C. and purified via reverse phase HPLC (10%-99% CH$_3$CN (0.035% TFA)/H$_2$O (0.05% TFA)) to give 4-fluoro-3-(trifluoromethyl)-N—((R)-1-(2-(2-hydroxyphenyl)-7-methylquinazolin-4-yl)pyrrolidin-3-yl)benzamide as the TFA salt. LC/MS: m/z 511.5 (M+H)$^+$ at 3.07 min (10%-99% CH$_3$CN (0.035% TFA)/H$_2$O (0.05% TFA)).

Example 333

3-Fluoro-N—((R)-1-(2-(2-hydroxyphenyl)-7-methylquinazolin-4-yl)pyrrolidin-3-yl)benzamide

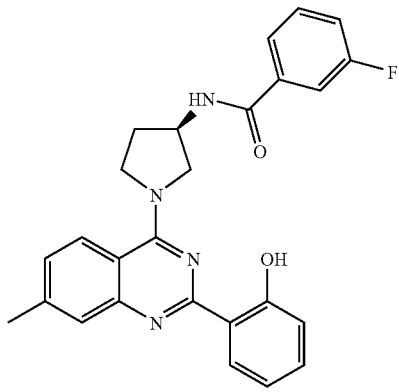

3-Fluoro-N—((R)-1-(2-(2-hydroxyphenyl)-7-methylquinazolin-4-yl)pyrrolidin-3-yl)benzamide 473
-continued

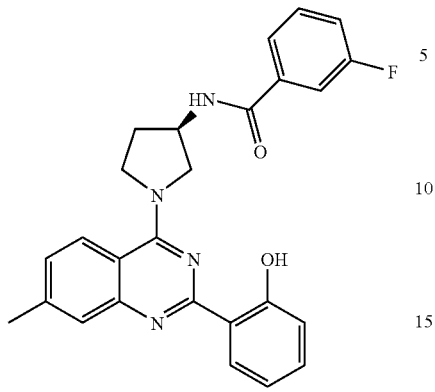

2-(4-((R)-3-Aminopyrrolidin-1-yl)-7-methylquinazolin-2-yl)phenol (50 mg, 0.16 mmol) was dissolved in 260 µL of anhydrous CH₂Cl₂ and cooled to 0° C. 3-Fluorobenzoyl chloride (30 mg, 0.18 mmol) dissolved in 260 µL of anhydrous CH₂Cl₂ was added dropwise to the mixture followed by triethylamine (21 mg, 28 µL, 0.20 mmol). The reaction was stirred for 20 minutes at 0° C. and purified via reverse phase HPLC (10%-99% CH₃CN (0.035% TFA)/H₂O (0.05% TFA)) to give 3-fluoro-N—((R)-1-(2-(2-hydroxyphenyl)-7-methylquinazolin-4-yl)pyrrolidin-3-yl)benzamide as the TFA salt. LC/MS: m/z 443.5 (M+H)⁺ at 2.83 min (10%-99% CH₃CN (0.035% TFA)/H₂O (0.05% TFA)).

Example 334

3-Fluoro-4-(trifluoromethyl)-N—((R)-1-(2-(2-hydroxyphenyl)-7-methylquinazolin-4-yl)pyrrolidin-3-yl)benzamide

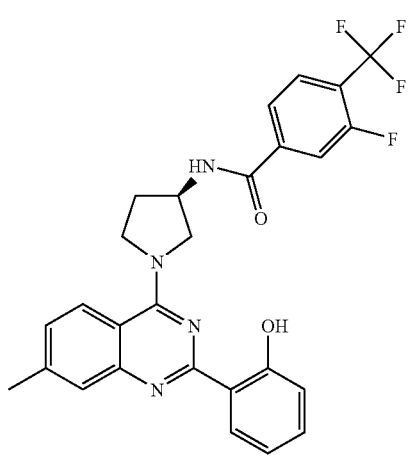

474

3-Fluoro-4-(trifluoromethyl)-N—((R)-1-(2-(2-hydroxyphenyl)-7-methylquinazolin-4-yl)pyrrolidin-3-yl)benzamide

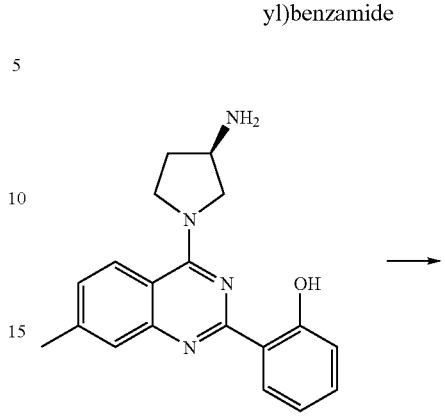

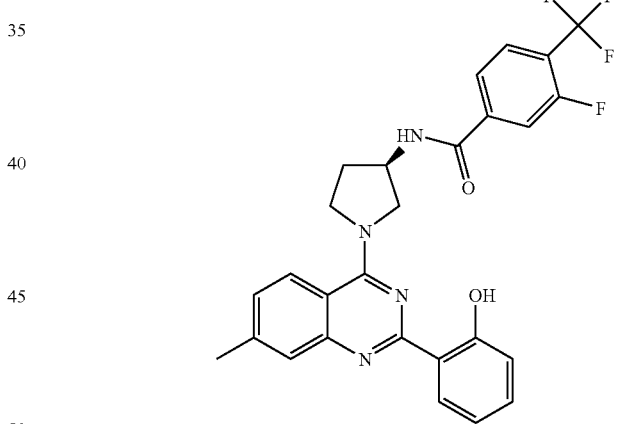

2-(4-((R)-3-Aminopyrrolidin-1-yl)-7-methylquinazolin-2-yl)phenol (50 mg, 0.16 mmol) was dissolved in 260 µL of anhydrous CH₂Cl₂ and cooled to 0° C. 3-Fluoro-4-(trifluoromethyl)benzoyl chloride (42 mg, 0.18 mmol) dissolved in 260 µL of anhydrous CH₂Cl₂ was added dropwise to the mixture followed by triethylamine (21 mg, 28 µL, 0.20 mmol). The reaction was stirred for 20 minutes at 0° C. and purified via reverse phase HPLC (10%-99% CH₃CN (0.035% TFA)/H₂O (0.05% TFA)) to give 3-fluoro-4-(trifluoromethyl)-N—((R)-1-(2-(2-hydroxyphenyl)-7-methylquinazolin-4-yl)pyrrolidin-3-yl)benzamide as the TFA salt. LC/MS: m/z 511.5 (M+H)⁺ at 3.1 min (10%-99% CH₃CN (0.035% TFA)/H₂O (0.05% TFA)).

Example 335

(S)-Tetrahydrofuran-3-yl (R)-1-(6-fluoro-2-(2-hydroxyphenyl)quinazolin-4-yl)pyrrolidin-3-ylcarbamate

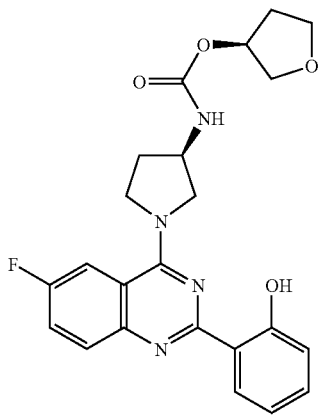

(S)-Tetrahydrofuran-3-yl (R)-1-(6-fluoro-2-(2-hydroxyphenyl)quinazolin-4-yl)pyrrolidin-3-ylcarbamate

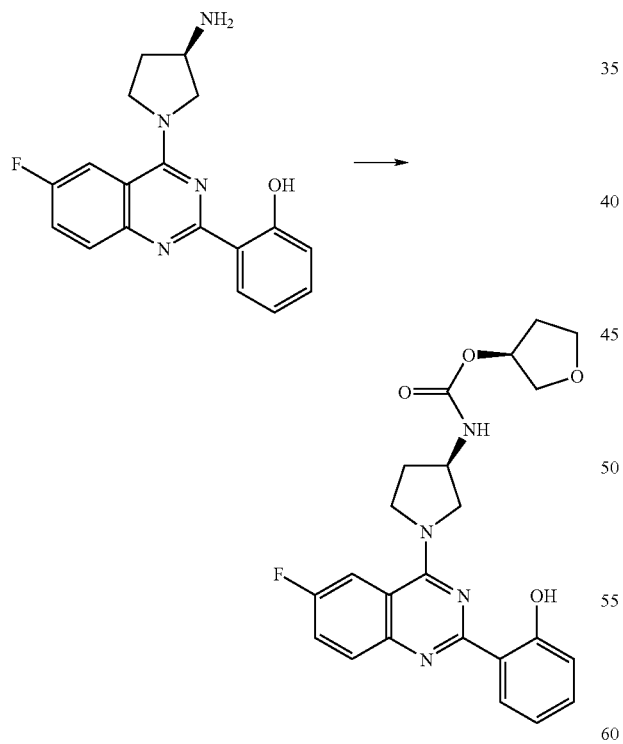

A solution of 2-(4-((R)-3-aminopyrrolidin-1-yl)-6-fluoroquinazolin-2-yl)phenol (0.03 g, 0.092 mmol) in DMF (1.0 mL) was cooled to −40° C. To this mixture was added triethylamine (26 µL, 0.184 mmol), followed by the addition of (S)-tetrahydrofuran-3-yl chloroformate (0.014 g, 0.092 mmol). After allowing the reaction to warm to room temperature the mixture was filtered, and purified via reverse phase HPLC (10%-99% CH$_3$CN (0.035% TFA)/H$_2$O (0.05% TFA)) to obtain (S)-tetrahydrofuran-3-yl (R)-1-(6-fluoro-2-(2-hydroxyphenyl)quinazolin-4-yl)pyrrolidin-3-ylcarbamate as the TFA salt. LC/MS: m/z 439.5 (M+H)$^+$ at 2.25 min (10%-99% CH$_3$CN (0.035% TFA)/H$_2$O (0.05% TFA)).

Method B (S)-Tetrahydrofuran-3-yl (R)-1-(tert-butoxycarbonyl)pyrrolidin-3-ylcarbamate

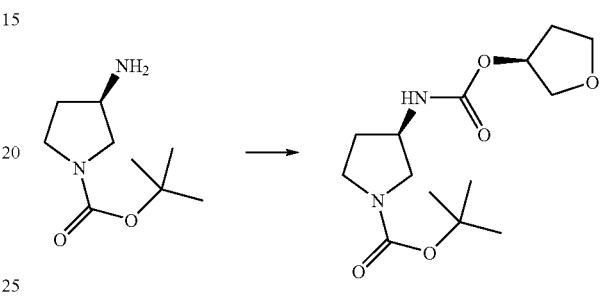

To a solution of (R)-tert-butyl 3-aminopyrrolidine-1-carboxylate (500 mg, 2.6 mmol) in 5 mL CH$_2$Cl$_2$ was added triethylamine (0.73 mL, 5.2 mmol), and the reaction was cooled to −20° C. (S)-tetrahydrofuran-3-yl chloroformate (525 mg, 3.48 mmol) was added in portions over a period of 10 minutes to the above reaction mixture. After allowing the reaction to warm to room temperature, it was quenched with water and extracted twice with CH$_2$Cl$_2$. The combined organic layers were dried over MgSO$_4$, filtered, and concentrated to afford (S)-tetrahydrofuran-3-yl (R)-1-(tert-butoxycarbonyl)pyrrolidin-3-ylcarbamate. Purification via silica gel chromatography using 0-20% EtOAc in CH$_2$Cl$_2$ gave (S)-tetrahydrofuran-3-yl (R)-1-(tert-butoxycarbonyl)pyrrolidin-3-ylcarbamate (490 mg, 63%). LC/MS: m/z 301.3 (M+H)$^+$ at 2.35 min (10%-99% CH$_3$CN (0.035% TFA)/H$_2$O (0.05% TFA)).

(S)-Tetrahydrofuran-3-yl (R)-pyrrolidin-3-ylcarbamate

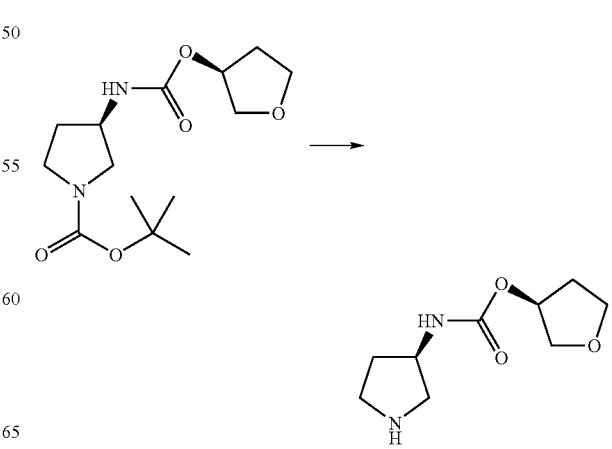

TFA (1 mL) was added to a solution of (S)-tetrahydrofuran-3-yl (R)-1-(tert-butoxycarbonyl)pyrrolidin-3-ylcarbamate (490 mg, 1.63 mmol) in 5 μL CH₂Cl₂. After stirring for 30 min, the reaction was quenched with NaOH and extracted twice with EtOAc. The organic extracts were combined, dried over MgSO₄, filtered, and concentrated to yield (S)-tetrahydrofuran-3-yl (R)-pyrrolidin-3-ylcarbamate (230 mg) which was used without further purification. LC/MS: m/z 201.3 (M+H)⁺ at 0.59 min (10%-99% CH₃CN (0.035% TFA)/H₂O (0.05% TFA)).

(S)-Tetrahydrofuran-3-yl (R)-1-(6-fluoro-2-(2-hydroxyphenyl)quinazolin-4-yl)pyrrolidin-3-ylcarbamate

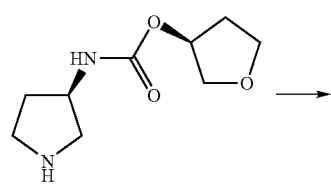

A mixture of (S)-tetrahydrofuran-3-yl (R)-pyrrolidin-3-ylcarbamate (225 mg, 1.12 mmol), 2-(4-chloro-6-fluoroquinazolin-2-yl)phenol (250 mg, 0.86 mmol), and triethylamine (0.240 mL, 1.72 mmol) in CH₂Cl₂ (10 mL) was stirred at room temperature. The reaction was complete in one hour. The reaction was quenched with water, the aqueous layer was extracted twice with CH₂Cl₂, and the combined organic extracts were dried over MgSO₄, filtered, and concentrated. Purification via silica gel chromatography using 0-10% EtOAc/CH₂Cl₂ gave (S)-tetrahydrofuran-3-yl (R)-1-(6-fluoro-2-(2-hydroxyphenyl)quinazolin-4-yl)pyrrolidin-3-ylcarbamate (250 mg, 66%). LC/MS: m/z 439.5 (M+H)⁺ at 2.40 min (10%-99% CH₃CN (0.035% TFA)/H₂O (0.05% TFA)). ¹H NMR (400 MHz, DMSO-d6) δ 8.43 (dd, J=7.8, 1.5 Hz, 1H), 7.99 (d, J=2.6 Hz, 1H), 7.87-7.91 (m, 1H), 7.74-7.79 (m, 1H), 7.70 (d, J=6.2 Hz, 1H), 7.35-7.39 (m, 1H), 6.91-6.96 (m, 2H), 5.15 (s, 1H), 4.21-4.25 (m, 2H), 4.12-4.14 (m, 1H), 4.01-4.06 (m, 1H), 3.87-3.89 (m, 1H), 3.65-3.78 (m, 4H), 2.02-2.26 (m, 3H), 1.82-1.89 (m, 1H) ppm.

(S)-Tetrahydrofuran-3-yl (R)-1-(6-fluoro-2-(2-hydroxyphenyl)quinazolin-4-yl)pyrrolidin-3-ylcarbamate hydrochloride

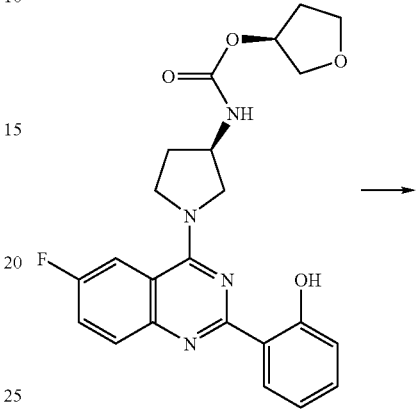

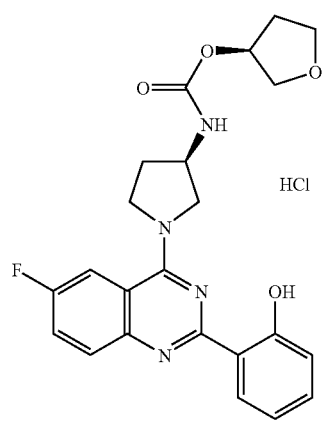

To a mixture of (S)-tetrahydrofuran-3-yl (R)-1-(6-fluoro-2-(2-hydroxyphenyl)quinazolin-4-yl)pyrrolidin-3-ylcarbamate (250 mg, 0.57 mmol) and CH₂Cl₂ (25 mL) was added a 2.0 M HCl solution in ether (0.285 mL, 0.57 mmol). After the addition of ether (40 mL), the reaction was stirred for 1 h. The resulting solid was filtered and dried to afford (S)-tetrahydrofuran-3-yl (R)-1-(6-fluoro-2-(2-hydroxyphenyl)quinazolin-4-yl)pyrrolidin-3-ylcarbamate hydrochloride. LC/MS: m/z 439.5 (M+H)⁺ at 2.25 min (10%-99% CH₃CN (0.035% TFA)/H₂O (0.05% TFA)). ¹H NMR (400 MHz, DMSO-d6) δ 8.18 (dd, J=8.1, 1.4 Hz, 1H), 8.00 (d, J=9.6 Hz, 1H), 7.90-7.94 (m, 1H), 7.78-7.83 (m, 1H), 7.45-7.49 (m, 1H), 7.00-7.03 (m, 2H), 5.10 (s, 1H), 4.09-4.25 (m, 4H), 3.90-3.92 (m, 1H), 3.62-3.75 (m, 4H), 2.22-2.27 (m, 1H), 2.03-2.14 (m, 2H), 1.83-1.91 (m, 1H) ppm.

Example 336

3-(Trifluoromethyl)-N—((R)-1-(2-(2-hydroxyphenyl)-7-methylquinazolin-4-yl)pyrrolidin-3-yl)benzamide

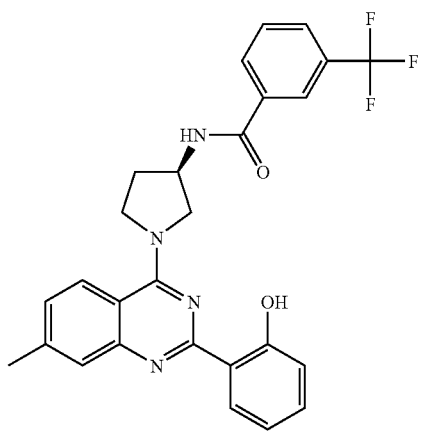

3-(Trifluoromethyl)-N—((R)-1-(2-(2-hydroxyphenyl)-7-methylquinazolin-4-yl)pyrrolidin-3-yl)benzamide

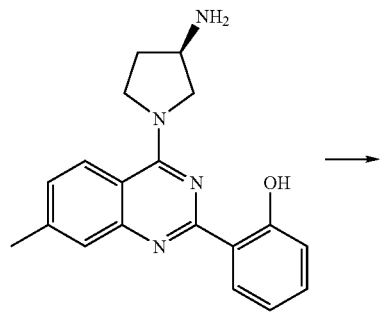

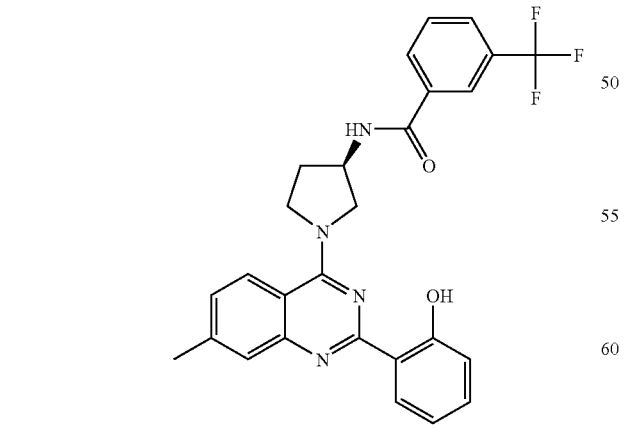

2-(4-((R)-3-Aminopyrrolidin-1-yl)-7-methylquinazolin-2-yl)phenol (130 mg, 0.406 mmol) was dissolved in 0.7 mL anhydrous CH₂Cl₂ and cooled to 0° C. 3-(Trifluoromethyl) benzoyl chloride (42 mg, 0.18 mmol) dissolved in 0.7 mL of anhydrous CH₂Cl₂ was added dropwise to the mixture followed by triethylamine (53 mg, 74 μL, 0.52 mmol). The reaction was stirred for 20 minutes at 0° C. and purified via reverse phase HPLC (10%-99% CH₃CN (0.035% TFA)/H₂O (0.05% TFA)) to give 3-(trifluoromethyl)-N—((R)-1-(2-(2-hydroxyphenyl)-7-methylquinazolin-4-yl)pyrrolidin-3-yl) benzamide as the TFA salt. LC/MS: m/z 493.5 (M+H)⁺ at 3.03 min (10%-99% CH₃CN (0.035% TFA)/H₂O (0.05% TFA)).

Example 337

(R)-Tetrahydrofuran-3-yl (R)-1-(6-fluoro-2-(2-hydroxyphenyl)quinazolin-4-yl)pyrrolidin-3-ylcarbamate

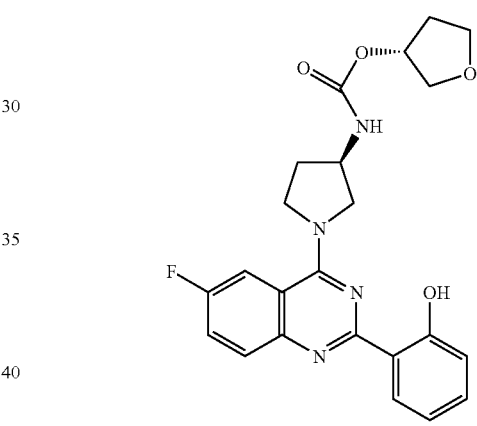

(R)-Tetrahydrofuran-3-yl (R)-1-(6-fluoro-2-(2-hydroxyphenyl)quinazolin-4-yl)pyrrolidin-3-ylcarbamate

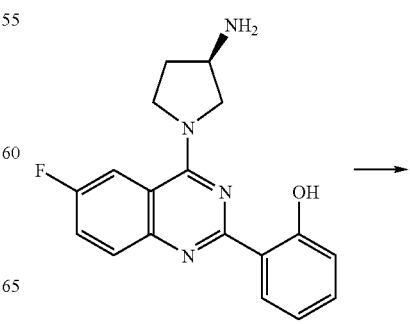

481
-continued

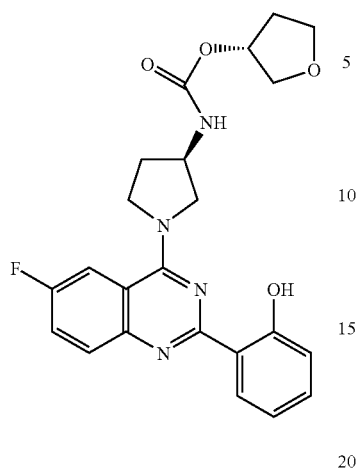

To a solution of 2-(4-((R)-3-aminopyrrolidin-1-yl)-6-fluoroquinazolin-2-yl)phenol (0.03 g, 0.092 mmol) in DMF (1.0 mL) was cooled to −40° C., triethylamine (26 µL, 0.184 mmol) was added, followed by the addition of (R)-tetrahydrofuran-3-yl chloroformate (0.014 g, 0.092 mmol). After warming to room temperature, the mixture was filtered, and purified via reverse phase HPLC (10%-99% CH$_3$CN (0.035% TFA)/H$_2$O (0.05% TFA)) to obtain (R)-tetrahydrofuran-3-yl (R)-1-(6-fluoro-2-(2-hydroxyphenyl)quinazolin-4-yl)pyrrolidin-3-ylcarbamate as the TFA salt. LC/MS: m/z 439.5 (M+H)$^+$ at 2.25 min (10%-99% CH$_3$CN (0.035% TFA)/H$_2$O (0.05% TFA)).

Example 338

N—((R)-1-(6-Fluoro-2-(2-hydroxyphenyl)quinazolin-4-yl)pyrrolidin-3-yl)-2-(tetrahydro-2H-pyran-4-yl)acetamide

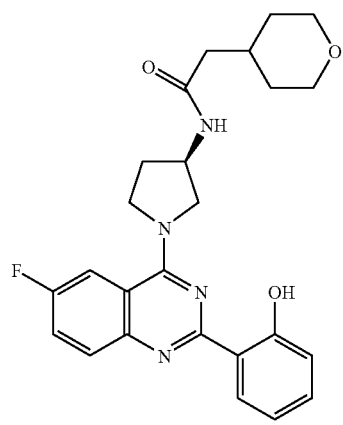

482

N—((R)-1-(6-Fluoro-2-(2-hydroxyphenyl)quinazolin-4-yl)pyrrolidin-3-yl)-2-(tetrahydro-2H-pyran-4-yl)acetamide

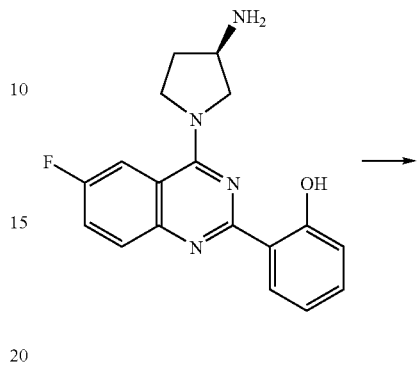

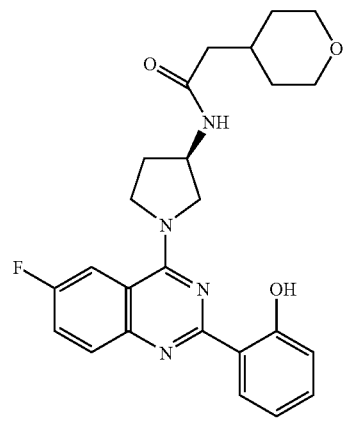

To a solution of 2-(4-((R)-3-aminopyrrolidin-1-yl)-6-fluoroquinazolin-2-yl)phenol(0.03 g, 0.092 mmol) in DMF (1.0 mL) was added 2-(tetrahydro-2H-pyran-4-yl)acetic acid (0.017 g, 0.12 mmol), followed by the addition of triethylamine (25.6 µL, 0.184 mmol) and HATU (0.045 g, 0.12 mmol). The reaction was stirred at room temperature for 2 h, filtered, and purified via reverse phase HPLC (10%-99% CH$_3$CN (0.035% TFA)/H$_2$O (0.05% TFA)) to obtain N—((R)-1-(6-fluoro-2-(2-hydroxyphenyl)quinazolin-4-yl)pyrrolidin-3-yl)-2-(tetrahydro-2H-pyran-4-yl)acetamide as the TFA salt. LC/MS: m/z 451.5 (M+H)$^+$ at 2.15 min (10%-99% CH$_3$CN (0.035% TFA)/H$_2$O (0.05% TFA)).

Example 339

(Tetrahydro-2H-pyran-2-yl)methyl (R)-1-(6-fluoro-2-(2-hydroxyphenyl)quinazolin-4-yl)pyrrolidin-3-ylcarbamate

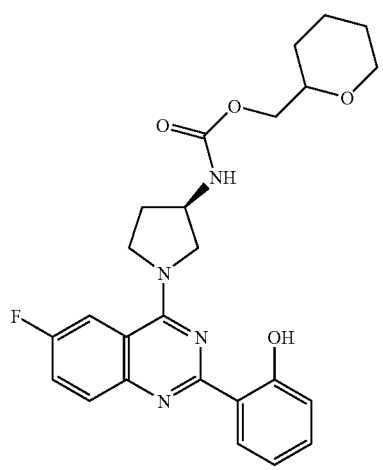

(Tetrahydro-2H-pyran-2-yl)methyl (R)-1-(6-fluoro-2-(2-hydroxyphenyl)quinazolin-4-yl)pyrrolidin-3-ylcarbamate

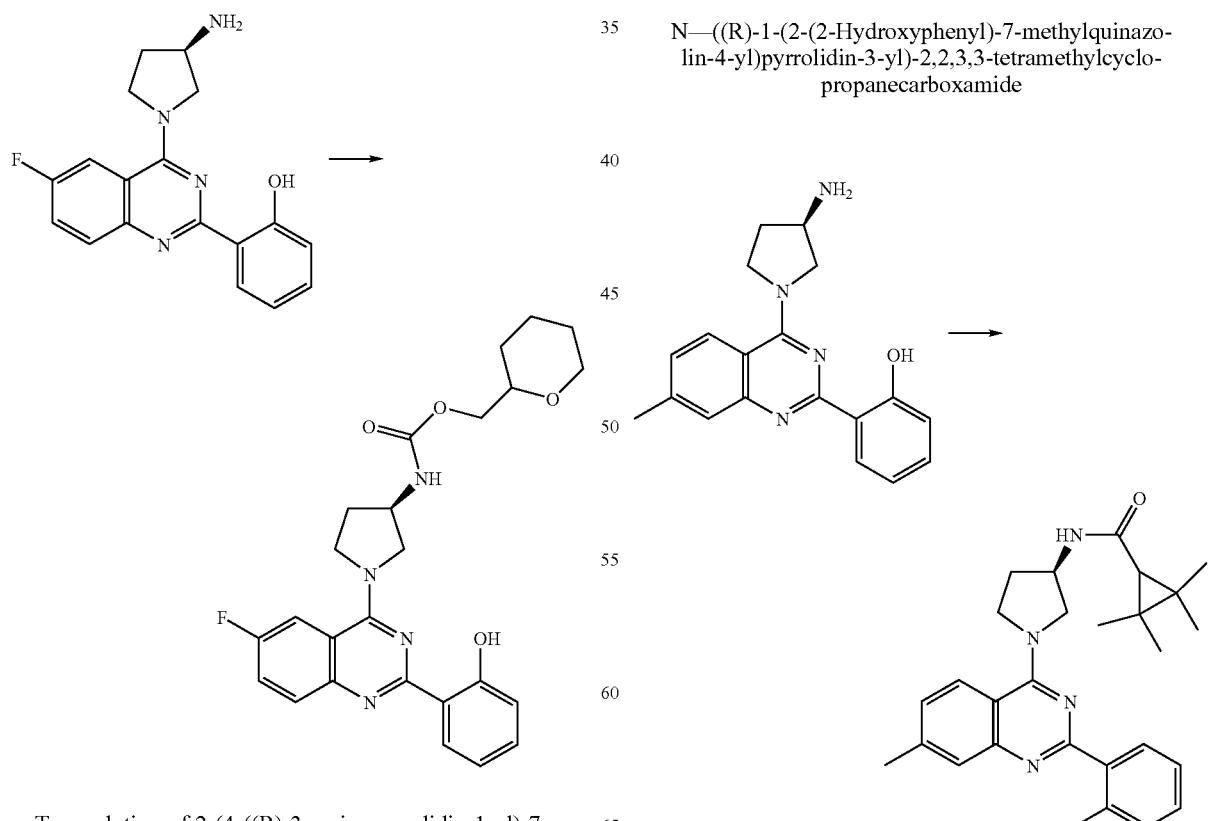

To a solution of 2-(4-((R)-3-aminopyrrolidin-1-yl)-7-methylquinazolin-2-yl)phenol (50 mg, 0.16 mmol) in DMSO (0.5 mL) at room temperature was added triethylamine (43 µL, 0.31 mmol), followed by the addition of (tetrahydro-2H-pyran-2-yl)methyl 1H-imidazole-1-carboxylate (39 mg, 0.13 mmol). The reaction was stirred at room temperature overnight, filtered, and purified via reverse phase HPLC (10%-99% $CH_3CN$ (0.035% TFA)/$H_2O$ (0.05% TFA)) to afford (tetrahydro-2H-pyran-2-yl)methyl (R)-1-(6-fluoro-2-(2-hydroxyphenyl)quinazolin-4-yl)pyrrolidin-3-ylcarbamate as the TFA salt. LC/MS: m/z 467.3 (M+H)$^+$ at 3.13 min (10%-99% $CH_3CN$ (0.035% TFA)/$H_2O$ (0.05% TFA)).

Example 340

N—((R)-1-(2-(2-Hydroxyphenyl)-7-methylquinazolin-4-yl)pyrrolidin-3-yl)-2,2,3,3-tetramethylcyclopropanecarboxamide

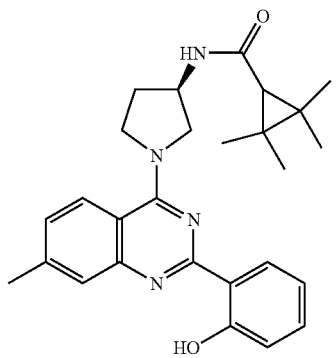

N—((R)-1-(2-(2-Hydroxyphenyl)-7-methylquinazolin-4-yl)pyrrolidin-3-yl)-2,2,3,3-tetramethylcyclopropanecarboxamide

485

2-(4-((R)-3-Aminopyrrolidin-1-yl)-6-fluoroquinazolin-2-yl)phenol (50 mg, 0.156 mmol) was dissolved in 0.52 mL of anhydrous CH$_2$Cl$_2$. 2,2,3,3-Tetramethylcyclopropanecarboxylic acid (26.63 mg, 0.18 mmol) was added, followed by triethylamine (22.14 mg, 30.49 μL, 0.22 mmol) and BOP (82.93 mg, 0.18 mmol). After stirring the mixture for 30 minutes at room temperature, it was filtered, and purified by reverse phase HPLC (10%-99% CH$_3$CN (0.035% TFA)/H$_2$O (0.05% TFA)) to give N—((R)-1-(2-(2-hydroxyphenyl)-7-methylquinazolin-4-yl)pyrrolidin-3-yl)-2,2,3,3-tetramethyl-cyclopropanecarboxamide as the TFA salt. LC/MS: m/z 445.4 (M+H)$^+$ at 2.95 min (10%-99% CH$_3$CN (0.035% TFA)/H$_2$O (0.05% TFA)).

Example 341

4-Fluoro-N—((R)-1-(2-(2-hydroxyphenyl)-7-methylquinazolin-4-yl)pyrrolidin-3-yl)benzamide

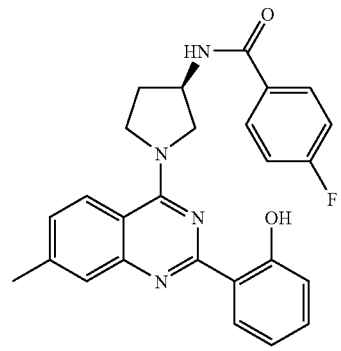

2-(4-((R)-3-Aminopyrrolidin-1-yl)-7-methylquinazolin-2-yl)phenol (50 mg, 0.16 mmol) was dissolved in 260 μL of anhydrous CH$_2$Cl$_2$ and cooled to 0° C. 4-Fluorobenzoyl chloride (25 mg, 0.15 mmol) dissolved in 260 μL of anhydrous CH$_2$Cl$_2$ was added dropwise to the mixture followed by triethylamine (19 mg, 26 μL, 0.18 mmol). The reaction was stirred for 15 minutes at 0° C. and purified via reverse phase HPLC (10%-99% CH$_3$CN (0.035% TFA)/H$_2$O (0.05% TFA)) to give 4-fluoro-N—((R)-1-(2-(2-hydroxyphenyl)-7-methylquinazolin-4-yl)pyrrolidin-3-yl)benzamide as the TFA salt. LC/MS: m/z 443.4 (M+H)$^+$ at 2.73 min (10%-99% CH$_3$CN (0.035% TFA)/H$_2$O (0.05% TFA)).

Example 342

3-(Dimethylamino)-N—((R)-1-(2-(2-hydroxyphenyl)-7-methylquinazolin-4-yl)pyrrolidin-3-yl)benzamide 4-Fluoro-N—((R)-1-(2-(2-hydroxyphenyl)-7-methylquinazolin-4-yl)pyrrolidin-3-yl)benzamide

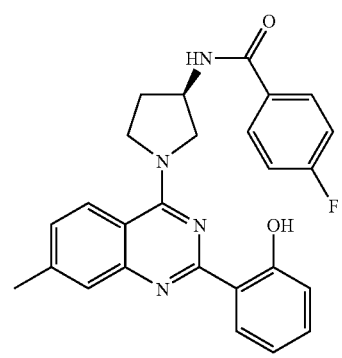

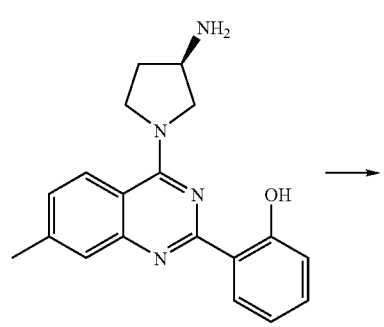

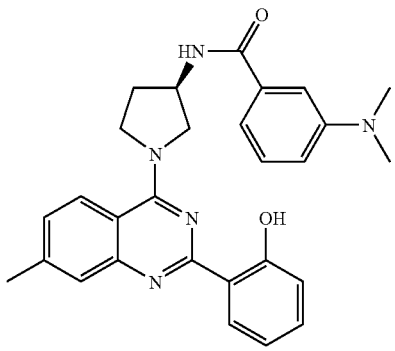

487

3-(Dimethylamino)-N—((R)-1-(2-(2-hydroxyphenyl)-7-methylquinazolin-4-yl)pyrrolidin-3-yl)benzamide

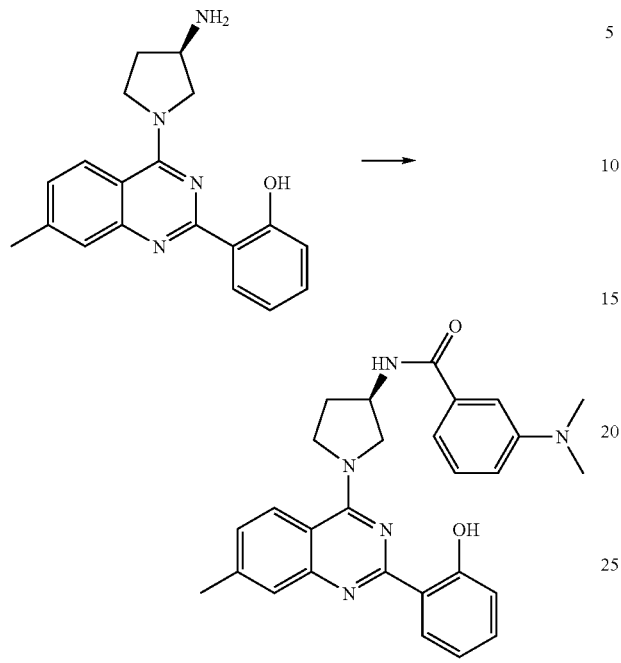

2-(4-((R)-3-Aminopyrrolidin-1-yl)-7-methylquinazolin-2-yl)phenol (50 mg, 0.16 mmol) was dissolved in 260 μL of anhydrous CH$_2$Cl$_2$ and cooled to 0° C. 3-(Dimethylamino) benzoyl chloride hydrochloride (34 mg, 0.15 mmol) dissolved in 260 μL of anhydrous CH$_2$Cl$_2$ was added dropwise to the mixture followed by triethylamine (32 mg, 44 μL, 0.31 mmol). The reaction was stirred for 1.5 hour at 0° C. and purified via reverse phase HPLC (10%-99% CH$_3$CN (0.035% TFA)/H$_2$O (0.05% TFA)) to give 3-(dimethylamino)-N—((R)-1-(2-(2-hydroxyphenyl)-7-methylquinazolin-4-yl)pyrrolidin-3-yl)benzamide as the TFA salt. LC/MS: m/z 468.4 (M+H)$^+$ at 2.39 min (10%-99% CH$_3$CN (0.035% TFA)/H$_2$O (0.05% TFA)).

Example 343

2-(Trifluoromethyl)-N—((R)-1-(2-(2-hydroxyphenyl)-7-methylquinazolin-4-yl)pyrrolidin-3-yl)benzamide

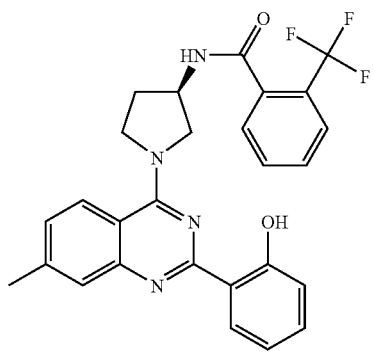

488

2-(Trifluoromethyl)-N—((R)-1-(2-(2-hydroxyphenyl)-7-methylquinazolin-4-yl)pyrrolidin-3-yl)benzamide

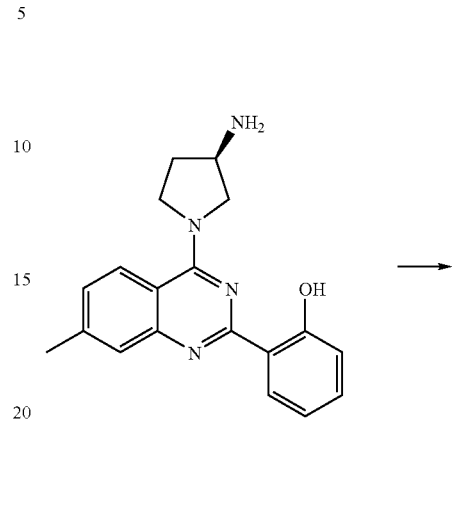

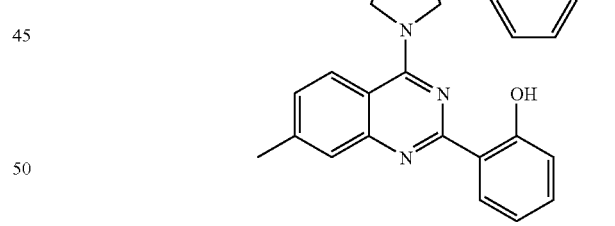

2-(4-((R)-3-Aminopyrrolidin-1-yl)-7-methylquinazolin-2-yl)phenol (50 mg, 0.16 mmol) was dissolved in 260 μL of anhydrous CH$_2$Cl$_2$ and cooled to 0° C. 2-(Trifluoromethyl) benzoyl chloride (39 mg, 0.18 mmol) dissolved in 260 μL of anhydrous CH$_2$Cl$_2$ was added dropwise to the mixture followed by triethylamine (21 mg, 28 μL, 0.20 mmol). The reaction was stirred for 20 minutes at 0° C. and purified via reverse phase HPLC (10%-99% CH$_3$CN (0.035% TFA)/H$_2$O (0.05% TFA)) to give 2-(trifluoromethyl)-N—((R)-1-(2-(2-hydroxyphenyl)-7-methylquinazolin-4-yl)pyrrolidin-3-yl)

benzamide as the TFA salt. LC/MS: m/z 493.4 (M+H)+ at 2.76 min (10%-99% CH₃CN (0.035% TFA)/H₂O (0.05% TFA)).

Example 344

2-Fluoro-N—((R)-1-(2-(2-hydroxyphenyl)-7-methylquinazolin-4-yl)pyrrolidin-3-yl)benzamide

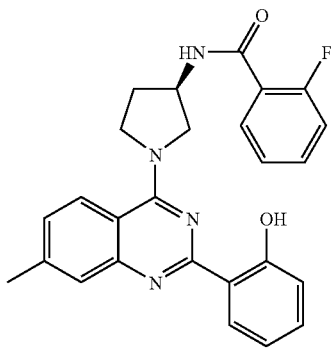

2-Fluoro-N—((R)-1-(2-(2-hydroxyphenyl)-7-methylquinazolin-4-yl)pyrrolidin-3-yl)benzamide

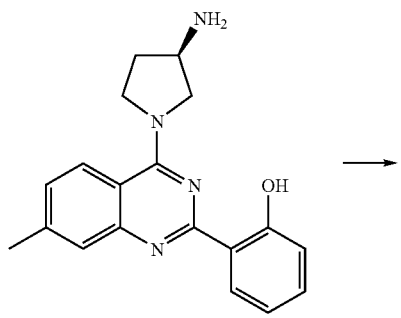

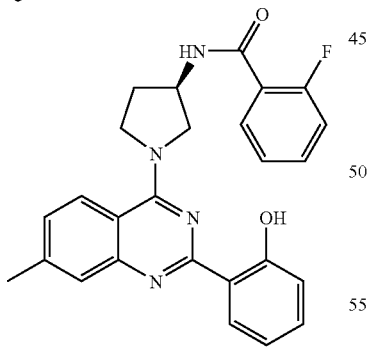

2-(4-((R)-3-Aminopyrrolidin-1-yl)-7-methylquinazolin-2-yl)phenol (50.6 mg, 0.158 mmol) was dissolved in 260 μL of anhydrous CH₂Cl₂ and cooled to 0° C. 2-Fluorobenzoyl chloride (27 mg, 0.17 mmol) dissolved in 260 μL of anhydrous CH₂Cl₂ was added dropwise to the mixture followed by triethylamine (21 mg, 28 μL, 0.20 mmol). The reaction was stirred for 15 minutes at 0° C. and purified via reverse phase HPLC (10%-99% CH₃CN (0.035% TFA)/H₂O (0.05% TFA)) to give 2-fluoro-N—((R)-1-(2-(2-hydroxyphenyl)-7-methylquinazolin-4-yl)pyrrolidin-3-yl)benzamide as the TFA salt. LC/MS: m/z 443.4 (M+H)+ at 2.69 min (10%-99% CH₃CN (0.035% TFA)/H₂O (0.05% TFA)).

Example 345

(S)-Tetrahydrofuran-3-yl (R)-1-(2-(2-fluoro-6-hydroxyphenyl)-7-methylquinazolin-4-yl)pyrrolidin-3-ylcarbamate

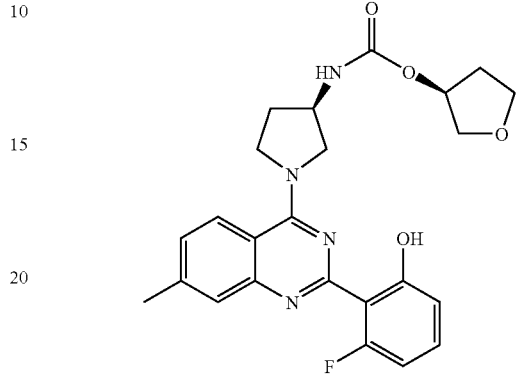

tert-Butyl (R)-1-(2-(2-fluoro-6-hydroxyphenyl)-7-methylquinazolin-4-yl)pyrrolidin-3-ylcarbamate

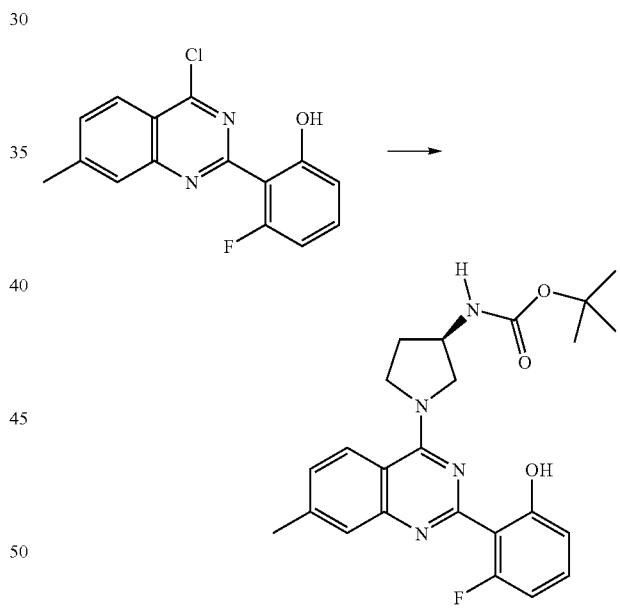

A solution of tert-butyl (R)-pyrrolidin-3-ylcarbamate (368 mg, 1.97 mmol) and triethylamine (0.46 mL, 3.28 mmol) in CH₂Cl₂ was rapidly added to a stirring solution of 2-(4-chloro-7-methylquinazolin-2-yl)-3-fluorophenol (475 mg, 1.65 mmol) in 15 mL CH₂Cl₂ at 0° C. under an N₂ atmosphere. The reaction was stirred for 1 h before it was quenched with water, and the aqueous layer was extracted twice with CH₂Cl₂. The combined organic extracts were dried over MgSO₄, filtered, and concentrated. Purification via silica gel chromatography using 0-10% EtOAc/CH₂Cl₂ yielded tert-butyl (R)-1-(2-(2-fluoro-6-hydroxyphenyl)-7-methylquinazolin-4-yl)pyrrolidin-3-ylcarbamate. LC/MS: m/z 439.5 (M+H)+ at 2.42 min (10%-99% CH₃CN (0.035% TFA)/H₂O (0.05% TFA)).

2-(4-((R)-3-Aminopyrrolidin-1-yl)-7-methylquinazolin-2-yl)-3-fluorophenol

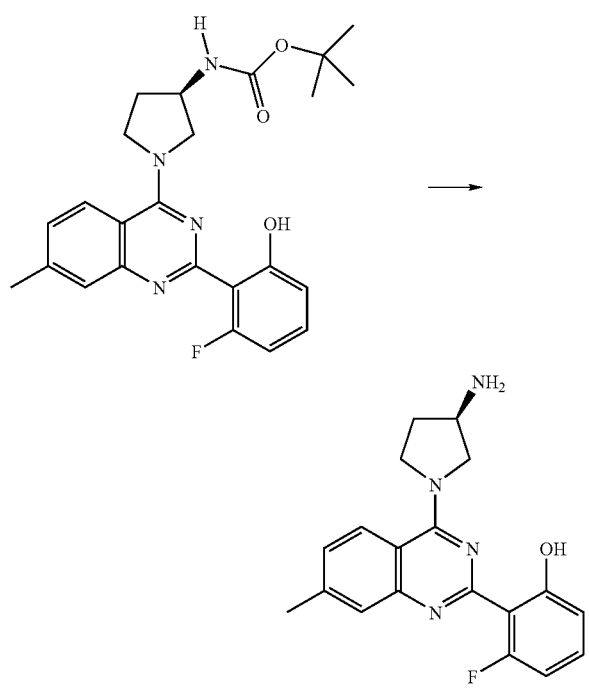

To a solution of tert-butyl (R)-1-(2-(2-fluoro-6-hydroxyphenyl)-7-methylquinazolin-4-yl)pyrrolidin-3-ylcarbamate (500 mg, 1.14 mmol) in CH$_2$Cl$_2$ (15 mL) was added TFA (5 mL). The mixture was stirred for 1 h and then neutralized with a 1 M NaOH solution, and the aqueous layer was extracted twice with CH$_2$Cl$_2$. The combined organic layers were dried over MgSO$_4$, filtered, and concentrated. Purification via silica gel chromatography using 3-20% EtOAc/CH$_2$Cl$_2$ gave 2-(4-((R)-3-aminopyrrolidin-1-yl)-7-methylquinazolin-2-yl)-3-fluorophenol. LC/MS: m/z 339.5 (M+H)$^+$ at 0.56 min (10%-99% CH$_3$CN (0.035% TFA)/H$_2$O (0.05% TFA)).

(S)-Tetrahydrofuran-3-yl (R)-1-(2-(2-fluoro-6-hydroxyphenyl)-7-methylquinazolin-4-yl)pyrrolidin-3-ylcarbamate

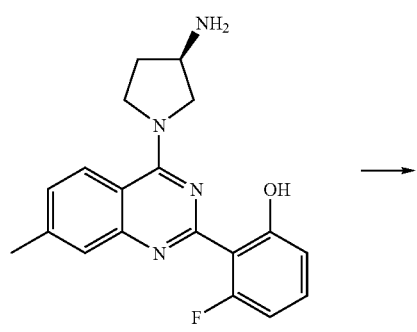

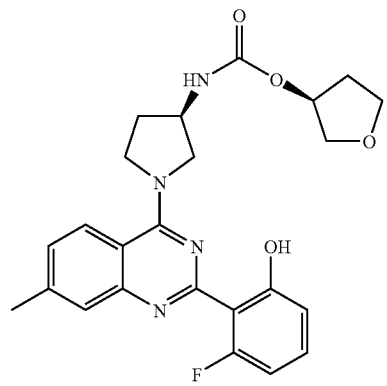

Method A

To a stirred solution of 2-(4-((R)-3-aminopyrrolidin-1-yl)-7-methylquinazolin-2-yl)-3-fluorophenol (40 mg, 0.12 mmol) in 800 μL of anhydrous DMF cooled to 0° C. was added (S)-tetrahydrofuran-3-yl chloroformate (20 mg, 19 μL, 0.13 mmol) dropwise, followed by the addition of triethylamine (24 mg, 33 μL, 0.23 mmol). The reaction was warmed to room temperature and stirred overnight, and the product purified via reverse phase HPLC (10%-99% CH$_3$CN (0.035% TFA)/H$_2$O (0.05% TFA)) to give (S)-tetrahydrofuran-3-yl (R)-1-(2-(2-fluoro-6-hydroxyphenyl)-7-methylquinazolin-4-yl)pyrrolidin-3-ylcarbamate as the TFA salt. LC/MS: m/z 453.3 (M+H)$^+$ at 2.05 min (10%-99% CH$_3$CN (0.035% TFA)/H$_2$O (0.05% TFA)).

Method B

At room temperature, N-ethyl-N-isopropylpropan-2-amine (155 mL, 0.88 mmol) was added to a solution of 2-(4-((R)-3-aminopyrrolidin-1-yl)-7-methylquinazolin-2-yl)-3-fluorophenol (150 mg, 0.40 mmol) in THF. The mixture was cooled in an ice bath, and (S)-tetrahydrofuran-3-yl chloroformate (63 mg, 0.42 mmol) was added slowly over a period of 10 minutes. After warming to room temperature, the reaction was quenched with water and extracted twice with CH$_2$Cl$_2$. The combined organic layers were dried over MgSO$_4$, filtered, and concentrated. Purification via silica gel chromatography using 0-10% EtOAc in CH$_2$Cl$_2$/hexanes (1:1) gave (S)-tetrahydrofuran-3-yl (R)-1-(2-(2-fluoro-6-hydroxyphenyl)-7-methylquinazolin-4-yl)pyrrolidin-3-ylcarbamate (160 mg, 84%). LC/MS: m/z 453.3 (M+H)$^+$ at 2.12 min (10%-99% CH$_3$CN (0.035% TFA)/H$_2$O (0.05% TFA)). $^1$H NMR (400 MHz, DMSO-d6) δ 8.18 (d, J=8.6 Hz, 1H), 7.70 (d, J=6.3 Hz, 1H), 7.58 (s, 1H), 7.29-7.38 (m, 2H), 6.76 (d, J=8.3 Hz, 1H), 6.67-6.72 (m, 1H), 5.14 (s, 1H), 4.23-4.24 (m, 1H), 3.99-4.13 (m, 3H), 3.64-3.85 (m, 5H), 2.50 (s, 3H), 2.07-2.22 (m, 2H), 2.00-2.03 (m, 1H), 1.85-1.90 (m, 1H) ppm.

(S)-Tetrahydrofuran-3-yl (R)-1-(2-(2-fluoro-6-hydroxyphenyl)-7-methylquinazolin-4-yl)pyrrolidin-3-ylcarbamate hydrochloride

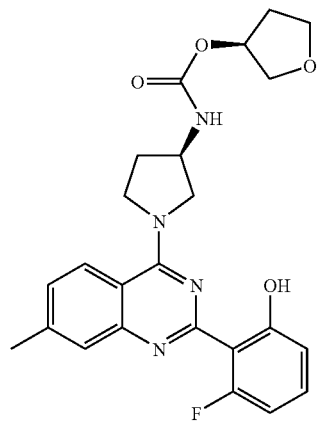

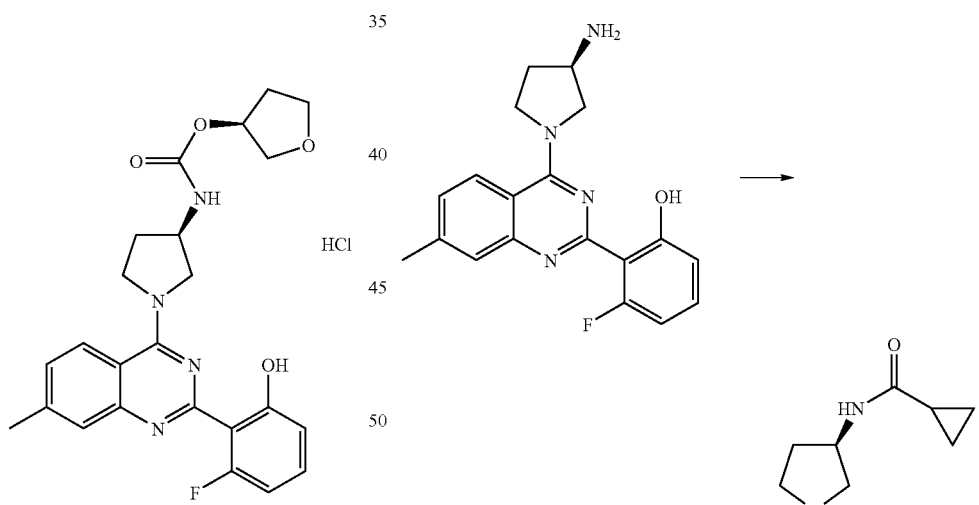

To a solution of (S)-tetrahydrofuran-3-yl (R)-1-(2-(2-fluoro-6-hydroxyphenyl)-7-methylquinazolin-4-yl)pyrrolidin-3-ylcarbamate (160 mg, 0.35 mmol) in 2 mL $CH_2Cl_2$ was added 2 M HCL solution in ether (0.176 mL, 0.35 mmol) resulting in precipitation of a solid. After the addition of 10 mL ether, the reaction was stirred for 30 minutes, filtered and the resulting solid was dried to obtain (S)-tetrahydrofuran-3-yl (R)-1-(2-(2-fluoro-6-hydroxyphenyl)-7-methylquinazolin-4-yl)pyrrolidin-3-ylcarbamate hydrochloride (130 mg, 76%)). LC/MS: m/z 453.3 (M+H)$^+$ at 2.13 min (10%-99% $CH_3CN$ (0.035% TFA)/$H_2O$ (0.05% TFA)). $^1$H NMR (400 MHz, DMSO-d6) δ 8.29 (s, 1H), 7.57 (s, 2H), 7.43-7.49 (m, 1H), 6.83-6.89 (m, 2H), 5.08 (s, 1H), 4.23-4.42 (m, 4H), 3.62-3.73 (m, 5H), 2.24-2.34 (m, 1H), 2.04-2.11 (m, 2H), 1.86-1.92 (m, 1H) ppm.

Example 346

N—((R)-1-(2-(2-Fluoro-6-hydroxyphenyl)-7-methylquinazolin-4-yl)pyrrolidin-3-yl)cyclopropanecarboxamide

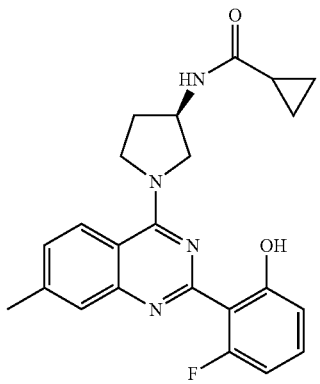

N—((R)-1-(2-(2-Fluoro-6-hydroxyphenyl)-7-methylquinazolin-4-yl)pyrrolidin-3-yl)cyclopropanecarboxamide Method A To a stirred solution of 2-(4-((R)-3-aminopyrrolidin-1-yl)-7-methylquinazolin-2-yl)-3-fluorophenol (40 mg, 0.12 mmol) in 800 µL of anhydrous DMF at 0° C. was added cyclopropanecarboxylic acid (11 mg, 0.13 mmol), followed by the addition of triethylamine (24 mg, 33 µL, 0.24 mmol) and HATU (60 mg, 0.16 mmol). The mixture was allowed to warm to room temperature and was stirred overnight. Filtration and purification via reverse phase HPLC (10%-99% $CH_3CN$ (0.035% TFA)/$H_2O$ (0.05% TFA)) gave N—((R)-1-(2-(2-fluoro-6-hydroxyphenyl)-7-methylquinazolin-4-yl)pyrrolidin-3-yl)cyclopropanecarboxamide as the TFA salt. LC/MS: m/z 407.5 $(M+H)^+$ at 2.2 min (10%-99% $CH_3CN$ (0.035% TFA)/$H_2O$ (0.05% TFA)).

Method B

To a solution of 2-(4-((R)-3-aminopyrrolidin-1-yl)-7-methylquinazolin-2-yl)-3-fluorophenol (100 mg, 0.295 mmol) in 10 mL DMF, at −20° C., was added cyclopropanecarboxylic acid (23 µL, 0.30 mmol), followed by the addition of triethylamine (82 µL, 0.59 mmol) and a solution of HATU (124 mg, 0.32 mmol) in 4 mL DMF. The mixture was warmed to room temperature and stirred for 1 h. Cold water was added to the reaction mixture which resulted in the formation of a precipitate which was collected by filtration and dissolved in $CH_2Cl_2$. The solution was then dried over $MgSO_4$, filtered, and concentrated to afford N—((R)-1-(2-(2-fluoro-6-hydroxyphenyl)-7-methylquinazolin-4-yl)pyrrolidin-3-yl)cyclopropanecarboxamide (80 mg, 66%) LC/MS: m/z 407.5 $(M+H)^+$ at 2.08 min (10%-99% $CH_3CN$ (0.035% TFA)/$H_2O$ (0.05% TFA)).

N—((R)-1-(2-(2-Fluoro-6-hydroxyphenyl)-7-methylquinazolin-4-yl)pyrrolidin-3-yl)cyclopropanecarboxamide hydrochloride

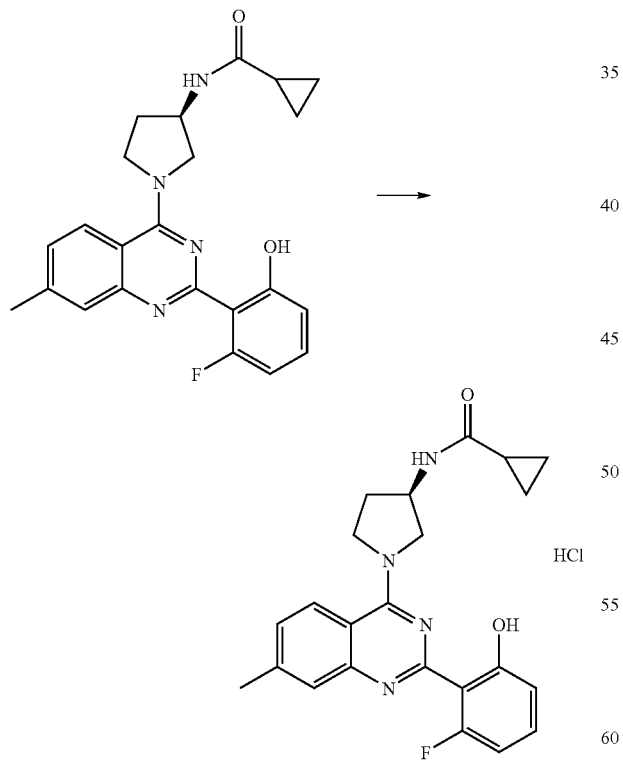

A 2 M HCl solution in ether (0.16 mL, 0.32 mmol) was added to a solution of N—((R)-1-(2-(2-fluoro-6-hydroxyphenyl)-7-methylquinazolin-4-yl)pyrrolidin-3-yl)cyclopropanecarboxamide (133 mg, 0.32 mmol) in $CH_2Cl_2$ (4 mL) under an $N_2$ atmosphere. Additional ether was then added (15 mL) and the reaction mixture was stirred for an hour. The formed precipitate was then filtered and dried to afford N—((R)-1-(2-(2-fluoro-6-hydroxyphenyl)-7-methylquinazolin-4-yl)pyrrolidin-3-yl)cyclopropanecarboxamide hydrochloride (135 mg, 95%). LC/MS: m/z 407.5 $(M+H)^+$ at 2.07 min (10%-99% $CH_3CN$ (0.035% TFA)/$H_2O$ (0.05% TFA)). $^1H$ NMR (400 MHz, DMSO-d6) δ 8.32 (d, J=7.6 Hz, 1H), 7.56-7.58 (m, 2H), 7.43-7.49 (m, 1H), 6.83-6.88 (m, 2H), 3.94-4.41 (m, 5H), 2.52 (s, 3H), 2.25-2.36 (m, 1H), 1.91-2.13 (m, 1H), 1.47-1.54 (m, 1H), 0.63-0.69 (m, 4H) ppm.

Example 347

N—((R)-1-(6-Fluoro-2-(2-hydroxyphenyl)quinazolin-4-yl)pyrrolidin-3-yl)isonicotinamide

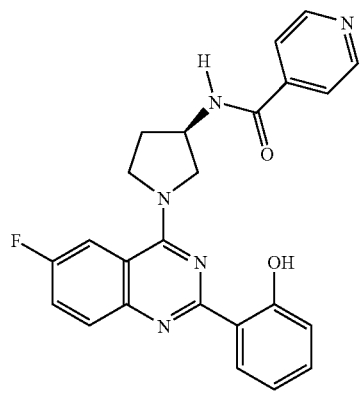

N—((R)-1-(6-Fluoro-2-(2-hydroxyphenyl)quinazolin-4-yl)pyrrolidin-3-yl)isonicotinamide

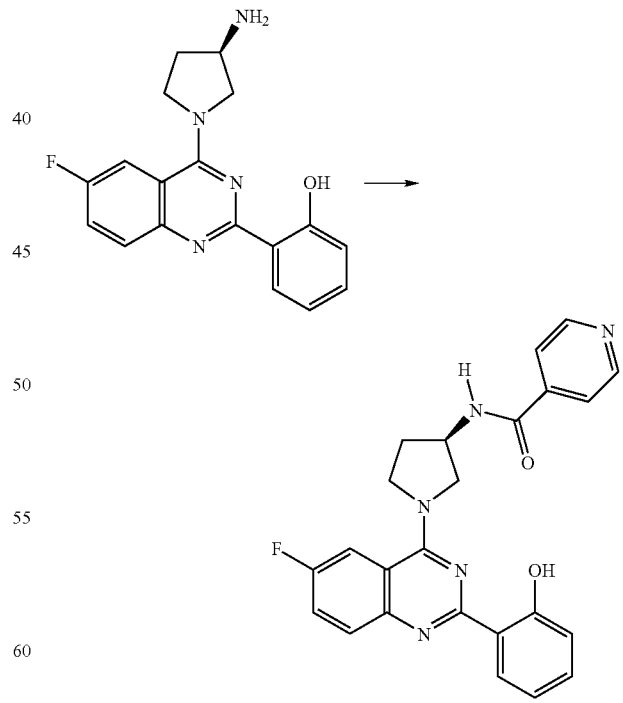

To a solution of 2-(4-((R)-3-aminopyrrolidin-1-yl)-6-fluoroquinazolin-2-yl)phenol (0.03 g, 0.09 mmol) in DMF (1.0 mL) was added isonicotinic acid (0.015 g, 0.12 mmol), followed by the addition of triethylamine (25 µL, 0.18 mmol)

and HATU (0.045 g, 0.12 mmol). The reaction was stirred at room temperature for 2 h, filtered, and purified using reverse phase HPLC (10%-99% CH₃CN (0.035% TFA)/H₂O (0.05% TFA)) to obtain N—((R)-1-(6-fluoro-2-(2-hydroxyphenyl)quinazolin-4-yl)pyrrolidin-3-yl)isonicotinamide as the TFA salt. LC/MS: m/z 430.5 (M+H)⁺ at 1.95 min (10%-99% CH₃CN (0.035% TFA)/H₂O (0.05% TFA)).

Example 348

N—((R)-1-(6-Fluoro-2-(2-hydroxyphenyl)quinazolin-4-yl)pyrrolidin-3-yl)picolinamide

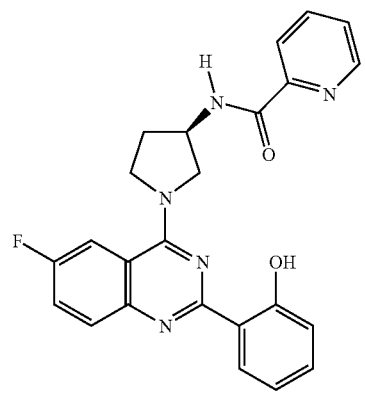

N—((R)-1-(6-Fluoro-2-(2-hydroxyphenyl)quinazolin-4-yl)pyrrolidin-3-yl)picolinamide

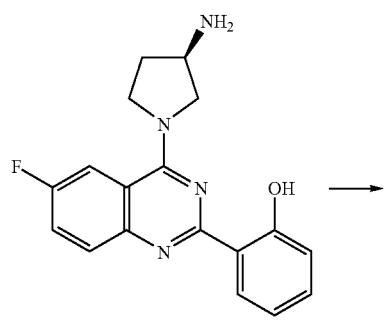

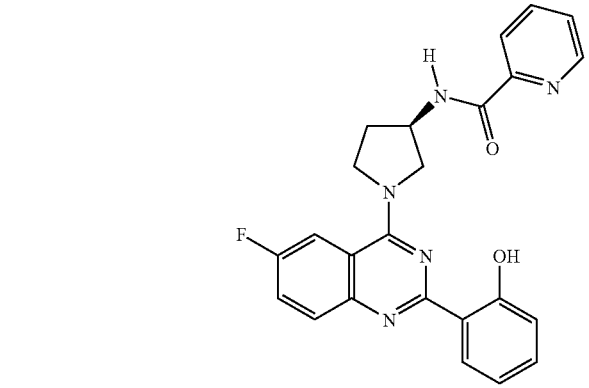

To a solution of 2-(4-((R)-3-aminopyrrolidin-1-yl)-6-fluoroquinazolin-2-yl)phenol (0.03 g, 0.09 mmol) in DMF (1.0 mL) was added picolinic acid (0.015 g, 0.12 mmol), followed by the addition of triethylamine (25 μL, 0.18 mmol) and HATU (0.045 g, 0.12 mmol). The reaction was stirred at room temperature for 2 h, filtered, and purified using reverse phase HPLC (10%-99% CH₃CN (0.035% TFA)/H₂O (0.05% TFA)) to obtain N—((R)-1-(6-fluoro-2-(2-hydroxyphenyl)quinazolin-4-yl)pyrrolidin-3-yl)picolinamide as the TFA salt. LC/MS: m/z 430.5 (M+H)⁺ at 2.43 min (10%-99% CH₃CN (0.035% TFA)/H₂O (0.05% TFA)).

Example 349

N—((R)-1-(6-Fluoro-2-(2-hydroxyphenyl)quinazolin-4-yl)pyrrolidin-3-yl)nicotinamide

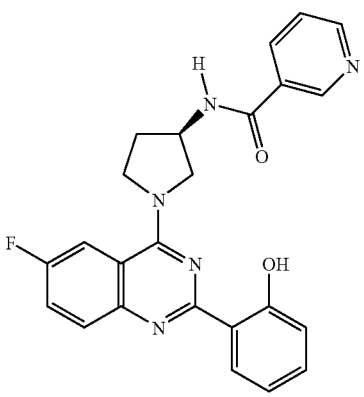

N—((R)-1-(6-Fluoro-2-(2-hydroxyphenyl)quinazolin-4-yl)pyrrolidin-3-yl)nicotinamide

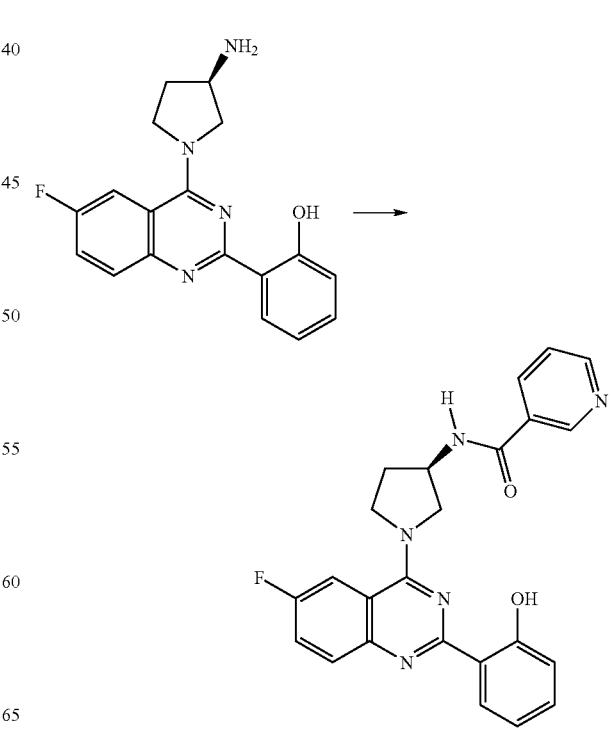

To a solution of 2-(4-((R)-3-aminopyrrolidin-1-yl)-6-fluoroquinazolin-2-yl)phenol (0.03 g, 0.09 mmol) in DMF (1.0 mL) was added nicotinic acid (0.015 g, 0.12 mmol), followed by the addition of triethylamine (25 μL, 0.18 mmol) and HATU (0.045 g, 0.12 mmol). The reaction was stirred at room temperature for 2 h, filtered, and purified using reverse phase HPLC (10%-99% CH$_3$CN (0.035% TFA)/H$_2$O (0.05% TFA)) to obtain N—((R)-1-(6-fluoro-2-(2-hydroxyphenyl)quinazolin-4-yl)pyrrolidin-3-yl)nicotinamide as the TFA salt. LC/MS: m/z 430.5 (M+H)$^+$ at 1.98 min (10%-99% CH$_3$CN (0.035% TFA)/H$_2$O (0.05% TFA)).

Example 350

N—((R)-1-(2-(2-Fluoro-6-hydroxyphenyl)-7-methylquinazolin-4-yl)pyrrolidin-3-yl)isonicotinamide

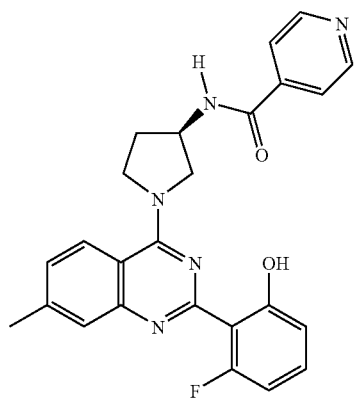

To a solution of 2-(4-((R)-3-aminopyrrolidin-1-yl)-7-methylquinazolin-2-yl)-3-fluorophenol (0.03 g, 0.09 mmol) in DMF (0.5 mL) was added isonicotinic acid (0.014 g, 0.12 mmol), followed by the addition of triethylamine (25 μL, 0.18 mmol) and HATU (0.045 g, 0.12 mmol). The reaction was stirred at room temperature for 2 h, filtered, and purified via reverse phase HPLC (10%-99% CH$_3$CN (0.035% TFA)/H$_2$O (0.05% TFA)) to obtain N—((R)-1-(2-(2-fluoro-6-hydroxyphenyl)-7-methylquinazolin-4-yl)pyrrolidin-3-yl)isonicotinamide as the TFA salt. LC/MS: m/z 444.5 (M+H)$^+$ at 1.85 min (10%-99% CH$_3$CN (0.035% TFA)/H$_2$O (0.05% TFA)).

Example 351

N—((R)-1-(2-(2-Fluoro-6-hydroxyphenyl)-7-methylquinazolin-4-yl)pyrrolidin-3-yl)picolinamide

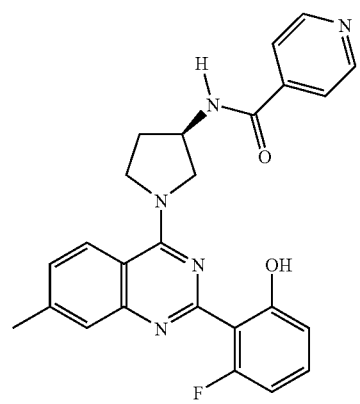

N—((R)-1-(2-(2-Fluoro-6-hydroxyphenyl)-7-methylquinazolin-4-yl)pyrrolidin-3-yl)isonicotinamide

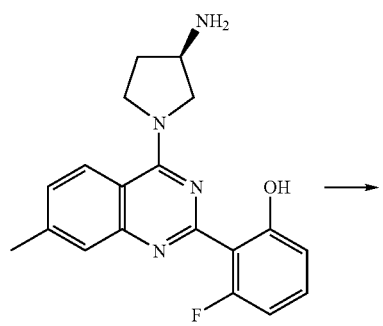

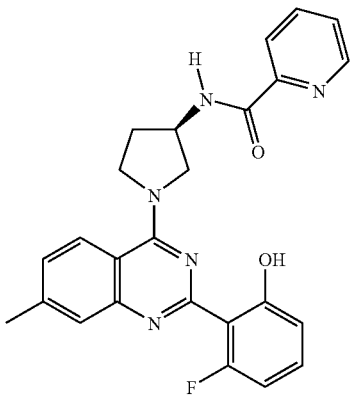

501

N—((R)-1-(2-(2-Fluoro-6-hydroxyphenyl)-7-methylquinazolin-4-yl)pyrrolidin-3-yl)picolinamide

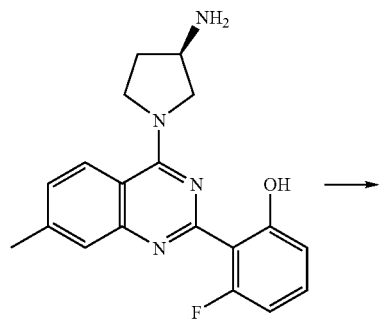

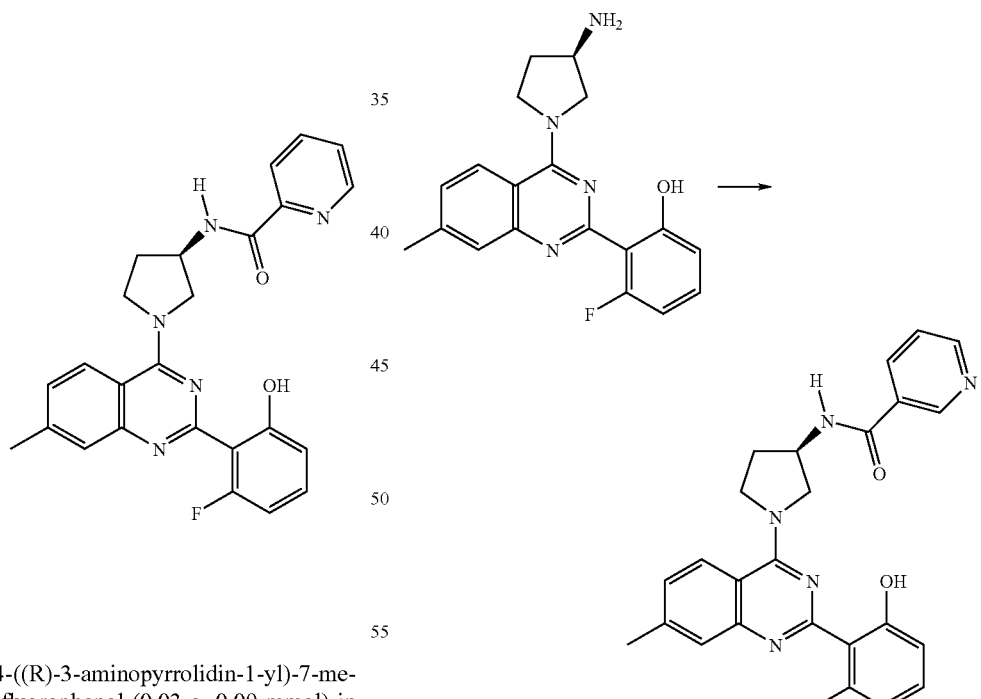

To a solution of 2-(4-((R)-3-aminopyrrolidin-1-yl)-7-methylquinazolin-2-yl)-3-fluorophenol (0.03 g, 0.09 mmol) in DMF (1.0 mL) was added picolinic acid (0.014 g, 0.12 mmol), followed by the addition of triethylamine (25 μL, 0.18 mmol) and HATU (0.045 g, 0.12 mmol). The reaction was stirred at room temperature for 2 h, filtered, and purified via reverse phase HPLC (10%-99% CH$_3$CN (0.035% TFA)/H$_2$O (0.05% TFA)) to obtain N—((R)-1-(2-(2-fluoro-6-hydroxyphenyl)-7-methylquinazolin-4-yl)pyrrolidin-3-yl)picolinamide as the TFA salt. LC/MS: m/z 444.5 (M+H)$^+$ at 2.24 min (10%-99% CH$_3$CN (0.035% TFA)/H$_2$O (0.05% TFA)).

502

Example 352

N—((R)-1-(2-(2-Fluoro-6-hydroxyphenyl)-7-methylquinazolin-4-yl)pyrrolidin-3-yl)nicotinamide

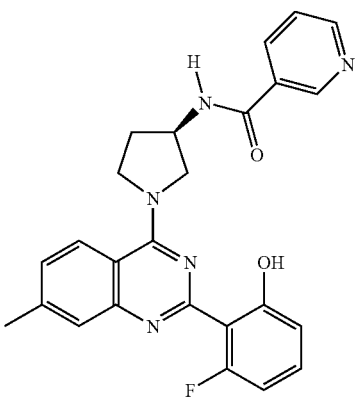

N—((R)-1-(2-(2-Fluoro-6-hydroxyphenyl)-7-methylquinazolin-4-yl)pyrrolidin-3-yl)nicotinamide To a solution of 2-(4-((R)-3-aminopyrrolidin-1-yl)-7-methylquinazolin-2-yl)-3-fluorophenol (0.03 g, 0.09 mmol) in DMF (1.0 mL) was added nicotinic acid (0.014 g, 0.12 mmol), followed by the addition of triethylamine (25 μL, 0.18 mmol) and HATU (0.045 g, 0.12 mmol). The reaction was stirred at room temperature for 2 h, filtered, and purified via reverse phase HPLC (10%-99% CH$_3$CN (0.035% TFA)/H$_2$O (0.05% TFA)) to obtain N—((R)-1-(2-(2-fluoro-6-hydroxyphenyl)-7-methylquinazolin-4-yl)pyrrolidin-3-yl)nicotinamide as the TFA salt. LC/MS: m/z 444.5 (M+H)$^+$ at 1.89 min (10%-99% CH$_3$CN (0.035% TFA)/H$_2$O (0.05% TFA)).

Example 353

N—((R)-1-(2-(2-Hydroxyphenyl)-7-methylquinazolin-4-yl)pyrrolidin-3-yl)isonicotinamide

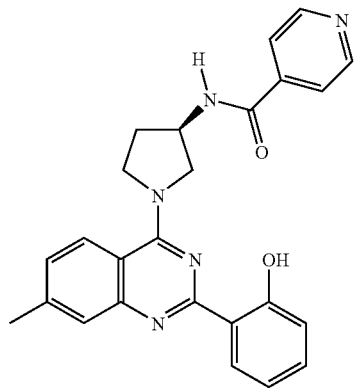

N—((R)-1-(2-(2-Hydroxyphenyl)-7-methylquinazolin-4-yl)pyrrolidin-3-yl)isonicotinamide

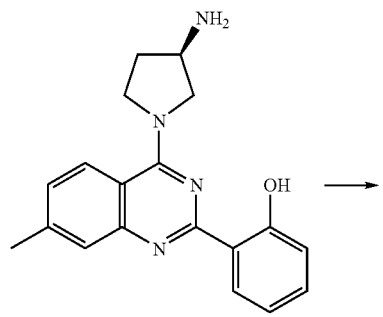

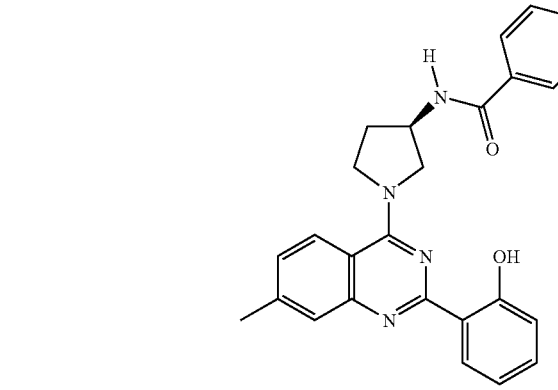

To a solution of 2-(4-((R)-3-aminopyrrolidin-1-yl)-7-methylquinazolin-2-yl)phenol (0.03 g, 0.09 mmol) in DMF (1.0 mL) was added isonicotinic acid (0.015 g, 0.12 mmol), followed by the addition of triethylamine (25 μL, 0.18 mmol) and HATU (0.045 g, 0.12 mmol). The reaction was stirred at room temperature for 2 h, filtered, and purified via reverse phase HPLC (10%-99% CH$_3$CN (0.035% TFA)/H$_2$O (0.05% TFA)) to obtain N—((R)-1-(2-(2-hydroxyphenyl)-7-methylquinazolin-4-yl)pyrrolidin-3-yl)isonicotinamide as the TFA salt. LC/MS: m/z 426.1 (M+H)$^+$ at 1.93 min (10%-99% CH$_3$CN (0.035% TFA)/H$_2$O (0.05% TFA)).

Example 354

N—((R)-1-(2-(2-Hydroxyphenyl)-7-methylquinazolin-4-yl)pyrrolidin-3-yl)picolinamide

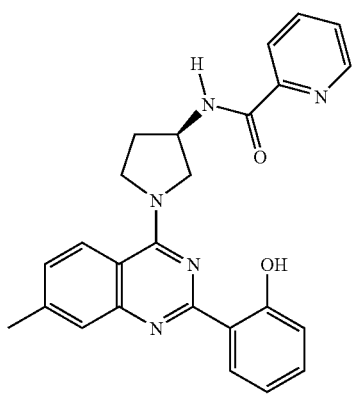

N—((R)-1-(2-(2-Hydroxyphenyl)-7-methylquinazolin-4-yl)pyrrolidin-3-yl)picolinamide

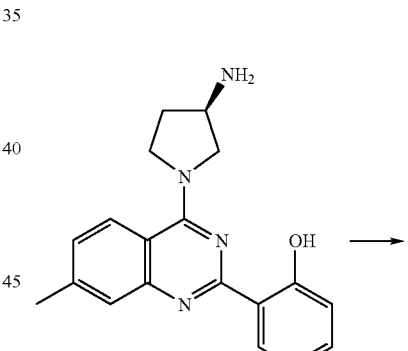

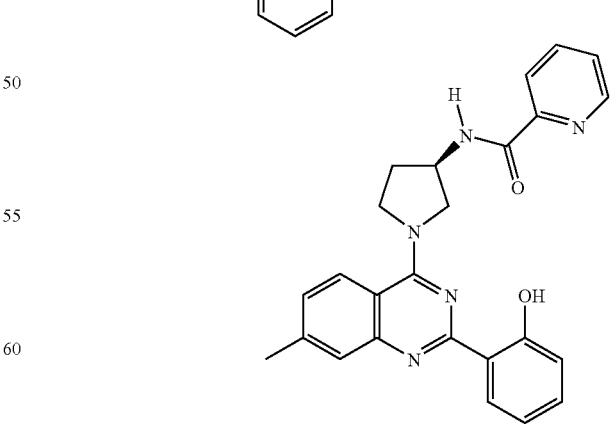

To a solution of 2-(4-((R)-3-aminopyrrolidin-1-yl)-7-methylquinazolin-2-yl)phenol (0.03 g, 0.09 mmol) in DMF (1.0 mL) was added picolinic acid (0.015 g, 0.12 mmol), followed by the addition of triethylamine (25 µL, 0.18 mmol) and HATU (0.045 g, 0.12 mmol). The reaction was stirred at room temperature for 2 h, filtered, and purified via reverse phase HPLC (10%-99% CH$_3$CN (0.035% TFA)/H$_2$O (0.05% TFA)) to obtain N—((R)-1-(2-(2-hydroxyphenyl)-7-methylquinazolin-4-yl)pyrrolidin-3-yl)picolinamide as the TFA salt. LC/MS: m/z 426.1 (M+H)$^+$ at 2.33 min (10%-99% CH$_3$CN (0.035% TFA)/H$_2$O (0.05% TFA)).

Example 355

(R)-Tetrahydrofuran-3-yl ((S)-1-(6-fluoro-2-(2-hydroxyphenyl)quinazolin-4-yl)pyrrolidin-3-yl)methylcarbamate

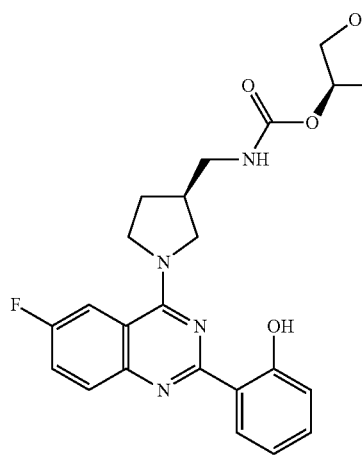

Benzyl ((S)-1-(tert-butoxycarbonyl)pyrrolidin-3-yl)methylcarbamate

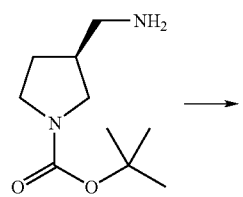

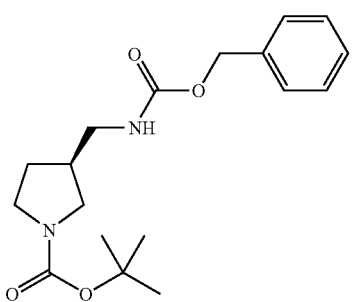

To a stirred solution of ((S)-1-(tert-butoxycarbonyl)pyrrolidin-3-yl)methylcarbamate (1.5 g, 4.48 mmol) in CH$_2$Cl$_2$ (20 mL) was slowly added TFA (5 mL). The reaction was stirred for 2 h. After removing the solvents under reduced pressure, the mixture was neutralized with a 1 M NaOH solution and extracted twice with CH$_2$Cl$_2$. The combined organic layers were dried over MgSO$_4$, filtered, and concentrated to afford benzyl ((R) -pyrrolidin-3-yl)methylcarbamate (800 mg, 76%). LC/MS: m/z 235.3 (M+H)$^+$ at 1.22 min (10%-99% CH$_3$CN (0.035% TFA)/H$_2$O (0.05% TFA)).

Benzyl ((R)-pyrrolidin-3-yl)methylcarbamate

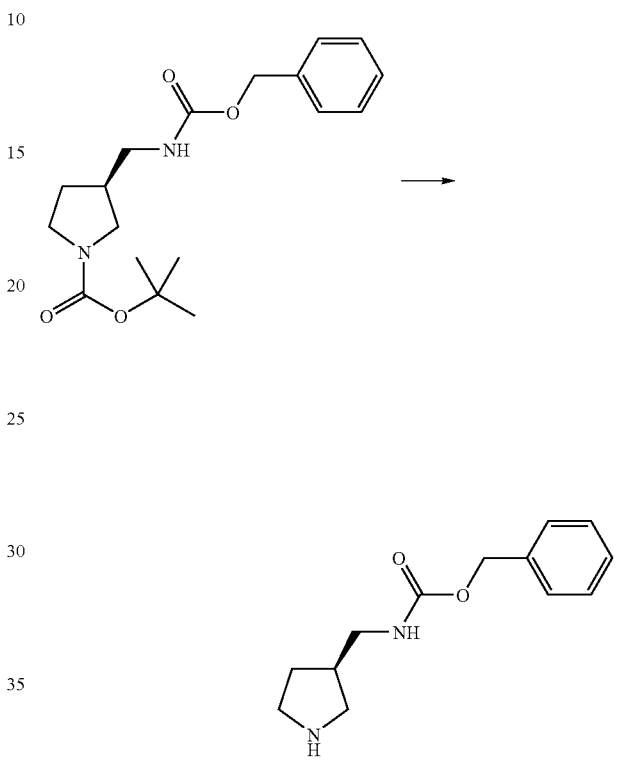

To a stirred solution of ((S)-1-(tert-butoxycarbonyl)pyrrolidin-3-yl)methylcarbamate (1.5 g, 4.48 mmol) in CH$_2$Cl$_2$ (20 mL) was slowly added TFA (5 mL). The reaction was stirred for 2 h. After removing the solvents under reduced pressure, the mixture was neutralized with a 1 M NaOH solution and extracted twice with CH$_2$Cl$_2$. The combined organic layers were dried over MgSO$_4$, filtered, and concentrated to afford benzyl ((R) -pyrrolidin-3-yl)methylcarbamate (800 mg, 76%). LC/MS: m/z 335.3 (M+H)$^+$ at 1.22 min (10%-99% CH$_3$CN (0.035% TFA)/H$_2$O (0.05% TFA)).

Benzyl ((S)-1-(6-fluoro-2-(2-hydroxyphenyl) quinazolin-4-yl)pyrrolidin-3-yl)methylcarbamate

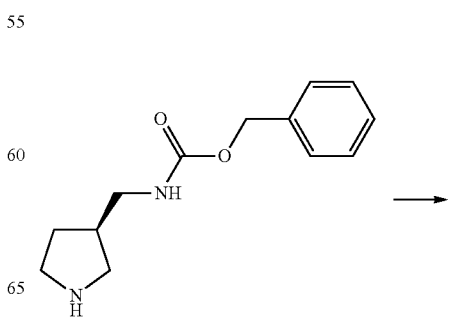

-continued

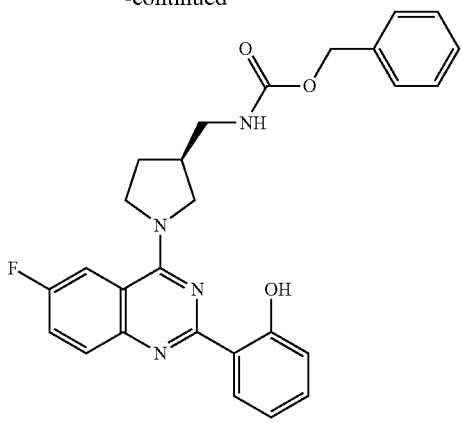

A solution of triethylamine (507 μL, 3.64 mmol) and benzyl ((R)-pyrrolidin-3-yl)methylcarbamate (0.47 g, 2 mmol) in CH₂Cl₂ was added dropwise to a solution of 2-(4-chloro-6-fluoroquinazolin-2-yl)phenol (0.5 g, 1.82 mmol) in CH₂Cl₂ (20 mL). The reaction was stirred at room temperature for 3 h. After quenching the reaction with water, the aqueous phase was extracted twice with CH₂Cl₂. The combined organic layers were dried over MgSO₄, filtered, and concentrated. Purification via silica gel chromatography using 5-10% EtOAc in CH₂Cl₂ yielded benzyl ((S)-1-(6-fluoro-2-(2-hydroxyphenyl)quinazolin-4-yl)pyrrolidin-3-yl)methylcarbamate. LC/MS: m/z 473.1 (M+H)⁺ at 2.91 min (10%-99% CH₃CN (0.035% TFA)/H₂O (0.05% TFA)).

2-(4-((S)-3-(Aminomethyl)pyrrolidin-1-yl)-6-fluoroquinazolin-2-yl)phenol

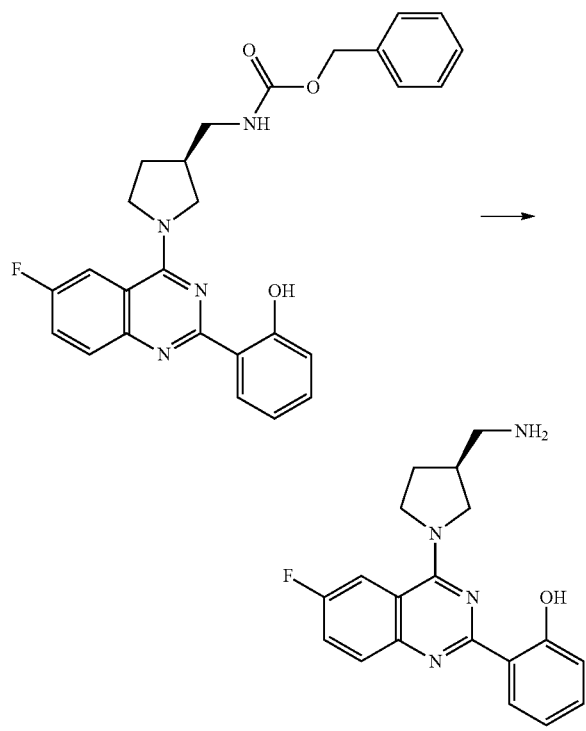

Under an N₂ atmosphere, a mixture of benzyl ((S)-1-(6-fluoro-2-(2-hydroxyphenyl)quinazolin-4-yl)pyrrolidin-3-yl)methylcarbamate (0.770 g, 1.6 mmol) and MeOH (5 mL) was added to Pd/C (77 mg, 10% weight Pd on carbon) weighed into a 100 mL flask. After the atmosphere in the flask was evacuated and purged with N₂ three times, the reaction mixture was vigorously stirred under an H₂ atmosphere at ambient pressure overnight and then filtered through a pad of Celite, concentrated, and dried to obtain 2-(4-((S)-3-(aminomethyl)pyrrolidin-1-yl)-6-fluoroquinazolin-2-yl)phenol (0.45 g, 81%). LC/MS: m/z 459.5 (M+H)⁺ at 2.81 min (10%-99% CH₃CN (0.035% TFA)/H₂O (0.05% TFA)).

(R)-Tetrahydrofuran-3-yl ((S)-1-(6-fluoro-2-(2-hydroxyphenyl)quinazolin-4-yl)pyrrolidin-3-yl)methylcarbamate

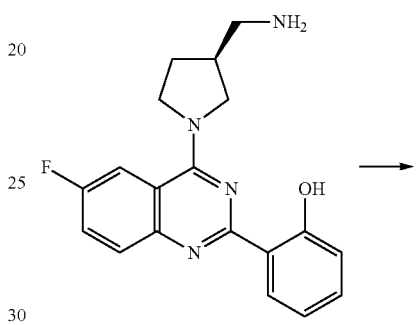

To a solution of 2-(4-((S)-3-(aminomethyl)pyrrolidin-1-yl)-6-fluoroquinazolin-2-yl)phenol (0.03 g, 0.09 mmol) in DMF (1.0 mL) at −60° C. (external temperature) was added triethylamine (25 mL, 0.18 mmol) and (R)-tetrahydrofuran-3-yl chloroformate (13 mg, 0.09 mmol). The reaction was warmed to room temperature, filtered, and purified via reverse phase HPLC (10%-99% CH₃CN (0.035% TFA)/H₂O (0.05% TFA)) to afford (R)-tetrahydrofuran-3-yl ((S)-1-(6-fluoro-2-(2-hydroxyphenyl)quinazolin-4-yl)pyrrolidin-3-yl)

methylcarbamate as the TFA salt. LC/MS: m/z 453.3 (M+H)+ at 2.29 min (10%-99% CH₃CN (0.035% TFA)/H₂O (0.05% TFA)).

Example 356

(S)-Tetrahydrofuran-3-yl ((S)-1-(6-fluoro-2-(2-hydroxyphenyl)quinazolin-4-yl)pyrrolidin-3-yl)methylcarbamate

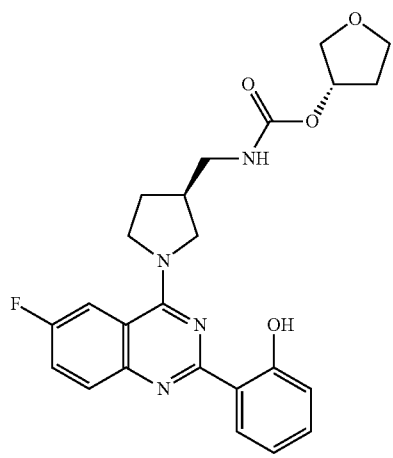

(S)-Tetrahydrofuran-3-yl ((S)-1-(6-fluoro-2-(2-hydroxyphenyl)quinazolin-4-yl)pyrrolidin-3-yl)methylcarbamate

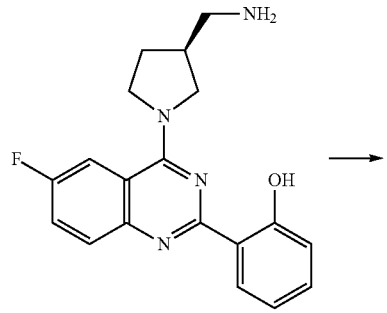

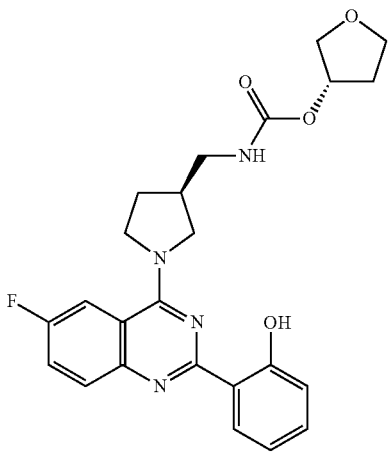

To a solution of 2-(4-((S)-3-(aminomethyl)pyrrolidin-1-yl)-6-fluoroquinazolin-2-yl)phenol (0.03 g, 0.09 mmol) in DMF (1.0 mL) at −60° C. (external temperature) was added triethylamine (25 mL, 0.18 mmol) and (S)-tetrahydrofuran-3-yl chloroformate (13 mg, 0.09 mmol). The reaction was warmed to room temperature, filtered, and purified via reverse phase HPLC (10%-99% CH₃CN (0.035% TFA)/H₂O (0.05% TFA)) to afford (S)-tetrahydrofuran-3-yl ((S)-1-(6-fluoro-2-(2-hydroxyphenyl)quinazolin-4-yl)pyrrolidin-3-yl) methylcarbamate as the TFA salt. LC/MS: m/z 453.3 (M+H)+ at 2.29 min (10%-99% CH₃CN (0.035% TFA)/H₂O (0.05% TFA)).

Example 357

N—(((S)-1-(6-Fluoro-2-(2-hydroxyphenyl)quinazolin-4-yl)pyrrolidin-3-yl)methyl)cyclopropanecarboxamide

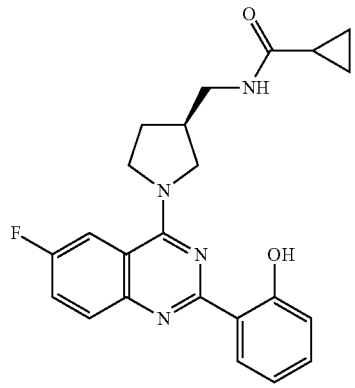

511

N—(((S)-1-(6-Fluoro-2-(2-hydroxyphenyl)quinazolin-4-yl)pyrrolidin-3-yl)methyl)cyclopropanecarboxamide

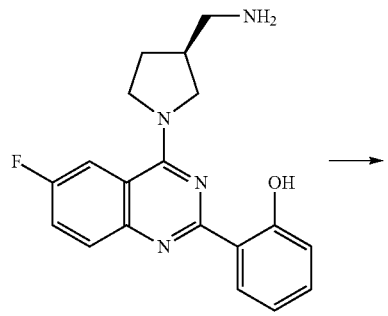

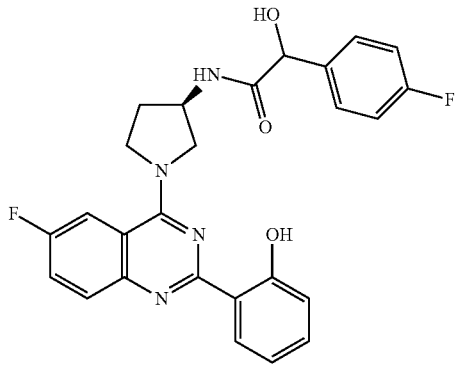

To a solution of 2-(4-((S)-3-(aminomethyl)pyrrolidin-1-yl)-6-fluoroquinazolin-2-yl)phenol (0.03 g, 0.09 mmol) and cyclopropanecarboxylic acid (10 mg, 0.12 mmol) in DMF (1.0 mL) was added triethylamine (25 μL, 0.18 mmol) followed by the addition of HATU (45 mg, 0.117 mmol). The reaction was stirred at room temperature for 2 h, filtered, and purified via reverse phase HPLC (10%-99% CH$_3$CN (0.035% TFA)/H$_2$O (0.05% TFA)) to obtain N—(((S)-1-(6-fluoro-2-(2-hydroxyphenyl)quinazolin-4-yl)pyrrolidin-3-yl)methyl)cyclopropanecarboxamide as the TFA salt. LC/MS: m/z 407.3 (M+H)$^+$ at 2.26 min (10%-99% CH$_3$CN (0.035% TFA)/H$_2$O (0.05% TFA)).

512

Example 358

N—((R)-1-(6-Fluoro-2-(2-hydroxyphenyl)quinazolin-4-yl)pyrrolidin-3-yl)-2-(4-fluorophenyl)-2-hydroxyacetamide N—((R)-1-(6-Fluoro-2-(2-hydroxyphenyl)quinazolin-4-yl)pyrrolidin-3-yl)-2-(4-fluorophenyl)-2-hydroxyacetamide

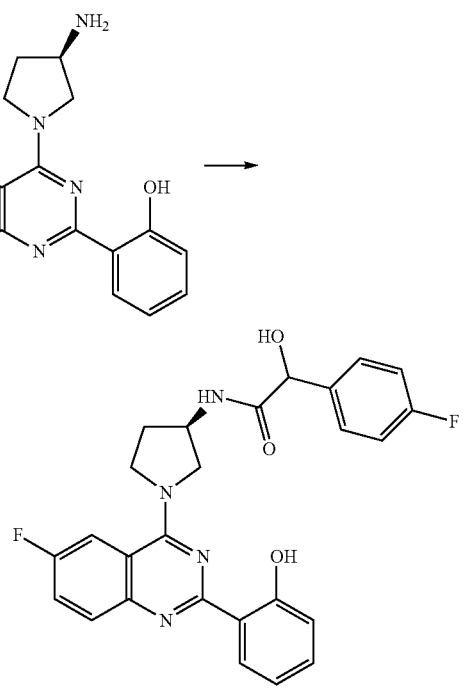

To a solution of 2-(4-((R)-3-aminopyrrolidin-1-yl)-6-fluoroquinazolin-2-yl)phenol (0.03 g, 0.09 mmol) in DMF (1.0 mL) was added 2-(4-fluorophenyl)-2-hydroxyacetic acid (20 mg, 0.12 mmol), followed by the addition of triethylamine (25 μL, 0.18 mmol) and HATU (0.045 g, 0.12 mmol). The reaction was stirred at room temperature for 2 h, filtered, and purified using reverse phase HPLC (10%-99% CH₃CN (0.035% TFA)/H₂O (0.05% TFA)) to obtain N—((R)-(6-fluoro-2-(2-hydroxyphenyl)quinazolin-4-yl)pyrrolidin-3-yl)-2-(4-fluorophenyl)-2-hydroxyacetamide as the TFA salt. LC/MS: m/z 477.3 (M+H)⁺ at 2.80 min (10%-99% CH₃CN (0.035% TFA)/H₂O (0.05% TFA)).

Example 359

N—((R)-1-(2-(2-Fluoro-6-hydroxyphenyl)-7-methylquinazolin-4-yl)pyrrolidin-3-yl)-2-(4-fluorophenyl)-2-hydroxyacetamide

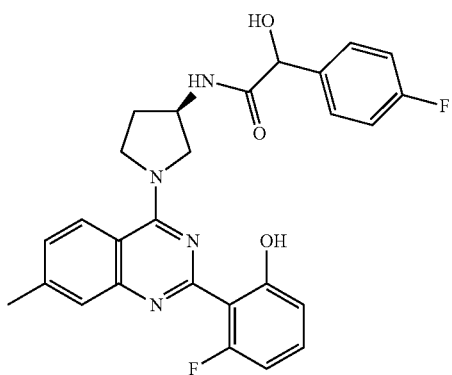

N—((R)-1-(2-(2-(2-Fluoro-6-hydroxyphenyl)-7-methylquinazolin-4-yl)pyrrolidin-3-yl)-2-(4-fluorophenyl)-2-hydroxyacetamide

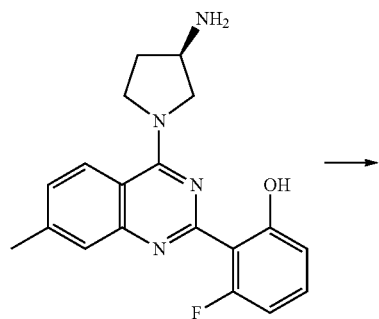

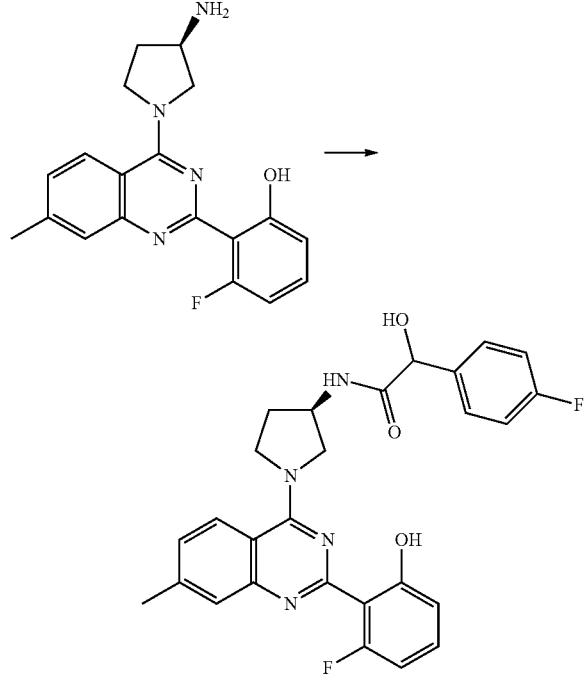

To a solution of 2-(4-((R)-3-aminopyrrolidin-1-yl)-7-methylquinazolin-2-yl)-3-fluorophenol (0.03 g, 0.09 mmol) in DMF (1.0 mL) was added 2-(4-fluorophenyl)-2-hydroxyacetic acid (0.020 g, 0.12 mmol), followed by the addition of triethylamine (25.6 μL, 0.184 mmol) and HATU (0.045 g, 0.12 mmol). The reaction was stirred at room temperature for 2 h, filtered, and purified using reverse phase HPLC (10%-99% CH₃CN (0.035% TFA)/H₂O (0.05% TFA)) to obtain N—((R)-1-(2-(2-fluoro-6-hydroxyphenyl)-7-methylquinazolin-4-yl)pyrrolidin-3-yl)-2-(4-fluorophenyl)-2-hydroxyacetamide as the TFA salt. LC/MS: m/z 4491.3 (M+H)⁺ at 2.46 min (10%-99% CH₃CN (0.035% TFA)/H₂O (0.05% TFA)).

Example 360

2-(4-Fluorophenyl)-2-hydroxy-N—((R)-1-(2-(2-hydroxyphenyl)-7-methylquinazolin-4-yl)pyrrolidin-3-yl)acetamide

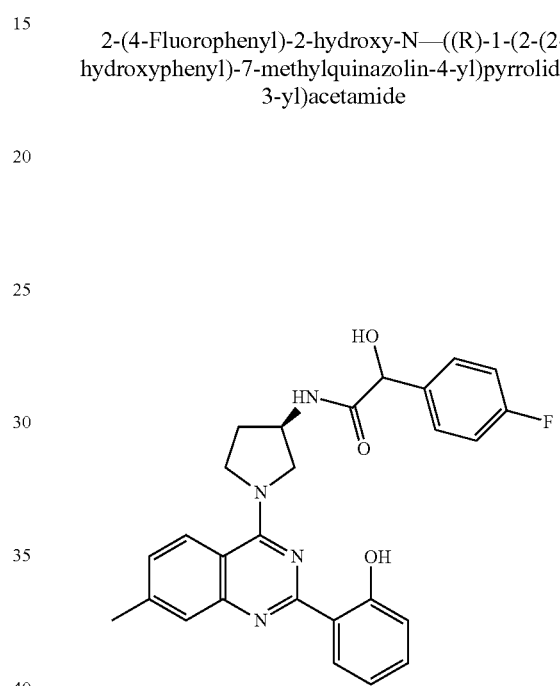

2-(4-Fluorophenyl)-2-hydroxy-N—((R)-1-(2-(2-hydroxyphenyl)-7-methylquinazolin-4-yl)pyrrolidin-3-yl)acetamide

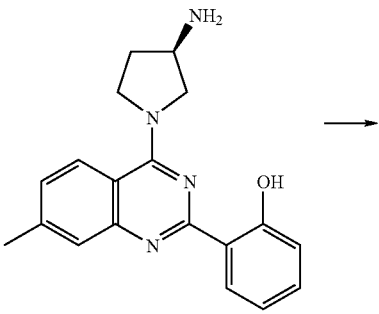

515
-continued

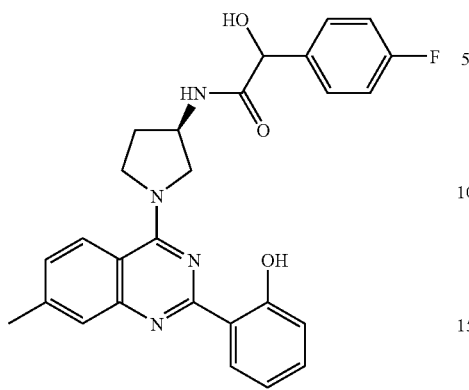

To a solution of 2-(4-((R)-3-aminopyrrolidin-1-yl)-7-methylquinazolin-2-yl)phenol (0.03 g, 0.09 mmol) in DMF (1.0 mL) was added 2-(4-fluorophenyl)-2-hydroxyacetic acid (0.02 g, 0.12 mmol), followed by the addition of triethylamine (25 μL, 0.18 mmol) and HATU (0.045 g, 0.12 mmol). The reaction was stirred at room temperature for 2 h, filtered, and purified using reverse phase HPLC (10%-99% CH$_3$CN (0.035% TFA)/H$_2$O (0.05% TFA)) to obtain 2-(4-fluorophenyl)-2-hydroxy-N—((R)-1-(2-(2-hydroxyphenyl)-7-methylquinazolin-4-yl)pyrrolidin-3-yl)acetamide as the TFA salt. LC/MS: m/z 473.1 (M+H)$^+$ at 2.32 min (10%-99% CH$_3$CN (0.035% TFA)/H$_2$O (0.05% TFA)).

Example 361

(2R)-2-Hydroxy-N—((R)-1-(2-(2-Hydroxyphenyl)-7-methylquinazolin-4-yl)pyrrolidin-3-yl)-4,4-dimethylpentanamide

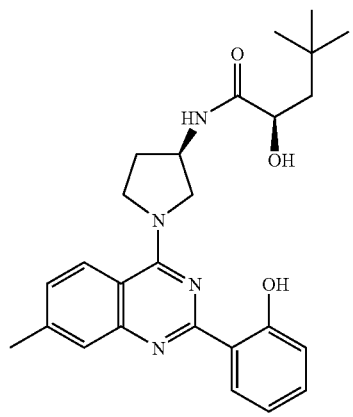

516

(2R)-2-Hydroxy-N—((R)-1-(2-(2-hydroxyphenyl)-7-methylquinazolin-4-yl)pyrrolidin-3-yl)-4,4-dimethylpentanamide

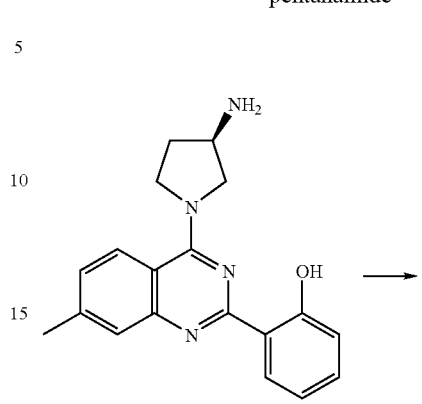

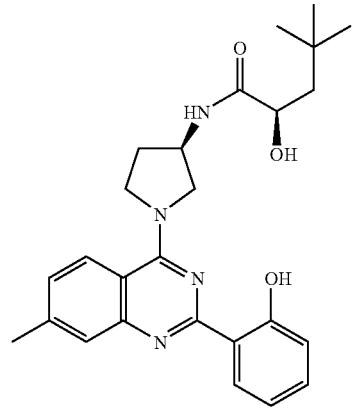

To a stirred solution of 2-(4-((R)-3-aminopyrrolidin-1-yl)-7-methylquinazolin-2-yl)phenol (50 mg, 0.16 mmol) in 1 mL of DMF cooled at 0° C. was added (R)-2-hydroxy-4,4-dimethylpentanoic acid (27.3 mg, 0.187 mmol), followed by the addition of triethylamine (32 mg, 44 μL, 0.31 mmol), then HATU (71.1 mg, 0.187 mmol). The reaction was stirred at 0° C. for 10 minutes, warmed to room temperature, filtered, and purified via reverse phase HPLC (10%-99% CH$_3$CN (0.035% TFA)/H$_2$O (0.05% TFA)) to afford (2R)-2-hydroxy-N—((R)-1-(2-(2-hydroxyphenyl)-7-methylquinazolin-4-yl)pyrrolidin-3-yl)-4,4-dimethylpentanamide as the TFA salt. LC/MS: m/z 449.3 (M+H)+ at 2.4 min (10%-99% CH$_3$CN (0.035% TFA)/H$_2$O (0.05% TFA)).

Example 362

Benzyl ((R)-1-(2-(2-hydroxyphenyl)-7-methylquinazolin-4-yl)pyrrolidin-3-yl)methylcarbamate

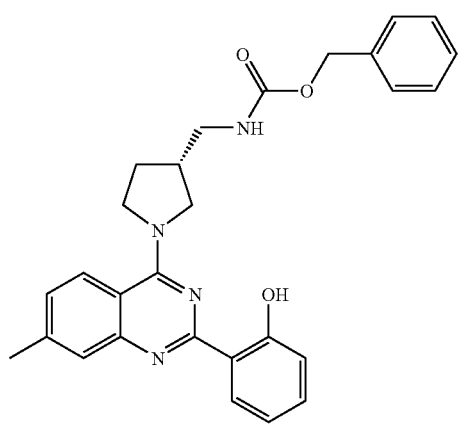

Benzyl ((R)-1-(2-(2-hydroxyphenyl)-7-methylquinazolin-4-yl)pyrrolidin-3-yl)methylcarbamate

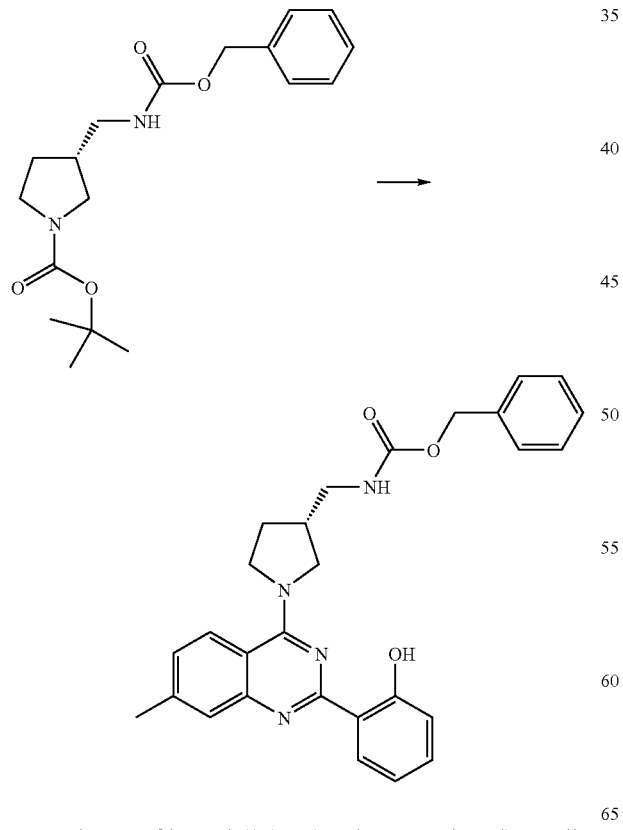

A mixture of benzyl ((R)-1-(tert-butoxycarbonyl)pyrrolidin-3-yl)methylcarbamate (0.20 g, 0.60 mmol) and 4 M HCl (10 mL) in dioxane was stirred at room temperature for 3 h. After evaporating the solvent under reduced pressure, the solid was triturated with Et$_2$O, dried under vacuum, and taken up in CH$_2$Cl$_2$ (10 mL). 2-(4-Chloro-7-methylquinazolin-2-yl)phenol (0.16 g, 0.60 mmol) was added to this solution, followed by the addition of triethylamine (0.25 mL, 1.8 mmol). The reaction mixture was stirred at room temperature overnight, then diluted with CH$_2$Cl$_2$ and washed with water. The combined organic layers were dried over Na$_2$SO$_4$, filtered, and concentrated. Purification via silica gel chromatography using 0-40% EtOAc in hexanes gave benzyl ((R)-1-(2-(2-hydroxyphenyl)-7-methylquinazolin-4-yl)pyrrolidin-3-yl)methylcarbamate as a colorless oil (0.19 g, 68% yield). LC/MS: m/z 469.1 (M+H)+ at 2.58 min (10%-99% CH$_3$CN (0.035% TFA)/H$_2$O (0.05% TFA)).

Example 363

Benzyl ((S)-1-(2-(2-hydroxyphenyl)-7-methylquinazolin-4-yl)pyrrolidin-3-yl)methylcarbamate

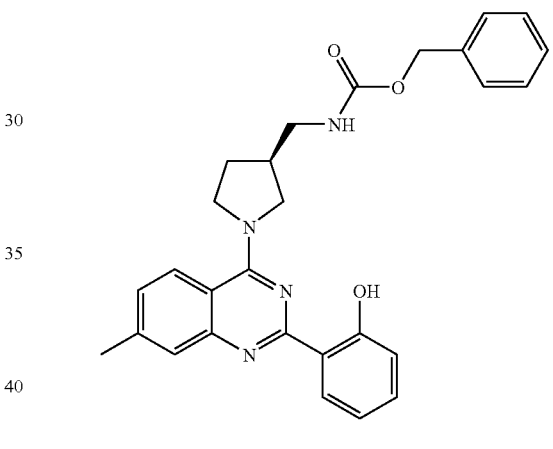

Benzyl ((S)-1-(2-(2-hydroxyphenyl)-7-methylquinazolin-4-yl)pyrrolidin-3-yl)methylcarbamate

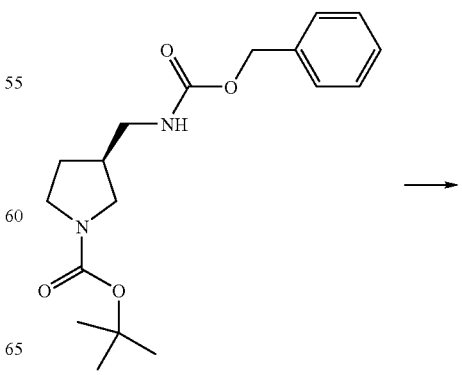

519
-continued

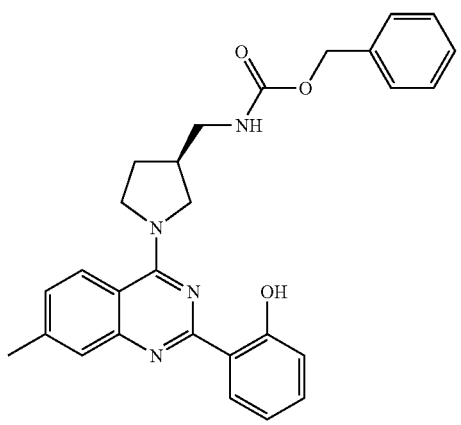

A mixture of benzyl ((S)-1-(tert-butoxycarbonyl)pyrrolidin-3-yl)methylcarbamate (0.20 g, 0.60 mmol) and 4 M HCl in dioxane (10 mL) was stirred for 3 h at room temperature. After evaporating the solvent under reduced pressure, the solid was triturated with Et$_2$O, dried under vacuum, and taken up in CH$_2$Cl$_2$ (10 mL). 2-(4-Chloro-7-methylquinazolin-2-yl)phenol (0.16 g, 0.60 mmol) was added to this solution, followed by the addition of triethylamine (0.25 mL, 1.8 mmol). The reaction mixture was stirred at room temperature overnight, then diluted with CH$_2$Cl$_2$ and washed with water. The combined organic layers were dried over Na$_2$SO$_4$, filtered, and concentrated. Purification via silica gel chromatography using 0-40% EtOAc in hexanes gave benzyl ((S)-1-(2-(2-hydroxyphenyl)-7-methylquinazolin-4-yl)pyrrolidin-3-yl)methylcarbamate as a colorless oil (0.19 g, 68% yield). LC/MS: m/z 469.1 (M+H)$^+$ at 2.58 min (10%-99% CH$_3$CN (0.035% TFA)/H$_2$O (0.05% TFA)).

Example 364

Ethyl ((S)-1-(2-(2-hydroxyphenyl)-7-methylquinazolin-4-yl)pyrrolidin-3-yl)methylcarbamate

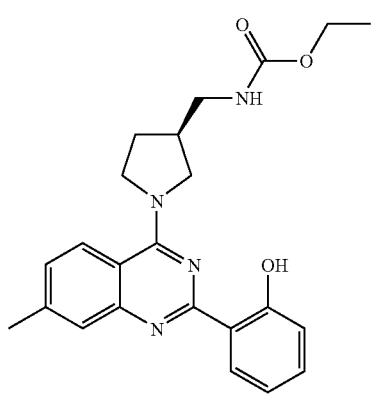

520

Ethyl ((S)-1-(2-(2-hydroxyphenyl)-7-methylquinazolin-4-yl)pyrrolidin-3-yl)methylcarbamate

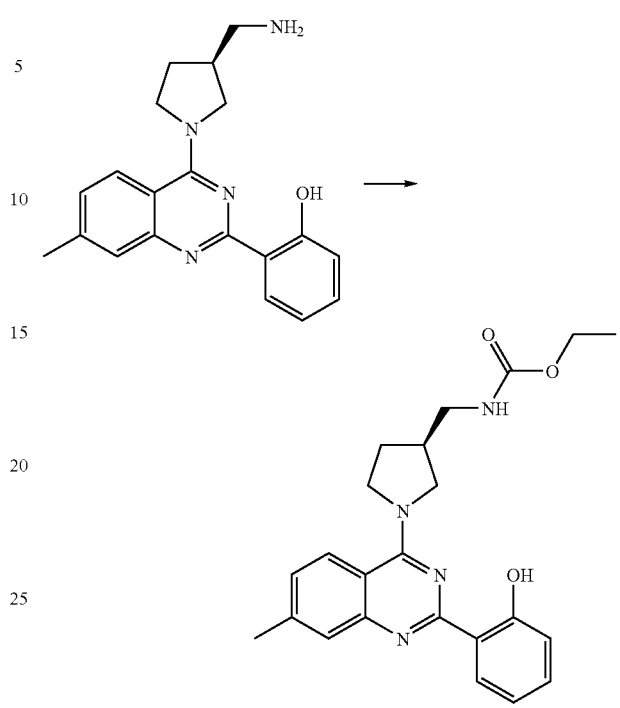

A solution of 2-(4-((S)-3-(aminomethyl)pyrrolidin-1-yl)-7-methylquinazolin-2-yl)phenol (25 mg, 0.075 mmol) in CH$_2$Cl$_2$ (1.0 mL) was cooled in an ice bath. To this mixture was added ethyl chloroformate (7.8 µL, 0.082 mmol), followed by triethylamine (21 µL, 0.15 mmol). After removing the ice bath, the reaction was stirred for 3 h at room temperature. Purification via preparative reverse phase HPLC (10%-99% CH$_3$CN (0.035% TFA)/H$_2$O (0.05% TFA)) gave ethyl ((S)-1-(2-(2-hydroxyphenyl)-7-methylquinazolin-4-yl)pyrrolidin-3-yl)methylcarbamate as the TFA salt. LC/MS: m/z 407.1 (M+H)$^+$ at 2.29 min (10%-99% CH$_3$CN (0.035% TFA)/H$_2$O (0.05% TFA)).

Example 365

Isobutyl ((S)-1-(2-(2-hydroxyphenyl)-7-methylquinazolin-4-yl)pyrrolidin-3-yl)methylcarbamate

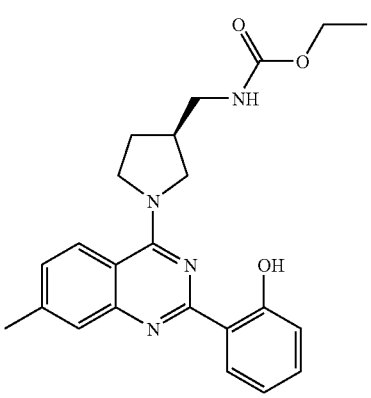

521

Isobutyl ((S)-1-(2-(2-hydroxyphenyl)-7-methylquinazolin-4-yl)pyrrolidin-3-yl)methylcarbamate

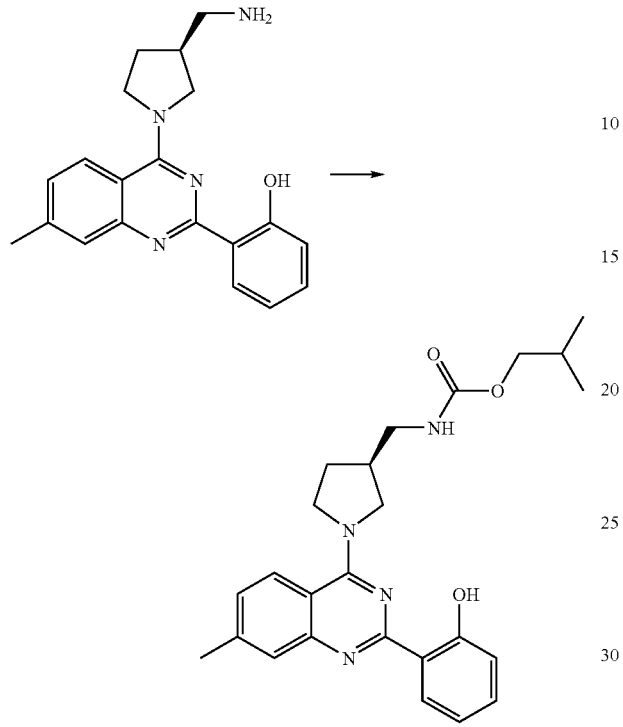

Method A

A solution of 2-(4-((S)-3-(aminomethyl)pyrrolidin-1-yl)-7-methylquinazolin-2-yl)phenol (25 mg, 0.075 mmol) in CH$_2$Cl$_2$ (1.0 mL) was cooled in an ice bath. To this mixture was added isobutyl chloroformate (11 μL, 0.082 mmol), followed by the addition of triethylamine (21 μL, 0.15 mmol). After removing the ice bath, the reaction was stirred for 3 h at room temperature. Purification via preparative reverse phase HPLC (10%-99% CH$_3$CN (0.035% TFA)/H$_2$O (0.05% TFA)) gave isobutyl ((S)-1-(2-(2-hydroxyphenyl)-7-methylquinazolin-4-yl)pyrrolidin-3-yl)methylcarbamate as the TFA salt. LC/MS: m/z 435.3 (M+H)$^+$ at 2.55 min (10%-99% CH$_3$CN (0.035% TFA)/H$_2$O (0.05% TFA)).

Method B

A mixture of 2-(4-((S)-3-(aminomethyl)pyrrolidin-1-yl)-7-methylquinazolin-2-yl)phenol (200 mg, 0.6 mmol), THF (6.0 mL), and CH$_2$Cl$_2$ was stirred under an N$_2$ atmosphere. Triethylamine (0.166 mL, 1.2 mmol) was added, and the reaction was cooled in an ice bath. To this was added 1 M isobutyl chloroformate solution (78 μL in 600 μL THF, 0.6 mmol). After allowing the reaction mixture to warm to room temperature, CH$_2$Cl$_2$ was added, and the organic solution washed twice with water, then dried over Na$_2$SO$_4$, filtered, and concentrated. Purification via silica gel chromatography using 0-20% EtOAc in CH$_2$Cl$_2$/hexanes (1:1) gave isobutyl ((S)-1-(2-(2-hydroxyphenyl)-7-methylquinazolin-4-yl)pyrrolidin-3-yl)methylcarbamate (183 mg, 70%). LC/MS: m/z 435.5 (M+H)$^+$ at 2.63 min (10%-99% CH$_3$CN (0.035% TFA)/H$_2$O (0.05% TFA)). LC/MS: m/z 435 (M+H)$^+$ at 2.63 min (10%-99% CH$_3$CN (0.035% TFA)/H$_2$O (0.05% TFA)). $^1$H NMR (400 MHz, DMSO-d6) δ 8.43 (dd, J=8.2, 1.8 Hz, 1H), 8.22 (d, J=8.7 Hz, 1H), 7.58 (s, 1H), 7.42-7.31 (m, 3H), 6.93-6.89 (m, 2H), 4.17-3.91 (m, 3H), 3.80-3.69 (m, 3H), 3.34-3.30 (m, 1H), 3.21-3.07 (m, 2H), 2.49 (s, 3H), 2.16-2.08 (m, 1H), 1.88-1.74 (m, 2H), 0.88 (d, J=6.7 Hz, 6H) ppm.

522

Isobutyl ((S)-1-(2-(2-hydroxyphenyl)-7-methylquinazolin-4-yl)pyrrolidin-3-yl)methylcarbamate hydrochloride

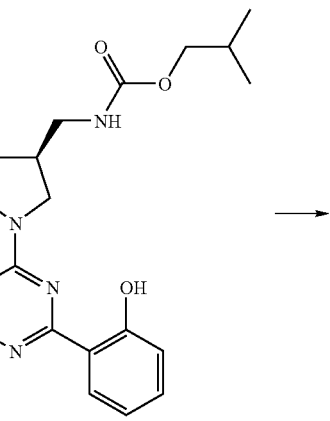

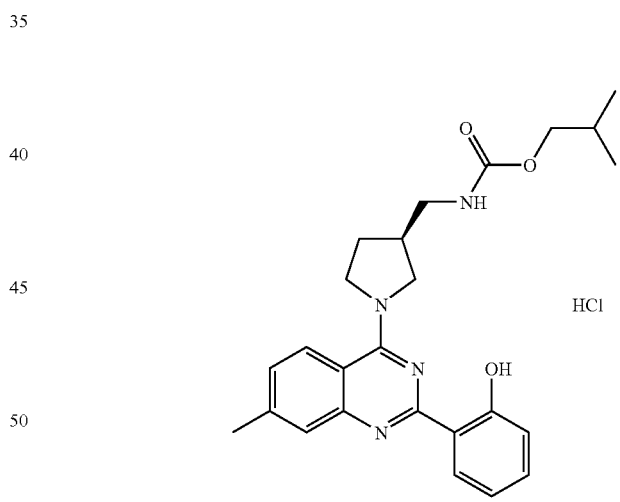

A solution of isobutyl ((S)-1-(2-(2-hydroxyphenyl)-7-methylquinazolin-4-yl)pyrrolidin-3-yl)methylcarbamate (183 mg, 0.42 mmol) in CH$_2$Cl$_2$ (1.5 mL) was stirred under an N$_2$ atmosphere. A 1.0 M HCl solution in ether (0.42 ml, 0.42 mmol) was added dropwise to this solution. After 10 minutes, 5 mL ether was added, and a precipitate formed which was filtered and dried to obtain isobutyl ((S)-1-(2-(2-hydroxyphenyl)-7-methylquinazolin-4-yl)pyrrolidin-3-yl)methylcarbamate hydrochloride (169 mg, 85%). LC/MS: m/z 435.5 (M+H)+at 2.64 min (10%-99% CH$_3$CN (0.035% TFA)/H$_2$O (0.05% TFA)). $^1$H NMR (400 MHz, DMSO-d6) δ 8.31 (d, J=8.7 Hz, 1H), 8.24 (d, J=6.8 Hz, 1H), 7.80 (s, 1H), 7.53-7.45 (m, 2H), 7.41-7.38 (m, 1H), 7.12 (d, J=8.2 Hz, 1H), 7.05-7.02

(m, 1H), 4.36-3.85 (m, 5H), 3.77-3.70 (m, 2H), 3.22-3.06 (m, 2H), 2.54 (s, 3H), 2.18-2.13 (m, 1H), 1.87-1.77 (m, 2H), 0.87 (d, J=6.7 Hz, 6H) ppm.

Example 366

2-Methoxyethyl ((S)-1-(2-(2-hydroxyphenyl)-7-methylquinazolin-4-yl)pyrrolidin-3-yl)methylcarbamate

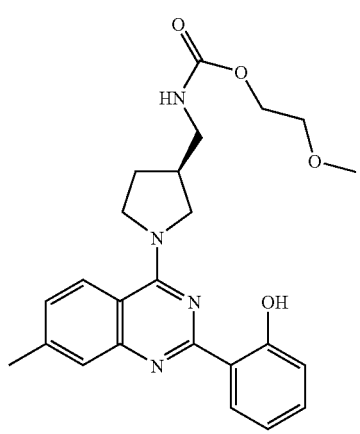

2-Methoxyethyl ((S)-1-(2-(2-hydroxyphenyl)-7-methylquinazolin-4-yl)pyrrolidin-3-yl)methylcarbamate Method A A solution of 2-(4-((S)-3-(aminomethyl)pyrrolidin-1-yl)-7-methylquinazolin-2-yl)phenol (25 mg, 0.075 mmol) in anhydrous $CH_2Cl_2$ was cooled in an ice bath. Then 2-methoxyethyl chloroformate (8.6 μL, 0.075 mmol) was added, followed by the addition of triethylamine (16 μL, 0.11 mmol). After removing the ice bath, the reaction was stirred at room temperature for 4 h. Water and saturated aqueous $NaHCO_3$ solution were added, and the reaction mixture was stirred at room temperature overnight. After separation of the aqueous and organic layers, the organic phase was dried over $Na_2SO_4$, filtered, and concentrated. Purification via preparative reverse phase HPLC (10%-99% $CH_3CN$ (0.035% TFA)/$H_2O$ (0.05% TFA)) gave 2-methoxyethyl ((S)-1-(2-(2-hydroxyphenyl)-7-methylquinazolin-4-yl)pyrrolidin-3-yl)methylcarbamate as the TFA salt. LC/MS (10%-99% $CH_3CN$ (0.035% TFA)/$H_2O$ (0.05% TFA)), m/z: M+1 obs=437.3; $t_R$=2.18 minutes.

Method B

A solution of 2-(4-((S)-3-(aminomethyl)pyrrolidin-1-yl)-7-methylquinazolin-2-yl)phenol (0.12 g, 0.35 mmol) and triethylamine (98 μL, 0.7 mmol) in anhydrous DMF (4.0 mL) was cooled in an ice bath. 2-Methoxyethyl chloroformate (40 mL, 0.35 mmol) was added, and the ice bath was removed. The solution was stirred at room temperature overnight. Purification via silica gel chromatography using 0-10% MeOH in $CH_2Cl_2$ gave 2-methoxyethyl ((S)-1-(2-(2-hydroxyphenyl)-7-methylquinazolin-4-yl)pyrrolidin-3-yl)methylcarbamate (0.12 g, 80%). LC/MS: m/z 437.5 (M+H)$^+$ at 2.20 min (10%-99% $CH_3CN$ (0.035% TFA)/$H_2O$ (0.05% TFA)).

2-Methoxyethyl ((S)-1-(2-(2-hydroxyphenyl)-7-methylquinazolin-4-yl)pyrrolidin-3-yl)methylcarbamate hydrochloride

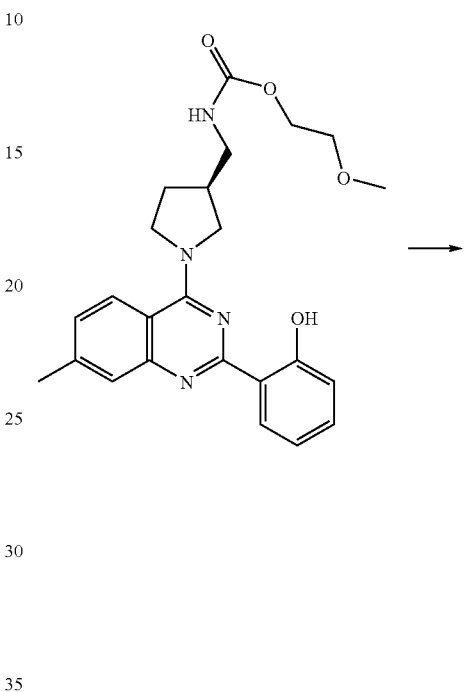

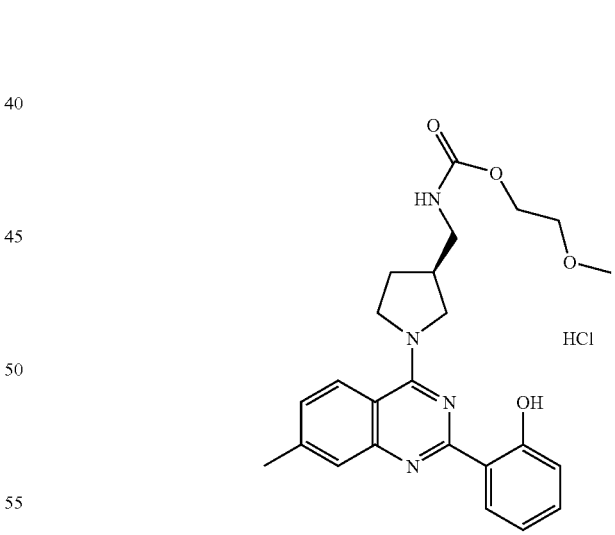

A 1.0 M HCl solution in $Et_2O$ (0.27 mL, 0.27 mmol) was slowly added to a stirring solution of 2-methoxyethyl ((S)-1-(2-(2-hydroxyphenyl)-7-methylquinazolin-4-yl)pyrrolidin-3-yl)methylcarbamate (0.12 g, 0.27 mmol) in $CH_2Cl_2$ (5 mL). The reaction was stirred for 30 minutes at room temperature, then $Et_2O$ was slowly added to the solution until a precipitate formed. After stirring for 1 h, the solid was filtered and washed with $Et_2O$ to obtain 2-methoxyethyl ((S)-1-(2-(2-hydroxyphenyl)-7-methylquinazolin-4-yl)pyrrolidin-3-yl)

methylcarbamate hydrochloride (0.10 g, 77%). LC/MS: m/z 437.1 (M+H)+ at 2.19 min (10%-99% CH3CN (0.035% TFA)/H2O (0.05% TFA)).

Example 367

Propyl ((S)-1-(2-(2-hydroxyphenyl)-7-methylquinazolin-4-yl)pyrrolidin-3-yl)methylcarbamate

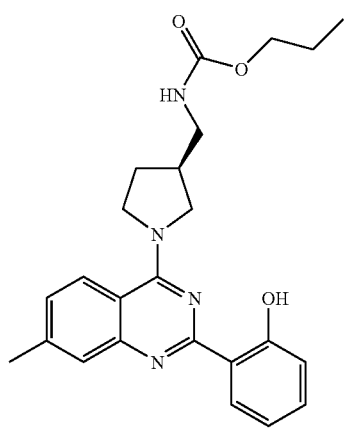

Propyl ((S)-1-(2-(2-hydroxyphenyl)-7-methylquinazolin-4-yl)pyrrolidin-3-yl)methylcarbamate

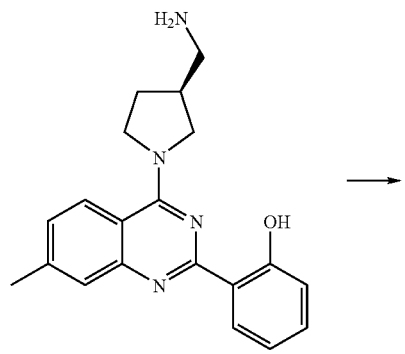

Method A

Propyl chloroformate (12 mg, 0.10 mmol) and triethylamine (30 mg, 42 µL, 0.30 mmol) were added to 2-(4-((S)-3-(aminomethyl)pyrrolidin-1-yl)-7-methylquinazolin-2-yl)phenol (33 mg, 0.10 mmol) in 1 mL anhydrous DMF. The reaction was stirred at room temperature overnight, filtered, and purified by reverse phase HPLC (10%-99% CH3CN (0.035% TFA)/H2O (0:05% TFA)) to give propyl ((S)-1-(2-(2-hydroxyphenyl)-7-methylquinazolin-4-yl)pyrrolidin-3-yl)methylcarbamate as the TFA salt. LC/MS: m/z 421.1 (M+H)+ at 2.43 min (10%-99% CH3CN (0.035% TFA)/H2O (0.05% TFA)).

Method B

A solution of 2-(4-((S)-3-(aminomethyl)pyrrolidin-1-yl)-7-methylquinazolin-2-yl)phenol (301 mg, 0.9 mmol) in CH2Cl2 (10 ml) was stirred under an N2 atmosphere. Triethylamine (0.25 mL, 1.8 mmol) was added, and the solution was cooled to −30° C. A 1 M propyl chloroformate solution (0.1 mL in 0.9 mL CH2Cl2, 0.9 mmol) was added, and the reaction mixture was allowed to warm to room temperature over a period of 30 minutes. After adding CH2Cl2 to the reaction mixture, it was washed 2 times with water, before it was dried over Na2SO4, filtered, and concentrated. Purification via silica gel chromatography using 0-20% EtOAc in CH2Cl2 gave propyl ((S)-1-(2-(2-hydroxyphenyl)-7-methylquinazolin-4-yl)pyrrolidin-3-yl)methylcarbamate (236 mg, 62%). LC/MS: m/z 421 (M+H)+ at 2.54 min (10%-99% CH3CN (0.035% TFA)/H2O (0.05% TFA)). 1H NMR (400 MHz, DMSO-d6) δ 8.43 (dd, J=8.2, 1.8 Hz, 1H), 8.21 (d, J=8.7 Hz, 1H), 7.58 (s, 1H), 7.39-7.31 (m, 3H), 6.93-6.89 (m, 2H), 4.09-3.86 (m, 6H), 3.78-3.73 (m, 1H), 3.21-3.09 (m, 2H), 2.49 (s, 3H), 2.15-2.09 (m, 1H), 1.83-1.74 (m, 1H), 1.62-1.48 (m, 2H), 0.89-0.86 (m, 3H) ppm.

Propyl ((S)-1-(2-(2-hydroxyphenyl)-7-methylquinazolin-4-yl)pyrrolidin-3-yl)methylcarbamate hydrochloride

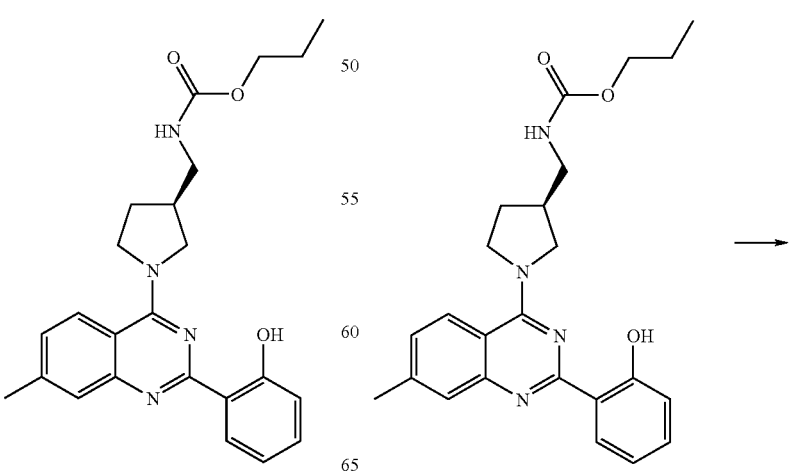

527
-continued

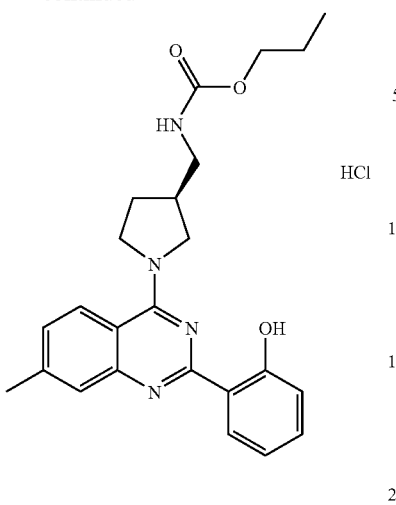

A solution of propyl ((S)-1-(2-(2-hydroxyphenyl)-7-methylquinazolin-4-yl)pyrrolidin-3-yl)methylcarbamate (232 mg, 0.552 mmol) in CH$_2$Cl$_2$ (2 mL) was stirred under an N$_2$ atmosphere. A 2.0 M HCl solution in ether (0.276 mL, 0.552 mmol) was added dropwise to this solution. After 10 minutes, ether (8 mL) was added until a precipitate formed, which was filtered and dried to obtain propyl ((S)-1-(2-(2-hydroxyphenyl)-7-methylquinazolin-4-yl)pyrrolidin-3-yl)methylcarbamate hydrochloride (223 mg, 88%). LC/MS: m/z 421 (M+H)$^+$ at 2.54 min (10%-99% CH$_3$CN (0.035% TFA)/H$_2$O (0.05% TFA)). $^1$H NMR (400 MHz, DMSO-d6) δ 8.31 (d, J=8.7 Hz, 1H), 8.24 (dd, J=7.9, 1.4 Hz, 1H), 7.82 (s, 1H), 7.54-7.49 (m, 2H), 7.41-7.37 (m, 1H), 7.14 (d, J=8.1 Hz, 1H), 7.06-7.02 (m, 1H), 4.29-3.78 (m, 7H), 3.24-3.08 (m, 2H), 2.54 (s, 3H), 2.18-2.12 (m, 1H), 1.84-1.79 (m, 1H), 1.59-1.50 (m, 2H), 0.87 (t, J=7.4 Hz, 3H) ppm.

Example 368

Isopropyl ((S)-1-(2-(2-hydroxyphenyl)-7-methylquinazolin-4-yl)pyrrolidin-3-yl)methylcarbamate

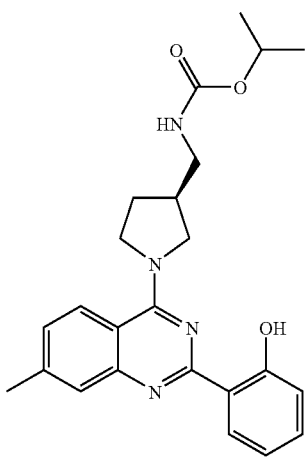

528

Isopropyl ((S)-1-(2-(2-hydroxyphenyl)-7-methylquinazolin-4-yl)pyrrolidin-3-yl)methylcarbamate

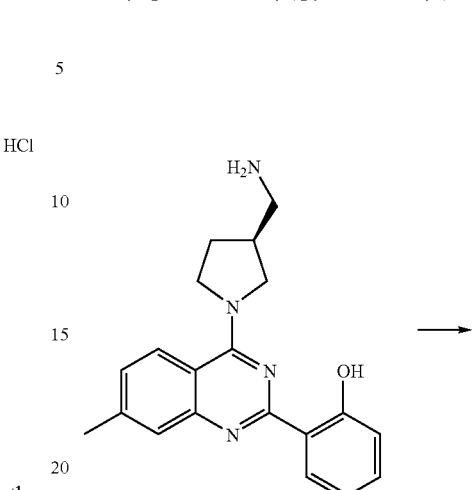

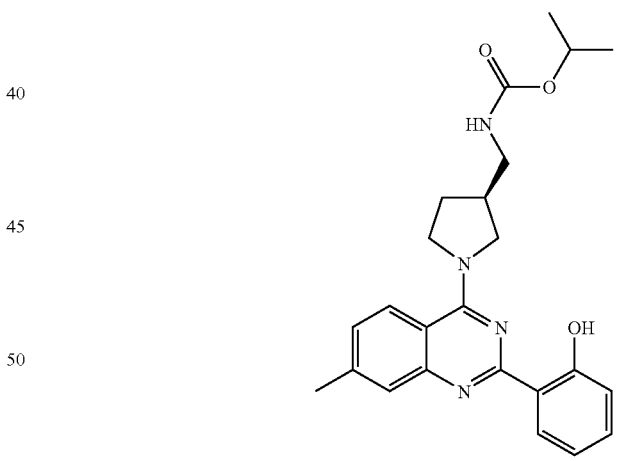

Isopropyl chloroformate (12 mg, 0.10 mmol) and triethylamine (30 mg, 42 μL, 0.30 mmol) were added to a solution of 2-(4-((S)-3-(aminomethyl)pyrrolidin-1-yl)-7-methylquinazolin-2-yl)phenol (33 mg, 0.10 mmol) in 1 mL anhydrous DMF. The reaction was stirred at room temperature overnight, filtered, and purified by reverse phase HPLC (10%-99% CH$_3$CN (0.035% TFA)/H$_2$O (0.05% TFA)) to give isopropyl ((S)-1-(2-(2-hydroxyphenyl)-7-methylquinazolin-4-yl)pyrrolidin-3-yl)methylcarbamate as the TFA salt. LC/MS: m/z 421.1 (M+H)+ at 2.42 min (10%-99% CH$_3$CN (0.035% TFA)/H$_2$O (0.05% TFA)).

Example 369

Neopentyl ((S)-1-(2-(2-hydroxyphenyl)-7-methylquinazolin-4-yl)pyrrolidin-3-yl)methylcarbamate

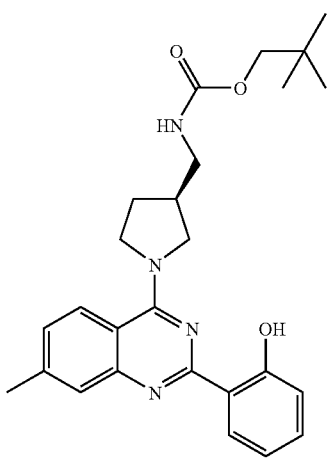

Neopentyl ((S)-1-(2-(2-hydroxyphenyl)-7-methylquinazolin-4-yl)pyrrolidin-3-yl)methylcarbamate

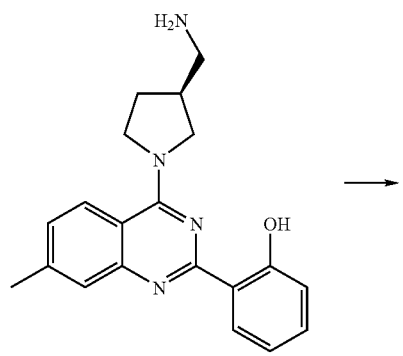

Method A

Neopentyl chloroformate (15 mg, 0.10 mmol) and triethylamine (30 mg, 42 µL, 0.30 mmol) were added to a solution of 2-(4-((S)-3-(aminomethyl)pyrrolidin-1-yl)-7-methylquinazolin-2-yl)phenol (33 mg, 0.10 mmol) in 1 mL anhydrous DMF. The reaction was stirred at room temperature overnight, filtered, and purified by reverse phase HPLC (10%-99% CH$_3$CN (0.035% TFA)/H$_2$O (0.05% TFA)) to give neopentyl ((S)-1-(2-(2-hydroxyphenyl)-7-methylquinazolin-4-yl)pyrrolidin-3-yl)methylcarbamate as the TFA salt. LC/MS: m/z 449.3 (M+H)+ at 2.67 min (10%-99% CH$_3$CN (0.035% TFA)/H$_2$O (0.05% TFA)).

Method B

A mixture of 2-(4-((S)-3-(aminomethyl)pyrrolidin-1-yl)-7-methylquinazolin-2-yl)phenol (200 mg, 0.6 mmol), DMF (6.0 mL), and DMF (1 mL) was stirred under an N$_2$ atmosphere. Triethylamine (0.166 mL, 1.2 mmol) was added, and the reaction was cooled in an ice bath. To this was added 1 M neopentyl chloroformate solution (89 µL in 600 µL THF, 0.6 mmol). After allowing the reaction mixture to warm to room temperature over a period of 30 minutes, CH$_2$Cl$_2$ was added to the reaction mixture, and it was washed once with water before it was dried over Na$_2$SO$_4$, filtered, and concentrated. Purification via silica gel chromatography using 0-20% EtOAc in CH$_2$Cl$_2$/hexanes (1:1) gave neopentyl ((S)-1-(2-(2-hydroxyphenyl)-7-methylquinazolin-4-yl)pyrrolidin-3-yl)methylcarbamate (222 mg, 94%). LC/MS: m/z 449 (M+H)+ at 2.73 min (10%-99% CH$_3$CN (0.035% TFA)/H$_2$O (0.05% TFA)). $^1$H NMR (400 MHz, acetic acid-d4) δ 8.42 (dd, J=8.1, 1.8 Hz, 1H), 8.20 (d, J=8.7 Hz, 1H), 7.57 (s, 1H), 7.40-7.29 (m, 3H), 6.92-6.89 (m, 2H), 4.11-3.92 (m, 3H), 3.78-3.61 (m, 3H), 3.33-3.28 (m, 1H), 3.23-3.10 (m, 2H), 2.49 (s, 3H), 2.16-2.08 (m, 1H), 1.83-1.75 (m, 1H), 0.89 (s, 9H) ppm.

Neopentyl ((S)-1-(2-(2-hydroxyphenyl)-7-methylquinazolin-4-yl)pyrrolidin-3-yl)methylcarbamate hydrochloride

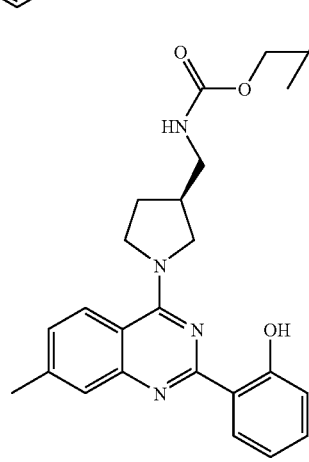 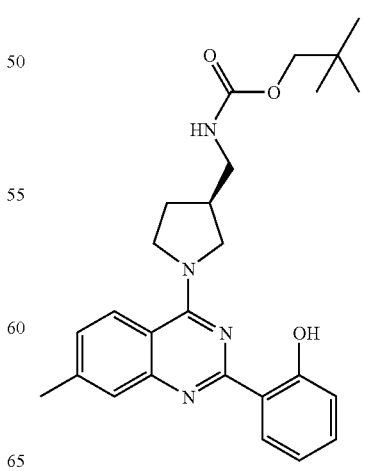

531
-continued

A solution of neopentyl ((S)-1-(2-(2-hydroxyphenyl)-7-methylquinazolin-4-yl)pyrrolidin-3-yl)methylcarbamate (215 mg, 0.48 mmol) in $CH_2Cl_2$ (2 ml) was stirred under an $N_2$ atmosphere. A 1.0 M HCl solution in ether (0.48 ml, 0.48 mmol) was added dropwise to this solution. After 10 minutes, ether (8 ml) was added until a precipitate formed, which was filtered and dried to obtain neopentyl ((S)-1-(2-(2-hydroxyphenyl)-7-methylquinazolin-4-yl)pyrrolidin-3-yl)methylcarbamate hydrochloride (214 mg, 92%). LC/MS: m/z 449 $(M+H)^+$ at 2.75 min (10%-99% $CH_3CN$ (0.035% TFA)/$H_2O$ (0.05% TFA)).

Example 370 tert-Butyl (S)-1-(2-(2-hydroxyphenyl)-7-methylquinazolin-4-yl)pyrrolidin-3-ylcarbamate 532
tert-Butyl (S)-1-(2-(2-hydroxyphenyl)-7-methylquinazolin-4-yl)pyrrolidin-3-ylcarbamate

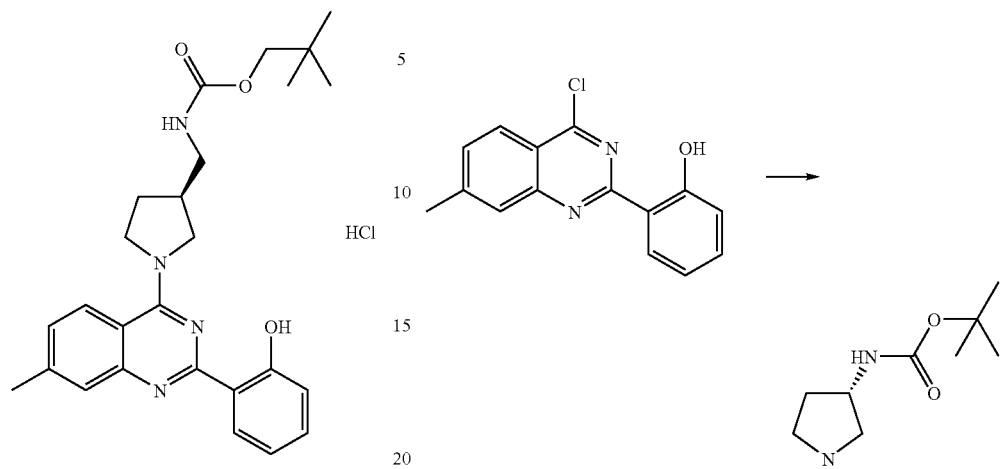

tert-Butyl (S)-pyrrolidin-3-ylcarbamate (245 mg, 1.31 mmol) was dissolved in 1.8 mL of anhydrous $CH_2Cl_2$ and cooled to 0° C. 2-(4-Chloro-7-methylquinazolin-2-yl)phenol (300 mg, 1.1 mmol) dissolved in 1.8 mL of anhydrous $CH_2Cl_2$ was added dropwise to the mixture followed by triethylamine (134 mg, 184 μL, 1.32 mmol). The reaction was allowed to warm to room temperature and was stirred overnight. Purification via silica gel chromatography using 10-100% ethyl acetate/hexanes gave tert-butyl (S)-1-(2-(2-hydroxyphenyl)-7-methylquinazolin-4-yl)pyrrolidin-3-ylcarbamate. LC/MS: m/z 421.0 $(M+H)^+$ at 2.84 min (10%-99% $CH_3CN$ (0.035% TFA)/$H_2O$ (0.05% TFA)).

Example 371

Isopropyl ((S)-1-(2-(2-fluoro-6-hydroxyphenyl)-7-methylquinazolin-4-yl)pyrrolidin-3-yl)methylcarbamate

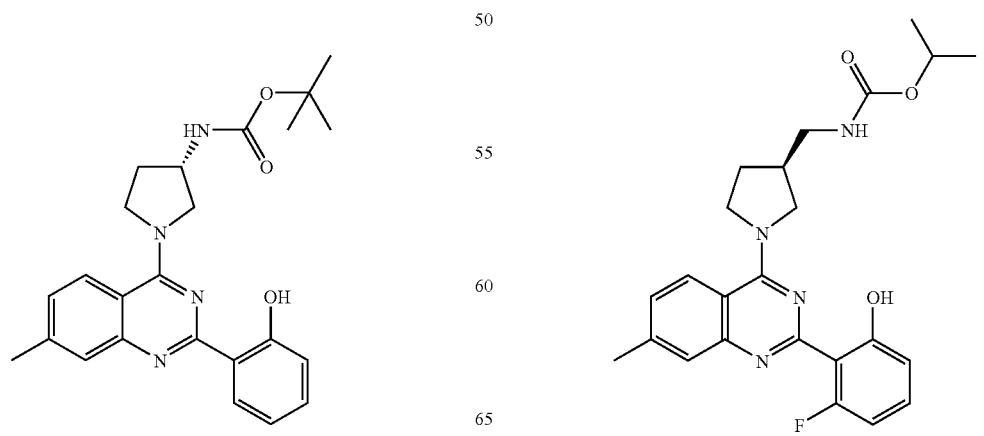

2-(4-((S)-3-(Aminomethyl)pyrrolidin-1-yl)-7-methylquinazolin-2-yl)-3-fluorophenol

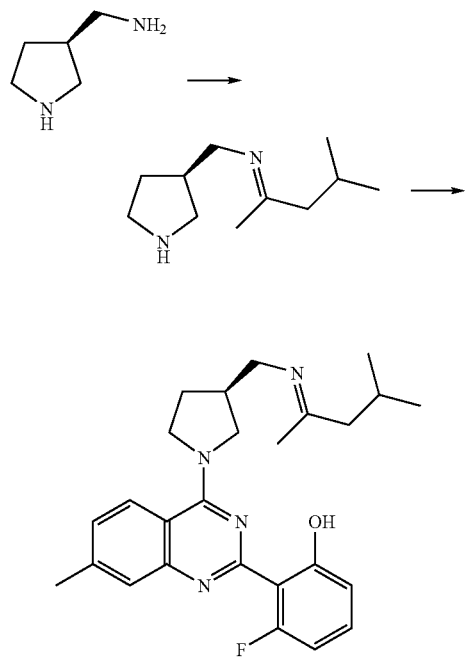

A mixture of ((S)-pyrrolidin-3-yl)methanamine (0.6 g, 6.0 mmol), Na$_2$CO$_3$ (2.2 g, 21 mmol) and methyl isobutyl ketone (12 mL, 6.0 mmol) under an N$_2$ atmosphere was refluxed overnight using a Dean Stark apparatus. After allowing the reaction to cool to room temperature, 2-(4-chloro-7-methylquinazolin-2-yl)-3-fluorophenol (1.73 g, 5.99 mmol) was added, and the mixture was stirred overnight at room temperature under an N$_2$ atmosphere. The reaction was then quenched with water. The aqueous layer was extracted twice with CH$_2$Cl$_2$. The organic extracts were combined, dried over Na$_2$SO$_4$, filtered, and concentrated to obtain a crude material containing 2-(4-((S)-3-((E)-(4-methylpentan-2-ylideneamino)methyl)pyrrolidin-1-yl)-7-methylquinazolin-2-yl)-3-fluorophenol which was then hydrolyzed by heating at 50° C. in 80 mL of a water/isopropanol mixture (1:1) for 6 hours. The reaction was cooled to room temperature, and the aqueous layer was extracted twice with CH$_2$Cl$_2$, dried over Na$_2$SO$_4$, filtered, and concentrated. Purification via silica gel chromatography using 5-20% MeOH and CH$_2$Cl$_2$ afforded 2-(4-((S)-3-(aminomethyl)pyrrolidin-1-yl)-7-methylquinazolin-2-yl)-3-fluorophenol (400 mg, 19% after 3 steps). LC/MS: m/z 353.1 (M+H)$^+$ at 1.22 min (10%-99% CH$_3$CN (0.035% TFA)/H$_2$O (0.05% TFA)).

Isopropyl ((S)-1-(2-(2-fluoro-6-hydroxyphenyl)-7-methylquinazolin-4-yl)pyrrolidin-3-yl)methylcarbamate

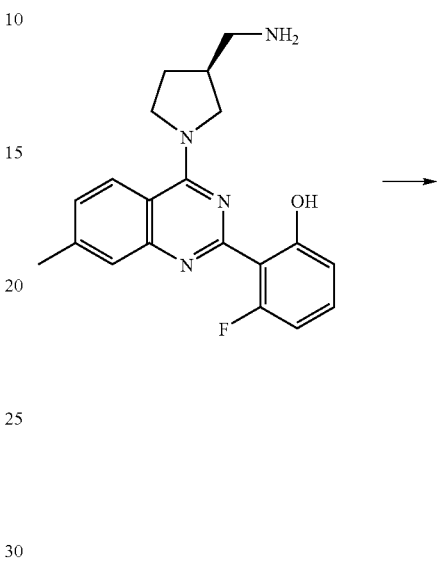

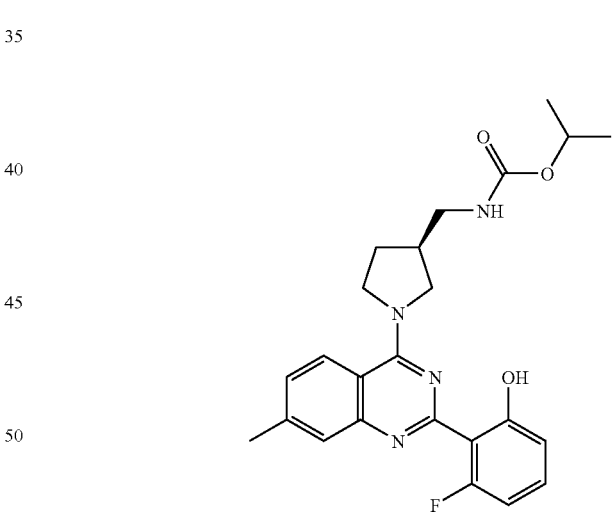

Isopropyl chloroformate (10 mg, 0.09 mmol) was added to a solution of 2-(4-((S)-3-(aminomethyl)pyrrolidin-1-yl)-7-methylquinazolin-2-yl)-3-fluorophenol (0.03 g, 0.09 mmol) and triethylamine (25 mL, 0.18 mmol) in DMF (0.6 mL) at −78° C. (external temperature). The reaction mixture was warmed to room temperature, filtered, and purified via reverse phase HPLC (10%-99% CH$_3$CN (0.035% TFA)/H$_2$O (0.05% TFA)) to afford isopropyl ((S)-1-(2-(2-fluoro-6-hydroxyphenyl)-7-methylquinazolin-4-yl)pyrrolidin-3-yl)methylcarbamate as the TFA salt. LC/MS: m/z 439.5 (M+H)$^+$ at 2.31 min (10%-99% CH$_3$CN (0.035% TFA)/H$_2$O (0.05% TFA)).

Example 372

Isobutyl ((S)-1-(2-(2-fluoro-6-hydroxyphenyl)-7-methylquinazolin-4-yl)pyrrolidin-3-yl)methylcarbamate

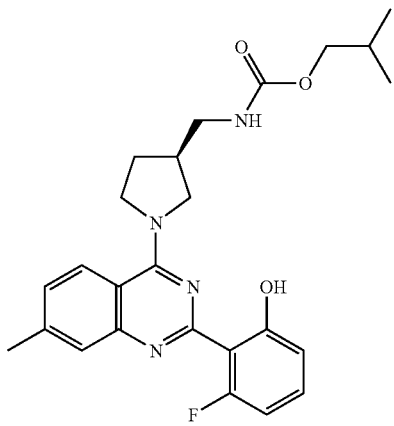

Isobutyl ((S)-1-(2-(2-fluoro-6-hydroxyphenyl)-7-methylquinazolin-4-yl)pyrrolidin-3-yl)methylcarbamate Isobutyl chloroformate (12 mg, 0.09 mmol) was added to a solution of 2-(4-((S)-3-(aminomethyl)pyrrolidin-1-yl)-7-methylquinazolin-2-yl)-3-fluorophenol (0.03 g, 0.09 mmol) and triethylamine (25 mL, 0.18 mmol) in DMF (0.6 mL) at −70° C. (external temperature). The reaction mixture was warmed to room temperature, filtered, and purified via reverse phase HPLC (10%-99% CH$_3$CN (0.035% TFA)/H$_2$O (0.05% TFA)) to afford isobutyl ((S)-1-(2-(2-fluoro-6-hydroxyphenyl)-7-methylquinazolin-4-yl)pyrrolidin-3-yl)methylcarbamate as the TFA salt. LC/MS: m/z 453.5 (M+H)$^+$ at 2.46 min (10%-99% CH$_3$CN (0.035% TFA)/H$_2$O (0.05% TFA)).

Example 373

2-Methoxyethyl ((S)-1-(2-(2-fluoro-6-hydroxyphenyl)-7-methylquinazolin-4-yl)pyrrolidin-3-yl)methylcarbamate

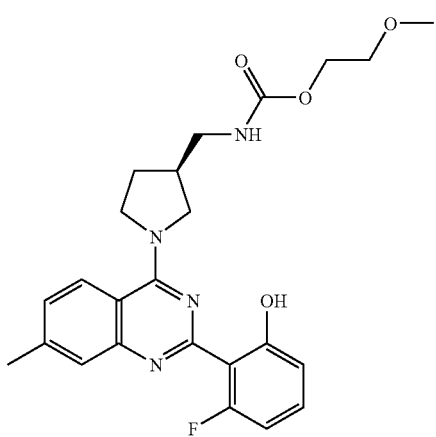

2-Methoxyethyl ((S)-1-(2-(2-fluoro-6-hydroxyphenyl)-7-methylquinazolin-4-yl)pyrrolidin-3-yl)methylcarbamate

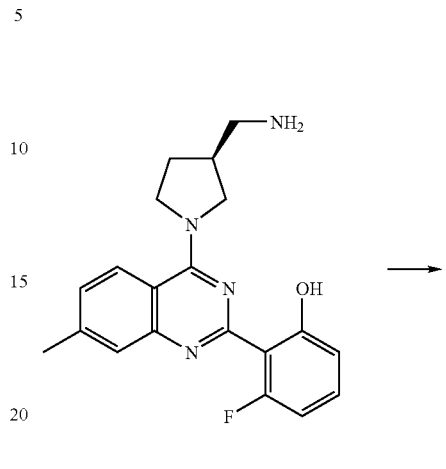

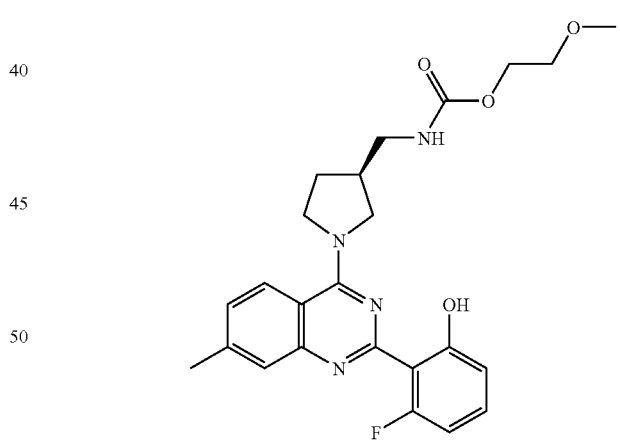

2-Methoxyethyl chloroformate (12 mg, 0.09 mmol) was added to a solution of 2-(4-((S)-3-(aminomethyl)pyrrolidin-1-yl)-7-methylquinazolin-2-yl)-3-fluorophenol (0.03 g, 0.09 mmol) and triethylamine (25 mL, 0.18 mmol) in DMF (0.6 mL) at −78° C. The reaction mixture was warmed to room temperature, filtered, and purified via reverse phase HPLC (10%-99% CH$_3$CN (0.035% TFA)/H$_2$O (0.05% TFA)) to afford 2-methoxyethyl ((S)-1-(2-(2-fluoro-6-hydroxyphenyl)-7-methylquinazolin-4-yl)pyrrolidin-3-yl)methylcarbamate as the TFA salt. LC/MS: m/z 455.5 (M+H)+ at 2.11 min (10%-99% CH$_3$CN (0.035% TFA)/H$_2$O (0.05% TFA)).

Example 374

Propyl ((S)-1-(6-fluoro-2-(2-hydroxyphenyl)quinazolin-4-yl)pyrrolidin-3-yl)methylcarbamate

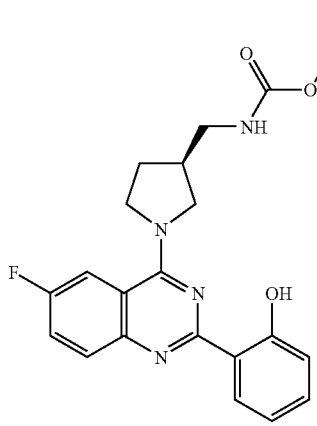

Propyl ((S)-1-(6-fluoro-2-(2-hydroxyphenyl)quinazolin-4-yl)pyrrolidin-3-yl)methylcarbamate

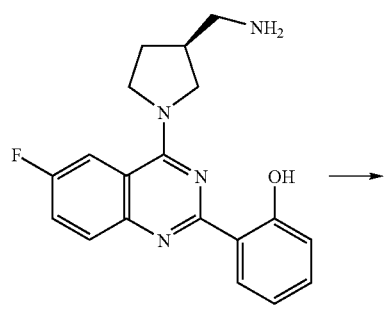

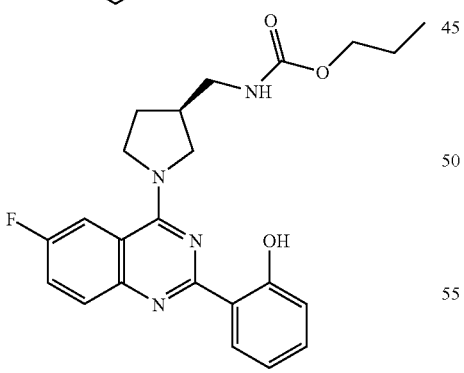

To a solution of 2-(4-((S)-3-(aminomethyl)pyrrolidin-1-yl)-6-fluoroquinazolin-2-yl)phenol (0.03 g, 0.09 mmol) in DMF (1.0 mL) at −60° C. (external temperature) was added triethylamine (25 mL, 0.18 mmol), followed by the addition of propyl chloroformate (11 mg, 0.09 mmol). The reaction was warmed to room temperature, filtered, and purified via reverse phase HPLC (10%-99% CH$_3$CN (0.035% TFA)/H$_2$O (0.05% TFA)) to afford propyl ((S)-1-(6-fluoro-2-(2-hydroxyphenyl)quinazolin-4-yl)pyrrolidin-3-yl)methylcarbamate as the TFA salt. LC/MS: m/z 425.3 (M+H)+ at 2.31 min (10%-99% CH$_3$CN (0.035% TFA)/H$_2$O (0.05% TFA)).

Example 375

Neopentyl ((S)-1-(6-fluoro-2-(2-hydroxyphenyl)quinazolin-4-yl)pyrrolidin-3-yl)methylcarbamate

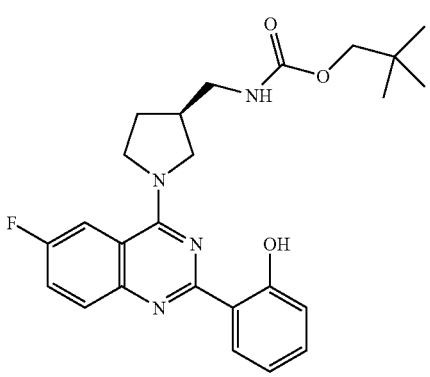

Neopentyl ((S)-1-(6-fluoro-2-(2-hydroxyphenyl)quinazolin-4-yl)pyrrolidin-3-yl)methylcarbamate

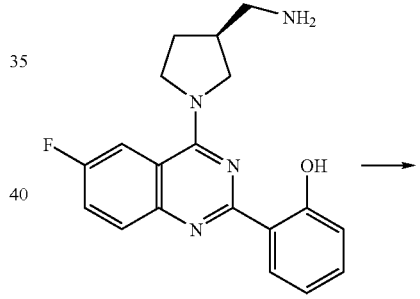

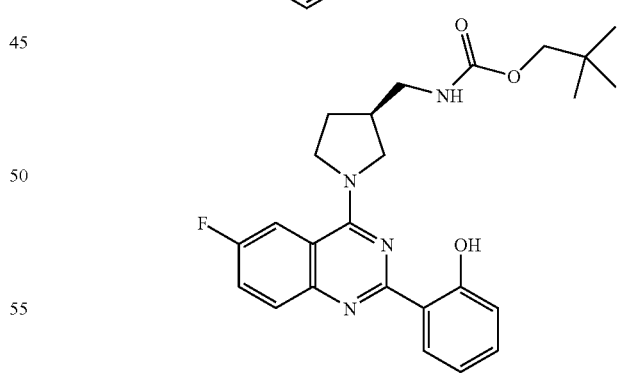

To a solution of 2-(4-((S)-3-(aminomethyl)pyrrolidin-1-yl)-6-fluoroquinazolin-2-yl)phenol (0.03 g, 0.09 mmol) in DMF (1.0 mL) at −60° C. (external temperature) was added triethylamine (25 mL, 0.18 mmol), followed by the addition of neopentyl chloroformate (13 mg, 0.09 mmol). The reaction was warmed to room temperature, filtered, and purified via reverse phase HPLC (10%-99% CH$_3$CN (0.035% TFA)/H$_2$O (0.05% TFA)) to afford neopentyl ((S)-1-(6-fluoro-2-(2-hydroxyphenyl)quinazolin-4-yl)pyrrolidin-3-yl)methylcarbamate as the TFA salt. LC/MS: m/z 453.5 (M+H)+ at 2.88 min (10%-99% CH$_3$CN (0.035% TFA)/H$_2$O (0.05% TFA)).

Example 376

Isobutyl ((S)-1-(6-fluoro-2-(2-hydroxyphenyl)quinazolin-4-yl)pyrrolidin-3-yl)methylcarbamate

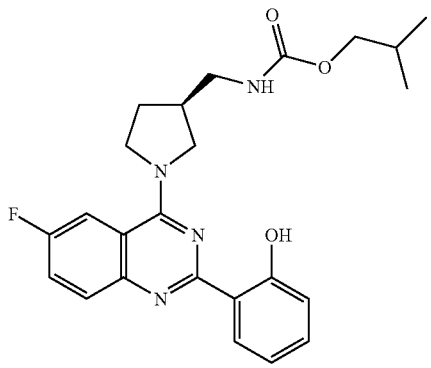

Isobutyl ((S)-1-(6-fluoro-2-(2-hydroxyphenyl)quinazolin-4-yl)pyrrolidin-3-yl)methylcarbamate

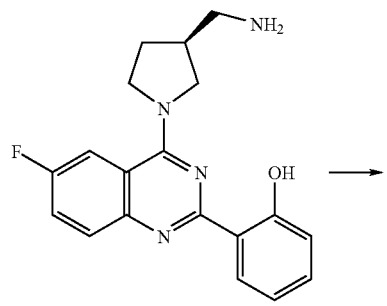

To a solution of 2-(4-((S)-3-(aminomethyl)pyrrolidin-1-yl)-6-fluoroquinazolin-2-yl)phenol (0.03 g, 0.09 mmol) in DMF (1.0 mL) at −60° C. (external temperature) was added triethylamine (25 mL, 0.18 mmol), followed by the addition of isobutyl chloroformate (12 mg, 0.09 mmol). The reaction was warmed to room temperature, and filtered and purification via reverse phase HPLC (10%-99% CH$_3$CN (0.035% TFA)/H$_2$O (0.05% TFA)) gave isobutyl ((S)-1-(6-fluoro-2-

(2-hydroxyphenyl)quinazolin-4-yl)pyrrolidin-3-yl)methylcarbamate as the TFA salt. LC/MS: m/z 439.5 (M+H)+ at 2.76 min (10%-99% CH$_3$CN (0.035% TFA)/H$_2$O (0.05% TFA)).

Example 377

2-Methoxyethyl ((S)-1-(6-fluoro-2-(2-hydroxyphenyl)quinazolin-4-yl)pyrrolidin-3-yl)methylcarbamate

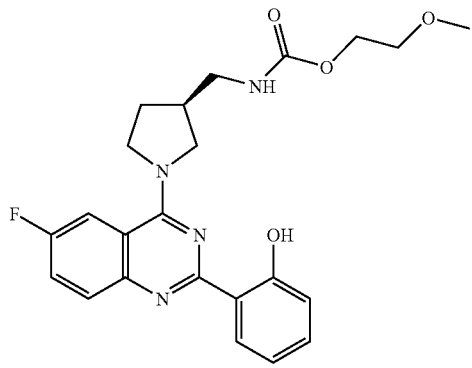

2-Methoxyethyl ((S)-1-(6-fluoro-2-(2-hydroxyphenyl)quinazolin-4-yl)pyrrolidin-3-yl)methylcarbamate

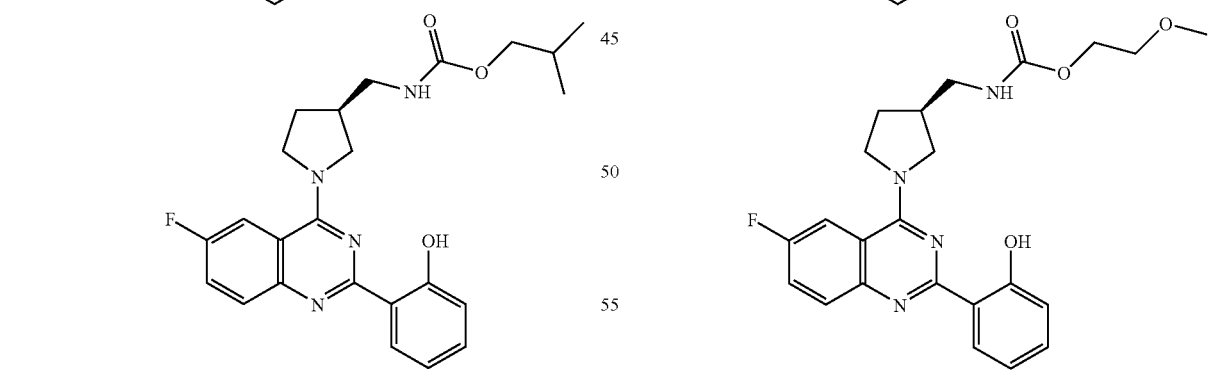

To a solution of 2-(4-((S)-3-(aminomethyl)pyrrolidin-1-yl)-6-fluoroquinazolin-2-yl)phenol (0.03 g, 0.09 mmol) in DMF (1.0 mL) at −60° C. (external temperature) was added triethylamine (25 mL, 0.18 mmol), followed by the addition of 2-methoxyethyl chloroformate (12 mg, 0.09 mmol). The reaction was warmed to room temperature, and filtered and purification via reverse phase HPLC (10%-99% CH$_3$CN (0.035% TFA)/H$_2$O (0.05% TFA)) gave 2-methoxyethyl ((S)-

1-(6-fluoro-2-(2-hydroxyphenyl)quinazolin-4-yl)pyrrolidin-3-yl)methylcarbamate as the TFA salt. LC/MS: m/z 441.5 (M+H)+ at 2.30 min (10%-99% CH₃CN (0.035% TFA)/H₂O (0.05% TFA)).

Example 401

1-(2-(2-Hydroxyphenyl)-7-methylquinazolin-4-yl)-N-((pyridin-4-yl)methyl)azetidine-3-carboxamide

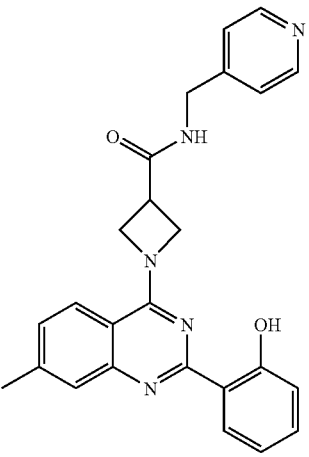

1-(2-(2-Hydroxyphenyl)-7-methylquinazolin-4-yl)azetidine-3-carboxylic acid

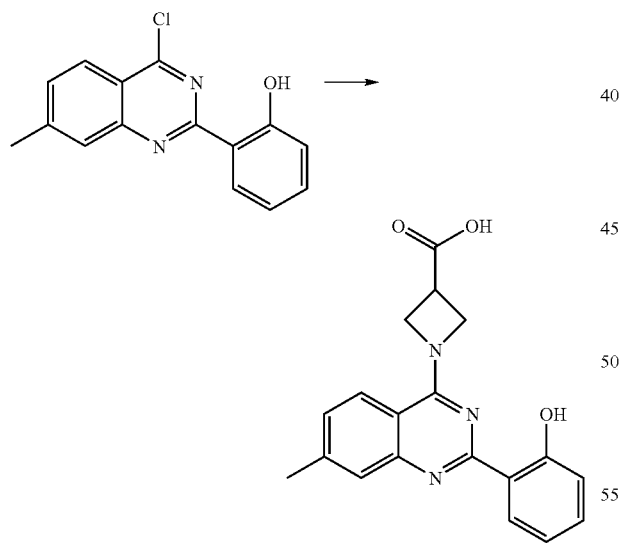

To a solution of 2-(4-chloro-7-methylquinazolin-2-yl)phenol (2.84 g, 10.5 mmol) and azetidine-3-carboxylic acid (1.06 g, 10.5 mmol) in DMF (100 mL) was added triethylamine (3.18 g, 4.39 mL, 31.5 mmol). The reaction was stirred at room temperature overnight then diluted with H₂O (400 mL). The pH of the solution was adjusted to 3-4 by addition of an aqueous 1 M HCl solution. The white precipitate then obtained was filtered, washed with H₂O, and purified by silica gel chromatography using 0-15% MeOH—CH₂Cl₂ giving 1-(2-(2-hydroxyphenyl)-7-methylquinazolin-4-yl)azetidine-3-carboxylic acid. LC/MS: m/z 336.3 (M+H)+ at 1.97 min (10%-99% CH₃CN (0.035% TFA)/H₂O (0.05% TFA)).

1-(2-(2-Hydroxyphenyl)-7-methylquinazolin-4-yl)-N-((pyridin-4-yl)methyl)azetidine-3-carboxamide

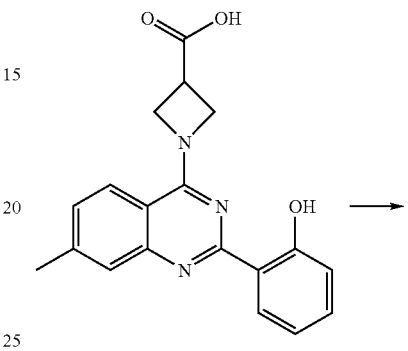

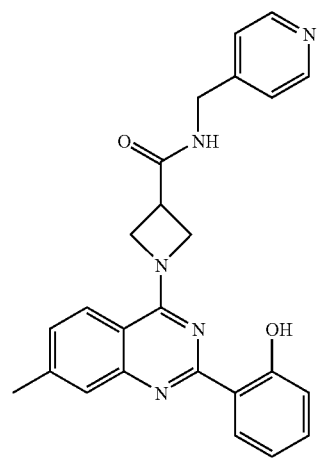

To a solution of 1-(2-(2-hydroxyphenyl)-7-methylquinazolin-4-yl)azetidine-3-carboxylic acid (34 mg, 0.1 mmol) and HATU (57 mg, 0.15 mmol) in DMF (1 mL) was added (pyridin-4-yl)methanamine (32 mg, 30 μL, 0.30 mmol). The reaction was stirred at room temperature overnight, filtered, and purified by reverse phase HPLC (10%-99% CH₃CN (0.035% TFA)/H₂O (0.05% TFA)) giving 1-(2-(2-hydroxyphenyl)-7-methylquinazolin-4-yl)-N-((pyridin-4-yl)methyl)azetidine-3-carboxamide as the TFA salt.

LC/MS: m/z 426.3 (M+H)+ at 1.72 min (10%-99% CH3CN (0.035% TFA)/H2O (0.05% TFA)).

Example 402

1-(2-(2-Hydroxyphenyl)-7-methylquinazolin-4-yl)-N-((pyridin-3-yl)methyl)azetidine-3-carboxamide

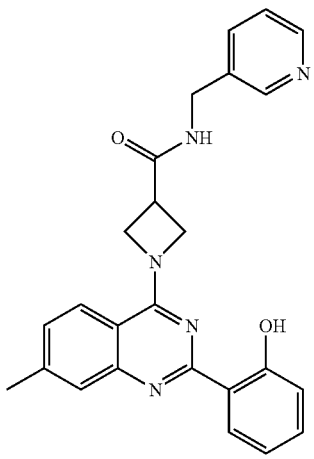

1-(2-(2-Hydroxyphenyl)-7-methylquinazolin-4-yl)azetidine-3-carboxylic acid

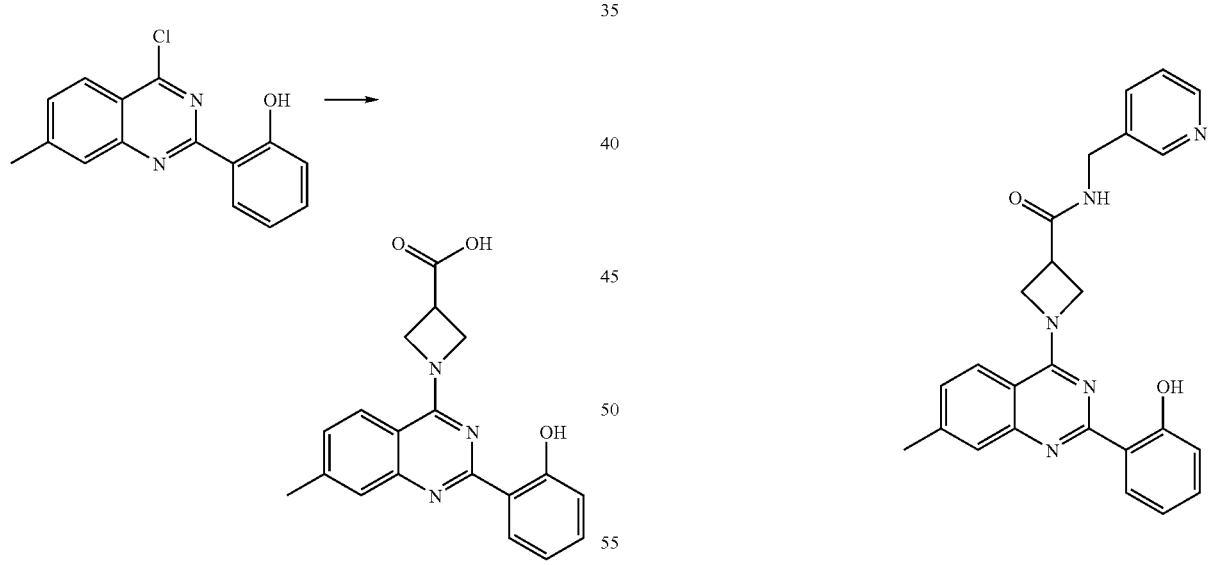

To a solution of 2-(4-chloro-7-methylquinazolin-2-yl)phenol (2.84 g, 10.5 mmol) and azetidine-3-carboxylic acid (1.06 g, 10.5 mmol) in DMF (100 mL) was added triethylamine (3.18 g, 4.39 mL, 31.5 mmol). The reaction was stirred at room temperature overnight then diluted with H2O (400 mL). The pH of the solution was adjusted to 3-4 by addition of an aqueous 1 M HCl solution. The white precipitate then obtained was filtered, washed with H2O, and purified by silica gel chromatography using 0-15% MeOH—CH2Cl2 giving 1-(2-(2-hydroxyphenyl)-7-methylquinazolin-4-yl)azetidine-3-carboxylic acid. LC/MS: m/z 336.3 (M+H)+ at 1.97 min (10%-99% CH3CN (0.035% TFA)/H2O (0.05% TFA)).

1-(2-(2-Hydroxyphenyl)-7-methylquinazolin-4-yl)-N-((pyridin-3-yl)methyl)azetidine-3-carboxamide

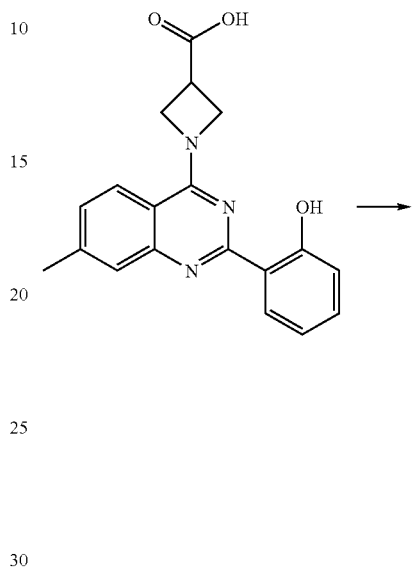

To a solution of 1-(2-(2-hydroxyphenyl)-7-methylquinazolin-4-yl)azetidine-3-carboxylic acid (34 mg, 0.1 mmol) and HATU (57 mg, 0.15 mmol) in DMF (1 mL) was added (pyridin-3-yl)methanamine (32 mg, 30 µL, 0.30 mmol). The reaction was stirred at room temperature overnight, filtered, and purified by reverse phase HPLC (10%-99% CH3CN (0.035% TFA)/H2O (0.05% TFA)) to give 1-(2-(2-hydroxyphenyl)-7-methylquinazolin-4-yl)-N-((pyridin-3-yl)methyl)azetidine-3-carboxamide as the TFA salt. LC/MS: m/z 426.3 (M+H)+ at 1.72 min (10%-99% CH3CN (0.035% TFA)/H2O (0.05% TFA)).

Example 403

N-(3-(Trifluoromethoxy)benzyl)-1-(2-(2-hydroxyphenyl)-7-methylquinazolin-4-yl)azetidine-3-carboxamide

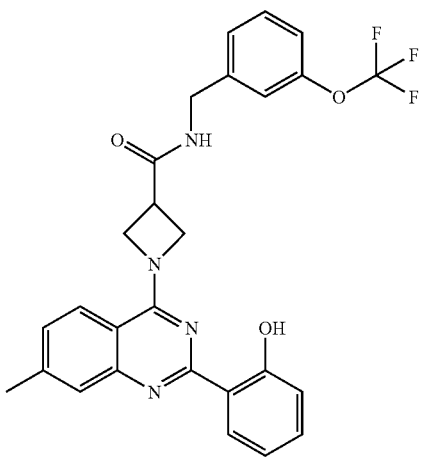

N-(3-(Trifluoromethoxy)benzyl)-1-(2-(2-hydroxyphenyl)-7-methylquinazolin-4-yl)azetidine-3-carboxamide

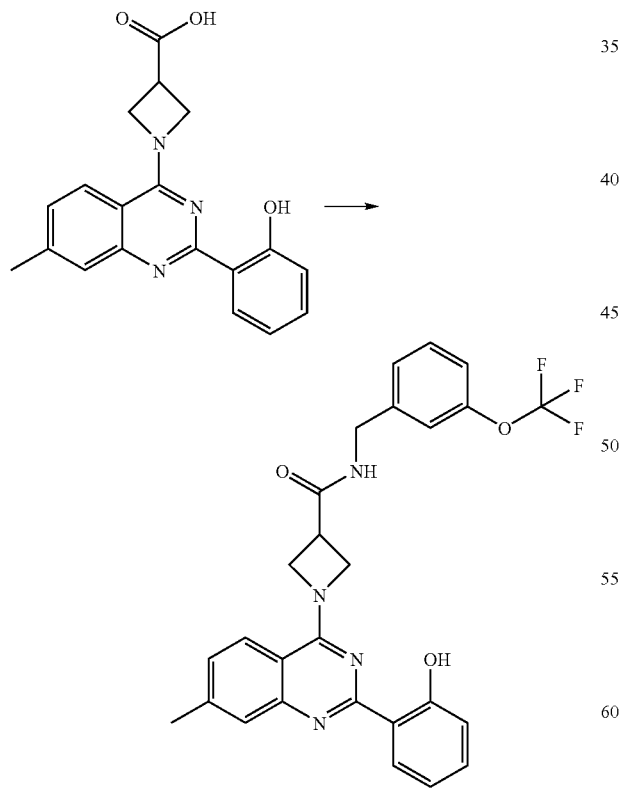

To a solution of 1-(2-(2-hydroxyphenyl)-7-methylquinazolin-4-yl)azetidine-3-carboxylic acid (34 mg, 0.10 mmol) and HATU (57 mg, 0.15 mmol) in DMF (1 mL) was added (3-(trifluoromethoxy)phenyl)methanamine (57 μL, 0.30 mmol). The reaction was stirred at room temperature overnight, filtered, and purified by reverse phase HPLC (10%-99% $CH_3CN$ (0.035% TFA)/$H_2O$ (0.05% TFA)) to give N-(3-(trifluoromethoxy)benzyl)-1-(2-(2-hydroxyphenyl)-7-methylquinazolin-4-yl)azetidine-3-carboxamide as the TFA salt. LC/MS: m/z 509.3 (M+H)+ at 2.73 min (10%-99% $CH_3CN$ (0.035% TFA)/$H_2O$ (0.05% TFA)).

Table 3 below recites analytical data for exemplary compounds of the present invention.

TABLE 3

| Cmpd No. | LC-MS M + 1 | LC-RT min |
|---|---|---|
| 101 | 449.3 | 2.79 |
| 102 | 421 | 2.48 |
| 103 | 499.3 | 2.97 |
| 104 | 464.5 | 2.03 |
| 105 | 447.1 | 2.32 |
| 106 | 465.5 | 2.47 |
| 107 | 442.5 | 1.97 |
| 108 | 407.5 | 2.21 |
| 109 | 393.1 | 2.04 |
| 110 | 461.1 | 2.56 |
| 111 | 453.5 | 3.21 |
| 112 | 461.3 | 2.49 |
| 113 | 421.1 | 2.76 |
| 114 | 474.3 | 1.19 |
| 115 | 421.3 | 2.51 |
| 116 | 442.5 | 1.96 |
| 117 | 439.5 | 2.79 |
| 118 | 393.3 | 2.22 |
| 119 | 465.2 | 2.5 |
| 120 | 435.3 | 2.65 |
| 121 | 393.3 | 2.21 |
| 122 | 435.3 | 2.56 |
| 123 | 465.3 | 2.5 |
| 124 | 407.5 | 2.29 |
| 125 | 453.4 | 2.79 |
| 126 | 471.2 | 2.93 |
| 127 | 445.5 | 3.32 |
| 128 | 451.5 | 2.62 |
| 129 | 407.5 | 2.31 |
| 130 | 469.3 | 2.87 |
| 131 | 469.4 | 2.88 |
| 132 | 456.5 | 2.04 |
| 133 | 454.3 | 1.94 |
| 134 | 421.1 | 2.46 |
| 135 | 467.1 | 2.59 |
| 136 | 453.3 | 3.02 |
| 137 | 407.3 | 2.28 |
| 138 | 453.3 | 2.43 |
| 139 | 439.5 | 2.95 |
| 140 | 485.5 | 2.94 |
| 141 | 459.3 | 2.13 |
| 142 | 446.3 | 3.17 |
| 143 | 439.5 | 2.99 |
| 144 | 435.3 | 2.9 |
| 145 | 437.3 | 2.04 |
| 146 | 455.5 | 2.45 |
| 147 | 453.3 | 2.4 |
| 148 | 439.5 | 2.8 |
| 149 | 465.5 | 2.23 |
| 150 | 449.3 | 2.22 |
| 151 | 435.5 | 2.13 |
| 152 | 456.5 | 2.02 |
| 153 | 453.4 | 2.73 |
| 154 | 436.3 | 1.94 |
| 155 | 477.5 | 2.96 |
| 156 | 474.3 | 1.19 |
| 157 | 485.4 | 3.02 |
| 158 | 403.5 | 2.34 |
| 159 | 421.3 | 2.6 |
| 160 | 467.3 | 3.13 |
| 162 | 467.3 | 2.33 |
| 163 | 453.3 | 2.25 |
| 164 | 451.3 | 2.18 |

TABLE 3-continued

| Cmpd No. | LC-MS M + 1 | LC-RT min |
|---|---|---|
| 165 | 421.3 | 2.4 |
| 166 | 434.53 | 2.61 |
| 167 | 491.3 | 2.46 |
| 168 | 435.3 | 2.91 |
| 169 | 577.4 | 2.5 |
| 170 | 473.1 | 2.63 |
| 171 | 517.5 | 3.49 |
| 172 | 465 | 2.77 |
| 173 | 393.1 | 2.03 |
| 174 | 407.5 | 2.41 |
| 175 | 460.5 | 2.33 |
| 176 | 435.5 | 2.62 |
| 177 | 447.1 | 2.53 |
| 178 | 447.3 | 2.5 |
| 179 | 427.2 | 2.59 |
| 180 | 435.2 | 2.88 |
| 181 | 435.3 | 2.69 |
| 182 | 435.3 | 2.5 |
| 183 | 435.3 | 2.5 |
| 184 | 449.3 | 2.5 |
| 185 | 449.3 | 2.56 |
| 186 | 419.3 | 2.9 |
| 187 | 419.3 | 2.38 |
| 188 | 467.5 | 2.58 |
| 189 | 433.5 | 2.59 |
| 190 | 477.2 | 2.83 |
| 191 | 435.5 | 2.81 |
| 192 | 393.3 | 2.7 |
| 193 | 435.5 | 2.54 |
| 194 | 553.1 | 2.42 |
| 195 | 421.3 | 3.43 |
| 196 | 405.5 | 2.68 |
| 197 | 435.5 | 3.2 |
| 201 | 454.5 | 1.87 |
| 203 | 449.3 | 2.34 |
| 204 | 449.3 | 2.33 |
| 205 | 433.3 | 2.33 |
| 206 | 433.5 | 2.34 |
| 207 | 449.5 | 2.34 |
| 208 | 449.5 | 2.33 |
| 209 | 447.5 | 2.27 |
| 210 | 463.5 | 2.34 |
| 211 | 463.5 | 2.34 |
| 212 | 417 | 2.3 |
| 213 | 453.5 | 1.98 |
| 214 | 463.5 | 2.32 |
| 215 | 463.5 | 2.36 |
| 216 | 463.5 | 2.35 |
| 217 | 463.5 | 2.35 |
| 218 | 447.5 | 2.02 |
| 219 | 477.4 | 2.84 |
| 220 | 447.5 | 2.19 |
| 221 | 461.5 | 2.22 |
| 222 | 531.3 | 3.08 |
| 223 | 468.3 | 1.86 |
| 224 | 437.1 | 2.54 |
| 225 | 468.6 | 2.19 |
| 226 | 417.5 | 2.3 |
| 227 | 470.5 | 1.98 |
| 228 | 470.5 | 1.98 |
| 229 | 513.3 | 2.82 |
| 230 | 447.3 | 2.21 |
| 231 | 481.1 | 2.17 |
| 232 | 463.3 | 2.58 |
| 233 | 421.2 | 2.17 |
| 234 | 449.2 | 2.42 |
| 235 | 407.5 | 2.04 |
| 236 | 407.3 | 2.08 |
| 237 | 407.5 | 2.09 |
| 238 | 435.3 | 2.4 |
| 239 | 461.1 | 2.4 |
| 240 | 435.5 | 2.29 |
| 241 | 421.1 | 2.24 |
| 242 | 421.3 | 2.18 |
| 243 | 421.3 | 2.18 |
| 244 | 421.3 | 2.18 |
| 245 | 449.3 | 2.45 |
| 246 | 475.1 | 2.46 |
| 247 | 435.3 | 2.31 |
| 248 | 435.3 | 2.24 |
| 249 | 481.3 | 2.42 |
| 250 | 449.5 | 2.77 |
| 251 | 421 | 2.48 |
| 252 | 449.3 | 2.8 |
| 253 | 449.5 | 2.78 |
| 254 | 421.1 | 2.5 |
| 255 | 435.5 | 2.61 |
| 256 | 435.5 | 2.61 |
| 257 | 451.1 | 2.34 |
| 258 | 441.5 | 2.6 |
| 259 | 435.2 | 3.03 |
| 260 | 467.1 | 2.56 |
| 261 | 469.1 | 2.2 |
| 262 | 439.3 | 2.31 |
| 264 | 435.1 | 2.6 |
| 265 | 449.3 | 2.72 |
| 266 | 449.2 | 2.55 |
| 267 | 449.3 | 2.58 |
| 268 | 449.1 | 2.54 |
| 269 | 449.5 | 2.57 |
| 270 | 435.2 | 2.88 |
| 271 | 447.2 | 2.46 |
| 272 | 449.2 | 2.57 |
| 273 | 449.2 | 2.57 |
| 274 | 463.4 | 2.42 |
| 275 | 463.4 | 2.43 |
| 276 | 433.2 | 2.33 |
| 277 | 433.2 | 2.32 |
| 278 | 449.2 | 2.85 |
| 279 | 435.4 | 2.61 |
| 280 | 491 | 2.73 |
| 281 | 505.2 | 2.71 |
| 282 | 435.5 | 2.8 |
| 283 | 433.2 | 2.33 |
| 301 | 435 | 2.41 |
| 302 | 419 | 2.35 |
| 303 | 419 | 2.34 |
| 304 | 435 | 2.39 |
| 305 | 449.3 | 2.18 |
| 306 | 449.3 | 2.16 |
| 307 | 449.3 | 2.18 |
| 308 | 433.5 | 2.11 |
| 309 | 455.2 | 2.81 |
| 310 | 433.5 | 2.13 |
| 311 | 403.7 | 2.17 |
| 312 | 389.2 | 2.38 |
| 313 | 441 | 2.78 |
| 314 | 463.4 | 2.66 |
| 315 | 432.5 | 2.24 |
| 316 | 433.5 | 2.05 |
| 317 | 447.3 | 2.07 |
| 318 | 454.3 | 1.79 |
| 319 | 456.5 | 1.85 |
| 320 | 456.5 | 1.84 |
| 321 | 499.3 | 2.57 |
| 322 | 454.4 | 2.08 |
| 323 | 445.4 | 2.85 |
| 324 | 460.4 | 2.1 |
| 325 | 509.5 | 2.71 |
| 326 | 455.3 | 2.43 |
| 327 | 450.3 | 2.39 |
| 328 | 426.3 | 1.91 |
| 329 | 393.3 | 2.23 |
| 330 | 465.4 | 2.88 |
| 331 | 477.3 | 2.81 |
| 332 | 511.5 | 3.07 |
| 333 | 443.5 | 2.83 |
| 334 | 511.5 | 3.1 |
| 335 | 439.5 | 2.25 |
| 336 | 493.5 | 3.03 |
| 337 | 439.5 | 2.25 |
| 338 | 451.5 | 2.15 |
| 339 | 467.3 | 2.5 |
| 340 | 445.4 | 2.95 |

TABLE 3-continued

| Cmpd No. | LC-MS M + 1 | LC-RT min |
|---|---|---|
| 341 | 443.4 | 2.73 |
| 342 | 468.4 | 2.39 |
| 343 | 493.4 | 2.76 |
| 344 | 443.3 | 2.69 |
| 345 | 453.3 | 2.05 |
| 346 | 407.5 | 2.2 |
| 347 | 430.5 | 1.95 |
| 348 | 430.5 | 2.43 |
| 349 | 430.5 | 1.98 |
| 350 | 444.5 | 1.85 |
| 351 | 444.5 | 2.24 |
| 352 | 444.5 | 1.89 |
| 353 | 426.1 | 1.93 |
| 354 | 426.1 | 2.33 |
| 355 | 453.3 | 2.29 |
| 356 | 453.3 | 2.29 |
| 357 | 407.3 | 2.26 |
| 358 | 477.3 | 2.8 |
| 359 | 491.3 | 2.24 |
| 360 | 473.1 | 2.32 |
| 361 | 449.3 | 2.4 |
| 362 | 469.1 | 2.58 |
| 363 | 469.1 | 2.58 |
| 364 | 407.7 | 2.3 |
| 365 | 435.3 | 2.57 |
| 366 | 437.3 | 2.18 |
| 367 | 421.1 | 2.44 |
| 368 | 421.1 | 2.43 |
| 369 | 449.3 | 2.67 |
| 370 | 421 | 2.84 |
| 371 | 439.5 | 2.31 |
| 372 | 453.5 | 2.46 |
| 373 | 455.5 | 2.11 |
| 374 | 425.3 | 2.31 |
| 375 | 453.5 | 2.88 |
| 376 | 439.5 | 2.76 |
| 377 | 441.5 | 2.3 |
| 378 | 491.2 | 2.58 |
| 379 | 441.2 | 2.72 |
| 380 | 419.5 | 2.5 |
| 401 | 426.3 | 1.72 |
| 402 | 426.3 | 1.72 |
| 403 | 509.3 | 2.73 |
| 404 | 393.2 | 1.95 |
| 405 | 421.2 | 2.29 |
| 406 | 421.2 | 2.2 |
| 407 | 435.4 | 2.23 |
| 408 | 435.4 | 2.16 |
| 409 | 421.2 | 2.15 |
| 410 | 421.1 | 2.4 |
| 411 | 435.2 | 2.24 |
| 412 | 405.2 | 2.09 |
| 413 | 435.4 | 2.16 |
| 414 | 435.2 | 2.17 |
| 415 | 449.2 | 2.25 |
| 416 | 435.3 | 2.25 |
| 417 | 419.4 | 2.06 |
| 418 | 421.2 | 2.57 |
| 419 | 423.2 | 2.15 |
| 420 | 407.2 | 2.42 |

Methods:

(A) Micromass MUX LCT 4 channel LC/MS, Waters 60F pump, Gilson 215 4 probe autosampler, Gilson 849 injection module, 1.5 mL/min/column flow rate, 10-99% CH$_3$CN (0.035% TFA)/H$_2$O (0.05% TFA) gradient, Phenomenex Luna 5u C18 columns (50×4.60 mm), Waters MUX UV-2488 UV detector, Cedex 75 ELSD detectors.

(B) PESciex API-150-EX LC/MS, Shimadzu LC-8A pumps, Gilson 215 autosampler, Gilson 819 injection module, 3.0 m/min flow rate, 10-99% CH$_3$CN (0.035% TFA)/H$_2$O (0.05% TFA) gradient, Phenomenex Luna 5u C18 column (50×4.60 mm), Shimadzu SPD-10A UV/Vis detector, Cedex 75 ELSD detector.

(C) PESciex API-150-EX LC/MS, Shimadzu LC-8A pumps, Gilson 215 autosampler, Gilson 819 injection module, 3.0 mL/min flow rate, 40-99% CH$_3$CN (0.035% TFA)/H$_2$O (0.05% TFA) gradient, Phenomenex Luna 5u C18 column (50×4.60 mm), Shimadzu SPD-10A UV/Vis detector, Cedex 75 ELSD detector.

Assays for Detecting and Measuring NaV Inhibition Properties of Compounds

A) Optical Methods for Assaying NaV Inhibition Properties of Compounds:

Compounds of the invention are useful as antagonists of voltage-gated sodium ion channels. Antagonist properties of test compounds were assessed as follows. Cells expressing the NaV of interest were placed into microtiter plates. After an incubation period, the cells were stained with fluorescent dyes sensitive to the transmembrane potential. The test compounds were added to the microtiter plate. The cells were stimulated with either a chemical or electrical means to evoke a NaV dependent membrane potential change from unblocked channels, which was detected and measured with trans-membrane potential-sensitive dyes. Antagonists were detected as a decreased membrane potential response to the stimulus. The optical membrane potential assay utilized voltage-sensitive FRET sensors described by Gonzalez and Tsien (See, Gonzalez, J. E. and R. Y. Tsien (1995) "Voltage sensing by fluorescence resonance energy transfer in single cells" *Biophys J* 69(4): 1272-80, and Gonzalez, J. E. and R. Y. Tsien (1997) "Improved indicators of cell membrane potential that use fluorescence resonance energy transfer" *Chem Biol* 4(4): 269-77) in combination with instrumentation for measuring fluorescence changes such as the Voltage/Ion Probe Reader (VIPR®) (See, Gonzalez, J. E., K. Oades, et al. (1999) "Cell-based assays and instrumentation for screening ion-channel targets" *Drug Discov Today* 4(9): 431-439).

B) VIPR® Optical Membrane Potential Assay Method with Chemical Stimulation

Cell Handling and Dye Loading 24 hours before the assay on VIPR, CHO cells endogenously expressing a NaV1.2 type voltage-gated NaV are seeded in 96-well poly-lysine coated plates at 60,000 cells per well. Other subtypes are performed in an analogous mode in a cell line expressing the NaV of interest.

1) On the day of the assay, medium is aspirated and cells are washed twice with 225 µL of Bath Solution #2 (BS#2).
2) A 15 uM CC2-DMPE solution is prepared by mixing 5 mM coumarin stock solution with 10% Pluronic 127 1:1 and then dissolving the mix in the appropriate volume of BS#2.
3) After bath solution is removed from the 96-well plates, the cells are loaded with 80 µL of the CC2-DMPE solution. Plates are incubated in the dark for 30 minutes at room temperature.
4) While the cells are being stained with coumarin, a 15 µL oxonol solution in BS#2 is prepared. In addition to DiSBAC$_2$(3), this solution should contain 0.75 mM ABSCl and 30 µL veratridine (prepared from 10 mM EtOH stock, Sigma #V-5754).
5) After 30 minutes, CC2-DMPE is removed and the cells are washed twice with 225 µL of BS#2. As before, the residual volume should be 40 µL.
6) Upon removing the bath, the cells are loaded with 80 µL of the DiSBAC$_2$(3) solution, after which test compound, dissolved in DMSO, is added to achieve the desired test concentration to each well from the drug addition plate and mixed thoroughly. The volume in the well should be roughly 121 µL. The cells are then incubated for 20-30 minutes.

7) Once the incubation is complete, the cells are ready to be assayed on VIPR® with a sodium add back protocol. 120 µL of Bath solution #1 is added to stimulate the NaV dependent depolarization. 200 µL tetracaine was used as an antagonist positive control for block of the NaV channel.

Analysis of VIPR® Data:

Data are analyzed and reported as normalized ratios of background-subtracted emission intensities measured in the 460 nm and 580 nm channels. Background intensities are then subtracted from each assay channel. Background intensities are obtained by measuring the emission intensities during the same time periods from identically treated assay wells in which there are no cells. The response as a function of time is then reported as the ratios obtained using the following formula:

$$R(t) = \frac{(intensity_{460nm} - background_{460nm})}{(intensity_{580nm} - background_{580nm})}$$

The data is further reduced by calculating the initial ($R_i$) and final ($R_f$) ratios. These are the average ratio values during part or all of the pre-stimulation period, and during sample points during the stimulation period. The response to the stimulus $R=R_f/R_i$ is then calculated. For the Na$^+$ addback analysis time windows, baseline is 2-7 sec and final response is sampled at 15-24 sec.

Control responses are obtained by performing assays in the presence of a compound with the desired properties (positive control), such as tetracaine, and in the absence of pharmacological agents (negative control). Responses to the negative (N) and positive (P) controls are calculated as above. The compound antagonist activity A is defined as:

$$A = \frac{R - P}{N - P} * 100.$$

where R is the ratio response of the test compound

Solutions [mM]

Bath Solution #1: NaCl 160, KCl 4.5, CaCl$_2$ 2, MgCl$_2$ 1, HEPES 10, pH 7.4 with NaOH Bath Solution #2 TMA-Cl 160, CaCl$_2$ 0.1, MgCl$_2$ 1, HEPES 10, pH 7.4 with KOH (final K Concentration ~5 mM)

CC2-DMPE: prepared as a 5 mM stock solution in DMSO and stored at −20° C.

DiSBAC$_2$(3): prepared as a 12 mM stock in DMSO and stored at −20° C.

ABSCl: prepared as a 200 mM stock in distilled H$_2$O and stored at room temperature Cell Culture CHO cells are grown in DMEM (Dulbecco's Modified Eagle Medium; GibcoBRL #10569-010) supplemented with 10% FBS (Fetal Bovine Serum, qualified; GibcoBRL #16140-071) and 1% Pen-Strep (Penicillin-Streptomycin; GibcoBRL #15140-122). Cells are grown in vented cap flasks, in 90% humidity and 10% CO$_2$, to 100% confluence. They are usually split by trypsinization 1:10 or 1:20, depending on scheduling needs, and grown for 2-3 days before the next split.

C) VIPR® Optical Membrane Potential Assay Method with Electrical Stimulation

The following is an example of how NaV1.3 inhibition activity is measured using the optical membrane potential method#2. Other subtypes are performed in an analogous mode in a cell line expressing the NaV of interest.

HEK293 cells stably expressing NaV1.3 are plated into 96-well microtiter plates. After an appropriate incubation period, the cells are stained with the voltage sensitive dyes CC2-DMPE/DiSBAC2(3) as follows.

Reagents:
100 mg/mL Pluronic F-127 (Sigma #P2443), in dry DMSO
10 mM DiSBAC$_2$(3) (Aurora #00-100-010) in dry DMSO
10 mM CC2-DMPE (Aurora #00-100-008) in dry DMSO
200 mM ABSCl in H$_2$O
Hank's Balanced Salt Solution (Hyclone #SH30268.02) supplemented with 10 mM HEPES (Gibco #15630-080)

Loading Protocol:

2×CC2-DMPE=20 µM CC2-DMPE: 10 mM CC2-DMPE is vortexed with an equivalent volume of 10% pluronic, followed by vortexing in required amount of HBSS containing 10 mM HEPES. Each cell plate will require 5 mL of 2×CC2-DMPE. 50 µL of 2× CC2-DMPE is to wells containing washed cells, resulting in a 10 µM final staining concentration. The cells are stained for 30 minutes in the dark at RT.

2×DISBAC$_2$(3) with ABSCl=6 µM DISBAC$_2$(3) and 1 mM ABSCl: The required amount of 10 mM DISBAC$_2$(3) is added to a 50 ml conical tube and mixed with 1 µL 10% pluronic for each mL of solution to be made and vortexed together. Then HBSS/HEPES is added to make up 2× solution. Finally, the ABSCl is added.

The 2×DiSBAC$_2$(3) solution can be used to solvate compound plates. Note that compound plates are made at 2× drug concentration. Wash stained plate again, leaving residual volume of 50 µL. Add 50 uL/well of the 2×DiSBAC$_2$(3) w/AB-SCl. Stain for 30 minutes in the dark at RT.

The electrical stimulation instrument and methods of use are described in ION Channel Assay Methods PCT/US01/21652, herein incorporated by reference. The instrument comprises a microtiter plate handler, an optical system for exciting the coumarin dye while simultaneously recording the coumarin and oxonol emissions, a waveform generator, a current- or voltage-controlled amplifier, and a device for inserting electrodes in well. Under integrated computer control, this instrument passes user-programmed electrical stimulus protocols to cells within the wells of the microtiter plate.

Reagents
Assay buffer #1
140 mM NaCl, 4.5 mM KCl, 2 mM CaCl$_2$, 1 mM MgCl$_2$, 10 mM HEPES, 10 mM glucose, pH 7.40, 330 mOsm
Pluronic stock (1000×): 100 mg/mL pluronic 127 in dry DMSO
Oxonol stock (3333×): 10 mM DiSBAC$_2$(3) in dry DMSO
Coumarin stock (1000×): 10 mM CC2-DMPE in dry DMSO
ABSCl stock (400×): 200 mM ABSCl in water Assay Protocol
1. Insert or use electrodes into each well to be assayed.
2. Use the current-controlled amplifier to deliver stimulation wave pulses for 3 s. Two seconds of pre-stimulus recording are performed to obtain the un-stimulated intensities. Five seconds of post-stimulation recording are performed to examine the relaxation to the resting state.

Data Analysis

Data are analyzed and reported as normalized ratios of background-subtracted emission intensities measured in the 460 nm and 580 nm channels. Background intensities are then subtracted from each assay channel. Background intensities are obtained by measuring the emission intensities during the same time periods from identically treated assay wells in which there are no cells. The response as a function of time is then reported as the ratios obtained using the following formula:

$$R(t) = \frac{(intensity_{460nm} - background_{460nm})}{(intensity_{580nm} - background_{580nm})}$$

The data is further reduced by calculating the initial ($R_i$) and final ($R_f$) ratios. These are the average ratio values during part or all of the pre-stimulation period, and during sample points during the stimulation period. The response to the stimulus $R=R_f/R_i$ is then calculated.

Control responses are obtained by performing assays in the presence of a compound with the desired properties (positive control), such as tetracaine, and in the absence of pharmacological agents (negative control). Responses to the negative (N) and positive (P) controls are calculated as above. The compound antagonist activity A is defined as:

$$A = \frac{R-P}{N-P} * 100.$$

where R is the ratio response of the test compound.

Electrophysiology Assays for NaV Activity and Inhibition of Test Compounds

Patch clamp electrophysiology was used to assess the efficacy and selectivity of sodium channel blockers in dorsal root ganglion neurons. Rat neurons were isolated from the dorsal root ganglions and maintained in culture for 2 to 10 days in the presence of NGF (50 ng/ml) (culture media consisted of NeurobasalA supplemented with B27, glutamine and antibiotics). Small diameter neurons (nociceptors, 8-12 μm in diameter) have been visually identified and probed with fine tip glass electrodes connected to an amplifier (Axon Instruments). The "voltage clamp" mode has been used to assess the compound's IC50 holding the cells at −60 mV. In addition, the "current clamp" mode has been employed to test the efficacy of the compounds in blocking action potential generation in response to current injections. The results of these experiments have contributed to the definition of the efficacy profile of the compounds.

Voltage-Clamp Assay in DRG Neurons

TTX-resistant sodium currents were recorded from DRG somata using the whole-cell variation of the patch clamp technique. Recordings were made at room temperature (~22° C.) with thick walled borosilicate glass electrodes (WPI; resistance 3-4 MΩ) using an Axopatch 200B amplifier (Axon Instruments). After establishing the whole-cell configuration, approximately 15 minutes were allowed for the pipette solution to equilibrate within the cell before beginning recording. Currents were lowpass filtered between 2-5 kHz and digitally sampled at 10 kHz. Series resistance was compensated 60-70% and was monitored continuously throughout the experiment. The liquid junction potential (−7 mV) between the intracellular pipette solution and the external recording solution was not accounted for in the data analysis. Test solutions were applied to the cells with a gravity driven fast perfusion system (SF-77; Warner Instruments).

Dose-response relationships were determined in voltage clamp mode by repeatedly depolarizing the cell from the experiment specific holding potential to a test potential of +10 mV once every 60 seconds. Blocking effects were allowed to plateau before proceeding to the next test concentration.

Solutions

Intracellular solution (in mM): Cs—F (130), NaCl (10), $MgCl_2$ (1), EGTA (1.5), $CaCl_2$ (0.1), HEPES (10), glucose (2), pH=7.42, 290 mOsm.

Extracellular solution (in mM): NaCl (138), $CaCl_2$ (1.26), KCl (5.33), $KH_2PO_4$ (0.44), $MgCl_2$ (0.5), $MgSO_4$ (0.41), $NaHCO_3$ (4), $Na_2HPO_4$ (0.3), glucose (5.6), HEPES (10), CdCl2 (0.4), NiCl2 (0.1), TTX ($0.25 \times 10^{-3}$).

Current-Clamp Assay for NaV Channel Inhibition Activity of Compounds

Cells were current-clamped in whole-cell configuration with a Multiplamp 700A amplifier (Axon Inst). Borosilicate pipettes (4-5 MOhm) were filled with (in mM):150 K-gluconate, 10 NaCl, 0.1 EGTA, 10 Hepes, 2 $MgCl_2$, (buffered to pH 7.34 with KOH). Cells were bathed in (in mM): 140 NaCl, 3 KCl, 1 MgCl, 1 CaCl, and 10 Hepes). Pipette potential was zeroed before seal formation; liquid junction potentials were not corrected during acquisition. Recordings were made at room temperature.

Following these procedures, representative compounds of the present invention were found to possess desired voltage gated sodium channel activity and selectivity.

Assays for Detecting and Measuring L-Type CaV 1.2 Inhibition Properties of Compounds A) Optical methods for assaying CaV inhibition properties of compounds:

Compounds of the invention are useful as antagonists of voltage-gated calcium ion channels. Antagonist properties of test compounds were assessed as follows. Cells expressing the CaV of interest were placed into microtiter plates. After an incubation period, the cells were stained with fluorescent dyes sensitive to the transmembrane potential. The test compounds were added to the microtiter plate. The cells were stimulated with electrical means to evoke a CaV dependent membrane potential change from unblocked channels, which was detected and measured with trans-membrane potential-sensitive dyes. Antagonists were detected as a decreased membrane potential response to the stimulus. The optical membrane potential assay utilized voltage-sensitive FRET sensors described by Gonzalez and Tsien (See, Gonzalez, J. E. and R. Y. Tsien (1995) "Voltage sensing by fluorescence resonance energy transfer in single cells" *Biophys J* 69(4): 1272-80, and Gonzalez, J. E. and R. Y. Tsien (1997) "Improved indicators of cell membrane potential that use fluorescence resonance energy transfer" *Chem Biol* 4(4): 269-77) in combination with instrumentation for measuring fluorescence changes such as the Voltage/Ion Probe Reader (VIPR®) (See, Gonzalez, J. E., K. Oades, et al. (1999) "Cell-based assays and instrumentation for screening ion-channel targets" *Drug Discov Today* 4(9): 431-439).

VIPR® optical membrane potential assay method with electrical stimulation Positive Control (100% Block)

The positive control for this assay was 125 uM mibefradil, achieved by adding 25 uL of 250 uM solution to the assay plates containing 25 uL of assay buffer. Each assay plate included positive control wells.

Negative Control (No Block)

The negative (baseline) control for this assay was DMSO. This was achieved by adding 25 uL of 1% DMSO (in assay buffer) to the assay plates containing 25 uL of assay buffer. Each assay plate included negative control wells.

Background Subtraction

Fluorescence background from plastic in assay plates (or from the assay buffer) was assessed by running a cell-free plate through the EVIPR under the same optical configuration. The average background values for each row and each wavelength were subtracted in MOD3 prior to ratio change and activity calculations.

Reagents
  Assay Buffers:
  Bath Y (Prepared by Vertex Lab Support)
  140 mM TMA-Cl
  4.5 mM KCl
  1 mM $MgCl_2$
  10 mM HEPES, pH7.4
  10 mM glucose
  Osmolarity=295mOsm (280-310 acceptable range)
  500 mM $BaCl_2$ (Sigma #B0750), in $H_2O$
  100 mg/mL Pluronic F-127 (Sigma #P2443), in dry DMSO
  10 mM $DiSBAC_2(3)$ (Aurora #00-100-010) in dry DMSO
  10 mM CC2-DMPE (Aurora #00-100-008) in dry DMSO
  200 mM Acid Yellow 17 (Aurora #VABSC) in $H_2O$
Assay Volume
  50 uL
DMSO Conc in Assay
  0.5% (1 uL of 75% DMSO/25% water, dilution factor of 160)
Incubation Time of Compounds
  20-25 minutes
Instrumentation
  This screen was conducted on the Allegro™ system. The system is diagrammed below: The Allegro™ is equipped with a compound plate storage unit (stacker). The stacker holds a set of trays (each tray holds 12 compound plates). The libraries were received from Compound Management, as pre-spotted (1 uL/well of compound and controls) intermediate plates in 384-well format, as a 1.6 mM stock solution in 75% DMSO/25% de-ionized $H_2O$. The plates are diluted in 80 uL oxonol dye solution to create a 2× stock. Three EVIPR readers are integrated to the Allegro system by a Mitsubishi robotic arm. Only one EVIPR was used per run.
Instrumentation Settings
  Optical:
  Read Frequency: 10 Hz
  Excitation Wavelength: 400 nm
  Emission Wavelengths: 460 nm and 560 nm
  Electrical Stimulation:
  Pulse Width: 11.1 ms
    Stimulation Current: 0.8 amps
    Stimulation Frequency: 90 Hz
  Pre-stimulation time: 2 s
  Stimulation time: 3 s
  Post-stimulation time: 1 s
  Waveform: Biphasic Square Wave
Plate Washer Settings:
  Settings for ELx405 washer will leave a residual volume of 25 uL.
  Plate Type: 384
  # of cycles: 3
  Soak/shake: No

| Dispense: | dispense volume | 100 |
|---|---|---|
|  | dispense flow rate | 1 |
|  | dispense height | 80 |
|  | horizontal disp pos | −20 |
|  | horiz y disp pos | −5 |
| Aspirate: | aspirate height | 48 |
|  | horizontal aspr pos | −18 |
|  | horiz y asp pos | −5 |
|  | aspiration rate | 0 |
|  | aspiration delay | 0 |
|  | final asp delay | 500 |

Assay Procedure
  Procedure run on HTS Allegro™:
    1. Carousel: Assay plates (Cell plates) loaded into carousel module #1 ($CO_2$=5%, ambient temperature and Rh)
    2. Barrier: Assay plates retrieved from carousel and passed through environmental barrier (The remaining steps are conducted at room temperature and ambient $CO_2$)
    3. Washer: Assay plates washed with Bath Y on Biotek ELx405.
    4. MultiReagent Dispenser (MRD): 25 uL of CC2-DMPE (and equal volume Pluronic) in Bath Y added to each well to make 10 uM.
    5. Barrier: Assay plates passed through barrier.
    6. Carousel: 30-minute incubation at room temperature.
    7. Barrier: Assay plates passed through barrier.
    8. Washer: Assay plates washed with Bath Y on Biotek ELx405
    9. High Density Transfer Station:
      a. 80 uL oxonol dye loading solution (4 uM DISBAC2(3), 1 mM VABSC and 30 mM $BaCl_2$ in BathY) added to compound plates (pre-spotted with 1 uL compound) using a Multiprop (offline)
      b. Plates mixed (3 times 20 uL) on CyBiWell (offline). Plates loaded onto compound tray.
      c. Compound tray retrieved from compound tray stacker and compound plate barcodes read.
      d. Assay plate barcode read and moved to SciClone deck
      e. 25 uL compound plus oxonol aspirated from compound plate on SciClone deck and transferred to assay plate.
        i. Final assay volume=50 uL
        ii. Final compound concentration=10 uM
      f. SciClone tips washed in DMSO and 5% ethanol in water to remove external carry-over.
    10. Carousel: Assay plates incubated for 20 minutes at RT
    11. Barrier: Assay plates passed through final barrier
    12. Mitsubishi Robotic Arm: Retrieves assay plate from barrier output, delivers cell plates to EVIPR 384-1, and sends command to initiate EVIPR run.
Assay Window
  Assay Window Criteria:
  Passing plates≦0.5, rejected plates>0.5

$$\text{Assay Window} = \frac{3(SD_{FullBlock} + SD_{Baseline})}{(AVE_{Baseline} - AVE_{FullBlock})} = 1 - Z'$$

Data Reduction
  The EVIPR files were reduced to decrease the amount of data pumped into the database. Two "windows" of interest were filtered out of each EVIPR file. Each window is a slice of the response measured in each well. The first window is measured before stimulation. The second window samples the peak of the response. The ratio of the two is used to determine the response size.
Data Analysis
  Once the data were collected on the VIPR, they were archived and uploaded, in reduced form, to Mod3. Once in Mod3, each individual assay plate was QC'ed (looking for acceptable window and dynamic range).
  Herg Assay
  hERG-inhibition was assayed in a Chinese Hamster Lung cell line (CHL) stably transduced with the structural gene for hERG. Cells express high numbers of hERG channels resulting in 500 pA to 1.5nA of hERG outward $K^+$ currents. The method used a planar patch instrument (IonWorks HT, Molecular Devices) that allowed medium-throughput electrophysiology measurements in 384-well format. The potency of hERG inhibition was measured at 1.1 µM, 3.3 µM, 10 µM, and 30 µM of the compound studied. The compound was added from a 3× aqueous addition buffer.

The compounds of the present invention exhibit a desirably low activity against hERG.

CYP-450 Isozyme Assay

Compound Preparation:
1. The desired compound was plated (2 mM in 75% DMSO/25% $H_2O$) with a Pieso Sample Distribution Robot (PSDR™) at 8mL per well.
2. The compound was centrifuged briefly at approximately 1000 rpm to shift the compound drop to the bottom of the well.
3. PVP 10K (excipient, 0.2% in 75% DMSO/25% $H_2O$) was plated with a PSDR™ at 100 nL per well.
4. The compound and PVP 10K were centrifuged briefly at approximately 1000 rpm to ensure an adequate mix of compound and excipient.
5. The dry-down of the plates was initiated using house vacuum for at least 3 hours.
6. The plates were transferred to a high vacuum (50 millitorr) apparatus and the dry-down process was continued for at least 15 hours.

The following assay protocol was employed for a desired CYP-450 isozyme (CYP3A4, CYP2C9, CYP1A2, CYP2C19, or CYP2D6).

Assay Protocol

All reagents below were added using a Flying Reagent Dispenser (FRD™).
1. 800 nL of $dH_2O$ was added to the 100% activity control, compound, and background control wells.
2. 800 nL of the appropriate control drug (3A4:clotrimazole, 2C9:miconazole, 1A2:ticlopidine, 2C19:lansoprazole, or 2D6:propanolol; 10 uM final dissolved in $dH_2O$) was added to the drug control wells.
3. 200 nL of 500 mM $K^+$ Phosphate buffer (pH 8.4) was added to the 100% activity control, drug control, and compound wells.
4. 600 nL of Control Insect Baculosomes (PanVera P2315) in 500 mM $K^+$ Phosphate Buffer (pH 8.4) was added to the background control wells. The calculation for this reagent was based on the protein concentration of the 100% activity control wells.
5. The plate was scanned for compound fluorescence using a NanoPlate™ Fluorescence Plate Reader (NPR™).
6. 200 mL of $NADP^+$ (Sigma, 100 µM final) and substrate in 100 mM $K^+$ Phosphate buffer (50 mM $K^+$ Phosphate buffer for 2C9 and 2C19) was added to all wells. Fluorogenic substrate (3A4:5 µM Vivid™ 3A4 Red, 2C9:1 µM Vivid™ 2C9 Green, 1A2:2 µM Vivid™ 1A2 Blue, 2C19:10 µM Vivid™ 2C19 Blue, and 2D6: 10 µM Vivid™ 2D6 Blue) was added at a final concentration corresponding to the $K_m$ of the substrate for its pertinent CYP450 isozyme.
7. 400 nL of the desired CYP450 isozyme and recycling buffer (3.3 mM glucose-6-phosphate, 0.4 units/ml glucose-6-phosphate dehydrogenase, 100 mM $MgCl_2$, and 0.00025% Antifoam 289; reagents obtained from Sigma) in 100 mM $K^+$ Phosphate Buffer (50 mM $K^+$ Phosphate buffer for 2C9 and 2C19) were added to the 100% activity control, drug control, and compound wells. The desired isozyme was added to obtain the following final concentrations of the desired isozyme: 5 nM CYP3A4, 10 nM CYP2C9, 5 nM CYP1A2, 5 nM CYP2C19, or 20 nM CYP2D6.
8. The plate was incubated for 60 minutes at room temperature.
9. The plate was scanned for solution fluorescence using a NanoPlate™ Fluorescence Plate Reader (NPR™).
10. The NPR™ data was converted into a format compatible with importation into a data visualizer and complete the analysis of data acquired.

The compounds of the present invention exhibit a desirably low activity against one or more of the CYP450 isozymes.

The activity of selected compounds of the present invention against NaV 1.8 channel is shown below in Table 4. In Table 4, the symbols have the following meaning: "+++" means <2 µM; "++" means between 2 µM and 10 µM; and "+" means >10 µM.

TABLE 4

| Cmpd # | IC50 |
|---|---|
| 101 | +++ |
| 102 | ++ |
| 103 | + |
| 104 | + |
| 105 | ++ |
| 106 | + |
| 107 | ++ |
| 108 | ++ |
| 109 | ++ |
| 110 | + |
| 111 | + |
| 112 | + |
| 113 | ++ |
| 114 | ++ |
| 115 | + |
| 116 | ++ |
| 117 | ++ |
| 118 | ++ |
| 119 | + |
| 120 | ++ |
| 121 | ++ |
| 122 | ++ |
| 123 | + |
| 124 | + |
| 125 | + |
| 126 | + |
| 127 | +++ |
| 128 | ++ |
| 129 | + |
| 130 | + |
| 131 | + |
| 132 | ++ |
| 133 | ++ |
| 134 | ++ |
| 135 | +++ |
| 136 | + |
| 137 | ++ |
| 138 | + |
| 139 | ++ |
| 140 | + |
| 141 | + |
| 142 | ++ |
| 143 | ++ |
| 144 | ++ |
| 145 | + |
| 146 | + |
| 147 | ++ |
| 148 | ++ |
| 149 | + |
| 150 | + |
| 151 | + |
| 152 | + |
| 153 | ++ |
| 154 | + |
| 155 | + |
| 156 | ++ |
| 157 | ++ |
| 158 | + |
| 159 | ++ |

TABLE 4-continued

| Cmpd # | IC50 |
|---|---|
| 160 | + |
| 162 | ++ |
| 163 | ++ |
| 164 | + |
| 165 | ++ |
| 166 | + |
| 167 | + |
| 168 | ++ |
| 169 | + |
| 170 | + |
| 172 | + |
| 173 | + |
| 174 | ++ |
| 175 | + |
| 176 | + |
| 177 | ++ |
| 178 | + |
| 179 | + |
| 180 | ++ |
| 181 | + |
| 182 | ++ |
| 183 | ++ |
| 184 | ++ |
| 185 | ++ |
| 186 | +++ |
| 187 | ++ |
| 188 | +++ |
| 189 | ++ |
| 190 | ++ |
| 191 | +++ |
| 192 | ++ |
| 193 | +++ |
| 194 | + |
| 195 | +++ |
| 196 | +++ |
| 197 | +++ |
| 201 | ++ |
| 203 | + |
| 204 | + |
| 205 | + |
| 206 | ++ |
| 207 | +++ |
| 208 | +++ |
| 210 | ++ |
| 211 | + |
| 212 | + |
| 213 | + |
| 214 | + |
| 215 | + |
| 216 | + |
| 217 | + |
| 218 | ++ |
| 219 | +++ |
| 220 | + |
| 221 | + |
| 222 | + |
| 223 | + |
| 224 | + |
| 225 | + |
| 226 | + |
| 227 | + |
| 228 | + |
| 229 | + |
| 230 | ++ |
| 231 | ++ |
| 232 | ++ |
| 233 | + |
| 234 | + |
| 235 | ++ |
| 236 | + |
| 237 | + |
| 238 | + |
| 239 | + |
| 240 | + |
| 241 | + |
| 242 | ++ |
| 243 | + |
| 244 | + |
| 245 | + |
| 246 | + |
| 247 | + |
| 248 | ++ |
| 249 | ++ |
| 250 | +++ |
| 251 | ++ |
| 252 | + |
| 253 | + |
| 254 | ++ |
| 255 | + |
| 256 | ++ |
| 257 | ++ |
| 258 | +++ |
| 259 | +++ |
| 260 | +++ |
| 261 | ++ |
| 262 | ++ |
| 264 | + |
| 265 | + |
| 266 | ++ |
| 267 | + |
| 268 | + |
| 269 | + |
| 270 | ++ |
| 271 | + |
| 272 | ++ |
| 273 | ++ |
| 274 | ++ |
| 275 | ++ |
| 276 | ++ |
| 277 | ++ |
| 278 | + |
| 279 | ++ |
| 280 | ++ |
| 281 | ++ |
| 282 | +++ |
| 283 | +++ |
| 301 | ++ |
| 302 | + |
| 303 | ++ |
| 304 | + |
| 305 | ++ |
| 306 | + |
| 307 | + |
| 308 | + |
| 309 | +++ |
| 310 | ++ |
| 311 | +++ |
| 312 | ++ |
| 314 | ++ |
| 315 | + |
| 316 | + |
| 317 | ++ |
| 318 | + |
| 319 | ++ |
| 320 | ++ |
| 321 | + |
| 322 | + |
| 323 | + |
| 324 | + |
| 325 | + |
| 326 | + |
| 327 | + |
| 328 | + |
| 329 | ++ |
| 335 | ++ |
| 337 | ++ |
| 338 | + |
| 339 | ++ |
| 340 | +++ |
| 342 | + |
| 345 | ++ |
| 346 | ++ |
| 347 | + |
| 348 | + |
| 349 | + |
| 350 | + |

TABLE 4-continued
| Cmpd # | IC50 |
|---|---|
| 351 | ++ |
| 352 | + |
| 353 | + |
| 354 | ++ |
| 355 | + |
| 356 | + |
| 357 | + |
| 358 | + |
| 359 | + |
| 360 | + |
| 361 | ++ |
| 362 | + |
| 363 | ++ |
| 364 | +++ |
| 365 | +++ |
| 366 | ++ |
| 367 | +++ |
| 368 | ++ |
| 369 | +++ |
| 370 | +++ |
| 371 | +++ |
| 372 | +++ |
| 373 | ++ |
| 374 | + |
| 375 | + |
| 376 | + |
| 377 | ++ |
| 401 | + |
| 402 | + |
| 403 | + |
| 404 | + |
| 405 | + |
| 406 | + |
| 407 | + |
| 408 | + |
| 409 | + |
| 410 | + |
| 411 | ++ |
| 412 | + |
| 413 | ++ |
| 414 | ++ |
| 415 | ++ |
| 416 | + |
| 417 | + |
| 418 | ++ |
| 419 | ++ |
| 420 | +++ |
We claim:
1. A compound selected from the group consisting of:
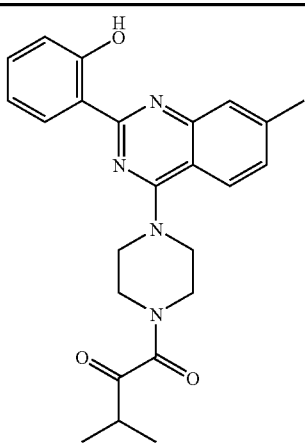
186
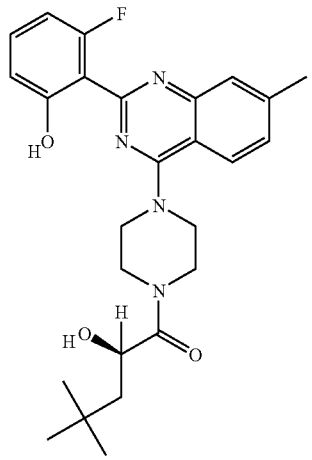
188
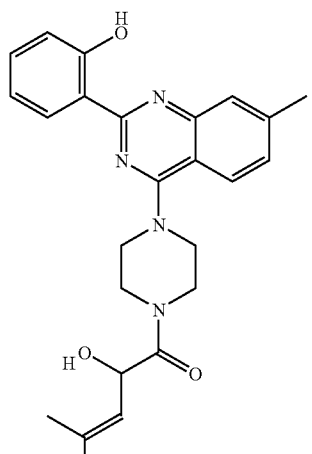
189
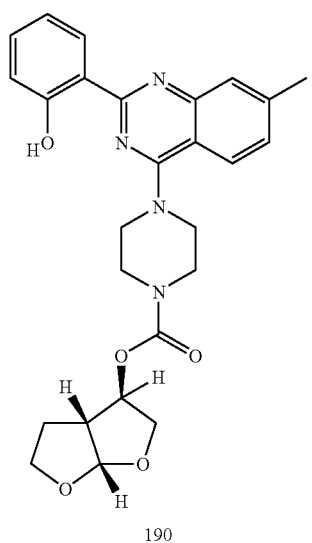
190

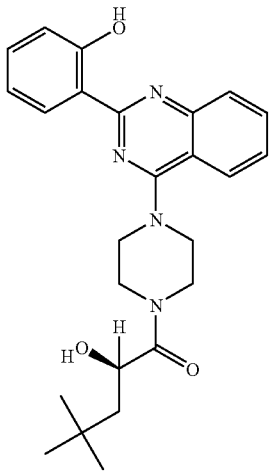
191
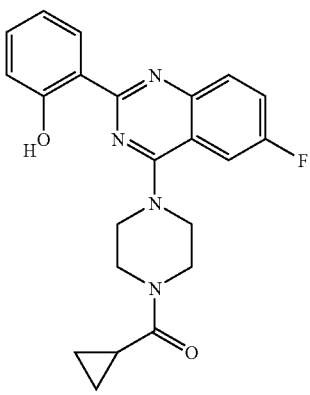
192
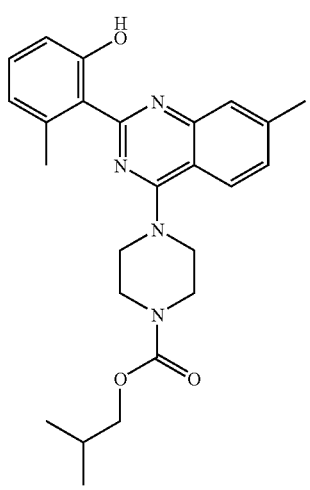
193
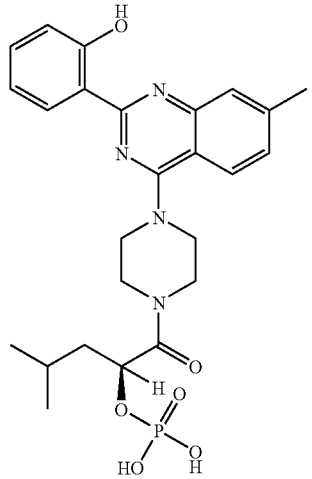
194
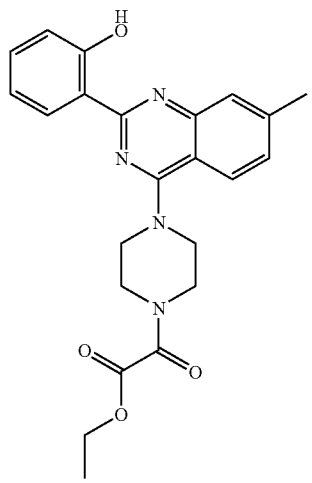
195
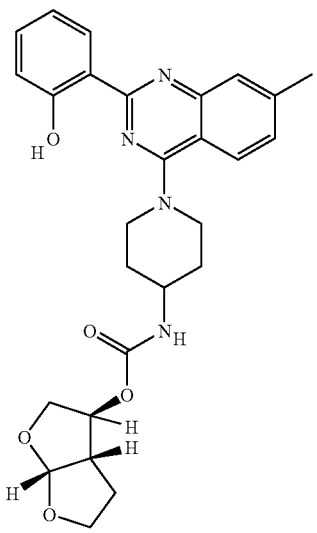
280

| 565 -continued | 566 -continued |
|---|---|
| 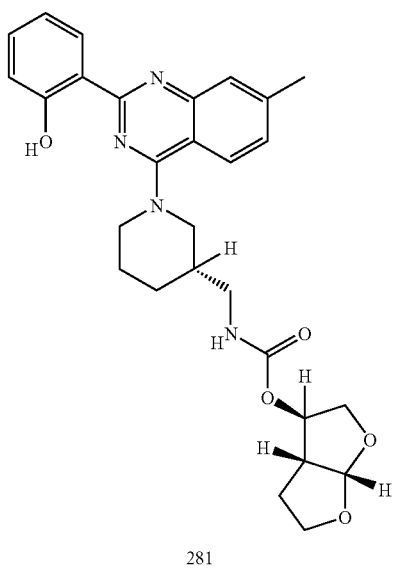 281 | 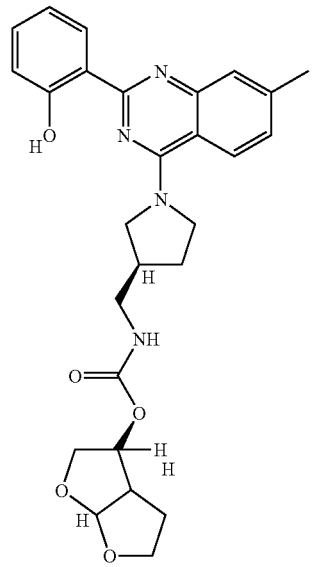 378 |
| 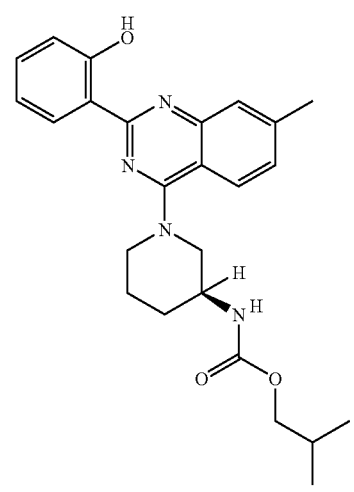 282 | 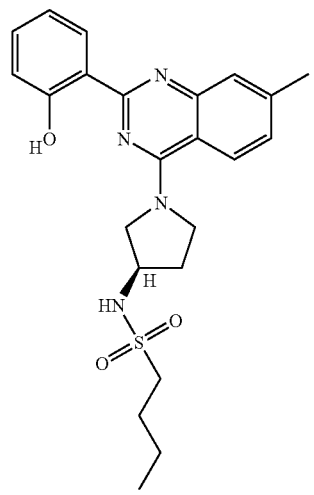 379 |
| 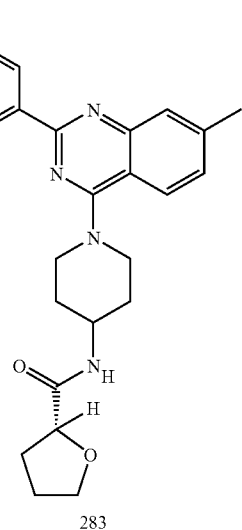 283 | 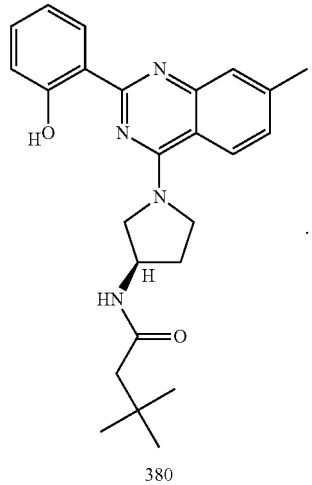 380 |

2. A pharmaceutical composition comprising a compound according to claim 1, and a pharmaceutically acceptable carrier.

3. A method for treating or lessening the severity of a disorder or condition selected from acute, chronic, neuropathic, or inflammatory pain, or severe pain said method comprising the step of administering to said patient an effective amount of a composition according to claim 2.

4. The method according to claim 3, wherein the condition or disorder is back pain, head pain, or neck pain.

5. The method according to claim 3, wherein the condition or disorder is severe pain, acute pain, postsurgical pain, back pain, or cancer pain.

\* \* \* \* \*